US012404306B2

(12) United States Patent
Brough et al.

(10) Patent No.: US 12,404,306 B2
(45) Date of Patent: Sep. 2, 2025

(54) HUMAN PAPILLOMAVIRUS VACCINES AND USES OF THE SAME

(71) Applicant: Precigen, Inc., Germantown, MD (US)

(72) Inventors: Douglas E. Brough, Germantown, MD (US); Cheryl G. Bolinger, Germantown, MD (US); Ramya Yarlagadda, Blacksburg, VA (US); Vinodhbabu Kurella, Blacksburg, VA (US); Prabakaran Ponraj, Blacksburg, VA (US); Simon Metenou, Germantown, MD (US); Kuan-Fu Ding, Blacksburg, VA (US)

(73) Assignee: Precigen, Inc., Germantown, MD (US)

( * ) Notice: Subject to any disclaimer, the term of this patent is extended or adjusted under 35 U.S.C. 154(b) by 1281 days.

(21) Appl. No.: 16/978,573

(22) PCT Filed: Mar. 6, 2019

(86) PCT No.: PCT/US2019/020933
§ 371 (c)(1),
(2) Date: Sep. 4, 2020

(87) PCT Pub. No.: WO2019/173465
PCT Pub. Date: Sep. 12, 2019

(65) Prior Publication Data

US 2021/0024586 A1 Jan. 28, 2021

Related U.S. Application Data

(60) Provisional application No. 62/639,354, filed on Mar. 6, 2018.

(51) Int. Cl.

| | |
|---|---|
| ***C07K 14/005*** | (2006.01) |
| ***A61K 39/12*** | (2006.01) |
| ***A61K 39/29*** | (2006.01) |
| ***A61K 48/00*** | (2006.01) |
| ***C07K 14/02*** | (2006.01) |
| ***C12N 7/00*** | (2006.01) |
| ***C12N 15/861*** | (2006.01) |

(52) U.S. Cl.
CPC ............ *C07K 14/005* (2013.01); *A61K 39/12* (2013.01); *A61K 39/292* (2013.01); *A61K 48/0066* (2013.01); *C07K 14/02* (2013.01); *C12N 7/00* (2013.01); *C12N 15/861* (2013.01); *C07K 2319/33* (2013.01); *C12N 2710/20022* (2013.01); *C12N 2710/20034* (2013.01)

(58) Field of Classification Search
None
See application file for complete search history.

(56) References Cited

U.S. PATENT DOCUMENTS

| | | | |
|---|---|---|---|
| 4,985,461 | A | 1/1991 | Hsu et al. |
| 5,117,057 | A | 5/1992 | Hsu et al. |
| 5,122,464 | A | 6/1992 | Wilson et al. |
| 5,225,443 | A | 7/1993 | Murphy et al. |
| 5,283,173 | A | 2/1994 | Fields et al. |
| 5,350,674 | A | 9/1994 | Boenisch et al. |
| 5,378,726 | A | 1/1995 | Yanagi et al. |
| 5,530,028 | A | 6/1996 | Lidert et al. |
| 5,585,362 | A | 12/1996 | Wilson et al. |
| 5,770,359 | A | 6/1998 | Wilson et al. |
| 5,837,511 | A | 11/1998 | Falck-Pedersen et al. |
| 5,851,806 | A | 12/1998 | Kovesdi et al. |
| 5,880,333 | A | 3/1999 | Goff et al. |
| 5,885,827 | A | 3/1999 | Wabl et al. |
| 5,994,106 | A | 11/1999 | Kovesdi et al. |
| 5,994,128 | A | 11/1999 | Fallaux et al. |
| 5,998,205 | A | 12/1999 | Hallenbeck et al. |
| 6,013,836 | A | 1/2000 | Hsu et al. |
| 6,033,908 | A | 3/2000 | Bout et al. |
| 6,127,175 | A | 10/2000 | Vigne et al. |
| 6,225,289 | B1 | 5/2001 | Kovesdi et al. |
| 6,265,173 | B1 | 7/2001 | Evans et al. |
| 6,482,616 | B1 | 11/2002 | Kovesdi et al. |
| 6,489,458 | B2 | 12/2002 | Hackett et al. |
| 6,514,943 | B2 | 2/2003 | Kovesdi et al. |
| 6,613,752 | B2 | 9/2003 | Kay et al. |
| 6,677,156 | B2 | 1/2004 | Brough et al. |
| 6,682,929 | B2 | 1/2004 | Brough et al. |

(Continued)

FOREIGN PATENT DOCUMENTS

| | | | |
|---|---|---|---|
| EP | 0234994 | B1 | 9/1991 |
| EP | 0461809 | B1 | 12/1994 |

(Continued)

OTHER PUBLICATIONS

Khatun, Sabera, et al. "Safety and immunogenicity profile of human papillomavirus-16/18 AS04 adjuvant cervical cancer vaccine: a randomized controlled trial in healthy adolescent girls of Bangladesh." Japanese journal of clinical oncology 42.1 (2012): 36-41. (Year: 2012).*

(Continued)

*Primary Examiner* — Kara D Johnson
*Assistant Examiner* — Constantina E Stavrou
(74) *Attorney, Agent, or Firm* — Barnes & Thornburg LLP; Gene J. Yao

(57) ABSTRACT

Provided herein are engineered human papilloma virus (HPV) molecular vaccine constructs. Vaccine constructs can also include ligand-inducible engineered gene switch systems for modulating expression of heterologous genes, such as a cytokines, in host cells.

12 Claims, 19 Drawing Sheets

Specification includes a Sequence Listing.

(56) References Cited

U.S. PATENT DOCUMENTS

| | | | |
|---|---|---|---|
| 7,091,038 B2 | 8/2006 | Palli et al. | |
| 7,148,203 B2 | 12/2006 | Hackett et al. | |
| 7,195,896 B2 | 3/2007 | Kovesdi et al. | |
| 7,531,326 B2 | 5/2009 | Kapitskaya et al. | |
| 7,563,879 B2 | 7/2009 | Palli | |
| 7,601,508 B2 | 10/2009 | Palli et al. | |
| 7,776,587 B2 | 8/2010 | Palli et al. | |
| 7,807,417 B2 | 10/2010 | Palli et al. | |
| 7,829,676 B2 | 11/2010 | Zhang et al. | |
| 7,919,269 B2 | 4/2011 | Zhang et al. | |
| 7,935,510 B2 | 5/2011 | Palli et al. | |
| 7,985,739 B2 | 7/2011 | Kay et al. | |
| 8,021,878 B2 | 9/2011 | Palli | |
| 8,030,067 B2 | 10/2011 | Zhang et al. | |
| 8,076,454 B2 | 12/2011 | Palli et al. | |
| 8,076,517 B2 | 12/2011 | Hormann et al. | |
| 8,105,825 B2 | 1/2012 | Dhadialla et al. | |
| 8,168,426 B2 | 5/2012 | Dhadialla et al. | |
| 8,202,718 B2 | 6/2012 | Palli et al. | |
| 8,227,432 B2 | 7/2012 | Hackett et al. | |
| 8,236,556 B2 | 8/2012 | Kapitskaya et al. | |
| 8,497,093 B2 | 7/2013 | Palli | |
| 8,598,409 B2 | 12/2013 | Kapitskaya et al. | |
| 8,603,950 B2 | 12/2013 | Bowers et al. | |
| 8,715,959 B2 | 5/2014 | Palli et al. | |
| 9,228,180 B2 | 1/2016 | Izsvak et al. | |
| 9,249,207 B2 | 2/2016 | Palli et al. | |
| 9,402,919 B2 | 8/2016 | Roeth et al. | |
| 9,492,482 B2 | 11/2016 | Beech et al. | |
| 9,493,540 B2 | 11/2016 | Palli et al. | |
| 2004/0049037 A1 | 3/2004 | Tice et al. | |
| 2004/0171651 A1 | 9/2004 | Hormann et al. | |
| 2005/0209283 A1 | 9/2005 | Hormann et al. | |
| 2005/0287161 A1 | 12/2005 | Dubin et al. | |
| 2006/0020146 A1 | 1/2006 | Hormann et al. | |
| 2006/0100416 A1 | 5/2006 | Palli et al. | |
| 2007/0203326 A1 | 8/2007 | Dedhar et al. | |
| 2008/0233650 A1 | 9/2008 | Gall et al. | |
| 2009/0123441 A1 | 5/2009 | Braughler et al. | |
| 2009/0136465 A1 | 5/2009 | Merenick et al. | |
| 2010/0175141 A1 | 7/2010 | Collins et al. | |
| 2011/0117072 A1 | 5/2011 | Izsvak et al. | |
| 2011/0212528 A1 | 9/2011 | Palli et al. | |
| 2011/0268766 A1 | 11/2011 | Beech et al. | |
| 2012/0167239 A1 | 6/2012 | Palli et al. | |
| 2013/0123199 A1 | 5/2013 | Lee | |
| 2013/0195800 A1 | 8/2013 | Roeth et al. | |
| 2013/0243805 A1 | 9/2013 | Apelian et al. | |
| 2015/0140025 A1* | 5/2015 | Wei | A61K 39/12 435/320.1 |
| 2016/0208285 A1 | 7/2016 | Roeth et al. | |

FOREIGN PATENT DOCUMENTS

| | | | |
|---|---|---|---|
| WO | WO-9208796 A1 | 5/1992 | |
| WO | WO-9428143 A1 | 12/1994 | |
| WO | WO-9428152 A1 | 12/1994 | |
| WO | WO-9502697 A1 | 1/1995 | |
| WO | WO-9516772 A1 | 6/1995 | |
| WO | WO-9534671 A1 | 12/1995 | |
| WO | WO-9622378 A1 | 7/1996 | |
| WO | WO-9700326 A1 | 1/1997 | |
| WO | 1997005164 A1 | 2/1997 | |
| WO | WO-9712986 A2 | 4/1997 | |
| WO | WO-9721826 A2 | 6/1997 | |
| WO | WO-9738117 A1 | 10/1997 | |
| WO | WO-9902683 A1 | 1/1999 | |
| WO | WO-9958155 A1 | 11/1999 | |
| WO | WO-0000628 B1 | 3/2000 | |
| WO | WO-0034444 A2 | 6/2000 | |
| WO | WO-0151528 A1 | 7/2001 | |
| WO | WO-0170816 A2 | 9/2001 | |
| WO | WO-0198333 A2 | 12/2001 | |
| WO | WO-0229075 A2 | 4/2002 | |
| WO | WO-02066612 A2 | 8/2002 | |
| WO | WO-02066613 A2 | 8/2002 | |
| WO | WO-02066614 A2 | 8/2002 | |
| WO | WO-02066615 A2 | 8/2002 | |
| WO | WO-03020879 A2 | 3/2003 | |
| WO | WO-03022311 A1 | 3/2003 | |
| WO | WO-03027266 A2 | 4/2003 | |
| WO | WO-03027289 A1 | 4/2003 | |
| WO | WO-2005108617 A2 | 11/2005 | |
| WO | WO-2008145745 A1 | 12/2008 | |
| WO | WO-2008153801 A1 | 12/2008 | |
| WO | WO-2009045370 A2 | 4/2009 | |
| WO | WO-2009048560 A1 | 4/2009 | |
| WO | WO-2010042189 A2 | 4/2010 | |
| WO | WO-2011119773 A1 | 9/2011 | |
| WO | WO-2012122025 A2 | 9/2012 | |
| WO | 2013/053008 A2 | 4/2013 | |
| WO | WO-2013052799 A2 | 4/2013 | |
| WO | WO-2013052811 A2 | 4/2013 | |
| WO | WO-2013052832 A2 | 4/2013 | |
| WO | 2013112549 A1 | 8/2013 | |
| WO | WO-2015095249 A1 | 6/2015 | |
| WO | 2015/106281 A1 | 7/2015 | |
| WO | 2016024255 A1 | 2/2016 | |
| WO | WO-2016048903 A1 | 3/2016 | |
| WO | WO-2016145146 A1 | 9/2016 | |
| WO | WO-2017037280 A1 | 3/2017 | |
| WO | WO-2017062953 A1 | 4/2017 | |
| WO | WO-2017070284 A1 | 4/2017 | |
| WO | WO-2017083750 A1 | 5/2017 | |
| WO | WO-2017096432 A1 | 6/2017 | |
| WO | WO-2017132547 A1 * | 8/2017 | A61K 35/74 |
| WO | 2017210649 A1 | 12/2017 | |
| WO | WO-2019173463 A1 | 9/2019 | |
| WO | WO-2019173465 A1 | 9/2019 | |

OTHER PUBLICATIONS

NCBI NIH ANKRD49 gene listing, https://www.ncbi.nlm.nih.gov/gene/54851. (Year: 2024).*

Tsang, Kwong Y., et al. "Identification and characterization of enhancer agonist human cytotoxic T-cell epitopes of the human papillomavirus type 16 (HPV16) E6/E7." Vaccine 35.19 (2017): 2605-2611. (Year: 2017).*

Paolini, Francesca, et al. "HPV 16 E5 oncoprotein is expressed in early stage carcinogenesis and can be a target of immunotherapy." Human Vaccines & Immunotherapeutics 13.2 (2017): 291-297. (Year: 2017).*

Cordeiro et al, Human Vaccine & Immunotherapeutics (2015), 11:45-52.

Martinez-Zapien et al, Nature (2016), 529:541-545.

Altschul, S.F., et al., "Basic Local Alignment Search Tool," Journal of Molecular Biology 215(3):403-410, Elsevier, United Kingdom (Oct. 1990).

Altschul, S.F., et al., "Gapped BLAST and PSI-BLAST: A New Generation of Protein Database Search Programs," Nucleic Acids Research 25(17):3389-3402, Oxford University Press, United Kingdom (Sep. 1997).

Bai, M., et al., "Mutations That Alter an Arg-gly-asp (Rgd) Sequence in the Adenovirus Type 2 Penton Base Protein Abolish Its Cell-rounding Activity and Delay Virus Reproduction in Flat Cells," Journal of Virology 67(9):5198-5205, American Society for Microbiology, United States (Sep. 1993).

Biegert, A., and Soding, J., "Sequence Context-specific Profiles for Homology Searching," Proc Natl Acad Sci USA 106(10):3770-3775, National Academy of Sciences, United States (Mar. 2009).

Bird, R.E., et al., "Single-chain Antigen-binding Proteins," Science 242(4877):423-426, Association for the Advancement of Science, United States (Oct. 1988).

Boulanger, P., et al., "Characterization of Adenovirus Protein Ix," The Journal of General Virology 44(3):783-800, Press for the Society for General Microbiology, United Kingdom (Sep. 1979).

Brash, D.E., et al., "Strontium Phosphate Transfection of Human Cells in Primary Culture: Stable Expression of the Simian Virus 40 Large-T-Antigen Gene in Primary Human Bronchial Epithelial

(56) References Cited

OTHER PUBLICATIONS

Cells," Molecular and Cellular Biology, 7(5):2031-2034, American Society for Microbiology, United States (May 1987).
Brough, D.E., et al., "Activation of Transgene Expression by Early Region 4 Is Responsible for a High Level of Persistent Transgene Expression From Adenovirus Vectors in Vivo," Journal of Virology 71(12):9206-9213, American Society for Microbiology, United States (Dec. 1997).
Chen, H.H., et al., "Persistence in Muscle of an Adenoviral Vector that Lacks all Viral Genes," Proc Natl Acad Sci USA 94(5):1645-1650, National Academy of Sciences, United States (Mar. 1997).
Chen, Y.F., et al., "Cytotoxic-t-lymphocyte Human Papillomavirus Type 16 E5 Peptide With Cpg-oligodeoxynucleotide Can Eliminate Tumor Growth in C57bl/6 Mice," Journal of Virology 78(3):1333-1343, American Society for Microbiology, United states (Feb. 2004).
Christopherson, K.S., et al., "Ecdysteroid-dependent Regulation of Genes in Mammalian Cells by a *Drosophila* Ecdysone Receptor and Chimeric Transactivators," Proc Natl Acad Sci USA 89(14):6314-6318, National Academy of Sciences, United States (1992).
Chroboczek, J., et al., "The Sequence of the Genome of Adenovirus Type 5 and Its Comparison With the Genome of Adenovirus Type 2," Virology 186(1):280-285, Academic Press, United States (Jan. 1992).
Colbere-Garapin, F., et al., "A New Dominant Hybrid Selective Marker for Higher Eukaryotic Cells," Journal of Molecular Biology 150(1):1-14, Academic Press, United Kingdom (Jul. 1981).
Conese, M., et al., "Gene therapy progress and prospects: episomally maintained self-replicating systems," Gene Therapy 11(24):1735-41, Nature Publishing Group, United Kingdom (2004).
Corpet, F, "Multiple Sequence Alignment With Hierarchical Clustering," Nucleic Acids Research 16(22):10881-10890, Oxford University Press, United Kingdom (Nov. 1988).
Crawford-Miksza, L.C., and Schnurr, D.P., "Analysis of 15 Adenovirus Hexon Proteins Reveals the Location and Structure of Seven Hypervariable Regions Containing Serotype-specific Residues," Journal of Virology 70(3): 1836-1844, American Society for Microbiology, United States (Mar. 1996).
Curiel, D.T., et al., "High-efficiency gene transfer mediated by adenovirus coupled to DNA-polylysine complexes," *Hum Gene Ther* 3(2):147-54, Mary Ann Liebert Inc., United States (1992).
Devaux, C., et al., "Structure of Adenovirus Fibre. I. Analysis of Crystals of Fibre From Adenovirus Serotypes 2 and 5 by Electron Microscopy and X-ray Crystallography," Journal of Molecular Biology 215(4):567-588, Academic Press, United Kingdom (Oct. 1990).
Field, J., et al., "Properties of the Adenovirus DNA Polymerase," The Journal of Biological Chemistry 259(15):9487-9495, American Society for Biochemistry and Molecular Biology, United States (Aug. 1984).
Funston, G.M., et al., "Expression of Heterologous Genes in Oncolytic Adenoviruses Using Picornaviral 2a Sequences That Trigger Ribosome Skipping," The Journal of General Virology 89(Pt 2):389-396, Cambridge Univ. Press for the Society for General Microbiology, United Kingdom (Feb. 2008).
Gall, J.G.D., et al., "Construction and Characterization of Hexon-chimeric Adenoviruses: Specification of Adenovirus Serotype," Journal of Virology 72(12):10260-10264, American Society for Microbiology, United States (Sep. 1998).
Genbank, "E3 14.7K [Human adenovirus 5]," Accession No. AP_000224.1, accessed at https://www.ncbi.nlm.nih.gov/protein/AP_000224, accessed on Dec. 10, 2020, 1 page.
GenBank, "E3 12.5K [Human adenovirus 5]," Accession No. AP_000218.1, accessed at https://www.ncbi.nlm.nih.gov/protein/56160551/, accessed on Dec. 10, 2020, 1 page.
GenBank, "Hepatitis B virus, complete genome," Accession No. Y07587.1, accessed at https://www.ncbi.nlm.nih.gov/nuccore/Y07587 on Dec. 15, 2020.
Ghosh-Choudhury, G., et al., "Protein Ix, A Minor Component of the Human Adenovirus Capsid, Is Essential for the Packaging of Full Length Genomes," The EMBO Journal 6(6):1733-1739, Wiley Blackwell, United Kingdom (Jun. 1987).
Ginsberg, H.S., et al., "A Proposed Terminology for the Adenovirus Antigens and Virion Morphological Subunits," Virology 28(4):782-783, Academic Press, United States (Apr. 1966).
Graham, F.L., et al., "Characteristics of a Human Cell Line Transformed by Dna From Human Adenovirus Type," The Journal of General Virology 36(1):59-74, Microbiology Society, United Kingdom (Jul. 1977).
Green, N.M., et al., "Evidence for a Repeating Cross Sheet Structure in the Adenovirus Fibre," The EMBO Journal 2(8):1357-1365, IRL Press Limited, United Kingdom (Jun. 1983).
Henikoff, S. and Henikoff, J.G., "Amino Acid Substitution Matrices from Protein Blocks," Proc Natl Acad Sci USA 89(22):10915-10919, National Academy of Sciences, United States (Nov. 1992).
Henry, L.J., et al., "Characterization of the Knob Domain of the Adenovirus Type 5 Fiber Protein Expressed in *Escherichia coli*," Journal of Virology 68(8): 5239-5246, American Society for Microbiology, United States (Aug. 1994).
Higgins, D.G and Sharp, P.M, "Clustal: A Package for Performing Multiple Sequence Alignment on a Microcomputer," Gene 73(1):237-244, Elsevier, Netherlands (Dec. 1988).
Higgins, D.G., and Sharp, P.M., "Fast and Sensitive Multiple Sequence Alignments on a Microcomputer," Computer Applications in the Biosciences 5(2):151-153, Oxford University Press, United Kingdom (Apr. 1989).
Holliger, P, and Hudson, P.J., "Engineered Antibody Fragments and the Rise of Single Domains," Nature Biotechnology 23(9):1126-1136, Nature Publishing Group, United Kingdom (2005).
Horwitz, M.S., "Adenoviridae and their replication" in *Virology*, $2^{nd}$ Edition, pp. 1679-1721, Fields B.N., Knipe D.M., Howley P.M., eds., Lippincott-Raven, United States (1990).
Huang, X., et al., "Parallelization of a Local Similarity Algorithm," Computer Applications in the Biosciences 8(2):155-165, Oxford University Press, United Kingdom (Apr. 1992).
Hurton, L.V., et al., "Tethered Il-15 Augments Antitumor Activity and Promotes a Stem-cell Memory Subset in Tumor-specific T Cells," Proc Natl Acad Sci USA 113(48): E7788-E7791, National Academy of Sciences, United States (Nov. 2016).
Huston, J.S., et al., "Protein Engineering of Antibody Binding Sites: Recovery of Specific Activity in an Anti-digoxin Single-chain Fv Analogue Produced in *Escherichia coli*," Proc Natl Acad Sci USA 85(16):5879-5883, National Academy of Sciences, United States (Aug. 1988).
International Search Report and Written Opinion for International Application No. PCT/US2019/020930, ISA/US, Alexandria, VA, mailed on Jul. 22, 2019, 12 pages.
International Search Report and Written Opinion for International Application No. PCT/US2019/020933, ISA/US, Alexandria, VA, mailed on Jul. 23, 2019, 13 pages.
Ivics, Z., et al., "Molecular Reconstruction of Sleeping Beauty, a Tc1-like Transposon From Fish, and Its Transposition in Human Cells," Cell 91(4):501-510, MIT Press, United States (Nov. 1997).
Jin, Z., et al., "The Hyperactive Sleeping Beauty Transposase Sb100x Improves the Genetic Modification of T Cells to Express a Chimeric Antigen Receptor," Gene Therapy 18(9):849-856, Macmillan Press Ltd, United Kingdom (Sep. 2011).
Johnston, S.A., "Biolistic Transformation: Microbes to Mice," Nature 346(6286):776-777, Nature Publishing Group, United Kingdom (Aug. 1990).
Jornvall, H., et al., "The Adenovirus Hexon Protein. The Primary Structure of the Polypeptide and Its Correlation With the Hexon Gene," The Journal of Biological Chemistry 256(12):6181-6186, American Society for Biochemistry and Molecular Biology, United States (Jun. 1981).
Kent, R.B., et al., "Ouabain resistance conferred by expression of the cDNA for a murine Na+, K+-ATPase alpha subunit," Science 237(4817):901-903, American Association for the Advancement of Science, United States (Aug. 1987).
Kochanek, S., "High-capacity Adenoviral Vectors for Gene Transfer and Somatic Gene Therapy," Human Gene Therapy 10(15):2451-2459, Mary Ann Liebert Inc., United States (Oct. 1999).

(56) References Cited

OTHER PUBLICATIONS

Lowy, I., et al., "Isolation of Transforming DNA: Cloning the Hamster aprt Gene," Cell 22(3):817-823, Cell Press, United States (Dec. 1980).
Lutz, P., et al., "The Product of the Adenovirus Intermediate Gene Ix Is a Transcriptional Activator," Journal of Virology 71(7): 5102-5109, American Society For Microbiology, United States (Jul. 1997).
Martinez-Zapien, D.M., et al., "Structure of the E6/E6AP/p53 complex required for HPV-mediated degradation of p53," Nature 529(7587):541-545, Nature Publishing Group, United Kingdom (Jan. 2016).
Mates, L., et al., "Molecular Evolution of a Novel Hyperactive Sleeping Beauty Transposase Enables Robust Stable Gene Transfer in Vertebrates," Nature Genetics 41(6):753-761, Nature Publishing Group, United Kingdom (Jun. 2009).
Mattila, P.S.,et al., "The Actions of Cyclosporin A and FK506 Suggest a Novel Step in the Activation of T Lymphocytes," EMBO J 9(13):4425-4433, Wiley Blackwell, United Kingdom (Dec. 1990).
Mitra, R., et al., "Functional Characterization of Piggybat from the Bat *Myotis lucifugus* Unveils an Active Mammalian DNA Transposon," Proc Natl Acad Sci USA 110(1):234-239, National Academy of Sciences, United States (Jan. 2013).
Morsy, M.A., et al., "An adenoviral vector deleted for all viral coding sequences results in enhanced safety and extended expression of a leptin transgene," Proc Natl Acad Sci USA 95(14):7866-71, National Academy of Sciences, United States (1998).
Mountford, P.S and Smith, A.G., "Internal Ribosome Entry Sites and Dicistronic Rnas In Mammalian Transgenesis," Trends in Genetics 11(5): 179-184, Elsevier Trends Journals, United Kingdom (May 1995).
Mulligan, R.C. and Berg, P., "Selection for Animal Cells that Express the *Escherichia coli* Gene Coding for Xanthine-guanine Phosphoribosyltransferase," Proc Natl Acad Sci USA 78(4):2072-2076, National Academy of Sciences, United States (Apr. 1981).
Mumtaz, S., et al., "Design of Liposomes for Circumventing the Reticuloendothelial Cells," Glycobiology 1(5):505-510, IRL Press at Oxford University Press, United Kingdom (Nov. 1991).
Needleman S.B., et al., "A General Method Applicable to the Search for Similarities in the Amino Acid Sequence of Two Proteins," Journal of Molecular Biology 48(3):443-453, Academic Press Inc., United States (Mar. 1970).
Neumann, R., et al., "Determination of the Nucleotide Sequence for The Penton-Base Gene of Human Adenovirus Type 5," Gene 69(1): 153-157, Elsevier B.V., Netherlands (Sep. 1988).
No., D., et al., "Ecdysone-inducible Gene Expression in Mammalian Cells and Transgenic Mice," Proc Natl Acad Sci USA 93(8):3346-3351, National Academy of Sciences, United States (Apr. 1996).
Novelli, A., and Boulanger, P.A., "Deletion analysis of functional domains in baculovirus-expressed adenovirus type 2 fiber," Virology 185(1):365-76, Elsevier, Netherlands (1991).
Nuclear Receptors Nomenclature Committee, "A Unified Nomenclature System for the Nuclear Receptor Superfamily," Cell 97(2):161-163, Cell Press, United States (Apr. 1999).
O'Hare, K., et al., "Transformation of Mouse Fibroblasts to Methotrexate Resistance by a Recombinant Plasmid Expressing a Prokaryotic Dihydrofolate Reductase," Proc Natl Acad Sci USA 78(3):1527-1531, National Academy of Sciences, United States (Mar. 1981).
Osbourn, J.K., et al., "Directed Selection of Mip-1 Alpha Neutralizing Ccr5 Antibodies from a Phage Display Human Antibody Library," Nature Biotechnology 16(8):778-781, Nature Publishing Group, United Kingdom (Aug. 1998).
Paul, W. E., ed., "Fundamental Immunology," 3rd Edition, pp. 353-363, Raven Press, United States (1993).
Pearson, W.R. and Lipman, D.J., "Improved Tools for Biological Sequence Comparison," Proc Natl Acad Sci USA 85(8):2444-2448, National Academy of Sciences, United States (Apr. 1988).
Pearson, W.R., "Using the FASTA Program to Search Protein and DNA Sequence Databases," Methods in Molecular Biology 24:307-331, Humana Press, United States (Feb. 1994).
Roberts, M.M., et al., "Three-Dimensional Structure of the Adenovirus Major Coat Protein Hexon," Science 232(4754):1148-1151, American Association for the Advancement of Science, United States (May 1986).
Rux, J.J., et al., "Structural and Phylogenetic Analysis of Adenovirus Hexons by Use of High-Resolution X-Ray Crystallographic, Molecular Modeling, and Sequence-Based Methods," Journal of Virology 77(17): 9553-9566, American Society for Microbiology, United States (Sep. 2003).
Santerre, R.F., et al., "Expression of Prokaryotic Genes for Hygromycin B and G418 Resistance as Dominant-selection Markers in Mouse L Cells," Gene 30(1-3):147-156, Elsevier, Netherlands (Oct. 1984).
Schirmbeck, R., et al., "Targeting Murine Immune Responses To Selected T Cell- or Antibody-Defined Determinants of the Hepatitis B Surface Antigen By Plasmid DNA Vaccines Encoding Chimeric Antigen," Journal of Immunology 166(2):1405-1413, American Association of Immunologists, United States (Jan. 2001).
Signas, C., et al., "Adenovirus 3 Fiber Polypeptide Gene: Implications for the Structure of the Fiber Protein," Journal of Virology 53(2):672-678, American Society For Microbiology, United States (Feb. 1985).
Smith, T.F., and Waterman, M.S., "Comparison of biosequences," *Advances in Applied Mathematics* 2(4):482-498, Academic Press Inc., United States (1981).
Soding, J., "Protein Homology Detection by Hmm-hmm Comparison," Bioinformatics 21(7):951-960, Oxford University Press, United Kingdom (Apr. 2005).
Soleimanjahi, H., et al., "Antitumor Response to a Codon-Optimized HPV-16 E7/HSP70 Fusion Antigen DNA Vaccine," Iranian Journal of Immunology 14(3):180-191, Shiraz University of Medical Sciences, Iran (Sep. 2017).
Stewart , P.L., et al., "Image Reconstruction Reveals the Complex Molecular Organization of Adenovirus," Cell 67(1):145-154, Cell Press, United States (Oct. 1991).
Stewart, P.L., et al., "Difference Imaging of Adenovirus: Bridging the Resolution Gap between X-Ray Crystallography and Electron Microscopy, " EMBO Journal 12(7):2589-2599, Wiley Blackwell, United Kingdom (Jul. 1993).
Suhr, S.T., et al., "High Level Transactivation by a Modified Bombyx Ecdysone Receptor in Mammalian Cells Without Exogenous Retinoid X Receptor," Proc Natl Acad Sci USA 95(14):7999-8004, National Academy of Sciences, United States (1998).
Szybalska, E.H. and Szybalski, W., "Genetics of Human Cess Line IV DNA-mediated Heritable Transformation of A Biochemical Trait," Proc Natl Acad Sci USA 48:2026-2034, National Academy of Sciences, United States (Dec. 1962).
Tsang, K.Y., et al., "Identification and characterization of enhancer agonist human cytotoxic T-cell epitopes of the human papillomavirus type 16 (HPV16) E6/E7," *Vaccine* 35(19):2605-2611, Elsevier, Netherlands (May 2017).
Ui-Tei, K., et al., "Sensitive Assay of RNA Interference in *Drosophila* and Chinese Hamster Cultured Cells Using Firefly Luciferase Gene as Target," FEBS Letters 479(3): 79-82, John Wiley & Sons, Inc., United States (Aug. 2000).
Van Oostrum, J., et al., "Molecular Composition of the Adenovirus Type 2 Virion," Journal of Virology 56(2):439-448, American Society for Microbiology, United States (Nov. 1985).
Wieking, B.G., et al., "A non-oncogenic HPV 16 E6/E7 vaccine enhances treatment of HPV expressing tumors," Cancer Gene Therapy 19(10):667-674, Nature Publishing Group, United Kingdom (Oct. 2012).
Wigler, M., et al., "Transfer of Purified Herpes Virus Thymidine Kinase Gene to Cultured Mouse Cells," Cell 11(1):223-232, Cell Press, United States (May 1977).
Wigler, M., et al., "Transformation of Mammalian Cells with an Amplifiable Dominant-Acting Gene," Proc Natl Acad Sci USA 77(6):3567-3570, National Academy of Sciences, United States (Jun. 1980).
Wilson, M.H., et al., "Piggybac Transposon-Mediated Gene Transfer in Human Cells," Molecular Therapy 15(1):139-145, Cell Press, United States (Jan. 2007).

(56) References Cited

OTHER PUBLICATIONS

Yan, J., et al., "Induction of antitumor immunity in vivo following delivery of a novel HPV-16 DNA vaccine encoding an E6/E7 fusion antigen," Vaccine 27(3):431-440, Elsevier Science, Netherlands (2009).
Yeh, H.Y., et al., "Human adenovirus type 41 contains two fibers," Virus Res 33(2):179-98, Elsevier, Netherlands (Aug. 1994).
Co-pending Application, U.S. Appl. No. 16/978,570, inventors Brough, D.E., et al., international filing date: Mar. 6, 2019 (Not Published).
Kaczkowski B. et al., "Integrative analyses reveal novel strategies in HPV11,-16 and -45 early infection", Sci. Rep., 2:515, Jul. 17, 2012.
Bin L. et al., "Ankyrin repeat domain 1 regulates innate immune responses against herpes simplex virus 1: A potential role in eczema herpeticum", J. Allergy Clin. Immunol., 141(6), pp. 2085-2093, Published online Jan. 31, 2018.
Kaczkowski et al., Sci. Rep., (2012), 2:515.
Bin et al., J. Allergy Clin. Immunol. (2018), 141:2085-2093.
Duncan et al., Virology (2013), 444:119-123.

* cited by examiner

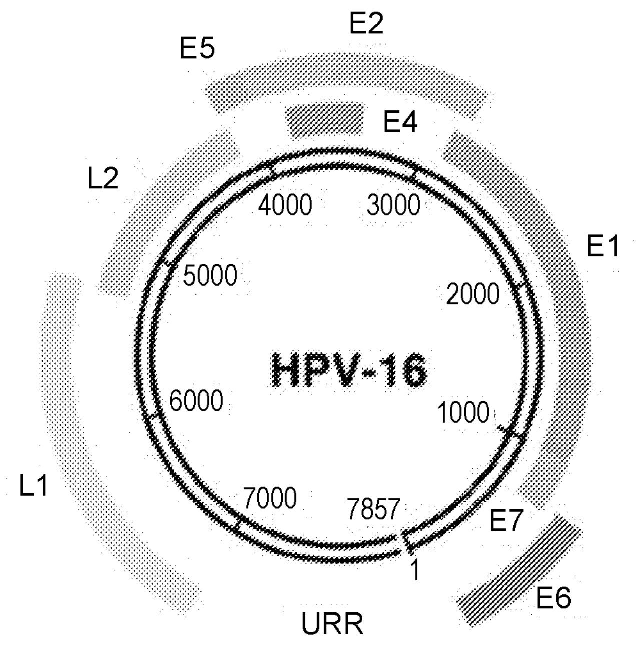

| Gene | Function |
|---|---|
| L1 | Major capsid protein. |
| L2 | Minor capsid protein. |
| E1 | Transcription factor, helicase activity.<br>Mediates episomal DNA replication. |
| E2 | Transcription factor. Regulates viral copy number. |
| E4 | Facilitates virion release. |
| E5 | Stimulates cell proliferation and prevents differentiation.<br>Downregulates surface MHC class I expression. |
| E6 | Deregulates cell cycle control through p53 inactivation/degradation. Induces malignant transformation together with E7. |
| E7 | Keeps cells active in the cell cycle through Rb inactivation. Induces malignant transformation alone and together with E6. |

FIG. 1

| Score | Expect | Method | Identities | Positives | Gaps |
|---|---|---|---|---|---|
| 585 bits(1507) | 0.0 | Compositional matrix adjust. | 365/566(64%) | 379/566(66%) | 134/566(23%) |

```
Query  4    RELTEVFEFAARYSRSDYIIFVYIPLADAKLPQLCTEVDNMLLMGTLGIVPLHAAVSADT   63
            +ELTEVFEFA +Y     IIFVYIPL   KLPQLCTEV   LLMGTLGIV         T
Sbjct  2    KELTEVFEFAKKY-----IIFVYIPLK-KKLPQLCTEVKK-LLMGTLGIV-------KKT   47

Query  64   LHEYMLDLRNRATDLSEEENDEIDGVNHQHLPARRMHDNLLIRCLRCPLILAARLAVLFL   123
            LHEYMLDL+      SEEENDEIDGVNHQHLPARR   NLLIRCLRC          LFL
Sbjct  48   LHEYMLDLKK-----SEEENDEIDGVNHQHLPARR-KKNLLIRCLRC--------KKLFL   93

Query  124  NTLSFVCPWCASSHADVKCIDFYSRIDDLKLPDLCTELALHWAAAVNNVQLFLNTLSFVG   183
            NTLSFVCPWCAS     KCIDFYSRI   KLPDLCTEL           QLFLNTLSFV
Sbjct  94   NTLSFVCPWCASKK---KCIDFYSRIKK-KLPDLCTEL---------KKQLFLNTLSFV-   139

Query  184  ANKFQQLFLNTLNNRVYDFAFRDLPLFLAAREGSYEKLTNTGLYNLANRLCIVYRDGNPY   243
              KFQQLFLNTL  +VYDFAFRDL           +KLTNTGLYNL  +LCIVYRDGNPY
Sbjct  140  -KKFQQLFLNTL-KKVYDFAFRDLK----------KKLTNTGLYNL-KKLCIVYRDGNPY   186

Query  244  AVCDDHMYMLDLQPETTPRDFAFRDLCIVYIVRLLDLEVSQTSKLTRQTDRTLGIVCPIA   303
            AVCD   YMLDLQPETT + FAFRDLCIVY                    +TLGIVCPI
Sbjct  187  AVCDKK-YMLDLQPETT-KKFAFRDLCIVY-------------------KKTLGIVCPIK   225

Query  304  ARYSRSDRTLEDLLMGVADATIHDIILECVDNMHLDKKQRFHNIPLHAAVSADTTLEQQY   363
                   RTLEDLLMGV   TIHDIILECV   HLDKKQRFHNI         TTLEQQY
Sbjct  226  K------RTLEDLLMGVK-KTIHDIILECVKK-HLDKKQRFHNI-------KKTTLEQQY   270

Query  364  NKPLCDLLRNRATDLCDSTLRLCVMHDRWTGRCMSCCPLILAARLAVSLQDIEITCVSHA   423
            NKPLCDLL+      CDSTLRLCV   RWTGRCMSCC          SLQDIEITCV
Sbjct  271  NKPLCDLLKK-----CDSTLRLCV-KKRWTGRCMSCC--------KKSLQDIEITCVKK-   315

Query  424  DVLCVQSTHVDIDDLAHYNIVTFCCLHWAAAVNNVDDLRAFQQLFLNTLSGANKISEYRH   483
              LCVQSTHVDI   AHYNIVTFCC          DDLRAFQQLFLNTLS   KISEYRH
Sbjct  316  --LCVQSTHVDIKK-AHYNIVTFCC--------KKDDLRAFQQLFLNTLS--KKISEYRH   362

Query  484  YCYNNRKLPQLCTELPLFLAAREGSYEKTVLELTEVANRRTLEDLLMGTDHMFAFKDLFV   543
            YCY  +KLPQLCTEL           +KTVLELTEV  +RTLEDLLMGT   FAFKDLFV
Sbjct  363  YCY-KKKLPQLCTELK----------KKTVLELTEV-KKRTLEDLLMGTKK-FAFKDLFV   409

Query  544  VPRDQLYNKPLCDVIVRTLQDIVLHL   569
            V + QLYNKPLCDV  +TLQDIVLHL
Sbjct  410  V-KKQLYNKPLCDV-KKTLQDIVLHL   433
```

FIG. 5A

```
(MOD-1755822) HPV 16 18 E6 E7 E5  ---------MFQDPQERPRKLPQLCTALQTTIHDIILECVYCKQQLLRREVYDFAFRDGC
(MOD-1755825) HPV 16 18 E6 E7 E5  klpqlctevMFQDPQERPRKLPQLCTALQTTIHDIILECVYCKQQLLRREVYDFAFRDGC

(MOD-1755822) HPV 16 18 E6 E7 E5  IVYRDGNPYAVCDKCLKFYSKISEYRHYCYSLYGTTLEQQYNKPLCDLLIRCINCQKPLC
(MOD-1755825) HPV 16 18 E6 E7 E5  IVYRDGNPYAVCDKCLKFYSKISEYRHYCYSLYGTTLEQQYNKPLCDLLIRCINCQKPLC

(MOD-1755822) HPV 16 18 E6 E7 E5  PEEKQRHLDKKQRFHNIRGRWTGRCMSCCRSSRTRRAAAA----------MPGDTPTLHE
(MOD-1755825) HPV 16 18 E6 E7 E5  PEEKQRHLDKKQRFHNIRGRWTGRCMSCCRSSRTRRAAAAqlynkplcdvMPGDTPTLHE

(MOD-1755822) HPV 16 18 E6 E7 E5  YMLDLQPETTDLYGYEQLNDSSEEEDEIDGPAGQAAPDRAHYNIVTFCCKCDSTLRRCVQ
(MOD-1755825) HPV 16 18 E6 E7 E5  YMLDLQPETTDLYGYEQLNDSSEEEDEIDGPAGQAAPDRAHYNIVTFCCKCDSTLRRCVQ

(MOD-1755822) HPV 16 18 E6 E7 E5  STHVDIRTLEDLLMGTLGIVCPICSQKP----------MTNLDTASTTLLACFLLCFCVL
(MOD-1755825) HPV 16 18 E6 E7 E5  STHVDIRTLEDLLMGTLGIVCPICSQKPrtledllmgvMTNLDTASTTLLACFLLCFCVL

(MOD-1755822) HPV 16 18 E6 E7 E5  LCVCLLIRPLLLSVSTYTRCFIVYIIFVYIPLFLIH---------MARFEDPTRRPYKLP
(MOD-1755825) HPV 16 18 E6 E7 E5  LCVCLLIRPLLLSVSTYTRCFIVYIIFVYIPLFLIHklpdlctevMARFEDPTRRPYKLP

(MOD-1755822) HPV 16 18 E6 E7 E5  DLCTALNTSLQDIEITCVYCKTVLELTEVFEFAFKDGFVVYRDSIPHAACHKCIDFYSRI
(MOD-1755825) HPV 16 18 E6 E7 E5  DLCTALNTSLQDIEITCVYCKTVLELTEVFEFAFKDGFVVYRDSIPHAACHKCIDFYSRI

(MOD-1755822) HPV 16 18 E6 E7 E5  RELRHYSDSVYGDTLEKLTNTGLYNLLIRCLRCQKPLNPAEKLRH----------EIDGV
(MOD-1755825) HPV 16 18 E6 E7 E5  RELRHYSDSVYGDTLEKLTNTGLYNLLIRCLRCQKPLNPAEKLRHkltntglynvEIDGV

(MOD-1755822) HPV 16 18 E6 E7 E5  NHQHLPARRAAPQRHTMLCMCCKCEARIERVVESSADDLRAFQQLFLNTLSFVCPWCASQ
(MOD-1755825) HPV 16 18 E6 E7 E5  NHQHLPARRAAPQRHTMLCMCCKCEARIERVVESSADDLRAFQQLFLNTLSFVCPWCASQ

(MOD-1755822) HPV 16 18 E6 E7 E5  Q----------MLSLIFLFCFCVCMYVCCHVPLLPSVVVITSPATAFTVYLLPMLLLHIH
(MOD-1755825) HPV 16 18 E6 E7 E5  QrafqqlflnvMLSLIFLFCFCVCMYVCCHVPLLPSVVVITSPATAFTVYLLPMLLLHIH

(MOD-1755822) HPV 16 18 E6 E7 E5  AILS
(MOD-1755825) HPV 16 18 E6 E7 E5  AILS
```

FIG. 8

(MOD-1755804) HPV- 16 E6(1-151) -------MFQDPQERPRKLPQLCTaLQTTIHDIILECVYCKQQLLRREVYDFAFRDgCIV
native seq mhqkrtaMFQDPQERPRKLPQLCTeLQTTIHDIILECVYCKQQLLRREVYDFAFRDlCIV (MOD-1755804) HPV- 16 E6(1-151) YRDGNPYAVCDKCLKFYSKISEYRHYCYSLYGTTLEQQYNKPLCDLLIRCINCQKPLCPE
native seq YRDGNPYAVCDKCLKFYSKISEYRHYCYSLYGTTLEQQYNKPLCDLLIRCINCQKPLCPE (MOD-1755804) HPV- 16 E6(1-151) EKQRHLDKKQRFHNIRGRWTGRCMSCCRSSRTRRaaaa
native seq EKQRHLDKKQRFHNIRGRWTGRCMSCCRSSRTRRetql

FIG. 9A

```
(MOD-1755805) HPV- 16 E7(1-98) n  MpGDTPTLHEYMLDLQPETTDLYgYEQLNDSSEEEDEIDGPAGQAaPDRAHYNIVTFCCK
native seq                        MhGDTPTLHEYMLDLQPETTDLYcYEQLNDSSEEEDEIDGPAGQAePDRAHYNIVTFCCK

(MOD-1755805) HPV- 16 E7(1-98) n  CDSTLRrCVQSTHVDIRTLEDLLMGTLGIVCPICSQKP
native seq                        CDSTLRlCVQSTHVDIRTLEDLLMGTLGIVCPICSQKP
```

FIG. 9B (MOD-1755806) HPV- 16 E5(1-40:58 MTNLDTASTTLLACFLLCFCVLLCVCLLIRPLLLSVSTYT-----------------RCF
native seq MTNLDTASTTLLACFLLCFCVLLCVCLLIRPLLLSVSTYTsliilvlllwitaasafRCF (MOD-1755806) HPV- 16 E5(1-40:58 IVYIIFVYIPLFLIH--------
native seq IVYIIFVYIPLFLIHtharflit

FIG. 9C

| | |
|---|---|
| (MOD-1755807) HPV- 18 E6(1-120) | MARFEDPTRRPYKLPDLCT**a**LNTSLQDIEITCVYCKTVLELTEVFEFAFKD**g**FVVYRDSI |
| seq | MARFEDPTRRPYKLPDLCT**e**LNTSLQDIEITCVYCKTVLELTEVFEFAFKD**l**FVVYRDSI |
| (MOD-1755807) HPV- 18 E6(1-120) | PHAACHKCIDFYSRIRELRHYSDSVYGDTLEKLTNTGLYNLLIRCLRCQKPLNPAEKLRH |
| seq | PHAACHKCIDFYSRIRELRHYSDSVYGDTLEKLTNTGLYNLLIRCLRCQKPLNPAEKLRH |
| (MOD-1755807) HPV- 18 E6(1-120) | -------------------------------------- |
| seq | lnekrrfhniaghyrgqchsccnrarqerlqrrretqv |

FIG. 10A

```
(MOD-1755808) HPV- 18 E7(40-105)  ---------------------------------------EIDGVNHQHLPARRAaPQRHT
native E7 seq                     mhgpkatlqdivlhlepqneipvdllcheqlsdseeendEIDGVNHQHLPARRAePQRHT

(MOD-1755808) HPV- 18 E7(40-105)  MLCMCCKCEARIErVVESSADDLRAFQQLFLNTLSFVCPWCASQQ
native E7 seq                     MLCMCCKCEARIKlVVESSADDLRAFQQLFLNTLSFVCPWCASQQ
```

FIG. 10B

```
(MOD-1755809) HPV- 18 E5(1-26:41  MLSLIFLFCFCVCMYVCCHVPLLPSV--------------VVITSPATAFTVY----LLP
native seq                        MLSLIFLFCFCVCMYVCCHVPLLPSVcmcayawvlvfvyiVVITSPATAFTVYvfcfLLP

(MOD-1755809) HPV- 18 E5(1-26:41  MLLLHIHAILS--
native seq                        MLLLHIHAILSlq
```

FIG. 10C

HUMAN PAPILLOMAVIRUS VACCINES AND USES OF THE SAME

The content of the electronically submitted sequence listing (Name: 2584_156PC01_SeqListing_ST25; Size: 444, 182 bytes; Date of Creation: Mar. 5, 2019) filed with this application is incorporated herein by reference in its entirety.

FIELD OF THE DISCLOSURE

The present disclosure relates to improved, broad-spectrum HPV molecular vaccines designed via use of advanced principles in bioinformatics and protein engineering.

BACKGROUND OF THE DISCLOSURE

Globally, tens of millions of people are currently infected with human papillomavirus (HPV), and millions more become newly infected each year. HPV has been determined to be a precursor of cervical and other cancers, such as head and neck cancers. Tens of thousands of women get cervical cancer each year. Currently, vaccinations can protect against diseases caused by HPV when given to recommended age groups; however, there is a tremendous need for HPV vaccines with broad coverage (against multiple HPV strains) and functionality against HPV-associated cancers.

The present disclosure relates to improved, broad-spectrum HPV molecular vaccines designed via use of advanced principles in bioinformatics and protein engineering. These novel HPV vaccines can be used as a therapeutic vaccine against HPV related diseases.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY OF THE DISCLOSURE

Provided herein is a non-naturally occurring polynucleotide encoding a polypeptide comprising at least one of one or more immune response-inducing human papilloma virus (HPV) polypeptides.

In some embodiments, said non-naturally occurring polynucleotide encodes a polypeptide comprising two or more HPV polypeptides. In some embodiments, said two or more HPV polypeptides comprise one or more HPV-16 immune response-inducing polypeptide sequences. In some embodiments, said HPV-16 peptide comprises at least one of an E5 peptide, an E6 peptide or an E7 peptide. In some embodiments, said HPV-16 peptide comprises an E5 peptide, and said E5 peptide has a sequence as shown in SEQ ID NO: 47. In some embodiments, said HPV-16 peptide comprises an E6 peptide, and said E6 peptide has a sequence as shown in SEQ ID NO: 45. In some embodiments, said HPV-16 peptide comprises an E7 peptide, and said E7 peptide has a sequence as shown in SEQ ID NO: 46. In some embodiments, said one or more HPV peptides comprises an HPV-18 peptide. In some embodiments, said HPV-18 peptide comprises at least one of an E5 peptide, an E6 peptide or an E7 peptide. In some embodiments, said HPV-18 peptide comprises an E5 peptide, and said E5 peptide has a sequence as shown in SEQ ID NO: 50. In some embodiments, said HPV-18 peptide comprises an E6 peptide, and said E6 peptide has a sequence as shown in SEQ ID NO: 48. In some embodiments, said HPV-18 peptide comprises an E7 peptide, and said E7 peptide has a sequence as shown in SEQ ID NO: 49. In some embodiments, said polypeptide has a sequence as shown in SEQ ID NO: 51. In some embodiments, at least one of said one or more HPV peptides is connected to an agonist peptide. In some embodiments, said agonist peptide has a sequence comprising an agonist peptide sequence as shown in Table 2. In some embodiments, said polypeptide has a sequence as shown in SEQ ID NO: 53.

Provided herein is a polynucleotide comprising any of the polynucleotides provided herein, further comprising one or more polynucleotides encoding a gene switch system for inducible control of heterologous gene expression, wherein heterologous gene expression is regulated by said gene switch system; and, wherein said heterologous gene comprises any of the polynucleotide described herein. In some embodiments, said gene switch system is an ecdysone receptor-based (EcR-based) gene switch system. In some embodiments, said one or more HPV polypeptides is for use in a vaccine.

Provided herein is a vector comprising any of the polynucleotides provided herein. In some embodiments, said vector is an adenoviral vector. In some embodiments, said adenoviral vector is a gorilla adenoviral vector.

Provided herein is a method of regulating the expression of a heterologous gene in a cell, the method comprising: introducing into said cell one or more polynucleotides that comprise (i) an repressible or inducible gene switch, and (ii) a heterologous immune response-inducing gene, wherein expression of said heterologous immune response-inducing gene is regulated by said gene switch, wherein said heterologous immune response-inducing gene encodes at least one of one or more HPV polypeptides; and exposing said cell to a compound in an amount sufficient to repress or induce expression of said heterologous immune response-inducing gene.

In some embodiments, said target cell is a mammalian cell in a method of regulating the expression of a heterologous gene in a cell described herein. In some embodiments, said gene switch comprises a ligand binding domain derived from at least one of an ecdysone receptor (EcR), a ubiquitous receptor, an orphan receptor 1, an NER-1, a steroid hormone nuclear receptor 1, a retinoid X receptor interacting protein-15, a liver X receptor β, a steroid hormone receptor like protein, a liver X receptor, a liver X receptor α, a farnesoid X receptor, a receptor interacting protein 14, and a famesol receptor.

Provided herein is an E6 peptide, wherein said E6 peptide comprises an E18A amino acid substitution and at least one of an L50G, E148A, T149A, Q150A and L151A amino acid substitution as compared to a wildtype E6 peptide. In some embodiments, said E6 peptide comprises said E18A amino acid substitution and said L50G, E148A, T149A, Q150A and L151A amino acid substitutions. In some embodiments, said E6 peptide has a sequence as shown in SEQ ID NO: 45. In some embodiments, said E6 peptide is fused to an agonist peptide. In some embodiments, said agonist peptide is fused to at least one of a C-terminus and an N-terminus of said E6 peptide. In some embodiments, said wildtype E6 peptide is from HPV-16.

Provided herein is an E6 peptide, wherein said E6 peptide comprises a deletion as compared to a wildtype E6 peptide, wherein said deletion comprises a C-terminus of said wildtype E6 peptide. In some embodiments, said deletion comprises amino acids from amino acid 121 to a C-terminus of said wildtype E6 peptide. In some embodiments, said E6 peptide comprises at least one of an E18A and L50G substitution as compared to said wildtype E6 peptide. In some embodiments, said wildtype E6 peptide is from HPV-18. In some embodiments, said E6 peptide has a sequence as shown in SEQ ID NO: 48.

Provided herein is an E7 peptide, wherein said E7 peptide comprises a deletion as compared to a wildtype E7 peptide, wherein said deletion comprises an N-terminus of said wildtype E7 peptide. In some embodiments, said deletion comprises amino acids 1-39 of said wildtype E7 peptide. In some embodiments, said E7 peptide comprises at least one of an E55A and L74R substitution as compared to said wildtype E7 peptide. In some embodiments, said wildtype E7 peptide is from HPV-18. In some embodiments, said E7 peptide has a sequence as shown in SEQ ID NO: 49.

Provided herein is an E5 peptide, wherein said E5 peptide comprises a deletion as compared to a wildtype E5 peptide, wherein said deletion comprises amino acids 41-57 of said wildtype E5 peptide. In some embodiments, said E5 peptide has a sequence as shown in SEQ ID NO: 47. In some embodiments, said wildtype E5 peptide is from HPV-16.

Provided herein is an E5 peptide, wherein said E5 peptide comprises a deletion as compared to a wildtype E5 peptide, wherein said deletion comprises at least one of amino acids 27-40 or amino acids 54-57 of said wildtype E5 peptide. In some embodiments, said E5 peptide has a sequence as shown in SEQ ID NO: 50. In some embodiments, said wildtype E5 peptide is from HPV-18.

Provided herein is a polypeptide construct comprising any one of the presently described E5, E6, and E7.

Provided herein is a polypeptide construct, wherein said polypeptide construct comprises an HPV-16 E6 peptide, wherein said HPV-16 E6 peptide comprises an E18A amino acid substitution and at least one of an L50G, E148A, T149A, Q150A and L151A amino acid substitution as compared to a wildtype HPV-16 E6 peptide. In some embodiments, said HPV-16 E6 peptide comprises said E18A amino acid substitution and said L50G, E148A, T149A, Q150A and L151A amino acid substitutions. In some embodiments, said HPV-16 E6 peptide has a sequence as shown in SEQ ID NO: 45. In some embodiments, said polypeptide construct further comprises an HPV-16 E7 peptide, wherein said HPV-16 E7 peptide comprises at least one of an H2P, C24G, E46A and L67R amino acid substitution as compared to a wildtype HPV-16 E7 peptide. In some embodiments, said HPV-16 E7 peptide comprises said H2P, C24G, E46A and L67R amino acid substitutions. In some embodiments, said HPV-16 E7 peptide has a sequence as shown in SEQ ID NO: 46. In some embodiments, said polypeptide construct further comprises an HPV-16 E5 peptide. In some embodiments, said HPV-16 E5 peptide comprises a deletion of one or more amino acids as compared to a wildtype HPV-16 E5 peptide. In some embodiments, said deletion comprises amino acids 41-57 of said wildtype HPV-16 E5 peptide. In some embodiments, said HPV-16 E5 peptide has a sequence as shown in SEQ ID NO: 47.

In some embodiments, said polypeptide construct comprising an HPV-16 E6 peptide, wherein said HPV-16 E6 peptide comprises an E18A amino acid substitution and at least one of an L50G, E148A, T149A, Q150A and L151A amino acid substitution as compared to a wildtype HPV-16 E6 peptide, further comprises an HPV-18 E6 peptide. In some embodiments, said HPV-18 E6 peptide comprises an E18A and L50G substitution as compared to a wildtype HPV-18 E6 peptide. In some embodiments, said HPV-18 E6 peptide comprises a deletion of at least one C-terminus amino acid relative to said wildtype HPV-18 E6 peptide. In some embodiments, said deletion comprises amino acids from amino acid 121 to said C-terminus of said wildtype HPV-18 E6 peptide. In some embodiments, said HPV-18 E6 peptide has a sequence as shown in SEQ ID NO: 48. In some embodiments, said polypeptide construct further comprises an HPV-18 E7 peptide. In some embodiments, said HPV-18 E7 peptide comprises an E55A and L74R substitution as compared to a wildtype HPV-18 E7 peptide. In some embodiments, said HPV-18 E7 peptide comprises a deletion of at least one amino acid from an N-terminus of said HPV-18 E7 peptide. In some embodiments, said deletion comprises amino acids 1-40 of said wildtype HPV-18 E7 peptide. In some embodiments, said HPV-18 E7 peptide has a sequence as shown in SEQ ID NO: 49. In some embodiments, said polypeptide construct further comprises an HPV-18 E5 peptide. In some embodiments, said HPV-18 E5 peptide comprises a deletion of at least one amino acid as compared to a wildtype HPV-18 E5 peptide. In some embodiments, said deletion comprises amino acids 27-40 or 54-57 of said wildtype HPV-18 E5 peptide. In some embodiments, said HPV-18 E5 peptide has a sequence as shown in SEQ ID NO: 50. In some embodiments, said polypeptide construct has a sequence as shown in SEQ ID NO: 51. In some embodiments, said polypeptide construct further comprises at least one agonist peptide. In some embodiments, said at least one agonist peptide has a sequence comprising an agonist peptide sequence as shown in Table 2. In some embodiments, said polypeptide construct has a sequence as shown in SEQ ID NO: 53.

Provided herein is a polypeptide construct comprising an ankyrin-like repeat domain and an HPV peptide. In some embodiments, said ankyrin-like repeat protein is a human ankyrin-like repeat protein. In some embodiments, said HPV peptide is linked to said ankyrin-like repeat protein by a linker. In some embodiments, said HPV peptide comprises at least one of an HPV-16 peptide or an HPV-18 peptide. In some embodiments, said HPV peptide comprises an HPV-16 peptide, and said HPV-16 peptide comprises at least one of an E5 peptide, an E6 peptide or an E7 peptide. In some embodiments, said HPV peptide comprises an HPV-18 peptide, and said HPV-18 peptide comprises at least one of an E6 peptide or an E7 peptide. In some embodiments, said HPV peptide comprises an HPV-16 E5 sequence, an HPV-16 E6 sequence, an HPV-16 E7 sequence, an HPV-18 E6 sequence or an HPV-18 E7 sequence as shown in Table 2. In some embodiments, said polypeptide construct has a sequence as shown in SEQ ID NO: 52. In some embodiments, said polypeptide construct further comprises at least one agonist peptide. In some embodiments, said polypeptide construct comprises three agonist peptides. In some embodiments, said polypeptide construct has a sequence as shown in SEQ ID NO: 54.

Provided herein is a polypeptide construct, wherein said polypeptide construct comprises at least two HPV amino acid sequences as shown in Table 2, wherein said at least two HPV amino acid sequences are connected by a peptide linker, wherein said peptide linker is a KK linker. In some embodiments, said at least two HPV amino acid sequences comprise at least one of an HPV-16 peptide or an HPV-18 peptide as shown in Table 2. In some embodiments, said at least two HPV amino acid sequences comprise an HPV-16 peptide, and said HPV-16 peptide comprises at least one of an HPV-16 E5 peptide, an HPV-16 E6 peptide or an HPV-16 E7 peptide as shown in Table 2. In some embodiments, said at least two HPV amino acid sequences comprise an HPV-18 peptide, and said HPV-18 peptide comprises at least one of an HPV-18 E6 peptide or an HPV-18 E7 peptide as shown in Table 2. In some embodiments, said at least two HPV amino acid sequences comprise each of the amino acid sequences as shown in Table 2. In some embodiments, said each of the amino acid sequences is connected to another of said each of the amino acid sequences by said KK linker. In some embodiments, said polypeptide construct has a sequence as shown in SEQ ID NO: 55. In some embodiments, any of the polypeptide constructs described herein is for use in a vaccine.

Provided herein is a polynucleotide encoding any of the presently described polypeptide constructs. Also provided herein is a vector comprising said polynucleotide. In some embodiments, said vector is an adenoviral vector. In some embodiments, said adenoviral vector is a gorilla adenoviral vector.

Provided herein is a vector, wherein said vector comprises a polynucleotide that encodes at least one HPV peptide, wherein said vector is an adenoviral vector.

Provided herein is a vector, wherein said vector comprises a polynucleotide that encodes at least one HPV peptide, wherein said vector is an adenoviral vector, wherein said adenoviral vector is a gorilla adenoviral vector.

In some embodiments, any of the polypeptide constructs described herein is for use in a vaccine. Also provided herein is a polynucleotide encoding any of the polypeptide constructs presently described. Also provided herein is a vector comprising said polynucleotide. In some embodiments, said vector is an adenoviral vector. In some embodiments, said adenoviral vector is a gorilla adenoviral vector.

BRIEF DESCRIPTION OF THE DRAWINGS

The features of the present disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1 is a schematic diagram of HPV genome. The HPV genomes includes seven early genes (E1 to E7) and two late genes (L1 and L2), and each gene has specific functions. E5, E6, and E7 genes are associated with cancer development.

FIG. 5A shows HPV design 5 (subject) mapped onto HPV design 4 (Query) using protein blast. Strong and weak binders were identified using netMHC. FIG. 5B shows density plots of HPV designs 4 and 5 which were extracted based on the mapped positions. Similar patterns in predicted strong/weak binding peptides were observed. The binding affinity predictions on the matched regions of HPV designs 4 and 5 were similar.

FIG. 8 shows a comparison of HPV design1 (MOD-1755822) and HPV design 3 (MOD-1755825).

FIG. 9A shows HPV16 E6 sequence alignment to wild-type HPV16 E6 from UP P03126. FIG. 9B shows HPV16 E7 sequence alignment to wildtype HPV16 E7 from UP P03129. FIG. 9C shows HPV16 E5 sequence alignment to wildtype HPV16 E5 from UP P06927.

FIG. 10A shows HPV18 E6 sequence alignment to wild-type HPV18E6 from UP P06463. FIG. 10B shows HPV18 E7 sequence alignment to wildtype HPV18E7 from UP P06788. FIG. 10C shows HPV18 E5 sequence alignment to wildtype HPV18E5 from UP P06792.

DETAILED DESCRIPTION OF THE DISCLOSURE

Figure 2:
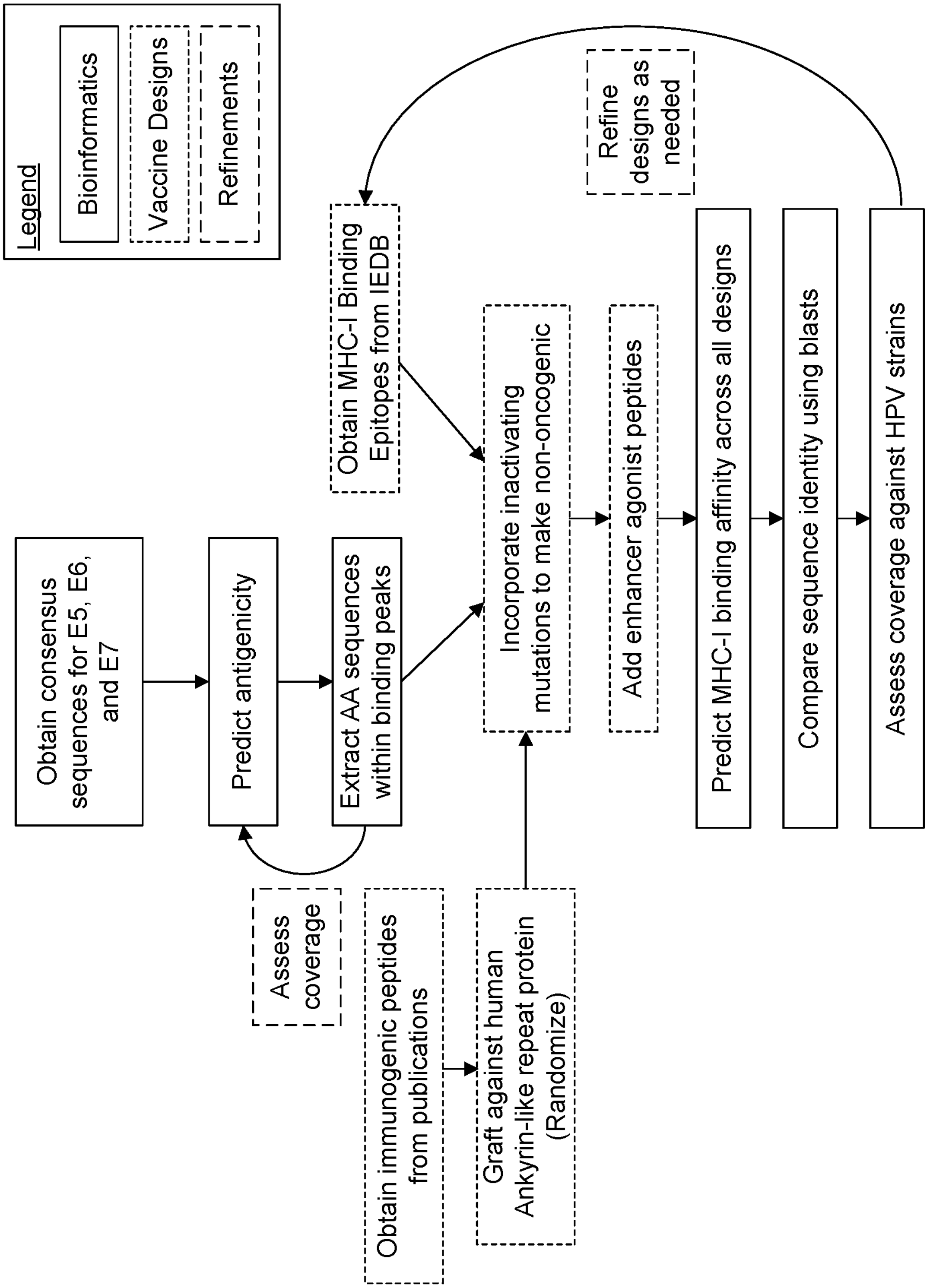
FIG. 2 is a schematic overall workflow implemented for designing HPV vaccine antigens.

The following description and examples illustrate embodiments of the present disclosure in detail.

It is to be understood that the present disclosure is not limited to the particular embodiments described herein and as such can vary. Those of skill in the art will recognize that there are variations and modifications of the present disclosure, which are encompassed within its scope.

All terms are intended to be understood as they would be understood by a person skilled in the art. Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

Although various features of the disclosure can be described in the context of a single embodiment, the features can also be provided separately or in any suitable combination. Conversely, although the present disclosure can be described herein in the context of separate embodiments for clarity, the present disclosure can also be implemented in a single embodiment.

The following definitions supplement those in the art and are directed to the current application and are not to be imputed to any related or unrelated case, e.g., to any commonly owned patent or application. Although any methods and materials similar or equivalent to those described herein can be used in the practice for testing of the present disclosure, the preferred materials and methods are described herein. Accordingly, the terminology used herein is for the purpose of describing particular embodiments only, and is not intended to be limiting.

Definitions

In this application, the use of the singular includes the plural unless specifically stated otherwise. It must be noted that, as used in the specification, the singular forms "a," "an" and "the" include plural referents unless the context clearly dictates otherwise.

In this application, the use of "or" means "and/or" unless stated otherwise. The terms "and/or" and "any combination thereof" and their grammatical equivalents as used herein, can be used interchangeably. These terms can convey that any combination is specifically contemplated. Solely for illustrative purposes, the following phrases "A, B, and/or C" or "A, B, C, or any combination thereof" can mean "A individually; B individually; C individually; A and B; B and C; A and C; and A, B, and C." The term "or" can be used conjunctively or disjunctively, unless the context specifically refers to a disjunctive use.

Furthermore, use of the term "including" as well as other forms, such as "include," "includes," and "included," is not limiting.

Reference in the specification to "some embodiments," "an embodiment," "one embodiment" or "other embodiments" means that a particular feature, structure, or characteristic described in connection with the embodiments is included in at least some embodiments, but not necessarily all embodiments, of the present disclosures.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the disclosure, and vice versa. Furthermore, compositions of the present disclosure can be used to achieve methods of the present disclosure.

The term "about" in relation to a reference numerical value and its grammatical equivalents as used herein can include the numerical value itself and a range of values plus or minus 10% from that numerical value.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. In another example, the amount "about 10" includes 10 and any amounts from 9 to 11. In yet another example, the term "about" in relation to a reference numerical value can also include a range of values plus or minus 10%, 9%, 8%, 7%, 6%, 5%, 4%, 3%, 2%, or 1% from that value. Alternatively, particularly with respect to biological systems or processes, the term "about" can mean within an order of magnitude, preferably within 5-fold, and more preferably within 2-fold, of a value. Where particular values are described in the application and claims, unless otherwise stated the term "about" meaning within an acceptable error range for the particular value should be assumed.

The term "isolated" and its grammatical equivalents as used herein refer to the removal of a nucleic acid from its natural environment. The term "purified" and its grammatical equivalents as used herein refer to a molecule or composition, whether removed from nature (including genomic DNA and mRNA) or synthesized (including cDNA) and/or amplified under laboratory conditions, that has been increased in purity, wherein "purity" is a relative term, not "absolute purity." It is to be understood, however, that nucleic acids and proteins can be formulated with diluents or adjuvants and still for practical purposes be isolated. For example, nucleic acids typically are mixed with an acceptable carrier or diluent when used for introduction into cells. The term "substantially purified" and its grammatical equivalents as used herein refer to a nucleic acid sequence, polypeptide, protein or other compound which is essentially free, i.e., is more than about 50% free of, more than about 70% free of, more than about 90% free of, the polynucleotides, proteins, polypeptides and other molecules that the nucleic acid, polypeptide, protein or other compound is naturally associated with.

"Polynucleotide", "oligonucleotide", "polynucleotide construct", "gene", "gene construct", "heterologous gene" and their grammatical equivalents as used herein refer to a polymeric form of nucleotides or nucleic acids of any length, either ribonucleotides or deoxyribonucleotides. This term refers only to the primary structure of the molecule. Thus, this term includes double and single stranded DNA, triplex DNA, as well as double and single stranded RNA. It also includes modified, for example, by methylation and/or by capping, and unmodified forms of the polynucleotide. The term is also meant to include molecules that include non-naturally occurring or synthetic nucleotides as well as nucleotide analogs. The nucleic acid sequences and vectors disclosed or contemplated herein can be introduced into a cell by, for example, transfection, transformation, or transduction.

"Transfection," "transformation," or "transduction" as used herein refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), Methods in Molecular Biology, Vol. 7, Gene Transfer and Expression Protocols, Humana Press (1991)); DEAE-dextran; electroporation; cationic liposome-mediated transfection; tungsten particle-facilitated microparticle bombardment (Johnston, *Nature,* 346: 776-777 (1990)); and strontium phosphate DNA co-precipitation (Brash et al., *Mol. Cell Biol.,* 7: 2031-2034 (1987)). Phage or viral vectors can be introduced into host cells, after growth of infectious particles in suitable packaging cells, many of which are commercially available.

"Polypeptide", "peptide" "polypeptide construct" and "peptide construct" and their grammatical equivalents as used herein refer to a polymer of amino acid residues. A "mature protein" is a protein which is full-length and which, optionally, includes glycosylation or other modifications typical for the protein in a given cellular environment. Polypeptides and proteins disclosed herein (including functional portions and functional variants thereof) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenyl serine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine. The present disclosure further contemplates that expression of polypeptides described herein in an engineered cell can be associated with post-translational modifications of one or more amino acids of the polypeptide constructs. Non-limiting examples of post-translational modifications include phosphorylation, acylation including acetylation and formylation, glycosylation (including N-linked and O-linked), amidation, hydroxylation, alkylation including methylation and ethylation, ubiquitylation, addition of pyrrolidone carboxylic acid, formation of disulfide bridges, sulfation, myristoylation, palmitoylation, isoprenylation, farnesylation, geranylation, glypiation, lipoylation and iodination.

Nucleic acids and/or nucleic acid sequences are "homologous" when they are derived, naturally or artificially, from a common ancestral nucleic acid or nucleic acid sequence. Proteins and/or protein sequences are "homologous" when their encoding DNAs are derived, naturally or artificially, from a common ancestral nucleic acid or nucleic acid sequence. The homologous molecules can be termed homologs. For example, any naturally occurring proteins, as described herein, can be modified by any available mutagenesis method. When expressed, this mutagenized nucleic acid encodes a polypeptide that is homologous to the protein encoded by the original nucleic acid. Homology is generally inferred from sequence identity between two or more nucleic acids or proteins (or sequences thereof). The precise percentage of identity between sequences that is useful in establishing homology varies with the nucleic acid and protein at issue, but as little as 25% sequence identity is routinely used to establish homology. Higher levels of sequence identity, e.g., 30%, 40%, 50%, 60%, 70%, 80%, 90%, 95% or 99% or more can also be used to establish homology. Methods for determining sequence identity percentages (e.g., BLASTP and BLASTN using default parameters) are described herein and are generally available.

The term "identical" and its grammatical equivalents as used herein or "sequence identity" in the context of two nucleic acid sequences or amino acid sequences of polypeptides refers to the residues in the two sequences which are the same when aligned for maximum correspondence over a specified comparison window. A "comparison window", as used herein, refers to a segment of at least about 20 contiguous positions, usually about 50 to about 200, more usually about 100 to about 150 in which a sequence can be compared to a reference sequence of the same number of contiguous positions after the two sequences are aligned optimally. Methods of alignment of sequences for comparison are well-known in the art. Optimal alignment of sequences for comparison can be conducted by the local homology algorithm of Smith and Waterman, *Adv. Appl. Math.*, 2:482 (1981); by the alignment algorithm of Needleman and Wunsch, *J. Mol. Biol.*, 48:443 (1970); by the search for similarity method of Pearson and Lipman, *Proc. Nat. Acad. Sci U.S.A.*, 85:2444 (1988); by computerized implementations of these algorithms (including, but not limited to CLUSTAL in the PC/Gene program by Intelligentics, Mountain View Calif., GAP, BESTFIT, BLAST, FASTA, and TFASTA in the Wisconsin Genetics Software Package, Genetics Computer Group (GCG), 575 Science Dr., Madison, Wis., U.S.A.); the CLUSTAL program is well described by Higgins and Sharp, *Gene*, 73:237-244 (1988) and Higgins and Sharp, *CABIOS*, 5:151-153 (1989); Corpet et al., *Nucleic Acids Res.*, 16:10881-10890 (1988); Huang et al., *Computer Applications in the Biosciences*, 8:155-165 (1992); and Pearson et al., *Methods in Molecular Biology*, 24:307-331 (1994). Alignment is also often performed by inspection and manual alignment. In one class of embodiments, the polypeptides herein are at least 80%, 85%, 90%, 98% 99% or 100% identical to a reference polypeptide, or a fragment thereof, e.g., as measured by BLASTP (or CLUSTAL, or any other available alignment software) using default parameters. Similarly, nucleic acids can also be described with reference to a starting nucleic acid, e.g., they can be 50%, 60%, 70%, 75%, 80%, 85%, 90%, 98%, 99% or 100% identical to a reference nucleic acid or a fragment thereof, e.g., as measured by BLASTN (or CLUSTAL, or any other available alignment software) using default parameters. When one molecule is said to have certain percentage of sequence identity with a larger molecule, it means that when the two molecules are optimally aligned, said percentage of residues in the smaller molecule finds a match residue in the larger molecule in accordance with the order by which the two molecules are optimally aligned.

The term "substantially identical" and its grammatical equivalents as applied to nucleic acid or amino acid sequences mean that a nucleic acid or amino acid sequence comprises a sequence that has at least 90% sequence identity or more, at least 95%, at least 98% and at least 99%, compared to a reference sequence using the programs described above, e.g., BLAST, using standard parameters. For example, the BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff, Proc. Natl. Acad. Sci. USA 89:10915 (1992)). Percentage of sequence identity is determined by comparing two optimally aligned sequences over a comparison window, wherein the portion of the polynucleotide sequence in the comparison window can comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. In embodiments, the substantial identity exists over a region of the sequences that is at least about 50 residues in length, over a region of at least about 100 residues, and in embodiments, the sequences are substantially identical over at least about 150 residues. In embodiments, the sequences are substantially identical over the entire length of the coding regions.

An "expression vector" or "vector" is any genetic element, e.g., a plasmid, chromosome, virus, transposon, behaving either as an autonomous unit of polynucleotide replication within a cell. (i.e. capable of replication under its own control) or being rendered capable of replication by insertion into a host cell chromosome, having attached to it another polynucleotide segment, so as to bring about the replication and/or expression of the attached segment. Suitable vectors include, but are not limited to, plasmids, transposons, bacteriophages and cosmids. Vectors can contain polynucleotide sequences which are necessary to effect ligation or insertion of the vector into a desired host cell and to effect the expression of the attached segment. Such sequences differ depending on the host organism; they include promoter sequences to effect transcription, enhancer sequences to increase transcription, ribosomal binding site sequences and transcription and translation termination sequences. Alternatively, expression vectors can be capable of directly expressing nucleic acid sequence products encoded therein without ligation or integration of the vector into host cell DNA sequences. In some embodiments, the vector is an "episomal expression vector" or "episome," which is able to replicate in a host cell, and persists as an extrachromosomal segment of DNA within the host cell in the presence of appropriate selective pressure (see, e.g., Conese et al., *Gene Therapy,* 11:1735-1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP). The vectors pREP4, pCEP4, pREP7, and pcDNA3.1 from Invitrogen (Carlsbad, Calif.) and pBK-CMV from Stratagene (La Jolla, Calif.) represent non-limiting examples of an episomal vector that uses T-antigen and the SV40 origin of replication in lieu of EBNA1 and oriP. Vector also can comprise a selectable marker gene.

The term "adenovirus," as used herein, refers to an adenovirus that retains the ability to participate in the adenovirus life cycle and has not been physically inactivated by, for example, disruption (e.g., sonication), denaturing (e.g., using heat or solvents), or cross-linkage (e.g., via formalin cross-linking). The "adenovirus life cycle" includes (1) virus binding and entry into cells, (2) transcription of the adenoviral genome and translation of adenovirus proteins, (3) replication of the adenoviral genome, and (4) viral particle assembly (see, e.g., Fields Virology, $5^{th}$ ed., Knipe et al. (eds.), Lippincott Williams & Wilkins, Philadelphia, PA (2006)). The term "adenoviral vector," as used herein, refers to an adenovirus in which the adenoviral genome has been manipulated to accommodate a nucleic acid sequence that is non-native with respect to the adenoviral genome. Typically, an adenoviral vector is generated by introducing one or more mutations (e.g., a deletion, insertion, or substitution) into the adenoviral genome of the adenovirus so as to accommodate the insertion of a non-native nucleic acid sequence, for example, for gene transfer, into the adenovirus.

The term "selectable marker gene" as used herein refers to a nucleic acid sequence that allows cells expressing the nucleic acid sequence to be specifically selected for or against, in the presence of a corresponding selective agent. Suitable selectable marker genes are known in the art and described in, e.g., International Patent Application Publications WO 1992/08796 and WO 1994/28143; Wigler et al., *Proc. Natl. Acad. Sci.* USA, 77: 3567 (1980); O'Hare et al., *Proc. Natl. Acad. Sci.* USA, 78: 1527 (1981); Mulligan & Berg, *Proc. Natl. Acad. Sci.* USA, 78: 2072 (1981); Colberre-Garapin et al., *J. Mol. Biol.,* 150:1 (1981); Santerre et al., *Gene,* 30: 147 (1984); Kent et al., *Science,* 237: 901-903 (1987); Wigler et al., *Cell,* 11: 223 (1977); Szybalska & Szybalski, *Proc. Natl. Acad. Sci.* USA, 48: 2026 (1962); Lowy et al., *Cell,* 22: 817 (1980); and U.S. Pat. Nos. 5,122,464 and 5,770,359.

The term "coding sequence" as used herein refers to a segment of a polynucleotide that codes for protein. The region or sequence is bounded nearer the 5' end by a start codon and nearer the 3' end with a stop codon. Coding sequences can also be referred to as open reading frames.

The term "operably linked" as used herein refers to refers to the physical and/or functional linkage of a DNA segment to another DNA segment in such a way as to allow the segments to function in their intended manners. A DNA sequence encoding a gene product is operably linked to a regulatory sequence when it is linked to the regulatory sequence, such as, for example, promoters, enhancers and/or silencers, in a manner which allows modulation of transcription of the DNA sequence, directly or indirectly. For example, a DNA sequence is operably linked to a promoter when it is ligated to the promoter downstream with respect to the transcription initiation site of the promoter, in the correct reading frame with respect to the transcription initiation site and allows transcription elongation to proceed through the DNA sequence. An enhancer or silencer is operably linked to a DNA sequence coding for a gene product when it is ligated to the DNA sequence in such a manner as to increase or decrease, respectively, the transcription of the DNA sequence. Enhancers and silencers can be located upstream, downstream or embedded within the coding regions of the DNA sequence. A DNA for a signal sequence is operably linked to DNA coding for a polypeptide if the signal sequence is expressed as a pre-protein that participates in the secretion of the polypeptide. Linkage of DNA sequences to regulatory sequences is typically accomplished by ligation at suitable restriction sites or via adapters or linkers inserted in the sequence using restriction endonucleases known to one of skill in the art.

The terms "induce", "induction" and its grammatical equivalents as used herein refer to an increase in nucleic acid sequence transcription, promoter activity and/or expression brought about by a transcriptional regulator, relative to some basal level of transcription.

The term "transcriptional regulator" refers to a biochemical element that acts to prevent or inhibit the transcription of a promoter-driven DNA sequence under certain environmental conditions (e.g., a repressor or nuclear inhibitory protein), or to permit or stimulate the transcription of the promoter-driven DNA sequence under certain environmental conditions (e.g., an inducer or an enhancer).

The term "enhancer" as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences. The term "Ig enhancers" refers to enhancer elements derived from enhancer regions mapped within the immunoglobulin (Ig) locus (such enhancers include for example, the heavy chain (mu) 5' enhancers, light chain (kappa) 5' enhancers, kappa and mu intronic enhancers, and 3' enhancers (see generally Paul W. E. (ed), Fundamental Immunology, 3rd Edition, Raven Press, New York (1993), pages 353-363; and U.S. Pat. No. 5,885,827).

The term "promoter" refers to a region of a polynucleotide that initiates transcription of a coding sequence. Promoters are located near the transcription start sites of genes, on the same strand and upstream on the DNA (towards the 5' region of the sense strand). Some promoters are constitutive as they are active in all circumstances in the cell, while others are regulated becoming active in response to specific stimuli, e.g., an inducible promoter. The term "promoter activity" and its grammatical equivalents as used herein refer to the extent of expression of nucleotide sequence that is operably linked to the promoter whose activity is being measured. Promoter activity can be measured directly by determining the amount of RNA transcript produced, for example by Northern blot analysis or indirectly by determining the amount of product coded for by the linked nucleic acid sequence, such as a reporter nucleic acid sequence linked to the promoter.

"Inducible promoter" as used herein refers to a promoter which is induced into activity by the presence or absence of transcriptional regulators, e.g., biotic or abiotic factors. Inducible promoters are useful because the expression of genes operably linked to them can be turned on or off at certain stages of development of an organism or in a particular tissue. Non-limiting examples of inducible promoters include alcohol-regulated promoters, tetracycline-regulated promoters, steroid-regulated promoters, metal-regulated promoters, pathogenesis-regulated promoters, temperature-regulated promoters and light-regulated promoters. The inducible promoter can be part of a gene switch or genetic switch. The inducible promoter can be a gene switch ligand inducible promoter. In some cases, an inducible promoter can be a small molecule ligand-inducible two polypeptide ecdysone receptor-based gene switch. In some cases, a gene switch can be selected from ecdysone-based receptor components as described in, but without limitation to, any of the systems described in: International Patent Applications WO 2001/070816; WO 2002/029075; WO 2002/066613; WO 2002/066614; WO 2002/066612; WO 2002/066615; WO 2003/027266; WO 2003/027289; WO 2005/108617; WO 2009/045370; WO 2009/048560; WO 2010/042189; WO 2010/042189; WO 2011/119773; and WO 2012/122025; and U.S. Pat. Nos. 7,091,038; 7,776,587; 7,807,417; 8,202,718; 8,105,825; 8,168,426; 7,531,326; 8,236,556; 8,598,409; 8,715,959; 7,601,508; 7,829,676; 7,919,269; 8,030,067; 7,563,879; 8,021,878; 8,497,093; 7,935,510; 8,076,454; 9,402,919; 9,493,540; 9,249,207; and 9,492,482, each of which is incorporated by reference in its entirety).

The term "gene switch" or "genetic switch" refers to the combination of a response element associated with a promoter, and for instance, an EcR based system, which, in the presence of one or more ligands, modulates the expression of a gene into which the response element and promoter are incorporated. Tightly regulated inducible gene expression systems or gene switches are useful for various applications such as gene therapy, large scale production of proteins in cells, cell based high throughput screening assays, functional genomics and regulation of traits in transgenic plants and animals. Such inducible gene expression systems can include ligand inducible heterologous gene expression systems.

"Sleeping Beauty (SB) Transposon System" refers a synthetic DNA transposon system for to introducing DNA sequences into the chromosomes of vertebrates. Some exemplary embodiments of the system are described, for example, in U.S. Pat. Nos. 6,489,458, 8,227,432, 9,228,180 and WO/2016/145146. The Sleeping Beauty transposon system is composed of a Sleeping Beauty (SB) transposase and a SB transposon. In embodiments, the Sleeping Beauty transposon system can include the SB11 transposon system, the SB100X transposon system, or the SB110 transposon system.

"Transposon" or "transposable element" (TE) is a vector DNA sequence that can change its position within the genome, sometimes creating or reversing mutations and altering the cell's genome size. Transposition often results in duplication of the TE. Class I TEs are copied in two stages: first they are transcribed from DNA to RNA, and the RNA produced is then reverse transcribed to DNA. This copied DNA is then inserted at a new position into the genome. The reverse transcription step is catalyzed by a reverse transcriptase, which can be encoded by the TE itself. The characteristics of retrotransposons are similar to retroviruses, such as HIV. The cut-and-paste transposition mechanism of class II TEs does not involve an RNA intermediate. The transpositions are catalyzed by several transposase enzymes. Some transposases non-specifically bind to any target site in DNA, whereas others bind to specific DNA sequence targets. The transposase makes a staggered cut at the target site resulting in single-strand 5' or 3' DNA overhangs (sticky ends). This step cuts out the DNA transposon, which is then ligated into a new target site; this process involves activity of a DNA polymerase that fills in gaps and of a DNA ligase that closes the sugar-phosphate backbone. This results in duplication of the target site. The insertion sites of DNA transposons can be identified by short direct repeats which can be created by the staggered cut in the target DNA and filling in by DNA polymerase, followed by a series of inverted repeats important for the TE excision by transposase. Cut-and-paste TEs can be duplicated if their transposition takes place during S phase of the cell cycle when a donor site has already been replicated, but a target site has not yet been replicated. Transposition can be classified as either autonomous or non-autonomous in both Class I and Class II TEs. Autonomous TEs can move by themselves while non-autonomous TEs require the presence of another TE to move. This is often because non-autonomous TEs lack transposase (for class II) or reverse transcriptase (for class I).

"Transposase" refers an enzyme that binds to the end of a transposon and catalyzes the movement of the transposon to another part of the genome by a cut and paste mechanism or a replicative transposition mechanism.

"T cell" or "T lymphocyte" as used herein is a type of lymphocyte that plays a central role in cell-mediated immunity. They can be distinguished from other lymphocytes, such as B cells and natural killer cells (NK cells), by the presence of a T-cell receptor (TCR) on the cell surface.

"T helper cells" ($T_H$ cells) assist other white blood cells in immunologic processes, including maturation of B cells into plasma cells and memory B cells, and activation of cytotoxic T cells and macrophages. These cells are also known as CD4+ T cells because they express the CD4 glycoprotein on their surfaces. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response. These cells can differentiate into one of several subtypes, including $T_H1$, $T_H2$, $T_H3$, $T_H9$, $T_H17$, $T_H22$ or $T_{FH}$ (T follicular helper cells), which secrete different cytokines to facilitate different types of immune responses. Signaling from the APCs directs T cells into particular subtypes.

"Cytotoxic T cells" (TC cells, or CTLs) or "cytotoxic T lymphocytes" destroy virus-infected cells and tumor cells, and are also implicated in transplant rejection. These cells are also known as CD8+ T cells since they express the CD8 glycoprotein at their surfaces. These cells recognize their targets by binding to antigen associated with MEW class I molecules, which are present on the surface of all nucleated cells. Through IL-10, adenosine, and other molecules secreted by regulatory T cells, the CD8+ cells can be inactivated to an anergic state, which prevents autoimmune diseases.

"Memory T cells" are a subset of antigen-specific T cells that persist long-term after an infection has resolved. They quickly expand to large numbers of effector T cells upon re-exposure to their cognate antigen, thus providing the immune system with memory against past infections. Memory T cells comprise three subtypes: central memory T cells ($T_{CM}$ cells) and two types of effector memory T cells ($T_{EM}$ cells and $T_{EMRA}$ cells). Memory cells can be either CD4+ or CD8+. Memory T cells typically express the cell surface proteins CD45RO, CD45RA and/or CCR7.

"Regulatory T cells" (Treg cells), formerly known as suppressor T cells, play a role in the maintenance of immunological tolerance. Their major role is to shut down T cell-mediated immunity toward the end of an immune reaction and to suppress autoreactive T cells that escaped the process of negative selection in the thymus.

"Natural killer T cells" (NKT cells—not to be confused with natural killer cells of the innate immune system) bridge the adaptive immune system with the innate immune system. Unlike conventional T cells that recognize peptide antigens presented by major histocompatibility complex (MHC) molecules, NKT cells recognize glycolipid antigen presented by a molecule called CD1d. Once activated, these cells can perform functions ascribed to both T helper ($T_H$) and cytotoxic T (TC) cells (i.e., cytokine production and release of cytolytic/cell killing molecules). They are also able to recognize and eliminate some tumor cells and cells infected with herpes viruses.

"Adoptive T cell transfer" refers to the isolation and ex vivo expansion of tumor specific T cells to achieve greater number of T cells than what could be obtained by vaccination alone or the patient's natural tumor response. The tumor specific T cells are then infused into patients with cancer in an attempt to give their immune system the ability to overwhelm remaining tumor via T cells which can attack and kill cancer. There are many forms of adoptive T cell therapy being used for cancer treatment; culturing tumor infiltrating lymphocytes or TIL, isolating and expanding one particular T cell or clone, and even using T cells that have been engineered to potently recognize and attack tumors.

"Antibody" as used herein refers to monoclonal or polyclonal antibodies. The term "monoclonal antibodies," as used herein, refers to antibodies that are produced by a single clone of B-cells and bind to the same epitope. In contrast, "polyclonal antibodies" refer to a population of antibodies that are produced by different B-cells and bind to different epitopes of the same antigen. A whole antibody typically consists of four polypeptides: two identical copies of a heavy (H) chain polypeptide and two identical copies of a light (L) chain polypeptide. Each of the heavy chains contains one N-terminal variable (VH) region and three C-terminal constant (CH1, CH2 and CH3) regions, and each light chain contains one N-terminal variable (VL) region and one C-terminal constant (CL) region. The variable regions of each pair of light and heavy chains form the antigen binding site of an antibody. The VH and VL regions have a similar general structure, with each region comprising four framework regions, whose sequences are relatively conserved. The framework regions are connected by three complementarity determining regions (CDRs). The three CDRs, known as CDR1, CDR2, and CDR3, form the "hypervariable region" of an antibody, which is responsible for antigen binding.

"Antibody like molecules" can be for example proteins that are members of the Ig-superfamily which are able to selectively bind a partner. MEW molecules and T cell receptors are such molecules. In one embodiment, the antibody-like molecule is an TCR. In one embodiment, the TCR has been modified to increase its MEW binding affinity.

The terms "fragment of an antibody," "antibody fragment," "functional fragment of an antibody," "antigen-binding portion" or its grammatical equivalents are used interchangeably herein to mean one or more fragments or portions of an antibody that retain the ability to specifically bind to an antigen (see, generally, Holliger et al., *Nat. Biotech.,* 23(9):1126-1129 (2005)). The antibody fragment desirably comprises, for example, one or more CDRs, the variable region (or portions thereof), the constant region (or portions thereof), or combinations thereof. Non-limiting examples of antibody fragments include (i) a Fab fragment, which is a monovalent fragment consisting of the VL, VH, CL, and CH1 domains; (ii) a F(ab')2 fragment, which is a bivalent fragment comprising two Fab fragments linked by a disulfide bridge at the stalk region; (iii) a Fv fragment consisting of the VL and VH domains of a single arm of an antibody; (iv) a single chain Fv (scFv), which is a monovalent molecule consisting of the two domains of the Fv fragment (i.e., VL and VH) joined by a synthetic linker which enables the two domains to be synthesized as a single polypeptide chain (see, e.g., Bird et al., *Science,* 242: 423-426 (1988); Huston et al., *Proc. Natl. Acad. Sci.* USA, 85: 5879-5883 (1988); and Osbourn et al., *Nat. Biotechnol.,* 16: 778 (1998)) and (v) a diabody, which is a dimer of polypeptide chains, wherein each polypeptide chain comprises a VH connected to a VL by a peptide linker that is too short to allow pairing between the VH and VL on the same polypeptide chain, thereby driving the pairing between the complementary domains on different VH-VL polypeptide chains to generate a dimeric molecule having two functional antigen binding sites. Antibody fragments are known in the art and are described in more detail in, e.g., U.S. Pat. No. 8,603,950.

"Antigen recognition moiety" or "antigen recognition domain" refers to a molecule or portion of a molecule that specifically binds to an antigen. In one embodiment, the antigen recognition moiety is an antibody, antibody like molecule or fragment thereof and the antigen is a tumor antigen.

The term "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz, G. E. and Schirmer, R. H., Principles of Protein Structure, Springer-Verlag, New York (1979)). According to such analyses, groups of amino acids can be defined where amino acids within a group exchange preferentially with each other, and therefore resemble each other most in their impact on the overall protein structure (Schulz, G. E. and Schirmer, R. H., supra). Examples of conservative mutations include amino acid substitutions of amino acids within the sub-groups above, for example, lysine for arginine and vice versa such that a positive charge can be maintained; glutamic acid for aspartic acid and vice versa such that a negative charge can be maintained; serine for threonine such that a free —OH can be maintained; and glutamine for asparagine such that a free —$NH_2$ can be maintained. Alternatively or additionally, the functional variants can comprise the amino acid sequence of the reference protein with at least one non-conservative amino acid substitution.

The term "non-conservative mutations" involve amino acid substitutions between different groups, for example, lysine for tryptophan, or phenylalanine for serine, etc. In this case, it is preferable for the non-conservative amino acid substitution to not interfere with, or inhibit the biological activity of, the functional variant. The non-conservative amino acid substitution can enhance the biological activity of the functional variant, such that the biological activity of the functional variant is increased as compared to the homologous parent protein.

The term "ankyrin" refers to a family of adaptor proteins that mediate the attachment of integral membrane proteins to the spectrin-actin based membrane cytoskeleton. Ankyrins have binding sites for the beta subunit of spectrin and at least 12 families of integral membrane proteins. This linkage is required to maintain the integrity of the plasma membranes and to anchor specific ion channels, ion exchangers and ion transporters in the plasma membrane. Ankyrins contain four functional domains: an N-terminal domain that contains 24 tandem ankyrin repeats, a central domain that binds to spectrin, a death domain that binds to proteins involved in apoptosis, and a C-terminal regulatory domain that is highly variable between different ankyrin proteins. The 24 tandem ankyrin repeats are responsible for the recognition of a wide range of membrane proteins. These 24 repeats contain 3 structurally distinct binding sites ranging from repeat 1-14. These binding sites are quasi-independent of each other and can be used in combination. The interactions the sites use to bind to membrane proteins are non-specific and consist of: hydrogen bonding, hydrophobic interactions and electrostatic interactions. These non-specific interactions gives ankyrin the property to recognize a large range of proteins as the sequence doesn't have to be conserved just the properties of the amino acids. The quasi-independence means that if a binding site is not used, it won't have a large effect on the overall binding. These two properties in combination give rise to large repertoire of proteins ankyrin can recognize. Ankyrins are encoded by three genes (ANK1, ANK2 and ANK3) in mammals. Each gene in turn produces multiple proteins through alternative splicing.

The term "proliferative disease" as referred to herein refers to a unifying concept in which excessive proliferation of cells and/or turnover of cellular matrix contributes significantly to the pathogenesis of the disease, including cancer.

"Patient" or "subject" as used herein refers to a mammalian subject diagnosed with or suspected of having or developing a proliferative disorder such as cancer. In some embodiments, the term "patient" refers to a mammalian subject with a higher than average likelihood of developing a proliferative disorder such as cancer. Exemplary patients can be humans, apes, dogs, pigs, cattle, cats, horses, goats, sheep, rodents and other mammalians that can benefit from the therapies disclosed herein. Exemplary human patients can be male and/or female. "Patient in need thereof" or "subject in need thereof" is referred to herein as a patient diagnosed with or suspected of having a disease or disorder, for instance, but not restricted to human papilloma virus (HPV) infection.

"Administering" is referred to herein as providing one or more compositions described herein to a patient or a subject. By way of example and not limitation, composition administration, e.g., injection, can be performed by intravenous (i.v.) injection, sub-cutaneous (s.c.) injection, intradermal (i.d.) injection, intraperitoneal (i.p.) injection, or intramuscular (i.m.) injection. One or more such routes can be employed. Parenteral administration can be, for example, by bolus injection or by gradual perfusion over time. Alternatively, or concurrently, administration can be by the oral route. Additionally, administration can also be by surgical deposition of a bolus or pellet of cells, or positioning of a medical device. In an embodiment, a composition of the present disclosure can comprise engineered cells or host cells expressing nucleic acid sequences described herein, or a vector comprising at least one nucleic acid sequence described herein, in an amount that is effective to treat or prevent proliferative disorders. A pharmaceutical composition can comprise a target cell population as described herein, in combination with one or more pharmaceutically or physiologically acceptable carriers, diluents or excipients. Such compositions can comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

As used herein, the term "treatment", "treating", or its grammatical equivalents refers to obtaining a desired pharmacologic and/or physiologic effect. In embodiments, the effect is therapeutic, i.e., the effect partially or completely cures a disease and/or adverse symptom attributable to the disease. To this end, the inventive method comprises administering a therapeutically effective amount of the composition comprising the host cells expressing the inventive nucleic acid sequence, or a vector comprising the inventive nucleic acid sequences.

The term "therapeutically effective amount", therapeutic amount", "immunologically effective amount", "anti-tumor effective amount", "tumor-inhibiting effective amount" or its grammatical equivalents refers to an amount effective, at dosages and for periods of time necessary, to achieve a desired therapeutic result. The therapeutically effective amount can vary according to factors such as the disease state, age, sex, and weight of the individual, and the ability of a composition described herein to elicit a desired response in one or more subjects. The precise amount of the compositions of the present disclosure to be administered can be determined by a physician with consideration of individual differences in age, weight, tumor size, extent of infection or metastasis, and condition of the patient (subject).

Alternatively, the pharmacologic and/or physiologic effect of administration of one or more compositions described herein to a patient or a subject of can be "prophylactic," i.e., the effect completely or partially prevents a disease or symptom thereof. A "prophylactically effective amount" refers to an amount effective, at dosages and for periods of time necessary, to achieve a desired prophylactic result (e.g., prevention of disease onset).

HPV Molecular Vaccine

Human papillomavirus (HPV) is a group of more than 200 related viruses. Each HPV virus in this large group is given a number which is called its HPV type (or serotype). HPV is a small, non-enveloped deoxyribonucleic acid (DNA) virus that infects skin or mucosal cells. The circular, double-stranded viral genome is approximately 8-kb in length. The genome encodes for seven early proteins (E1 to E7) responsible for virus replication and two late proteins (L1 and L2), which are the viral structural proteins. As depicted in FIG. 1, each gene has specific functions. At least 13 of more than 200 known HPV types can cause cancer of the cervix and are associated with other anogenital cancers and cancers of the head and neck. The two most common "high-risk" serotypes (HPV-16 and HPV-18) cause approximately 70% of all cervical cancers. In HPV-16 and HPV-18, two primary oncoproteins, E6 and E7, are constitutively expressed by HPV-associated tumors and are critical for the induction and maintenance of cellular transformation in HPV-infected cells. Recent evidence also suggests the E5 protein also impacts viral transformation. HPV types 16, 18, 31, 33, 35, 39, 45, 51, 52, 56, 58, 59, 68, 73, and 82 are considered carcinogenic. Two "low-risk" HPV 6 and 11 are known to cause genital warts, a common benign condition of the external genitalia that causes significant morbidity. HPV is highly transmissible, with peak incidence soon after the onset of sexual activity, and most persons acquire infection at some time in their lives.

Prophylactic vaccines composed of virus-like particles, only induce immunity to the capsid structure and not to the non-structural proteins responsible for cell transformation. Initial HPV studies in animal models showed that inoculation with species-specific papillomaviruses induced an immune response that conferred protection against homologous virus challenge. However, native papillomaviruses are not good substrates for vaccine development as they cannot be grown easily in tissue culture. Subsequent studies were initiated on the production of viral particles from expression of the structural proteins in heterologous expression systems, such as yeast or baculovirus vectors. Results showed that expression of L1 alone led to the production of virus-like particles (VLPs) which morphologically resemble the authentic HPV virions but contain no viral DNA. These VLPs are produced by self-assembly of the L1 protein when expressed in a heterologous cell substrate. In animal studies, VLPs were shown to protect against high dose experimental infection by homologous virus. HPV VLPs are highly immunogenic in mice or rabbits, and the resulting antibodies have been shown to be neutralizing and type restricted when tested in a pseudovirion neutralization assay. Immunization with denatured particles does not result in the production of neutralizing antibodies, or protect from experimental virus challenge, indicating that neutralizing epitopes are conformation dependent.

Provided herein are compositions, kits, and systems comprising methods of making HPV recombinant vaccines. The HPV recombinant vaccines (e.g., HPV designs 1-5) in the present disclosure are engineered through protein engineering of E5, E6, and E7. These vaccines include a greater protein level sequence consensus amongst different HPV-16 and HPV-18 isolates. Moreover, they include genetically modified mutations to avoid oncogenic activities, improve their expression, and trigger broader immune response. Also provided herein are multi-epitope recombinant antigens containing immunogenic epitopes of the E5, E6, and E7 proteins. Along with the present HPV vaccine designs, certain enhancer agonist peptides previously shown to activate HPV-specific T cells are included. In some embodiments, the agonist peptides comprise one or more peptide sequences as shown in Table 2.

Each HPV vaccine antigen design was inspired via inventor-selected combinatorial use of bioinformatics analysis and in silico protein engineering methods (e.g., selection of antigenic sequences based on consensus sequences, antigenicity predictions, and T cell epitope mapping, targeted to induce MHC-I binding and cytokine production following T cell activation). The overall workflow of the presently disclosed HPV vaccine designs is shown in FIG. 2 and is further detailed in Example 2.

The naturally existing sequence variations on numerous HPV strains present a significant hurdle to the development of effective, broad spectrum HPV vaccines. As a solution to this problem, the present vaccine design approach utilizes advanced bioinformatics and protein engineering approaches to select and design antigen sequences with broad coverage of T cell epitopes, novel mutations, and enhancer agonist peptides. Drawing on information available of extended coverage of antigen regions with CTL-specific epitopes and in silico prediction results, the designed HPV vaccine antigens are targeted to induce robust HPV-16 and HPV-18 specific responses and provide therapeutic benefit to persons at risk of HPV-derived cancers.

Figure 6:
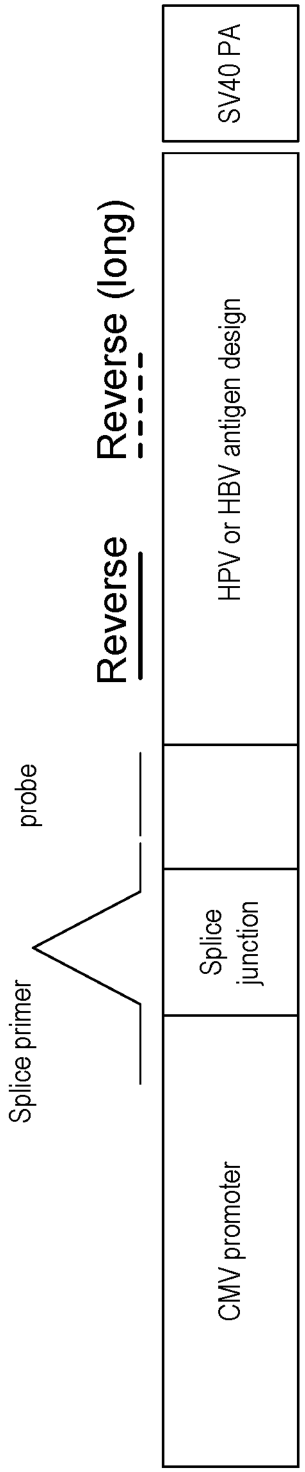
FIG. 6 is a schematic illustration showing short and long primer and probe sets generated for RNA qPCR relative expression assay. Specific primers were designed for each HPV antigen design.

The present disclosure provides five HPV antigen designs (HPV designs 1-5) constructed in a multi-deleted gorilla adenovector (GC46). Detailed methods for each of the HPV antigen designs are elaborated in Examples 1-3. For RNA qPCR relative expression assay, 5'-TGCCAAGAGTGACGTGTCCA-3' (SEQ ID NO: 110) was used as a splice primer, and 5'-CCCAGGTCCAACTGCAGCCGG-3' (SEQ ID NO: 111) was used as a splice probe. Specific primers designed for each antigen were used as reverse primers (FIG. 6).

Delivery System

Gorilla Adenovirus Shuttle Vector

Certain aspects of the present disclosure are directed to a vector comprising a polynucleotide encoding a polypeptide comprising one or more immune response-inducing HPV polypeptides described herein. In certain embodiments, the vector is a viral vector. In particular embodiments, the vector is an adenoviral vector. Adenoviruses are generally associated with benign pathologies in humans, and the genomes of adenoviruses isolated from a variety of species, including humans, have been extensively studied. Adenovirus is a medium-sized (90-100 nm), non-enveloped icosahedral virus containing approximately 36 kb of double-stranded DNA. The adenovirus capsid mediates the key interactions of the early stages of the infection of a cell by the virus, and is required for packaging adenovirus genomes at the end of the adenovirus life cycle. The capsid comprises 252 capsomeres, which includes 240 hexons, 12 penton base proteins, and 12 fibers (Ginsberg et al., *Virology,* 28: 782-83 (1966)). The hexon comprises three identical proteins, namely polypeptide II (Roberts et al., *Science,* 232: 1148-51 (1986)). The penton base comprises five identical proteins and the fiber comprises three identical proteins. Proteins IIIa, VI, and IX are present in the adenoviral coat and are believed to stabilize the viral capsid (Stewart et al., *Cell,* 67: 145-54 (1991), and Stewart et al., *EMBO J.,* 12(7): 2589-99 (1993)). The expression of the capsid proteins, with the exception of pIX, is dependent on the adenovirus polymerase protein. Therefore, major components of an adenovirus particle are expressed from the genome only when the polymerase protein gene is present and expressed.

Several features of adenoviruses make them ideal vehicles for transferring genetic material to cells for therapeutic applications (i.e., "gene therapy"), or for use as antigen delivery systems for vaccine applications. For example, adenoviruses can be produced in high titers (e.g., about $10^{13}$ particle units (pu)), and can transfer genetic material to non-replicating and replicating cells. The adenoviral genome can be manipulated to carry a large amount of exogenous DNA (up to about 8 kb), and the adenoviral capsid can potentiate the transfer of even longer sequences (Curiel et al., *Hum. Gene Ther.,* 3: 147-154 (1992)). Additionally, adenoviruses generally do not integrate into the host cell chromosome, but rather are maintained as a linear episome, thereby minimizing the likelihood that a recombinant adenovirus will interfere with normal cell function.

In some embodiments, the adenovirus described herein is isolated from a gorilla. There are four widely recognized gorilla subspecies within the two species of Eastern Gorilla (*Gorilla beringei*) and Western Gorilla (*Gorilla gorilla*). The Western Gorilla species includes the subspecies Western Lowland Gorilla (*Gorilla gorilla gorilla*) and Cross River Gorilla (*Gorilla gorilla diehli*). The Eastern Gorilla species includes the subspecies Mountain Gorilla (*Gorilla beringei beringei*) and Eastern Lowland Gorilla (*Gorilla beringei graueri*) (see, e.g., Wilson and Reeder, eds., *Mammalian Species of the World,* 3rd ed., Johns Hopkins University Press, Baltimore, Maryland (2005)). In some embodiments, the adenovirus of the present disclosure is isolated from Mountain Gorilla (*Gorilla beringei beringei*).

Various Gorilla adenoviruses or adenoviral vectors are described in International Patent Application Publications WO 2013/052832; WO 2013/052811; and WO 2013 052799, each of which is herein incorporated by reference in its entirety.

The genomes of several such adenoviruses have been analyzed, and it has been determined that the adenovirus can have the nucleic acid sequence of, for example, SEQ ID NO: 21, SEQ ID NO: 22, SEQ ID NO: 23, SEQ ID NO: 24, or SEQ ID NO: 25, each of which includes a number of sub-sequences that serve to uniquely define the adenovirus, namely the nucleic acid sequences SEQ ID NOs: 1-10, and amino acid sequences SEQ ID NOs: 11-20. SEQ ID NOs: 6-10 encode the amino acid sequences of SEQ ID NOs: 16-20, respectively. SEQ ID NOs: 1-5 are a subset of the nucleic acid sequences of SEQ ID NOs: 6-10, respectively. SEQ ID NOs: 11-15 are a subset of the amino acid sequences of SEQ ID NOs: 16-20, respectively.

The adenovirus can be modified in the same manner as previously known adenoviruses to be used as an adenoviral vector, e.g., a gene delivery vehicle. The adenovirus and adenoviral vector can be replication-competent, conditionally replication-competent, or replication-deficient.

A replication-competent adenovirus or adenoviral vector can replicate in typical host cells, i.e., cells typically capable of being infected by an adenovirus. A replication-competent adenovirus or adenoviral vector can have one or more mutations as compared to the wild-type adenovirus (e.g., one or more deletions, insertions, and/or substitutions) in the adenoviral genome that do not inhibit viral replication in host cells. For example, the adenovirus or adenoviral vector can have a partial or entire deletion of the adenoviral early region known as the E3 region, which is not essential for propagation of the adenovirus or adenoviral genome.

A conditionally-replicating adenovirus or adenoviral vector is an adenovirus or adenoviral vector that has been engineered to replicate under pre-determined conditions. For example, replication-essential gene functions, e.g., gene functions encoded by the adenoviral early regions, can be operably linked to an inducible, repressible, or tissue-specific transcription control sequence, e.g., promoter. In such an embodiment, replication requires the presence or absence of specific factors that interact with the transcription control sequence. Conditionally-replicating adenoviral vectors are further described in U.S. Pat. No. 5,998,205.

A replication-deficient adenovirus or adenoviral vector is an adenovirus or adenoviral vector that requires complementation of one or more gene functions or regions of the adenoviral genome that are required for replication, as a result of, for example, a deficiency in one or more replication-essential gene function or regions, such that the adenovirus or adenoviral vector does not replicate in typical host cells, especially those in a human to be infected by the adenovirus or adenoviral vector.

A deficiency in a gene function or genomic region, as used herein, is defined as a disruption (e.g., deletion) of sufficient genetic material of the adenoviral genome to obliterate or impair the function of the gene (e.g., such that the function of the gene product is reduced by at least about 2-fold, 5-fold, 10-fold, 20-fold, 30-fold, or 50-fold) whose nucleic acid sequence was disrupted (e.g., deleted) in whole or in part. Deletion of an entire gene region often is not required for disruption of a replication-essential gene function. However, for the purpose of providing sufficient space in the adenoviral genome for one or more transgenes, removal of a majority of one or more gene regions can be desirable. While deletion of genetic material is preferred, mutation of genetic material by addition or substitution also is appropriate for disrupting gene function. Replication-essential gene functions are those gene functions that are required for adenovirus replication (e.g., propagation) and are encoded by, for example, the adenoviral early regions (e.g., the E1, E2, and E4 regions), late regions (e.g., the L1, L2, L3, L4, and L5 regions), genes involved in viral packaging (e.g., the IVa2 gene), and virus-associated RNAs (e.g., VA-RNA-1 and/or VA-RNA-2).

Whether the adenovirus or adenoviral vector is replication-competent or replication-deficient, the adenovirus or adenoviral vector retains at least a portion of the adenoviral genome. The adenovirus or adenoviral vector can comprise any portion of the adenoviral genome, including protein coding and non-protein coding regions. Desirably, the adenovirus or adenoviral vector comprises at least one nucleic acid sequence that encodes an adenovirus protein. The adenovirus or adenoviral vector can comprise a nucleic acid sequence that encodes any suitable adenovirus protein, such as, for example, a protein encoded by any one of the early region genes (i.e., E1A, E1B, E2A, E2B, E3, and/or E4 regions), or a protein encoded by any one of the late region genes, which encode the virus structural proteins (i.e., L1, L2, L3, L4, and L5 regions).

The adenovirus or adenoviral vector desirably comprises one or more nucleic acid sequences that encode the pIX protein, the DNA polymerase protein, the penton protein, the hexon protein, and/or the fiber protein. The adenovirus or adenoviral vector can comprise a full-length nucleic acid sequence that encodes a full-length amino acid sequence of an adenovirus protein. Alternatively, the adenovirus or adenoviral vector can comprise a portion of a full-length nucleic acid sequence that encodes a portion of a full-length amino acid sequence of an adenovirus protein.

A "portion" of a nucleic acid sequence comprises at least ten nucleotides (e.g., about 10 to about 5000 nucleotides). Preferably, a "portion" of a nucleic acid sequence comprises 10 or more (e.g., 15 or more, 20 or more, 25 or more, 30 or more, 35 or more, 40 or more, 45 or more, 50 or more, or 100 or more) nucleotides, but less than 5,000 (e.g., 4900 or less, 4000 or less, 3000 or less, 2000 or less, 1000 or less, 800 or less, 500 or less, 300 or less, or 100 or less)

nucleotides. Preferably, a portion of a nucleic acid sequence is about 10 to about 3500 nucleotides (e.g., about 10, 20, 30, 50, 100, 300, 500, 700, 1000, 1500, 2000, 2500, or 3000 nucleotides), about 10 to about 1000 nucleotides (e.g., about 25, 55, 125, 325, 525, 725, or 925 nucleotides), or about 10 to about 500 nucleotides (e.g., about 15, 30, 40, 50, 60, 70, 80, 90, 150, 175, 250, 275, 350, 375, 450, 475, 480, 490, 495, or 499 nucleotides), or a range defined by any two of the foregoing values. More preferably, a "portion" of a nucleic acid sequence comprises no more than about 3200 nucleotides (e.g., about 10 to about 3200 nucleotides, about 10 to about 3000 nucleotides, or about 30 to about 500 nucleotides, or a range defined by any two of the foregoing values).

A "portion" of an amino acid sequence comprises at least three amino acids (e.g., about 3 to about 1,200 amino acids). Preferably, a "portion" of an amino acid sequence comprises 3 or more (e.g., 5 or more, 10 or more, 15 or more, 20 or more, 25 or more, 30 or more, 40 or more, or 50 or more) amino acids, but less than 1,200 (e.g., 1,000 or less, 800 or less, 700 or less, 600 or less, 500 or less, 400 or less, 300 or less, 200 or less, or 100 or less) amino acids. Preferably, a portion of an amino acid sequence is about 3 to about 500 amino acids (e.g., about 10, 100, 200, 300, 400, or 500 amino acids), about 3 to about 300 amino acids (e.g., about 20, 50, 75, 95, 150, 175, or 200 amino acids), or about 3 to about 100 amino acids (e.g., about 15, 25, 35, 40, 45, 60, 65, 70, 80, 85, 90, 95, or 99 amino acids), or a range defined by any two of the foregoing values. More preferably, a "portion" of an amino acid sequence comprises no more than about 500 amino acids (e.g., about 3 to about 400 amino acids, about 10 to about 250 amino acids, or about 50 to about 100 amino acids, or a range defined by any two of the foregoing values).

The adenovirus pIX protein is present in the adenovirus capsid, has been shown to strengthen hexon nonamer interactions, and is essential for the packaging of full-length genomes (see, e.g., Boulanger et al., *J Gen. Virol.,* 44: 783-800 (1979); Horwitz M. S., "Adenoviridae and their replication" in *Virology,* 2$^{nd}$ ed., B. N. Fields et al. (eds.), Raven Press, Ltd., New York, pp. 1679-1721 (1990), Ghosh-Choudhury et al., *EMBO J.,* 6: 1733-1739 (1987), and van Oostrum et al, *J. Virol.,* 56: 439-448 (1985)). In addition to its contribution to adenovirus structure, pIX also has been shown to exhibit transcriptional properties, such as stimulation of adenovirus major late promoter (MLP) activity (see, e.g., Lutz et al., *J. Virol.,* 71(7): 5102-5109 (1997)). Nucleic acid sequences that encode all or a portion of an adenovirus pIX protein include, for example, SEQ ID NO: 6 and SEQ ID NO: 1. Amino acid sequences that comprise a full-length pIX protein, or a portion thereof, include, for example, SEQ ID NO: 16 and SEQ ID NO: 11.

The adenovirus DNA polymerase protein is essential for viral DNA replication both in vitro and in vivo. The polymerase co-purifies in a complex with the precursor (pTP) of the terminal protein (TP), which is covalently attached to the 5' ends of adenovirus DNA (Field et al., *J. Biol. Chem.,* 259: 9487-9495 (1984)). Both the adenovirus DNA polymerase and pTP are encoded by the E2 region. The polymerase protein is required for the expression of all the structural proteins except for pIX. Without the gene sequence for polymerase protein, polymerase protein is not produced. As a result, the viral genome is not replicated, the Major Late Promoter is not activated, and the capsid proteins are not expressed. Nucleic acid sequences that encode all or a portion of an adenovirus DNA polymerase protein include, for example, SEQ ID NO: 7 and SEQ ID NO: 2. Amino acid sequences that comprise a full-length adenovirus DNA polymerase, or a portion thereof, include, for example, SEQ ID NO: 17 and SEQ ID NO: 12.

The adenovirus hexon protein is the largest and most abundant protein in the adenovirus capsid. The hexon protein is essential for virus capsid assembly, determination of the icosahedral symmetry of the capsid (which in turn defines the limits on capsid volume and DNA packaging size), and integrity of the capsid. In addition, hexon is a primary target for modification in order to reduce neutralization of adenoviral vectors (see, e.g., Gall et al., *J. Virol.,* 72: 10260-264 (1998), and Rux et al., *J. Virol.,* 77(17): 9553-9566 (2003)). The major structural features of the hexon protein are shared by adenoviruses across serotypes, but the hexon protein differs in size and immunological properties between serotypes (Jornvall et al., *J. Biol. Chem.,* 256(12): 6181-6186 (1981)). A comparison of 15 adenovirus hexon proteins revealed that the predominant antigenic and serotype-specific regions of the hexon appear to be in loops 1 and 2 (i.e., LI or l1, and LII or l2, respectively), within which are seven discrete hypervariable regions (HVR1 to HVR7) varying in length and sequence between adenoviral serotypes (Crawford-Miksza et al., *J. Virol.,* 70(3): 1836-1844 (1996)). Nucleic acid sequences that encode all or a portion of an adenovirus hexon protein include, for example, SEQ ID NO: 9 and SEQ ID NO: 4. Amino acid sequences that comprise a full-length adenovirus hexon protein, or a portion thereof, include, for example, SEQ ID NO: 19 and SEQ ID NO: 14.

The adenovirus fiber protein is a homotrimer of the adenoviral polypeptide IV that has three domains: the tail, shaft, and knob. (Devaux et al., *J. Molec. Biol.,* 215: 567-88 (1990), Yeh et al., *Virus Res.,* 33: 179-98 (1991)). The fiber protein mediates primary viral binding to receptors on the cell surface via the knob and the shaft domains (Henry et al., *J. Virol.,* 68(8): 5239-46 (1994)). The amino acid sequences for trimerization are located in the knob, which appears necessary for the amino terminus of the fiber (the tail) to properly associate with the penton base (Novelli et al., *Virology,* 185: 365-76 (1991)). In addition to recognizing cell receptors and binding the penton base, the fiber contributes to serotype identity. Fiber proteins from different adenoviral serotypes differ considerably (see, e.g., Green et al., *EMBO J.,* 2: 1357-65 (1983), Chroboczek et al., *Virology,* 186: 280-85 (1992), and Signas et al., *J. Virol.,* 53: 672-78 (1985)). Thus, the fiber protein has multiple functions key to the life cycle of adenovirus. Nucleic acid sequences that encode all or a portion of an adenovirus fiber protein include, for example, SEQ ID NO: 10 and SEQ ID NO: 5. Amino acid sequences that comprise a full-length adenovirus fiber protein, or a portion thereof, include, for example, SEQ ID NO: 20 and SEQ ID NO: 15.

The adenovirus penton base protein is located at the vertices of the icosahedral capsid and comprises five identical monomers. The penton base protein provides a structure for bridging the hexon proteins on multiple facets of the icosahedral capsid, and provides the essential interface for the fiber protein to be incorporated in the capsid. Each monomer of the penton base contains an RGD tripeptide motif (Neumann et al., *Gene,* 69: 153-157 (1988)). The RGD tripeptide mediates binding to αv integrins and adenoviruses that have point mutations in the RGD sequence of the penton base are restricted in their ability to infect cells (Bai et al., *J. Virol.,* 67: 5198-5205 (1993)). Thus, the penton base protein is essential for the architecture of the capsid and for maximum efficiency of virus-cell interaction. Nucleic acid sequences that encode all or a portion of an adenovirus penton base protein include, for example, SEQ ID NO: 8 and SEQ ID NO: 3. Amino acid sequences that comprise a full-length adenovirus penton base protein, or a portion thereof, include, for example, SEQ ID NO: 18 and SEQ ID NO: 13.

Nucleic acid or amino acid sequence "identity," as described herein, can be determined by comparing a nucleic acid or amino acid sequence of interest to a reference nucleic acid or amino acid sequence. The numbers of nucleotides or amino acid residues that have been changed and/or modified (such as, e.g., by point mutations, insertions, or deletions) in the reference sequence so as to result in the sequence of interest are counted. The total number of such changes is subtracted from the total length of the sequence of interest, and the difference is divided by the length of the sequence of interest and expressed as a percentage. A number of mathematical algorithms for obtaining the optimal alignment and calculating identity between two or more sequences are known and incorporated into a number of available software programs. Examples of such programs include CLUSTAL-W, T-Coffee, and ALIGN (for alignment of nucleic acid and amino acid sequences), BLAST programs (e.g., BLAST 2.1, BL2SEQ, and later versions thereof) and FASTA programs (e.g., FASTA3x, FASTM, and SSEARCH) (for sequence alignment and sequence similarity searches). Sequence alignment algorithms also are disclosed in, for example, Altschul et al., *J. Molecular Biol.*, 215(3): 403-410 (1990), Beigert et al., *Proc. Natl. Acad. Sci.* USA, 106(10): 3770-3775 (2009), Durbin et al., eds., *Biological Sequence Analysis: Probabilistic Models of Proteins and Nucleic Acids*, Cambridge University Press, Cambridge, UK (2009), Soding, *Bioinformatics,* 21(7): 951-960 (2005), Altschul et al., *Nucleic Acids Res.*, 25(17): 3389-3402 (1997), and Gusfield, *Algorithms on Strings, Trees and Sequences*, Cambridge University Press, Cambridge UK (1997)).

The adenovirus or adenoviral vector can comprise one, two, three, four, or all five of the aforementioned sequences alone or in any combination. In this respect, the adenovirus or adenoviral vector can comprise any combination of any two of the aforementioned sequences, any combination of any three of the aforementioned sequences, any combination of any four of the aforementioned sequences, or all five of the aforementioned sequences.

As discussed herein, the adenovirus or adenoviral vector can be replication-competent, conditionally-replicating, or replication-deficient. Preferably, the adenovirus or adenoviral vector is replication-deficient, such that the replication-deficient adenovirus or adenoviral vector requires complementation of at least one replication-essential gene function of one or more regions of the adenoviral genome for propagation (e.g., to form adenoviral vector particles).

The replication-deficient adenovirus or adenoviral vector can be modified in any suitable manner to cause the deficiencies in the one or more replication-essential gene functions in one or more regions of the adenoviral genome for propagation. The complementation of the deficiencies in the one or more replication-essential gene functions of one or more regions of the adenoviral genome refers to the use of exogenous means to provide the deficient replication-essential gene functions. Such complementation can be effected in any suitable manner, for example, by using complementing cells and/or exogenous DNA (e.g., helper adenovirus) encoding the disrupted replication-essential gene functions.

The adenovirus or adenoviral vector can be deficient in one or more replication-essential gene functions of only the early regions (i.e., E1-E4 regions) of the adenoviral genome, only the late regions (i.e., L1-L5 regions) of the adenoviral genome, both the early and late regions of the adenoviral genome, or all adenoviral genes (i.e., a high capacity adenovector (HC-Ad). See Morsy et al., *Proc. Natl. Acad. Sci.* USA, 95: 965-976 (1998); Chen et al., *Proc. Natl. Acad. Sci.* USA, 94: 1645-1650 (1997); and Kochanek et al., *Hum. Gene Ther.,* 10: 2451-2459 (1999). Examples of replication-deficient adenoviral vectors are disclosed in U.S. Pat. Nos. 5,837,511; 5,851,806; 5,994,106; 6,127,175; 6,482,616; and 7,195,896, and International Patent Application Publications WO 1994/028152, WO 1995/002697, WO 1995/016772, WO 1995/034671, WO 1996/022378, WO 1997/012986, WO 1997/021826, and WO 2003/022311.

The early regions of the adenoviral genome include the E1, E2, E3, and E4 regions. The E1 region comprises the E1A and E1B subregions, and one or more deficiencies in replication-essential gene functions in the E1 region can include one or more deficiencies in replication-essential gene functions in either or both of the E1A and E1B subregions, thereby requiring complementation of the E1A subregion and/or the E1B subregion of the adenoviral genome for the adenovirus or adenoviral vector to propagate (e.g., to form adenoviral vector particles). The E2 region comprises the E2A and E2B subregions, and one or more deficiencies in replication-essential gene functions in the E2 region can include one or more deficiencies in replication-essential gene functions in either or both of the E2A and E2B subregions, thereby requiring complementation of the E2A subregion and/or the E2B subregion of the adenoviral genome for the adenovirus or adenoviral vector to propagate (e.g., to form adenoviral vector particles).

The E3 region does not include any replication-essential gene functions, such that a deletion of the E3 region in part or in whole does not require complementation of any gene functions in the E3 region for the adenovirus or adenoviral vector to propagate (e.g., to form adenoviral vector particles). In the context of the present disclosure, the E3 region is defined as the region that initiates with the open reading frame that encodes a protein with high homology to the 12.5K protein from the E3 region of human adenovirus 5 (NCBI reference sequence AP_000218) and ends with the open reading frame that encodes a protein with high homology to the 14.7K protein from the E3 region of human adenovirus 5 (NCBI reference sequence AP_000224.1). The E3 region can be deleted in whole or in part, or retained in whole or in part. The size of the deletion can be tailored so as to retain an adenovirus or adenoviral vector whose genome closely matches the optimum genome packaging size. A larger deletion will accommodate the insertion of larger heterologous nucleic acid sequences in the adenovirus or adenoviral genome. In one embodiment of the present disclosure, the L4 polyadenylation signal sequences, which reside in the E3 region, are retained.

The E4 region comprises multiple open reading frames (ORFs). An adenovirus or adenoviral vector with a deletion of all of the open reading frames of the E4 region except ORF6, and in some cases ORF3, does not require complementation of any gene functions in the E4 region for the adenovirus or adenoviral vector to propagate (e.g., to form adenoviral vector particles). Conversely, an adenovirus or adenoviral vector with a disruption or deletion of ORF6, and in some cases ORF3, of the E4 region (e.g., with a deficiency in a replication-essential gene function based in ORF6 and/or ORF3 of the E4 region), with or without a disruption or deletion of any of the other open reading frames of the E4 region or the native E4 promoter, polyadenylation sequence, and/or the right-side inverted terminal repeat (ITR), requires complementation of the E4 region (specifically, of ORF6 and/or ORF3 of the E4 region) for the adenovirus or adenoviral vector to propagate (e.g., to form adenoviral vector particles). The late regions of the adenoviral genome include the L1, L2, L3, L4, and L5 regions. The adenovirus or adenoviral vector also can have a mutation in the major late promoter (MLP), as discussed in International Patent Application Publication WO 2000/000628, which can render the adenovirus or adenoviral vector replication-deficient if desired.

The one or more regions of the adenoviral genome that contain one or more deficiencies in replication-essential gene functions desirably are one or more early regions of the adenoviral genome, i.e., the E1, E2, and/or E4 regions, optionally with the deletion in part or in whole of the E3 region.

The replication-deficient adenovirus or adenoviral vector also can have one or more mutations as compared to the wild-type adenovirus (e.g., one or more deletions, insertions, and/or substitutions) in the adenoviral genome that do not inhibit viral replication in host cells. Thus, in addition to one or more deficiencies in replication-essential gene functions, the adenovirus or adenoviral vector can be deficient in other respects that are not replication-essential. For example, the adenovirus or adenoviral vector can have a partial or entire deletion of the adenoviral early region known as the E3 region, which is not essential for propagation of the adenovirus or adenoviral genome.

In one embodiment, the adenovirus or adenoviral vector is replication-deficient and requires, at most, complementation of the E1 region or the E4 region of the adenoviral genome, for propagation (e.g., to form adenoviral vector particles). Thus, the replication-deficient adenovirus or adenoviral vector requires complementation of at least one replication-essential gene function of the E1A subregion and/or the E1B region of the adenoviral genome (denoted an E1-deficient adenoviral vector) or the E4 region of the adenoviral genome (denoted an E4-deficient adenoviral vector) for propagation (e.g., to form adenoviral vector particles). The adenovirus or adenoviral vector can be deficient in at least one replication-essential gene function (desirably all replication-essential gene functions) of the E1 region of the adenoviral genome and at least one gene function of the nonessential E3 region of the adenoviral genome (denoted an E1/E3-deficient adenoviral vector). The adenovirus or adenoviral vector can be deficient in at least one replication-essential gene function (desirably all replication-essential gene functions) of the E4 region of the adenoviral genome and at least one gene function of the nonessential E3 region of the adenoviral genome (denoted an E3/E4-deficient adenoviral vector).

In one embodiment, the adenovirus or adenoviral vector is replication-deficient and requires, at most, complementation of the E2 region, preferably the E2A subregion, of the adenoviral genome, for propagation (e.g., to form adenoviral vector particles). Thus, the replication-deficient adenovirus or adenoviral vector requires complementation of at least one replication-essential gene function of the E2A subregion of the adenoviral genome (denoted an E2A-deficient adenoviral vector) for propagation (e.g., to form adenoviral vector particles). The adenovirus or adenoviral vector can be deficient in at least one replication-essential gene function (desirably all replication-essential gene functions) of the E2A region of the adenoviral genome and at least one gene function of the nonessential E3 region of the adenoviral genome (denoted an E2A/E3-deficient adenoviral vector).

In one embodiment, the adenovirus or adenoviral vector is replication-deficient and requires, at most, complementation of the E1 and E4 regions of the adenoviral genome for propagation (e.g., to form adenoviral vector particles). Thus, the replication-deficient adenovirus or adenoviral vector requires complementation of at least one replication-essential gene function of both the E1 and E4 regions of the adenoviral genome (denoted an E1/E4-deficient adenoviral vector) for propagation (e.g., to form adenoviral vector particles). The adenovirus or adenoviral vector can be deficient in at least one replication-essential gene function (desirably all replication-essential gene functions) of the E1 region of the adenoviral genome, at least one replication-essential gene function of the E4 region of the adenoviral genome, and at least one gene function of the nonessential E3 region of the adenoviral genome (denoted an E1/E3/E4-deficient adenoviral vector). The adenovirus or adenoviral vector preferably requires, at most, complementation of the E1 region of the adenoviral genome for propagation, and does not require complementation of any other deficiency of the adenoviral genome for propagation. More preferably, the adenovirus or adenoviral vector requires, at most, complementation of the E1 and E4 regions of the adenoviral genome for propagation, and does not require complementation of any other deficiency of the adenoviral genome for propagation.

The adenovirus or adenoviral vector, when deficient in multiple replication-essential gene functions of the adenoviral genome (e.g., an E1/E4-deficient adenoviral vector), can include a spacer sequence to provide viral growth in a complementing cell line similar to that achieved by adenoviruses or adenoviral vectors deficient in a single replication-essential gene function (e.g., an E1-deficient adenoviral vector). The spacer sequence can contain any nucleotide sequence or sequences which are of a desired length, such as sequences at least about 15 base pairs (e.g., between about 15 nucleotides and about 12,000 nucleotides), preferably about 100 nucleotides to about 10,000 nucleotides, more preferably about 500 nucleotides to about 8,000 nucleotides, even more preferably about 1,500 nucleotides to about 6,000 nucleotides, and most preferably about 2,000 to about 3,000 nucleotides in length, or a range defined by any two of the foregoing values. The spacer sequence can be coding or non-coding and native or non-native with respect to the adenoviral genome, but does not restore the replication-essential function to the deficient region. The spacer also can contain an expression cassette. More preferably, the spacer comprises a polyadenylation sequence and/or a gene that is non-native with respect to the adenovirus or adenoviral vector. The use of a spacer in an adenoviral vector is further described in, for example, U.S. Pat. No. 5,851,806 and International Patent Application Publication WO 1997/021826.

By removing all or part of the adenoviral genome, for example, the E1, E3, and E4 regions of the adenoviral genome, the resulting adenovirus or adenoviral vector is able to accept inserts of exogenous nucleic acid sequences while retaining the ability to be packaged into adenoviral capsids. An exogenous nucleic acid sequence can be inserted at any position in the adenoviral genome so long as insertion in the position allows for the formation of adenovirus or the adenoviral vector particle. The exogenous nucleic acid sequence preferably is positioned in the E1 region, the E3 region, or the E4 region of the adenoviral genome.

The replication-deficient adenovirus or adenoviral vector of the present disclosure can be produced in complementing cell lines that provide gene functions not present in the replication-deficient adenovirus or adenoviral vector, but required for viral propagation, at appropriate levels in order to generate high titers of viral vector stock. Such complementing cell lines are known and include, but are not limited to, 293 cells (described in, e.g., Graham et al., *J. Gen. Virol.,* 36: 59-72 (1977)), PER.C6 cells (described in, e.g., International Patent Application Publication WO 1997/000326, and U.S. Pat. Nos. 5,994,128 and 6,033,908), and 293-ORF6 cells (described in, e.g., International Patent Application Publication WO 95/34671 and Brough et al., *J. Virol.,* 71: 9206-9213 (1997)). Other suitable complementing cell lines to produce the replication-deficient adenovirus or adenoviral vector of the present disclosure include complementing cells that have been generated to propagate adenoviral vectors encoding transgenes whose expression inhibits viral growth in host cells (see, e.g., U.S. Patent Application Publication No. 2008/0233650). Additional suitable complementing cells are described in, for example, U.S. Pat. Nos. 6,677,156 and 6,682,929, and International Patent Application Publication WO 2003/020879. In some instances, the cellular genome need not comprise nucleic acid sequences, the gene products of which complement for all of the deficiencies of a replication-deficient adenoviral vector. One or more replication-essential gene functions lacking in a replication-deficient adenoviral vector can be supplied by a helper virus, e.g., an adenoviral vector that supplies in trans one or more essential gene functions required for replication of the replication-deficient adenovirus or adenoviral vector. Alternatively, the inventive adenovirus or adenoviral vector can comprise a non-native replication-essential gene that complements for the one or more replication-essential gene functions lacking in the inventive replication-deficient adenovirus or adenoviral vector. For example, an E1/E4-deficient adenoviral vector can be engineered to contain a nucleic acid sequence encoding E4 ORF 6 that is obtained or derived from a different adenovirus (e.g., an adenovirus of a different serotype than the inventive adenovirus or adenoviral vector, or an adenovirus of a different species than the inventive adenovirus or adenoviral vector).

The adenovirus or adenoviral vector can further comprise a transgene. The term “transgene” is defined herein as a non-native nucleic acid sequence that is operably linked to appropriate regulatory elements (e.g., a promoter), such that the non-native nucleic acid sequence can be expressed to produce a protein (e.g., peptide or polypeptide). The regulatory elements (e.g., promoter) can be native or non-native to the adenovirus or adenoviral vector.

A “non-native” nucleic acid sequence is any nucleic acid sequence (e.g., DNA, RNA, or cDNA sequence) that is not a naturally occurring nucleic acid sequence of an adenovirus in a naturally occurring position. Thus, the non-native nucleic acid sequence can be naturally found in an adenovirus, but located at a non-native position within the adenoviral genome and/or operably linked to a non-native promoter. The terms “non-native nucleic acid sequence,” “heterologous nucleic acid sequence,” and “exogenous nucleic acid sequence” are synonymous and can be used interchangeably in the context of the present disclosure. The non-native nucleic acid sequence preferably is DNA and preferably encodes a protein (i.e., one or more nucleic acid sequences encoding one or more proteins).

The non-native nucleic acid sequence can encode a therapeutic protein that can be used to prophylactically or therapeutically treat a mammal for a disease. Examples of suitable therapeutic proteins include cytokines, toxins, tumor suppressor proteins, growth factors, hormones, receptors, mitogens, immunoglobulins, neuropeptides, neurotransmitters, and enzymes. Alternatively, the non-native nucleic acid sequence can encode an antigen of a pathogen (e.g., a bacterium or a virus), and the adenovirus or adenoviral vector can be used as a vaccine.

Viral Based Delivery System

The present disclosure also provides delivery systems, such as viral-based systems, in which a nucleic acid described herein is inserted. Representative viral expression vectors include, but are not limited to, adeno-associated viral vectors, adenovirus-based vectors, lentivirus-based vectors, retroviral vectors, and herpes virus-based vectors. In an embodiment, the viral vector is a lentivirus vector. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In an additional embodiment, the viral vector is an adeno-associated viral vector. In a further embodiment, the viral vector is a retroviral vector. In general, and in embodiments, a suitable vector contains an origin of replication functional in at least one organism, a promoter sequence, convenient restriction endonuclease sites, and one or more selectable markers.

Additional suitable vectors include integrating expression vectors, which can randomly integrate into the host cell’s DNA, or can include a recombination site to enable the specific recombination between the expression vector and the host cell’s chromosome. Such integrating expression vectors can utilize the endogenous expression control sequences of the host cell’s chromosomes to effect expression of the desired protein. Examples of vectors that integrate in a site specific manner include, for example, components of the flp-in system from Invitrogen (Carlsbad, Calif.) (e.g., pcDNATM5/FRT), or the cre-lox system, such as can be found in the pExchange-6 Core Vectors from Stratagene (La Jolla, Calif.). Examples of vectors that randomly integrate into host cell chromosomes include, for example, pcDNA3.1 (when introduced in the absence of T-antigen) from Invitrogen (Carlsbad, Calif.), and pCI or pFN10A (ACT) FLEXI™ from Promega (Madison, Wis.). Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto.

However, other constitutive promoter sequences can also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the present disclosure should not be limited to the use of constitutive promoters. Inducible promoters are also contemplated as part of the present disclosure. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

Reporter genes can be used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes can include genes encoding luciferase, beta-galactosidase, chloramphenicol acetyl transferase, secreted alkaline phosphatase, or the green fluorescent protein gene (e.g., Ui-Tei et al., FEBS Letters 479: 79-82 (2000)). Suitable expression systems are well known and can be prepared using known techniques or obtained commercially. In general, the construct with the minimal 5' flanking region showing the highest level of expression of reporter gene is identified as the promoter. Such promoter regions can be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (Molecular Cloning: A Laboratory Manual, Cold Spring Harbor Laboratory, New York (2001)). In embodiments, a method for the introduction of a polynucleotide into a host cell is calcium phosphate transfection or polyethylenimine (PEI) Transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Non-Viral Based Delivery System

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

The use of lipid formulations is contemplated for the introduction of the nucleic acids into a host cell (in vitro, ex vivo or in vivo). In another aspect, the nucleic acid can be associated with a lipid. The nucleic acid associated with a lipid can be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they can be present in a bilayer structure, as micelles, or with a "collapsed" structure. They can also simply be interspersed in a solution, possibly forming aggregates that are not uniform in size or shape. Lipids are fatty substances which can be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids can be obtained from Avanti Polar Lipids, Inc. (Birmingham, Ala.). Stock solutions of lipids in chloroform or chloroform/methanol can be stored at about −20o C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., *Glycobiology* 5: 505-10 (1991)). However, compositions that have different structures in solution than the normal vesicular structure are also encompassed. For example, the lipids can assume a micellar structure or merely exist as nonuniform aggregates of lipid molecules. Also contemplated are lipofectamine-nucleic acid complexes.

In some instances, polynucleotides encoding polypeptides can also be introduced into cells using non-viral based delivery systems, such as the "Sleeping Beauty (SB) Transposon System," which refers a synthetic DNA transposon system for introducing DNA sequences into the chromosomes of vertebrates. Some exemplary embodiments of the system are described, for example, in U.S. Pat. Nos. 6,489,458 and 8,227,432. The Sleeping Beauty transposon system is composed of a Sleeping Beauty (SB) transposase and a SB transposon. In embodiments, the Sleeping Beauty transposon system can include the SB11 transposon system, the SB100X transposon system, or the SB110 transposon system.

DNA transposons translocate from one DNA site to another in a simple, cut-and-paste manner. Transposition is a precise process in which a defined DNA segment is excised from one DNA molecule and moved to another site in the same or different DNA molecule or genome. As do other Tc1/mariner-type transposases, SB transposase inserts a transposon into a TA dinucleotide base pair in a recipient DNA sequence. The insertion site can be elsewhere in the same DNA molecule, or in another DNA molecule (or chromosome). In mammalian genomes, including humans, there are approximately 200 million TA sites. The TA insertion site is duplicated in the process of transposon integration. This duplication of the TA sequence is a hallmark of transposition and used to ascertain the mechanism in some experiments. The transposase can be encoded either within the transposon or the transposase can be supplied by another source, for instance a DNA or mRNA source, in which case the transposon becomes a non-autonomous element. Non-autonomous transposons are most useful as genetic tools because after insertion they cannot independently continue to excise and re-insert. SB transposons envisaged to be used as non-viral vectors for introduction of genes into genomes of vertebrate animals and for gene therapy.

Regardless of the method used to introduce exogenous nucleic acids into a host cell or otherwise expose a cell to the inhibitor of the present disclosure, in order to confirm the presence of the recombinant DNA sequence in the host cell, a variety of assays can be performed. Such assays include, for example, molecular assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the present disclosure.

In embodiments, a modified effector cell described herein and other genetic elements are delivered to a cell using the SB11 transposon system, the SB100X transposon system, the SB110 transposon system, the piggyBac transposon system (see, e.g., Wilson et al, "PiggyBac Transposon-mediated Gene Transfer in Human Cells," *Molecular Therapy* 15:139-145 (2007), incorporated herein by reference in its entirety) and/or the piggyBac transposon system (see, e.g., Mitra et al., "Functional characterization of piggyBac from the bat Myotis lucifugus unveils an active mammalian DNA transposon," *Proc. Natl. Acad. Sci USA* 110:234-239 (2013). Additional transposases and transposon systems are provided in U.S. Pat. Nos. 6,489,458; 6,613,752, 7,148,203; 7,985,739; 8,227,432; 9,228,180; U.S. Patent Pub. No. 2011/0117072; Mates et al., *Nat Genet,* 41(6):753-61 (2009). doi: 10.1038/ng.343. Epub 2009 May 3, *Gene Ther.,* 18(9):849-56 (2011). doi: 10.1038/gt.2011.40. Epub 2011 Mar. 31 and in Ivics et al., *Cell,* 91(4):501-10, (1997), each of which is incorporated herein by reference in their entirety.

Additional suitable non-viral systems can include integrating expression vectors, which can randomly integrate into the host cell's DNA, or can include a recombination site to enable the specific recombination between the expression vector and the host cell's chromosome. Targeted integration of transgenes into predefined genetic loci is a desirable goal for many applications. First, a first recombination site for a site-specific recombinase is inserted at a genomic site, either at a random or at a predetermined location. Subsequently, the cells are transfected with a plasmid carrying the gene or DNA of interest and the second recombination site and a source for recombinase (expression plasmid, RNA, protein, or virus-expressing recombinase). Recombination between the first and second recombination sites leads to integration of plasmid DNA.

Such integrating expression vectors can utilize the endogenous expression control sequences of the host cell's chromosomes to effect expression of the desired protein. In some embodiments, targeted integration is promoted by the presence of sequences on the donor polynucleotide that are homologous to sequences flanking the integration site. For example, targeted integration using the donor polynucleotides described herein can be achieved following conventional transfection techniques, e.g. techniques used to create gene knockouts or knockins by homologous recombination. In other embodiments, targeted integration is promoted both by the presence of sequences on the donor polynucleotide that are homologous to sequences flanking the integration site, and by contacting the cells with donor polynucleotide in the presence of a site-specific recombinase. By a site-specific recombinase, or simply a recombinase, it is meant is a polypeptide that catalyzes conservative site-specific recombination between its compatible recombination sites. As used herein, a site-specific recombinase includes native polypeptides as well as derivatives, variants and/or fragments that retain activity, and native polynucleotides, derivatives, variants, and/or fragments that encode a recombinase that retains activity.

Also provided herein is a system for integrating heterologous genes in a host cell, said system comprising one or more gene expression cassettes. In some instances, the system includes a first gene expression cassette comprising a first polynucleotide encoding a first polypeptide construct. In other instances, the system can include a second gene expression cassette comprising a second polynucleotide encoding a second polypeptide construct. In yet other instances, the system can include a third gene expression cassette. In one embodiment, one of the gene expression cassettes can comprise a gene switch polynucleotide encoding one or more of: (i) a transactivation domain; (ii) nuclear receptor ligand binding domain; (iii) a DNA-binding domain; and (iv) ecdysone receptor binding domain. In another embodiment, the system further includes recombinant attachment sites; and a serine recombinase; such that upon contacting said host cell with at least said first gene expression cassette, in the presence of said serine recombinase, said heterologous genes are integrated in said host cell.

In some instances, the system further comprises a ligand; such that upon contacting said host cell, in the presence of said ligand, said heterologous gene are expressed in said host cell. In one instance, the system also includes recombinant attachment sites. In some instances, one recombination attachment site is a phage genomic recombination attachment site (attP) or a bacterial genomic recombination attachment site (attB). In one instance, the host cell is an eukaryotic cell. In another instance, the host cell is a human cell. In further instances, the host cell is a T cell or NK cell.

Promoters

"Promoter" refers to a region of a polynucleotide that initiates transcription of a coding sequence. Promoters are located near the transcription start sites of genes, on the same strand and upstream on the DNA (towards the 5' region of the sense strand). Some promoters are constitutive as they are active in all circumstances in the cell, while others are regulated becoming active in response to specific stimuli, e.g., an inducible promoter. Yet other promoters are tissue specific or activated promoters, including but not limited to T-cell specific promoters.

The term “promoter activity” and its grammatical equivalents as used herein refer to the extent of expression of nucleotide sequence that is operably linked to the promoter whose activity is being measured. Promoter activity can be measured directly by determining the amount of RNA transcript produced, for example by Northern blot analysis or indirectly by determining the amount of product coded for by the linked nucleic acid sequence, such as a reporter nucleic acid sequence linked to the promoter.

“Inducible promoter” as used herein refers to a promoter which is induced into activity by the presence or absence of transcriptional regulators, e.g., biotic or abiotic factors. Inducible promoters are useful because the expression of genes operably linked to them can be turned on or off at certain stages of development of an organism or in a particular tissue. Examples of inducible promoters are alcohol-regulated promoters, tetracycline-regulated promoters, steroid-regulated promoters, metal-regulated promoters, pathogenesis-regulated promoters, temperature-regulated promoters and light-regulated promoters. In one embodiment, the inducible promoter is part of a genetic switch. The inducible promoter can be a gene switch ligand inducible promoter. In some cases, an inducible promoter can be a small molecule ligand-inducible two polypeptide ecdysone receptor-based gene switch, such as RHEOSWITCH® gene switch. In some cases, a gene switch can be selected from ecdysone-based receptor components as described in, but without limitation to, any of the systems described in: PCT/US2001/009050 (WO 2001/070816); U.S. Pat. Nos. 7,091,038; 7,776,587; 7,807,417; 8,202,718; PCT/US2001/030608 (WO 2002/029075); U.S. Pat. Nos. 8,105,825; 8,168,426; PCT/1J52002/005235 (WO 2002/066613); U.S. application Ser. No. 10/468,200 (U.S. Pub. No. 20120167239); PCT/US2002/005706 (WO 2002/066614); U.S. Pat. Nos. 7,531,326; 8,236,556; 8,598,409; PCT/U52002/005090 (WO 2002/066612); U.S. Pat. No. 8,715,959 (U.S. Pub. No. 20060100416); PCT/US2002/005234 (WO 2003/027266); U.S. Pat. Nos. 7,601,508; 7,829,676; 7,919,269; 8,030,067; PCT/US2002/005708 (WO 2002/066615); U.S. application Ser. No. 10/468,192 (U.S. Pub. No. 20110212528); PCT/US2002/005026 (WO 2003/027289); U.S. Pat. Nos. 7,563,879; 8,021,878; 8,497,093; PCT/US2005/015089 (WO 2005/108617); U.S. Pat. Nos. 7,935,510; 8,076,454; PCT/U52008/011270 (WO 2009/045370); U.S. application Ser. No. 12/241,018 (U.S. Pub. No. 20090136465); PCT/US2008/011563 (WO 2009/048560); U.S. application Ser. No. 12/247,738 (U.S. Pub. No. 20090123441); PCT/US2009/005510 (WO 2010/042189); U.S. application Ser. No. 13/123,129 (U.S. Pub. No. 20110268766); PCT/US2011/029682 (WO 2011/119773); U.S. application Ser. No. 13/636,473 (U.S. Pub. No. 20130195800); PCT/US2012/027515 (WO 2012/122025); and, U.S. Pat. No. 9,402,919 each of which is incorporated by reference in its entirety).

Provided herein are methods comprising administering to a subject at least one non-viral vector comprising a polynucleotide encoding a polypeptide sequence described herein comprising at least two functional proteins or portions thereof; at least one promoter; and at least one engineered recombination site; wherein said at least one promoter drives expression of said at least two functional proteins. In some cases, at least one promoter can be constitutive. In some cases, at least one promoter can be tissue-specific. In some cases, at least one promoter can be inducible. In some cases, an inducible promoter is a small molecule ligand-inducible two polypeptide ecdysone receptor-based gene switch. In other cases, a combination of promoters wherein at least one promoter can be inducible and at least one promoter can be activation specific can be utilized.

An inducible promoter utilizes a ligand for dose-regulated control of expression of said at least two genes. In some cases, a ligand can be selected from a group consisting of ecdysteroid, 9-cis-retinoic acid, synthetic analogs of retinoic acid, N,N'-diacylhydrazines, oxadiazolines, dibenzoylalkyl cyanohydrazines, N-alkyl-N,N'-diaroylhydrazines, N-acyl-N-alkylcarbonylhydrazines, N-aroyl-N-alkyl-N'-aroylhydrazines, arnidoketones, 3,5-di-tert-butyl-4-hydroxy-N-isobutyl-benzamide, 8-O-acetylharpagide, oxysterols, 22(R) hydroxycholesterol, 24(S) hydroxycholesterol, 25-epoxycholesterol, T0901317, 5-alpha-6-alpha-epoxycholesterol-3-sulfate (ECHS), 7-ketocholesterol-3-sulfate, framesol, bile acids, 1,1-biphosphonate esters, juvenile hormone III, RG-115819 (3,5-Dimethyl-benzoic acid N-(1-ethyl-2,2-dimethyl-propyl)-N'-(2-methyl-3-methoxy-benzoyl)-hydrazide-), RG-115932 ((R)-3,5-Dimethyl-benzoic acid N-(1-tert-butyl-butyl)-N'-(2-ethyl-3-methoxy-benzoyl)-hydrazide), and RG-115830 (3,5-Dimethyl-benzoic acid N-(1-tert-butyl-butyl)-N'-(2-ethyl-3-methoxy-benzoyl)-hydrazide), and any combination thereof.

In some embodiments, a promoter is an inducible promoter. In some embodiments, a promoter is a non-inducible promoter. In some cases, a promoter can be a tissue-specific promoter. Herein “tissue-specific” refers to regulated expression of a gene in a subset of tissues or cell types. In some cases, a tissue-specific promoter can be regulated spatially such that the promoter drives expression only in certain tissues or cell types of an organism. In other cases, a tissue-specific promoter can be regulated temporally such that the promoter drives expression in a cell type or tissue differently across time, including during development of an organism. In some cases, a tissue-specific promoter is regulated both spatially and temporally. In certain embodiments, a tissue-specific promoter is activated in certain cell types either constitutively or intermittently at particular times or stages of the cell type. For example, a tissue-specific promoter can be a promoter that is activated when a specific cell such as a T cell or a NK cell is activated. T cells can be activated in a variety of ways, for example, when presented with peptide antigens by MHC class II molecules.

In one case, at least one promoter is an engineered promoter or variants thereof. As described herein, the promoter can incorporate minimal promoter sequences from IL-2 and one or more of the following: nuclear factor of activated T-cells (NFAT) response element(s); NFIL2D response element, NFkB/TCF response element, NF_AT/NFIL2B response element or NFIL2A/OCT response element. Examples of response elements are described in Mattila et al., i EMBO J. 9(13):4425-33 (1990); incorporated herein in its entirety.

In some embodiments, at least one promoter comprises IL-2 core promoter (SEQ ID NO: 26). In one embodiment, at least one promoter comprises IL-2 minimal promoter (SEQ ID NO: 27). In another embodiment, at least one promoter comprises IL-2 enhancer and promoter variant (SEQ ID NOS: 26-28). In yet another embodiment, at least one promoter comprises NF-κB binding site (SEQ ID NOS: 30-32). In some embodiments, at least one promoter comprises $(NF\text{-}\kappa B)_1$-IL2 promoter variant (SEQ ID NO: 30). In some embodiments, at least one promoter comprises $(NF\text{-}\kappa B)_3$-IL2 promoter variant (SEQ ID NO: 31). In some embodiments, at least one promoter comprises $(NF\text{-}\kappa B)_6$-IL2 promoter variant (SEQ ID NO: 32). In one embodiment, at least one promoter comprises 1× nuclear factor of activated T-cells (NFAT) response elements-IL2 promoter variant (SEQ ID NO: 33). In another embodiment, at least one promoter comprises 3× NFAT response element (SEQ ID NOS: 34-35). In yet another embodiment, at least one promoter comprises 6×NFAT response elements-IL2 promoter variant (SEQ ID NOS: 36-39). In some embodiments, at least one promoter comprises human EF1A1 promoter variant (SEQ ID NOS: 40-41). In some embodiment, at least one promoter comprises human EF1A1 promoter and enhancer (SEQ ID NO: 42). In some embodiments, at least one promoter comprises human UBC promoter (SEQ ID NO: 43). In some embodiments, at least one promoter comprises 6 site GAL4-inducible proximal factor binding element (PFB). In some embodiment, at least one promoter comprises synthetic minimal promoter 1 (inducible promoter) (SEQ ID NO: 44).

Use of gene switch for ligand inducible control of IL-12 expression described herein can improve the safety profile of IL-12 by for example allowing for regulated expression and improving therapeutic index. However, a condition for ligand dose dependent expression of IL-12 using gene switch(es) is the presence or absence of activator ligand (e.g. veledimex). In certain embodiments, an additional conditional control for induction of IL-12 expression is contemplated. Gene switch components under the control of T cell activated specific promoters are provided. This results in conditional expression (e.g., T cell activation) of gene switch components necessary for veledimex controlled expression of transgene(s) under control of a gene switch. In some embodiments, this results in preferential expression of cytokines such as IL-12 or IL-15 by tumor specific T cells when veledimex is present and T cells are activated. This can lead to increased localized levels of gene switch controlled transgene expression.

For example, T cell activation specific expression of gene switch components can be controlled by promoter comprising Nuclear Factor of Activated T-cells (NFAT) response element(s). NFAT transcription factors are key modulators of effector T-cell states. NFATs are early transcriptional checkpoint progressively driving exhaustion. NFATs are quickly activated in T cells following TCR stimulation and form a protein complex with AP-1 induced by appropriate co-stimulation signaling and regulate effector genes and T-cell functions. NFAT response element(s) can be fused with other minimal promoter sequences (e.g. IL2 minimal promoter) to drive expression of transgenes in response to T cell activation.

Other examples of activation specific promoters include but are not limited to interleukin-2 (IL2) promoter and Programmed Death (PD)-1 (CD279) promoter. Gene switch components can also be conditionally expressed upon immune cell activation by fusing binding sites for other nuclear factors like NF-κB of proinflammatory signaling pathway to minimal promoter sequence (e.g. IL2).

In certain embodiments, the promoter can be any one or more of: IL-2 core promoter, IL-2 minimal promoter, IL-2 enhancer and promoter variant, $(NF\text{-}\kappa B)_1$-IL2 promoter variant, $(NF\text{-}\kappa B)_3$-IL2 promoter variant, $(NF\text{-}\kappa B)_6$-IL2 promoter variant, 1× NFAT response elements-IL2 promoter variant, 3×NFAT response elements-IL2 promoter variant, 6×NFAT response elements-IL2 promoter variant, human EEF1A1 promoter variant, human EEF1A1 promoter and enhancer, human UBC promoter and synthetic minimal promoter 1. In certain embodiments, the promoter nucleotides can comprise SEQ ID NOs: 26-44.

Gene Switch

Provided herein are gene switch polypeptides, polynucleotides encoding ligand-inducible gene switch polypeptides, and methods and systems incorporating these polypeptides and/or polynucleotides. In certain aspects, the present disclosure is directed to a polynucleotide comprising one or more polynucleotides encoding a gene switch system for inducible control of heterologous gene expression, wherein the heterologous gene expression is regulated by said gene switch system; and, wherein said heterologous gene comprises a polynucleotide encoding a polypeptide comprising one or more immune response-inducing human papilloma virus (HPV) polypeptides, disclosed herein.

The term "gene switch" refers to the combination of a response element associated with a promoter, and for instance, an EcR based system which, in the presence of one or more ligands, modulates the expression of a gene into which the response element and promoter are incorporated. Tightly regulated inducible gene expression systems or gene switches are useful for various applications such as gene therapy, large scale production of proteins in cells, cell based high throughput screening assays, functional genomics and regulation of traits in transgenic plants and animals. Such inducible gene expression systems can include ligand inducible heterologous gene expression systems.

An early version of EcR-based gene switch used *Drosophila melanogaster* EcR (DmEcR) and *Mus musculus* RXR (MmRXR) polypeptides and showed that these receptors in the presence of steroid, ponasteroneA, transactivate reporter genes in mammalian cell lines and transgenic mice (Christopherson et al., *Proc. Natl. Acad. Sci.* USA 89(14):6314-18 (1992); No et al., *Proc. Natl. Acad. Sci.* USA 93(8):3346-51 (1996)). Later, Suhr et al. (*Proc. Natl. Acad. Sci.* USA 95(14):7999-8004 (1998)) showed that non-steroidal ecdysone agonist, tebufenozide, induced high level of transactivation of reporter genes in mammalian cells through *Bombyx mori* EcR (BmEcR) in the absence of exogenous heterodimer partner.

International Patent Applications No. PCT/US97/05330 (WO 97/38117) and PCT/US99/08381 (WO99/58155) disclose methods for modulating the expression of an exogenous gene in which a DNA construct comprising the exogenous gene and an ecdysone response element is activated by a second DNA construct comprising an ecdysone receptor that, in the presence of a ligand therefor, and optionally in the presence of a receptor capable of acting as a silent partner, binds to the ecdysone response element to induce gene expression. In this example, the ecdysone receptor was isolated from *Drosophila melanogaster*. Typically, such systems require the presence of the silent partner, preferably retinoid X receptor (RXR), in order to provide optimum activation. In mammalian cells, insect ecdysone receptor (EcR) is capable of heterodimerizing with mammalian retinoid X receptor (RXR) and, thereby, be used to regulate expression of target genes or heterologous genes in a ligand dependent manner. International Patent Application No. PCT/US98/14215 (WO 99/02683) discloses that the ecdysone receptor isolated from the silk moth *Bombyx mori* is functional in mammalian systems without the need for an exogenous dimer partner.

U.S. Pat. No. 6,265,173 discloses that various members of the steroid/thyroid superfamily of receptors can combine with *Drosophila melanogaster* ultraspiracle receptor (USP) or fragments thereof comprising at least the dimerization domain of USP for use in a gene expression system. U.S. Pat. No. 5,880,333 discloses a *Drosophila melanogaster* EcR and ultraspiracle (USP) heterodimer system used in plants in which the transactivation domain and the DNA binding domain are positioned on two different hybrid proteins. In each of these cases, the transactivation domain and the DNA binding domain (either as native EcR as in International Patent Application No. PCT/US98/14215 or as modified EcR as in International Patent Application No. PCT/US97/05330) were incorporated into a single molecule and the other heterodimeric partners, either USP or RXR, were used in their native state.

International Patent Application No. PCT/US01/0905 discloses an ecdysone receptor-based inducible gene expression system in which the transactivation and DNA binding domains are separated from each other by placing them on two different proteins results in greatly reduced background activity in the absence of a ligand and significantly increased activity over background in the presence of a ligand. This two-hybrid system is a significantly improved inducible gene expression modulation system compared to the two systems disclosed in applications PCT/US97/05330 and PCT/US98/14215. The two-hybrid system is believed to exploit the ability of a pair of interacting proteins to bring the transcription activation domain into a more favorable position relative to the DNA binding domain such that when the DNA binding domain binds to the DNA binding site on the gene, the transactivation domain more effectively activates the promoter (see, for example, U.S. Pat. No. 5,283,173). The two-hybrid gene expression system comprises two gene expression cassettes; the first encoding a DNA binding domain fused to a nuclear receptor polypeptide, and the second encoding a transactivation domain fused to a different nuclear receptor polypeptide. In the presence of ligand, it is believed that a conformational change is induced which promotes interaction of the first polypeptide with the second polypeptide thereby resulting in dimerization of the DNA binding domain and the transactivation domain. Since the DNA binding and transactivation domains reside on two different molecules, the background activity in the absence of ligand is greatly reduced.

Another surprising discovery was that certain modifications of the two-hybrid system could also provide improved sensitivity to non-steroidal ligands for example, diacylhydrazines, when compared to steroidal ligands for example, ponasterone A ("PonA") or muristerone A ("MurA"). That is, when compared to steroids, the non-steroidal ligands provided higher gene transcription activity at a lower ligand concentration. Furthermore, the two-hybrid system avoids some side effects due to overexpression of RXR that can occur when unmodified RXR is used as a switching partner. In a preferred two-hybrid system, native DNA binding and transactivation domains of EcR or RXR are eliminated and as a result, these hybrid molecules have less chance of interacting with other steroid hormone receptors present in the cell, thereby resulting in reduced side effects.

The ecdysone receptor (EcR) is a member of the nuclear receptor superfamily and is classified into subfamily 1, group H (referred to herein as "Group H nuclear receptors"). The members of each group share 40-60% amino acid identity in the E (ligand binding) domain (Laudet et al., A Unified Nomenclature System for the Nuclear Receptor Subfamily, 1999; *Cell* 97: 161-163). In addition to the ecdysone receptor, other members of this nuclear receptor subfamily 1, group H include: ubiquitous receptor (UR), Orphan receptor 1 (OR-1), steroid hormone nuclear receptor 1 (NER-1), RXR interacting protein-15 (RIP-15), liver x receptor β (LXRβ), steroid hormone receptor like protein (RLD-1), liver x receptor (LXR), liver x receptor α (LXRα), farnesoid x receptor (FXR), receptor interacting protein 14 (RIP-14), and farnesol receptor (HRR-1).

In some cases, an inducible promoter can be a small molecule ligand-inducible two polypeptide ecdysone receptor-based gene switch, such as Intrexon Corporation's RHEOSWITCH® gene switch. In some cases, a gene switch can be selected from ecdysone-based receptor components as described in, but without limitation to, any of the systems described in: PCT/US2001/009050 (WO 2001/070816); U.S. Pat. Nos. 7,091,038; 7,776,587; 7,807,417; 8,202,718; PCT/US2001/030608 (WO 2002/029075); U.S. Pat. Nos. 8,105,825; 8,168,426; PCT/1J52002/005235 (WO 2002/066613); U.S. application Ser. No. 10/468,200 (U.S. Pub. No. 20120167239); PCT/US2002/005706 (WO 2002/066614); U.S. Pat. Nos. 7,531,326; 8,236,556; 8,598,409; PCT/U52002/005090 (WO 2002/066612); U.S. Pat. No. 8,715,959 (U.S. Pub. No. 20060100416); PCT/US2002/005234 (WO 2003/027266); U.S. Pat. Nos. 7,601,508; 7,829,676; 7,919,269; 8,030,067; PCT/U52002/005708 (WO 2002/066615); U.S. application Ser. No. 10/468,192 (U.S. Pub. No. 20110212528); PCT/US2002/005026 (WO 2003/027289); U.S. Pat. Nos. 7,563,879; 8,021,878; 8,497,093; PCT/US2005/015089 (WO 2005/108617); U.S. Pat. Nos. 7,935,510; 8,076,454; PCT/U52008/011270 (WO 2009/045370); U.S. application Ser. No. 12/241,018 (U.S. Pub. No. 20090136465); PCT/US2008/011563 (WO 2009/048560); U.S. application Ser. No. 12/247,738 (U.S. Pub. No. 20090123441); PCT/US2009/005510 (WO 2010/042189); U.S. application Ser. No. 13/123,129 (U.S. Pub. No. 20110268766); PCT/US2011/029682 (WO 2011/119773); U.S. application Ser. No. 13/636,473 (U.S. Pub. No. 20130195800); PCT/US2012/027515 (WO 2012/122025); and, U.S. Pat. No. 9,402,919 each of which is incorporated by reference in its entirety.

Provided are systems for modulating the expression of a heterologous gene and an interleukin in a host cell, comprising polynucleotides expressing gene-switch polypeptides disclosed herein.

In some embodiments are systems for modulating the expression of a heterologous gene and a cytokine in a host cell, comprising a first gene expression cassette comprising a first polynucleotide encoding a first polypeptide; a second gene expression cassette comprising a second polynucleotide encoding a second polypeptide; and a ligand; wherein said first and second polypeptides comprise one or more of: (i) a transactivation domain; (ii) a DNA-binding domain; and (iii) a ligand binding domain; (iv) said heterologous gene; and (vi) said cytokine such that upon contacting said host cell with said first gene expression cassette and said second gene expression cassette in the presence of said ligand, said heterologous gene and said cytokine are expressed in said host cell. In some cases, the heterologous gene comprises an antigen binding polypeptide described herein. In some cases, the cytokine comprises at least one chemokine, interferon, interleukin, lymphokine, tumor necrosis factor, or variant or combination thereof. In some cases, the cytokine is an interleukin. In some cases the interleukin is at least one of IL12, IL2, IL15, IL21, and functional variants and fragments thereof. In some embodiments, the cytokines can be membrane bound or secreted. In other embodiments, the cytokines can be intracellular. The interleukin can comprise membrane bound IL-15 (mbIL-15) or a fusion of IL-15 and IL-15Rα. In some embodiments, a mbIL-15 is a membrane-bound chimeric IL-15 which can be co-expressed with a modified effector cell described herein. In some embodiments, the mbIL-15 comprises a full-length IL-15 (e.g., a native IL-15 polypeptide) or fragment or variant thereof, fused in frame with a full length IL-15Rα, functional fragment or variant thereof. In some cases, the IL-15 is indirectly linked to the IL-15Rα through a linker. In some instances, the mbIL-15 is as described in Hurton et al., "Tethered IL-15 augments antitumor activity and promotes a stem-cell memory subset in tumor-specific T cells." *Proc. Natl. Acad. Sci.* USA 113(48):E7788-E7797 (2016). In another aspect, the interleukin can comprise IL-12 In some embodiments, the IL-12 is a single chain IL-12 (scIL-12), protease sensitive IL-12, destabilized IL-12, membrane bound IL-12, intercalated IL-12. In some instances, the IL-12 variants are as described in WO2015/095249, WO2016/048903, WO2017/062953, all of which is incorporated by reference in their entireties.

Provided herein are polynucleotides encoding gene switch polypeptides, wherein said gene switch polypeptides comprise: a) a first gene switch polypeptide comprising a DNA-binding domain fused to a nuclear receptor ligand binding domain, and b) a second gene switch polypeptide comprising a transactivation domain fused to a nuclear receptor ligand binding domain, wherein the first gene switch polypeptide and the second gene switch polypeptide are connected by a linker. In some cases, the linker can be a linker described herein, for instance GSG linker, furinlink, a 2A linker such as F/T2A, T2A, p2A, GSG-p2A, variants and derivatives thereof. In other instances, the linker can be an IRES.

In some cases, the DNA binding domain (DBD) comprises a DBD described herein, for instance at least one of GAL4 (GAL4 DBD), a LexA DBD, a transcription factor DBD, a steroid/thyroid hormone nuclear receptor superfamily member DBD, a bacterial LacZ DBD, and a yeast DBD. The transactivation domain can comprise a transactivation domain described herein, for instance one of a VP16 transactivation domain, a p53 transactivation domain and a B42 acidic activator transactivation domain. The Nuclear receptor ligand binding domain can comprise at least one of a ecdysone receptor (EcR), a ubiquitous receptor, an orphan receptor 1, a NER-1, a steroid hormone nuclear receptor 1, a retinoid X receptor interacting protein-15, a liver X receptor β, a steroid hormone receptor like protein, a liver X receptor, a liver X receptor α, a farnesoid X receptor, a receptor interacting protein 14, and a famesol receptor.

In some cases, the gene switch polypeptides connected by a polypeptide linker or ribosome-skipping sequence exhibit improved dose-dependent ligand-inducible control of gene expression compared to a ligand-inducible gene switch wherein the gene switch polypeptides are connected by non-coding sequences, such as an IRES. In some cases, the gene switch polypeptides connected by a 2A linker can exhibit improved dose-dependent ligand-inducible control of heterologous gene expression compared to a gene switch wherein said gene switch polypeptides are separated by an IRES.

In some embodiments, the gene switch comprises a VP16 transactivation domain. In one embodiment, the gene switch comprises at least one of an ecdysone receptor (EcR), a ubiquitous receptor, an orphan receptor 1, a NER-1, a steroid hormone nuclear receptor 1, a retinoid X receptor interacting protein-15, a liver X receptor β, a steroid hormone receptor like protein, a liver X receptor, a liver X receptor α, a farnesoid X receptor, a receptor interacting protein 14, and a famesol receptor. In another embodiment, a DNA-binding domain (DBD) of the gene switch comprises at least one of GAL4 (GAL4 DBD), a LexA DBD, a transcription factor DBD, a steroid/thyroid hormone nuclear receptor superfamily member DBD, a bacterial LacZ DBD, and a yeast DBD. In yet another case, the gene switch further comprises at least one of ultraspiracle protein (USP), retinoid receptor X (RXR), functional fragments and variants thereof wherein said functional fragments and variants are capable of binding to an EcR.

The polypeptides and polynucleotides as described herein can be expressed in an engineered cell. Herein an engineered cell is a cell which has been modified from its natural or endogenous state. An example of an engineered cell is a cell described herein which has been modified (e.g., by transfection of a polynucleotide into the cell) to encode for example, gene switch polypeptides, gene of interest (GOI), cell tags, heterologous genes and any other polypeptides and polynucleotides described herein.

Ligands

In some embodiments, a ligand used for inducible gene switch regulation can be selected from any of, but without limitation to, following: N-[(1R)-1-(1,1-dimethylethyl)butyl]-N-(2-ethyl-3-methoxybenzoyl)-3,5-dimethylbenzohydrazide (also referred to as veledimex), (2S,3R,5R,9R,10R,13R,14S,17R)-17-[(2S,3R)-3,6-dihydroxy-6-methylheptan-2-yl]-2,3,14-trihydroxy-10,13-dimethyl-2,3,4,5,9,11,12,15,16,17-decahydro-1H-cyclopenta[a]phenanthren-6-one; N'-(3,5-Dimethylbenzoyl)-N'-[(3R)-2,2-dimethyl-3-hexanyl]-2-ethyl-3-methoxybenzohydrazide; 5-Methyl-2,3-dihydro-benzo[1,4]dioxine-6-carboxylic acid N'-(3,5-dimethyl-benzoyl)-N'-(1-ethyl-2,2-dimethyl-propyl)-hydrazide; 5-Methyl-2,3-dihydro-benzo[1,4]dioxine-6-carboxylic acid N'-(3,5-dimethoxy-4-methyl-benzoyl)-N'-(1-ethyl-2,2-dimethyl-propyl)-hydrazide; 5-Methyl-2,3-dihydro-benzo[1,4]dioxine-6-carboxylic acid N'-(1-tert-butyl-butyl)-N'-(3,5-dimethyl-benzoyl)-hydrazide; 5-Methyl-2,3-dihydro-benzo[1,4]dioxine-6-carboxylic acid N'-(1-tert-butyl-butyl)-N'-(3,5-dimethoxy-4-methyl-benzoyl)-hydrazide; 5-Ethyl-2,3-dihydro-benzo[1,4]dioxine-6-carboxylic acid N'-(3,5-dimethyl-benzoyl)-N'-(1-ethyl-2,2-dimethyl-propyl)-hydrazide; 5-Ethyl-2,3-dihydro-benzo[1,4]dioxine-6-carboxylic acid N'-(3,5-dimethoxy-4-methyl-benzoyl)-N'-(1-ethyl-2,2-dimethyl-propyl)-hydrazide; 5-Ethyl-2,3-dihydro-benzo[1,4]dioxine-6-carboxylic acid N'-(1-tert-butyl-butyl)-N'-(3,5-dimethyl-benzoyl)-hydrazide; 5-Ethyl-2,3-dihydro-benzo[1,4]dioxine-6-carboxylic acid N'-(1-tert-butyl-butyl)-N'-(3,5-dimethoxy-4-methyl-benzoyl)-hydrazide; 3,5-Dimethyl-benzoic acid N-(1-ethyl-2,2-dimethyl-propyl)-N'-(3-methoxy-2-methyl-benzoyl)-hydrazide; 3,5-Dimethoxy-4-methyl-benzoic acid N-(1-ethyl-2,2-dimethyl-propyl)-N'-(3-methoxy-2-methyl-benzoyl)-hydrazide; 3,5-Dimethyl-benzoic acid N-(1-tert-butyl-butyl)-N'-(3-methoxy-2-methyl-benzoyl)-hydrazide; 3,5-Dimethoxy-4-methyl-benzoic acid N-(1-tert-butyl-butyl)-N'-(3-methoxy-2-methyl-benzoyl)-hydrazide; 3,5-Dimethyl-benzoic acid N-(1-ethyl-2,2-dimethyl-propyl)-N'-(2-ethyl-3-methoxy-benzoyl)-hydrazide; 3,5-Dimethoxy-4-methyl-benzoic acid N-(1-ethyl-2,2-dimethyl-propyl)-N'-(2-ethyl-3-methoxy-benzoyl)-hydrazide; 3,5-Dimethyl-benzoic acid N-(1-tert-butyl-butyl)-N'-(2-ethyl-3-methoxy-benzoyl)-hydrazide; 3,5-Dimethoxy-4-methyl-benzoic acid N-(1-tert-butyl-butyl)-N'-(2-ethyl-3-methoxy-benzoyl)-hydrazide; 2-Methoxy-nicotinic acid N-(1-tert-butyl-pentyl)-N'-(4-ethyl-benzoyl)-hydrazide; 3,5-Dimethyl-benzoic acid N-(2,2-dimethyl-1-phenyl-propyl)-N'-(4-ethyl-benzoyl)-hydrazide; 3,5-Dimethyl-benzoic acid N-(1-tert-butyl-pentyl)-N'-(3-methoxy-2-methyl-benzoyl)-hydrazide; and 3,5-Dimethoxy-4-methyl-benzoic acid N-(1-tert-butyl-pentyl)-N'-(3-methoxy-2-methyl-benzoyl)-hydrazide.

In some cases, a ligand used for dose-regulated control of ecdysone receptor-based inducible gene switch can be selected from any of, but without limitation to, an ecdysteroid, such as ecdysone, 20-hydroxyecdysone, ponasterone A, muristerone A, and the like, 9-cis-retinoic acid, synthetic analogs of retinoic acid, N,N'-diacylhydrazines such as those disclosed in U.S. Pat. Nos. 6,013,836; 5,117,057; 5,530,028; and 5,378,726 and U.S. Published Application Nos. 2005/0209283 and 2006/0020146; oxadiazolines as described in U.S. Published Application No. 2004/0171651; dibenzoylalkyl cyanohydrazines such as those disclosed in European Application No. 461,809; N-alkyl-N,N'-diaroylhydrazines such as those disclosed in U.S. Pat. No. 5,225,443; N-acyl-N-alkylcarbonylhydrazines such as those disclosed in European Application No. 234,994; N-aroyl-N-alkyl-N'-aroylhydrazines such as those described in U.S. Pat. No. 4,985,461; arnidoketones such as those described in U.S. Published Application No. 2004/0049037; each of which is incorporated herein by reference and other similar materials including 3,5-di-tert-butyl-4-hydroxy-N-isobutyl-benzamide, 8-O-acetylharpagide, oxysterols, 22(R) hydroxycholesterol, 24(S) hydroxycholesterol, 25-epoxycholesterol, T0901317, 5-alpha-6-alpha-epoxycholesterol-3-sulfate (ECHS), 7-ketocholesterol-3-sulfate, framesol, bile acids, 1,1-biphosphonate esters, juvenile hormone III, and the like. Examples of diacylhydrazine ligands useful in the present disclosure include RG-115819 (3,5-Dimethyl-benzoic acid N-(1-ethyl-2,2-dimethyl-propyl)-N'-(2-methyl-3-methoxy-benzoyl)-hydrazide-), RG-115932 ((R)-3,5-Dimethyl-benzoic acid N-(1-tert-butyl-butyl)-N'-(2-ethy 1-3-methoxy-benzoyl)-hydrazide), and RG-115830 (3,5-Dimethyl-benzoic acid N-(1-tert-butyl-butyl)-N'-(2-ethyl-3-methoxy-benzoyl)-hydrazide). See, e.g., U.S. patent application Ser. No. 12/155,111, and PCT Appl. No. PCT/US2008/006757, both of which are incorporated herein by reference in their entireties.

Cytokines

In certain embodiments, HPV vaccine antigens provided herein may be co-delivered and/or co-expressed (e.g., as part of the same HPV antigen delivery vector or via a separate vector) along with other cytokines. Provided herein are polynucleotides encoding gene-switch polypeptides and a cytokine, or variant or derivative thereof, and methods and systems incorporating the same. Cytokine is a category of small proteins between about 5-20 kDa that are involved in cell signaling. In some instances, cytokines include chemokines, interferons, interleukins, colony-stimulating factors or tumor necrosis factors. In some embodiments, chemokines play a role as a chemoattractant to guide the migration of cells, and is classified into four subfamilies: CXC, CC, CX3C, and XC. Exemplary chemokines include chemokines from the CC subfamily: CCL1, CCL2 (MCP-1), CCL3, CCL4, CCL5 (RANTES), CCL6, CCL7, CCL8, CCL9 (or CCL10), CCL11, CCL12, CCL13, CCL14, CCL15, CCL16, CCL17, CCL18, CCL19, CCL20, CCL21, CCL22, CCL23, CCL24, CCL25, CCL26, CCL27, and CCL28; the CXC subfamily: CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, and CXCL17; the XC subfamily: XCL1 and XCL2; and the CX3C subfamily CX3CL1.

In certain embodiments, HPV vaccine antigens provided herein may be co-delivered and/or co-expressed (e.g., as part of the same HPV antigen delivery vector or via a separate vector) along with interferons. Interferons (IFNs) comprise interferon type I (e.g. IFN-α, IFN-β, IFN-ε, IFN-κ, and IFN-ω), interferon type II (e.g. IFN-γ), and interferon type III. In some embodiments, IFN-α is further classified into about 13 subtypes including IFNA1, IFNA2, IFNA4, IFNA5, IFNA6, IFNA7, IFNA8, IFNA10, IFNA13, IFNA14, IFNA16, IFNA17, and IFNA21.

In certain embodiments, HPV vaccine antigens provided herein may be co-delivered and/or co-expressed (e.g., as part of the same HPV antigen delivery vector or via a separate vector) along with other interleukins. Interleukins are expressed by leukocytes or white blood cells and they promote the development and differentiation of T and B lymphocytes and hematopoietic cells. Exemplary interleukines include IL-1, IL-2, IL-3, IL-4, IL-5, IL-6, IL-7, IL-8 (CXCL8), IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-35, and IL-36. In some embodiments, interleukins are IL-2, IL-12, IL-15, IL-21 or a fusion of IL-15 and IL-15α.

In some aspects, the interleukin can comprise IL-12. In some embodiments, the IL-12 is a single chain IL-12 (scIL-12), protease sensitive IL-12, destabilized IL-12, membrane bound IL-12, intercalated IL-12. In some instances, the IL-12. variants are as described in WO2015/095249, WO2016/048903, WO2017/062953, all of which is incorporated by reference in their entireties.

In some embodiments, an interleukin comprises mbIL-15. In some embodiments, a mbIL-15 is a membrane-bound chimeric IL-15 which can be co-expressed with a modified effector cell described herein. In some embodiments, the mbIL-15 comprises a full-length IL-15 (e.g., a native IL-15 polypeptide) or fragment or variant thereof, fused in frame with a full length IL-15Rα, functional fragment or variant thereof. In some cases, the IL-15 is indirectly linked to the IL-15Rα through a linker. In some instances, the mbIL-15 is as described in Hurton et al., "Tethered IL-15 augments antitumor activity and promotes a stem-cell memory subset in tumor-specific T cells," PNAS 2016.

In certain embodiments, HPV vaccine antigens provided herein may be co-delivered and/or co-expressed (e.g., as part of the same HPV antigen delivery vector or via a separate vector) along with tumor necrosis factors. Tumor necrosis factors (TNFs) are a group of cytokines that modulate apoptosis. In some instances, there are about 19 members within the TNF family, including, not limited to, TNFα, lymphotoxin-alpha (LT-alpha), lymphotoxin-beta (LT-beta), T cell antigen gp39 (CD40L), CD27L, CD30L, FASL, 4-1BBL, OX40L, and TNF-related apoptosis inducing ligand (TRAIL).

In certain embodiments, HPV vaccine antigens provided herein may be co-delivered and/or co-expressed (e.g., as part of the same HPV antigen delivery vector or via a separate vector) along with colony stimulating factors. Colony-stimulating factors (CSFs) are secreted glycoproteins that interact with receptor proteins on the surface of hemopoietic stem cells, which subsequently modulates cell proliferation and differentiation into specific kind of blood cells. In some instances, a CSF comprises macrophage colony-stimulating factor, granulocyte macrophage colony-stimulating factor (GM-CSF), granulocyte colony-stimulating factor (G-CSF) or promegapoietin.

In some embodiments, the cytokine is a membrane-bound cytokine, which is co-expressed with a chimeric antigen receptor described herein. In some embodiments, one or more methods described herein further comprise administration of a cytokine. In some instances, the cytokine comprises a chemokine, an interferon, an interleukin, a colony-stimulating factor or a tumor necrosis factor. In some instances, one or more methods described herein further comprise administration of a cytokine selected from a chemokine, an interferon, an interleukin, a colony-stimulating factor or a tumor necrosis factor. In some instances, one or more methods described herein further comprise administration of a cytokine selected from IL2, IL7, IL12, IL15, a fusion of IL-15 and IL-15Rα, IL21, IFNγ or TNF-α.

Interleukin-12

Figure 11:
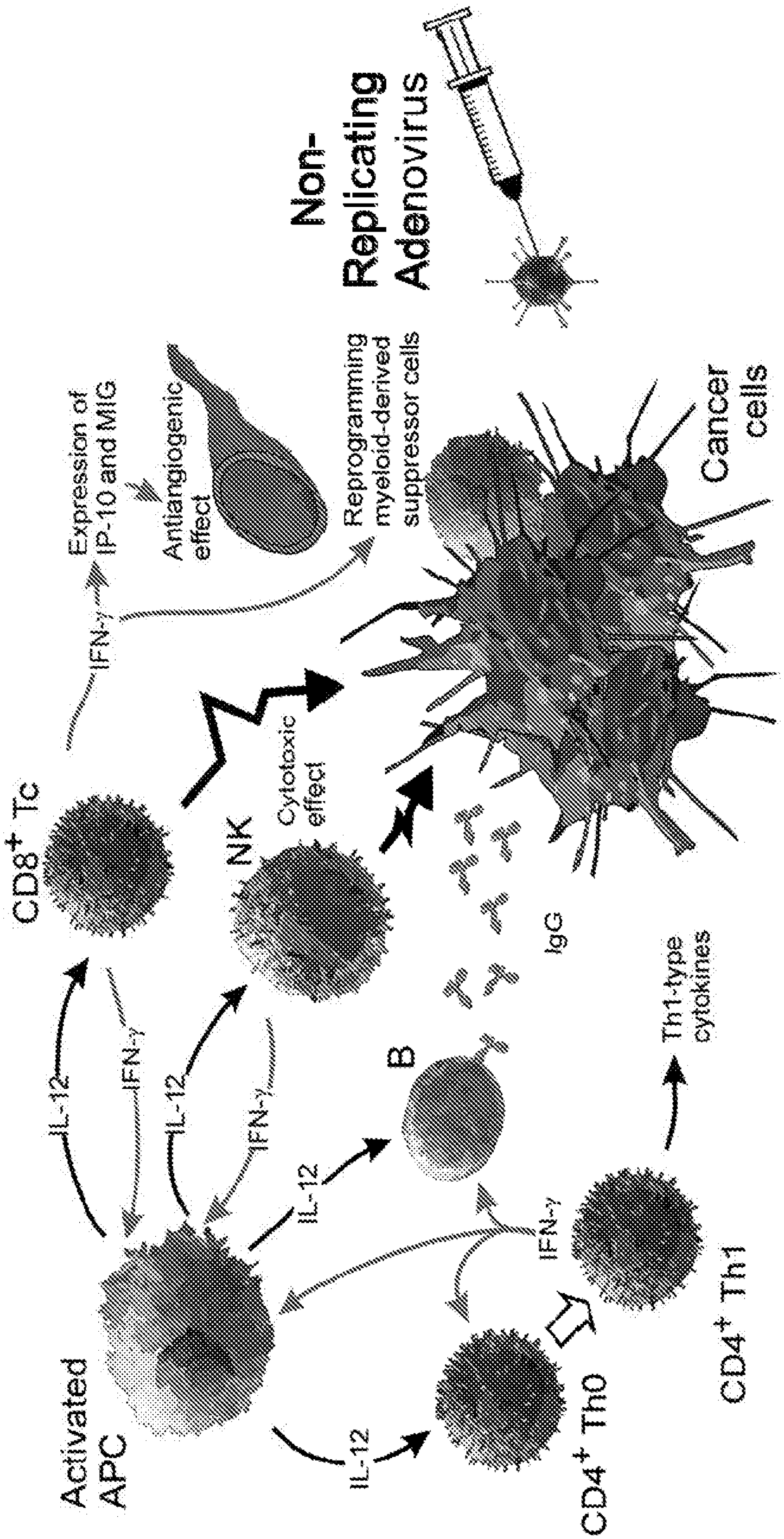
FIG. 11 shows an overview of IL-12 promoting immune response by activating NK cells and T cells.

In particular embodiments, HPV vaccine antigens provided herein may be co-delivered and/or co-expressed (e.g., as part of the same HPV antigen delivery vector or via a separate vector) along with Interleukin-12. Interleukin 12 (IL-12) is an interleukin that is naturally produced by dendritic cells, macrophages, neutrophils, and human B-lymphoblastoid cells (NC-37) in response to antigenic stimulation. IL-12 is composed of a bundle of four alpha helices. It is a heterodimeric cytokine encoded by two separate genes, IL-12A (p35) and IL-12B (p40). The active heterodimer (referred to as p'70), and a homodimer of p40 are formed following protein synthesis. IL-12 is the master regulator of the immune system. IL-12 promotes immune response by activating NK cells and T cells (FIG. 11).

Figure 12:
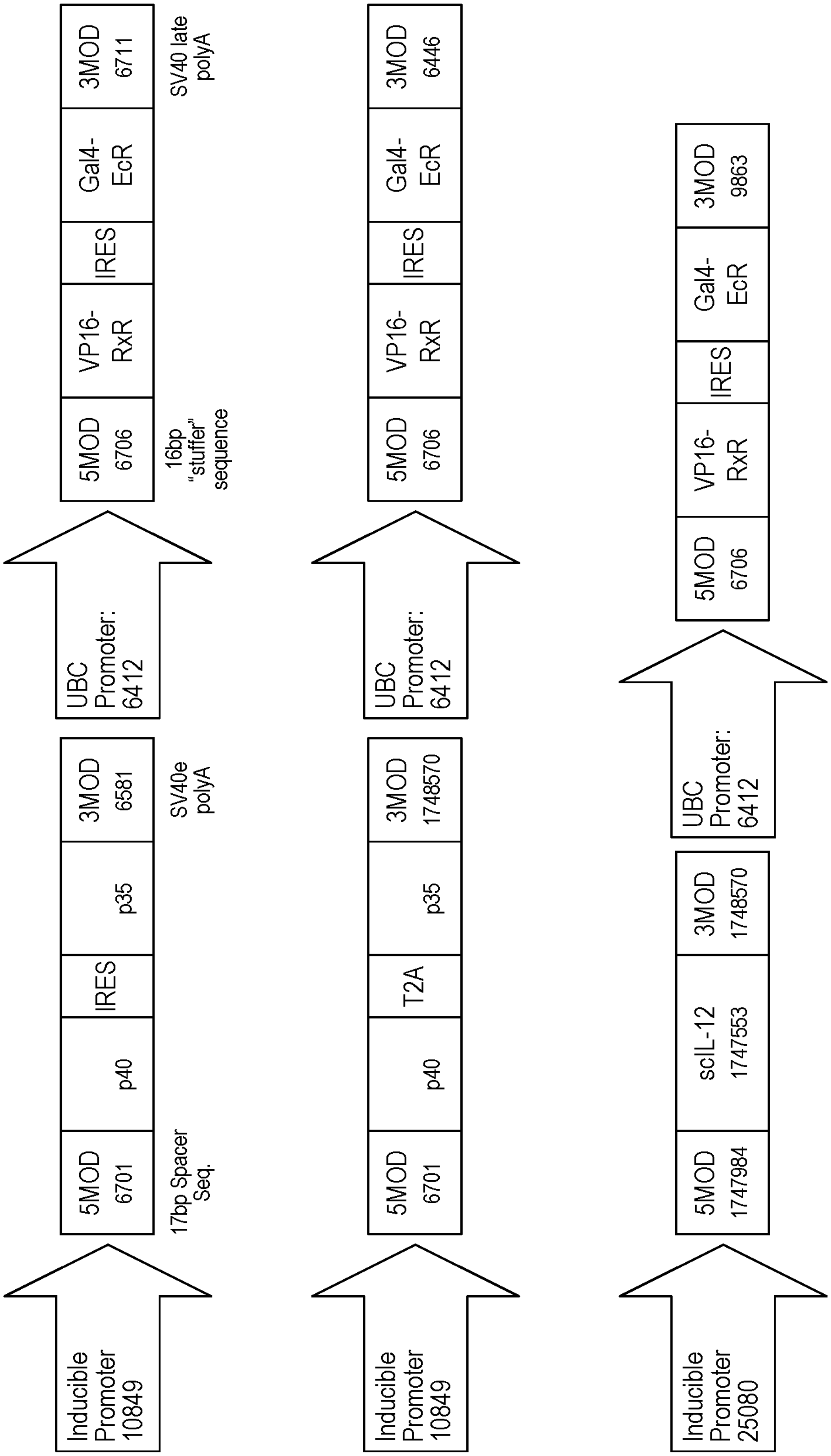
FIG. 12 shows various structural components of diverse IL-12 ligand-inducible gene switch vector systems.

Provided herein are compositions, kits, and system comprising and methods of making HPV recombinant vaccines. The present disclosure provides HPV antigen designs (HPV designs 1-5) constructed in a multi-deleted gorilla adenovector (GC46) (SEQ ID NOS: 61-63). Also provided herein are polynucleotides encoding gene-switch polypeptides and IL-12 or variant or derivative thereof, and methods and systems incorporating the same (FIG. 12).

Linkers

Also disclosed are constructs comprising a linker to facilitate the expression and functionality of the polynucleotides and polypeptides described herein. In some embodiments, a polynucleotide linker can be utilized in a polynucleotide described herein. A polynucleotide linker can be a double-stranded segment of DNA containing desired restriction sites that can be added to create end structures that are compatible with a vector comprising a polynucleotide described herein. In some cases, a polynucleotide linker can be useful for modifying vectors comprising polynucleotides described herein. For example, a vector modification comprising a polynucleotide linker can be a change in a multiple cloning site, or the addition of a poly-histidine tail. Polynucleotide linkers can also be used to adapt the ends of blunt insert DNA for cloning into a vector cleaved with a restriction enzyme with cohesive end termini. The use of polynucleotide linkers can be more efficient than a blunt ligation into a vector and can provide a method of releasing an insert from a vector in downstream applications. In some cases an insert can be a polynucleotide sequence encoding polypeptides useful for therapeutic applications. In some cases, a linker can be a cleavable linker.

A polynucleotide linker can be an oligomer. A polynucleotide linker can be a DNA double strand, single strand, or a combination thereof. In some cases, a linker can be RNA. A polynucleotide linker can be ligated into a vector comprising a polynucleotide described herein by a T4 ligase in some cases. To facilitate a ligation an excess of polynucleotide linkers can be added to a composition comprising an insert and a vector. In some cases, an insert and vector are pre-treated before a linker is introduced. For example, pre-treatment with a methylase can prevent unwanted cleavage of insert DNA.

In certain embodiments, two or more polypeptides encoded by a polynucleotide described herein can be separated by an intervening sequence encoding an intervening linker polypeptide. Herein the term "intervening linker polypeptide" referring to an amino acid sequence separating two or more polypeptides encoded by a polynucleotide is distinguished from the term "peptide linker" which refers to the sequence of amino acids which is optionally included in a polypeptide construct disclosed herein to connect the transmembrane domain to the cell surface polypeptide (e.g., comprising a truncated variant of a natural polypeptide). In certain cases, the intervening linker is a cleavage-susceptible intervening linker polypeptide. In some embodiments, the linker is a cleavable or ribosome skipping linker. In some embodiments, the cleavable linker or ribosome skipping linker sequence is selected from the group consisting of 2A, GSG-2A, GSG linker, SGSG linker, furinlink variants and derivatives thereof. In some embodiments, the 2A linker is a p2A linker, a T2A linker, F2A linker or E2A linker. In some embodiments, polypeptides of interest are expressed as fusion proteins linked by a cleavage-susceptible intervening linker polypeptide. In certain embodiments, cleavage-susceptible intervening linker polypeptide(s) can be any one or more of: F/T2A, T2A, p2A, 2A, GSG-p2A, GSG linker, and furinlink variants. Linkers (polynucleotide and polypeptide sequences) as disclosed in PCT/US2016/061668 (WO2017083750) published 18 May 2017 are incorporated by reference herein. In certain embodiments, the linker polypeptide comprises disclosed in the table below:

TABLE 1

Linker amino acid sequences and polynucleotide sequences

| Linker Name | SEQ ID NO: | Polynucleotide Sequence (5′ to 3′ where applicable) | SEQ ID NO: | Amino Acids Sequence (5′ to 3′ where applicable) |
|---|---|---|---|---|
| Whitlow Linker | 64 | GGCAGCACCTCCGGCAGCG GCAAGCCTGGCAGCGGCGA GGGCAGCACCAAGGGC | 81 | GSTSGSGKPGSGEGSTKG |
| Linker | 65 | TCTGGCGGAGGATCTGGAG GAGGCGGATCTGGAGGAGG AGGCAGTGGAGGCGGAGGA TCTGGCGGAGGATCTCTGCA G | 82 | SGGGSGGGGSGGGGSGGG GSGGGSLQ |
| GSG linker | 66 | GGAAGCGGA | 83 | GSG |
| SGSG linker | 67 | AGTGGCAGCGGC | 84 | SGSG |
| (G4S)3 linker | 68 | GGTGGCGGTGGCTCGGGCG GTGGTGGGTCGGGTGGCGG CGGATCT | 85 | GGGGSGGGGSGGGGS |

TABLE 1-continued

Linker amino acid sequences and polynucleotide sequences

| Linker Name | SEQ ID NO: | Polynucleotide Sequence (5' to 3' where applicable) | SEQ ID NO: | Amino Acids Sequence (5' to 3' where applicable) |
|---|---|---|---|---|
| Furin cleavage site/ Furinlink1 | 69 | CGTGCAAAGCGT | 86 | RAKR |
| Fmdv | 70 | AGAGCCAAGAGGGCACCGG TGAAACAGACTTTGAATTTT GACCTTCTGAAGTTGGCAGG AGACGTTGAGTCCAACCCTG GGCCC | 87 | RAKRAPVKQTLNFDLLKL AGDVESNPGP |
| Thosea asigna virus 2A region (T2A) | 71 | GAGGGCAGAGGAAGTCTGC TAACATGCGGTGACGTCGA GGAGAATCCTGGACCT | 88 | EGRGSLLTCGDVEENPGP |
| Furin-GSG-T2A | 72 | AGAGCTAAGAGGGGAAGCG GAGAGGGCAGAGGAAGTCT GCTAACATGCGGTGACGTCG AGGAGAATCCTGGACCT | 89 | RAKRGSGEGRGSLLTCGD VEENPGP |
| Furin-SGSG-T2A | 73 | AGGGCCAAGAGGAGTGGCA GCGGCGAGGGCAGAGGAAG TCTTCTAACATGCGGTGACG TGGAGGAGAATCCCGGCCC T | 90 | RAKRSGSGEGRGSLLTCGD VEENPGP |
| Porcine teschovirus-1 2A region (P2A) | 74 | GCAACGAACTTCTCTCTCCT AAAACAGGCTGGTGATGTG GAGGAGAATCCTGGTCCA | 91 | ATNFSLLKQAGDVEENPGP |
| GSG-P2A | 75 | GGAAGCGGAGCTACTAACT TCAGCCTGCTGAAGCAGGCT GGAGACGTGGAGGAGAACC CTGGACCT | 92 | GSGATNFSLLKQAGDVEE NPGP |
| Equine rhinitis A virus 2A region (E2A) | 76 | CAGTGTACTAATTATGCTCT CTTGAAATTGGCTGGAGATG TTGAGAGCAACCCTGGACCT | 93 | QCTNYALLKLAGDVESNP GP |
| Foot-and-mouth disease virus 2A region (F2A) | 77 | GTCAAACAGACCCTAAACTT TGATCTGCTAAAACTGGCCG GGGATGTGGAAAGTAATCC CGGCCCC | 94 | VKQTLNFDLLKLAGDVES NPGP |
| FP2A | 78 | CGTGCAAAGCGTGCACCGG TGAAACAGGGAAGCGGAGC TACTAACTTCAGCCTGCTGA AGCAGGCTGGAGACGTGGA GGAGAACCCTGGACCT | 95 | RAKRAPVKQGSGATNFSLL KQAGDVEENPGP |
| Linker-GSG | 79 | GCACCGGTGAAACAGGGAA GCGGA | 96 | APVKQGSG |
| Linker | 80 | GCACCGGTGAAACAG | 97 | APVKQ |

In some embodiments, an intervening linker polypeptide comprises an amino acid sequence having at least 70%, 75%, 80%, 85%, 90%, 95%, 99%, 99.5% or 100% identity with the amino acid sequence of Whitlow linker (SEQ ID NO: 64), GSG linker (SEQ ID NO: 66), SGSG linker (SEQ ID NO: 67), (G4S)3 linker (SEQ ID NO: 68), Furin cleavage site/Furlink1 (SEQ ID NO: 69), Fmdv linker (SEQ ID NO: 70), *Thosea asigna* virus 2A region (T2A) (SEQ ID NO: 71), Furin-GSG-T2A (SEQ ID NO: 72), Furin-SGSG-T2A (SEQ ID NO: 73), porcine teschovirus-1 2A region (P2A) (SEQ ID NO: 74), GSG-P2A (SEQ ID NO: 75), equine rhinitis A virus 2A region (E2A) (SEQ ID NO: 76), or foot-and-mouth disease virus 2A region (F2A) (SEQ ID NO: 78) (Table 1). In some cases, an intervening linker polypeptide comprises an amino acid sequence having at least 70%, 75%, 80%, 85%, 90%, 95%, 99%, 99.5% or 100% identity with the amino acid sequence of linkers (SEQ ID NOS: 65, 79 80) In some cases, a viral 2A sequence can be used. 2A elements can be shorter than IRES, having from 5 to 100 base pairs. In some cases, a 2A sequence can have 5, 10, 15, 20, 25, 30, 35, 40, 45, 50, 55, 60, 65, 70, 75, 80, 85, 90, or 100 nucleotides in length. 2A linked genes can be expressed in one single open reading frame and "self-cleavage" can occur co-translationally between the last two amino acids, GP, at the C-terminus of the 2A polypeptide, giving rise to equal amounts of co-expressed proteins.

A viral 2A sequence can be about 20 amino acids. In some cases, a viral 2A sequence can contain a consensus motif Asp-Val/Ile-Glu-X-Asn-Pro-Gly-Pro. A consensus motif sequence can act co-translationally. For example, formation of a normal peptide bond between a glycine and proline residue can be prevented, which can result in ribosomal skipping and cleavage of a nascent polypeptide. This effect can produce multiple genes at equimolar levels.

A 2A peptide can allow translation of multiple proteins in a single open reading frame into a polypeptide that can be subsequently cleaved into individual polypeptide through a ribosome-skipping mechanism (Funston et al., *J. Gen. Virol.* 89(Pt 2):389-96 (2008)). In some embodiments, a 2A sequence can include: F/T2A, T2A, p2A, 2A, T2A, E2A, F2A, and BmCPV2A, BmIFV2A, and any combination thereof.

In some cases, a vector can comprise an IRES sequence and a 2A linker sequence. In other cases, expression of multiple genes linked with 2A peptides can be facilitated by a spacer sequence (GSG) ahead of the 2A peptides. In some cases, constructs can combine a spacers, linkers, adaptors, promoters, or combinations thereof. For example, a linker can have a spacer (SGSG or GSG or Whitlow linker) and furin linker (R-A-K-R) cleavage site with different 2A peptides. A spacer can be an I-Ceui. In some cases, a linker can be engineered. For example, a linker can be designed to comprise chemical characteristics such as hydrophobicity. In some cases, at least two linker sequences can produce the same protein. In other cases, multiple linkers can be used in a vector. For example, genes of interest can be separated by at least two linkers.

In certain embodiments, two or more polypeptides encoded by a polynucleotide described herein can be separated by an intervening sequence encoding a linker polypeptide. In certain cases, the linker is a cleavage-susceptible linker. In some embodiments, polypeptides of interest are expressed as fusion proteins linked by a cleavage-susceptible linker polypeptide. In certain embodiments, cleavage-susceptible linker polypeptide(s) can be any one or two of: Furinlink, fmdv, p2a, GSG-p2a, and/or fp2a described below. In some cases, a linker is APVKQGSG (SEQ ID NO: 96).

In certain cases, a linker polypeptide can comprise an amino acid sequence "RAKR" (SEQ ID NO: 86). In certain cases, a Furin linker polypeptide can be encoded by a polynucleotide sequence polynucleotide sequence comprising "CGTGCAAAGCGT" (SEQ ID NO: 69) or "AGAGCTAAGAGG" (SEQ ID NO: 112).

In some embodiments, a linker can be utilized in a polynucleotide described herein. A linker can be a flexible linker, a rigid linker, an in vivo cleavable linker, or any combination thereof. In some cases, a linker can link functional domains together (as in flexible and rigid linkers) or releasing free functional domain in vivo as in in vivo cleavable linkers.

Linkers can improve biological activity, increase expression yield, and achieving desirable pharmacokinetic profiles. A linker can also comprise hydrazone, peptide, disulfide, or thioesther.

In some cases, a linker sequence described herein can include a flexible linker. Flexible linkers can be applied when a joined domain requires a certain degree of movement or interaction. Flexible linkers can be composed of small, non-polar (e.g., Gly) or polar (e.g., Ser or Thr) amino acids. A flexible linker can have sequences consisting primarily of stretches of Gly and Ser residues ("GS" linker). An example of a flexible linker can have the sequence of (Gly-Gly-Gly-Gly-Ser)n (SEQ ID NO: 85). By adjusting the copy number "n", the length of this exemplary GS linker can be optimized to achieve appropriate separation of functional domains, or to maintain necessary inter-domain interactions. Besides GS linkers, other flexible linkers can be utilized for recombinant fusion proteins. In some cases, flexible linkers can also be rich in small or polar amino acids such as Gly and Ser, but can contain additional amino acids such as Thr and Ala to maintain flexibility. In other cases, polar amino acids such as Lys and Glu can be used to improve solubility.

Flexible linkers included in linker sequences described herein, can be rich in small or polar amino acids such as Gly and Ser to provide good flexibility and solubility. Flexible linkers can be suitable choices when certain movements or interactions are desired for fusion protein domains. In addition, although flexible linkers cannot have rigid structures, they can serve as a passive linker to keep a distance between functional domains. The length of flexible linkers can be adjusted to allow for proper folding or to achieve optimal biological activity of the fusion proteins.

A linker described herein can further include a rigid linker in some cases. A rigid linker can be utilized to maintain a fixed distance between domains of a polypeptide. Examples of rigid linkers can be: Alpha helix-forming linkers, Pro-rich sequence, (XP)n, X-Pro backbone, A(EAAAK)nA (n=2-5), to name a few. Rigid linkers can exhibit relatively stiff structures by adopting α-helical structures or by containing multiple Pro residues in some cases.

A linker described herein can be cleavable in some cases. In other cases a linker is not cleavable. Linkers that are not cleavable can covalently join functional domains together to act as one molecule throughout an in vivo processes or an ex vivo process. A linker can also be cleavable in vivo. A cleavable linker can be introduced to release free functional domains in vivo. A cleavable linker can be cleaved by the presence of reducing reagents, proteases, to name a few. For example, a reduction of a disulfide bond can be utilized to produce a cleavable linker. In the case of a disulfide linker, a cleavage event through disulfide exchange with a thiol, such as glutathione, could produce a cleavage. In other cases, an in vivo cleavage of a linker in a recombinant fusion protein can also be carried out by proteases that can be expressed in vivo under pathological conditions (e.g. cancer or inflammation), in specific cells or tissues, or constrained within certain cellular compartments. In some cases, a cleavable linker can allow for targeted cleavage. For example, the specificity of many proteases can offer slower cleavage of a linker in constrained compartments. A cleavable linker can also comprise hydrazone, peptides, disulfide, or thioesther. For example, a hydrazone can confer serum stability. In other cases, a hydrazone can allow for cleavage in an acidic compartment. An acidic compartment can have a pH up to 7. A linker can also include a thioether. A thioether can be nonreducible A thioether can be designed for intracellular proteolytic degradation.

In certain embodiments, an fmdv linker polypeptide comprises a sequence that can be at least about 45%, 50%, 55%, 60%, 65%, 70%, 75%, 80%, 85%, 90%, 95%, 97%, 98%, 99% or 100% identical to SEQ ID NO: 87. In certain embodiments, an fmdv linker polypeptide is one or more of the linkers encoded in a single vector linking two or more fusion proteins. In certain cases, an fmdv linker polypeptide can be encoded by a polynucleotide open reading frame (ORF) nucleic acid sequence. In some cases, an ORF encoding fmdv comprises or consists of a sequence of SEQ ID NO: 70). In certain embodiments, a polynucleotide encoding fmdv is at least 45%, 50%, 55%, 60%, 65%, 70%, 75%, 80%, 85%, 90%, 95%, 97%, 98%, 99% or 100% identical to SEQ ID NO: 70).

In certain cases, a linker polypeptide can be a "p2a" linker. In certain embodiments, a p2a polypeptide can comprise a sequence that can be about at least 45%, 50%, 55%, 60%, 65%, 70%, 75%, 80%, 85%, 90%, 95%, 97%, 98%, 99% or 100% identical to SEQ ID NO: 91). In certain embodiments, the p2a linker polypeptide can be one or more of the linkers encoded in a single vector linking two or more fusion proteins. In some cases, a p2a linker polypeptide can be encoded by a polynucleotide open reading frame (ORF) nucleic acid sequence. In certain embodiments, an ORF encoding p2a comprises or consists of the sequence of SEQ ID NO: 74). In certain cases, a polynucleotide encoding p2a can be or can be about at least 45%, 50%, 55%, 60%, 65%, 70%, 75%, 80%, 85%, 90%, 95%, 97%, 98%, 99% or 100% identical to SEQ ID NO: 74).

In some cases, a linker polypeptide can be a "GSG-p2a" linker. In certain embodiments, a GSG-p2a linker polypeptide can comprise a sequence that can be about at least 45%, 50%, 55%, 60%, 65%, 70%, 75%, 80%, 85%, 90%, 95%, 97%, 98%, 99% or 100% identical to SEQ ID NO: 92). In certain embodiments, a GSG-p2a linker polypeptide can be one or more of the linkers encoded in a single vector linking two or more fusion proteins. In some cases, a GSG-p2a linker polypeptide can be encoded by a polynucleotide open-reading frame (ORF) nucleic acid sequence. An ORF encoding GSG p2a can comprise the sequence of SEQ ID NO: 75). In some cases, a polynucleotide encoding GSG-p2a can be or can be about at least 45%, 50%, 55%, 60%, 65%, 70%, 75%, 80%, 85%, 90%, 95%, 97%, 98%, 99% or 100% identical to SEQ ID NO: 75).

A linker polypeptide can be an "fp2a" linker as provided herein. In certain embodiments, a fp2a linker polypeptide can comprise a sequence that can be about at least 45%, 50%, 55%, 60%, 65%, 70%, 75%, 80%, 85%, 90%, 95%, 97%, 98%, 99% or 100% identical to SEQ ID NO: 95). In certain cases, an fp2a linker polypeptide can be one or more of the linkers encoded in a single vector linking two or more fusion proteins. In some cases, a fp2a linker polypeptide can be encoded by a polynucleotide open reading frame (ORF) nucleic acid sequence. In certain embodiments, a polynucleotide encoding an fp2a linker can be or can be about at least 45%, 50%, 55%, 60%, 65%, 70%, 75%, 80%, 85%, 90%, 95%, 97%, 98%, 99% or 100% identical to SEQ ID NO: 78).

In some cases, a linker can be engineered. For example, a linker can be designed to comprise chemical characteristics such as hydrophobicity. In some cases, at least two linker sequences can produce the same protein. A sequence can be or can be about 45%, 50%, 55%, 60%, 65%, 70%, 75%, 80%, 85%, 90%, 95%, 96%, 97%, 98%, 99%, or 100% identical to a polypeptide sequence of SEQ ID NO 82, 96 or 97. In other cases, multiple linkers can be used in a vector. For example, genes of interest, and one or more gene switch polypeptide sequences described herein can be separated by at least two linkers. In some cases, genes can be separated by 2, 3, 4, 5, 6, 7, 8, 9, or up to 10 linkers.

A linker can be an engineered linker. Methods of designing linkers can be computational. In some cases, computational methods can include graphic techniques. Computation methods can be used to search for suitable peptides from libraries of three-dimensional peptide structures derived from databases. For example, a Brookhaven Protein Data Bank (PDB) can be used to span the distance in space between selected amino acids of a linker.

In some embodiments are polynucleotides encoding a polypeptide construct comprising a furin polypeptide and a 2A polypeptide, wherein the furin polypeptide and the 2A polypeptide are connected by a polypeptide linker comprising at least three hydrophobic amino acids. In some cases, at least three hydrophobic amino acids are selected from the list consisting of glycine (Gly)(G), alanine (Ala)(A), valine (Val)(V), leucine (Leu)(L), isoleucine (Ile)(I), proline (Pro) (P), phenylalanine (Phe)(F), methionine (Met)(M), tryptophan (Trp)(W). In some cases, a polypeptide linker can also include one or more GS linker sequences, for instance (GS)n, (SG)n, (GSG)n, and (SGSG)n, wherein n can be any number from zero to fifteen.

Provided are methods of obtaining an improved expression of a polypeptide construct comprising: providing a polynucleotide encoding said polypeptide construct comprising a first functional polypeptide and a second functional polypeptide, wherein said first functional polypeptide and second functional polypeptide are connected by a linker polypeptide comprising a sequence with at least 60% identity to the sequence APVKQ; and expressing said polynucleotide in a host cell, wherein said expressing results in an improved expression of the polypeptide construct as compared to a corresponding polypeptide construct that does not have a linker polypeptide comprising a sequence with at least 60% identity to the sequence APVKQ.

IRES Elements

Also disclosed herein are constructs comprising an IRES element to facilitate the expression and functionality of the polynucleotides and polypeptides described herein. The term "internal ribosome entry site (IRES)" as used herein can be intended to mean internal ribosomal entry site. In a vector comprising an IRES sequence, a first gene can be translated by a cap-dependent, ribosome scanning, mechanism with its own 5'-UTR, whereas translation of a subsequent gene can be accomplished by direct recruitment of a ribosome to an IRES in a cap-independent manner. An IRES sequence can allow eukaryotic ribosomes to bind and begin translation without binding to a 5' capped end. An IRES sequence can allow expression of multiple genes from one transcript (Mountford and Smith, *Trends Genet.* 11(5):179-84 (1995)).

The term "CAP" or "cap" as used herein refers to a modified nucleotide, generally a 7-methyl guanosine, linked 3' to 5' (7meG-ppp-G), to the 5' end of a eukaryotic mRNA, that serves as a required element in the normal translation initiation pathway during expression of protein from that mRNA.

In certain cases, an IRES region can be derived from a virus, such as picornavirus, encephalomyocarditis virus, hepatitis C virus IRES sequence. In other cases, an IRES sequence can be derived from an encephalomyocarditis virus. The term "EMCV" or "encephalomyocarditis virus" as used herein refers to any member isolate or strain of the encephalomyocarditis virus species of the genus of the family Picornaviridae. Examples are: EMCV-R (Rueckert) strain virus, Columbia-SK virus. In some cases, a cellular IRES element, such as eukaryotic initiation factor 4G, immunoglobulin heavy chain binding protein, c-myc proto-oncogene, vascular endothelial growth factor, fibroblast growth factor-1 IRES, or any combination or modification thereof can be used. In some cases, a cellular IRES can have increased gene expression when compared to a viral IRES.

An IRES sequence of viral, cellular or a combination thereof can be utilized in a vector. An IRES can be from encephalomyocarditis (EMCV) or poliovirus (PV). In some cases, an IRES element is selected from a group consisting of Poliovirus (PV), Encephalomyelitis virus (EMCV), Foot-and-mouth disease virus (FMDV), Porcine teschovirus-1 (PTV-1), Aichivirus (AiV), Seneca Valley virus (SVV), Hepatitis C virus (HCV), Classical swine fever virus (CSFV), Human immunodeficiency virus-2 (HIV-2), Human immunodeficiency virus-1 (HIV-1), Moloney murine leukemia virus (MoMLV), Feline immunodeficiency virus (FIV), Mouse mammary tumor virus (MMTV), Human cytomegalovirus latency (pUL138), Epstein-Barr virus (EBNA-1), Herpes virus Marek's disease (MDV RLORF9), SV40 polycistronic 19S (SV40 19S), Rhopalosiphum padi virus (RhPV), Cricket paralysis virus (CrPV), Ectropis obliqua picorna-like virus (EoPV), Plautia stali intestine virus (PSIV), Triatoma virus (TrV), Bee paralysis dicistrovirus (IAPV, KBV), Black currant reversion virus (BRV), Pelargonium flower break virus (PFBV), Hibiscus chlorotic ringspot virus (HCRSV), Crucifer-infecting tobamovirus (CrTMV), Potato leaf roll polerovirus (PLRV), Tobacco etch virus (TEV), Giardiavirus (GLV), Leishmania RNA virus-1 (LRV-1), and combinations or modifications thereof. In some cases, an IRES is selected from a group consisting of Apaf-1, XIAP, HIAP2/c-IAP1, DAP5, Bcl-2, c-myc, CAT-1, INR, Differentiation LEF-1, PDGF2, HIF-1a, VEGF, FGF2, BiP, BAG-1, CIRP, p53, SHMT1, PITSL-REp58, CDK1, Rpr, hid, hsp70, grim, skl, Antennapedia, dFoxO, dInR, Adh-Adhr, HSP101, ADH, URE-2, GPR1, NCE102, YMR181a, MSN1, BOI1, FLO8, GIC1, and any combination or modification thereof. When an IRES element is included between two open reading frames (ORFs), initiation of translation can occur by a canonical 5'-m7GpppN cap-dependent mechanism in a first ORF and a cap-independent mechanism in a second ORF downstream of the IRES element.

In some cases, genes can be linked by an internal ribosomal entry site (IRES). An IRES can allow simultaneous expression of multiple genes. For example, an IRES sequence can permit production of multiple proteins from a single mRNA transcript. A ribosome can bind to an IRES in a 5'-cap independent manner and initiate translation.

In some cases, an IRES sequence can be or can be about 500 base pairs. An IRES sequence can be from 300 base pairs to 1000 base pairs. For example, an IRES can be 300, 350, 400, 450, 500, 550, 600, 650, 700, 750, 800, 850, 900, 950, or 1000 base pairs long.

In some cases, expression of a downstream gene within a vector comprising an IRES sequence can be reduced. For example, a gene following an IRES sequence can have reduced expression over a gene preceding an IRES sequence. Reduced expression can be from 1% to 99% reduction over a preceding gene.

Methods of Regulating Expression

In one embodiment, a method of regulating the expression of a heterologous gene in an engineered cell is provided. Polynucleotides encoding for gene switch polypeptides for ligand inducible control of a heterologous gene expression, an antigen binding polypeptide and a heterologous gene is provided. In some instances, the polynucleotides are in one or more gene expression cassettes as depicted in any one of FIGS. 1 through 16. In another instance, the polynucleotides are incorporated into an engineered cell via viral or non-viral vectors. Viral vectors can include lentiviral vectors, retroviral vectors or adenoviral vectors. Non-viral vectors can include Sleeping Beauty transposons. In other instances, the polynucleotides are incorporated into an engineered cell via recombinases or gene editing techniques. Examples of recombinases are serine recombinases as described herein. Examples of gene editing techniques can include CRISPR or Argonaute systems. Herein a "CRISPR gene editing system" of "CRISPR system" refers to any RNA-guided Cas protein-mediated process for targeting a change in DNA sequence to a specific region of a genome. Herein "Argonaute gene editing system" refers to any single-stranded DNA guided Argonaute endonuclease-mediated process for targeting a change in DNA sequence to a specific region of a genome.

Pharmaceutical Compostions and Dosage

The present disclosure provides a composition comprising the adenovirus or adenoviral vector described herein and a carrier therefor (e.g., a pharmaceutically acceptable carrier). The composition desirably is a physiologically acceptable (e.g., pharmaceutically acceptable) composition, which comprises a carrier, preferably a physiologically (e.g., pharmaceutically) acceptable carrier, and the adenovirus or adenoviral vector. Any suitable carrier can be used within the context of the present disclosure, and such carriers are well known in the art. The choice of carrier will be determined, in part, by the particular use of the composition (e.g., administration to an animal) and the particular method used to administer the composition. Ideally, in the context of replication-deficient adenoviral vectors, the pharmaceutical composition preferably is free of replication-competent adenovirus. The pharmaceutical composition optionally can be sterile.

Suitable compositions include aqueous and non-aqueous isotonic sterile solutions, which can contain anti-oxidants, buffers, and bacteriostats, and aqueous and non-aqueous sterile suspensions that can include suspending agents, solubilizers, thickening agents, stabilizers, and preservatives. The composition can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets. Preferably, the carrier is a buffered saline solution. More preferably, the adenovirus or adenoviral vector is part of a composition formulated to protect the adenovirus or adenoviral vector from damage prior to administration. For example, the composition can be formulated to reduce loss of the adenovirus or adenoviral vector on devices used to prepare, store, or administer the adenovirus or adenoviral vector, such as glassware, syringes, or needles. The composition can be formulated to decrease the light sensitivity and/or temperature sensitivity of the adenovirus or adenoviral vector. To this end, the composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a composition will extend the shelf life of the adenovirus or adenoviral vector, and facilitate its administration. Formulations for adenovirus or adenoviral vector-containing compositions are further described in, for example, U.S. Pat. Nos. 6,225,289, 6,514,943, and International Patent Application Publication WO 2000/034444.

The composition also can be formulated to enhance transduction efficiency. In addition, one of ordinary skill in the art will appreciate that the adenovirus or adenoviral vector can be present in a composition with other therapeutic or biologically-active agents. For example, factors that control inflammation, such as ibuprofen or steroids, can be part of the composition to reduce swelling and inflammation associated with in vivo administration of the adenovirus or adenoviral vector. If the adenovirus or adenoviral vector is used to deliver an antigen-encoding nucleic acid sequence to a host, immune system stimulators or adjuvants, e.g., interleukins, lipopolysaccharide, or double-stranded RNA, can be administered to enhance or modify any immune response to the antigen. Antibiotics, i.e., microbicides and fungicides, can be present to treat existing infection and/or reduce the risk of future infection, such as infection associated with gene transfer procedures.

In some embodiments, disclosed herein are compositions comprising a polynucleotide or polypeptide disclosed herein for administration in a subject. In some instances, are modified effector cell compositions encoding a polynucleotide or polypeptide disclosed herein, and optionally containing a cytokine and/or an additional therapeutic agent. In some instances, also included herein are vectors encoding gene-switch polypeptides for regulating expression of a chimeric antigen receptor for modification of an effector cell.

In some instances, pharmaceutical compositions of a modified effector cell or a vector encoding gene-switch polypeptides and a chimeric antigen receptor are formulated in a conventional manner using one or more physiologically acceptable carriers including excipients and auxiliaries which facilitate processing of the active compounds into preparations which can be used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

Pharmaceutical compositions are optionally manufactured in a conventional manner, such as, by way of example only, by means of conventional mixing, dissolving, granulating, dragee-making, levigating, emulsifying, encapsulating, entrapping or compression processes.

In certain embodiments, compositions can also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In other embodiments, compositions can also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

The pharmaceutical compositions described herein are administered by any suitable administration route, including but not limited to, oral, parenteral (e.g., intravenous, subcutaneous, intramuscular, intracerebral, intracerebroventricular, intra-articular, intraperitoneal, or intracranial), intranasal, buccal, sublingual, or rectal administration routes. In some instances, the pharmaceutical composition is formulated for parenteral (e.g., intravenous, subcutaneous, intramuscular, intracerebral, intracerebroventricular, intra-articular, intraperitoneal, or intracranial) administration.

The pharmaceutical compositions described herein are formulated into any suitable dosage form, including but not limited to, aqueous oral dispersions, liquids, gels, syrups, elixirs, slurries, suspensions and the like, for oral ingestion by an individual to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations. In some embodiments, the pharmaceutical compositions are formulated into capsules. In some embodiments, the pharmaceutical compositions are formulated into solutions (for example, for IV administration). In some cases, the pharmaceutical composition is formulated as an infusion. In some cases, the pharmaceutical composition is formulated as an injection.

The pharmaceutical solid dosage forms described herein optionally include a compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof.

In still other aspects, using standard coating procedures, such as those described in Remington's Pharmaceutical Sciences, 20th Edition (2000), a film coating is provided around the compositions. In some embodiments, the compositions are formulated into particles (for example for administration by capsule) and some or all of the particles are coated. In some embodiments, the compositions are formulated into particles (for example for administration by capsule) and some or all of the particles are microencapsulated. In some embodiments, the compositions are formulated into particles (for example for administration by capsule) and some or all of the particles are not microencapsulated and are uncoated.

In certain embodiments, compositions provided herein can also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

"Antifoaming agents" reduce foaming during processing which can result in coagulation of aqueous dispersions, bubbles in the finished film, or generally impair processing. Exemplary anti-foaming agents include silicon emulsions or sorbitan sesquoleate.

"Antioxidants" include, for example, butylated hydroxytoluene (BHT), sodium ascorbate, ascorbic acid, sodium metabisulfite and tocopherol. In certain embodiments, antioxidants enhance chemical stability where required.

Formulations described herein can benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

A "carrier" or "carrier materials" include any commonly used excipients in pharmaceutics and should be selected on the basis of compatibility with compounds disclosed herein, such as, compounds of ibrutinib and An anticancer agent, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" can include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitator with one or more diffusion facilitator can also be used in the present compositions.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants can be included to enhance physical stability or for other purposes.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Kits/Article of Manufacture

Disclosed herein, in certain embodiments, are kits and articles of manufacture for use with one or more methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

A kit typically includes labels listing contents and/or instructions for use, and package inserts with instructions for use. A set of instructions will also typically be included.

In some embodiments, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

EXAMPLES

These examples are provided for illustrative purposes only and not to limit the scope of the claims provided herein.

Example 1

Antigenicity Bioinformatics Workflow for HPV Vaccine Designs

Generating Consensus Sequences

Sample sequences for E5, E6, and E7 (for HPV16, HPV 17, HPV31, HPV33, and HPV45, serotypes determined to have a higher predisposition for cancer) were downloaded, converted to FASTQ files, and imported into R statistical program. Individual AA sequences were read into R using the biostrings package (readAAStringSet function). Multiple sequence alignments were performed using the ClustalW algorithm in the msa R package. For each subgroup/subtype, consensus sequences were generated and output to PDF/FASTQ files using the msaPrettyPrint function.

Predicting Binding Affinity

Figure 7A:
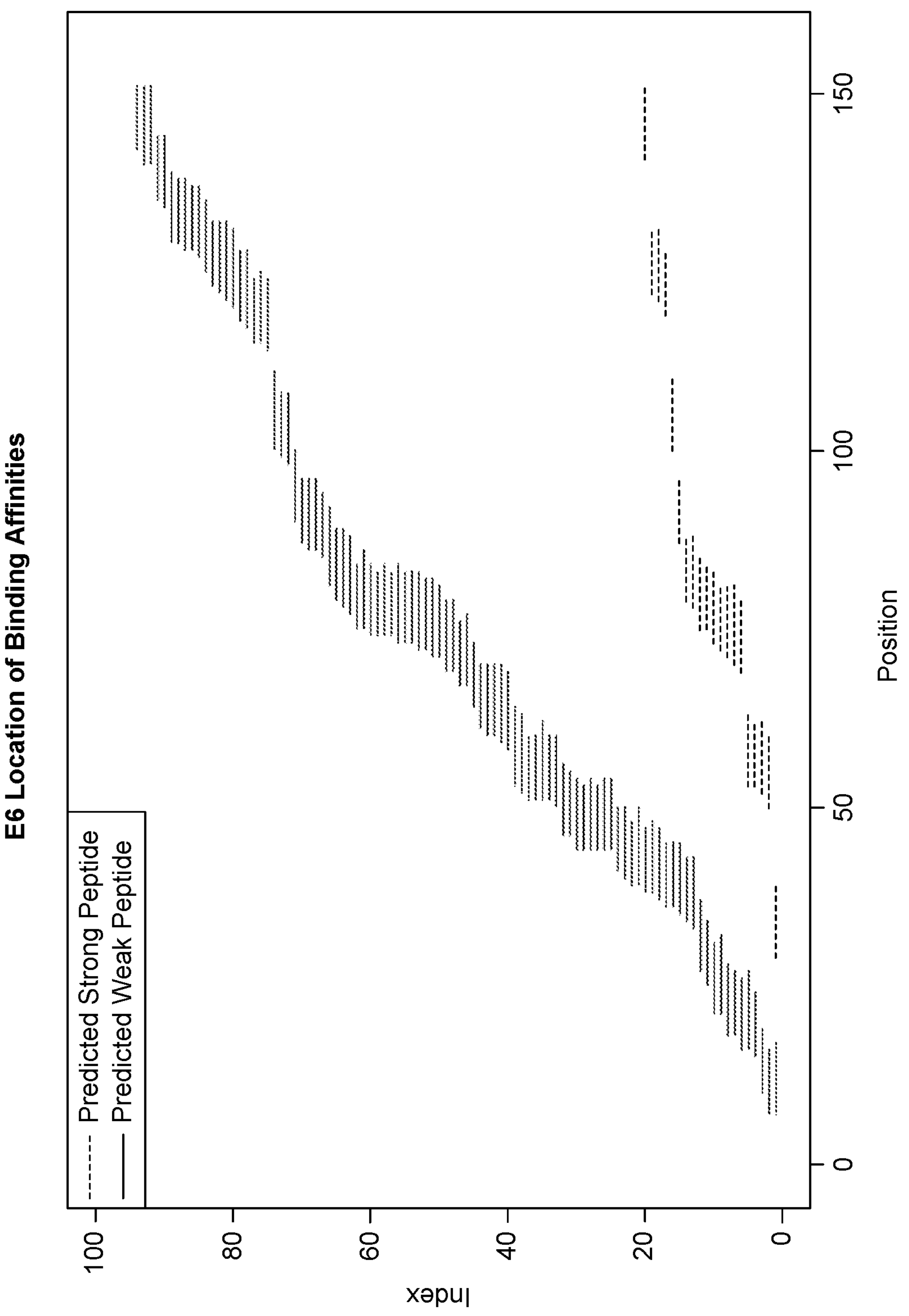
FIG. 7A shows NetMHC 4.0 antigenicity predictions. Predicted strong and weak binding peptide indices are plotted against peptide locations.
Figure 7B:
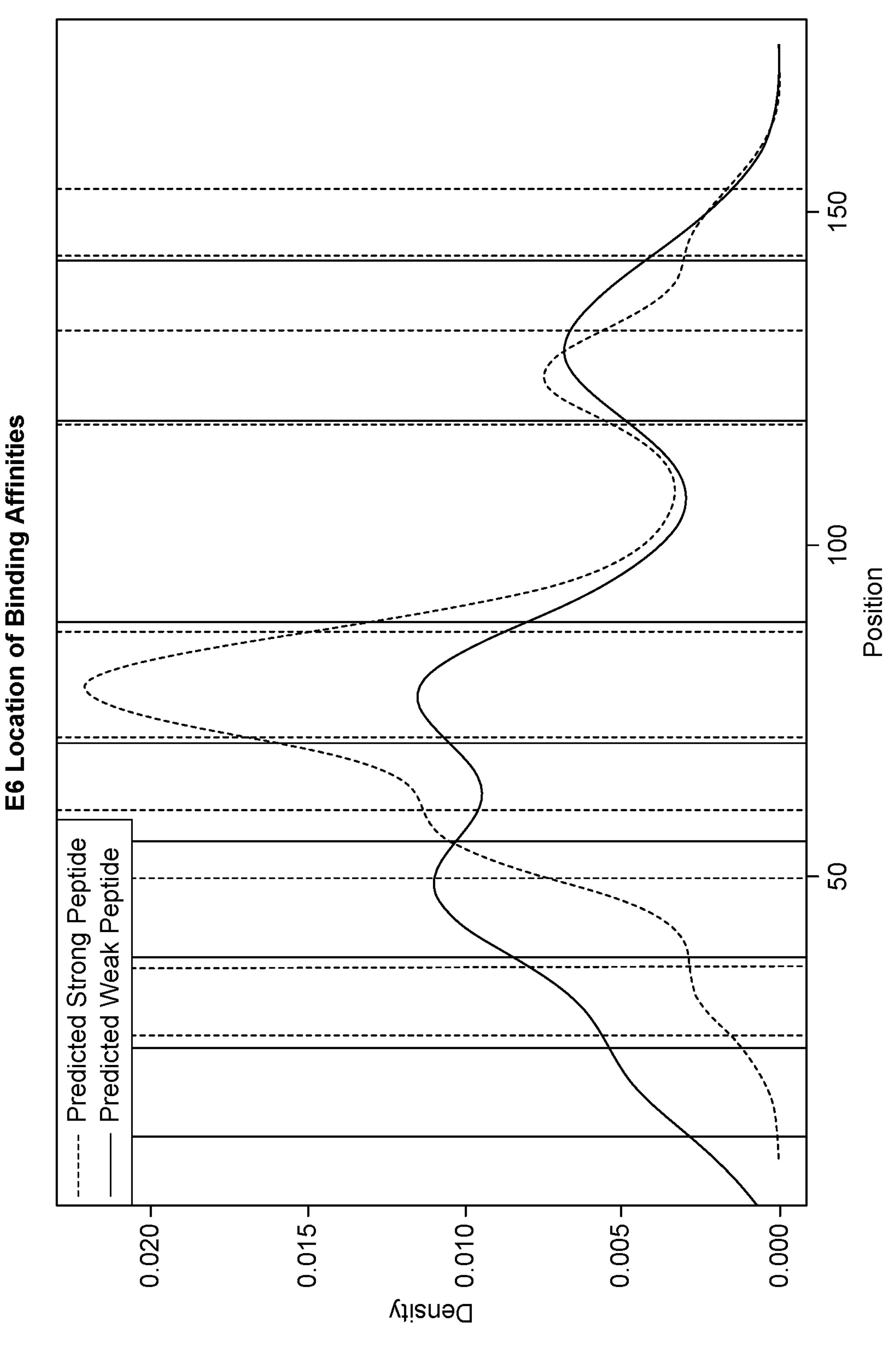
FIG. 7B shows NetMHC 4.0 antigenicity prediction density plot. First/second order differentials are employed in order to identify peaks.
Figure 7C:
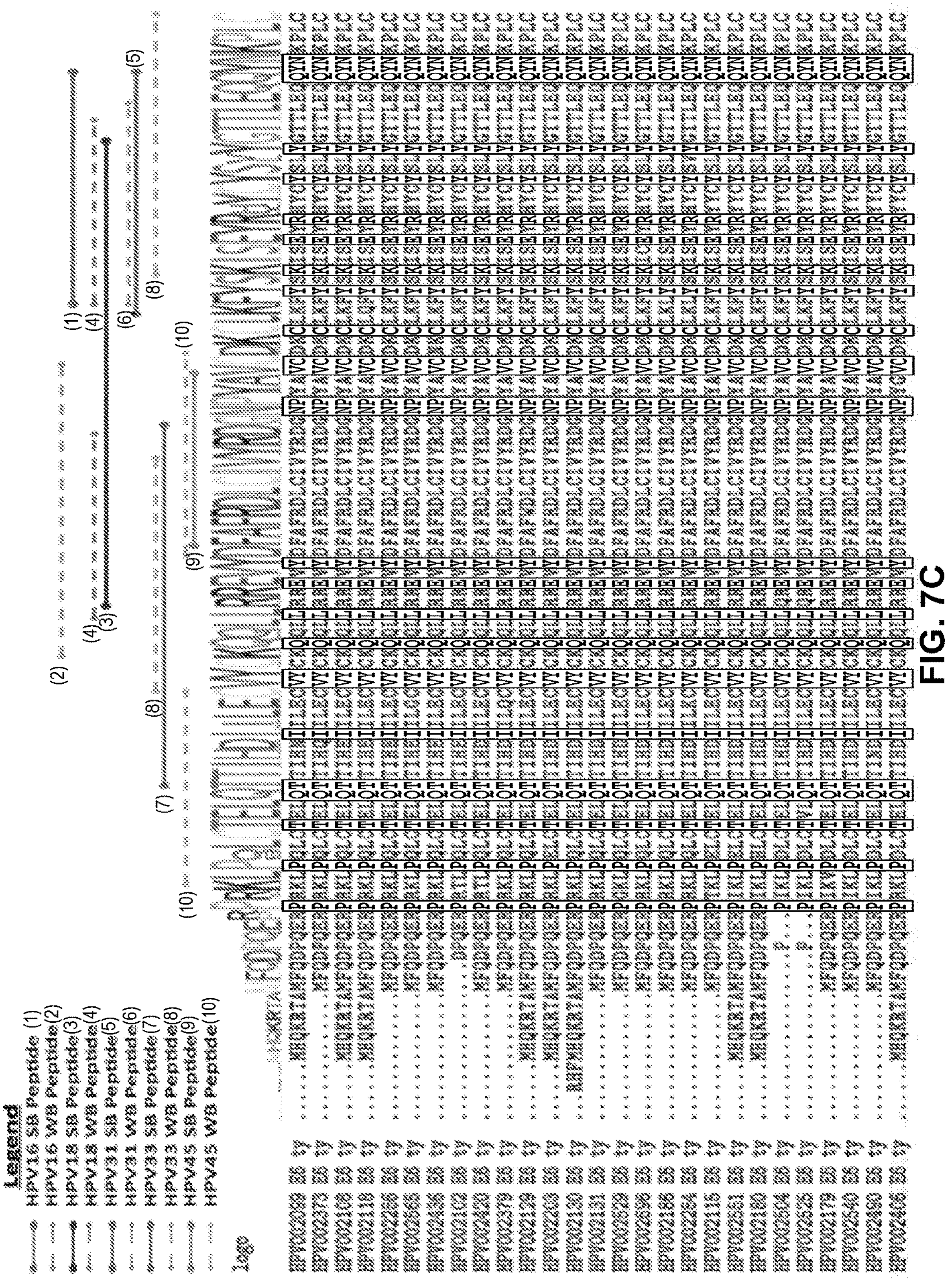
FIG. 7C shows amino acid sequences aligned against consensus sequences in order to determine coverage across HPV subtypes.

NetMHC 4.0 was applied to each consensus sequence to predict binding affinity against all major MHC-I alleles (HLA-A0101, HLA-A0201, HLA-A0301, HLA-A2402, HLA-A2601, HLA-B0702, HLA-B0801, HLA-B2705, HLA-B3901, HLA-B4001, HLA-B5801, and HLA-B1501). NetMHC 4.0 uses artificial neural networks to predict the binding affinity of peptide sequences. This analysis was performed for HPV16, HPV18, HPV31, HPV33, and HPV45. Thresholds were arbitrarily established at 0.5% (strong binders) and 2% (weak binders) ranks. Peptides with predicted binding affinity greater than 99.5% were classified as strong binders, and peptides with predicted binding affinity greater than 98% were classified as weak binders. The position of each AA within the peptide sequences were extracted and used to generate density curves (FIG. 7A and FIG. 7B). Using these density curves, first and second order differentials were calculated to determine peaks for strong and weak binders (FIG. 7C). Finally, the union of these positions was used to extract AA sequences likely to elicit a response.

Predicting Binding Affinity in HPV16, HPV18, HPV31, HPV33, and HPV45

Previous studies have shown that HPV strains 16, 18, 31, 33, and 45 were precursors for cervical carcinoma. To identify candidate peptides with broad coverage across these strains, binding affinity was predicted within each strain. The sequences with strong/weak binding affinity predictions were extracted. Using protein blast, these sequences were aligned against the consensus sequences across all five strains. Alignments were plotted for all five serotypes and coverage was assessed.

Example 2

HPV Antigen Designs

Naturally existing sequence variations on HPV strains could potentially hinder the development of effective HPV vaccines. To address this concern, the present vaccine design approach utilized bioinformatics and protein engineering methods to select and design antigens with broader coverage of T cell epitopes, novel mutations, and enhancer agonist peptides. Drawing on available information of extended coverage of antigen regions with CTL-specific epitopes and in silico prediction results, the designed HPV vaccine antigens can induce robust HPV-16 and HPV-18 specific responses and potentially benefit patients at high risk of HPV-derived cancers.

The new HPV vaccines include the following engineered proteins, peptides and/or modifications:

1) truncated E5 regions that fused with E6 and E7 domains of HPV16 and HPV18;
2) newly designed point mutations that can potentially abrogate p53 binding with the known PTPN13 binding mutants (Weiking et al., *Cancer Gene Ther.* 19(10:667-74 (2012). doi: 10.1038/cgt.2012.55. Epub 2012 Aug. 24);
3) a novel truncation in HPV18 E6 non-immunogenic region at the C-terminus and application of p53 binding knockout mutants;
4) a novel truncation of HPV18 E7 non-immunogenic region at the N-terminus and incorporating pRb, Mi2B mutants (Weiking et al., 2012); and/or
5) agonist peptides from Tsang, et al., *Vaccine* 35(19): 2605-2611 (2017) doi: 10.1016/j.vaccine.2017.03.025. Epub 2017 Apr. 4 in the newly designed HPV vaccine constructs.

HPV Design 1

Figure 3:
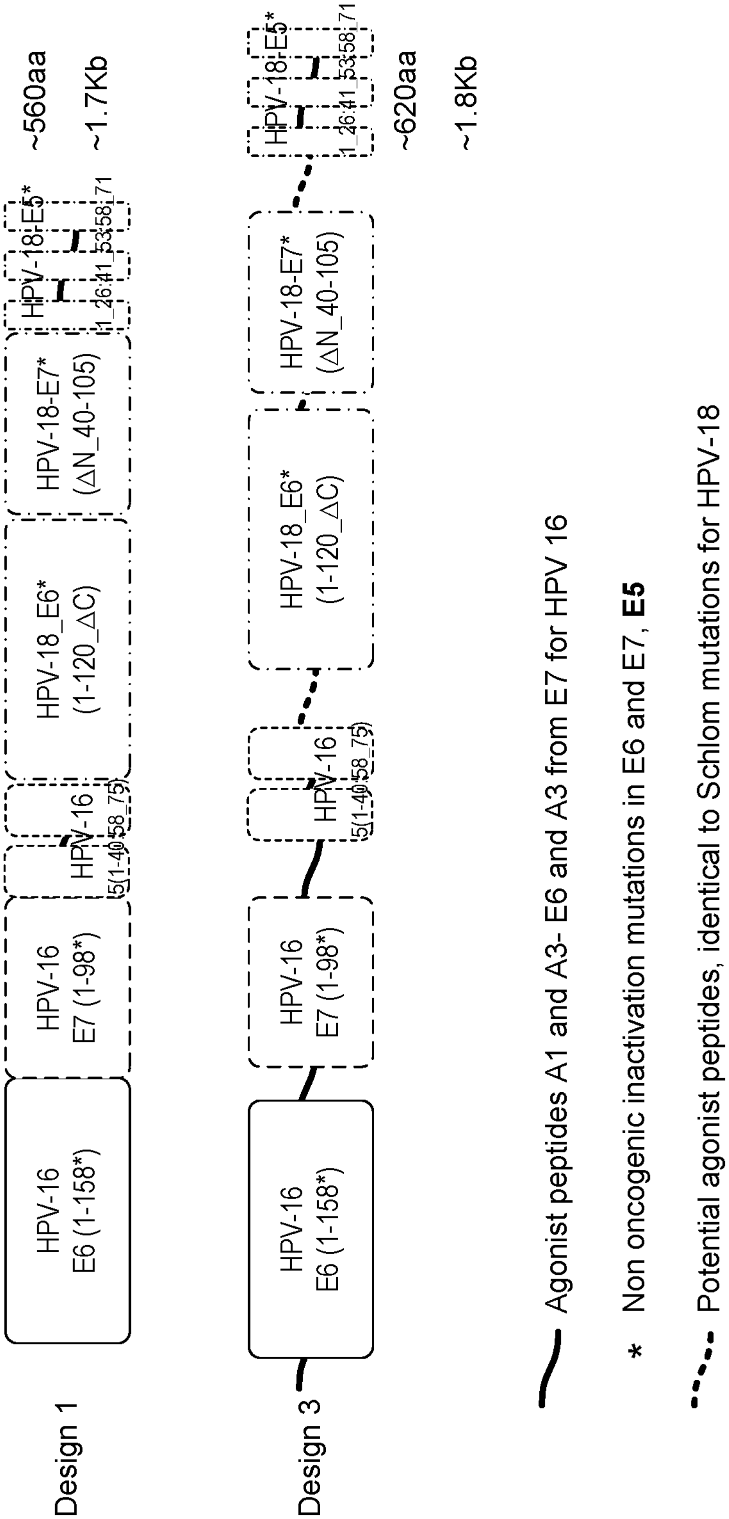
FIG. 3 is schematic diagrams of HPV16 and HPV18 antigenic designs for HPV design 1 and HPV design 3. Consensus sequence information was utilized to select HPV16/HPV18 reference sequences for the design which included all major variants. The vaccine composition comprising different E6, E7 and E5 protein components with domain boundaries and mutation information is shown. These different domains contain most prevalent peptides deduced from IEDB predictions for MHC-I binding. HPV design 3 is similar to HPV design 1 with the addition of enhancer agonist peptides.

Consensus sequence information was utilized to select HPV 16/18 reference sequences for the design which included all major variants. The vaccine composition comprising different E6, E7 and E5 protein components with domain boundaries and mutation information is shown in FIG. 3. The reference sequence for E6 was obtained from the Human Papillomavirus T cell Antigen Database (Bioinformatics Core at Cancer Vaccine Center, Dana-Farber Cancer Institute). Reference sequences for E5 and E7 were obtained from the Papilloma Virus Episteme (PaVE) database.

Figure 4B:
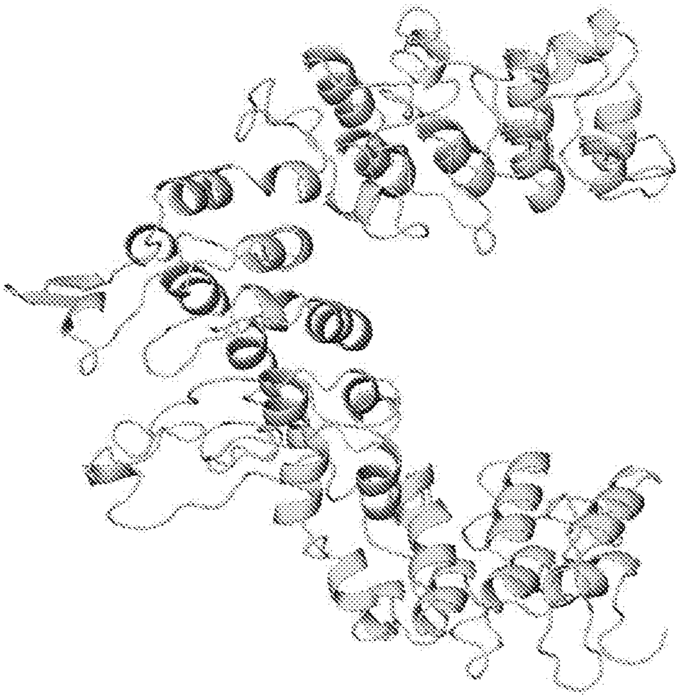
FIG. 4A and FIG. 4B show a homology model of HPV design 2 and HPV design 4, respectively. A homology model is used to assess the overall structural feature and to compare the HPV design against native ankyrin repeats. HPV designs are shown in the same orientation and suggest different structural conformations due to shuffled peptides although maintaining the same overall fold.
Figure 4A:
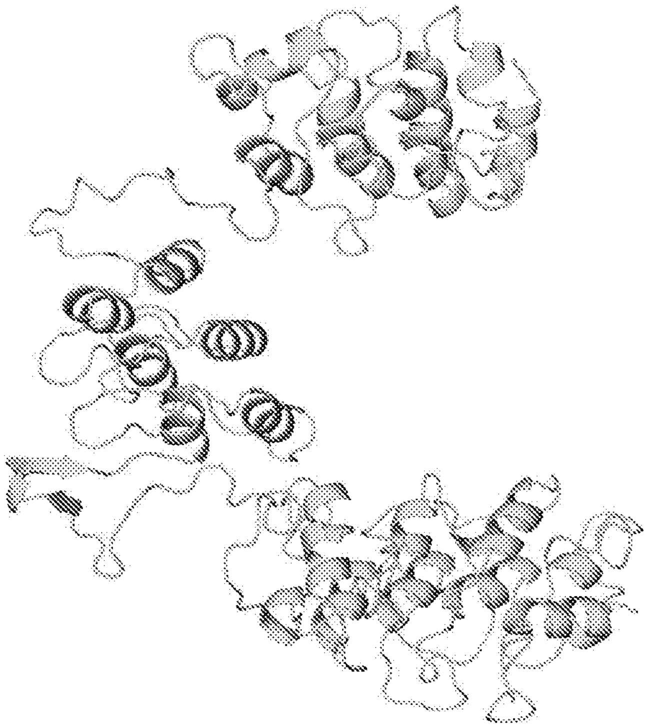

The design for HPV16 and HPV18 E5 were inspired via a combination of in silico predictions (IEDB and netMHC) and, for HPV16 also included findings of Chen et al., J Virol. 78(3):1333-43 (2004); whereas, the design for HPV18 included N terminal residues (1-26) and C terminal residues (41-53, 58-71) (see, FIGS. 4A and 4B).

Inactivating mutations for HPV16 and HPV18 were introduced into E6 and E7 peptide sequences in order prevent oncogenicity (Weiking et al., 2012 October; 19(10):667-74. doi: 10.1038/cgt.2012.55. Epub 2012 Aug. 24). For HPV16 E6, these mutations were E18A, L50G and alanine replacement from 148-151 (ETQL to AAAA). For HPV16 E7, four mutations (H2P, C24G, E46A, and L67R) were included (Weiking et al., 2012). For HPV18 E6, two mutations were included (E18A and L52G). For HPV18 E6, only the N terminus portion was predicted to contain MHC-I binding epitopes (IEBD and netMHC analysis), thus, residues starting at amino acid 121 were removed from these designs. An additional mutation was included in E6 in order to further abrogate its interaction with the p53 protein (Martinez-Zapien et al., *Nature* 529(7587):541-45 (2016)). For HPV18 E7, two mutations (Weiking et al., 2012) were included (E55A and L74R) and residues from (1-40) were removed because HPV-18 E7 contained majority of the predicted MHC-I binding epitopes (IEDB and netMHC predictions) in the C terminal region.

HPV Design 2

For designing recombinant multi-epitope proteins as HPV vaccine antigens, a total of 32 key immunogenic peptides, as listed in Table 2, were selected. These peptides included CTL specific peptides from E6 (HPV-16/-18), E7 (HPV-16/-18) and E5 (HPV16) genes. Most of these CTL epitopes were reported with multiple immunological assays, immuno-proteomics, and were included in IEDB resource and netMHC predictions. The novelty of this antigen design is to graft the CTL peptides on to a human ankyrin repeat protein scaffold for possible generation of new protein bearing T cell epitopes and or proteasome cleavage sites.

Human Ankyrin-like repeat ("ALR") protein (PDB code 1QYM) was selected as a scaffold on to which CTL peptides were assembled randomly, enabling different types of protein linker sequences embedded between the peptides. ALR proteins have generally high expression and high stability; the ALR protein provides a scaffold for the HPV peptides and could create novel CTLs. Caution was taken by random shuffling of the peptides to prevent any reformation of E6 and E7 oncogenic proteins.

A homology model (FIG. 4A) was used to assess the overall structural feature and to compare the design against native ankyrin repeats. This model suggested that the grafted CTL peptides on an ankyrin scaffold should retain their tertiary structure. It is expected that the scaffold amino acids connecting those peptides could serve as "linkers" and potentially create new CTL epitopes and or agonist peptide epitopes.

TABLE 2

Peptides from E5 (HPV16), E6 (HPV16 and HPV18), and E7 (HPV16 and HPV18) along with agonist peptides used to assemble multi-epitope vaccine constructs

| SEQ | HPV16-E6 (9) | SEQ | HPV16-E7 (8) | SEQ | HPV16-E5 (1) |
|---|---|---|---|---|---|

TABLE 2-continued

Peptides from E5 (HPV16), E6 (HPV16 and HPV18), and E7 (HPV16 and HPV18) along with agonist peptides used to assemble multi-epitope vaccine constructs

| | | | | | |
|---|---|---|---|---|---|
| 113 | HLDKKQRFHNI | 122 | LCVQSTHVDI | 130 | YIIFVYIPL |
| 114 | RWTGRCMSCC | 123 | RTLEDLLMGT | | |
| 115 | TTLEQQYNKPLCDLL | 124 | TLGIVCPI | | |
| 116 | ISEYRHYCY | 125 | LLMGTLGIV | | |
| 117 | VYDFAFRDL | 126 | TLHEYMLDL | | |
| 118 | TIHDIILECV | 127 | AHYNIVTFCC | | |
| 119 | KLPQLCTEL | 128 | YMLDLQPETT | | |
| 120 | FAFRDLCIVY | 129 | CDSTLRLCV | | |
| 121 | LCIVYRDGNPYAVCD | | | | |
| SEQ | HPV18-E6 (8) | SEQ | HPV18-E7 (6) | SEQ | Agonist peptides (3) |
| 131 | KLTNTGLYNL | 139 | DDLRAFQQLFLNTLS | 145 | KLPQLCTEV |
| 132 | KCIDFYSRI | 140 | FQQLFLNTL | 146 | QLYNKPLCDV |
| 133 | FAFKDLFVV | 141 | QLFLNTLSFV | 147 | RTLEDLLMGV |
| 134 | NLLIRCLRC | 142 | LFLNTLSFVCPWCAS | | |
| 135 | KLPDLCTEL | 143 | TLQDIVLHL | | |
| 136 | ELTEVFEFA | 144 | SEEENDEIDGVNHQHLPARR | | |
| 137 | SLQDIEITCV | | | | |
| 138 | KTVLELTEV | | | | |

HPV Design 3

Design 3 is similar to Design 1 with the addition of enhancer agonist peptides (FIG. 3). Overall, designs 1 and 3 contain all necessary sequences from each E5, E6, and E7 (FIGS. 4A and 4B). These were inspired via inventor-selected combinations using guidance from in silico epitope prediction analysis and available information on MHC-I binding and cytokine production following T cell activation.

For HPV16, this design includes: (1) peptides from Tsang et al., *Vaccine* 35(19):2605-2611 (2017) doi: 10.1016/j.vaccine.2017.03.025. Epub 2017 Apr. 4—three peptides that exhibit better MHC-I binding and elicit more robust cytotoxic T cell lymphocyte (CTL) response comprising mutations in E6 (L19V and Q91L/L99V) and mutation in E7 (T86V); (3) two enhancer peptides fused to the inactivated N and C terminus of E6; and (4) one enhancer peptide fused to the inactivated C terminus of E7.

For HPV18, this design includes: (1) three peptides with identical mutations to mimic enhancer agonist peptides similar to peptides of HPV16 (Tsang et al., 2017) comprising the mutations in E6 (L21V and L101V); and (2) two potential mimic enhancer agonists fused to N and C terminus regions of E6 and another agonist mimic fused to the C terminal region of E7. Since HPV18 naturally had the aforementioned mutations in E6 (Q91L) and E7 (T95V) naturally, no additional modifications were needed.

HPV Design 4

This design was based on Design 2, utilizing the same ankyrin repeat approach. However, Design 4 includes an additional three unique agonist peptides from the peptides of Tsang et al., 2017 for a total of 35 key immunogenic peptides (Table 2). The order of peptides grafted on the scaffold was again randomized in order to be different from Design 2 and for the potential to generate different CTL epitopes. A homology model of Design 4 was generated (FIG. 4B). The homology of this design was found similar to the Design 2, but indicated local structural variations.

HPV Design 5

This design is a multi-epitope vaccine, designed by selecting all 35 key immunogenic peptides shown in Table 2. It was assembled with a charged dipeptide KK residue. Advantages of this design include potential for cleavage at "KK" residues and random modification with the "K" residue added at CTL epitopes.

Example 3

Assessing the Predicted Binding Affinities of HPV Vaccine Constructs

Figure 5B:
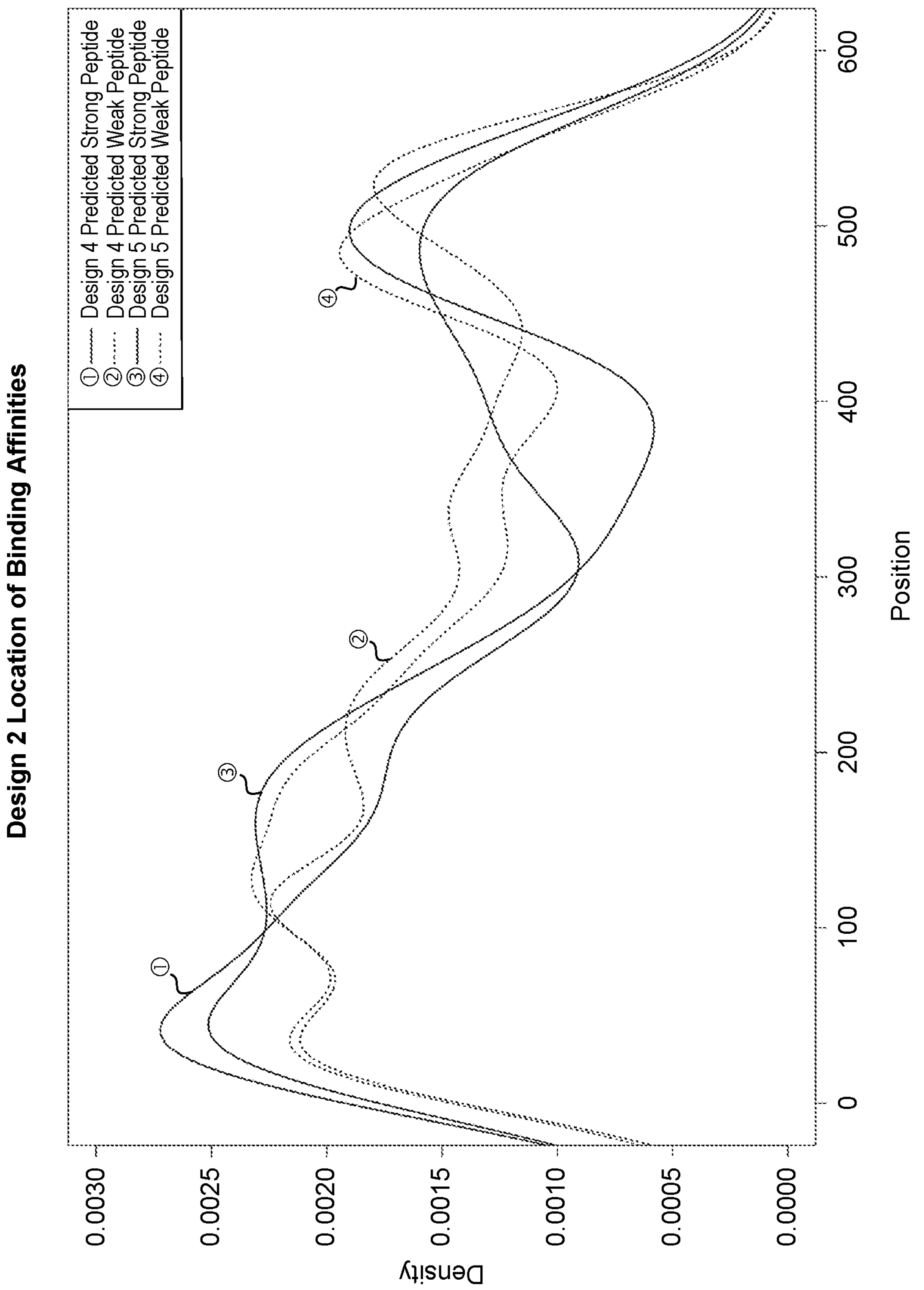

Bioinformatics predictions for the binding affinity for each design were carried out. Entire sequences were loaded into NetMHC, which was used to assess antigenicity and extent of coverage against various HPV genotypes. It should be noted that Designs 4 and 5 use the same 35 peptides. The main difference is that Design 4 peptides were grafted on Ankyrin protein and Design 5 peptides were connected by "KK" linkers (FIG. 5A). Ultimately, the binding affinity predictions on the matched regions of both designs were similar (FIG. 5B). The HPV designs were compared among themselves (Tables 3 and 4) and with reference sequences which are shown in FIG. 8, FIGS. 9A-9C, and FIGS. 10A-10C.

TABLE 3

| HPV16 Design Elements (HPV Designs 1 and 3) | | |
|---|---|---|
| MOD | HPV type | Rationale |
| 1755804 | HPV16 E6 non oncogenic | Inclusion of p53 and PTPN13 binding site mutations [E18A, L50G, ETQL - AAAA]. These mutations do not allow E6/E7 to degrade p53, pRb, PTPN13, or activate telomerase: Martinez-Zapien et al., 2016; Weiking et al., 2012 |
| 1755805 | HPV16 E7 non oncogenic | Removal of Rb and Mi2B binding sites; prior art in Etubics E7 |
| 1755806 | HPV16 E5 (1-40, 58-75) | Novel truncation of E5 with removal of 2 immuno-dominant regions |
| 1755814 | HPV16 E6 A1 peptide (L19V) | Agonistic peptides |
| 1755815 | HPV16 E6 A3 peptide (Q91L/L99V) | Agonistic peptides |
| 1755816 | HPV16 E7 A3 peptide (T86V) | Agonistic peptides |

TABLE 4

| HPV18 Design Elements (HPV Designs 1 and 3) | | |
|---|---|---|
| MOD | HPV type | Notes |
| 1755807 | HPV18 E6 non oncogenic | Novel C terminal truncated E6 domain (1-120) and inclusion of p53 binding sites mutations [E18A, L50G]; Martinez-Zapien et al., 2016; Weiking et al., 2012 |
| 1755808 | HPV18 E7 non oncogenic | Novel N terminal truncated E7 domain (40-105), and inclusion of Rb and Mi2B binding mutants [E46A, L67R]; Weiking et al., 2012 |
| 1755809 | HPV18 E5 (1-26: 41-53: 58-71) | Novel truncation of E5 with removal of 2 immuno-dominant regions |
| 1755817 | HPV18 E6 A1 peptide (L21V) | Agonistic peptides |
| 1755818 | HPV18 E6 A3 peptide (L101V) | Agonistic peptides |
| 1755819 | HPV18 E7 A3 peptide (T95V) | Agonistic peptides |

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The present application claims benefit to U.S. Provisional Application No. 62/639,354 filed Mar. 6, 2018, which is incorporated herein by reference in its entirety.

EMBODIMENTS

E1. A non-naturally occurring polynucleotide encoding a polypeptide comprising one or more immune response-inducing human papilloma virus (HPV) polypeptides.

E2. The polynucleotide of E1, wherein said non-naturally occurring polynucleotide encodes a polypeptide comprising two or more HPV polypeptides.

E3. The polynucleotide of E2, wherein said two or more HPV polypeptides comprise one or more HPV-16 immune response-inducing polypeptide sequences.

E4. The polynucleotide of E3, wherein said HPV-16 peptide comprises at least one of an E5 peptide, an E6 peptide or an E7 peptide.

E5. The polynucleotide of E3 or E4, wherein said HPV-16 peptide comprises an E5 peptide, and said E5 peptide has a sequence as shown in SEQ ID NO: 47.

E6. The polynucleotide of any one of E3 to E5, wherein said HPV-16 peptide comprises an E6 peptide, and said E6 peptide has a sequence as shown in SEQ ID NO: 45.

E7. The polynucleotide of any one of E3 to E6, wherein said HPV-16 peptide comprises an E7 peptide, and said E7 peptide has a sequence as shown in SEQ ID NO: 46.

E8. The polynucleotide of any one of E1 to E7, wherein said one or more HPV peptides comprises an HPV-18 peptide.

E9. The polynucleotide of E8, wherein said HPV-18 peptide comprises at least one of an E5 peptide, an E6 peptide or an E7 peptide.

E10. The polynucleotide of E8 or 9, wherein said HPV-18 peptide comprises an E5 peptide, and said E5 peptide has a sequence as shown in SEQ ID NO: 50.

E11. The polynucleotide of any one of E8 to 10, wherein said HPV-18 peptide comprises an E6 peptide, and said E6 peptide has a sequence as shown in SEQ ID NO: 48.

E12. The polynucleotide of any one of E8 to 10, wherein said HPV-18 peptide comprises an E7 peptide, and said E7 peptide has a sequence as shown in SEQ ID NO: 49.

E13. The polynucleotide of any one of E1 to E12, wherein said polypeptide has a sequence as shown in SEQ ID NO: 51.

E14. The polynucleotide of any one of E1 to E13, wherein at least one of said one or more HPV polypeptides is connected to an agonist peptide.

E15. The polynucleotide of E14, wherein said agonist peptide has a sequence comprising an agonist peptide sequence as shown in Table 2.

E16. The polynucleotide of E14 or E15, wherein said polypeptide has a sequence as shown in SEQ ID NO: 53.

E17. A polynucleotide comprising the polynucleotide of any one of E1 to E16, further comprising one or more polynucleotides encoding a gene switch system for inducible control of heterologous gene expression, wherein said heterologous gene expression is regulated by said gene switch system; and, wherein said heterologous gene comprises the polynucleotide of any one of E1 to E16.

E18. The polynucleotide of E17, wherein said gene switch system is an ecdysone receptor-based (EcR-based) gene switch system.

E19. The polynucleotide of any one of E1 to E18, wherein said one or more HPV polypeptides is for use in a vaccine.

E20. A vector comprising the polynucleotide of any one of E1 to E19.

E21. The vector of E20, wherein said vector is an adenoviral vector.

E22. The vector of E21, wherein said adenoviral vector is a gorilla adenoviral vector.

E23. A method of regulating the expression of a heterologous gene in a cell, the method comprising: introducing into said cell one or more polynucleotides that comprise (i) an repressible or inducible gene switch, and (ii) a heterologous immune response-inducing gene, wherein expression of said heterologous immune response-inducing gene is regulated by said gene switch, wherein said heterologous immune response-inducing gene encodes one or more HPV polypeptides; and exposing said cell to a compound in an amount sufficient to repress or induce expression of said heterologous immune response-inducing gene.

E24. The method of E23, wherein said target cell is a mammalian cell.

E25. The method of E23 or E24, wherein said gene switch comprises a ligand binding domain derived from at least one of an ecdysone receptor (EcR), a ubiquitous receptor, an orphan receptor 1, an NER-1, a steroid hormone nuclear receptor 1, a retinoid X receptor interacting protein-15, a liver X receptor β, a steroid hormone receptor like protein, a liver X receptor, a liver X receptor α, a farnesoid X receptor, a receptor interacting protein 14, and a famesol receptor.

E26. An E6 peptide, wherein said E6 peptide comprises an E18A amino acid substitution and at least one of an L50G, E148A, T149A, Q150A and L151A amino acid substitution as compared to a wildtype E6 peptide.

E27. The E6 peptide of E26, wherein said E6 peptide comprises said E18A amino acid substitution and said L50G, E148A, T149A, Q150A and L151A amino acid substitutions.

E28. The E6 peptide of E26, wherein said E6 peptide has a sequence as shown in SEQ ID NO: 45.

E29. The E6 peptide of any one of E26 to E28, wherein said E6 peptide is fused to an agonist peptide.

E30. The E6 peptide of E29, wherein said agonist peptide is fused to at least one of a C-terminus and an N-terminus of said E6 peptide.

E31. The E6 peptide of any one of E26 to E30, wherein said wildtype E6 peptide is from HPV-16.

E32. An E6 peptide, wherein said E6 peptide comprises a deletion as compared to a wildtype E6 peptide, wherein said deletion comprises a C-terminus of said wildtype E6 peptide.

E33. The E6 peptide of E32, wherein said deletion comprises amino acids from amino acid 121 to a C-terminus of said wildtype E6 peptide.

E34. The E6 peptide of E32 or E33, wherein said E6 peptide comprises at least one of an E18A and L50G substitution as compared to said wildtype E6 peptide.

E35. The E6 peptide of any one of E32 to E34, wherein said wildtype E6 peptide is from HPV-18.

E36. The E6 peptide of any one of E32 to E35, wherein said E6 peptide has a sequence as shown in SEQ ID NO: 48.

E37. An E7 peptide, wherein said E7 peptide comprises a deletion as compared to a wildtype E7 peptide, wherein said deletion comprises an N-terminus of said wildtype E7 peptide.

E38. The E7 peptide of E37, wherein said deletion comprises amino acids 1-39 of said wildtype E7 peptide.

E39. The E7 peptide of E37 or E38, wherein said E7 peptide comprises at least one of an E55A and L74R substitution as compared to said wildtype E7 peptide.

E40. The E7 peptide of any one of E37 to E39, wherein said wildtype E7 peptide is from HPV-18.

E41. The E7 peptide of any one of E37 to E40, wherein said E7 peptide has a sequence as shown in SEQ ID NO: 49.

E42. An E5 peptide, wherein said E5 peptide comprises a deletion as compared to a wildtype E5 peptide, wherein said deletion comprises amino acids 41-57 of said wildtype E5 peptide.

E43. The E5 peptide of E42, wherein said E5 peptide has a sequence as shown in SEQ ID NO: 47.

E44. The E5 peptide of E42 or E43, wherein said wildtype E5 peptide is from HPV-16.

E45. An E5 peptide, wherein said E5 peptide comprises a deletion as compared to a wildtype E5 peptide, wherein said deletion comprises at least one of amino acids 27-40 or amino acids 54-57 of said wildtype E5 peptide.

E46. The E5 peptide of E45, wherein said E5 peptide has a sequence as shown in SEQ ID NO: 50.

E47. The E5 peptide of E45 or E46, wherein said wildtype E5 peptide is from HPV-18.

E48. A polypeptide construct comprising the peptide of any one of E26 to E47.

E49. A polypeptide construct, wherein said polypeptide construct comprises an HPV-16 E6 peptide, wherein said HPV-16 E6 peptide comprises an E18A amino acid substitution and at least one of an L50G, E148A, T149A, Q150A and L151A amino acid substitution as compared to a wildtype HPV-16 E6 peptide.

E50. The polypeptide construct of E49, wherein said HPV-16 E6 peptide comprises said E18A amino acid substitution and said L50G, E148A, T149A, Q150A and L151A amino acid substitutions.

E51. The polypeptide construct of E49 or E50, wherein said HPV-16 E6 peptide has a sequence as shown in SEQ ID NO: 45.

E52. The polypeptide construct of any one of E49 to E51, wherein said polypeptide construct further comprises an HPV-16 E7 peptide, wherein said HPV-16 E7 peptide comprises at least one of an H2P, C24G, E46A and L67R amino acid substitution as compared to a wildtype HPV-16 E7 peptide.

E53. The polypeptide construct of E52, wherein said HPV-16 E7 peptide comprises said H2P, C24G, E46A and L67R amino acid substitutions.

E54. The polypeptide construct of E53, wherein said HPV-16 E7 peptide has a sequence as shown in SEQ ID NO: 46.

E55. The polypeptide construct of any one of E49 to E54, wherein said polypeptide construct further comprises an HPV-16 E5 peptide.

E56. The polypeptide construct of E55, wherein said HPV-16 E5 peptide comprises a deletion of one or more amino acids as compared to a wildtype HPV-16 E5 peptide.

E57. The polypeptide construct of E56, wherein said deletion comprises amino acids 41-57 of said wildtype HPV-16 E5 peptide.

E58. The polypeptide construct of any one of E55 to E57, wherein said HPV-16 E5 peptide has a sequence as shown in SEQ ID NO: 47.

E59. The polypeptide construct of any one of E49 to E58, wherein said polypeptide further comprises an HPV-18 E6 peptide.

E60. The polypeptide construct of E59, wherein said HPV-18 E6 peptide comprises an E18A and L50G substitution as compared to a wildtype HPV-18 E6 peptide.

E61. The polypeptide construct of E59 or E60, wherein said HPV-18 E6 peptide comprises a deletion of at least one C-terminus amino acid relative to said wildtype HPV-18 E6 peptide.

E62. The polypeptide construct of E61, wherein said deletion comprises amino acids from amino acid 121 to said C-terminus of said wildtype HPV-18 E6 peptide.

E63. The polypeptide construct of any one of E59 to E62, wherein said HPV-18 E6 peptide has a sequence as shown in SEQ ID NO: 48.

E64. The polypeptide construct of any one of E49 to E63, wherein said polypeptide construct further comprises an HPV-18 E7 peptide.

E65. The polypeptide construct of E64, wherein said HPV-18 E7 peptide comprises an E55A and L74R substitution as compared to a wildtype HPV-18 E7 peptide.

E66. The polypeptide construct of E64 or E65, wherein said HPV-18 E7 peptide comprises a deletion of at least one amino acid from an N-terminus of said HPV-18 E7 peptide.

E67. The polypeptide construct of E66, wherein said deletion comprises amino acids 1-40 of said wildtype HPV-18 E7 peptide.

E68. The polypeptide construct of any one of E64 to E67, wherein said HPV-18 E7 peptide has a sequence as shown in SEQ ID NO: 49.

E69. The polypeptide construct of any one of E59 to E68, wherein said polypeptide construct further comprises an HPV-18 E5 peptide.

E70. The polypeptide construct of E69, wherein said HPV-18 E5 peptide comprises a deletion of at least one amino acid as compared to a wildtype HPV-18 E5 peptide.

E71. The polypeptide construct of E70, wherein said deletion comprises amino acids 27-40 or 54-57 of said wildtype HPV-18 E5 peptide.

E72. The polypeptide construct of any one of E69 to E71, wherein said HPV-18 E5 peptide has a sequence as shown in SEQ ID NO: 50.

E73. The polypeptide construct of any one of E59 to E72, wherein said polypeptide construct has a sequence as shown in SEQ ID NO: 51.

E74. The polypeptide construct of any one of E5973, wherein said polypeptide construct further comprises at least one agonist peptide.

E75. The polypeptide construct of E74, wherein said at least one agonist peptide has a sequence comprising an agonist peptide sequence as shown in Table 2.

E76. The polypeptide construct of E74 or E75, wherein said polypeptide construct has a sequence as shown in SEQ ID NO: 53.

E77. A polypeptide construct comprising an ankyrin-like repeat domain and an HPV peptide.

E78. The polypeptide construct of E77, wherein said ankyrin-like repeat protein is a human ankyrin-like repeat protein.

E79. The polypeptide construct of E77 or E78, wherein said HPV peptide is linked to said ankyrin-like repeat protein by a linker.

E80. The polypeptide construct of any one of E77 to E79, wherein said HPV peptide comprises at least one of an HPV-16 peptide or an HPV-18 peptide.

E81. The polypeptide construct of any one of E77 to E80, wherein said HPV peptide comprises an HPV-16 peptide, and said HPV-16 peptide comprises at least one of an E5 peptide, an E6 peptide or an E7 peptide.

E82. The polypeptide construct of any one of E77 to E81, wherein said HPV peptide comprises an HPV-18 peptide, and said HPV-18 peptide comprises at least one of an E6 peptide or an E7 peptide.

E83. The polypeptide construct of any one of E77 to E82, wherein said HPV peptide comprises an HPV-16 E5 sequence, an HPV-16 E6 sequence, an HPV-16 E7 sequence, an HPV-18 E6 sequence or an HPV-18 E7 sequence as shown in Table 2.

E84. The polypeptide construct of any one of E77 to E83, wherein said polypeptide construct has a sequence as shown in SEQ ID NO: 52.

E85. The polypeptide construct of any one of E77 to E84, wherein said polypeptide construct further comprises at least one agonist peptide.

E86. The polypeptide construct of E85, wherein said polypeptide construct comprises three agonist peptides.

E87. The polypeptide construct of E86, wherein said polypeptide construct has a sequence as shown in SEQ ID NO: 54.

E88. A polypeptide construct, wherein said polypeptide construct comprises at least two HPV amino acid sequences as shown in Table 2, wherein said at least two HPV amino acid sequences are connected by a peptide linker, wherein said peptide linker is a KK linker.

E89. The polypeptide construct of E88, wherein said at least two HPV amino acid sequences comprise at least one of an HPV-16 peptide or an HPV-18 peptide as shown in Table 2.

E90. The polypeptide construct of E88 or E89, wherein said at least two HPV amino acid sequences comprise an HPV-16 peptide, and said HPV-16 peptide comprises at least one of an HPV-16 E5 peptide, an HPV-16 E6 peptide or an HPV-16 E7 peptide as shown in Table 2.

E91. The polypeptide construct of any one of E88 to E90, wherein said at least two HPV amino acid sequences comprise an HPV-18 peptide, and said HPV-18 peptide comprises at least one of an HPV-18 E6 peptide or an HPV-18 E7 peptide as shown in Table 2.

E92. The polypeptide construct of any one of E88 to E91, wherein said at least two HPV amino acid sequences comprise each of the amino acid sequences as shown in Table 2.

E93. The polypeptide construct of E92, wherein said each of the amino acid sequences is connected to another of said each of the amino acid sequences by said KK linker.

E94. The polypeptide construct of any one of E88 to E93, wherein said polypeptide construct has a sequence as shown in SEQ ID NO: 55.

E95. The polypeptide construct of any one of E48 to E94 for use in a vaccine.

E96. A polynucleotide encoding the polypeptide construct of any one of E58 to E95.

E97. A vector comprising the polynucleotide of E96.

E98. The vector of E97, wherein said vector is an adenoviral vector.

E99. The vector of E98, wherein said adenoviral vector is a gorilla adenoviral vector.

E100. A vector, wherein said vector comprises a polynucleotide that encodes at least one HPV peptide, wherein said vector is an adenoviral vector.

E101. A vector, wherein said vector comprises a polynucleotide that encodes at least one HPV peptide, wherein said vector is an adenoviral vector, wherein said adenoviral vector is a gorilla adenoviral vector.

Provided herein is a representative reference list of certain sequences included in embodiments provided herein (Table 5).

TABLE 5

| Polynucleotide/Amino Acid Sequences | |
|---|---|
| SEQ ID NO: | Description |
| 1 | Adenovirus pIX fragment nucleotides |
| 2 | Adenovirus DNA polymerase fragment nucleotides |
| 3 | Adenovirus penton base protein fragment nucleotides |
| 4 | Adenovirus hexon protein fragment nucleotides |
| 5 | Adenovirus fiber protein fragment nucleotides |
| 6 | Adenovirus pIX nucleotides |
| 7 | Adenovirus DNA polymerase nucleotides |
| 8 | Adenovirus penton base protein nucleotides |
| 9 | Adenovirus hexon protein nucleotides |
| 10 | Adenovirus fiber protein nucleotides |
| 11 | Adenovirus pIX protein fragment |
| 12 | Adenovirus DNA polymerase fragment |
| 13 | Adenovirus penton base protein fragment |
| 14 | Adenovirus hexon protein fragment |
| 15 | Adenovirus fiber protein fragment |
| 16 | Adenovirus pIX amino acids |
| 17 | Adenovirus DNA polymerase amino acids |
| 18 | Adenovirus penton base protein |
| 19 | Adenovirus hexon protein |
| 20 | Adenovirus fiber protein |
| 21 | Adenovirus vector nucleotide sequences |
| 22 | Adenovirus vector nucleotide sequences |
| 23 | Adenovirus vector nucleotide sequences |
| 24 | Adenovirus vector nucleotide sequences |
| 25 | Adenovirus vector nucleotide sequences |
| 26 | IL-2 core promoter |
| 27 | IL-2 minimal promoter |
| 28 | IL-2 enhancer and promoter variant |
| 29 | L-2 enhancer and promoter variant |
| 30 | $(NF-\kappa B)_1$-IL2 promoter variant |
| 31 | $(NF-\kappa B)_3$-IL2 promoter variant |
| 32 | $(NF-\kappa B)_6$-IL2 promoter variant |
| 33 | 1X NFAT response elements-IL2 promoter variant |
| 34 | 3X NFAT response elements-IL2 promoter variant |
| 35 | 3X NFAT response elements-IL2 promoter variant |
| 36 | 6X NFAT response elements-IL2 promoter variant |
| 37 | 6X NFAT response elements-IL2 promoter variant |
| 38 | 6X NFAT response elements-IL2 promoter variant |
| 39 | 6X NFAT response elements-IL2 promoter variant |
| 40 | human EEF1A1 promoter variant |
| 41 | human EEF1A1 promoter variant |
| 42 | human EEF1A1 promoter and enhancer |
| 43 | human UBC promoter |
| 44 | synthetic minimal promoter 1 |
| 45 | HPV antigen design 1 HPV16 E6 amino acids |
| 46 | HPV antigen design 1 HPV16 E7 amino acids |
| 47 | HPV antigen design 1 HPV16 E5 amino acids |
| 48 | HPV antigen design 1 HPV18 E6 amino acids |
| 49 | HPV antigen design 1 HPV18 E7 amino acids |
| 50 | HPV antigen design 1 HPV18 E5 amino acids |
| 51 | HPV antigen design 1 amino acids |
| 52 | HPV antigen design 2 amino acids |
| 53 | HPV antigen design 3 amino acids |
| 54 | HPV antigen design 4 amino acids |
| 55 | HPV antigen design 5 amino acids |
| 56 | HPV antigen design 1 full nucleotide sequences of gorilla adenovirus shuttle plasmid |
| 57 | HPV antigen design 2 full nucleotide sequences of gorilla adenovirus shuttle plasmid |
| 58 | HPV antigen design 3 full nucleotide sequences of gorilla adenovirus shuttle plasmid |
| 59 | HPV antigen design 4 full nucleotide sequences of gorilla adenovirus shuttle plasmid |
| 60 | HPV antigen design 5 full nucleotide sequences of gorilla adenovirus shuttle plasmid |
| 61 | GCAd-RTS-IL12 design 1 |
| 62 | GCAd-RTS-IL12 design 2 |
| 63 | GCAd-RTS-IL12 design 3 |

What is claimed is:

1. A polynucleotide encoding a polypeptide construct comprising the amino acid sequence of SEQ ID NO: 52 or 54.

2. A vector comprising the polynucleotide of claim 1.

3. The vector of claim 2, wherein the vector is an adenoviral vector.

4. The polynucleotide of claim 1, wherein the polypeptide construct comprises the amino acid sequence of SEQ ID NO: 54.

5. The polynucleotide of claim 1, wherein the polypeptide construct comprises the amino acid sequence of SEQ ID NO: 52.

6. The vector of claim 3, wherein the adenoviral vector is a gorilla adenoviral vector.

7. The vector of claim 6, wherein the gorilla adenoviral vector does not comprise an E1 region.

8. The vector of claim 6, wherein the gorilla adenoviral vector does not comprise an E4 region.

9. The vector of claim 6, wherein the gorilla adenoviral vector does not comprise an E1 region or an E4 region.

10. The vector of claim 6, wherein the gorilla adenoviral vector is a GC46 vector.

11. The vector of claim 6, wherein the polynucleotide is under the control of an immediate early cytomegalovirus (CMV) promoter.

12. A method of vaccinating a subject against human papilloma virus, the method comprising administering to the subject the vector of claim 6.

* * * * *

SEQUENCE LISTING

```
<160> NUMBER OF SEQ ID NOS: 147

<210> SEQ ID NO 1
<211> LENGTH: 30
<212> TYPE: DNA
<213> ORGANISM: Artificial sequence
<220> FEATURE:
<223> OTHER INFORMATION: Adenovirus pIX fragment nucleotides

<400> SEQUENCE: 1

agctctttgg tggcgagcgg cgcggcctct                                        30


<210> SEQ ID NO 2
<211> LENGTH: 439
<212> TYPE: DNA
<213> ORGANISM: Artificial sequence
<220> FEATURE:
<223> OTHER INFORMATION: Adenovirus DNA polymerase fragment nucleotides

<400> SEQUENCE: 2

aacatcaata cctcaaagtc atggtcaggg acactttcgc cctcacccac acctccctcc       60

gcaaggcggc gcaggcctac gcgctgcccg tggagaaggg ctgttgcccc taccaggccg      120

tcaaccagtt ctacatgcta ggctcttacc gttcggacac ggacgggttt cccctccaag      180

agtactggaa agaccgcgaa gagttcgtcc tcaaccgcga gctgtggaaa aagaaggggg      240

aggataagta tgacatcatc cgcgagaccc tcgactactg cgcgctcgac gtccaggtca      300
```

-continued ccgccgagct ggtgcacaag ctgcgcgagt cctacgcctc cttcgtcagg gactcggtgg 360
gcttgcaaga agcaagcttc aacgtcttcc agcggcccac catctcctcc aactcccatg 420
ccatcttcag gcagatcgc 439

<210> SEQ ID NO 3
<211> LENGTH: 34
<212> TYPE: DNA
<213> ORGANISM: Artificial sequence
<220> FEATURE:
<223> OTHER INFORMATION: Adenovirus penton base protein fragment nucleotides

<400> SEQUENCE: 3
actgaggctg cggctaaggc tgaggtcgaa gcca 34

<210> SEQ ID NO 4
<211> LENGTH: 45
<212> TYPE: DNA
<213> ORGANISM: Artificial sequence
<220> FEATURE:
<223> OTHER INFORMATION: Adenovirus hexon protein fragment nucleotides

<400> SEQUENCE: 4
ataggtgtgg atgccacaca ggcgggagat aaccctatat atgct 45

<210> SEQ ID NO 5
<211> LENGTH: 30
<212> TYPE: DNA
<213> ORGANISM: Artificial sequence
<220> FEATURE:
<223> OTHER INFORMATION: Adenovirus fiber protein fragment nucleotides

<400> SEQUENCE: 5
gtagcaggcc ccctagctgt ggccaatggc 30

<210> SEQ ID NO 6
<211> LENGTH: 399
<212> TYPE: DNA
<213> ORGANISM: Artificial sequence
<220> FEATURE:
<223> OTHER INFORMATION: Adenovirus pIX nucleotides

<400> SEQUENCE: 6
atgagcgaca ccggcaacag ctttgatgga agcatcttta gcccctatct gacagtgcgc 60
atgcctcact gggctggagt gcgtcagaat gtgatgggtt ccaacgtgga tggacgcccc 120
gttctgcctt caaattcgtc tacaatggcc tacgcgaccg tgggaggaac tccgctggac 180
gccgcgacct ccgccgccgc ctccgccgcc gccgcgaccg cgcgcagcat ggctacggac 240
ctttacagct ctttggtggc gagcggcgcg gcctctcgcg cgtctgctcg ggatgagaaa 300
ctgaccgctc tgctgcttaa actggaagac ttgacccggg agctgggtca actgacccag 360
caggtctcca gcttgcgtga gagcagcctt gcctccccc 399

<210> SEQ ID NO 7
<211> LENGTH: 3168
<212> TYPE: DNA
<213> ORGANISM: Artificial sequence
<220> FEATURE:
<223> OTHER INFORMATION: Adenovirus DNA polymerase nucleotides

<400> SEQUENCE: 7
atggacagct ccaatgtgcg cgatgtcgtc atcaaactcc gcccgccgag cgccgagatc 60

-continued

```
tggacctgcg gctctcgcgg cgtggtggtc tgctccacca tcgccctcca ggagacagat    120
gctggcggcc agacaaccaa agtagaagac caccagccac acgggacccc aggcggggga    180
cttagattcc cgctgcgctt cctcgtcaga ggtcgccagg ttcacctcgt gcaagatata    240
caacccgtgc agcgctgcca gtactgcggt cgcttttaca aaagccagca cgagtgctcg    300
gcccgcagac gggacttcta ctttcaccac atcaacagcc aatcctccaa ctggtggcgg    360
gagatccagt tcttcccgat cggctctcat cctcgcacgg agcgcctctt tgtcacctac    420
gatgtagaga cctacacttg gatgggagcc tttggcaagc agctcgtgcc cttcatgctg    480
gtcatgaaac tgggggggcga cgaggctctg gtcgccgccg cgcgcgacct cgcccgagag    540
ctcagatggg accccctggga gaaagacccc ctcaccttct actgcatcac ccccgaaaag    600
atggccgtgg ggcgacagtt cagaaccttc cgcgaccgcc tgcagaccct catggcccgc    660
gacctctggc gatccttcct ggcggccaac cctcacttgc aagactgggc cctggaggag    720
cacggcctgg aatcgcccga ggagctcacc tacgaggaac tcaaaaagct cccctccatc    780
aagggccagc cccgcttttt ggagctctac atcgtgggcc acaacataaa cggctttgac    840
gagatcgtcc tggccgccca ggtcatcaac aaccgctcct cggtcccagg gccctttcgc    900
atcaccagaa acttcatgcc tcgagcgggg aagatcctct tcaatgacct caccttctcc    960
ctgcccaacc cgcgctccaa aaagcgcacg gactacaccc tgtgggaaca gggcggctgc   1020
gatgacacag acttcaaaca tcaatacctc aaagtcatgg tcagggacac tttcgccctc   1080
acccacacct ccctccgcaa ggcggcgcag gcctacgcgc tgcccgtgga gaagggctgt   1140
tgcccctacc aggccgtcaa ccagttctac atgctaggct cttaccgttc ggacacggac   1200
gggtttcccc tccaagagta ctggaaagac cgcgaagagt tcgtcctcaa ccgcgagctg   1260
tggaaaaaga agggggagga taagtatgac atcatccgcg agaccctcga ctactgcgcg   1320
ctcgacgtcc aggtcaccgc cgagctggtg cacaagctgc gcgagtccta cgcctccttc   1380
gtcagggact cggtgggctt gcaagaagca agcttcaacg tcttccagcg gcccaccatc   1440
tcctccaact cccatgccat cttcaggcag atcgccttcc gcgccgagcg cccccagcgc   1500
accaacctcg ggcccaacat gctggccccc tcccacgagc tctatgacta cgtgcgcgcc   1560
agcatccgcg gggggcgctg ctaccccacc tacctcggca tcctcaggga accccctgtac   1620
gtgtatgaca tctgcggcat gtacgcctcc gcgctcaccc accccatgcc ctggggcccg   1680
cccctcaacc cctacgagcg cgcgctcgcc gcccgcgaat ggcagcgggc tctggacatg   1740
caagcttgca agatcgacta ctttgacccg cgcttgctcc ccggggtctt caccatcgac   1800
gcggaccccc caaacgagga ccagctggac cccctacccc ccttctgctc gcgcaagggc   1860
ggccgcctct gctggaccaa cgagcgcctg cgcggcgagg tcgccaccag cgtcgacatg   1920
gtcaccctgc acaaccgagg ctggagggtg cgcctaatcc cagacgagcg caccaccgtc   1980
ttccccgagt ggaagtgcgt ggcccgcgag tacgtgcaac tcaacatcgc ggccaaggag   2040
cgagccgacc gcgacaaaaa ccagaccctg cgctccatcg ccaagctgct ctcccaacgcc   2100
ctctacgggt cgttcgccac caagcttgac aacaaaaaaa tagtgttttc tgaccagatg   2160
gacccaggta ccctcaaagg tatcacctcc ggacaggtga acatcaaatc ctcctcattt   2220
ttagaaactg acaacctgag cgctgaggtc atgcccgcct tcgagaggga atacttaccc   2280
cagcagctgg ccctcgcaga cagcgatgcg gaagagagtg aagatgaaag ggcgcccacc   2340
ccccttttata cccccccgtc gggaaccccc ggtcacgtgt cctacaccta caagccaatc   2400
acttttctgg acgcggagga gggggacatg tgcctgcaca ccctggagaa ggtggacccg   2460
```

-continued

```
ctagtggaca acgaccgcta cccctcccac gtggcctcct tcgtcctggc ctggacgcgg   2520

gccttcgtct cagagtggtc agagtttctc tacgaggagg acagaggcac tccgctggaa   2580

gacaggcccc tgaagtcggt ctacggggac acggacagcc tcttcgtcac cgagaaggga   2640

caccgcctca tggagagccg aggtaagaaa cgcatcaaaa agcatggggg caacctggtt   2700

tttgaccctg accgcccgga gctcacttgg ctggtggaat gcgagacggt ctgcgcttcc   2760

tgcggcgcgg acgcctactc cccagagtcc gtgtttctcg ctcccaagct ctacgccctg   2820

aagagcctgc agtgcccctc gtgcggcgcc acctccaagg gaaagctccg cgccaagggg   2880

cacgccgccg agggtctcga ctacgagacc atggtcaaat gctacctggc cgacgcgcag   2940

ggcgaagagc ggcagcgatt cagcaccagc agaaccagcc tcaagcgcac cctggccagc   3000

gcccaacccg gagcgcaccc cttcaccgtg acccagacca ccctgacgag gaccctgcgc   3060

ccatggaagg acatgactct ggccccgctg gacgcccatc ggctggtgcc ctacagcgaa   3120

agccgcccca acccgcgaaa cgaggagatc tgctggatcg agatgccg                3168


<210> SEQ ID NO 8
<211> LENGTH: 1974
<212> TYPE: DNA
<213> ORGANISM: Artificial sequence
<220> FEATURE:
<223> OTHER INFORMATION: Adenovirus penton base protein nucleotides

<400> SEQUENCE: 8

atgcggcgcg cggcgatgtt cgaggagggg cctcccccct cttacgagag cgcgatgggg     60

atttctcctg cggcgcccct gcagcctccc tacgtgcctc ctcggtacct gcaacctaca    120

ggggggagaa atagcatctg ttactctgag ctgcagcccc tgtacgatac caccagactg    180

tacctggtgg acaacaagtc cgcggacgtg gcctccctga actaccagaa cgaccacagc    240

gatttttga ccacggtgat ccaaaaacaac gacttcaccc caaccgaggc cagcacccag    300

accataaacc tggataacag gtcgaactgg ggcggcgacc tgaagaccat cttgcacacc    360

aacatgccca acgtgaacga gttcatgttc accaactctt ttaaggcgcg ggtgatggtg    420

gcgcgcgagc agggggaggc gaagtacgag tgggtggact tcacgctgcc cgagggcaac    480

tactcagaga ccatgactct cgacctgatg aacaatgcga tcgtggaaca ctatctgaaa    540

gtgggcaggc agaacggggt gaaggaaagc gatatcgggg tcaagtttga caccagaaac    600

ttccgtctgg gctgggaccc cgtgaccggg ctggtcatgc cgggggtcta caccaacgag    660

gcctttcatc ccgacatagt gcttctgccc ggctgtgggg tggacttcac ccagagccgg    720

ctgagcaacc tgctgggcat tcgcaagcgg cagcctttcc aggagggttt caagatcacc    780

tatgaggatc tgaagggggg caacattccc gcgctccttg atctggacgc ctacgaggag    840

agcttgaaac ccgaggagag cgctggcgac agcggcgaga gtggcgagga gcaagccggc    900

ggcggtggcg gcgcgtcggt agaaaacgaa agtacgcccg cagtggcggc ggacgctgcg    960

gaggtcgagc cggaggccat gcagcaggac gcagaggagg gcgcacagga gggcgcgcag   1020

aaggacatga acgatgggga gatcagggga gacacattcg ccacccgggg cgaagaaaaa   1080

gaggcagagg cggcggcggc ggcgacggcg gaggccgaaa ccgaggttga ggcagaggca   1140

gagcccgaga ccgaagttat ggaagacatg aatgatggag aacgtagggg cgacacgttc   1200

gccacccggg gcgaagagaa ggcggcggag gcagaagccg cggctgagga ggcggctgcg   1260

gctgcggcca agactgaggc tgcggctaag gctgaggtcg aagccaatgt tgcggttgag   1320
```

-continued gctcaggctg aggaggaggc ggcggctgaa gcagttaagg aaaaggccca ggcagagcag 1380
gaagagaaaa aacctgtcat tcaacctcta aaagaagata gcaaaaagcg cagttacaac 1440
gtcatcgagg gcagcacctt tacccagtac cgcagctggt acctggcgta caactacggc 1500
gacccggtca agggggtgcg ctcgtggacc ctgctctgca cgccggacgt cacctgcggc 1560
tccgagcaga tgtactggtc gctgccgaac atgatgcaag acccggtgac cttccgctcc 1620
acgcggcagg ttagcaactt cccggtggtg ggcgccgaac tgctgcccgt gcactccaag 1680
agtttttaca acgagcaggc cgtctactcc cagctgatcc gccaggccac ctctctgacc 1740
cacgtgttca atcgctttcc cgagaaccag attttggcgc gcccgccggc ccccaccatc 1800
accaccgtga gtgaaaacgt tcctgccctc acagatcacg ggacgctacc gctgcgcaac 1860
agcatctcag gagtccagcg agtgaccatt actgacgcca gacgccggac ctgcccctac 1920
gtttacaagg ccttgggcat agtctcgccg cgcgtcctct ccagtcgcac tttt 1974

<210> SEQ ID NO 9
<211> LENGTH: 2877
<212> TYPE: DNA
<213> ORGANISM: Artificial sequence
<220> FEATURE:
<223> OTHER INFORMATION: Adenovirus hexon protein nucleotides

<400> SEQUENCE: 9
atggcgaccc catcgatgat gcctcagtgg tcgtacatgc acatctcggg ccaggacgct 60
tcggagtacc tgagccccgg gctggtgcag ttcgcccgcg ccacagacac ctacttcaac 120
atgagtaaca agttcaggaa ccccactgtg gcgcccaccc acgatgtgac cacggaccgg 180
tcgcagcgcc tgacgctgcg gttcatcccc gtggatcggg aggacaccgc ctactcttac 240
aaggcgcggt tcacgctggc cgtgggcgac aaccgcgtgc tggacatggc ctccacttac 300
tttgacatca ggggggtgct ggacaggggc cccaccttca agccctactc gggtactgcc 360
tacaactccc tggcccccaa gggcgctccc aattcttgcg agtgggaaca agatgaacca 420
gctcaggcag caatagctga agatgaagaa gaacttgaag aagaacaagc tcaggacgaa 480
caggcgccca ctaagaaaac ccatgtatac gcccaggcac ctctttctgg tgaaaaaatt 540
actaaggatg gtttgcaaat aggtgtggat gccacacagg cgggagataa ccctatatat 600
gctgataaaa cattccaacc cgaacctcag ataggtgagt ctcagtggaa cgaggctgat 660
gccacagtag caggaggcag agtcttaaaa aagaccaccc ctatgagacc ttgctatgga 720
tcctatgcca aacctactaa tgccaatggc ggtcaaggga tcatggtggc caatgatcag 780
ggagcgcttg aatctaaagt tgagatgcaa tttttctcca ccacaacgtc tcttaatgta 840
agggaaggtg aaaacaatct tcagccaaaa gtagtgctat acagcgaaga tgttaacttg 900
gaatcccctg acactcattt gtcttacaaa cctaaaaagg atgacaccaa ctctaaaatc 960
atgttgggtc agcaagccat gcccaacaga cccaacctca ttgcttttag ggacaacttt 1020
attggactta tgtactacaa cagcacaggc aacatgggag tgctggcagg acaggcctcc 1080
cagctaaacg ctgtggtaga cttgcaagac agaaacacag agctgtcata ccaactgatg 1140
cttgattcca ttggagacag atcaagatac ttttccatgt ggaaccaggc agtggacagc 1200
tatgacccag atgtcagaat cattgaaaac catggggttg aagatgagct gcccaactat 1260
tgctttcccc tgggcggtat tggaattaca gacacatacc agtgcataaa accaaccgca 1320
gctgctaata acactacatg gtctaaggat gaagaattta gtgatcgcaa tgaaataggg 1380
gtgggaaaca acttcgccat ggagatcaac atccaggcca acctctggag gaacttcctc 1440
tatgcgaacg tggggctcta cctgccagac aagctcaagt acaaccccac caacgtggac 1500
atctctgaca accccaacac ctatgactac atgaacaagc gtgtggtggc tcccggcctg 1560
gtggactgct ttgtcaatgt gggagccagg tggtccctgg actacatgga caacgtcaac 1620
cccttcaacc accaccgcaa tgcgggtctg cgctaccgct ccatgatcct gggcaacggg 1680
cgctacgtgc ccttccacat tcaggtgccc cagaagttct ttgccatcaa gaacctcctc 1740
ctcctgccgg gctcctacac ttacgagtgg aacttcagga aggatgtcaa catggtcctg 1800
cagagctctc tgggcaatga ccttagggtg gacggggcca gcatcaagtt tgacagcgtc 1860
accctctatg ctaccttctt ccccatggct cacaacaccg cctccacgct cgaggccatg 1920
ctgaggaacg acaccaacga ccagtccttc aatgactacc tctctggggc caacatgctc 1980
taccccatcc ccgccaaggc caccaacgtg cccatctcca ttccctctcg caactgggcc 2040
gccttcagag gctgggcctt tacccgcctt aagaccaagg aaacccccctc cctgggctcg 2100 ggttttgacc cctactttgt ctactcggga tccatcccct acctggatgg caccttctac 2160
ctcaaccaca cttttaagaa gatatccatc atgtatgact cctccgtcag ctggccgggc 2220
aatgaccgcc tgctcacccc caatgagttc gaggtcaagc gcgccgtgga cggcgagggc 2280
tacaacgtgg cccagtgcaa catgaccaag gactggttcc tggtgcagat gctggccaac 2340
tacaacatag gctaccaggg cttctacatc ccagagagct acaaggacag gatgtactcc 2400
ttcttcagaa atttccaacc catgagcagg caggtggtgg acgagaccaa atacaaggac 2460
tatcaggcca ttggcatcac tcaccagcac aacaactcgg gattcgtggg ctacctggct 2520
cccaccatgc gcgaggggca ggcctacccc gccaacttcc cctacccgtt gataggcaaa 2580
accgcggtcg acagcgtcac ccagaaaaag ttcctctgcg accgcaccct ctggcgcatc 2640
cccttctcta gcaacttcat gtccatgggt gcgctcacgg acctgggcca gaacctgctc 2700
tatgccaact ccgcccatgc gctggacatg acttttgagg tggaccccat ggacgagccc 2760
acccttctct atattgtgtt tgaagtgttc gacgtggtca gagtgcacca gccgcaccgc 2820
ggtgtcatcg agaccgtgta cctgcgcacg cccttctcgg ccggcaacgc caccacc 2877

<210> SEQ ID NO 10
<211> LENGTH: 1749
<212> TYPE: DNA
<213> ORGANISM: Artificial sequence
<220> FEATURE:
<223> OTHER INFORMATION: Adenovirus fiber protein nucleotides

<400> SEQUENCE: 10
atgaaacgcg cgagatcgtc tgacgagacc ttcaaccccg tgtacccccta cgataccgag 60 atcgctccga cttctgtccc tttccttacc cctccctttg tgtcatccgc aggaatgcaa 120
gaaaatccag ctggggtgct gtccctgcac ttgtcagagc cccttaccac ccacaatggg 180
gccctgactc taaaaatggg gggcggcctg accctggaca aggaagggaa tctcacttcc 240
caaaacatca ccagtgtcga tccccctctc aaaaaaagca agaacaacat cagccttcag 300
accgccgcac ccctcgccgt cagctccggg gccctaacac tttttgccac tccccccccta 360 gcggtcagtg gtgacaacct tactgtgcag tctcaggccc ctctcacttt ggaagactca 420
aaactaactc tggccaccaa aggaccccta actgtgtccg aaggcaaact tgtcctagaa 480
acagaggctc ccctgcatgc aagtgacagc agcagcctgg gccttagcgt tacggcccca 540
cttagcatta acaatgacag cctaggacta gatctgcagg cacccattgt ctctcaaaat 600

-continued

```
ggaaaactgg ctctaaatgt agcaggcccc ctagctgtgg ccaatggcat taatgctttg      660
acagtaggca caggcaaagg tattggtcta aatgaaacca gcactcactt gcaagcaaag      720
ttggtcgccc ccctaggctt tgataccaat ggcaacatta agctaagcgt tgcaggaggc      780
atgagactaa ataatgacac acttatacta gatgtaaact acccatttga agctcaaggc      840
caactaagtc taagagtggg ccagggtccg ctgtatgtag attctagcag ccataacctg      900
accattagat gccttagagg attatacata acatcgtcta ataaccaaac cggtctagag      960
gccaacataa aactaacaaa aggccttgtc tatgatggaa atgccatagc agtcaatgtt     1020
ggtcaaggat tgcaatacag cactactgcc acatcggaag gtgtgtatcc tatacagtct     1080
aagataggtt tgggaatgga atatgatacc aacggagcca tgatgacaaa actaggctct     1140
ggactaagct ttgacaattc aggagccatt gtagtgggaa acaaaaatga tgacaggctt     1200
actctgtgga ctacaccaga cccatctcct aactgtagaa tttattctga aaaagatact     1260
aaactaacct tggtgctgac taagtgtggc agccaaatcc taggcacagt atctgccctt     1320
gctgtcagag gcagccttgc gcccatcact aatgcatcca gcatagtcca aatatttcta     1380
agatttgatg aaaatggact attgatgagc aactcatcgc tagacggtga ttactggaat     1440
tacagaaatg gggactccac taatagcaca ccatatacaa atgcagtagg ctttatgcct     1500
aatctagcag cctatcctaa aggtcaggct acagctgcaa aaagcagtat tgtaagccag     1560
gtatacatgg atggtgacac tactaaacct ataacactaa aaataaactt caatggcatt     1620
gatgaaacaa cagaaaatac ccctgttagt aaatattcca tgacattctc atggagctgg     1680
cccaccgcaa gctacatagg ccacactttt gcaacaaact cttttacttt ctcctacatc     1740
gcccaagaa                                                             1749
```

<210> SEQ ID NO 11
<211> LENGTH: 10
<212> TYPE: PRT
<213> ORGANISM: Artificial sequence
<220> FEATURE:
<223> OTHER INFORMATION: Adenovirus pIX protein fragment

<400> SEQUENCE: 11

Ser Ser Leu Val Ala Ser Gly Ala Ala Ser
1               5                   10

<210> SEQ ID NO 12
<211> LENGTH: 147
<212> TYPE: PRT
<213> ORGANISM: Artificial sequence
<220> FEATURE:
<223> OTHER INFORMATION: Adenovirus DNA polymerase fragment

<400> SEQUENCE: 12

Lys His Gln Tyr Leu Lys Val Met Val Arg Asp Thr Phe Ala Leu Thr
1               5                   10                  15

His Thr Ser Leu Arg Lys Ala Ala Gln Ala Tyr Ala Leu Pro Val Glu
            20                  25                  30

Lys Gly Cys Cys Pro Tyr Gln Ala Val Asn Gln Phe Tyr Met Leu Gly
        35                  40                  45

Ser Tyr Arg Ser Asp Thr Asp Gly Phe Pro Leu Gln Glu Tyr Trp Lys
    50                  55                  60

Asp Arg Glu Glu Phe Val Leu Asn Arg Glu Leu Trp Lys Lys Lys Gly
65                  70                  75                  80

Glu Asp Lys Tyr Asp Ile Ile Arg Glu Thr Leu Asp Tyr Cys Ala Leu

-continued

```
                85                  90                  95

Asp Val Gln Val Thr Ala Glu Leu Val His Lys Leu Arg Glu Ser Tyr
            100                 105                 110

Ala Ser Phe Val Arg Asp Ser Val Gly Leu Gln Glu Ala Ser Phe Asn
        115                 120                 125

Val Phe Gln Arg Pro Thr Ile Ser Ser Asn Ser His Ala Ile Phe Arg
    130                 135                 140

Gln Ile Ala
145


<210> SEQ ID NO 13
<211> LENGTH: 15
<212> TYPE: PRT
<213> ORGANISM: Artificial sequence
<220> FEATURE:
<223> OTHER INFORMATION: Adenovirus penton base protein fragment

<400> SEQUENCE: 13

Lys Thr Glu Ala Ala Ala Lys Ala Glu Val Glu Ala Asn Val Ala
1               5                   10                  15


<210> SEQ ID NO 14
<211> LENGTH: 15
<212> TYPE: PRT
<213> ORGANISM: Artificial sequence
<220> FEATURE:
<223> OTHER INFORMATION: Adenovirus hexon protein fragment

<400> SEQUENCE: 14

Ile Gly Val Asp Ala Thr Gln Ala Gly Asp Asn Pro Ile Tyr Ala
1               5                   10                  15


<210> SEQ ID NO 15
<211> LENGTH: 15
<212> TYPE: PRT
<213> ORGANISM: Artificial sequence
<220> FEATURE:
<223> OTHER INFORMATION: Adenovirus fiber protein fragment

<400> SEQUENCE: 15

Leu Asn Val Ala Gly Pro Leu Ala Val Ala Asn Gly Ile Asn Ala
1               5                   10                  15


<210> SEQ ID NO 16
<211> LENGTH: 133
<212> TYPE: PRT
<213> ORGANISM: Artificial sequence
<220> FEATURE:
<223> OTHER INFORMATION: Adenovirus pIX amino acids

<400> SEQUENCE: 16

Met Ser Asp Thr Gly Asn Ser Phe Asp Gly Ser Ile Phe Ser Pro Tyr
1               5                   10                  15

Leu Thr Val Arg Met Pro His Trp Ala Gly Val Arg Gln Asn Val Met
            20                  25                  30

Gly Ser Asn Val Asp Gly Arg Pro Val Leu Pro Ser Asn Ser Ser Thr
        35                  40                  45

Met Ala Tyr Ala Thr Val Gly Gly Thr Pro Leu Asp Ala Ala Thr Ser
    50                  55                  60

Ala Ala Ala Ser Ala Ala Ala Ala Thr Ala Arg Ser Met Ala Thr Asp
65                  70                  75                  80

Leu Tyr Ser Ser Leu Val Ala Ser Gly Ala Ala Ser Arg Ala Ser Ala
```

-continued

```
                85                  90                  95

Arg Asp Glu Lys Leu Thr Ala Leu Leu Leu Lys Leu Glu Asp Leu Thr
            100                 105                 110

Arg Glu Leu Gly Gln Leu Thr Gln Gln Val Ser Ser Leu Arg Glu Ser
        115                 120                 125

Ser Leu Ala Ser Pro
    130


<210> SEQ ID NO 17
<211> LENGTH: 1056
<212> TYPE: PRT
<213> ORGANISM: Artificial sequence
<220> FEATURE:
<223> OTHER INFORMATION: Adenovirus DNA polymerase amino acids

<400> SEQUENCE: 17

Met Asp Ser Ser Asn Val Arg Asp Val Val Ile Lys Leu Arg Pro Pro
1               5                   10                  15

Ser Ala Glu Ile Trp Thr Cys Gly Ser Arg Gly Val Val Val Cys Ser
            20                  25                  30

Thr Ile Ala Leu Gln Glu Thr Asp Ala Gly Gly Gln Thr Thr Lys Val
        35                  40                  45

Glu Asp His Gln Pro His Gly Thr Pro Gly Gly Gly Leu Arg Phe Pro
    50                  55                  60

Leu Arg Phe Leu Val Arg Gly Arg Gln Val His Leu Val Gln Asp Ile
65                  70                  75                  80

Gln Pro Val Gln Arg Cys Gln Tyr Cys Gly Arg Phe Tyr Lys Ser Gln
                85                  90                  95

His Glu Cys Ser Ala Arg Arg Arg Asp Phe Tyr Phe His His Ile Asn
            100                 105                 110

Ser Gln Ser Ser Asn Trp Trp Arg Glu Ile Gln Phe Phe Pro Ile Gly
        115                 120                 125

Ser His Pro Arg Thr Glu Arg Leu Phe Val Thr Tyr Asp Val Glu Thr
    130                 135                 140

Tyr Thr Trp Met Gly Ala Phe Gly Lys Gln Leu Val Pro Phe Met Leu
145                 150                 155                 160

Val Met Lys Leu Gly Gly Asp Glu Ala Leu Val Ala Ala Ala Arg Asp
                165                 170                 175

Leu Ala Arg Glu Leu Arg Trp Asp Pro Trp Glu Lys Asp Pro Leu Thr
            180                 185                 190

Phe Tyr Cys Ile Thr Pro Glu Lys Met Ala Val Gly Arg Gln Phe Arg
        195                 200                 205

Thr Phe Arg Asp Arg Leu Gln Thr Leu Met Ala Arg Asp Leu Trp Arg
    210                 215                 220

Ser Phe Leu Ala Ala Asn Pro His Leu Gln Asp Trp Ala Leu Glu Glu
225                 230                 235                 240

His Gly Leu Glu Ser Pro Glu Glu Leu Thr Tyr Glu Glu Leu Lys Lys
                245                 250                 255

Leu Pro Ser Ile Lys Gly Gln Pro Arg Phe Leu Glu Leu Tyr Ile Val
            260                 265                 270

Gly His Asn Ile Asn Gly Phe Asp Glu Ile Val Leu Ala Ala Gln Val
        275                 280                 285

Ile Asn Asn Arg Ser Ser Val Pro Gly Pro Phe Arg Ile Thr Arg Asn
    290                 295                 300

Phe Met Pro Arg Ala Gly Lys Ile Leu Phe Asn Asp Leu Thr Phe Ser
```

-continued

```
305                 310                 315                 320

Leu Pro Asn Pro Arg Ser Lys Lys Arg Thr Asp Tyr Thr Leu Trp Glu
                325                 330                 335

Gln Gly Gly Cys Asp Asp Thr Asp Phe Lys His Gln Tyr Leu Lys Val
            340                 345                 350

Met Val Arg Asp Thr Phe Ala Leu Thr His Thr Ser Leu Arg Lys Ala
        355                 360                 365

Ala Gln Ala Tyr Ala Leu Pro Val Glu Lys Gly Cys Cys Pro Tyr Gln
    370                 375                 380

Ala Val Asn Gln Phe Tyr Met Leu Gly Ser Tyr Arg Ser Asp Thr Asp
385                 390                 395                 400

Gly Phe Pro Leu Gln Glu Tyr Trp Lys Asp Arg Glu Glu Phe Val Leu
                405                 410                 415

Asn Arg Glu Leu Trp Lys Lys Lys Gly Glu Asp Lys Tyr Asp Ile Ile
            420                 425                 430

Arg Glu Thr Leu Asp Tyr Cys Ala Leu Asp Val Gln Val Thr Ala Glu
        435                 440                 445

Leu Val His Lys Leu Arg Glu Ser Tyr Ala Ser Phe Val Arg Asp Ser
    450                 455                 460

Val Gly Leu Gln Glu Ala Ser Phe Asn Val Phe Gln Arg Pro Thr Ile
465                 470                 475                 480

Ser Ser Asn Ser His Ala Ile Phe Arg Gln Ile Ala Phe Arg Ala Glu
                485                 490                 495

Arg Pro Gln Arg Thr Asn Leu Gly Pro Asn Met Leu Ala Pro Ser His
            500                 505                 510

Glu Leu Tyr Asp Tyr Val Arg Ala Ser Ile Arg Gly Gly Arg Cys Tyr
        515                 520                 525

Pro Thr Tyr Leu Gly Ile Leu Arg Glu Pro Leu Tyr Val Tyr Asp Ile
    530                 535                 540

Cys Gly Met Tyr Ala Ser Ala Leu Thr His Pro Met Pro Trp Gly Pro
545                 550                 555                 560

Pro Leu Asn Pro Tyr Glu Arg Ala Leu Ala Ala Arg Glu Trp Gln Arg
                565                 570                 575

Ala Leu Asp Met Gln Ala Cys Lys Ile Asp Tyr Phe Asp Pro Arg Leu
            580                 585                 590

Leu Pro Gly Val Phe Thr Ile Asp Ala Asp Pro Pro Asn Glu Asp Gln
        595                 600                 605

Leu Asp Pro Leu Pro Pro Phe Cys Ser Arg Lys Gly Gly Arg Leu Cys
    610                 615                 620

Trp Thr Asn Glu Arg Leu Arg Gly Glu Val Ala Thr Ser Val Asp Met
625                 630                 635                 640

Val Thr Leu His Asn Arg Gly Trp Arg Val Arg Leu Ile Pro Asp Glu
                645                 650                 655

Arg Thr Thr Val Phe Pro Glu Trp Lys Cys Val Ala Arg Glu Tyr Val
            660                 665                 670

Gln Leu Asn Ile Ala Ala Lys Glu Arg Ala Asp Arg Asp Lys Asn Gln
        675                 680                 685

Thr Leu Arg Ser Ile Ala Lys Leu Leu Ser Asn Ala Leu Tyr Gly Ser
    690                 695                 700

Phe Ala Thr Lys Leu Asp Asn Lys Lys Ile Val Phe Ser Asp Gln Met
705                 710                 715                 720

Asp Pro Gly Thr Leu Lys Gly Ile Thr Ser Gly Gln Val Asn Ile Lys
                725                 730                 735
```

Ser Ser Ser Phe Leu Glu Thr Asp Asn Leu Ser Ala Glu Val Met Pro
740 745 750

Ala Phe Glu Arg Glu Tyr Leu Pro Gln Gln Leu Ala Leu Ala Asp Ser
755 760 765

Asp Ala Glu Glu Ser Glu Asp Glu Arg Ala Pro Thr Pro Phe Tyr Thr
770 775 780

Pro Pro Ser Gly Thr Pro Gly His Val Ser Tyr Thr Tyr Lys Pro Ile
785 790 795 800

Thr Phe Leu Asp Ala Glu Glu Gly Asp Met Cys Leu His Thr Leu Glu
805 810 815

Lys Val Asp Pro Leu Val Asp Asn Asp Arg Tyr Pro Ser His Val Ala
820 825 830

Ser Phe Val Leu Ala Trp Thr Arg Ala Phe Val Ser Glu Trp Ser Glu
835 840 845

Phe Leu Tyr Glu Glu Asp Arg Gly Thr Pro Leu Glu Asp Arg Pro Leu
850 855 860

Lys Ser Val Tyr Gly Asp Thr Asp Ser Leu Phe Val Thr Glu Lys Gly
865 870 875 880

His Arg Leu Met Glu Ser Arg Gly Lys Lys Arg Ile Lys Lys His Gly
885 890 895

Gly Asn Leu Val Phe Asp Pro Asp Arg Pro Glu Leu Thr Trp Leu Val
900 905 910

Glu Cys Glu Thr Val Cys Ala Ser Cys Gly Ala Asp Ala Tyr Ser Pro
915 920 925

Glu Ser Val Phe Leu Ala Pro Lys Leu Tyr Ala Leu Lys Ser Leu Gln
930 935 940

Cys Pro Ser Cys Gly Ala Thr Ser Lys Gly Lys Leu Arg Ala Lys Gly
945 950 955 960

His Ala Ala Glu Gly Leu Asp Tyr Glu Thr Met Val Lys Cys Tyr Leu
965 970 975

Ala Asp Ala Gln Gly Glu Glu Arg Gln Arg Phe Ser Thr Ser Arg Thr
980 985 990

Ser Leu Lys Arg Thr Leu Ala Ser Ala Gln Pro Gly Ala His Pro Phe
995 1000 1005

Thr Val Thr Gln Thr Thr Leu Thr Arg Thr Leu Arg Pro Trp Lys
1010 1015 1020

Asp Met Thr Leu Ala Pro Leu Asp Ala His Arg Leu Val Pro Tyr
1025 1030 1035

Ser Glu Ser Arg Pro Asn Pro Arg Asn Glu Glu Ile Cys Trp Ile
1040 1045 1050

Glu Met Pro
1055

<210> SEQ ID NO 18
<211> LENGTH: 658
<212> TYPE: PRT
<213> ORGANISM: Artificial sequence
<220> FEATURE:
<223> OTHER INFORMATION: Adenovirus penton base protein

<400> SEQUENCE: 18

Met Arg Arg Ala Ala Met Phe Glu Glu Gly Pro Pro Pro Ser Tyr Glu
1 5 10 15

Ser Ala Met Gly Ile Ser Pro Ala Ala Pro Leu Gln Pro Pro Tyr Val
20 25 30

-continued

```
Pro Pro Arg Tyr Leu Gln Pro Thr Gly Gly Arg Asn Ser Ile Cys Tyr
        35                  40                  45

Ser Glu Leu Gln Pro Leu Tyr Asp Thr Thr Arg Leu Tyr Leu Val Asp
    50                  55                  60

Asn Lys Ser Ala Asp Val Ala Ser Leu Asn Tyr Gln Asn Asp His Ser
65                  70                  75                  80

Asp Phe Leu Thr Thr Val Ile Gln Asn Asn Asp Phe Thr Pro Thr Glu
                85                  90                  95

Ala Ser Thr Gln Thr Ile Asn Leu Asp Asn Arg Ser Asn Trp Gly Gly
            100                 105                 110

Asp Leu Lys Thr Ile Leu His Thr Asn Met Pro Asn Val Asn Glu Phe
        115                 120                 125

Met Phe Thr Asn Ser Phe Lys Ala Arg Val Met Val Ala Arg Glu Gln
    130                 135                 140

Gly Glu Ala Lys Tyr Glu Trp Val Asp Phe Thr Leu Pro Glu Gly Asn
145                 150                 155                 160

Tyr Ser Glu Thr Met Thr Leu Asp Leu Met Asn Asn Ala Ile Val Glu
                165                 170                 175

His Tyr Leu Lys Val Gly Arg Gln Asn Gly Val Lys Glu Ser Asp Ile
            180                 185                 190

Gly Val Lys Phe Asp Thr Arg Asn Phe Arg Leu Gly Trp Asp Pro Val
        195                 200                 205

Thr Gly Leu Val Met Pro Gly Val Tyr Thr Asn Glu Ala Phe His Pro
    210                 215                 220

Asp Ile Val Leu Leu Pro Gly Cys Gly Val Asp Phe Thr Gln Ser Arg
225                 230                 235                 240

Leu Ser Asn Leu Leu Gly Ile Arg Lys Arg Gln Pro Phe Gln Glu Gly
                245                 250                 255

Phe Lys Ile Thr Tyr Glu Asp Leu Lys Gly Gly Asn Ile Pro Ala Leu
            260                 265                 270

Leu Asp Leu Asp Ala Tyr Glu Glu Ser Leu Lys Pro Glu Glu Ser Ala
        275                 280                 285

Gly Asp Ser Gly Glu Ser Gly Glu Glu Gln Ala Gly Gly Gly Gly Gly
    290                 295                 300

Ala Ser Val Glu Asn Glu Ser Thr Pro Ala Val Ala Ala Asp Ala Ala
305                 310                 315                 320

Glu Val Glu Pro Glu Ala Met Gln Gln Asp Ala Glu Glu Gly Ala Gln
                325                 330                 335

Glu Gly Ala Gln Lys Asp Met Asn Asp Gly Glu Ile Arg Gly Asp Thr
            340                 345                 350

Phe Ala Thr Arg Gly Glu Glu Lys Glu Ala Glu Ala Ala Ala Ala Ala
        355                 360                 365

Thr Ala Glu Ala Glu Thr Glu Val Glu Ala Glu Ala Glu Pro Glu Thr
    370                 375                 380

Glu Val Met Glu Asp Met Asn Asp Gly Glu Arg Arg Gly Asp Thr Phe
385                 390                 395                 400

Ala Thr Arg Gly Glu Glu Lys Ala Ala Glu Ala Glu Ala Ala Ala Glu
                405                 410                 415

Glu Ala Ala Ala Ala Ala Ala Lys Thr Glu Ala Ala Ala Lys Ala Glu
            420                 425                 430

Val Glu Ala Asn Val Ala Val Glu Ala Gln Ala Glu Glu Glu Ala Ala
        435                 440                 445
```

```
Ala Glu Ala Val Lys Glu Lys Ala Gln Ala Glu Gln Glu Glu Lys Lys
    450                 455                 460

Pro Val Ile Gln Pro Leu Lys Glu Asp Ser Lys Lys Arg Ser Tyr Asn
465                 470                 475                 480

Val Ile Glu Gly Ser Thr Phe Thr Gln Tyr Arg Ser Trp Tyr Leu Ala
                485                 490                 495

Tyr Asn Tyr Gly Asp Pro Val Lys Gly Val Arg Ser Trp Thr Leu Leu
            500                 505                 510

Cys Thr Pro Asp Val Thr Cys Gly Ser Glu Gln Met Tyr Trp Ser Leu
        515                 520                 525

Pro Asn Met Met Gln Asp Pro Val Thr Phe Arg Ser Thr Arg Gln Val
    530                 535                 540

Ser Asn Phe Pro Val Val Gly Ala Glu Leu Leu Pro Val His Ser Lys
545                 550                 555                 560

Ser Phe Tyr Asn Glu Gln Ala Val Tyr Ser Gln Leu Ile Arg Gln Ala
                565                 570                 575

Thr Ser Leu Thr His Val Phe Asn Arg Phe Pro Glu Asn Gln Ile Leu
            580                 585                 590

Ala Arg Pro Pro Ala Pro Thr Ile Thr Thr Val Ser Glu Asn Val Pro
        595                 600                 605

Ala Leu Thr Asp His Gly Thr Leu Pro Leu Arg Asn Ser Ile Ser Gly
    610                 615                 620

Val Gln Arg Val Thr Ile Thr Asp Ala Arg Arg Arg Thr Cys Pro Tyr
625                 630                 635                 640

Val Tyr Lys Ala Leu Gly Ile Val Ser Pro Arg Val Leu Ser Ser Arg
                645                 650                 655

Thr Phe


<210> SEQ ID NO 19
<211> LENGTH: 959
<212> TYPE: PRT
<213> ORGANISM: Artificial sequence
<220> FEATURE:
<223> OTHER INFORMATION: Adenovirus hexon protein

<400> SEQUENCE: 19

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Asn Met Ser Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ser Leu Ala Pro Lys Gly
        115                 120                 125

Ala Pro Asn Ser Cys Glu Trp Glu Gln Asp Glu Pro Ala Gln Ala Ala
    130                 135                 140

Ile Ala Glu Asp Glu Glu Glu Leu Glu Glu Glu Gln Ala Gln Asp Glu
```

-continued

```
145                 150                 155                 160

Gln Ala Pro Thr Lys Lys Thr His Val Tyr Ala Gln Ala Pro Leu Ser
                165                 170                 175

Gly Glu Lys Ile Thr Lys Asp Gly Leu Gln Ile Gly Val Asp Ala Thr
            180                 185                 190

Gln Ala Gly Asp Asn Pro Ile Tyr Ala Asp Lys Thr Phe Gln Pro Glu
        195                 200                 205

Pro Gln Ile Gly Glu Ser Gln Trp Asn Glu Ala Asp Ala Thr Val Ala
    210                 215                 220

Gly Gly Arg Val Leu Lys Lys Thr Thr Pro Met Arg Pro Cys Tyr Gly
225                 230                 235                 240

Ser Tyr Ala Lys Pro Thr Asn Ala Asn Gly Gly Gln Gly Ile Met Val
                245                 250                 255

Ala Asn Asp Gln Gly Ala Leu Glu Ser Lys Val Glu Met Gln Phe Phe
            260                 265                 270

Ser Thr Thr Thr Ser Leu Asn Val Arg Glu Gly Glu Asn Asn Leu Gln
        275                 280                 285

Pro Lys Val Val Leu Tyr Ser Glu Asp Val Asn Leu Glu Ser Pro Asp
    290                 295                 300

Thr His Leu Ser Tyr Lys Pro Lys Lys Asp Asp Thr Asn Ser Lys Ile
305                 310                 315                 320

Met Leu Gly Gln Gln Ala Met Pro Asn Arg Pro Asn Leu Ile Ala Phe
                325                 330                 335

Arg Asp Asn Phe Ile Gly Leu Met Tyr Tyr Asn Ser Thr Gly Asn Met
            340                 345                 350

Gly Val Leu Ala Gly Gln Ala Ser Gln Leu Asn Ala Val Val Asp Leu
        355                 360                 365

Gln Asp Arg Asn Thr Glu Leu Ser Tyr Gln Leu Met Leu Asp Ser Ile
    370                 375                 380

Gly Asp Arg Ser Arg Tyr Phe Ser Met Trp Asn Gln Ala Val Asp Ser
385                 390                 395                 400

Tyr Asp Pro Asp Val Arg Ile Ile Glu Asn His Gly Val Glu Asp Glu
                405                 410                 415

Leu Pro Asn Tyr Cys Phe Pro Leu Gly Gly Ile Gly Ile Thr Asp Thr
            420                 425                 430

Tyr Gln Cys Ile Lys Pro Thr Ala Ala Ala Asn Asn Thr Thr Trp Ser
        435                 440                 445

Lys Asp Glu Glu Phe Ser Asp Arg Asn Glu Ile Gly Val Gly Asn Asn
    450                 455                 460

Phe Ala Met Glu Ile Asn Ile Gln Ala Asn Leu Trp Arg Asn Phe Leu
465                 470                 475                 480

Tyr Ala Asn Val Gly Leu Tyr Leu Pro Asp Lys Leu Lys Tyr Asn Pro
                485                 490                 495

Thr Asn Val Asp Ile Ser Asp Asn Pro Asn Thr Tyr Asp Tyr Met Asn
            500                 505                 510

Lys Arg Val Val Ala Pro Gly Leu Val Asp Cys Phe Val Asn Val Gly
        515                 520                 525

Ala Arg Trp Ser Leu Asp Tyr Met Asp Asn Val Asn Pro Phe Asn His
    530                 535                 540

His Arg Asn Ala Gly Leu Arg Tyr Arg Ser Met Ile Leu Gly Asn Gly
545                 550                 555                 560

Arg Tyr Val Pro Phe His Ile Gln Val Pro Gln Lys Phe Phe Ala Ile
                565                 570                 575
```

```
Lys Asn Leu Leu Leu Leu Pro Gly Ser Tyr Thr Tyr Glu Trp Asn Phe
            580                 585                 590

Arg Lys Asp Val Asn Met Val Leu Gln Ser Ser Leu Gly Asn Asp Leu
        595                 600                 605

Arg Val Asp Gly Ala Ser Ile Lys Phe Asp Ser Val Thr Leu Tyr Ala
    610                 615                 620

Thr Phe Phe Pro Met Ala His Asn Thr Ala Ser Thr Leu Glu Ala Met
625                 630                 635                 640

Leu Arg Asn Asp Thr Asn Asp Gln Ser Phe Asn Asp Tyr Leu Ser Gly
                645                 650                 655

Ala Asn Met Leu Tyr Pro Ile Pro Ala Lys Ala Thr Asn Val Pro Ile
            660                 665                 670

Ser Ile Pro Ser Arg Asn Trp Ala Ala Phe Arg Gly Trp Ala Phe Thr
        675                 680                 685

Arg Leu Lys Thr Lys Glu Thr Pro Ser Leu Gly Ser Gly Phe Asp Pro
    690                 695                 700

Tyr Phe Val Tyr Ser Gly Ser Ile Pro Tyr Leu Asp Gly Thr Phe Tyr
705                 710                 715                 720

Leu Asn His Thr Phe Lys Lys Ile Ser Ile Met Tyr Asp Ser Ser Val
                725                 730                 735

Ser Trp Pro Gly Asn Asp Arg Leu Leu Thr Pro Asn Glu Phe Glu Val
            740                 745                 750

Lys Arg Ala Val Asp Gly Glu Gly Tyr Asn Val Ala Gln Cys Asn Met
        755                 760                 765

Thr Lys Asp Trp Phe Leu Val Gln Met Leu Ala Asn Tyr Asn Ile Gly
    770                 775                 780

Tyr Gln Gly Phe Tyr Ile Pro Glu Ser Tyr Lys Asp Arg Met Tyr Ser
785                 790                 795                 800

Phe Phe Arg Asn Phe Gln Pro Met Ser Arg Gln Val Val Asp Glu Thr
                805                 810                 815

Lys Tyr Lys Asp Tyr Gln Ala Ile Gly Ile Thr His Gln His Asn Asn
            820                 825                 830

Ser Gly Phe Val Gly Tyr Leu Ala Pro Thr Met Arg Glu Gly Gln Ala
        835                 840                 845

Tyr Pro Ala Asn Phe Pro Tyr Pro Leu Ile Gly Lys Thr Ala Val Asp
    850                 855                 860

Ser Val Thr Gln Lys Lys Phe Leu Cys Asp Arg Thr Leu Trp Arg Ile
865                 870                 875                 880

Pro Phe Ser Ser Asn Phe Met Ser Met Gly Ala Leu Thr Asp Leu Gly
                885                 890                 895

Gln Asn Leu Leu Tyr Ala Asn Ser Ala His Ala Leu Asp Met Thr Phe
            900                 905                 910

Glu Val Asp Pro Met Asp Glu Pro Thr Leu Leu Tyr Ile Val Phe Glu
        915                 920                 925

Val Phe Asp Val Val Arg Val His Gln Pro His Arg Gly Val Ile Glu
    930                 935                 940

Thr Val Tyr Leu Arg Thr Pro Phe Ser Ala Gly Asn Ala Thr Thr
945                 950                 955
```

<210> SEQ ID NO 20
<211> LENGTH: 583
<212> TYPE: PRT
<213> ORGANISM: Artificial sequence
<220> FEATURE:

<223> OTHER INFORMATION: Adenovirus fiber protein

<400> SEQUENCE: 20

Met Lys Arg Ala Arg Ser Ser Asp Glu Thr Phe Asn Pro Val Tyr Pro
1 5 10 15

Tyr Asp Thr Glu Ile Ala Pro Thr Ser Val Pro Phe Leu Thr Pro Pro
20 25 30

Phe Val Ser Ser Ala Gly Met Gln Glu Asn Pro Ala Gly Val Leu Ser
35 40 45

Leu His Leu Ser Glu Pro Leu Thr Thr His Asn Gly Ala Leu Thr Leu
50 55 60

Lys Met Gly Gly Gly Leu Thr Leu Asp Lys Glu Gly Asn Leu Thr Ser
65 70 75 80

Gln Asn Ile Thr Ser Val Asp Pro Pro Leu Lys Lys Ser Lys Asn Asn
85 90 95

Ile Ser Leu Gln Thr Ala Ala Pro Leu Ala Val Ser Ser Gly Ala Leu
100 105 110

Thr Leu Phe Ala Thr Pro Pro Leu Ala Val Ser Gly Asp Asn Leu Thr
115 120 125

Val Gln Ser Gln Ala Pro Leu Thr Leu Glu Asp Ser Lys Leu Thr Leu
130 135 140

Ala Thr Lys Gly Pro Leu Thr Val Ser Glu Gly Lys Leu Val Leu Glu
145 150 155 160

Thr Glu Ala Pro Leu His Ala Ser Asp Ser Ser Ser Leu Gly Leu Ser
165 170 175

Val Thr Ala Pro Leu Ser Ile Asn Asn Asp Ser Leu Gly Leu Asp Leu
180 185 190

Gln Ala Pro Ile Val Ser Gln Asn Gly Lys Leu Ala Leu Asn Val Ala
195 200 205

Gly Pro Leu Ala Val Ala Asn Gly Ile Asn Ala Leu Thr Val Gly Thr
210 215 220

Gly Lys Gly Ile Gly Leu Asn Glu Thr Ser Thr His Leu Gln Ala Lys
225 230 235 240

Leu Val Ala Pro Leu Gly Phe Asp Thr Asn Gly Asn Ile Lys Leu Ser
245 250 255

Val Ala Gly Gly Met Arg Leu Asn Asn Asp Thr Leu Ile Leu Asp Val
260 265 270

Asn Tyr Pro Phe Glu Ala Gln Gly Gln Leu Ser Leu Arg Val Gly Gln
275 280 285

Gly Pro Leu Tyr Val Asp Ser Ser Ser His Asn Leu Thr Ile Arg Cys
290 295 300

Leu Arg Gly Leu Tyr Ile Thr Ser Ser Asn Asn Gln Thr Gly Leu Glu
305 310 315 320

Ala Asn Ile Lys Leu Thr Lys Gly Leu Val Tyr Asp Gly Asn Ala Ile
325 330 335

Ala Val Asn Val Gly Gln Gly Leu Gln Tyr Ser Thr Thr Ala Thr Ser
340 345 350

Glu Gly Val Tyr Pro Ile Gln Ser Lys Ile Gly Leu Gly Met Glu Tyr
355 360 365

Asp Thr Asn Gly Ala Met Met Thr Lys Leu Gly Ser Gly Leu Ser Phe
370 375 380

Asp Asn Ser Gly Ala Ile Val Val Gly Asn Lys Asn Asp Asp Arg Leu
385 390 395 400

```
Thr Leu Trp Thr Thr Pro Asp Pro Ser Pro Asn Cys Arg Ile Tyr Ser
                405                 410                 415

Glu Lys Asp Thr Lys Leu Thr Leu Val Leu Thr Lys Cys Gly Ser Gln
            420                 425                 430

Ile Leu Gly Thr Val Ser Ala Leu Ala Val Arg Gly Ser Leu Ala Pro
        435                 440                 445

Ile Thr Asn Ala Ser Ser Ile Val Gln Ile Phe Leu Arg Phe Asp Glu
    450                 455                 460

Asn Gly Leu Leu Met Ser Asn Ser Ser Leu Asp Gly Asp Tyr Trp Asn
465                 470                 475                 480

Tyr Arg Asn Gly Asp Ser Thr Asn Ser Thr Pro Tyr Thr Asn Ala Val
                485                 490                 495

Gly Phe Met Pro Asn Leu Ala Ala Tyr Pro Lys Gly Gln Ala Thr Ala
            500                 505                 510

Ala Lys Ser Ser Ile Val Ser Gln Val Tyr Met Asp Gly Asp Thr Thr
        515                 520                 525

Lys Pro Ile Thr Leu Lys Ile Asn Phe Asn Gly Ile Asp Glu Thr Thr
    530                 535                 540

Glu Asn Thr Pro Val Ser Lys Tyr Ser Met Thr Phe Ser Trp Ser Trp
545                 550                 555                 560

Pro Thr Ala Ser Tyr Ile Gly His Thr Phe Ala Thr Asn Ser Phe Thr
                565                 570                 575

Phe Ser Tyr Ile Ala Gln Glu
            580
```

<210> SEQ ID NO 21
<211> LENGTH: 32728
<212> TYPE: DNA
<213> ORGANISM: Artificial sequence
<220> FEATURE:
<223> OTHER INFORMATION: Adenovirus vector nucleotide sequences

<400> SEQUENCE: 21

```
catcatcaat aatatacctt attttggatt gtggccaata tgataatgag gtgggcgggg     60

agaggcgggg cgggtgacgt aggacgcgcg agtagggttg ggaggtgtgg cggaagtgtg    120

gcatttgcaa gtgggaggag ctcacatgca agcttccgtc gcggaaaatg tgacgttttt    180

gatgagcgcc gcctacctcc ggaagtgcca attttcgcgc gcttttcacc ggatatcgta    240

gtaattttgg gcgggaccat gtaagatttg gccattttcg cgcgaaaagt gaaacgggga    300

agtgaaaact gaataatagg gcgttagtca tagcgcgtaa tatttaccga gggccgaggg    360

actttgaccg attacgtgga ggactcgccc aggtgttttt tacgtgaatt tccgcgttcc    420

gggtcaaagt ctccgttttt attgtcaccg tcatttgacg cggagggtat ttaaacccgc    480

tgcgctcctc aagaggccac tcttgagtgc cagcgagaag agttttctcc tctgctccgc    540

ttcggtgatc gaaaaatgag acacatagcc tgcactccgg gtcttttgtc cggtcgggcg    600

gcggccgagc ttttggacgc tttgatcaat gatgtcctaa gcgatgattt tccgtctact    660

acccacttta gcccacctac tcttcacgaa ctgtacgatc tggatgtact ggtggatgtg    720

aacgatccca acgaggaggc ggtttctgcg ttttttcccg agtctgcgct gttggccgct    780

caggagggat ttgacctaca cactccgccg cctattttag agtctccgct gccggagccc    840

agtggtatac cttatatgcc tgaactgctt cccgaagtgg tagacctgac ctgccacgag    900

cctggctttc cgcccagcga cgatgagggt gagccttttg ttttagactt tgctgagata    960

cctgggcacg gttgcaggtc ttgtgcatat catcagaggg ttaccggaga ccccgaggtt   1020
```

-continued

```
aagtgttcgc tgtgctatat gaggatgacc tcttccttta tctacagtaa gtttttgtct   1080
aggtgggctt ttgggtaggt gggttttgtg tcagaacagg tgtaaacgtt gcttgtgttt   1140
tttgtacctg taggtccggt gtccgagcca gacccggagc ccgaccgcga tcccgagccg   1200
gatcccgagc ctcctcgcag gacaaggaaa ctaccttcca ttctgtgcaa gtctcagaca   1260
cctgtaagga ccagcgaggc agacagcacc gactctggca cttctacctc tccccctgaa   1320
attcacccag tggttcctct gggtatacat aaacctgttg ctgttaaagt ttgcgggcga   1380
cgccctgcag tacagtgcat tgaggacttg cttcacgatc ccgaggaacc tttggacttg   1440
agccttaaac gccctaggca ataaacccca cctaagtaat aaaccccacc taagtaataa   1500
accctgccgc ccttggttat tgagatgacg cccaatgttt gcttttgaat gacttcatgt   1560
gtgtaataaa agtgagtgtg atcataggtc tcttgtttgt ctgggcgggg cttaagggta   1620
tataagtctc ttggggctaa acttggttac acttgacccc aatggaggcg tgggggtgct   1680
tggaggagtt tgcggacgtg cgccgtttgc tggacgagag ctctagcaat acctatacta   1740
tttggaggta tctgtggggc tctactcagg ccaagttggt ttccagaatt aagcaggatt   1800
acaagtgcga ttttgaagag ctttttagtt cctgcggtga gcttttgcaa tccttgaatc   1860
tgggccatca ggctattttc caggaaaagg ttctctcgac tttggatttt tccactcccg   1920
ggcgcaccgc cgcttgtgtg gcttttgtgt cttttgtgca agataaatgg agcgaggaga   1980
cccacctgag tcacggctac gtactggatt tcatggcgat ggctctttgg agggctcaca   2040
acaaatggaa gattcagaag gaactgtacg gttccgccct acgtcgtcca cttctgtcgc   2100
gacaggggct gaggtttccc gaccatcggc agcatcagaa tctggaagac gagtcggagg   2160
agcgagcgga ggagaagatc agcttgagag ccggcctgga ccctcctcag gaggaatgaa   2220
tctcccgcag gtggttgacc tgtttccaga actgagacgg gtcctgacta tcagggagga   2280
tggtcagttt gtgaagaagt ttaagaggga tcggggtgag ggagatgatg aggcggctag   2340
caatttagct tttagtctga tgactcgcca ccgaccggaa tgtattacct atcagcagat   2400
taaggagagt tgtgccaacg agctggatct tttgggtcag aagtatagca tagaacagct   2460
taccacttac tggcttcagc ctggggatga ttgggaagag gcgatcaggg tgtatgcaaa   2520
ggtggccctg cggcccgatt gcaagtataa gattactaag ttggttaata ttagaaactg   2580
ctgctatatt tctgggaacg gggccgaagt ggagatagat actcaggaca gggtggcttt   2640
taggtgttgc atgataaaca tgtggcccgg gatactgggg atggatgggg tggtattcat   2700
gaatgtgagg tttacgggcc ccaactttaa tggcacggtg ttcatgggca acaccaactt   2760
gctcctgcat ggtgcgagtt tctatgggtt taataacacc tgtatagagg cctggaccga   2820
tgtaaaggtt cgaggttgtt ccttttatag ctgttggaag gcggtggtgt gtcgccctaa   2880
aagcaggggt tctgtgaaaa aatgcttgtt tgaaaggtgc accttaggca tcctctctga   2940
gggcaactcc agggtgcgcc ataatgtggc ttcgaactgc ggttgcttca tgcaagtgaa   3000
gggggtgagc gttatcaagc ataactcggt gtgtggaaac tgcgaggatc gcgcctccca   3060
gatgctgacc tgctttgatg gcaactgtca cctgttgaag accattcata taagcagcca   3120
ccccagaaag gcctggcccg tgtttgagca taacatcttg acccgctgct ccttgcatct   3180
gggggtcagg aggggtatgt tcctgcctta ccagtgtaac tttagccaca ctaaaatcct   3240
gctggaaccc gagtgcatga ccaaggtcag cctgaatggt gtgtttgatg tgactctgaa   3300
aatctggaag gtgctgaggt atgatgagac caggaccagg tgccgaccct gcgagtgcgg   3360
```

-continued

```
cggcaagcac atgagaaatc agcctgtgat gttggatgtg accgaggagc ttaggcctga   3420
ccatctggtg ctggcctgca ccagggccga gtttgggtct agcgatgagg ataccgattg   3480
aggtgggtaa ggtgggcgtg gctagaaggg tggggcgtgt ataaattggg ggtctaaggg   3540
tctctctgtt ttgtcttgca acagccgccg ccatgagcga caccggcaac agctttgatg   3600
gaagcatctt tagcccctat ctgacagtgc gcatgcctca ctgggctgga gtgcgtcaga   3660
atgtgatggg ttccaacgtg gatggacgcc ccgttctgcc ttcaaattcg tctacaatgg   3720
cctacgcgac cgtgggagga actccgctgg acgccgcgac ctccgccgcc gcctccgccg   3780
ccgccgcgac cgcgcgcagc atggctacgg acctttacag ctctttggtg gcgagcggcg   3840
cggcctctcg cgcgtctgct cgggatgaga aactgaccgc tctgctgctt aaactggaag   3900
acttgacccg ggagctgggt caactgaccc agcaggtctc cagcttgcgt gagagcagcc   3960
ttgcctcccc ctaatggccc ataatataaa taaaagccag tctgtttgga ttaagcaagt   4020
gtatgttctt tatttaactc tccgcgcgcg gtaagcccgg gaccagcggt ctcggtcgtt   4080
tagggtgcgg tggattcttt ccaacacgtg gtacaggtgg ctctggatgt ttagatacat   4140
gggcatgagt ccatccctgg ggtggaggta gcaccactgc agagcttcgt gctcgggggt   4200
ggtgttgtat atgatccagt cgtagcagga gcgctgggcg tggtgctgaa aaatgtcctt   4260
aagcaagagg cttatagcta gggggaggcc cttggtgtaa gtgtttacaa atctgctcag   4320
ttgggagggg tgcatccggg gggatataat gtgcatcttg gactggattt ttaggttggc   4380
tatgttccca cccagatccc ttctgggatt catgttgtgc aggaccacca gcacggtata   4440
tccagtgcac ttgggaaatt tatcgtggag cttagacggg aatgcatgga agaacttgga   4500
gacgcccttg tggcctccca gattttccat acattcgtcc atgatgatgg caatgggccc   4560
gtgggaagct gcctgagcaa aaatgtttct gggatcgctc acatcgtagt tatgttccag   4620
ggtgaggtca tcataggaca tctttacgaa tcggggggcgg agggtcccgg actgggggat   4680
gatggtaccc tcgggccccg gggcgtagtt cccctcacag atctgcatct cccaggcttt   4740
catttcagag ggagggatca tatccacctg cggagcgatg aaaaacacag tttctggcgc   4800
aggggagatt aactgggatg agagcaggtt tctgagcagc tgtgactttc cacagccggt   4860
gggcccatat atcacgccta tcaccggctg cagctggtag ttaagagagc tgcagctgcc   4920
gtcctcccgg agcagggggg ccacctcgtt cagcatatcc ctgacgtgga tgttctccct   4980
gaccaattcc gccagaaggc gctcgccgcc cagcgaaagc agctcttgca aggaagcaaa   5040
atttttcagc ggttttaggc cgtcggccgt gggcatgttt ttcagcgtct gggtcagcag   5100
ttccagcctg tcccacagct cggtgatgtg ctctacggca tctcgatcca gcagatctcc   5160
tcgtttcgcg ggttggggcg gctttcgctg tagggcacca gccgatgggc gtccagcggg   5220
gccagagtca tgtccttcca tgggcgcagg gtcctcgtca gggtggtctg ggtcacggtg   5280
aaggggtgcg ctccgggttg ggcgctggcc agggtgcgct tgaggctggt tctgctggtg   5340
ctgaatcgct gccgctcttc gccctgcgcg tcggccaggt agcatttgac catggtctcg   5400
tagtcgagac cctcggcggc gtgccccttg gcgcggagct ttcccttgga ggtggcgccg   5460
cacgaggggc actgcaggct cttcagggcg tagagcttgg gagcgagaaa cacggactct   5520
ggggagtagg cgtccgcgcc gcaggaagcg cagaccgtct cgcattccac cagccaagtg   5580
agctccgggc ggtcagggtc aaaaaccagg ttgcccccat gctttttgat gcgtttctta   5640
cctcggctct ccatgaggcg gtgtcccttc tcggtgacga agaggctgtc cgtgtccccg   5700
tagaccgact tcaggggcct gtcttccagc ggagtgcctc tgtcctcctc gtagagaaac   5760
```

-continued tctgaccact ctgagacgaa ggcccgcgtc caggccagga cgaaggaggc cacgtgggag 5820
gggtagcggt cgttgtccac tagcgggtcc accttctcca gggtgtgcag gcacatgtcc 5880
ccctcctccg cgtccagaaa agtgattggc ttgtaggtgt aggacacgtg accgggggtt 5940
cccgacgggg gggtataaaa gggggtgggc gccctttcat cttcactctc ttccgcatcg 6000
ctgtctgcga gggccagctg ctggggtaag tattccctct cgaaggcggg catgacctca 6060
gcgctcaggt tgtcagtttc taaaaatgag gaggatttga tgttcacctg tccggaggtg 6120 ataccttga gggtacctgg gtccatctgg tcagaaaaca ctattttttt gttgtcaagc 6180
ttggtggcga acgacccgta gagggcgttg gagagcagct tggcgatgga gcgcagggtc 6240
tggtttttgt cgcggtcggc tcgctccttg gccgcgatgt tgagttgcac gtactcgcgg 6300
gccacgcact tccactcggg gaagacggtg gtgcgctcgt ctgggattag gcgcaccctc 6360
cagcctcggt tgtgcagggt gaccatgtcg acgctggtgg cgacctcgcc gcgcaggcgc 6420
tcgttggtcc agcagaggcg gccgcccttg cgcgagcaga agggggggtag ggggtccagc 6480 tggtcctcgt ttgggggtc cgcgtcgatg gtgaagaccc cggggagcaa gcgcgggtca 6540
aagtagtcga tcttgcaagc ttgcatgtcc agagcccgct gccattcgcg ggcggcgagc 6600
gcgcgctcgt aggggttgag gggcgggccc cagggcatgg ggtgggtgag cgcggaggcg 6660
tacatgccgc agatgtcata cacgtacagg ggttccctga ggatgccgag gtaggtgggg 6720
tagcagcgcc ccccgcggat gctggcgcgc acgtagtcat agagctcgtg ggaggggggcc 6780 agcatgttgg gcccgaggtt ggtgcgctgg gggcgctcgg cgcggaaggc gatctgcctg 6840
aagatggcat gggagttgga ggagatggtg ggccgctgga agacgttgaa gcttgcttct 6900
tgcaagccca ccgagtccct gacgaaggag gcgtaggact cgcgcagctt gtgcaccagc 6960
tcggcggtga cctggacgtc gagcgcgcag tagtcgaggg tctcgcggat gatgtcatac 7020
ttatcctccc ccttcttttt ccacagctcg cggttgagga cgaactcttc gcggtctttc 7080
cagtactctt ggaggggaaa cccgtccgtg tccgaacggt aagagcctag catgtagaac 7140
tggttgacgg cctggtaggg gcaacagccc ttctccacgg gcagcgcgta ggcctgcgcc 7200
gccttgcgga gggaggtgtg ggtgagggcg aaagtgtccc tgaccatgac tttgaggtat 7260
tgatgtttga agtctgtgtc atcgcagccg ccctgttccc acagggtgta gtccgtgcgc 7320
tttttggagc gcgggttggg cagggagaag gtgaggtcat tgaagaggat cttccccgct 7380
cgaggcatga agtttctggt gatgcgaaag ggccctggga ccgaggagcg gttgttgatg 7440
acctgggcgg ccaggacgat ctcgtcaaag ccgtttatgt tgtggcccac gatgtagagc 7500
tccaaaaagc ggggctggcc cttgatggag gggagctttt tgagttcctc gtaggtgagc 7560
tcctcgggcg attccaggcc gtgctcctcc agggcccagt cttgcaagtg agggttggcc 7620
gccaggaagg atcgccagag gtcgcgggcc atgagggtct gcaggcggtc gcggaaggtt 7680
ctgaactgtc gccccacggc catcttttcg ggggtgatgc agtagaaggt gagggggtct 7740
ttctcccagg ggtcccatct gagctctcgg gcgaggtcgc gcgcggcggc gaccagagcc 7800
tcgtcgcccc ccagtttcat gaccagcatg aagggcacga gctgcttgcc aaaggctccc 7860
atccaagtgt aggtctctac atcgtaggtg acaaagaggc gctccgtgcg aggatgagag 7920
ccgatcggga agaactggat ctcccgccac cagttggagg attggctgtt gatgtggtga 7980
aagtagaagt cccgtctgcg ggccgagcac tcgtgctggc ttttgtaaaa gcgaccgcag 8040
tactggcagc gctgcacggg ttgtatatct tgcacgaggt gaacctggcg acctctgacg 8100

-continued

```
aggaagcgca gcgggaatct aagtcccccg cctggggtcc cgtgtggctg gtggtcttct   8160
actttggttg tctggccgcc agcatctgtc tcctggaggg cgatggtgga gcagaccacc   8220
acgccgcgag agccgcaggt ccagatctcg gcgctcggcg ggcggagttt gatgacgaca   8280
tcgcgcacat tggagctgtc catggtctcc agctcccgcg gcggcaggtc agctgggagt   8340
tcctggaggt tcacctcgca gagacgggtc aaggcgcggg cagtgttgag atggtatctg   8400
atttcaaggg gcgtgttggc ggcggagtcg atggcttgca ggaggccgca gccccggggg   8460
gccacgatgg ttccccgcgg ggcgcgaggg gaggcggaag ctgggggtgt gttcagaagc   8520
ggtgacgcgg gcgggccccc ggaggtaggg ggggttccgg ccccacaggc atgggcggca   8580
ggggcacgtc ttcgccgcgc gcgggcaggg gctggtgctg gctccgaaga gcgcttgcgt   8640
gcgcgacgac gcgacggttg gtgtcctgta tctgacgcct ctgagtgaag accacgggtc   8700
ccgtgacctt gaacctgaaa gagagttcga cagaatcaat ctcggcatcg ttgacagcgg   8760
cctggcgcag gatctcctgc acgtcgcccg agttgtcctg gtaggcgatc tctgccatga   8820
actgctcgat ctcttcttcc tggagatctc ctcgtccggc gcgctccacg gtggccgcca   8880
ggtcgttgga gatgcgaccc atgagctgtg agaaggcgtt gagcccgccc tcgttccaga   8940
cccggctgta gaccacgccc ccctcggcgt cgcgagcgcg catgaccacc tgggccaggt   9000
tgagctccac gtgtcgcgtg aagacggcgt agttgcgcag gcgctggaaa aggtagttca   9060
gggtggtggc ggtgtgctcg gcgacgaaga agtacatgac ccagcgccgc aacgtggatt   9120
cattgatgtc ccccaaggcc tccaggcgct ccatggcctc gtagaagtcc acggcgaagt   9180
tgaaaaactg ggagttgcga gcggacacgg tcaactcctc ctccagaaga cggatgagct   9240
cggcgacagt gttgcgcacc tcgcgctcga aggccacggg gggcgcttct tcctcttcca   9300
cctcttcttc catgatcgct tcttcttctt cctcagccgg gacgggaggg ggcggcggcg   9360
gcgggggagg ggcgcggcgg cggcggcggc gcaccgggag gcggtcgatg aagcgctcga   9420
tcatctcccc ccgcatgcgg cgcatggtct cggtgacggc gcggccgttc tcccgggggc   9480
gcagctcgaa gacgccgcct ctcatctcgc cgcggggcga gcggccgtga ggtagcgaga   9540
cggcgctgac tatgcatctt aacaattgct gtgtaggtac accgccgagg gacctgattg   9600
agtccagatc caccggatcc gaaaaccttt ggaggaaagc gtctatccag tcgcagtcgc   9660
aaggtaggct gagcaccgtg gcgggcgggg gcgggtctgg agagttcctg gcggagatgc   9720
tgctgatgat gtaattaaag taggcggtct tgagaaggcg gatggtggac aggagcacca   9780
tgtctttggg tccggcctgt tggatgcgga ggcggtcggc catgccccag gcctcgttct   9840
gacaccggcg caggtctttg tagtagtctt gcatgagtct ttccaccggc acctcttctc   9900
cttcctcttc tccatctcgc cggtggtttc tcgcgccgcc catgcgcgtg accccaaagc   9960
ccctgagcgg ctgcagcagg gccaggtcgg cgaccacgcg ctcggccaag atggcctgct  10020
gcacctgagt gagggtcctc tcgaagtcat ccatgtccac gaagcggtgg taggcgcccg  10080
tgttgatggt gtaggtgcag ttggccatga cggaccagtt gacggtctgg tgtcccggct  10140
gcgagagctc cgtgtaccgc aggcgcgaga aggcgcggga atcgaacacg tagtcgttgc  10200
aagtccgcac cagatactgg tagcccacca ggaagtgcgg cggaggttgg cgatagaggg  10260
gccagcgctg ggtggcgggg gcgccgggcg ccaggtcttc cagcatgagg cggtggtatc  10320
cgtagatgta cctggacatc caggtgatgc cggcggcggt ggtggtggcg cgcgcgtagt  10380
cgcggacccg gttccagatg tttcgcaggg gcgagaagtg ttccatggtc ggcacgctct  10440
ggccggtgag gcgcgcgcag tcgttgacgc tctatacaca cacaaaaacg aaagcgttta  10500
```

cagggctttc gttctgtagc ctggaggaaa gtaaatgggt tgggttgcgg tgtgccccgg 10560
ttcgagacca agctgagctc ggccggctga agccgcagct aacgtggtat tggcagtccc 10620
gtctcgaccc aggccctgta tcctccagga tacggtcgag agccctttg ctttcttggc 10680 caagcgcccg tggcgcgatc tgggatagat ggtcgcgatg agaggacaaa agcggctcgc 10740
ttccgtagtc tggagaaaca atcgccaggg ttgcgttgcg gcgtaccccg gttcgagccc 10800
ctatggcggc ttgaatcggc cggaaccgcg gctaacgagg gccgtggcag ccccgtcctc 10860
aggaccccgc cagccgactt ctccagttac gggagcgagc cccttttgtt ttttattttt 10920
tagatgcatc ccgtgctgcg gcagatgcgc ccctcgcccc ggcccgatca gcagcagcaa 10980
cagcaggcat gcagaccccc ctctcccctt tccgccccgg tcaccacggc cgcggcggcc 11040
gtgtcgggcg cggggggcgc gctggagtca gatgagccac cgcggcggcg acctaggcag 11100
tatctggact tggaagaggg cgagggactg gcgcggctgg gggcgaactc tccagagcgc 11160
cacccgcggg tgcagttgaa aagggacgcg cgcgaggcgt acctgccgcg gcagaacctg 11220
tttcgcgacc gcgggggcga ggagcccgag gagatgcgag actgcaggtt ccaagcgggg 11280
cgcgagctgc ggcgcgggct ggacagacag cgcctgctgc gcgaggagga ctttgagccc 11340
gacacgcaga cgggcatcag ccccgcgcgc gcgcacgtag ccgcggccga cctggtgacc 11400
gcctacgagc agacggtaaa ccaggagcgc aacttccaaa agagcttcaa caaccacgtg 11460
cgcacgctgg tggcgcgcga ggaggtgacc ctgggtctca tgcatctgtg ggacctggtg 11520
gaggcgatcg tgcagaaccc cagcagcaag cccctgaccg cgcagctgtt cctggtggtg 11580
cagcacagca gggacaacga ggccttcagg gaggcgctgc tgaacatcac cgagccggag 11640
gggcgctggc tcctggacct gataaacatc ctgcagagca tagtggtgca ggagcgcagc 11700
ctgagcctgg ccgagaaggt ggcggccatc aactactcta tgctgagcct gggcaagttc 11760
tacgcccgca agatctacaa gaccccctac gtgcccatag acaaggaggt gaagatagac 11820
agcttctaca tgcgcatggc gctgaaggtg ctgaccctga gcgacgacct gggagtgtac 11880
cgcaacgagc gcatccacaa ggccgtgagc gccagccggc ggcgcgagct gagcgaccgc 11940
gagctgatgc acagtctgca gcgcgcgctg accggcgcgg gcgagggcga cagggaggtc 12000
gagtcctact tcgacatggg ggccgacctg cactggcagc cgagccgccg cgccctggag 12060
gcggcggggg cgtacggcgg ccccctggcg gccgatgacc aggaagagga ggactatgag 12120
ctagaggagg gcgagtacct ggaggactga cctggctggt ggtgttttgg tatagatgca 12180
agatccgaac gtggcggacc cggcggtccg ggcggcgctg caaagccagc cgtccggcat 12240
taactcctct gacgactggg ccgcggccat gggtcgcatc atggccctga ccgcgcgcaa 12300
ccccgaggct ttcaggcagc agcctcaggc caaccggctg gcggccatct tggaagcggt 12360
agtgcccgcg cgctccaacc ccacccacga gaaggtgctg gccatagtca acgcgctggc 12420
ggagagcagg gccatccgcg cggacgaggc cggactggtg tacgatgcgc tgctgcagcg 12480
ggtggcgcgg tacaacagcg gcaacgtgca gaccaacctg gaccgcctgg tgacggacgt 12540
gcgcgaggcc gtggcgcagc gcgagcgctt gcatcaggac ggtaacctgg gctcgctggt 12600
ggcgctaaac gccttcctca gcacccagcc ggccaacgta ccgcgggggc aggaggacta 12660
caccaacttt ttgagcgcgc tgcggctgat ggtgaccgag gtccctcaga gcgaggtgta 12720
ccagtcgggg cccgactact tcttccagac cagcagacag ggcttgcaaa ccgtgaacct 12780
gagccaggct ttcaagaacc tgcgggggct gtggggagtg aaggcgccca ccggcgaccg 12840

-continued

```
ggctacggtg tccagcctgc taacccccaa ctcgcgcctg ctgctgctgc tgatcgcgcc  12900
cttcacggac agcgggagcg tctcgcggga gacctatctg ggccacctgc tgacgctgta  12960
ccgcgaggcc atcgggcagg cgcaggtgga cgagcacacc ttccaagaga tcaccagcgt  13020
gagccacgcg ctggggcagg aggacacggg cagcctgcag gcgaccctga actacctgct  13080
gaccaacagg cggcagaaga ttcccacgct gcacagcctg acccaggagg aggagcgcat  13140
cttgcgctac gtgcagcaga gcgtgagcct gaacctgatg cgcgacggcg tgacgcccag  13200
cgtggcgctg gacatgaccg cgcgcaacat ggaaccgggc atgtacgcct cccaccggcc  13260
gtttatcaac cgcctgatgg actacttgca tcgggcggcg gccgtgaacc ccgagtactt  13320
cactaatgcc attctgaatc cccactggat gccccctccg ggtttctaca acggggactt  13380
tgaggtgccc gaggtcaacg acgggttcct ctgggatgac atggatgaca gtgtgttctc  13440
acccaacccg ctgcgcgccg cgtctctgcg attgaaggag ggctctgaca gggaaggacc  13500
gaggagtctg gcctcctccc tggctctggg agcggtgggc gccacgggcg cggcggcgcg  13560
gggcagtagc cccttcccca gcctggcaga ctctctgaac agcgggcggg tgagcaggcc  13620
ccgcttgcta ggcgaggagg agtatctgaa caactccctg ctgcagcccg cgagggacaa  13680
gaacgctcag cggcagcagt ttcccaacaa tgggatagag agcctggtgg acaagatgtc  13740
cagatggaag acgtatgcgc aggagtacaa ggagtgggag gaccgccagc cgcggccctt  13800
gccgcccct aggcagcgct ggcagcggcg cgcgtccaac cgccgctgga ggcaggggcc  13860
cgaggacgat gatgactctg cagatgacag cagcgtgttg gacctgggcg ggagcgggaa  13920
cccctttcg cacctgcgcc cacgcctggg caagatgttt taaaagaaaa aaaaaataaa  13980
actcaccaag gccatggcga cgagcgttgg tttttgttc ccttccttag tatgcggcgc  14040
gcggcgatgt tcgaggaggg gcctcccccc tcttacgaga gcgcgatggg gatttctcct  14100
gcggcgcccc tgcagcctcc ctacgtgcct cctcggtacc tgcaacctac agggggggaga  14160
aatagcatct gttactctga gctgcagccc ctgtacgata ccaccagact gtacctggtg  14220
gacaacaagt ccgcggacgt ggcctccctg aactaccaga acgaccacag cgattttttg  14280
accacggtga tccaaaacaa cgacttcacc ccaaccgagg ccagcaccca gaccataaac  14340
ctggataaca ggtcgaactg gggcggcgac ctgaagacca tcttgcacac caacatgccc  14400
aacgtgaacg agttcatgtt caccaactct tttaaggcgc gggtgatggt ggcgcgcgag  14460
cagggggagg cgaagtacga gtgggtggac ttcacgctgc ccgagggcaa ctactcagag  14520
accatgactc tcgacctgat gaacaatgcg atcgtggaac actatctgaa agtgggcagg  14580
cagaacgggg tgaaggaaag cgatatcggg gtcaagtttg acaccagaaa cttccgtctg  14640
ggctgggacc ccgtgaccgg gctggtcatg ccgggggtct acaccaacga ggcctttcat  14700
cccgacatag tgcttctgcc cggctgtggg gtggacttca cccagagccg gctgagcaac  14760
ctgctgggca ttcgcaagcg gcagcctttc caggagggtt tcaagatcac ctatgaggat  14820
ctgaaggggg gcaacattcc cgcgctcctt gatctggacg cctacgagga gagcttgaaa  14880
cccgaggaga gcgctggcga cagcggcgag agtggcgagg agcaagccgg cggcggtggc  14940
ggcgcgtcgg tagaaaacga aagtacgccc gcagtggcgg cggacgctgc ggaggtcgag  15000
ccggaggcca tgcagcagga cgcagaggag ggcgcacagg agggcgcgca gaaggacatg  15060
aacgatgggg agatcagggg agacacattc gccacccggg gcgaagaaaa agaggcagag  15120
gcggcggcgg cggcgacggc ggaggccgaa accgaggttg aggcagaggc agagcccgag  15180
accgaagtta tggaagacat gaatgatgga gaacgtaggg gcgacacgtt cgccacccgg  15240
```

-continued

```
ggcgaagaga aggcggcgga ggcagaagcc gcggctgagg aggcggctgc ggctgcggcc  15300
aagactgagg ctgcggctaa ggctgaggtc gaagccaatg ttgcggttga ggctcaggct  15360
gaggaggagg cggcggctga agcagttaag gaaaaggccc aggcagagca ggaagagaaa  15420
aaacctgtca ttcaacctct aaaagaagat agcaaaaagc gcagttacaa cgtcatcgag  15480
ggcagcacct ttacccagta ccgcagctgg tacctggcgt acaactacgg cgacccggtc  15540
aagggggtgc gctcgtggac cctgctctgc acgccggacg tcacctgcgg ctccgagcag  15600
atgtactggt cgctgccgaa catgatgcaa gacccggtga ccttccgctc cacgcggcag  15660
gttagcaact tcccggtggt gggcgccgaa ctgctgcccg tgcactccaa gagtttttac  15720
aacgagcagg ccgtctactc ccagctgatc cgccaggcca cctctctgac ccacgtgttc  15780
aatcgctttc ccgagaacca gattttggcg cgcccgccgg cccccaccat caccaccgtg  15840
agtgaaaacg ttcctgccct cacagatcac gggacgctac cgctgcgcaa cagcatctca  15900
ggagtccagc gagtgaccat tactgacgcc agacgccgga cctgccccta cgtttacaag  15960
gccttgggca tagtctcgcc gcgcgtcctc tccagtcgca ctttttaaaa cacatctacc  16020
cacacgttcc aaaatcatgt ccgtactcat ctcacccagc aacaacaccg gctgggggct  16080
gcgcgcgccc agcaagatgt ttggaggggc gaggaagcgc tccgaccagc accctgtgcg  16140
cgtgcgcggc cactaccgcg cgccctgggg agcgcacaag cgcgggcgca cagggcgcac  16200
cactgtggac gacgtcattg actccgtagt ggagcaagcg cgccactaca cacccggcgc  16260
gccgaccgcc cccgccgtgt ccaccgtgga ccaggcgatc gaaagcgtgg tacagggcgc  16320
gcggcactat gccaacctta aaagtcgccg ccgccgcgtg gcccgccgcc atcgccggag  16380
accccgggcc accgccgccg cgcgccttac taaggctctg ctcaggcgcg ccaggcgaac  16440
tggccaccgg gccgccatga gggccgcacg gcgggctgcc gctgccgcaa gcgtcgtggc  16500
cccgcgggca cgaaggcgcg cggccgctgc cgccgccgcc gccatttcca gcttggcctc  16560
gacgcggcgc ggtaacatat actgggtgcg cgactcggta accggcacgc gggtacccgt  16620
gcgctttcgc cccccgcgga attagcacaa gacaacatac acactgagtc tcctgctgtt  16680
gtgtatccca gcggcgaccg tcagcagcgg cgacatgtcc aagcgcaaaa ttaaagaaga  16740
gatgctccag gtcatcgcgc cggagatcta tgggcccccg aagaaggagg aggatgatta  16800
caagccccgc aagctaaagc gggtcaaaaa gaaaaagaaa gatgatgatg acgaggcggt  16860
ggagtttgtc cgccgcatgg cacccaggcg ccccgtgcag tggaagggcc ggcgcgtgca  16920
gcgcgttttg cgcccccggca ccgcggtggt cttcacgccc ggcgagcgct ccacgcgcac  16980
tttcaagcgg gtgtacgatg aggtgtacgg cgacgaggac ctgttggagc aggccaacca  17040
gcgctttggg gagtttgcat atgggaaacg gccccgcgag agtctaaaag aggacctgct  17100
ggcgctaccg ctggacgagg gcaatcccac cccgagtctg aagccggtaa ccctgcaaca  17160
ggtgctgcct ttgagcgcgc ccagcgagca taagcgaggg ttgaagcgcg aaggcgggga  17220
cctggcgccc accgtgcagt tgatggtgcc caagcggcag aagctggagg acgtgctgga  17280
gaaaatgaaa gtagagcccg ggatccagcc cgagatcaag gtccgcccca tcaagcaggt  17340
ggcgcccggc gtgggagtcc agaccgtgga cgttaggatt cccacggagg agatggaaac  17400
ccaaaccgcc actccctctt cggcggccag cgccaccacc ggcaccgctt cggtagaggt  17460
gcagacggac ccctggctac ccgccaccgc tgttgccgcc gccgcccccc gttcgcgcgg  17520
gcgcaagaga aattatccag cggccagcgc gctcatgccc cagtacgcac tgcatccatc  17580
```

-continued

```
catcgtgccc acccccggct accgcgggta ctcgtaccgc ccgcgcagat cagccggcac  17640
tcgcggccgc cgccgccgtg cgaccacaac cagccgccgc cgtcgccgcc gccgccagcc  17700
agtgctgacc cccgtgtctg taaggaaggt ggctcgctcg gggagcacgc tggtggtgcc  17760
cagagcgcgc taccacccca gcatcgttta aagccggtct ctgtatggtt cttgcagata  17820
tggccctcac ttgtcgcctc cgcttcccgg tgccgggata ccgaggaaga actcaccgcc  17880
gcagaggcat ggcgggcagc ggtctccgcg gcggccgtcg ccatcgccgg cgcgcaaaaa  17940
gcaggcgcat gcgcggcggt gtgctgcctc tgctaatccc gctaatcgcc gcggcgatcg  18000
gtgccgtacc cgggatcgcc tccgtggccc tgcaggcgtc ccagaaacgt tgactcttgc  18060
aaccttgcaa gcttgcattt tttggaggaa aaataaaaaa aagtctagac tctcacgctc  18120
gcttggtcct gtgactattt tgtagaaaaa aagatggaag acatcaactt tgcgtcgctg  18180
gccccgcgtc acggctcgcg cccgttcatg ggagactgga cagatatcgg caccagcaat  18240
atgagcggtg gcgccttcag ctggggcagt ctgtggagcg gccttaaaaa ttttggttcc  18300
accattaaga actatggcaa caaagcgtgg aacagcagca cgggccagat gctgagagac  18360
aagttgaaag agcagaactt ccaggagaag gtggcgcagg gcctggcctc tggcatcagc  18420
ggggtggtgg acatagctaa ccaggccgtg cagaaaaaga taaacagtca tctggacccc  18480
cgtcctcagg tggaggaaat gcctccagcg atggagacgg tgtctcccga gggcaaaggc  18540
gaaaagcgcc cgcggcccga cagagaagag accctggtgt cacacaccga ggagccgccc  18600
tcttacgagg aggcagtcaa ggccggcctg cccaccactc gccccatagc ccccatggcc  18660
accggtgtgg tgggccacag gcaacacact cccgcaacac tagatctgcc cccgccgtcc  18720
gagccgccgc gccagccaaa ggcggcgacg gtgcccgctc cctccacttc cgccgccaac  18780
agagtgcccc tgcgccgcgc cgcgagcggc ccccgggcct cgcgagttag cggcaactgg  18840
cagagcacac tgaacagcat cgtgggcctg ggagtgagga gtgtgaagcg ccgccgttgc  18900
tactgaatga gcaagctagc taacgtgttg tatgtgtgta tgcgtcctat gtcgccgcca  18960
gaggagctgt tgagccgccg gcgccgtctg cactccagcg aatttcaaga tggcgacccc  19020
atcgatgatg cctcagtggt cgtacatgca catctcgggc caggacgctt cggagtacct  19080
gagccccggg ctggtgcagt tcgcccgcgc cacagacacc tacttcaaca tgagtaacaa  19140
gttcaggaac cccactgtgg cgcccaccca cgatgtgacc acggaccggt cgcagcgcct  19200
gacgctgcgg ttcatccccg tggatcggga ggacaccgcc tactcttaca aggcgcggtt  19260
cacgctggcc gtgggcgaca accgcgtgct ggacatggcc tccacttact ttgacatcag  19320
gggggtgctg gacaggggcc ccaccttcaa gccctactcg ggtactgcct acaactccct  19380
ggcccccaag ggcgctccca attcttgcga gtgggaacaa gatgaaccag ctcaggcagc  19440
aatagctgaa gatgaagaag aacttgaaga agaacaagct caggacgaac aggcgcccac  19500
taagaaaacc catgtatacg cccaggcacc tctttctggt gaaaaaatta ctaaggatgg  19560
tttgcaaata ggtgtggatg ccacacaggc gggagataac cctatatatg ctgataaaac  19620
attccaaccc gaacctcaga taggtgagtc tcagtggaac gaggctgatg ccacagtagc  19680
aggaggcaga gtcttaaaaa agaccacccc tatgagacct tgctatggat cctatgccaa  19740
acctactaat gccaatggcg gtcaagggat catggtggcc aatgatcagg gagcgcttga  19800
atctaaagtt gagatgcaat tttctccac cacaacgtct cttaatgtaa gggaaggtga  19860
aaacaatctt cagccaaaag tagtgctata cagcgaagat gttaacttgg aatcccctga  19920
cactcatttg tcttacaaac ctaaaaagga tgacaccaac tctaaaatca tgttgggtca  19980
```

gcaagccatg cccaacagac ccaacctcat tgcttttagg gacaacttta ttggacttat 20040
gtactacaac agcacaggca acatgggagt gctggcagga caggcctccc agctaaacgc 20100
tgtggtagac ttgcaagaca gaaacacaga gctgtcatac caactgatgc ttgattccat 20160
tggagacaga tcaagatact tttccatgtg gaaccaggca gtggacagct atgacccaga 20220
tgtcagaatc attgaaaacc atggggttga agatgagctg cccaactatt gctttcccct 20280
gggcggtatt ggaattacag acacatacca gtgcataaaa ccaaccgcag ctgctaataa 20340
cactacatgg tctaaggatg aagaatttag tgatcgcaat gaaatagggg tgggaaacaa 20400
cttcgccatg gagatcaaca tccaggccaa cctctggagg aacttcctct atgcgaacgt 20460
ggggctctac ctgccagaca agctcaagta caacccccacc aacgtggaca tctctgacaa 20520
ccccaacacc tatgactaca tgaacaagcg tgtggtggct cccggcctgg tggactgctt 20580
tgtcaatgtg ggagccaggt ggtccctgga ctacatggac aacgtcaacc ccttcaacca 20640
ccaccgcaat gcgggtctgc gctaccgctc catgatcctg ggcaacgggc gctacgtgcc 20700
cttccacatt caggtgcccc agaagttctt tgccatcaag aacctcctcc tcctgccggg 20760
ctcctacact tacgagtgga acttcaggaa ggatgtcaac atggtcctgc agagctctct 20820
gggcaatgac cttagggtgg acggggccag catcaagttt gacagcgtca ccctctatgc 20880
taccttcttc cccatggctc acaacaccgc ctccacgctc gaggccatgc tgaggaacga 20940
caccaacgac cagtccttca atgactacct ctctggggcc aacatgctct accccatccc 21000
cgccaaggcc accaacgtgc ccatctccat tccctctcgc aactgggccg ccttcagagg 21060
ctgggccttt acccgcctta agaccaagga aaccccctcc ctgggctcgg gttttgaccc 21120
ctactttgtc tactcgggat ccatccccta cctggatggc accttctacc tcaaccacac 21180
ttttaagaag atatccatca tgtatgactc ctccgtcagc tggccgggca atgaccgcct 21240
gctcaccccc aatgagttcg aggtcaagcg cgccgtggac ggcgagggct acaacgtggc 21300
ccagtgcaac atgaccaagg actggttcct ggtgcagatg ctggccaact acaacatagg 21360
ctaccagggc ttctacatcc cagagagcta caaggacagg atgtactcct tcttcagaaa 21420
tttccaaccc atgagcaggc aggtggtgga cgagaccaaa tacaaggact atcaggccat 21480
tggcatcact caccagcaca acaactcggg attcgtgggc tacctggctc ccaccatgcg 21540
cgaggggcag gcctaccccg ccaacttccc ctacccgttg ataggcaaaa ccgcggtcga 21600
cagcgtcacc cagaaaaagt tcctctgcga ccgcaccctc tggcgcatcc ccttctctag 21660
caacttcatg tccatgggtg cgctcacgga cctgggccag aacctgctct atgccaactc 21720
cgcccatgcg ctggacatga cttttgaggt ggaccccatg gacgagccca cccttctcta 21780
tattgtgttt gaagtgttcg acgtggtcag agtgcaccag ccgcaccgcg gtgtcatcga 21840
gaccgtgtac ctgcgcacgc ccttctcggc cggcaacgcc accacctaag gagacagcgc 21900
cgccgcctgc atgacgggtt ccaccgagca agagctcagg gccatcgcca gagacctggg 21960
atgcggaccc tattttttgg gcacctatga caaacgcttc ccgggcttca tctcccgaga 22020
caagctcgcc tgcgccatcg tcaacacggc cgcgcgcgag accgggggcg tgcactggct 22080
ggcctttggc tgggacccgc gctccaaaac ctgctacctc ttcgacccct ttggcttctc 22140
cgatcagcgc ctcagacaga tctatgagtt tgagtacgag gggctgctgc gccgcagcgc 22200
gcttgcctcc tcgcccgacc gctgcatcac ccttgagaag tccaccgaga ccgtgcaggg 22260
gccccactcg gccgcctgcg gtctcttctg ctgcatgttt ttgcacgcct ttgtgcgctg 22320

-continued gccccagagt cccatggatc gcaaccccac catgaacttg ctcaagggag tgcccaacgc 22380
catgctccag agcccccagg tccagcccac cctgcgccac aaccaggaac agctctaccg 22440
cttcctggag cgccactccc cctacttccg cagtcacagc gcgcacatcc ggggggccac 22500
ctctttctgc cacttgcaag aaaacatgca agacggaaaa tgatgtacag ctcgcttttt 22560
aataaatgta aagactgtgc actttattta tacacgggct ctttctggtt atttattcaa 22620
caccgccgtc gccatctaga aatcgaaagg gttctgccgc gcgtcgccgt gcgccacggg 22680
cagagacacg ttgcgatact ggaagcggct cgcccactta aactcgggca ccaccatgcg 22740
gggcagtggt tcctcgggga agttctcgcc ccacagggtg cgggtcagct gcagcgcgct 22800
caggaggtcg ggagccgaga tcttgaagtc gcagttgggg ccggaaccct gcgcgcgcga 22860
gttgcggtac acggggttgc agcactggaa caccagcagg gccggattat gcacgctggc 22920
cagcaggctc tcgtcgctga tcatgtcgct gtccagatcc tccgcgttgc tcagggcgaa 22980
cggggtcatc ttgcagacct gcctgcccag gaaaggcggc agcccgggct tgccgttgca 23040
gtcgcagcgc aggggcatca gcaggtgccc gcggcccgac tgcgcctgcg ggtacagcgc 23100
gcgcatgaag gcttcgatct gcctgaaagc cacctgcgtc ttggctccct ccgaaaagaa 23160
catcccacag gacttgctgg agaactggtt cgcgggacag ctggcatcgt gcaggcagca 23220
gcgcgcgtcg gtgttggcga tctgcaccac gttgcgaccc caccggttct tcactatctt 23280
ggccttggaa gcctgctcct tcagcgcgcg ctggccgttc tcgctggtca catccatctc 23340
tatcacctgc tccttgttga tcatgtttgt accgtgcaga cacttcaggt cgccctccgt 23400
ctgggtgcag cggtgctccc acagcgcgca accggtgggc tcccaatttt tgtgggtcac 23460
ccccgcgtag gcctgcaggt aggcctgcaa gaagcgcccc atcatggcca caaaggtctt 23520
ctggctcgta aaggtcagct gcaggccgcg atgctcttcg ttcagccagg tcttgcagat 23580
ggcggccagc gcctcggtct gctcgggcag catcctaaaa tttgtcttca ggtcgttatc 23640
cacgtggtac ttgtccatca tggcgcgcgc cgcctccatg cccttctccc aggcggacac 23700
catgggcagg cttagggggt ttatcacttc caccggcgag gacaccgtac tttcgatttc 23760
ttcttcctcc ccctcttccc ggcgcgcgcc cacgctgctg cgcgctctca ccgcctgcac 23820
caaggggtcg tcttcaggca agcgccgcac cgagcgcttg ccgcccttga cctgcttaat 23880
cagcaccggc gggttgctga agcccaccat ggtcagcgcc gcctgctctt cttcgtcttc 23940
gctgtctacc actatctctg gggaagggct tctccgctct gcggcggcgc gcttcttttt 24000
tttcttggga gcggccgtga tggagtccgc cacggcgacg gaggtcgagg gcgtggggct 24060
gggggtgcgc ggtaccaggg cctcgtcgcc ctcggactct tcctctgact ccaggcggcg 24120
gcggagtcgc ttctttgggg gcgcgcgcgt cagcggcggc ggagacgggg acggggacgg 24180
ggacgggacg ccctccacag gggtggtctt cgcgcagacc ccgcggccgc gctcgggggt 24240
cttctcgagc tggtcttggt cccgactggc cattgtatcc tcctcctcct aggcagagag 24300
acataaggag tctatcatgc aagtcgagaa ggaggagagc ttaaccaccc cctctgagac 24360
cgccgatgcg cccgccgtcg ccgtcgcccc cgctgccgcc gacgcgcccg ccacaccgag 24420
cgacaccccc gcggaccccc ccgccgacgc acccctgttc gaggaagcgg ccgtggagca 24480
ggacccgggc tttgtctcgg cagaggagga tttgcgagag gaggaggata aggagaagaa 24540
gccctcagtg ccaaaagatg ataaagagca agacgagcac gacgcagatg cacaccaggg 24600
tgaagtcggg cggggggacg gagggcatga cggcgccgac tacctagacg aagggaacga 24660
cgtgctcttg aagcacctgc atcgtcagtg cgccattgtt tgcgacgctc tgcaggagcg 24720
cagcgaagtg cccctcagcg tggcggaggt cagccacgcc tacgagctca gcctcttctc 24780
cccccgggtg cccccccgcc gccgcgaaaa cggcacatgc gagcccaacc cgcgcctcaa 24840
cttctacccc gcctttgtgg tacccgaggt cctggccacc tatcacatct tctttcaaaa 24900
ttgcaagatc cccctctcgt gccgcgccaa ccgtagccgc gccgataaga tgctggccct 24960
gcgccagggc gaccacatac ctgatatcgc cgctttggaa gatgtaccaa agatcttcga 25020
gggtctgggt cgcaacgaga agcgggcagc aaactctctg caacaggaaa acagcgaaaa 25080
tgagagtcac accggggtac tggtggagct cgagggcgac aacgcccgcc tggcggtggt 25140
caagcgcagc atcgaggtca cccactttgc ctaccccgcg ctaaacctgc cccccaaagt 25200
catgaacgcg gccatggacg ggctgatcat gcgccgcggc cggcccctcg ctccagatgc 25260
aaacttgcat gaggagaccg aggacggcca gcccgtggtc agcgacgagc agctggcgcg 25320
ctggctggag accgcggacc ccgccgaact ggaggagcgg cgcaagatga tgatggccgt 25380
ggtgctggtc accgtagagc tggagtgtct gcagcgcttc ttcggcgacc ccgagatgca 25440
gagaaaggtc gaggagaccc tgcactacac cttccgccag ggctacgtgc gccaggcttg 25500
caagatctcc aacgtggagc tcagcaacct ggtgtcctac ctgggcatct tgcatgagaa 25560
ccgcctcggg cagagcgtgc tgcactccac cctgcgcggg gaggcgcgcc gcgactacgt 25620
gcgcgactgc gtttacctct tcctctgcta cacctggcag acggccatgg gggtctggca 25680
gcagtgcctg gaggagcgca acctcaagga gctggagaag ctcctgcagc gcgcgctcaa 25740
agatctctgg acgggctaca acgagcgctc ggtggccgcc gcgctggccg acctcatctt 25800
ccccgagcgc ctgctcaaaa ccctccagca ggggctgccc gacttcacca gccaaagcat 25860
gttgcaaaac ttcaggaact ttatcctgga gcgttctggc atcctacccg ccacctgctg 25920
cgccctgccc agcgactttg tcccccctcgt gtaccgcgag tgccccccgc cgctgtgggg 25980
tcactgctac ctgttccaac tggccaacta cctgtcctac cacgcggacc tcatggagga 26040
ctccagcggc gaggggctca tggagtgcca ctgccgctgc aacctctgca cgccccaccg 26100
ctccctggtc tgcaacaccc aactgctcag cgagagtcag attatcggta ccttcgagct 26160
acagggtccg tcctcctcag acgagaagtc cgcggctccg ggctaaaac tcactccggg 26220
gctgtggact tccgcctacc tgcgcaaatt tgtacctgaa gactaccacg cccacgagat 26280
caggttttac gaagaccaat cccgcccgcc caaggcggag ctgaccgcct gcgtcatcac 26340
ccagggcgag atcctaggcc aattgcaagc catccaaaaa gcccgccaag actttttgct 26400
gaagaagggt cggggggtgt atctggaccc ccagtcgggt gaggagctca acccggttcc 26460
cccgctgccg ccgccgcggg accttgcttc ccaggataag catcgccatg gctcccagaa 26520
agaagcagca gcggccgcca ctgccgccac ccccacatgct ggaggaagag gaggaatact 26580
gggacagtca ggcagaggag gtttcggacg aggaggagcc ggagacggag atggaagagt 26640
gggaggagga cagcttagac gaggaggctt ccgaagccga agaggcagac gcaacaccgt 26700
caccctcggc cgcagccccc tcgcaggcgc ccccgaagtc cgctcccagc atcagcagca 26760
acagcagcgc tataacctcc gctcctccac cgccgcgacc cacggccgac cgcagaccca 26820
accgtagatg ggacaccacc ggaaccgggg ccggtaagtc ctccgggaga ggcaagcaag 26880
cgcagcgcca aggctaccgc tcgtggcgcg ctcacaagaa cgccatagtc gcttgcttgc 26940
aagactgcgg ggggaacatc tccttcgccc gccgcttcct gctcttccac cacggtgtgg 27000
ccttcccccg taacgtcctg cattactacc gtcatctcta cagcccctac tgcggcggca 27060

-continued

```
gtgagccaga gacggtcggc ggcggcggcg gcgcccgttt cggcgcctag gaagacccag  27120
ggcaagactt cagccaagaa actcgcggcg gccgcggcga acgcggtcgc gggggccctg  27180
cgcctgacgg tgaacgaacc cctgtcgacc cgcgaactga ggaaccgaat cttccccact  27240
ctctatgcca tcttccagca gagcagaggg caggatcagg aactgaaagt aaaaaacagg  27300
tctctgcgct ccctcacccg cagctgtctg tatcacaaga gcgaagacca gcttcggcgc  27360
acgctggagg acgctgaggc actcttcagc aaatactgcg cgctcactct taaggactag  27420
ctccgcgccc ttctcgaatt taggcgggaa cgcctacgtc atcgcagcgc cgccgtcatg  27480
agcaaggaca ttcccacgcc atacatgtgg agctatcagc cgcagatggg actcgcggcg  27540
ggcgcctccc aagactactc cacccgcatg aactggctca gtgccggccc acacatgatc  27600
tcacaggtta atgatatccg cacccatcga aaccaaatat tggtggagca ggcggcaatt  27660
accaccacgc cccgcaataa tcccaacccc agggagtggc ccgcgtccct ggtgtatcag  27720
gaaattcccg gccccaccac cgtactactt ccgcgtgatt cccaggccga agtccaaatg  27780
actaactcag gggcacagct cgcgggcggc tgtcgtcaca gggtgcggcc tcctcgccag  27840
ggtataactc acctggagat ccgaggcaga ggtattcagc tcaacgacga gtcggtgagc  27900
tcctcgctcg gtctcagacc tgacgggacc ttccagatag ccggagccgg ccgatcttcc  27960
ttcacgcccc gccaggcgta cctgactctg caaagctcgt cctcggcgcc gcgctcgggc  28020
ggcatcggga ctctccagtt cgtgcaggag tttgtgccct cggtctactt caaccccttc  28080
tcgggctctc ccggtcgcta cccggaccag ttcatctcga actttgacgc cgcgagggac  28140
tcggtggacg gctacgactg aatgtcgggt ggacccggtg cagagcaact tcgcctgaag  28200
cacctcgacc actgccgccg ccctcagtgc tttgcccgct gtcagaccgg tgagttccag  28260
tacttttccc tgcccgactc gcacccggac ggcccggcgc acggggtgcg ctttttcatc  28320
ccgagtcagg tgcgctctac cctaatcagg gagtttaccg cccgtcccct actggcggag  28380
ttggaaaagg ggccttctat cctaaccatt gcctgcatct gctctaaccc tggattgcac  28440
caagatcttt gctgtcattt gtgtgctgag tataataaag gctgagatca gaatctactc  28500
gggctcctgt cgccatcctg tcaacgccac cgtccaagcc cggcccgatc agcccgaggt  28560
gaacctcacc tgcggtctgc accggcgcct gaggaaatac ctagcttggt actacaacag  28620
cactcccttt gtggtttaca acagctttga ccaggacggg gtctcactga gggataacct  28680
ctcgaacctg agctactcca tcaggaagaa cagcaccctc gagctacttc ctccttacct  28740
gcccgggact taccagtgtg tcaccggtcc ctgcacccac acccacctgt tgatcgtaaa  28800
cgactctctt ccgagaacag acctcaataa ctcctcttcg cagttcccca gaacaggagg  28860
tgagctcagg aaaccccggg taaagaaggg tggacgagag ttaacacttg tggggtttct  28920
ggtgtatgtg acgctggtgg tggctctttt gattaaggct tttccttcca tgtctgaact  28980
ctccctcttc ttttatgaac aactcgacta gtgctaacgg gaccctaccc aacgaatcgg  29040
gattgaatat cggtaaccag gttgcagttt cacttttgat taccttcata gtcctcttcc  29100
tgctagtgct gtcgcttctg tgcctgcgga tcgggggctg ctgcatccac gtttatatct  29160
ggtgctggct gtttagaagg ttcggagacc atcgcaggta gaataaacat gctgctgctt  29220
accctctttg tcctggcgct ggccgccagc tgccaagcct tttccgaggc tgactttata  29280
gagccccagt gtaatgtgac ttttaaagcc catgcacagc gttgtcatac tataatcaaa  29340
tgtgccaccg aacacgatga ataccttatc cagtataaag ataaatcaca caaagtggca  29400
cttgttgaca tctggaaacc cgaagaccct ttggaataca atgtgaccgt tttccagggt  29460
```

-continued

```
gacctcttca aaatttacaa ttacactttc ccatttgacc agatgtgtga ctttgtcatg  29520
tacatggaaa agcagcacaa gctgtggcct ccgactcccc agggctgtgt ggaaaatcca  29580
ggctctttct gcatgatctc tctctgtgta actgtgctgg cactaatact cacgcttttg  29640
tatatcagat ttaaatcaag gcaaagcttc attgatgaaa agaaaatgcc ttaatcgctt  29700
tcacgcttga ttgctaacac cgggtttttta tccgcagaat gattggaatc accctactaa  29760
tcacctccct ccttgcgatt gcccatgggt tggaacgaat cgaagtccct gtgggggcca  29820
atgttaccct ggtggggcct gtcggcaatg ctacattaat gtgggaaaaa tatactaaaa  29880
atcaatgggt ctcttactgc actaacaaaa atagccacaa gcccagagcc atctgcgatg  29940
ggcaaaatct aaccttgatt gatgttcaat tgctggatgc gggctactat tatgggcagc  30000
tgggtacaat gattaattac tggagacccc acagagatta catgctccac gtagtaaagg  30060
gtccccttag cagcccaccc actaccacct ctactacccc cactaccacc actactccca  30120
ccaccagcac tgccgcccag cctcctcata gcagaacaac cacttttatc aattccaagt  30180
cccactcccc ccacattgcc ggcgggccct ccgcctcaga ctccgaaacc accgagatct  30240
gcttctgcaa atgctctgac gccattgccc aggatttgga agatcacgag gaagatgagc  30300
atgacttcgc agatgcatgc caggcatcag agccagaagc gctgccggtg gccctcaaac  30360
agtatgcaga cccccacacc acccccgacc ttcctccacc ttcccagaag ccaagtttcc  30420
tgggggaaaa tgaaactctg cctctctcca tactcgctct gacatctgtt gctatgttga  30480
ccgctctgct ggtgcttcta tgctctatat gctacctgat ctgctgcaga aagaaaaaat  30540
ctcacggcca tgctcaccag cccctcatgc acttccctta ccctccagag ctgggcgacc  30600
acaaacttta agtctgcagt aactatctgc ccatcccttg tcagtcgaca gcgatgagcc  30660
ccactaatct aacggcctct ggacttacaa catcgtctct taatgagacc accgctcctc  30720
aagacctgta cgatggtgtc tccgcgctgg ttaaccagtg ggatcacctg ggcatatggt  30780
ggctcctcat aggagcagtg accctgtgcc taatcctggt ctggatcatc tgctgcatca  30840
aaagcagaag acccaggcgg cggcccatct acaggccctt tgtcatcaca cctgaagatg  30900
atgatgacac cacttccagg ctgcagaggc taaagcagct actcttctct tttacagcat  30960
ggtaaattga atcatgcctc gcattttcat ctacttgtct ctccttccac tttttctggg  31020
ctcttctaca ttggccgctg tgtcccacat cgaggtagac tgcctcacgc ccttcacagt  31080
ctacctgctt ttcggctttg tcatctgcac ctttgtctgc agcgttatca ctgtagtgat  31140
ctgcttcata cagtgcatcg actacgtctg cgtgcgggtg gcttacttta gacaccaccc  31200
ccagtatcgc aacagggaca tagcggctct cctaagactt gtttaaaatc atggccaaat  31260
taactgtgat tggtcttctg atcatctgct gcgtcctagc cgcgattggg actcaagctc  31320
ctaccaccac cagcgctccc agaaagagac atgtatcctg cagcttcaag cgtccctgga  31380
atatacccca atgctttact gatgaacctg aaatctcttt ggcttggtac ttcagcgtca  31440
ccgcccttct tatcttctgc agtacggtta ttgcccttgc catctaccct tcccttgacc  31500
tgggctggaa tgctgtcaac tctatggaat atcccacctt cccagaacca gacctgccag  31560
acctggttgt tctaaacgcg tttcctcctc ctgctcccgt tcaaaatcag tttcgccctc  31620
cgtcccccac gcccactgag gtcagctact ttaatctaac aggcggagat gactgaaaac  31680
ctagacctag aaatggacgg tctctgcagc gagcaacgca cactagagag gcgccggcaa  31740
aaagagctcg agcgtcttaa acaagagctc caagacgcgg tggccataca ccagtgcaaa  31800
```

```
aaaggtgtct tctgtctggt aaaacaggcc acgctcacct atgaaaaaac aggtgacacc  31860

caccgcctag gatacaagct gcccacacag cgccaaaagt tcgccctcat gataggcgaa  31920

caacccatca ccgtgaccca gcactccgtg gagacagaag gctgcataca tgctccctgt  31980

aggggcgctg actgcctcta caccttgatc aaaaccctct gcggtctcag agaccttatc  32040

cctttcaatt aatcataact gtaatcaata aaaaatcact tacttgaaat ctgatagcaa  32100

gcctctgtcc aattttttca gcaacacttc cttcccctcc tcccaactct ggtactctag  32160

gcgcctccta gctgcaaact tcctccacag tctgaaggga atgtcagatt cctcctcctg  32220

tccctccgca cccacgatct tcatgttgtt gcagatgaaa cgcgcgagat cgtctgacga  32280

gaccttcaac cccgtgtacc cctacgatac cgagatcgct ccgacttctg tccctttcct  32340

taccoctccc tttgtgtcat ccgcaggaat gcaagaaaat ccagctgggg tgctgtccct  32400

gcacttgtca gagccccta ccacccacaa tggggccctg actctaaaaa tggggggcgg  32460

cctgaccctg gacaaggaag ggaatctcac ttcccaaaac atcaccagtg tcgatccccc  32520

tctcaaaaaa agcaagaaca acatcagcct tcagaccgcc gcacccctcg ccgtcagctc  32580

cggggcccta acacttttg ccactccccc cctagcggtc agtggtgaca accttactgt  32640

gcagtctcag gcccctctca ctttggaaga ctcaaaacta actctggcca ccaaaggacc  32700

cctaactgtg tccgaaggca aacttgtc                                     32728
```

<210> SEQ ID NO 22
<211> LENGTH: 32728
<212> TYPE: DNA
<213> ORGANISM: Artificial sequence
<220> FEATURE:
<223> OTHER INFORMATION: Adenovirus vector nucleotide sequences

<400> SEQUENCE: 22

```
catcatcaat aatatacctt attttggatt gtggccaata tgataatgag gtgggcgggg     60

agaggcgggg cgggtgacgt aggacgcgcg agtagggttg ggaggtgtgg cggaagtgtg    120

gcatttgcaa gtgggaggag ctcacatgca agcttccgtc gcggaaaatg tgacgttttt    180

gatgagcgcc gcctacctcc ggaagtgcca attttcgcgc gcttttcacc ggatatcgta    240

gtaattttgg gcgggaccat gtaagatttg gccattttcg cgcgaaaagt gaaacgggga    300

agtgaaaact gaataatagg gcgttagtca tagcgcgtaa tatttaccga gggccgaggg    360

actttgaccg attacgtgga ggactcgccc aggtgttttt tacgtgaatt tccgcgttcc    420

gggtcaaagt ctccgttttt attgtcaccg tcatttgacg cggagggtat ttaaacccgc    480

tgcgctcctc aagaggccac tcttgagtgc cagcgagaag agttttctcc tctgctccgc    540

ttcggtgatc gaaaaatgag acacatagcc tgcactccgg gtcttttgtc cggtcgggcg    600

gcggccgagc ttttggacgc tttgatcaat gatgtcctaa gcgatgattt tccgtctact    660

acccacttta gcccacctac tcttcacgaa ctgtacgatc tggatgtact ggtggatgtg    720

aacgatccca acgaggaggc ggtttctgcg ttttttcccg agtctgcgct gttggccgct    780

caggagggat ttgacctaca cactccgccg cctattttag agtctccgct gccggagccc    840

agtggtatac cttatatgcc tgaactgctt cccgaagtgg tagacctgac ctgccacgag    900

cctggctttc cgcccagcga cgatgagggt gagccttttg ttttagactt tgctgagata    960

cctgggcacg gttgcaggtc ttgtgcatat catcagaggg ttaccggaga ccccgaggtt   1020

aagtgttcgc tgtgctatat gaggatgacc tcttccttta tctacagtaa gtttttgtct   1080

aggtgggctt ttgggtaggt gggttttgtg tcagaacagg tgtaaacgtt gcttgtgttt   1140
```

-continued

```
tttgtacctg taggtccggt gtccgagcca gacccggagc ccgaccgcga tcccgagccg   1200
gatcccgagc ctcctcgcag gacaaggaaa ctaccttcca ttctgtgcaa gtctcagaca   1260
cctgtaagga ccagcgaggc agacagcacc gactctggca cttctacctc tccccctgaa   1320
attcacccag tggttcctct gggtatacat aaacctgttg ctgttaaagt ttgcgggcga   1380
cgccctgcag tacagtgcat tgaggacttg cttcacgatc ccgaggaacc tttggacttg   1440
agccttaaac gccctaggca ataaacccca cctaagtaat aaaccccacc taagtaataa   1500
accctgccgc ccttggttat tgagatgacg cccaatgttt gcttttgaat gacttcatgt   1560
gtgtaataaa agtgagtgtg atcataggtc tcttgtttgt ctgggcgggg cttaagggta   1620
tataagtctc ttggggctaa acttggttac acttgacccc aatggaggcg tgggggtgct   1680
tggaggagtt tgcggacgtg cgccgtttgc tggacgagag ctctagcaat acctatacta   1740
tttggaggta tctgtggggc tctactcagg ccaagttggt ttccagaatt aagcaggatt   1800
acaagtgcga ttttgaagag ctttttagtt cctgcggtga gcttttgcaa tccttgaatc   1860
tgggccatca ggctattttc caggaaaagg ttctctcgac tttggatttt tccactcccg   1920
ggcgcaccgc cgcttgtgtg gcttttgtgt cttttgtgca agataaatgg agcgaggaga   1980
cccacctgag tcacggctac gtactggatt tcatggcgat ggctctttgg agggctcaca   2040
acaaatggaa gattcagaag gaactgtacg gttccgccct acgtcgtcca cttctgtcgc   2100
gacaggggct gaggtttccc gaccatcggc agcatcagaa tctggaagac gagtcggagg   2160
agcgagcgga ggagaagatc agcttgagag ccggcctgga ccctcctcag gaggaatgaa   2220
tctcccgcag gtggttgacc tgtttccaga actgagacgg gtcctgacta tcagggagga   2280
tggtcagttt gtgaagaagt ttaagaggga tcggggtgag ggagatgatg aggcggctag   2340
caatttagct tttagtctga tgactcgcca ccgaccggaa tgtattacct atcagcagat   2400
taaggagagt tgtgccaacg agctggatct tttgggtcag aagtatagca tagaacagct   2460
taccacttac tggcttcagc ctggggatga ttgggaagag gcgatcaggg tgtatgcaaa   2520
ggtggccctg cggcccgatt gcaagtataa gattactaag ttggttaata ttagaaactg   2580
ctgctatatt tctgggaacg gggccgaagt ggagatagat actcaggaca gggtggcttt   2640
taggtgttgc atgataaaca tgtggcccgg gatactgggg atggatgggg tggtattcat   2700
gaatgtgagg tttacgggcc ccaactttaa tggcacggtg ttcatgggca acaccaactt   2760
gctcctgcat ggtgcgagtt tctatgggtt taataacacc tgtatagagg cctggaccga   2820
tgtaaaggtt cgaggttgtt ccttttatag ctgttggaag gcggtggtgt gtcgccctaa   2880
aagcaggggt tctgtgaaaa aatgcttgtt tgaaaggtgc accttaggca tcctctctga   2940
gggcaactcc agggtgcgcc ataatgtggc ttcgaactgc ggttgcttca tgcaagtgaa   3000
gggggtgagc gttatcaagc ataactcggt gtgtggaaac tgcgaggatc gcgcctccca   3060
gatgctgacc tgctttgatg gcaactgtca cctgttgaag accattcata taagcagcca   3120
ccccagaaag gcctggcccg tgtttgagca taacatcttg acccgctgct ccttgcatct   3180
gggggtcagg aggggtatgt tcctgcctta ccagtgtaac tttagccaca ctaaaatcct   3240
gctggaaccc gagtgcatga ccaaggtcag cctgaatggt gtgtttgatg tgactctgaa   3300
aatctggaag gtgctgaggt atgatgagac caggaccagg tgccgaccct gcgagtgcgg   3360
cggcaagcac atgagaaatc agcctgtgat gttggatgtg accgaggagc ttaggcctga   3420
ccatctggtg ctggcctgca ccagggccga gtttgggtct agcgatgagg ataccgattg   3480
```

-continued aggtgggtaa ggtgggcgtg gctagaaggg tggggcgtgt ataaattggg ggtctaaggg 3540
tctctctgtt ttgtcttgca acagccgccg ccatgagcga caccggcaac agctttgatg 3600
gaagcatctt tagcccctat ctgacagtgc gcatgcctca ctgggctgga gtgcgtcaga 3660
atgtgatggg ttccaacgtg gatggacgcc ccgttctgcc ttcaaattcg tctacaatgg 3720
cctacgcgac cgtgggagga actccgctgg acgccgcgac ctccgccgcc gcctccgccg 3780
ccgccgcgac cgcgcgcagc atggctacgg acctttacag ctctttggtg gcgagcggcg 3840
cggcctctcg cgcgtctgct cgggatgaga aactgaccgc tctgctgctt aaactggaag 3900
acttgacccg ggagctgggt caactgaccc agcaggtctc cagcttgcgt gagagcagcc 3960
ttgcctcccc ctaatggccc ataatataaa taaaagccag tctgtttgga ttaagcaagt 4020
gtatgttctt tatttaactc tccgcgcgcg gtaagcccgg gaccagcggt ctcggtcgtt 4080
tagggtgcgg tggattcttt ccaacacgtg gtacaggtgg ctctggatgt ttagatacat 4140
gggcatgagt ccatccctgg ggtggaggta gcaccactgc agagcttcgt gctcgggggt 4200
ggtgttgtat atgatccagt cgtagcagga gcgctgggcg tggtgctgaa aaatgtcctt 4260
aagcaagagg cttatagcta gggggaggcc cttggtgtaa gtgtttacaa atctgctcag 4320
ttgggagggg tgcatccggg gggatataat gtgcatcttg gactggattt ttaggttggc 4380
tatgttccca cccagatccc ttctgggatt catgttgtgc aggaccacca gcacggtata 4440
tccagtgcac ttgggaaatt tatcgtggag cttagacggg aatgcatgga agaacttgga 4500
gacgcccttg tggcctccca gattttccat acattcgtcc atgatgatgg caatgggccc 4560
gtgggaagct gcctgagcaa aaatgtttct gggatcgctc acatcgtagt tatgttccag 4620
ggtgaggtca tcataggaca tctttacgaa tcgggggcgg agggtcccgg actgggggat 4680
gatggtaccc tcgggccccg gggcgtagtt cccctcacag atctgcatct cccaggcttt 4740
catttcagag ggagggatca tatccacctg cggagcgatg aaaaacacag tttctggcgc 4800
aggggagatt aactgggatg agagcaggtt tctgagcagc tgtgactttc cacagccggt 4860
gggcccatat atcacgccta tcaccggctg cagctggtag ttaagagagc tgcagctgcc 4920
gtcctcccgg agcagggggg ccacctcgtt cagcatatcc ctgacgtgga tgttctccct 4980
gaccaattcc gccagaaggc gctcgccgcc cagcgaaagc agctcttgca aggaagcaaa 5040
atttttcagc ggttttaggc cgtcggccgt gggcatgttt ttcagcgtct gggtcagcag 5100
ttccagcctg tcccacagct cggtgatgtg ctctacggca tctcgatcca gcagatctcc 5160
tcgtttcgcg ggttggggcg gctttcgctg tagggcacca gccgatgggc gtccagcggg 5220
gccagagtca tgtccttcca tgggcgcagg gtcctcgtca gggtggtctg ggtcacggtg 5280
aaggggtgcg ctccgggttg ggcgctggcc agggtgcgct tgaggctggt tctgctggtg 5340
ctgaatcgct gccgctcttc gccctgcgcg tcggccaggt agcatttgac catggtctcg 5400
tagtcgagac cctcggcggc gtgccccttg gcgcggagct ttcccttgga ggtggcgccg 5460
cacgaggggc actgcaggct cttcagggcg tagagcttgg gagcgagaaa cacggactct 5520
ggggagtagg cgtccgcgcc gcaggaagcg cagaccgtct cgcattccac cagccaagtg 5580
agctccgggc ggtcagggtc aaaaaccagg ttgcccccat gctttttgat gcgtttctta 5640
cctcggctct ccatgaggcg gtgtcccttc tcggtgacga agaggctgtc cgtgtccccg 5700
tagaccgact tcaggggcct gtcttccagc ggagtgcctc tgtcctcctc gtagagaaac 5760
tctgaccact ctgagacgaa ggcccgcgtc caggccagga cgaaggaggc cacgtgggag 5820
gggtagcggt cgttgtccac tagcgggtcc accttctcca gggtgtgcag gcacatgtcc 5880

-continued

```
ccctcctccg cgtccagaaa agtgattggc ttgtaggtgt aggacacgtg accgggggtt   5940
cccgacgggg gggtataaaa gggggtgggc gccctttcat cttcactctc ttccgcatcg   6000
ctgtctgcga gggccagctg ctggggtaag tattccctct cgaaggcggg catgacctca   6060
gcgctcaggt tgtcagtttc taaaaatgag gaggatttga tgttcacctg tccggaggtg   6120
ataccttga gggtacctgg gtccatctgg tcagaaaaca ctattttttt gttgtcaagc    6180
ttggtggcga acgacccgta gagggcgttg gagagcagct tggcgatgga gcgcagggtc   6240
tggtttttgt cgcggtcggc tcgctccttg gccgcgatgt tgagttgcac gtactcgcgg   6300
gccacgcact tccactcggg gaagacggtg gtgcgctcgt ctgggattag gcgcaccctc   6360
cagcctcggt tgtgcagggt gaccatgtcg acgctggtgg cgacctcgcc gcgcaggcgc   6420
tcgttggtcc agcagaggcg gccgcccttg cgcgagcaga agggggtag ggggtccagc    6480
tggtcctcgt ttgggggtc cgcgtcgatg gtgaagaccc cggggagcaa gcgcgggtca    6540
aagtagtcga tcttgcaagc ttgcatgtcc agagcccgct gccattcgcg ggcggcgagc   6600
gcgcgctcgt aggggttgag gggcgggccc cagggcatgg ggtgggtgag cgcggaggcg   6660
tacatgccgc agatgtcata cacgtacagg ggttccctga ggatgccgag gtaggtgggg   6720
tagcagcgcc ccccgcggat gctggcgcgc acgtagtcat agagctcgtg ggaggggggcc  6780
agcatgttgg gcccgaggtt ggtgcgctgg gggcgctcgg cgcggaaggc gatctgcctg   6840
aagatggcat gggagttgga ggagatggtg ggccgctgga agacgttgaa gcttgcttct   6900
tgcaagccca ccgagtccct gacgaaggag gcgtaggact cgcgcagctt gtgcaccagc   6960
tcggcggtga cctggacgtc gagcgcgcag tagtcgaggg tctcgcggat gatgtcatac   7020
ttatcctccc ccttcttttt ccacagctcg cggttgagga cgaactcttc gcggtctttc   7080
cagtactctt ggaggggaaa cccgtccgtg tccgaacggt aagagcctag catgtagaac   7140
tggttgacgg cctggtaggg gcaacagccc ttctccacgg gcagcgcgta ggcctgcgcc   7200
gccttgcgga gggaggtgtg ggtgagggcg aaagtgtccc tgaccatgac tttgaggtat   7260
tgatgtttga agtctgtgtc atcgcagccg ccctgttccc acagggtgta gtccgtgcgc   7320
tttttggagc gcgggttggg cagggagaag gtgaggtcat tgaagaggat cttccccgct   7380
cgaggcatga agtttctggt gatgcgaaag ggccctggga ccgaggagcg gttgttgatg   7440
acctgggcgg ccaggacgat ctcgtcaaag ccgtttatgt tgtggcccac gatgtagagc   7500
tccaaaaagc ggggctggcc cttgatggag gggagctttt tgagttcctc gtaggtgagc   7560
tcctcgggcg attccaggcc gtgctcctcc agggcccagt cttgcaagtg agggttggcc   7620
gccaggaagg atcgccagag gtcgcgggcc atgagggtct gcaggcggtc gcggaaggtt   7680
ctgaactgtc gccccacggc catcttttcg ggggtgatgc agtagaaggt gagggggtct   7740
ttctcccagg ggtcccatct gagctctcgg gcgaggtcgc gcgcggcggc gaccagagcc   7800
tcgtcgcccc ccagtttcat gaccagcatg aagggcacga gctgcttgcc aaaggctccc   7860
atccaagtgt aggtctctac atcgtaggtg acaaagaggc gctccgtgcg aggatgagag   7920
ccgatcggga agaactggat ctcccgccac cagttggagg attggctgtt gatgtggtga   7980
aagtagaagt cccgtctgcg ggccgagcac tcgtgctggc ttttgtaaaa gcgaccgcag   8040
tactggcagc gctgcacggg ttgtatatct tgcacgaggt gaacctggcg acctctgacg   8100
aggaagcgca gcgggaatct aagtcccccg cctggggtcc cgtgtggctg gtggtcttct   8160
actttggttg tctggccgcc agcatctgtc tcctggaggg cgatggtgga gcagaccacc   8220
```

-continued

```
acgccgcgag agccgcaggt ccagatctcg gcgctcggcg ggcggagttt gatgacgaca   8280
tcgcgcacat tggagctgtc catggtctcc agctcccgcg gcggcaggtc agctgggagt   8340
tcctggaggt tcacctcgca gagacgggtc aaggcgcggg cagtgttgag atggtatctg   8400
atttcaaggg gcgtgttggc ggcggagtcg atggcttgca ggaggccgca gccccggggg   8460
gccacgatgg ttccccgcgg ggcgcgaggg gaggcggaag ctgggggtgt gttcagaagc   8520
ggtgacgcgg gcgggccccc ggaggtaggg ggggttccgg ccccacaggc atgggcggca   8580
ggggcacgtc ttcgccgcgc gcgggcaggg gctggtgctg gctccgaaga gcgcttgcgt   8640
gcgcgacgac gcgacggttg gtgtcctgta tctgacgcct ctgagtgaag accacgggtc   8700
ccgtgacctt gaacctgaaa gagagttcga cagaatcaat ctcggcatcg ttgacagcgg   8760
cctggcgcag gatctcctgc acgtcgcccg agttgtcctg gtaggcgatc tctgccatga   8820
actgctcgat ctcttcttcc tggagatctc ctcgtccggc gcgctccacg gtggccgcca   8880
ggtcgttgga gatgcgaccc atgagctgtg agaaggcgtt gagcccgccc tcgttccaga   8940
cccggctgta gaccacgccc ccctcggcgt cgcgagcgcg catgaccacc tgggccaggt   9000
tgagctccac gtgtcgcgtg aagacggcgt agttgcgcag gcgctggaaa aggtagttca   9060
gggtggtggc ggtgtgctcg gcgacgaaga agtacatgac ccagcgccgc aacgtggatt   9120
cattgatgtc ccccaaggcc tccaggcgct ccatggcctc gtagaagtcc acggcgaagt   9180
tgaaaaactg ggagttgcga gcggacacgg tcaactcctc ctccagaaga cggatgagct   9240
cggcgacagt gttgcgcacc tcgcgctcga aggccacggg gggcgcttct tcctcttcca   9300
cctcttcttc catgatcgct tcttcttctt cctcagccgg gacgggaggg ggcggcggcg   9360
gcgggggagg ggcgcggcgg cggcggcggc gcaccgggag gcggtcgatg aagcgctcga   9420
tcatctcccc ccgcatgcgg cgcatggtct cggtgacggc gcggccgttc tcccgggggc   9480
gcagctcgaa gacgccgcct ctcatctcgc cgcggggcga gcggccgtga ggtagcgaga   9540
cggcgctgac tatgcatctt aacaattgct gtgtaggtac accgccgagg gacctgattg   9600
agtccagatc caccggatcc gaaaaccttt ggaggaaagc gtctatccag tcgcagtcgc   9660
aaggtaggct gagcaccgtg gcgggcgggg gcgggtctgg agagttcctg gcggagatgc   9720
tgctgatgat gtaattaaag taggcggtct tgagaaggcg gatggtggac aggagcacca   9780
tgtctttggg tccggcctgt tggatgcgga ggcggtcggc catgccccag gcctcgttct   9840
gacaccggcg caggtctttg tagtagtctt gcatgagtct ttccaccggc acctcttctc   9900
cttcctcttc tccatctcgc cggtggtttc tcgcgccgcc catgcgcgtg accccaaagc   9960
ccctgagcgg ctgcagcagg gccaggtcgg cgaccacgcg ctcggccaag atggcctgct  10020
gcacctgagt gagggtcctc tcgaagtcat ccatgtccac gaagcggtgg taggcgcccg  10080
tgttgatggt gtaggtgcag ttggccatga cggaccagtt gacggtctgg tgtcccggct  10140
gcgagagctc cgtgtaccgc aggcgcgaga aggcgcggga atcgaacacg tagtcgttgc  10200
aagtccgcac cagatactgg tagcccacca ggaagtgcgg cggaggttgg cgatagaggg  10260
gccagcgctg ggtggcgggg gcgccgggcg ccaggtcttc cagcatgagg cggtggtatc  10320
cgtagatgta cctggacatc caggtgatgc cggcggcggt ggtggtggcg cgcgcgtagt  10380
cgcggacccg gttccagatg tttcgcaggg gcgagaagtg ttccatggtc ggcacgctct  10440
ggccggtgag gcgcgcgcag tcgttgacgc tctatacaca cacaaaaacg aaagcgttta  10500
cagggctttc gttctgtagc ctggaggaaa gtaaatgggt tgggttgcgg tgtgccccgg  10560
ttcgagacca agctgagctc ggccggctga agccgcagct aacgtggtat tggcagtccc  10620
```

-continued

```
gtctcgaccc aggccctgta tcctccagga tacggtcgag agccctttttg ctttcttggc  10680
caagcgcccg tggcgcgatc tgggatagat ggtcgcgatg agaggacaaa agcggctcgc  10740
ttccgtagtc tggagaaaca atcgccaggg ttgcgttgcg gcgtaccccg gttcgagccc  10800
ctatggcggc ttgaatcggc cggaaccgcg gctaacgagg gccgtggcag ccccgtcctc  10860
aggaccccgc cagccgactt ctccagttac gggagcgagc cccttttgtt ttttattttt  10920
tagatgcatc ccgtgctgcg gcagatgcgc ccctcgcccc ggcccgatca gcagcagcaa  10980
cagcaggcat gcagaccccc ctctcccctt tccgccccgg tcaccacggc cgcggcggcc  11040
gtgtcgggcg cggggggcgc gctggagtca gatgagccac cgcggcggcg acctaggcag  11100
tatctggact tggaagaggg cgagggactg gcgcggctgg gggcgaactc tccagagcgc  11160
cacccgcggg tgcagttgaa aagggacgcg cgcgaggcgt acctgccgcg gcagaacctg  11220
tttcgcgacc gcgggggcga ggagcccgag gagatgcgag actgcaggtt ccaagcgggg  11280
cgcgagctgc ggcgcgggct ggacagacag cgcctgctgc gcgaggagga ctttgagccc  11340
gacacgcaga cgggcatcag ccccgcgcgc gcgcacgtag ccgcggccga cctggtgacc  11400
gcctacgagc agacggtaaa ccaggagcgc aacttccaaa agagcttcaa caaccacgtg  11460
cgcacgctgg tggcgcgcga ggaggtgacc ctgggtctca tgcatctgtg ggacctggtg  11520
gaggcgatcg tgcagaaccc cagcagcaag cccctgaccg cgcagctgtt cctggtggtg  11580
cagcacagca gggacaacga ggccttcagg gaggcgctgc tgaacatcac cgagccggag  11640
gggcgctggc tcctggacct gataaacatc ctgcagagca tagtggtgca ggagcgcagc  11700
ctgagcctgg ccgagaaggt ggcggccatc aactactcta tgctgagcct gggcaagttc  11760
tacgcccgca agatctacaa gaccccctac gtgcccatag acaaggaggt gaagatagac  11820
agcttctaca tgcgcatggc gctgaaggtg ctgaccctga gcgacgacct gggagtgtac  11880
cgcaacgagc gcatccacaa ggccgtgagc gccagccggc ggcgcgagct gagcgaccgc  11940
gagctgatgc acagtctgca gcgcgcgctg accggcgcgg gcgagggcga cagggaggtc  12000
gagtcctact tcgacatggg ggccgacctg cactggcagc cgagccgccg cgccctggag  12060
gcggcggggg cgtacggcgg ccccctggcg gccgatgacc aggaagagga ggactatgag  12120
ctagaggagg gcgagtacct ggaggactga cctggctggt ggtgttttgg tatagatgca  12180
agatccgaac gtggcggacc cggcggtccg ggcggcgctg caaagccagc cgtccggcat  12240
taactcctct gacgactggg ccgcggccat gggtcgcatc atggccctga ccgcgcgcaa  12300
ccccgaggct ttcaggcagc agcctcaggc caaccggctg gcggccatct tggaagcggt  12360
agtgcccgcg cgctccaacc ccacccacga gaaggtgctg gccatagtca acgcgctggc  12420
ggagagcagg gccatccgcg cggacgaggc cggactggtg tacgatgcgc tgctgcagcg  12480
ggtggcgcgg tacaacagcg gcaacgtgca gaccaacctg gaccgcctgg tgacggacgt  12540
gcgcgaggcc gtggcgcagc gcgagcgctt gcatcaggac ggtaacctgg gctcgctggt  12600
ggcgctaaac gccttcctca gcacccagcc ggccaacgta ccgcgggggc aggaggacta  12660
caccaacttt ttgagcgcgc tgcggctgat ggtgaccgag gtccctcaga gcgaggtgta  12720
ccagtcgggg cccgactact tcttccagac cagcagacag ggcttgcaaa ccgtgaacct  12780
gagccaggct ttcaagaacc tgcgggggct gtggggagtg aaggcgccca ccggcgaccg  12840
ggctacggtg tccagcctgc taacccccaa ctcgcgcctg ctgctgctgc tgatcgcgcc  12900
cttcacggac agcgggagcg tctcgcggga gacctatctg ggccacctgc tgacgctgta  12960
```

-continued

```
ccgcgaggcc atcgggcagg cgcaggtgga cgagcacacc ttccaagaga tcaccagcgt  13020
gagccacgcg ctggggcagg aggacacggg cagcctgcag gcgaccctga actacctgct  13080
gaccaacagg cggcagaaga ttcccacgct gcacagcctg acccaggagg aggagcgcat  13140
cttgcgctac gtgcagcaga gcgtgagcct gaacctgatg cgcgacggcg tgacgcccag  13200
cgtggcgctg gacatgaccg cgcgcaacat ggaaccgggc atgtacgcct cccaccggcc  13260
gtttatcaac cgcctgatgg actacttgca tcgggcggcg gccgtgaacc ccgagtactt  13320
cactaatgcc attctgaatc cccactggat gccccctccg ggtttctaca acggggactt  13380
tgaggtgccc gaggtcaacg acgggttcct ctgggatgac atggatgaca gtgtgttctc  13440
acccaacccg ctgcgcgccg cgtctctgcg attgaaggag ggctctgaca gggaaggacc  13500
gaggagtctg gcctcctccc tggctctggg agcggtgggc gccacgggcg cggcggcgcg  13560
gggcagtagc cccttcccca gcctggcaga ctctctgaac agcgggcggg tgagcaggcc  13620
ccgcttgcta ggcgaggagg agtatctgaa caactccctg ctgcagcccg cgagggacaa  13680
gaacgctcag cggcagcagt ttcccaacaa tgggatagag agcctggtgg acaagatgtc  13740
cagatggaag acgtatgcgc aggagtacaa ggagtgggag gaccgccagc cgcggccctt  13800
gccgcccccct aggcagcgct ggcagcggcg cgcgtccaac cgccgctgga ggcaggggcc  13860
cgaggacgat gatgactctg cagatgacag cagcgtgttg gacctgggcg ggagcgggaa  13920
cccctttcg cacctgcgcc cacgcctggg caagatgttt taaaagaaaa aaaaaaataa  13980
aactcaccaa ggccatggcg acgagcgttg gttttttgtt cccttcctta gtatgcggcg  14040
cgcggcgatg ttcgaggagg ggcctccccc ctcttacgag agcgcgatgg ggatttctcc  14100
tgcggcgccc ctgcagcctc cctacgtgcc tcctcggtac ctgcaaccta caggggggag  14160
aaatagcatc tgttactctg agctgcagcc cctgtacgat accaccagac tgtacctggt  14220
ggacaacaag tccgcggacg tggcctccct gaactaccag aacgaccaca gcgatttttt  14280
gaccacggtg atccaaaaca acgacttcac cccaaccgag gccagcaccc agaccataaa  14340
cctggataac aggtcgaact ggggcggcga cctgaagacc atcttgcaca ccaacatgcc  14400
caacgtgaac gagttcatgt tcaccaactc ttttaaggcg cgggtgatgg tggcgcgcga  14460
gcagggggag gcgaagtacg agtgggtgga cttcacgctg cccgagggca actactcaga  14520
gaccatgact ctcgacctga tgaacaatgc gatcgtggaa cactatctga aagtgggcag  14580
gcagaacggg gtgaaggaaa gcgatatcgg ggtcaagttt gacaccagaa acttccgtct  14640
gggctgggac cccgtgaccg ggctggtcat gccgggggtc tacaccaacg aggcctttca  14700
tcccgacata gtgcttctgc ccggctgtgg ggtggacttc acccagagcc ggctgagcaa  14760
cctgctgggc attcgcaagc ggcagccttt ccaggagggt ttcaagatca cctatgagga  14820
tctgaagggg ggcaacattc ccgcgctcct tgatctggac gcctacgagg agagcttgaa  14880
acccgaggag agcgctggcg acagcggcga gagtggcgag gagcaagccg gcggcggtgg  14940
cggcgcgtcg gtagaaaacg aaagtacgcc cgcagtggcg gcggacgctg cggaggtcga  15000
gccggaggcc atgcagcagg acgcagagga gggcgcacag gagggcgcgc agaaggacat  15060
gaacgatggg gagatcaggg gagacacatt cgccacccgg ggcgaagaaa aagaggcaga  15120
ggcggcggcg gcggcgacgg cggaggccga aaccgaggtt gaggcagagg cagagcccga  15180
gaccgaagtt atggaagaca tgaatgatgg agaacgtagg ggcgacacgt tcgccacccg  15240
gggcgaagag aaggcggcgg aggcagaagc cgcggctgag gaggcggctg cggctgcggc  15300
caagactgag gctgcggcta aggctgaggt cgaagccaat gttgcggttg aggctcaggc  15360
```

tgaggaggag gcggcggctg aagcagttaa ggaaaaggcc caggcagagc aggaagagaa 15420
aaaacctgtc attcaacctc taaaagaaga tagcaaaaag cgcagttaca acgtcatcga 15480
gggcagcacc tttacccagt accgcagctg gtacctggcg tacaactacg gcgacccggt 15540
caagggggtg cgctcgtgga ccctgctctg cacgccggac gtcacctgcg gctccgagca 15600
gatgtactgg tcgctgccga acatgatgca agacccggtg accttccgct ccacgcggca 15660
ggttagcaac ttcccggtgg tgggcgccga actgctgccc gtgcactcca agagttttta 15720
caacgagcag gccgtctact cccagctgat ccgccaggcc acctctctga cccacgtgtt 15780
caatcgcttt cccgagaacc agattttggc gcgcccgccg gcccccacca tcaccaccgt 15840
gagtgaaaac gttcctgccc tcacagatca cgggacgcta ccgctgcgca acagcatctc 15900
aggagtccag cgagtgacca ttactgacgc cagacgccgg acctgcccct acgtttacaa 15960
ggccttgggc atagtctcgc cgcgcgtcct ctccagtcgc actttttaaa acacatctac 16020
ccacacgttc caaaatcatg tccgtactca tctcacccag caacaacacc ggctgggggc 16080
tgcgcgcgcc cagcaagatg tttggagggg cgaggaagcg ctccgaccag caccctgtgc 16140
gcgtgcgcgg ccactaccgc gcgccctggg gagcgcacaa gcgcgggcgc acagggcgca 16200
ccactgtgga cgacgtcatt gactccgtag tggagcaagc gcgccactac acacccggcg 16260
cgccgaccgc ccccgccgtg tccaccgtgg accaggcgat cgaaagcgtg gtacagggcg 16320
cgcggcacta tgccaacctt aaaagtcgcc gccgccgcgt ggcccgccgc catcgccgga 16380
gaccccgggc caccgccgcc gcgcgcctta ctaaggctct gctcaggcgc gccaggcgaa 16440
ctggccaccg ggccgccatg agggccgcac ggcgggctgc cgctgccgca agcgtcgtgg 16500
ccccgcgggc acgaaggcgc gcggccgctg ccgccgccgc cgccatttcc agcttggcct 16560
cgacgcggcg cggtaacata tactgggtgc gcgactcggt aaccggcacg cgggtacccg 16620
tgcgctttcg ccccccgcgg aattagcaca agacaacata cacactgagt ctcctgctgt 16680
tgtgtatccc agcggcgacc gtcagcagcg gcgacatgtc caagcgcaaa attaaagaag 16740
agatgctcca ggtcatcgcg ccggagatct atgggccccc gaagaaggag gaggatgatt 16800
acaagccccg caagctaaag cgggtcaaaa agaaaaagaa agatgatgat gacgaggcgg 16860
tggagtttgt ccgccgcatg gcacccaggc gccccgtgca gtggaagggc cggcgcgtgc 16920
agcgcgtttt gcgccccggc accgcggtgg tcttcacgcc cggcgagcgc tccacgcgca 16980
ctttcaagcg ggtgtacgat gaggtgtacg gcgacgagga cctgttggag caggccaacc 17040
agcgctttgg ggagtttgca tatgggaaac ggccccgcga gagtctaaaa gaggacctgc 17100
tggcgctacc gctggacgag ggcaatccca ccccgagtct gaagccggta accctgcaac 17160
aggtgctgcc tttgagcgcg cccagcgagc ataagcgagg gttgaagcgc gaaggcgggg 17220
acctggcgcc caccgtgcag ttgatggtgc ccaagcggca gaagctggag gacgtgctgg 17280
agaaaatgaa agtagagccc gggatccagc ccgagatcaa ggtccgcccc atcaagcagg 17340
tggcgcccgg cgtgggagtc cagaccgtgg acgttaggat tcccacggag gagatggaaa 17400
cccaaaccgc cactccctct tcggcggcca gcgccaccac cggcaccgct tcggtagagg 17460
tgcagacgga cccctggcta cccgccaccg ctgttgccgc cgccgccccc cgttcgcgcg 17520
ggcgcaagag aaattatcca gcggccagcg cgctcatgcc ccagtacgca ctgcatccat 17580
ccatcgtgcc cacccccggc taccgcgggt actcgtaccg cccgcgcaga tcagccggca 17640
ctcgcggccg ccgccgccgt gcgaccacaa ccagccgccg ccgtcgccgc cgccgccagc 17700

-continued

```
cagtgctgac ccccgtgtct gtaaggaagg tggctcgctc ggggagcacg ctggtggtgc  17760
ccagagcgcg ctaccacccc agcatcgttt aaagccggtc tctgtatggt tcttgcagat  17820
atggccctca cttgtcgcct ccgcttcccg gtgccgggat accgaggaag aactcaccgc  17880
cgcagaggca tggcgggcag cggtctccgc ggcggccgtc gccatcgccg gcgcgcaaaa  17940
agcaggcgca tgcgcggcgg tgtgctgcct ctgctaatcc cgctaatcgc cgcggcgatc  18000
ggtgccgtac ccgggatcgc ctccgtggcc ctgcaggcgt cccagaaacg ttgactcttg  18060
caaccttgca agcttgcatt ttttggagga aaaaataaaa aaaaagtcta gactctcacg  18120
ctcgcttggt cctgtgacta ttttgtagaa aaaaagatgg aagacatcaa ctttgcgtcg  18180
ctggccccgc gtcacggctc gcgcccgttc atgggagact ggacagatat cggcaccagc  18240
aatatgagcg gtggcgcctt cagctggggc agtctgtgga gcggccttaa aaattttggt  18300
tccaccatta agaactatgg caacaaagcg tggaacagca gcacgggcca gatgctgaga  18360
gacaagttga aagagcagaa cttccaggag aaggtggcgc agggcctggc ctctggcatc  18420
agcggggtgg tggacatagc taaccaggcc gtgcagaaaa agataaacag tcatctggac  18480
ccccgtcctc aggtggagga aatgcctcca gcgatggaga cggtgtctcc cgagggcaaa  18540
ggcgaaaagc gcccgcggcc cgacagagaa gagaccctgg tgtcacacac cgaggagccg  18600
ccctcttacg aggaggcagt caaggccggc ctgcccacca ctcgccccat agcccccatg  18660
gccaccggtg tggtgggcca caggcaacac actcccgcaa cactagatct gcccccgccg  18720
tccgagccgc cgcgccagcc aaaggcggcg acggtgcccg ctccctccac ttccgccgcc  18780
aacagagtgc ccctgcgccg cgccgcgagc ggcccccggg cctcgcgagt tagcggcaac  18840
tggcagagca cactgaacag catcgtgggc ctgggagtga ggagtgtgaa gcgccgccgt  18900
tgctactgaa tgagcaagct agctaacgtg ttgtatgtgt gtatgcgtcc tatgtcgccg  18960
ccagaggagc tgttgagccg ccggcgccgt ctgcactcca gcgaatttca agatggcgac  19020
cccatcgatg atgcctcagt ggtcgtacat gcacatctcg ggccaggacg cttcggagta  19080
cctgagcccc gggctggtgc agttcgcccg cgccacagac acctacttca acatgagtaa  19140
caagttcagg aaccccactg tggcgcccac ccacgatgtg accacggacc ggtcgcagcg  19200
cctgacgctg cggttcatcc ccgtggatcg ggaggacacc gcctactctt acaaggcgcg  19260
gttcacgctg gccgtgggcg acaaccgcgt gctggacatg gcctccactt actttgacat  19320
caggggggtg ctggacaggg gccccacctt caagccctac tcgggtactg cctacaactc  19380
cctggccccc aagggcgctc ccaattcttg cgagtgggaa caagatgaac cagctcaggc  19440
agcaatagct gaagatgaag aagaacttga agaagaacaa gctcaggacg aacaggcgcc  19500
cactaagaaa acccatgtat acgcccaggc acctctttct ggtgaaaaaa ttactaagga  19560
tggtttgcaa ataggtgtgg atgccacaca ggcgggagat aaccctatat atgctgataa  19620
aacattccaa cccgaacctc agataggtga gtctcagtgg aacgaggctg atgccacagt  19680
agcaggaggc agagtcttaa aaaagaccac ccctatgaga ccttgctatg gatcctatgc  19740
caaacctact aatgccaatg gcggtcaagg gatcatggtg gccaatgatc agggagcgct  19800
tgaatctaaa gttgagatgc aatttttctc caccacaacg tctcttaatg taagggaagg  19860
tgaaaacaat cttcagccaa aagtagtgct atacagcgaa gatgttaact tggaatcccc  19920
tgacactcat ttgtcttaca aacctaaaaa ggatgacacc aactctaaaa tcatgttggg  19980
tcagcaagcc atgcccaaca gacccaacct cattgctttt agggacaact ttattggact  20040
tatgtactac aacagcacag gcaacatggg agtgctggca ggacaggcct cccagctaaa  20100
```

cgctgtggta gacttgcaag acagaaacac agagctgtca taccaactga tgcttgattc 20160
cattggagac agatcaagat acttttccat gtggaaccag gcagtggaca gctatgaccc 20220
agatgtcaga atcattgaaa accatggggt tgaagatgag ctgcccaact attgctttcc 20280
cctgggcggt attggaatta cagacacata ccagtgcata aaaccaaccg cagctgctaa 20340
taacactaca tggtctaagg atgaagaatt tagtgatcgc aatgaaatag gggtgggaaa 20400
caacttcgcc atggagatca acatccaggc caacctctgg aggaacttcc tctatgcgaa 20460
cgtggggctc tacctgccag acaagctcaa gtacaacccc accaacgtgg acatctctga 20520
caaccccaac acctatgact acatgaacaa gcgtgtggtg gctcccggcc tggtggactg 20580
ctttgtcaat gtgggagcca ggtggtccct ggactacatg gacaacgtca accccttcaa 20640
ccaccaccgc aatgcgggtc tgcgctaccg ctccatgatc ctgggcaacg ggcgctacgt 20700
gcccttccac attcaggtgc cccagaagtt ctttgccatc aagaacctcc tcctcctgcc 20760
gggctcctac acttacgagt ggaacttcag gaaggatgtc aacatggtcc tgcagagctc 20820
tctgggcaat gaccttaggg tggacggggc cagcatcaag tttgacagcg tcaccctcta 20880
tgctaccttc ttccccatgg ctcacaacac cgcctccacg ctcgaggcca tgctgaggaa 20940
cgacaccaac gaccagtcct tcaatgacta cctctctggg gccaacatgc tctaccccat 21000
ccccgccaag gccaccaacg tgcccatctc cattccctct cgcaactggg ccgccttcag 21060
aggctgggcc tttacccgcc ttaagaccaa ggaaaccccc tccctgggct cgggttttga 21120
cccctacttt gtctactcgg gatccatccc ctacctggat ggcaccttct acctcaacca 21180
cacttttaag aagatatcca tcatgtatga ctcctccgtc agctggccgg gcaatgaccg 21240
cctgctcacc cccaatgagt tcgaggtcaa gcgcgccgtg gacggcgagg gctacaacgt 21300
ggcccagtgc aacatgacca aggactggtt cctggtgcag atgctggcca actacaacat 21360
aggctaccag ggcttctaca tcccagagag ctacaaggac aggatgtact ccttcttcag 21420
aaatttccaa cccatgagca ggcaggtggt ggacgagacc aaatacaagg actatcaggc 21480
cattggcatc actcaccagc acaacaactc gggattcgtg ggctacctgg ctcccaccat 21540
gcgcgagggg caggcctacc ccgccaactt cccctacccg ttgataggca aaaccgcggt 21600
cgacagcgtc acccagaaaa agttcctctg cgaccgcacc ctctggcgca tccccttctc 21660
tagcaacttc atgtccatgg gtgcgctcac ggacctgggc cagaacctgc tctatgccaa 21720
ctccgcccat gcgctggaca tgacttttga ggtggacccc atggacgagc ccacccttct 21780
ctatattgtg tttgaagtgt tcgacgtggt cagagtgcac cagccgcacc gcggtgtcat 21840
cgagaccgtg tacctgcgca cgcccttctc ggccggcaac gccaccacct aaggagacag 21900
cgccgccgcc tgcatgacgg gttccaccga gcaagagctc agggccatcg ccagagacct 21960
gggatgcgga ccctattttt tgggcaccta tgacaaacgc ttcccgggct tcatctcccg 22020
agacaagctc gcctgcgcca tcgtcaacac ggccgcgcgc gagaccgggg gcgtgcactg 22080
gctggccttt ggctgggacc cgcgctccaa aacctgctac ctcttcgacc cctttggctt 22140
ctccgatcag cgcctcagac agatctatga gtttgagtac gaggggctgc tgcgccgcag 22200
cgcgcttgcc tcctcgcccg accgctgcat cacccttgag aagtccaccg agaccgtgca 22260
ggggccccac tcggccgcct gcggtctctt ctgctgcatg tttttgcacg cctttgtgcg 22320
ctggccccag agtcccatgg atcgcaaccc caccatgaac ttgctcaagg gagtgcccaa 22380
cgccatgctc cagagccccc aggtccagcc caccctgcgc cacaaccagg aacagctcta 22440

-continued

```
ccgcttcctg gagcgccact cccccctactt ccgcagtcac agcgcgcaca tccggggggc  22500
cacctctttc tgccacttgc aagaaaacat gcaagacgga aaatgatgta cagctcgctt  22560
tttaataaat gtaaagactg tgcactttat ttatacacgg gctctttctg gttatttatt  22620
caacaccgcc gtcgccatct agaaatcgaa agggttctgc cgcgcgtcgc cgtgcgccac  22680
gggcagagac acgttgcgat actggaagcg gctcgcccac ttaaactcgg gcaccaccat  22740
gcggggcagt ggttcctcgg ggaagttctc gccccacagg gtgcgggtca gctgcagcgc  22800
gctcaggagg tcgggagccg agatcttgaa gtcgcagttg gggccggaac cctgcgcgcg  22860
cgagttgcgg tacacggggt tgcagcactg gaacaccagc agggccggat tatgcacgct  22920
ggccagcagg ctctcgtcgc tgatcatgtc gctgtccaga tcctccgcgt tgctcagggc  22980
gaacggggtc atcttgcaga cctgcctgcc caggaaaggc ggcagcccgg gcttgccgtt  23040
gcagtcgcag cgcaggggca tcagcaggtg cccgcggccc gactgcgcct gcgggtacag  23100
cgcgcgcatg aaggcttcga tctgcctgaa agccacctgc gtcttggctc cctccgaaaa  23160
gaacatccca caggacttgc tggagaactg gttcgcggga cagctggcat cgtgcaggca  23220
gcagcgcgcg tcggtgttgg cgatctgcac cacgttgcga ccccaccggt tcttcactat  23280
cttggccttg gaagcctgct ccttcagcgc gcgctggccg ttctcgctgg tcacatccat  23340
ctctatcacc tgctccttgt tgatcatgtt tgtaccgtgc agacacttca ggtcgccctc  23400
cgtctgggtg cagcggtgct cccacagcgc gcaaccggtg ggctcccaat ttttgtgggt  23460
cacccccgcg taggcctgca ggtaggcctg caagaagcgc cccatcatgg ccacaaaggt  23520
cttctggctc gtaaaggtca gctgcaggcc gcgatgctct tcgttcagcc aggtcttgca  23580
gatggcggcc agcgcctcgg tctgctcggg cagcatccta aaatttgtct tcaggtcgtt  23640
atccacgtgg tacttgtcca tcatggcgcg cgccgcctcc atgcccttct cccaggcgga  23700
caccatgggc aggcttaggg ggtttatcac ttccaccggc gaggacaccg tactttcgat  23760
ttcttcttcc tcccccctctt cccggcgcgc gcccacgctg ctgcgcgctc tcaccgcctg  23820
caccaagggg tcgtcttcag gcaagcgccg caccgagcgc ttgccgccct tgacctgctt  23880
aatcagcacc ggcgggttgc tgaagcccac catggtcagc gccgcctgct cttcttcgtc  23940
ttcgctgtct accactatct ctggggaagg gcttctccgc tctgcggcgg cgcgcttctt  24000
tttttcttg ggagcggccg tgatggagtc cgccacggcg acggaggtcg agggcgtggg  24060
gctgggggtg cgcggtacca gggcctcgtc gccctcggac tcttcctctg actccaggcg  24120
gcggcggagt cgcttctttg ggggcgcgcg cgtcagcggc ggcggagacg gggacgggga  24180
cggggacggg acgccctcca caggggggtgg tcttcgcgca gacccgcggc cgcgctcggg  24240
ggtcttctcg agctggtctt ggtcccgact ggccattgta tcctcctcct cctaggcaga  24300
gagacataag gagtctatca tgcaagtcga gaaggaggag agcttaacca ccccctctga  24360
gaccgccgat gcgcccgccg tcgccgtcgc ccccgctgcc gccgacgcgc ccgccacacc  24420
gagcgacacc cccgcggacc cccccgccga cgcacccctg ttcgaggaag cggccgtgga  24480
gcaggacccg ggctttgtct cggcagagga ggatttgcga gaggaggagg ataaggagaa  24540
gaagccctca gtgccaaaag atgataaaga gcaagacgag cacgacgcag atgcacacca  24600
gggtgaagtc gggcgggggg acggagggca tgacggcgcc gactacctag acgaagggaa  24660
cgacgtgctc ttgaagcacc tgcatcgtca gtgcgccatt gtttgcgacg ctctgcagga  24720
gcgcagcgaa gtgcccctca gcgtggcgga ggtcagccac gcctacgagc tcagcctctt  24780
ctccccccgg gtgccccccc gccgccgcga aaacggcaca tgcgagccca acccgcgcct  24840
```

-continued caacttctac cccgcctttg tggtacccga ggtcctggcc acctatcaca tcttctttca 24900
aaattgcaag atccccctct cgtgccgcgc caaccgtagc cgcgccgata agatgctggc 24960
cctgcgccag ggcgaccaca tacctgatat cgccgctttg gaagatgtac caaagatctt 25020
cgagggtctg ggtcgcaacg agaagcgggc agcaaactct ctgcaacagg aaaacagcga 25080
aaatgagagt cacaccgggg tactggtgga gctcgagggc gacaacgccc gcctggcggt 25140
ggtcaagcgc agcatcgagg tcacccactt tgcctacccc gcgctaaacc tgccccccaa 25200
agtcatgaac gcggccatgg acgggctgat catgcgccgc ggccggcccc tcgctccaga 25260
tgcaaacttg catgaggaga ccgaggacgg ccagcccgtg gtcagcgacg agcagctggc 25320
gcgctggctg gagaccgcgg accccgccga actggaggag cggcgcaaga tgatgatggc 25380
cgtggtgctg gtcaccgtag agctggagtg tctgcagcgc ttcttcggcg accccgagat 25440
gcagagaaag gtcgaggaga ccctgcacta caccttccgc cagggctacg tgcgccaggc 25500
ttgcaagatc tccaacgtgg agctcagcaa cctggtgtcc tacctgggca tcttgcatga 25560
gaaccgcctc gggcagagcg tgctgcactc caccctgcgc ggggaggcgc gccgcgacta 25620
cgtgcgcgac tgcgtttacc tcttcctctg ctacacctgg cagacggcca tgggggtctg 25680
gcagcagtgc ctggaggagc gcaacctcaa ggagctggag aagctcctgc agcgcgcgct 25740
caaagatctc tggacgggct acaacgagcg ctcggtggcc gccgcgctgg ccgacctcat 25800
cttccccgag cgcctgctca aaaccctcca gcaggggctg cccgacttca ccagccaaag 25860
catgttgcaa aacttcagga actttatcct ggagcgttct ggcatcctac ccgccacctg 25920
ctgcgccctg cccagcgact ttgtccccct cgtgtaccgc gagtgccccc cgccgctgtg 25980
gggtcactgc tacctgttcc aactggccaa ctacctgtcc taccacgcgg acctcatgga 26040
ggactccagc ggcgaggggc tcatggagtg ccactgccgc tgcaacctct gcacgcccca 26100
ccgctccctg gtctgcaaca cccaactgct cagcgagagt cagattatcg gtaccttcga 26160
gctacagggt ccgtcctcct cagacgagaa gtccgcggct ccggggctaa aactcactcc 26220
ggggctgtgg acttccgcct acctgcgcaa atttgtacct gaagactacc acgcccacga 26280
gatcaggttt tacgaagacc aatcccgccc gcccaaggcg gagctgaccg cctgcgtcat 26340
cacccagggc gagatcctag gccaattgca agccatccaa aaagcccgcc aagacttttt 26400
gctgaagaag ggtcgggggg tgtatctgga cccccagtcg ggtgaggagc tcaacccggt 26460
tcccccgctg ccgccgccgc gggaccttgc ttcccaggat aagcatcgcc atggctccca 26520
gaaagaagca gcagcggccg ccactgccgc caccccacat gctggaggaa gaggaggaat 26580
actgggacag tcaggcagag gaggtttcgg acgaggagga gccggagacg gagatggaag 26640
agtgggagga ggacagctta gacgaggagg cttccgaagc cgaagaggca gacgcaacac 26700
cgtcaccctc ggccgcagcc ccctcgcagg cgcccccgaa gtccgctccc agcatcagca 26760
gcaacagcag cgctataacc tccgctcctc caccgccgcg acccacggcc gaccgcagac 26820
ccaaccgtag atgggacacc accggaaccg gggccggtaa gtcctccggg agaggcaagc 26880
aagcgcagcg ccaaggctac cgctcgtggc gcgctcacaa gaacgccata gtcgcttgct 26940
tgcaagactg cggggggaac atctccttcg cccgccgctt cctgctcttc caccacggtg 27000
tggccttccc ccgtaacgtc ctgcattact accgtcatct ctacagcccc tactgcggcg 27060
gcagtgagcc agagacggtc ggcggcggcg gcggcgcccg tttcggcgcc taggaagacc 27120
cagggcaaga cttcagccaa gaaactcgcg gcggccgcgg cgaacgcggt cgcgggggcc 27180

-continued

```
ctgcgcctga cggtgaacga acccctgtcg acccgcgaac tgaggaaccg aatcttcccc  27240
actctctatg ccatcttcca gcagagcaga gggcaggatc aggaactgaa agtaaaaaac  27300
aggtctctgc gctccctcac ccgcagctgt ctgtatcaca agagcgaaga ccagcttcgg  27360
cgcacgctgg aggacgctga ggcactcttc agcaaatact gcgcgctcac tcttaaggac  27420
tagctccgcg cccttctcga atttaggcgg gaacgcctac gtcatcgcag cgccgccgtc  27480
atgagcaagg acattcccac gccatacatg tggagctatc agccgcagat gggactcgcg  27540
gcgggcgcct cccaagacta ctccacccgc atgaactggc tcagtgccgg cccacacatg  27600
atctcacagg ttaatgatat ccgcacccat cgaaaccaaa tattggtgga gcaggcggca  27660
attaccacca cgccccgcaa taatcccaac cccagggagt ggcccgcgtc cctggtgtat  27720
caggaaattc ccggccccac caccgtacta cttccgcgtg attcccaggc cgaagtccaa  27780
atgactaact caggggcaca gctcgcgggc ggctgtcgtc acagggtgcg gcctcctcgc  27840
cagggtataa ctcacctgga gatccgaggc agaggtattc agctcaacga cgagtcggtg  27900
agctcctcgc tcggtctcag acctgacggg accttccaga tagccggagc cggccgatct  27960
tccttcacgc cccgccaggc gtacctgact ctgcaaagct cgtcctcggc gccgcgctcg  28020
ggcggcatcg ggactctcca gttcgtgcag gagtttgtgc cctcggtcta cttcaacccc  28080
ttctcgggct ctcccggtcg ctacccggac cagttcatct cgaactttga cgccgcgagg  28140
gactcggtgg acggctacga ctgaatgtcg ggtggacccg gtgcagagca acttcgcctg  28200
aagcacctcg accactgccg ccgccctcag tgctttgccc gctgtcagac cggtgagttc  28260
cagtactttt ccctgcccga ctcgcacccg gacggcccgg cgcacggggt gcgcttttc  28320
atcccgagtc aggtgcgctc taccctaatc agggagttta ccgcccgtcc cctactggcg  28380
gagttggaaa aggggccttc tatcctaacc attgcctgca tctgctctaa ccctggattg  28440
caccaagatc tttgctgtca tttgtgtgct gagtataata aaggctgaga tcagaatcta  28500
ctcgggctcc tgtcgccatc ctgtcaacgc caccgtccaa gcccggcccg atcagcccga  28560
ggtgaacctc acctgcggtc tgcaccggcg cctgaggaaa tacctagctt ggtactacaa  28620
cagcactccc tttgtggttt acaacagctt tgaccaggac ggggtctcac tgagggataa  28680
cctctcgaac ctgagctact ccatcaggaa gaacagcacc ctcgagctac ttcctcctta  28740
cctgcccggg acttaccagt gtgtcaccgg tccctgcacc cacacccacc tgttgatcgt  28800
aaacgactct cttccgagaa cagacctcaa taactcctct tcgcagttcc ccagaacagg  28860
aggtgagctc aggaaacccc gggtaaagaa gggtggacga gagttaacac ttgtggggtt  28920
tctggtgtat gtgacgctgg tggtggctct tttgattaag gcttttcctt ccatgtctga  28980
actctccctc ttcttttatg aacaactcga ctagtgctaa cgggacccta cccaacgaat  29040
cgggattgaa tatcggtaac caggttgcag tttcactttt gattaccttc atagtcctct  29100
tcctgctagt gctgtcgctt ctgtgcctgc ggatcggggg ctgctgcatc cacgtttata  29160
tctggtgctg gctgtttaga aggttcggag accatcgcag gtagaataaa catgctgctg  29220
cttaccctct ttgtcctggc gctggccgcc agctgccaag ccttttccga ggctgacttt  29280
atagagcccc agtgtaatgt gacttttaaa gcccatgcac agcgttgtca tactataatc  29340
aaatgtgcca ccgaacacga tgaatacctt atccagtata aagataaatc acacaaagtg  29400
gcacttgttg acatctggaa acccgaagac cctttggaat acaatgtgac cgttttccag  29460
ggtgacctct tcaaaattta caattacact ttcccatttg accagatgtg tgactttgtc  29520
atgtacatgg aaaagcagca caagctgtgg cctccgactc cccagggctg tgtggaaaat  29580
```

ccaggctctt tctgcatgat ctctctctgt gtaactgtgc tggcactaat actcacgctt 29640
ttgtatatca gatttaaatc aaggcaaagc ttcattgatg aaaagaaaat gccttaatcg 29700
ctttcacgct tgattgctaa caccgggttt ttatccgcag aatgattgga atcaccctac 29760
taatcacctc cctccttgcg attgcccatg ggttggaacg aatcgaagtc cctgtggggg 29820
ccaatgttac cctggtgggg cctgtcggca atgctacatt aatgtgggaa aaatatacta 29880
aaaatcaatg ggtctcttac tgcactaaca aaaatagcca caagcccaga gccatctgcg 29940
atgggcaaaa tctaaccttg attgatgttc aattgctgga tgcgggctac tattatgggc 30000
agctgggtac aatgattaat tactggagac cccacagaga ttacatgctc cacgtagtaa 30060
agggtcccct tagcagccca cccactacca cctctactac ccccactacc accactactc 30120
ccaccaccag cactgccgcc cagcctcctc atagcagaac aaccactttt atcaattcca 30180
agtcccactc cccccacatt gccggcgggc cctccgcctc agactccgaa accaccgaga 30240
tctgcttctg caaatgctct gacgccattg cccaggattt ggaagatcac gaggaagatg 30300
agcatgactt cgcagatgca tgccaggcat cagagccaga agcgctgccg gtggccctca 30360
aacagtatgc agacccccac accacccccg accttcctcc accttcccag aagccaagtt 30420
tcctggggga aaatgaaact ctgcctctct ccatactcgc tctgacatct gttgctatgt 30480
tgaccgctct gctggtgctt ctatgctcta tatgctacct gatctgctgc agaaagaaaa 30540
aatctcacgg ccatgctcac cagcccctca tgcacttccc ttaccctcca gagctgggcg 30600
accacaaact ttaagtctgc agtaactatc tgcccatccc ttgtcagtcg acagcgatga 30660
gccccactaa tctaacggcc tctggactta caacatcgtc tcttaatgag accaccgctc 30720
ctcaagacct gtacgatggt gtctccgcgc tggttaacca gtgggatcac ctgggcatat 30780
ggtggctcct cataggagca gtgaccctgt gcctaatcct ggtctggatc atctgctgca 30840
tcaaaagcag aagacccagg cggcggccca tctacaggcc ctttgtcatc acacctgaag 30900
atgatgatga caccacttcc aggctgcaga ggctaaagca gctactcttc tcttttacag 30960
catggtaaat tgaatcatgc ctcgcatttt catctacttg tctctccttc cactttttct 31020
gggctcttct acattggccg ctgtgtccca catcgaggta gactgcctca cgcccttcac 31080
agtctacctg cttttcggct ttgtcatctg cacctttgtc tgcagcgtta tcactgtagt 31140
gatctgcttc atacagtgca tcgactacgt ctgcgtgcgg gtggcttact ttagacacca 31200
cccccagtat cgcaacaggg acatagcggc tctcctaaga cttgtttaaa atcatggcca 31260
aattaactgt gattggtctt ctgatcatct gctgcgtcct agccgcgatt gggactcaag 31320
ctcctaccac caccagcgct cccagaaaga gacatgtatc ctgcagcttc aagcgtccct 31380
ggaatatacc ccaatgcttt actgatgaac ctgaaatctc tttggcttgg tacttcagcg 31440
tcaccgccct tcttatcttc tgcagtacgg ttattgccct tgccatctac ccttcccttg 31500
acctgggctg gaatgctgtc aactctatgg aatatcccac cttcccagaa ccagacctgc 31560
cagacctggt tgttctaaac gcgtttcctc ctcctgctcc cgttcaaaat cagtttcgcc 31620
ctccgtcccc cacgcccact gaggtcagct actttaatct aacaggcgga gatgactgaa 31680
aacctagacc tagaaatgga cggtctctgc agcgagcaac gcacactaga gaggcgccgg 31740
caaaaagagc tcgagcgtct taaacaagag ctccaagacg cggtggccat acaccagtgc 31800
aaaaaaggtg tcttctgtct ggtaaaacag gccacgctca cctatgaaaa aacaggtgac 31860
acccaccgcc taggatacaa gctgcccaca cagcgccaaa agttcgccct catgataggc 31920

-continued

```
gaacaaccca tcaccgtgac ccagcactcc gtggagacag aaggctgcat acatgctccc  31980
tgtaggggcg ctgactgcct ctacaccttg atcaaaaccc tctgcggtct cagagacctt  32040
atccctttca attaatcata actgtaatca ataaaaaatc acttacttga aatctgatag  32100
caagcctctg tccaattttt tcagcaacac ttccttcccc tcctcccaac tctggtactc  32160
taggcgcctc ctagctgcaa acttcctcca cagtctgaag ggaatgtcag attcctcctc  32220
ctgtccctcc gcacccacga tcttcatgtt gttgcagatg aaacgcgcga gatcgtctga  32280
cgagaccttc aaccccgtgt accccctacga taccgagatc gctccgactt ctgtcccttt  32340
ccttacccct ccctttgtgt catccgcagg aatgcaagaa aatccagctg ggtgctgtc  32400
cctgcacttg tcagagcccc ttaccaccca caatggggcc ctgactctaa aaatgggggg  32460
cggcctgacc ctggacaagg aagggaatct cacttcccaa aacatcacca gtgtcgatcc  32520
ccctctcaaa aaaagcaaga acaacatcag ccttcagacc gccgcacccc tcgccgtcag  32580
ctccggggcc ctaacacttt ttgccactcc ccccctagcg gtcagtggtg acaaccttac  32640
tgtgcagtct caggcccctc tcactttgga agactcaaaa ctaactctgg ccaccaaagg  32700
acccctaact gtgtccgaag gcaaactt                                    32728
```

<210> SEQ ID NO 23
<211> LENGTH: 32728
<212> TYPE: DNA
<213> ORGANISM: Artificial sequence
<220> FEATURE:
<223> OTHER INFORMATION: Adenovirus vector nucleotide sequences

<400> SEQUENCE: 23

```
ataatatacc ttattttgga ttgtggccaa tatgataatg aggtgggcgg ggagaggcgg     60
ggcgggtgac gtaggacgcg cgagtagggt tgggaggtgt ggcggaagtg tggcatttgc    120
aagtgggagg agctcacatg caagcttccg tcgcggaaaa tgtgacgttt ttgatgagcg    180
ccgcctacct ccggaagtgc caattttcgc gcgcttttca ccggatatcg tagtaatttt    240
gggcgggacc atgtaagatt tggccatttt cgcgcgaaaa gtgaaacggg gaagtgaaaa    300
ctgaataata gggcgttagt catagcgcgt aatatttacc gagggccgag ggactttgac    360
cgattacgtg gaggactcgc ccaggtgttt tttacgtgaa tttccgcgtt ccgggtcaaa    420
gtctccgttt ttattgtcac cgtcatttga cgcggagggt atttaaaccc gctgcgctcc    480
tcaagaggcc actcttgagt gccagcgaga agagttttct cctctgctcc gcttcggtga    540
tcgaaaaatg agacacatag cctgcactcc gggtcttttg tccggtcggg cggcggccga    600
gcttttggac gctttgatca atgatgtcct aagcgatgat tttccgtcta ctacccactt    660
tagcccacct actcttcacg aactgtacga tctggatgta ctggtggatg tgaacgatcc    720
caacgaggag gcggtttctg cgttttttcc cgagtctgcg ctgttggccg ctcaggaggg    780
atttgaccta cacactccgc cgcctatttt agagtctccg ctgccggagc ccagtggtat    840
accttatatg cctgaactgc ttcccgaagt ggtagacctg acctgccacg agcctggctt    900
tccgcccagc gacgatgagg gtgagccttt tgttttagac tttgctgaga tacctgggca    960
cggttgcagg tcttgtgcat atcatcagag ggttaccgga gaccccgagg ttaagtgttc   1020
gctgtgctat atgaggatga cctcttcctt tatctacagt aagtttttgt ctaggtgggc   1080
ttttgggtag gtgggttttg tgtcagaaca ggtgtaaacg ttgcttgtgt tttttgtacc   1140
tgtaggtccg gtgtccgagc cagacccgga gcccgaccgc gatcccgagc cggatcccga   1200
gcctcctcgc aggacaagga aactaccttc cattctgtgc aagtctcaga cacctgtaag   1260
```

gaccagcgag gcagacagca ccgactctgg cacttctacc tctcccctg aaattcaccc 1320
agtggttcct ctgggtatac ataaacctgt tgctgttaaa gtttgcgggc gacgccctgc 1380
agtacagtgc attgaggact tgcttcacga tcccgaggaa cctttggact tgagccttaa 1440
acgccctagg caataaaccc cacctaagta ataaacccca cctaagtaat aaaccctgcc 1500
gcccttggtt attgagatga cgcccaatgt ttgcttttga atgacttcat gtgtgtaata 1560
aaagtgagtg tgatcatagg tctcttgttt gtctgggcgg ggcttaaggg tatataagtc 1620
tcttggggct aaacttggtt acacttgacc ccaatggagg cgtgggggtg cttggaggag 1680
tttgcggacg tgcgccgttt gctggacgag agctctagca atacctatac tatttggagg 1740
tatctgtggg gctctactca ggccaagttg gtttccagaa ttaagcagga ttacaagtgc 1800
gattttgaag agctttttag ttcctgcggt gagcttttgc aatccttgaa tctgggccat 1860
caggctattt tccaggaaaa ggttctctcg actttggatt tttccactcc cgggcgcacc 1920
gccgcttgtg tggcttttgt gtcttttgtg caagataaat ggagcgagga gacccacctg 1980
agtcacggct acgtactgga tttcatggcg atggctcttt ggagggctca caacaaatgg 2040
aagattcaga aggaactgta cggttccgcc ctacgtcgtc cacttctgtc gcgacagggg 2100
ctgaggtttc ccgaccatcg gcagcatcag aatctggaag acgagtcgga ggagcgagcg 2160
gaggagaaga tcagcttgag agccggcctg gaccctcctc aggaggaatg aatctcccgc 2220
aggtggttga cctgtttcca gaactgagac gggtcctgac tatcagggag gatggtcagt 2280
ttgtgaagaa gtttaagagg gatcggggtg agggagatga tgaggcggct agcaatttag 2340
cttttagtct gatgactcgc caccgaccgg aatgtattac ctatcagcag attaaggaga 2400
gttgtgccaa cgagctggat cttttgggtc agaagtatag catagaacag cttaccactt 2460
actggcttca gcctggggat gattgggaag aggcgatcag ggtgtatgca aaggtggccc 2520
tgcggcccga ttgcaagtat aagattacta agttggttaa tattagaaac tgctgctata 2580
tttctgggaa cggggccgaa gtggagatag atactcagga cagggtggct tttaggtgtt 2640
gcatgataaa catgtggccc gggatactgg ggatggatgg ggtggtattc atgaatgtga 2700
ggtttacggg ccccaacttt aatggcacgg tgttcatggg caacaccaac ttgctcctgc 2760
atggtgcgag tttctatggg tttaataaca cctgtataga ggcctggacc gatgtaaagg 2820
ttcgaggttg ttccttttat agctgttgga aggcggtggt gtgtcgccct aaaagcaggg 2880
gttctgtgaa aaaatgcttg tttgaaaggt gcaccttagg catcctctct gagggcaact 2940
ccagggtgcg ccataatgtg gcttcgaact gcggttgctt catgcaagtg aagggggtga 3000
gcgttatcaa gcataactcg gtgtgtggaa actgcgagga tcgcgcctcc cagatgctga 3060
cctgctttga tggcaactgt cacctgttga agaccattca tataagcagc caccccagaa 3120
aggcctggcc cgtgtttgag cataacatct tgacccgctg ctccttgcat ctgggggtca 3180
ggaggggtat gttcctgcct taccagtgta actttagcca cactaaaatc ctgctggaac 3240
ccgagtgcat gaccaaggtc agcctgaatg gtgtgtttga tgtgactctg aaaatctgga 3300
aggtgctgag gtatgatgag accaggacca ggtgccgacc ctgcgagtgc ggcggcaagc 3360
acatgagaaa tcagcctgtg atgttggatg tgaccgagga gcttaggcct gaccatctgg 3420
tgctggcctg caccagggcc gagtttgggt ctagcgatga ggataccgat tgaggtgggt 3480
aaggtgggcg tggctagaag ggtggggcgt gtataaattg gggtctaag ggtctctctg 3540
ttttgtcttg caacagccgc cgccatgagc gacaccggca acagctttga tggaagcatc 3600

-continued

```
tttagcccct atctgacagt gcgcatgcct cactgggctg gagtgcgtca gaatgtgatg   3660
ggttccaacg tggatggacg ccccgttctg ccttcaaatt cgtctacaat ggcctacgcg   3720
accgtgggag gaactccgct ggacgccgcg acctccgccg ccgcctccgc cgccgccgcg   3780
accgcgcgca gcatggctac ggacctttac agctctttgg tggcgagcgg cgcggcctct   3840
cgcgcgtctg ctcgggatga gaaactgacc gctctgctgc ttaaactgga agacttgacc   3900
cgggagctgg gtcaactgac ccagcaggtc tccagcttgc gtgagagcag ccttgcctcc   3960
ccctaatggc ccataatata aataaaagcc agtctgtttg gattaagcaa gtgtatgttc   4020
tttatttaac tctccgcgcg cggtaagccc gggaccagcg gtctcggtcg tttagggtgc   4080
ggtggattct ttccaacacg tggtacaggt ggctctggat gtttagatac atgggcatga   4140
gtccatccct ggggtggagg tagcaccact gcagagcttc gtgctcgggg gtggtgttgt   4200
atatgatcca gtcgtagcag gagcgctggg cgtggtgctg aaaaatgtcc ttaagcaaga   4260
ggcttatagc taggggggagg cccttggtgt aagtgtttac aaatctgctc agttgggagg   4320
ggtgcatccg gggggatata atgtgcatct tggactggat ttttaggttg gctatgttcc   4380
cacccagatc ccttctggga ttcatgttgt gcaggaccac cagcacggta tatccagtgc   4440
acttgggaaa tttatcgtgg agcttagacg ggaatgcatg gaagaacttg gagacgccct   4500
tgtggcctcc cagattttcc atacattcgt ccatgatgat ggcaatgggc ccgtgggaag   4560
ctgcctgagc aaaaatgttt ctgggatcgc tcacatcgta gttatgttcc agggtgaggt   4620
catcatagga catctttacg aatcgggggc ggagggtccc ggactggggg atgatggtac   4680
cctcgggccc cggggcgtag ttcccctcac agatctgcat ctcccaggct ttcatttcag   4740
agggagggat catatccacc tgcggagcga tgaaaaacac agtttctggc gcagggggaga   4800
ttaactggga tgagagcagg tttctgagca gctgtgactt tccacagccg gtgggcccat   4860
atatcacgcc tatcaccggc tgcagctggt agttaagaga gctgcagctg ccgtcctccc   4920
ggagcagggg ggccacctcg ttcagcatat ccctgacgtg gatgttctcc ctgaccaatt   4980
ccgccagaag gcgctcgccg cccagcgaaa gcagctcttg caaggaagca aatttttca   5040
gcggttttag gccgtcggcc gtgggcatgt ttttcagcgt ctgggtcagc agttccagcc   5100
tgtcccacag ctcggtgatg tgctctacgg catctcgatc cagcagatct cctcgtttcg   5160
cgggttgggg cggctttcgc tgtagggcac cagccgatgg gcgtccagcg ggccagagt   5220
catgtccttc catgggcgca gggtcctcgt cagggtggtc tgggtcacgg tgaaggggtg   5280
cgctccgggt tgggcgctgg ccagggtgcg cttgaggctg gttctgctgg tgctgaatcg   5340
ctgccgctct tcgccctgcg cgtcggccag gtagcatttg accatggtct cgtagtcgag   5400
accctcggcg gcgtgcccct tggcgcggag ctttcccttg gaggtggcgc cgcacgaggg   5460
gcactgcagg ctcttcaggg cgtagagctt gggagcgaga aacacggact ctggggagta   5520
ggcgtccgcg ccgcaggaag cgcagaccgt ctcgcattcc accagccaag tgagctccgg   5580
gcggtcaggg tcaaaaacca ggttgccccc atgcttttg atgcgtttct tacctcggct   5640
ctccatgagg cggtgtccct tctcggtgac gaagaggctg tccgtgtccc cgtagaccga   5700
cttcaggggc ctgtcttcca gcggagtgcc tctgtcctcc tcgtagagaa actctgacca   5760
ctctgagacg aaggcccgcg tccaggccag gacgaaggag gccacgtggg aggggtagcg   5820
gtcgttgtcc actagcgggt ccaccttctc cagggtgtgc aggcacatgt ccccctcctc   5880
cgcgtccaga aaagtgattg gcttgtaggt gtaggacacg tgaccggggg ttcccgacgg   5940
gggggtataa aagggggtgg gcgccctttc atcttcactc tcttccgcat cgctgtctgc   6000
```

gagggccagc tgctggggta agtattccct ctcgaaggcg ggcatgacct cagcgctcag 6060
gttgtcagtt tctaaaaatg aggaggattt gatgttcacc tgtccggagg tgataccttt 6120
gagggtacct gggtccatct ggtcagaaaa cactattttt ttgttgtcaa gcttggtggc 6180
gaacgacccg tagagggcgt tggagagcag cttggcgatg gagcgcaggg tctggttttt 6240
gtcgcggtcg gctcgctcct tggccgcgat gttgagttgc acgtactcgc gggccacgca 6300
cttccactcg gggaagacgg tggtgcgctc gtctgggatt aggcgcaccc tccagcctcg 6360
gttgtgcagg gtgaccatgt cgacgctggt ggcgacctcg ccgcgcaggc gctcgttggt 6420
ccagcagagg cggccgccct tgcgcgagca gaaggggggt agggggtcca gctggtcctc 6480
gtttgggggg tccgcgtcga tggtgaagac cccggggagc aagcgcgggt caaagtagtc 6540
gatcttgcaa gcttgcatgt ccagagcccg ctgccattcg cgggcggcga gcgcgcgctc 6600
gtaggggttg aggggcgggc cccagggcat ggggtgggtg agcgcggagg cgtacatgcc 6660
gcagatgtca tacacgtaca ggggttccct gaggatgccg aggtaggtgg ggtagcagcg 6720
ccccccgcgg atgctggcgc gcacgtagtc atagagctcg tgggaggggg ccagcatgtt 6780
gggcccgagg ttggtgcgct gggggcgctc ggcgcggaag gcgatctgcc tgaagatggc 6840
atgggagttg gaggagatgg tgggccgctg gaagacgttg aagcttgctt cttgcaagcc 6900
caccgagtcc ctgacgaagg aggcgtagga ctcgcgcagc ttgtgcacca gctcggcggt 6960
gacctggacg tcgagcgcgc agtagtcgag ggtctcgcgg atgatgtcat acttatcctc 7020
ccccttcttt ttccacagct cgcggttgag gacgaactct tcgcggtctt tccagtactc 7080
ttggagggga aacccgtccg tgtccgaacg gtaagagcct agcatgtaga actggttgac 7140
ggcctggtag gggcaacagc ccttctccac gggcagcgcg taggcctgcg ccgccttgcg 7200
gagggaggtg tgggtgaggg cgaaagtgtc cctgaccatg actttgaggt attgatgttt 7260
gaagtctgtg tcatcgcagc cgccctgttc ccacagggtg tagtccgtgc gctttttgga 7320
gcgcgggttg ggcagggaga aggtgaggtc attgaagagg atcttccccg ctcgaggcat 7380
gaagtttctg gtgatgcgaa agggccctgg gaccgaggag cggttgttga tgacctgggc 7440
ggccaggacg atctcgtcaa agccgtttat gttgtggccc acgatgtaga gctccaaaaa 7500
gcggggctgg cccttgatgg aggggagctt tttgagttcc tcgtaggtga gctcctcggg 7560
cgattccagg ccgtgctcct ccagggccca gtcttgcaag tgagggttgg ccgccaggaa 7620
ggatcgccag aggtcgcggg ccatgagggt ctgcaggcgg tcgcggaagg ttctgaactg 7680
tcgccccacg gccatctttt cggggggtgat gcagtagaag gtgagggggt ctttctccca 7740
ggggtcccat ctgagctctc gggcgaggtc gcgcgcggcg gcgaccagag cctcgtcgcc 7800
ccccagtttc atgaccagca tgaagggcac gagctgcttg ccaaaggctc ccatccaagt 7860
gtaggtctct acatcgtagg tgacaaagag gcgctccgtg cgaggatgag agccgatcgg 7920
gaagaactgg atctcccgcc accagttgga ggattggctg ttgatgtggt gaaagtagaa 7980
gtcccgtctg cgggccgagc actcgtgctg gcttttgtaa aagcgaccgc agtactggca 8040
gcgctgcacg ggttgtatat cttgcacgag gtgaacctgg cgacctctga cgaggaagcg 8100
cagcgggaat ctaagtcccc cgcctggggt cccgtgtggc tggtggtctt ctactttggt 8160
tgtctggccg ccagcatctg tctcctggag ggcgatggtg gagcagacca ccacgccgcg 8220
agagccgcag gtccagatct cggcgctcgg cgggcggagt ttgatgacga catcgcgcac 8280
attggagctg tccatggtct ccagctcccg cggcggcagg tcagctggga gttcctggag 8340

-continued

```
gttcacctcg cagagacggg tcaaggcgcg ggcagtgttg agatggtatc tgatttcaag   8400
gggcgtgttg gcggcggagt cgatggcttg caggaggccg cagccccggg gggccacgat   8460
ggttccccgc ggggcgcgag gggaggcgga agctgggggt gtgttcagaa gcggtgacgc   8520
gggcgggccc ccggaggtag ggggggttcc ggccccacag gcatgggcgg caggggcacg   8580
tcttcgccgc gcgcgggcag gggctggtgc tggctccgaa gagcgcttgc gtgcgcgacg   8640
acgcgacggt tggtgtcctg tatctgacgc ctctgagtga agaccacggg tcccgtgacc   8700
ttgaacctga aagagagttc gacagaatca atctcggcat cgttgacagc ggcctggcgc   8760
aggatctcct gcacgtcgcc cgagttgtcc tggtaggcga tctctgccat gaactgctcg   8820
atctcttctt cctggagatc tcctcgtccg gcgcgctcca cggtggccgc caggtcgttg   8880
gagatgcgac ccatgagctg tgagaaggcg ttgagcccgc cctcgttcca gacccggctg   8940
tagaccacgc ccccctcggc gtcgcgagcg cgcatgacca cctgggccag gttgagctcc   9000
acgtgtcgcg tgaagacggc gtagttgcgc aggcgctgga aaaggtagtt cagggtggtg   9060
gcggtgtgct cggcgacgaa gaagtacatg acccagcgcc gcaacgtgga ttcattgatg   9120
tcccccaagg cctccaggcg ctccatggcc tcgtagaagt ccacggcgaa gttgaaaaac   9180
tgggagttgc gagcggacac ggtcaactcc tcctccagaa gacggatgag ctcggcgaca   9240
gtgttgcgca cctcgcgctc gaaggccacg gggggcgctt cttcctcttc cacctcttct   9300
tccatgatcg cttcttcttc ttcctcagcc gggacgggag gggggcggcgg cggcggggga   9360
ggggcgcggc ggcggcggcg gcgcaccggg aggcggtcga tgaagcgctc gatcatctcc   9420
ccccgcatgc ggcgcatggt ctcggtgacg gcgcggccgt tctcccgggg gcgcagctcg   9480
aagacgccgc ctctcatctc gccgcggggc gagcggccgt gaggtagcga gacggcgctg   9540
actatgcatc ttaacaattg ctgtgtaggt acaccgccga gggacctgat tgagtccaga   9600
tccaccggat ccgaaaacct ttggaggaaa gcgtctatcc agtcgcagtc gcaaggtagg   9660
ctgagcaccg tggcgggcgg gggcgggtct ggagagttcc tggcggagat gctgctgatg   9720
atgtaattaa agtaggcggt cttgagaagg cggatggtgg acaggagcac catgtctttg   9780
ggtccggcct gttggatgcg gaggcggtcg gccatgcccc aggcctcgtt ctgacaccgg   9840
cgcaggtctt tgtagtagtc ttgcatgagt ctttccaccg gcacctcttc tccttcctct   9900
tctccatctc gccggtggtt tctcgcgccg cccatgcgcg tgaccccaaa gcccctgagc   9960
ggctgcagca gggccaggtc ggcgaccacg cgctcggcca agatggcctg ctgcacctga  10020
gtgagggtcc tctcgaagtc atccatgtcc acgaagcggt ggtaggcgcc cgtgttgatg  10080
gtgtaggtgc agttggccat gacggaccag ttgacggtct ggtgtcccgg ctgcgagagc  10140
tccgtgtacc gcaggcgcga gaaggcgcgg gaatcgaaca cgtagtcgtt gcaagtccgc  10200
accagatact ggtagcccac caggaagtgc ggcggaggtt ggcgatagag gggccagcgc  10260
tgggtggcgg gggcgccggg cgccaggtct tccagcatga ggcggtggta tccgtagatg  10320
tacctggaca tccaggtgat gccggcggcg gtggtggtgg cgcgcgcgta gtcgcggacc  10380
cggttccaga tgtttcgcag gggcgagaag tgttccatgg tcggcacgct ctggccggtg  10440
aggcgcgcgc agtcgttgac gctctataca cacacaaaaa cgaaagcgtt tacagggctt  10500
tcgttctgta gcctggagga aagtaaatgg gttgggttgc ggtgtgcccc ggttcgagac  10560
caagctgagc tcggccggct gaagccgcag ctaacgtggt attggcagtc ccgtctcgac  10620
ccaggccctg tatcctccag gatacggtcg agagcccttt tgctttcttg gccaagcgcc  10680
cgtggcgcga tctgggatag atggtcgcga tgagaggaca aaagcggctc gcttccgtag  10740
```

tctggagaaa caatcgccag ggttgcgttg cggcgtaccc cggttcgagc ccctatggcg 10800
gcttgaatcg gccggaaccg cggctaacga gggccgtggc agccccgtcc tcaggacccc 10860
gccagccgac ttctccagtt acgggagcga gccccttttg ttttttattt tttagatgca 10920
tcccgtgctg cggcagatgc gcccctcgcc ccggcccgat cagcagcagc aacagcaggc 10980
atgcagaccc ccctctcccc tttccgcccc ggtcaccacg gccgcggcgg ccgtgtcggg 11040 cgcgggggc gcgctggagt cagatgagcc accgcggcgg cgacctaggc agtatctgga 11100
cttggaagag ggcgagggac tggcgcggct gggggcgaac tctccagagc gccacccgcg 11160
ggtgcagttg aaaagggacg cgcgcgaggc gtacctgccg cggcagaacc tgtttcgcga 11220
ccgcgggggc gaggagcccg aggagatgcg agactgcagg ttccaagcgg ggcgcgagct 11280
gcggcgcggg ctggacagac agcgcctgct gcgcgaggag gactttgagc ccgacacgca 11340
gacgggcatc agccccgcgc gcgcgcacgt agccgcggcc gacctggtga ccgcctacga 11400
gcagacggta aaccaggagc gcaacttcca aaagagcttc aacaaccacg tgcgcacgct 11460
ggtggcgcgc gaggaggtga ccctgggtct catgcatctg tgggacctgg tggaggcgat 11520
cgtgcagaac cccagcagca agcccctgac cgcgcagctg ttcctggtgg tgcagcacag 11580
cagggacaac gaggccttca gggaggcgct gctgaacatc accgagccgg aggggcgctg 11640
gctcctggac ctgataaaca tcctgcagag catagtggtg caggagcgca gcctgagcct 11700
ggccgagaag gtggcggcca tcaactactc tatgctgagc ctgggcaagt tctacgcccg 11760
caagatctac aagaccccct acgtgcccat agacaaggag gtgaagatag acagcttcta 11820
catgcgcatg gcgctgaagg tgctgaccct gagcgacgac ctgggagtgt accgcaacga 11880
gcgcatccac aaggccgtga gcgccagccg gcggcgcgag ctgagcgacc gcgagctgat 11940
gcacagtctg cagcgcgcgc tgaccggcgc gggcgagggc gacagggagg tcgagtccta 12000
cttcgacatg gggggccgacc tgcactggca gccgagccgc cgcgccctgg aggcggcggg 12060
ggcgtacggc ggccccctgg cggccgatga ccaggaagag gaggactatg agctagagga 12120
gggcgagtac ctggaggact gacctggctg gtggtgtttt ggtatagatg caagatccga 12180
acgtggcgga cccggcggtc cgggcggcgc tgcaaagcca gccgtccggc attaactcct 12240
ctgacgactg ggccgcggcc atgggtcgca tcatggccct gaccgcgcgc aaccccgagg 12300
ctttcaggca gcagcctcag gccaaccggc tggcggccat cttggaagcg gtagtgcccg 12360
cgcgctccaa ccccacccac gagaaggtgc tggccatagt caacgcgctg gcggagagca 12420
gggccatccg cgcggacgag gccggactgg tgtacgatgc gctgctgcag cgggtggcgc 12480
ggtacaacag cggcaacgtg cagaccaacc tggaccgcct ggtgacggac gtgcgcgagg 12540
ccgtggcgca gcgcgagcgc ttgcatcagg acggtaacct gggctcgctg gtggcgctaa 12600
acgccttcct cagcacccag ccggccaacg taccgcgggg gcaggaggac tacaccaact 12660
ttttgagcgc gctgcggctg atggtgaccg aggtccctca gagcgaggtg taccagtcgg 12720
ggcccgacta cttcttccag accagcagac agggcttgca aaccgtgaac ctgagccagg 12780
ctttcaagaa cctgcggggg ctgtggggag tgaaggcgcc caccggcgac cgggctacgg 12840
tgtccagcct gctaaccccc aactcgcgcc tgctgctgct gctgatcgcg cccttcacgg 12900
acagcgggag cgtctcgcgg gagacctatc tgggccacct gctgacgctg taccgcgagg 12960
ccatcgggca ggcgcaggtg gacgagcaca ccttccaaga gatcaccagc gtgagccacg 13020
cgctggggca ggaggacacg ggcagcctgc aggcgaccct gaactacctg ctgaccaaca 13080

-continued

```
ggcggcagaa gattcccacg ctgcacagcc tgacccagga ggaggagcgc atcttgcgct  13140
acgtgcagca gagcgtgagc ctgaacctga tgcgcgacgg cgtgacgccc agcgtggcgc  13200
tggacatgac cgcgcgcaac atggaaccgg gcatgtacgc ctcccaccgg ccgtttatca  13260
accgcctgat ggactacttg catcgggcgg cggccgtgaa ccccgagtac ttcactaatg  13320
ccattctgaa tccccactgg atgcccccctc cgggtttcta caacggggac tttgaggtgc  13380
ccgaggtcaa cgacgggttc ctctgggatg acatggatga cagtgtgttc tcacccaacc  13440
cgctgcgcgc cgcgtctctg cgattgaagg agggctctga cagggaagga ccgaggagtc  13500
tggcctcctc cctggctctg ggagcggtgg gcgccacggg cgcggcggcg cggggcagta  13560
gcccccttccc cagcctggca gactctctga acagcgggcg ggtgagcagg ccccgcttgc  13620
taggcgagga ggagtatctg aacaactccc tgctgcagcc cgcgagggac aagaacgctc  13680
agcggcagca gtttcccaac aatgggatag agagcctggt ggacaagatg tccagatgga  13740
agacgtatgc gcaggagtac aaggagtggg aggaccgcca gccgcggccc ttgccgcccc  13800
ctaggcagcg ctggcagcgg cgcgcgtcca accgccgctg gaggcagggg cccgaggacg  13860
atgatgactc tgcagatgac agcagcgtgt tggacctggg cgggagcggg aaccccctttt  13920
cgcacctgcg cccacgcctg ggcaagatgt tttaaaagaa aaaaaaaata aaactcacca  13980
aggccatggc gacgagcgtt ggtttttttgt tcccttcctt agtatgcggc gcgcggcgat  14040
gttcgaggag ggcctccccc cctcttacga gagcgcgatg ggatttctc ctgcggcgcc  14100
cctgcagcct ccctacgtgc ctcctcggta cctgcaacct acagggggga gaaatagcat  14160
ctgttactct gagctgcagc ccctgtacga taccaccaga ctgtacctgg tggacaacaa  14220
gtccgcggac gtggcctccc tgaactacca gaacgaccac agcgattttt tgaccacggt  14280
gatccaaaac aacgacttca ccccaaccga ggccagcacc cagaccataa acctggataa  14340
caggtcgaac tggggcggcg acctgaagac catcttgcac accaacatgc ccaacgtgaa  14400
cgagttcatg ttcaccaact cttttaaggc gcgggtgatg gtggcgcgcg agcagggggga  14460
ggcgaagtac gagtgggtgg acttcacgct gcccgagggc aactactcag agaccatgac  14520
tctcgacctg atgaacaatg cgatcgtgga acactatctg aaagtgggca ggcagaacgg  14580
ggtgaaggaa agcgatatcg ggtcaagtt tgacaccaga aacttccgtc tgggctggga  14640
ccccgtgacc gggctggtca tgccgggggt ctacaccaac gaggcctttc atcccgacat  14700
agtgcttctg cccggctgtg ggtggactt cacccagagc cggctgagca acctgctggg  14760
cattcgcaag cggcagcctt tccaggaggg tttcaagatc acctatgagg atctgaaggg  14820
gggcaacatt cccgcgctcc ttgatctgga cgcctacgag gagagcttga aacccgagga  14880
gagcgctggc gacagcggcg agagtggcga ggagcaagcc ggcggcggtg gcggcgcgtc  14940
ggtagaaaac gaaagtacgc ccgcagtggc ggcggacgct gcggaggtcg agccggaggc  15000
catgcagcag gacgcagagg agggcgcaca ggagggcgcg cagaaggaca tgaacgatgg  15060
ggagatcagg ggagacacat tcgccacccg gggcgaagaa aaagaggcag aggcggcggc  15120
ggcggcgacg gcggaggccg aaaccgaggt tgaggcagag gcagagcccg agaccgaagt  15180
tatggaagac atgaatgatg gagaacgtag gggcgacacg ttcgccaccc ggggcgaaga  15240
gaaggcggcg gaggcagaag ccgcggctga ggaggcggct gcggctgcgg ccaagactga  15300
ggctgcggct aaggctgagg tcgaagccaa tgttgcggtt gaggctcagg ctgaggagga  15360
ggcggcggct gaagcagtta aggaaaaggc ccaggcagag caggaagaga aaaaacctgt  15420
cattcaacct ctaaaagaag atagcaaaaa gcgcagttac aacgtcatcg agggcagcac  15480
```

-continued

```
ctttacccag taccgcagct ggtacctggc gtacaactac ggcgacccgg tcaagggggt  15540
gcgctcgtgg accctgctct gcacgccgga cgtcacctgc ggctccgagc agatgtactg  15600
gtcgctgccg aacatgatgc aagacccggt gaccttccgc tccacgcggc aggttagcaa  15660
cttcccggtg gtgggcgccg aactgctgcc cgtgcactcc aagagttttt acaacgagca  15720
ggccgtctac tcccagctga tccgccaggc cacctctctg acccacgtgt tcaatcgctt  15780
tcccgagaac cagattttgg cgcgcccgcc ggcccccacc atcaccaccg tgagtgaaaa  15840
cgttcctgcc ctcacagatc acgggacgct accgctgcgc aacagcatct caggagtcca  15900
gcgagtgacc attactgacg ccagacgccg gacctgcccc tacgtttaca aggccttggg  15960
catagtctcg ccgcgcgtcc tctccagtcg cactttttaa aacacatcta cccacacgtt  16020
ccaaaatcat gtccgtactc atctcaccca gcaacaacac cggctggggg ctgcgcgcgc  16080
ccagcaagat gtttggaggg gcgaggaagc gctccgacca gcaccctgtg cgcgtgcgcg  16140
gccactaccg cgcgccctgg ggagcgcaca agcgcgggcg cacagggcgc accactgtgg  16200
acgacgtcat tgactccgta gtggagcaag cgcgccacta cacacccggc gcgccgaccg  16260
cccccgccgt gtccaccgtg gaccaggcga tcgaaagcgt ggtacagggc gcgcggcact  16320
atgccaacct taaaagtcgc cgccgccgcg tggcccgccg ccatcgccgg agaccccggg  16380
ccaccgccgc cgcgcgcctt actaaggctc tgctcaggcg cgccaggcga actggccacc  16440
gggccgccat gagggccgca cggcgggctg ccgctgccgc aagcgtcgtg gccccgcggg  16500
cacgaaggcg cgcggccgct gccgccgccg ccgccatttc cagcttggcc tcgacgcggc  16560
gcggtaacat atactgggtg cgcgactcgg taaccggcac gcgggtaccc gtgcgctttc  16620
gcccccgcg gaattagcac aagacaacat acacactgag tctcctgctg ttgtgtatcc  16680
cagcggcgac cgtcagcagc ggcgacatgt ccaagcgcaa aattaaagaa gagatgctcc  16740
aggtcatcgc gccggagatc tatgggcccc cgaagaagga ggaggatgat tacaagcccc  16800
gcaagctaaa gcgggtcaaa aagaaaaaga aagatgatga tgacgaggcg gtggagtttg  16860
tccgccgcat ggcacccagg cgccccgtgc agtggaaggg ccggcgcgtg cagcgcgttt  16920
tgcgccccgg caccgcggtg gtcttcacgc ccggcgagcg ctccacgcgc actttcaagc  16980
gggtgtacga tgaggtgtac ggcgacgagg acctgttgga gcaggccaac cagcgctttg  17040
gggagtttgc atatgggaaa cggccccgcg agagtctaaa agaggacctg ctggcgctac  17100
cgctggacga gggcaatccc accccgagtc tgaagccggt aaccctgcaa caggtgctgc  17160
ctttgagcgc gcccagcgag cataagcgag ggttgaagcg cgaaggcggg gacctggcgc  17220
ccaccgtgca gttgatggtg cccaagcggc agaagctgga ggacgtgctg gagaaaatga  17280
aagtagagcc cgggatccag cccgagatca aggtccgccc catcaagcag gtggcgcccg  17340
gcgtgggagt ccagaccgtg gacgttagga ttcccacgga ggagatggaa acccaaaccg  17400
ccactccctc ttcggcggcc agcgccacca ccggcaccgc ttcggtagag gtgcagacgg  17460
acccctggct acccgccacc gctgttgccg ccgccgcccc ccgttcgcgc gggcgcaaga  17520
gaaattatcc agcggccagc gcgctcatgc cccagtacgc actgcatcca tccatcgtgc  17580
ccacccccgg ctaccgcggg tactcgtacc gcccgcgcag atcagccggc actcgcggcc  17640
gccgccgccg tgcgaccaca accagccgcc gccgtcgccg ccgccgccag ccagtgctga  17700
cccccgtgtc tgtaaggaag gtggctcgct cggggagcac gctggtggtg cccagagcgc  17760
gctaccaccc cagcatcgtt taaagccggt ctctgtatgg ttcttgcaga tatggccctc  17820
```

-continued

```
acttgtcgcc tccgcttccc ggtgccggga taccgaggaa gaactcaccg ccgcagaggc  17880
atggcgggca gcggtctccg cggcggccgt cgccatcgcc ggcgcgcaaa aagcaggcgc  17940
atgcgcggcg gtgtgctgcc tctgctaatc ccgctaatcg ccgcggcgat cggtgccgta  18000
cccgggatcg cctccgtggc cctgcaggcg tcccagaaac gttgactctt gcaaccttgc  18060
aagcttgcat tttttggagg aaaaataaaa aaaagtctag actctcacgc tcgcttggtc  18120
ctgtgactat tttgtagaaa aaaagatgga agacatcaac tttgcgtcgc tggccccgcg  18180
tcacggctcg cgcccgttca tgggagactg gacagatatc ggcaccagca atatgagcgg  18240
tggcgccttc agctggggca gtctgtggag cggccttaaa aattttggtt ccaccattaa  18300
gaactatggc aacaaagcgt ggaacagcag cacgggccag atgctgagag acaagttgaa  18360
agagcagaac ttccaggaga aggtggcgca gggcctggcc tctggcatca gcggggtggt  18420
ggacatagct aaccaggccg tgcagaaaaa gataaacagt catctggacc cccgtcctca  18480
ggtggaggaa atgcctccag cgatggagac ggtgtctccc gagggcaaag gcgaaaagcg  18540
cccgcggccc gacagagaag agaccctggt gtcacacacc gaggagccgc cctcttacga  18600
ggaggcagtc aaggccggcc tgcccaccac tcgccccata gcccccatgg ccaccggtgt  18660
ggtgggccac aggcaacaca ctcccgcaac actagatctg cccccgccgt ccgagccgcc  18720
gcgccagcca aaggcggcga cggtgcccgc tccctccact tccgccgcca acagagtgcc  18780
cctgcgccgc gccgcgagcg gcccccgggc ctcgcgagtt agcggcaact ggcagagcac  18840
actgaacagc atcgtgggcc tgggagtgag gagtgtgaag cgccgccgtt gctactgaat  18900
gagcaagcta gctaacgtgt tgtatgtgtg tatgcgtcct atgtcgccgc cagaggagct  18960
gttgagccgc cggcgccgtc tgcactccag cgaatttcaa gatggcgacc ccatcgatga  19020
tgcctcagtg gtcgtacatg cacatctcgg gccaggacgc ttcggagtac ctgagccccg  19080
ggctggtgca gttcgcccgc gccacagaca cctacttcaa catgagtaac aagttcagga  19140
accccactgt ggcgcccacc cacgatgtga ccacggaccg gtcgcagcgc ctgacgctgc  19200
ggttcatccc cgtggatcgg gaggacaccg cctactctta caaggcgcgg ttcacgctgg  19260
ccgtgggcga caaccgcgtg ctggacatgg cctccactta ctttgacatc aggggggtgc  19320
tggacagggg ccccaccttc aagccctact cgggtactgc ctacaactcc ctggccccca  19380
agggcgctcc caattcttgc gagtgggaac aagatgaacc agctcaggca gcaatagctg  19440
aagatgaaga agaacttgaa gaagaacaag ctcaggacga acaggcgccc actaagaaaa  19500
cccatgtata cgcccaggca cctctttctg gtgaaaaaat tactaaggat ggtttgcaaa  19560
taggtgtgga tgccacacag gcgggagata accctatata tgctgataaa acattccaac  19620
ccgaacctca gataggtgag tctcagtgga acgaggctga tgccacagta gcaggaggca  19680
gagtcttaaa aaagaccacc cctatgagac cttgctatgg atcctatgcc aaacctacta  19740
atgccaatgg cggtcaaggg atcatggtgg ccaatgatca gggagcgctt gaatctaaag  19800
ttgagatgca atttttctcc accacaacgt ctcttaatgt aagggaaggt gaaaacaatc  19860
ttcagccaaa agtagtgcta tacagcgaag atgttaactt ggaatcccct gacactcatt  19920
tgtcttacaa acctaaaaag gatgacacca actctaaaat catgttgggt cagcaagcca  19980
tgcccaacag acccaacctc attgctttta gggacaactt tattggactt atgtactaca  20040
acagcacagg caacatggga gtgctggcag gacaggcctc ccagctaaac gctgtggtag  20100
acttgcaaga cagaaacaca gagctgtcat accaactgat gcttgattcc attggagaca  20160
gatcaagata cttttccatg tggaaccagg cagtggacag ctatgaccca gatgtcagaa  20220
```

tcattgaaaa ccatggggtt gaagatgagc tgcccaacta ttgctttccc ctgggcggta 20280
ttggaattac agacacatac cagtgcataa aaccaaccgc agctgctaat aacactacat 20340
ggtctaagga tgaagaattt agtgatcgca atgaaatagg ggtgggaaac aacttcgcca 20400
tggagatcaa catccaggcc aacctctgga ggaacttcct ctatgcgaac gtggggctct 20460
acctgccaga caagctcaag tacaacccca ccaacgtgga catctctgac aaccccaaca 20520
cctatgacta catgaacaag cgtgtggtgg ctcccggcct ggtggactgc tttgtcaatg 20580
tgggagccag gtggtccctg gactacatgg acaacgtcaa ccccttcaac caccaccgca 20640
atgcgggtct gcgctaccgc tccatgatcc tgggcaacgg gcgctacgtg cccttccaca 20700
ttcaggtgcc ccagaagttc tttgccatca agaacctcct cctcctgccg ggctcctaca 20760
cttacgagtg gaacttcagg aaggatgtca acatggtcct gcagagctct ctgggcaatg 20820
accttagggt ggacggggcc agcatcaagt ttgacagcgt caccctctat gctaccttct 20880
tccccatggc tcacaacacc gcctccacgc tcgaggccat gctgaggaac gacaccaacg 20940
accagtcctt caatgactac ctctctgggg ccaacatgct ctaccccatc cccgccaagg 21000
ccaccaacgt gcccatctcc attccctctc gcaactgggc cgccttcaga ggctgggcct 21060
ttacccgcct taagaccaag gaaacccccct ccctgggctc gggttttgac ccctactttg 21120
tctactcggg atccatcccc tacctggatg gcaccttcta cctcaaccac acttttaaga 21180
agatatccat catgtatgac tcctccgtca gctggccggg caatgaccgc ctgctcaccc 21240
ccaatgagtt cgaggtcaag cgcgccgtgg acggcgaggg ctacaacgtg gcccagtgca 21300
acatgaccaa ggactggttc ctggtgcaga tgctggccaa ctacaacata ggctaccagg 21360
gcttctacat cccagagagc tacaaggaca ggatgtactc cttcttcaga aatttccaac 21420
ccatgagcag gcaggtggtg gacgagacca aatacaagga ctatcaggcc attggcatca 21480
ctcaccagca caacaactcg ggattcgtgg gctacctggc tcccaccatg cgcgaggggc 21540
aggcctaccc cgccaacttc ccctacccgt tgataggcaa aaccgcggtc gacagcgtca 21600
cccagaaaaa gttcctctgc gaccgcaccc tctggcgcat cccctctct agcaacttca 21660 tgtccatggg tgcgctcacg gacctgggcc agaacctgct ctatgccaac tccgcccatg 21720
cgctggacat gacttttgag gtggacccca tggacgagcc caccttctc tatattgtgt 21780 ttgaagtgtt cgacgtggtc agagtgcacc agccgcaccg cggtgtcatc gagaccgtgt 21840
acctgcgcac gcccttctcg gccggcaacg ccaccaccta aggagacagc gccgccgcct 21900
gcatgacggg ttccaccgag caagagctca gggccatcgc cagagacctg ggatgcggac 21960
cctatttttt gggcacctat gacaaacgct tcccgggctt catctcccga gacaagctcg 22020
cctgcgccat cgtcaacacg gccgcgcgcg agaccggggg cgtgcactgg ctggcctttg 22080
gctgggaccc gcgctccaaa acctgctacc tcttcgaccc ctttggcttc tccgatcagc 22140
gcctcagaca gatctatgag tttgagtacg aggggctgct gcgccgcagc gcgcttgcct 22200
cctcgcccga ccgctgcatc acccttgaga agtccaccga gaccgtgcag gggccccact 22260
cggccgcctg cggtctcttc tgctgcatgt ttttgcacgc ctttgtgcgc tggccccaga 22320
gtcccatgga tcgcaacccc accatgaact tgctcaaggg agtgcccaac gccatgctcc 22380
agagccccca ggtccagccc accctgcgcc acaaccagga acagctctac cgcttcctgg 22440
agcgccactc cccctacttc cgcagtcaca gcgcgcacat ccggggggcc acctctttct 22500
gccacttgca agaaaacatg caagacggaa aatgatgtac agctcgcttt ttaataaatg 22560
taaagactgt gcactttatt tatacacggg ctctttctgg ttatttattc aacaccgccg 22620
tcgccatcta gaaatcgaaa gggttctgcc gcgcgtcgcc gtgcgccacg ggcagagaca 22680
cgttgcgata ctggaagcgg ctcgcccact taaactcggg caccaccatg cggggcagtg 22740
gttcctcggg gaagttctcg ccccacaggg tgcgggtcag ctgcagcgcg ctcaggaggt 22800
cgggagccga gatcttgaag tcgcagttgg ggccggaacc ctgcgcgcgc gagttgcggt 22860
acacggggtt gcagcactgg aacaccagca gggccggatt atgcacgctg gccagcaggc 22920
tctcgtcgct gatcatgtcg ctgtccagat cctccgcgtt gctcagggcg aacggggtca 22980
tcttgcagac ctgcctgccc aggaaaggcg gcagcccggg cttgccgttg cagtcgcagc 23040
gcaggggcat cagcaggtgc ccgcggcccg actgcgcctg cgggtacagc gcgcgcatga 23100
aggcttcgat ctgcctgaaa gccacctgcg tcttggctcc ctccgaaaag aacatcccac 23160
aggacttgct ggagaactgg ttcgcgggac agctggcatc gtgcaggcag cagcgcgcgt 23220
cggtgttggc gatctgcacc acgttgcgac cccaccggtt cttcactatc ttggccttgg 23280
aagcctgctc cttcagcgcg cgctggccgt tctcgctggt cacatccatc tctatcacct 23340
gctccttgtt gatcatgttt gtaccgtgca gacacttcag gtcgccctcc gtctgggtgc 23400
agcggtgctc ccacagcgcg caaccggtgg gctcccaatt tttgtgggtc acccccgcgt 23460
aggcctgcag gtaggcctgc aagaagcgcc ccatcatggc cacaaaggtc ttctggctcg 23520
taaaggtcag ctgcaggccg cgatgctctt cgttcagcca ggtcttgcag atggcggcca 23580
gcgcctcggt ctgctcgggc agcatcctaa aatttgtctt caggtcgtta tccacgtggt 23640
acttgtccat catggcgcgc gccgcctcca tgcccttctc ccaggcggac accatgggca 23700
ggcttagggg gtttatcact tccaccggcg aggacaccgt actttcgatt tcttcttcct 23760
ccccctcttc ccggcgcgcg cccacgctgc tgcgcgctct caccgcctgc accaaggggt 23820
cgtcttcagg caagcgccgc accgagcgct tgccgccctt gacctgctta atcagcaccg 23880
gcgggttgct gaagcccacc atggtcagcg ccgcctgctc ttcttcgtct tcgctgtcta 23940
ccactatctc tggggaaggg cttctccgct ctgcggcggc gcgcttcttt tttttcttgg 24000
gagcggccgt gatggagtcc gccacggcga cggaggtcga gggcgtgggg ctgggggtgc 24060
gcggtaccag ggcctcgtcg ccctcggact cttcctctga ctccaggcgg cggcggagtc 24120
gcttctttgg gggcgcgcgc gtcagcggcg gcggagacgg ggacggggac ggggacggga 24180
cgccctccac agggggtggt cttcgcgcag acccgcggcc gcgctcgggg gtcttctcga 24240
gctggtcttg gtcccgactg gccattgtat cctcctcctc ctaggcagag agacataagg 24300
agtctatcat gcaagtcgag aaggaggaga gcttaaccac cccctctgag accgccgatg 24360
cgcccgccgt cgccgtcgcc cccgctgccg ccgacgcgcc cgccacaccg agcgacaccc 24420
ccgcggaccc ccccgccgac gcacccctgt tcgaggaagc ggccgtggag caggacccgg 24480
gctttgtctc ggcagaggag gatttgcgag aggaggagga taaggagaag aagccctcag 24540
tgccaaaaga tgataaagag caagacgagc acgacgcaga tgcacaccag ggtgaagtcg 24600
ggcgggggga cggagggcat gacggcgccg actacctaga cgaagggaac gacgtgctct 24660
tgaagcacct gcatcgtcag tgcgccattg tttgcgacgc tctgcaggag cgcagcgaag 24720
tgcccctcag cgtggcggag gtcagccacg cctacgagct cagcctcttc tccccccggg 24780
tgcccccccg ccgccgcgaa aacggcacat gcgagcccaa cccgcgcctc aacttctacc 24840
ccgcctttgt ggtacccgag gtcctggcca cctatcacat cttctttcaa aattgcaaga 24900
tccccctctc gtgccgcgcc aaccgtagcc gcgccgataa gatgctggcc ctgcgccagg 24960
gcgaccacat acctgatatc gccgctttgg aagatgtacc aaagatcttc gagggtctgg 25020
gtcgcaacga gaagcgggca gcaaactctc tgcaacagga aaacagcgaa aatgagagtc 25080
acaccggggt actggtggag ctcgagggcg acaacgcccg cctggcggtg gtcaagcgca 25140
gcatcgaggt cacccacttt gcctaccccg cgctaaacct gccccccaaa gtcatgaacg 25200
cggccatgga cgggctgatc atgcgccgcg gccggcccct cgctccagat gcaaacttgc 25260
atgaggagac cgaggacggc cagcccgtgg tcagcgacga gcagctggcg cgctggctgg 25320
agaccgcgga ccccgccgaa ctggaggagc ggcgcaagat gatgatggcc gtggtgctgg 25380
tcaccgtaga gctggagtgt ctgcagcgct tcttcggcga ccccgagatg cagagaaagg 25440
tcgaggagac cctgcactac accttccgcc agggctacgt gcgccaggct tgcaagatct 25500
ccaacgtgga gctcagcaac ctggtgtcct acctgggcat cttgcatgag aaccgcctcg 25560
ggcagagcgt gctgcactcc accctgcgcg gggaggcgcg ccgcgactac gtgcgcgact 25620
gcgtttacct cttcctctgc tacacctggc agacggccat gggggtctgg cagcagtgcc 25680
tggaggagcg caacctcaag gagctggaga agctcctgca gcgcgcgctc aaagatctct 25740
ggacgggcta caacgagcgc tcggtggccg ccgcgctggc cgacctcatc ttccccgagc 25800
gcctgctcaa aaccctccag caggggctgc ccgacttcac cagccaaagc atgttgcaaa 25860
acttcaggaa ctttatcctg gagcgttctg gcatcctacc cgccacctgc tgcgccctgc 25920
ccagcgactt tgtcccccctc gtgtaccgcg agtgcccccc gccgctgtgg ggtcactgct 25980
acctgttcca actggccaac tacctgtcct accacgcgga cctcatggag gactccagcg 26040
gcgaggggct catggagtgc cactgccgct gcaacctctg cacgccccac cgctccctgg 26100
tctgcaacac ccaactgctc agcgagagtc agattatcgg taccttcgag ctacagggtc 26160
cgtcctcctc agacgagaag tccgcggctc cggggctaaa actcactccg gggctgtgga 26220
cttccgccta cctgcgcaaa tttgtacctg aagactacca cgcccacgag atcaggtttt 26280
acgaagacca atcccgcccg cccaaggcgg agctgaccgc ctgcgtcatc acccagggcg 26340
agatcctagg ccaattgcaa gccatccaaa aagcccgcca agactttttg ctgaagaagg 26400
gtcgggggt gtatctggac ccccagtcgg gtgaggagct caacccggtt cccccgctgc 26460
cgccgccgcg ggaccttgct tcccaggata agcatcgcca tggctcccag aaagaagcag 26520
cagcggccgc cactgccgcc accccacatg ctggaggaag aggaggaata ctgggacagt 26580
caggcagagg aggtttcgga cgaggaggag ccggagacgg agatggaaga gtgggaggag 26640
gacagcttag acgaggaggc ttccgaagcc gaagaggcag acgcaacacc gtcaccctcg 26700
gccgcagccc cctcgcaggc gcccccgaag tccgctccca gcatcagcag caacagcagc 26760
gctataacct ccgctcctcc accgccgcga cccacggccg accgcagacc caaccgtaga 26820
tgggacacca ccggaaccgg ggccggtaag tcctccggga gaggcaagca agcgcagcgc 26880
caaggctacc gctcgtggcg cgctcacaag aacgccatag tcgcttgctt gcaagactgc 26940
gggggaaca tctccttcgc ccgccgcttc ctgctcttcc accacggtgt ggccttcccc 27000
cgtaacgtcc tgcattacta ccgtcatctc tacagcccct actgcggcgg cagtgagcca 27060
gagacggtcg gcggcggcgg cggcgcccgt ttcggcgcct aggaagaccc agggcaagac 27120
ttcagccaag aaactcgcgg cggccgcggc gaacgcggtc gcgggggccc tgcgcctgac 27180
ggtgaacgaa cccctgtcga cccgcgaact gaggaaccga atcttcccca ctctctatgc 27240
catcttccag cagagcagag ggcaggatca ggaactgaaa gtaaaaaaca ggtctctgcg 27300
ctccctcacc cgcagctgtc tgtatcacaa gagcgaagac cagcttcggc gcacgctgga 27360
ggacgctgag gcactcttca gcaaatactg cgcgctcact cttaaggact agctccgcgc 27420
ccttctcgaa tttaggcggg aacgcctacg tcatcgcagc gccgccgtca tgagcaagga 27480
cattcccacg ccatacatgt ggagctatca gccgcagatg ggactcgcgg cgggcgcctc 27540
ccaagactac tccacccgca tgaactggct cagtgccggc ccacacatga tctcacaggt 27600
taatgatatc cgcacccatc gaaaccaaat attggtggag caggcggcaa ttaccaccac 27660
gccccgcaat aatcccaacc ccagggagtg gcccgcgtcc ctggtgtatc aggaaattcc 27720
cggccccacc accgtactac ttccgcgtga ttcccaggcc gaagtccaaa tgactaactc 27780
aggggcacag ctcgcgggcg gctgtcgtca cagggtgcgg cctcctcgcc agggtataac 27840
tcacctggag atccgaggca gaggtattca gctcaacgac gagtcggtga gctcctcgct 27900
cggtctcaga cctgacggga ccttccagat agccggagcc ggccgatctt ccttcacgcc 27960
ccgccaggcg tacctgactc tgcaaagctc gtcctcggcg ccgcgctcgg gcggcatcgg 28020
gactctccag ttcgtgcagg agtttgtgcc ctcggtctac ttcaacccct tctcgggctc 28080
tcccggtcgc tacccggacc agttcatctc gaactttgac gccgcgaggg actcggtgga 28140
cggctacgac tgaatgtcgg gtggacccgg tgcagagcaa cttcgcctga agcacctcga 28200
ccactgccgc cgccctcagt gctttgcccg ctgtcagacc ggtgagttcc agtacttttc 28260
cctgcccgac tcgcacccgg acggcccggc gcacggggtg cgctttttca tcccgagtca 28320
ggtgcgctct accctaatca gggagtttac cgcccgtccc ctactggcgg agttggaaaa 28380
ggggccttct atcctaacca ttgcctgcat ctgctctaac cctggattgc accaagatct 28440
ttgctgtcat ttgtgtgctg agtataataa aggctgagat cagaatctac tcgggctcct 28500
gtcgccatcc tgtcaacgcc accgtccaag cccggcccga tcagcccgag gtgaacctca 28560
cctgcggtct gcaccggcgc ctgaggaaat acctagcttg gtactacaac agcactccct 28620
ttgtggttta caacagcttt gaccaggacg gggtctcact gagggataac ctctcgaacc 28680
tgagctactc catcaggaag aacagcaccc tcgagctact tcctccttac ctgcccggga 28740
cttaccagtg tgtcaccggt ccctgcaccc acacccacct gttgatcgta aacgactctc 28800
ttccgagaac agacctcaat aactcctctt cgcagttccc cagaacagga ggtgagctca 28860
ggaaaccccg ggtaaagaag ggtggacgag agttaacact tgtggggttt ctggtgtatg 28920
tgacgctggt ggtggctctt ttgattaagg cttttccttc catgtctgaa ctctccctct 28980
tcttttatga acaactcgac tagtgctaac gggaccctac ccaacgaatc gggattgaat 29040
atcggtaacc aggttgcagt ttcactttg attaccttca tagtcctctt cctgctagtg 29100
ctgtcgcttc tgtgcctgcg gatcgggggc tgctgcatcc acgtttatat ctggtgctgg 29160
ctgtttagaa ggttcggaga ccatcgcagg tagaataaac atgctgctgc ttaccctctt 29220
tgtcctggcg ctggccgcca gctgccaagc cttttccgag gctgacttta tagagcccca 29280
gtgtaatgtg actttaaag cccatgcaca gcgttgtcat actataatca aatgtgccac 29340
cgaacacgat gaataccta tccagtataa agataaatca cacaaagtgg cacttgttga 29400
catctggaaa cccgaagacc ctttggaata caatgtgacc gttttccagg gtgacctctt 29460
caaaatttac aattacactt tcccatttga ccagatgtgt gactttgtca tgtacatgga 29520
aaagcagcac aagctgtggc ctccgactcc ccagggctgt gtggaaaatc caggctcttt 29580
ctgcatgatc tctctctgtg taactgtgct ggcactaata ctcacgcttt tgtatatcag 29640
atttaaatca aggcaaagct tcattgatga aaagaaaatg ccttaatcgc tttcacgctt 29700

-continued gattgctaac accgggtttt tatccgcaga atgattggaa tcaccctact aatcacctcc 29760
ctccttgcga ttgcccatgg gttggaacga atcgaagtcc ctgtgggggc caatgttacc 29820
ctggtggggc ctgtcggcaa tgctacatta atgtgggaaa aatatactaa aaatcaatgg 29880
gtctcttact gcactaacaa aaatagccac aagcccagag ccatctgcga tgggcaaaat 29940
ctaaccttga ttgatgttca attgctggat gcgggctact attatgggca gctgggtaca 30000
atgattaatt actggagacc ccacagagat tacatgctcc acgtagtaaa gggtcccctt 30060
agcagcccac ccactaccac ctctactacc cccactacca ccactactcc caccaccagc 30120
actgccgccc agcctcctca tagcagaaca accactttta tcaattccaa gtcccactcc 30180
ccccacattg ccggcgggcc ctccgcctca gactccgaaa ccaccgagat ctgcttctgc 30240
aaatgctctg acgccattgc ccaggatttg gaagatcacg aggaagatga gcatgacttc 30300
gcagatgcat gccaggcatc agagccagaa gcgctgccgg tggccctcaa acagtatgca 30360
gacccccaca ccacccccga ccttcctcca ccttcccaga agccaagttt cctgggggaa 30420
aatgaaactc tgcctctctc catactcgct ctgacatctg ttgctatgtt gaccgctctg 30480
ctggtgcttc tatgctctat atgctacctg atctgctgca gaaagaaaaa atctcacggc 30540
catgctcacc agcccctcat gcacttccct taccctccag agctgggcga ccacaaactt 30600
taagtctgca gtaactatct gcccatccct tgtcagtcga cagcgatgag ccccactaat 30660
ctaacggcct ctggacttac aacatcgtct cttaatgaga ccaccgctcc tcaagacctg 30720
tacgatggtg tctccgcgct ggttaaccag tgggatcacc tgggcatatg gtggctcctc 30780
ataggagcag tgaccctgtg cctaatcctg gtctggatca tctgctgcat caaaagcaga 30840
agacccaggc ggcggcccat ctacaggccc tttgtcatca cacctgaaga tgatgatgac 30900
accacttcca ggctgcagag gctaaagcag ctactcttct cttttacagc atggtaaatt 30960
gaatcatgcc tcgcattttc atctacttgt ctctccttcc actttttctg ggctcttcta 31020
cattggccgc tgtgtcccac atcgaggtag actgcctcac gcccttcaca gtctacctgc 31080
ttttcggctt tgtcatctgc acctttgtct gcagcgttat cactgtagtg atctgcttca 31140
tacagtgcat cgactacgtc tgcgtgcggg tggcttactt tagacaccac ccccagtatc 31200
gcaacaggga catagcggct ctcctaagac ttgtttaaaa tcatggccaa attaactgtg 31260
attggtcttc tgatcatctg ctgcgtccta gccgcgattg ggactcaagc tcctaccacc 31320
accagcgctc ccagaaagag acatgtatcc tgcagcttca agcgtccctg gaatataccc 31380
caatgcttta ctgatgaacc tgaaatctct ttggcttggt acttcagcgt caccgccctt 31440
cttatcttct gcagtacggt tattgccctt gccatctacc cttcccttga cctgggctgg 31500
aatgctgtca actctatgga atatcccacc ttcccagaac cagacctgcc agacctggtt 31560
gttctaaacg cgtttcctcc tcctgctccc gttcaaaatc agtttcgccc tccgtccccc 31620
acgcccactg aggtcagcta ctttaatcta acaggcggag atgactgaaa acctagacct 31680
agaaatggac ggtctctgca gcgagcaacg cacactagag aggcgccggc aaaaagagct 31740
cgagcgtctt aaacaagagc tccaagacgc ggtggccata caccagtgca aaaaaggtgt 31800
cttctgtctg gtaaaacagg ccacgctcac ctatgaaaaa acaggtgaca cccaccgcct 31860
aggatacaag ctgcccacac agcgccaaaa gttcgccctc atgataggcg aacaacccat 31920
caccgtgacc cagcactccg tggagacaga aggctgcata catgctccct gtagggggcgc 31980 tgactgcctc tacaccttga tcaaaaccct ctgcggtctc agagacctta tccctttcaa 32040
ttaatcataa ctgtaatcaa taaaaaatca cttacttgaa atctgatagc aagcctctgt 32100
ccaatttttt cagcaacact tccttcccct cctcccaact ctggtactct aggcgcctcc 32160
tagctgcaaa cttcctccac agtctgaagg gaatgtcaga ttcctcctcc tgtccctccg 32220
cacccacgat cttcatgttg ttgcagatga aacgcgcgag atcgtctgac gagaccttca 32280
accccgtgta cccctacgat accgagatcg ctccgacttc tgtccctttc cttacccctc 32340
cctttgtgtc atccgcagga atgcaagaaa atccagctgg ggtgctgtcc ctgcacttgt 32400
cagagcccct taccacccac aatggggccc tgactctaaa aatggggggc ggcctgaccc 32460
tggacaagga agggaatctc acttcccaaa acatcaccag tgtcgatccc cctctcaaaa 32520
aaagcaagaa caacatcagc cttcagaccg ccgcacccct cgccgtcagc tccggggccc 32580
taacactttt tgccactccc cccctagcgg tcagtggtga caaccttact gtgcagtctc 32640
aggcccctct cactttggaa gactcaaaac taactctggc caccaaagga cccctaactg 32700
tgtccgaagg caaacttgtc ctagaaac 32728

<210> SEQ ID NO 24
<211> LENGTH: 32728
<212> TYPE: DNA
<213> ORGANISM: Artificial sequence
<220> FEATURE:
<223> OTHER INFORMATION: Adenovirus vector nucleotide sequences

<400> SEQUENCE: 24
ataatatacc ttattttgga ttgtggccaa tatgataatg aggtgggcgg ggagaggcgg 60
ggcgggtgac gtaggacgcg cgagtagggt tgggaggtgt ggcggaagtg tggcatttgc 120
aagtgggagg agctcacatg caagcttccg tcgcggaaaa tgtgacgttt ttgatgagcg 180
ccgcctacct ccggaagtgc caattttcgc gcgcttttca ccggatatcg tagtaatttt 240
gggcgggacc atgtaagatt tggccatttt cgcgcgaaaa gtgaaacggg gaagtgaaaa 300
ctgaataata gggcgttagt catagcgcgt aatatttacc gagggccgag ggactttgac 360
cgattacgtg gaggactcgc ccaggtgttt tttacgtgaa tttccgcgtt ccgggtcaaa 420
gtctccgttt ttattgtcac cgtcatttga cgcggagggt atttaaaccc gctgcgctcc 480
tcaagaggcc actcttgagt gccagcgaga agagttttct cctctgctcc gcttcggtga 540
tcgaaaaatg agacacatag cctgcactcc gggtcttttg tccggtcggg cggcggccga 600
gcttttggac gctttgatca atgatgtcct aagcgatgat tttccgtcta ctacccactt 660
tagcccacct actcttcacg aactgtacga tctggatgta ctggtggatg tgaacgatcc 720
caacgaggag gcggtttctg cgtttttttcc cgagtctgcg ctgttggccg ctcaggaggg 780
atttgaccta cacactccgc cgcctatttt agagtctccg ctgccggagc ccagtggtat 840
accttatatg cctgaactgc ttcccgaagt ggtagacctg acctgccacg agcctggctt 900
tccgcccagc gacgatgagg gtgagccttt tgttttagac tttgctgaga tacctgggca 960
cggttgcagg tcttgtgcat atcatcagag ggttaccgga gaccccgagg ttaagtgttc 1020
gctgtgctat atgaggatga cctcttcctt tatctacagt aagtttttgt ctaggtgggc 1080
ttttgggtag gtgggttttg tgtcagaaca ggtgtaaacg ttgcttgtgt tttttgtacc 1140
tgtaggtccg gtgtccgagc cagacccgga gcccgaccgc gatcccgagc cggatcccga 1200
gcctcctcgc aggacaagga aactaccttc cattctgtgc aagtctcaga cacctgtaag 1260
gaccagcgag gcagacagca ccgactctgg cacttctacc tctcccccctg aaattcaccc 1320 agtggttcct ctgggtatac ataaacctgt tgctgttaaa gtttgcgggc gacgccctgc 1380

-continued

```
agtacagtgc attgaggact tgcttcacga tcccgaggaa cctttggact tgagccttaa   1440
acgccctagg caataaaccc cacctaagta ataaacccca cctaagtaat aaaccctgcc   1500
gcccttggtt attgagatga cgcccaatgt ttgcttttga atgacttcat gtgtgtaata   1560
aaagtgagtg tgatcatagg tctcttgttt gtctgggcgg ggcttaaggg tatataagtc   1620
tcttggggct aaacttggtt acacttgacc ccaatggagg cgtgggggtg cttggaggag   1680
tttgcggacg tgcgccgttt gctggacgag agctctagca atacctatac tatttggagg   1740
tatctgtggg gctctactca ggccaagttg gtttccagaa ttaagcagga ttacaagtgc   1800
gattttgaag agctttttag ttcctgcggt gagcttttgc aatccttgaa tctgggccat   1860
caggctattt tccaggaaaa ggttctctcg actttggatt tttccactcc cgggcgcacc   1920
gccgcttgtg tggcttttgt gtcttttgtg caagataaat ggagcgagga gacccacctg   1980
agtcacggct acgtactgga tttcatggcg atggctcttt ggagggctca caacaaatgg   2040
aagattcaga aggaactgta cggttccgcc ctacgtcgtc cacttctgtc gcgacagggg   2100
ctgaggtttc ccgaccatcg gcagcatcag aatctggaag acgagtcgga ggagcgagcg   2160
gaggagaaga tcagcttgag agccggcctg gaccctcctc aggaggaatg aatctcccgc   2220
aggtggttga cctgtttcca gaactgagac gggtcctgac tatcagggag gatggtcagt   2280
ttgtgaagaa gtttaagagg gatcggggtg agggagatga tgaggcggct agcaatttag   2340
cttttagtct gatgactcgc caccgaccgg aatgtattac ctatcagcag attaaggaga   2400
gttgtgccaa cgagctggat cttttgggtc agaagtatag catagaacag cttaccactt   2460
actggcttca gcctggggat gattgggaag aggcgatcag ggtgtatgca aaggtggccc   2520
tgcggcccga ttgcaagtat aagattacta agttggttaa tattagaaac tgctgctata   2580
tttctgggaa cggggccgaa gtggagatag atactcagga cagggtggct tttaggtgtt   2640
gcatgataaa catgtggccc gggatactgg ggatggatgg ggtggtattc atgaatgtga   2700
ggtttacggg ccccaacttt aatggcacgg tgttcatggg caacaccaac ttgctcctgc   2760
atggtgcgag tttctatggg tttaataaca cctgtataga ggcctggacc gatgtaaagg   2820
ttcgaggttg ttccttttat agctgttgga aggcggtggt gtgtcgccct aaaagcaggg   2880
gttctgtgaa aaaatgcttg tttgaaaggt gcaccttagg catcctctct gagggcaact   2940
ccagggtgcg ccataatgtg gcttcgaact gcggttgctt catgcaagtg aagggggtga   3000
gcgttatcaa gcataactcg gtgtgtggaa actgcgagga tcgcgcctcc cagatgctga   3060
cctgctttga tggcaactgt cacctgttga agaccattca tataagcagc caccccagaa   3120
aggcctggcc cgtgtttgag cataacatct tgacccgctg ctccttgcat ctgggggtca   3180
ggaggggtat gttcctgcct taccagtgta actttagcca cactaaaatc ctgctggaac   3240
ccgagtgcat gaccaaggtc agcctgaatg gtgtgtttga tgtgactctg aaaatctgga   3300
aggtgctgag gtatgatgag accaggacca ggtgccgacc ctgcgagtgc ggcggcaagc   3360
acatgagaaa tcagcctgtg atgttggatg tgaccgagga gcttaggcct gaccatctgg   3420
tgctggcctg caccagggcc gagtttgggt ctagcgatga ggataccgat tgaggtgggt   3480
aaggtgggcg tggctagaag ggtggggcgt gtataaattg gggtctaagg ggtctctctg   3540
ttttgtcttg caacagccgc cgccatgagc gacaccggca acagctttga tggaagcatc   3600
tttagcccct atctgacagt gcgcatgcct cactgggctg gagtgcgtca gaatgtgatg   3660
ggttccaacg tggatggacg ccccgttctg ccttcaaatt cgtctacaat ggcctacgcg   3720
```

-continued

```
accgtgggag gaactccgct ggacgccgcg acctccgccg ccgcctccgc cgccgccgcg   3780
accgcgcgca gcatggctac ggacctttac agctctttgg tggcgagcgg cgcggcctct   3840
cgcgcgtctg ctcgggatga gaaactgacc gctctgctgc ttaaactgga agacttgacc   3900
cgggagctgg gtcaactgac ccagcaggtc tccagcttgc gtgagagcag ccttgcctcc   3960
ccctaatggc ccataatata aataaaagcc agtctgtttg gattaagcaa gtgtatgttc   4020
tttatttaac tctccgcgcg cggtaagccc gggaccagcg gtctcggtcg tttagggtgc   4080
ggtggattct ttccaacacg tggtacaggt ggctctggat gtttagatac atgggcatga   4140
gtccatccct ggggtggagg tagcaccact gcagagcttc gtgctcgggg gtggtgttgt   4200
atatgatcca gtcgtagcag gagcgctggg cgtggtgctg aaaaatgtcc ttaagcaaga   4260
ggcttatagc taggggggagg cccttggtgt aagtgtttac aaatctgctc agttgggagg   4320
ggtgcatccg gggggatata atgtgcatct tggactggat tttaggttg gctatgttcc   4380
cacccagatc ccttctggga ttcatgttgt gcaggaccac cagcacggta tatccagtgc   4440
acttgggaaa tttatcgtgg agcttagacg ggaatgcatg gaagaacttg gagacgccct   4500
tgtggcctcc cagattttcc atacattcgt ccatgatgat ggcaatgggc ccgtgggaag   4560
ctgcctgagc aaaaatgttt ctgggatcgc tcacatcgta gttatgttcc agggtgaggt   4620
catcatagga catctttacg aatcgggggc ggagggtccc ggactggggg atgatggtac   4680
cctcgggccc cggggcgtag ttcccctcac agatctgcat ctcccaggct ttcatttcag   4740
agggagggat catatccacc tgcggagcga tgaaaaacac agtttctggc gcaggggaga   4800
ttaactggga tgagagcagg tttctgagca gctgtgactt tccacagccg gtgggcccat   4860
atatcacgcc tatcaccggc tgcagctggt agttaagaga gctgcagctg ccgtcctccc   4920
ggagcagggg ggccacctcg ttcagcatat ccctgacgtg gatgttctcc ctgaccaatt   4980
ccgccagaag gcgctcgccg cccagcgaaa gcagctcttg caaggaagca aaatttttca   5040
gcggttttag gccgtcggcc gtgggcatgt ttttcagcgt ctgggtcagc agttccagcc   5100
tgtcccacag ctcggtgatg tgctctacgg catctcgatc cagcagatct cctcgtttcg   5160
cgggttgggg cggctttcgc tgtagggcac cagccgatgg gcgtccagcg gggccagagt   5220
catgtccttc catgggcgca gggtcctcgt cagggtggtc tgggtcacgg tgaaggggtg   5280
cgctccgggt tgggcgctgg ccagggtgcg cttgaggctg gttctgctgg tgctgaatcg   5340
ctgccgctct tcgccctgcg cgtcggccag gtagcatttg accatggtct cgtagtcgag   5400
accctcggcg gcgtgcccct tggcgcggag ctttcccttg gaggtggcgc cgcacgaggg   5460
gcactgcagg ctcttcaggg cgtagagctt gggagcgaga aacacggact ctggggagta   5520
ggcgtccgcg ccgcaggaag cgcagaccgt ctcgcattcc accagccaag tgagctccgg   5580
gcggtcaggg tcaaaaacca ggttgccccc atgctttttg atgcgtttct tacctcggct   5640
ctccatgagg cggtgtccct tctcggtgac gaagaggctg tccgtgtccc cgtagaccga   5700
cttcaggggc ctgtcttcca gcggagtgcc tctgtcctcc tcgtagagaa actctgacca   5760
ctctgagacg aaggcccgcg tccaggccag gacgaaggag gccacgtggg aggggtagcg   5820
gtcgttgtcc actagcgggt ccaccttctc cagggtgtgc aggcacatgt ccccctcctc   5880
cgcgtccaga aaagtgattg gcttgtaggt gtaggacacg tgaccggggg ttcccgacgg   5940
gggggtataa aagggggtgg gcgccctttc atcttcactc tcttccgcat cgctgtctgc   6000
gagggccagc tgctggggta agtattccct ctcgaaggcg ggcatgacct cagcgctcag   6060
gttgtcagtt tctaaaaatg aggaggattt gatgttcacc tgtccggagg tgatacccttt   6120
```

gagggtacct gggtccatct ggtcagaaaa cactattttt ttgttgtcaa gcttggtggc 6180
gaacgacccg tagagggcgt tggagagcag cttggcgatg gagcgcaggg tctggttttt 6240
gtcgcggtcg gctcgctcct tggccgcgat gttgagttgc acgtactcgc gggccacgca 6300
cttccactcg gggaagacgg tggtgcgctc gtctgggatt aggcgcaccc tccagcctcg 6360
gttgtgcagg gtgaccatgt cgacgctggt ggcgacctcg ccgcgcaggc gctcgttggt 6420
ccagcagagg cggccgccct tgcgcgagca gaaggggggt agggggtcca gctggtcctc 6480
gtttgggggg tccgcgtcga tggtgaagac cccggggagc aagcgcgggt caaagtagtc 6540
gatcttgcaa gcttgcatgt ccagagcccg ctgccattcg cgggcggcga gcgcgcgctc 6600
gtaggggttg aggggcgggc cccagggcat ggggtgggtg agcgcggagg cgtacatgcc 6660
gcagatgtca tacacgtaca ggggttccct gaggatgccg aggtaggtgg ggtagcagcg 6720
ccccccgcgg atgctggcgc gcacgtagtc atagagctcg tgggaggggg ccagcatgtt 6780
gggcccgagg ttggtgcgct gggggcgctc ggcgcggaag gcgatctgcc tgaagatggc 6840
atgggagttg gaggagatgg tgggccgctg gaagacgttg aagcttgctt cttgcaagcc 6900
caccgagtcc ctgacgaagg aggcgtagga ctcgcgcagc ttgtgcacca gctcggcggt 6960
gacctggacg tcgagcgcgc agtagtcgag ggtctcgcgg atgatgtcat acttatcctc 7020
ccccttcttt ttccacagct cgcggttgag gacgaactct tcgcggtctt tccagtactc 7080
ttggagggga aacccgtccg tgtccgaacg gtaagagcct agcatgtaga actggttgac 7140
ggcctggtag ggcaacagc ccttctccac gggcagcgcg taggcctgcg ccgccttgcg 7200
gagggaggtg tgggtgaggg cgaaagtgtc cctgaccatg actttgaggt attgatgttt 7260
gaagtctgtg tcatcgcagc cgccctgttc ccacagggtg tagtccgtgc gctttttgga 7320
gcgcgggttg ggcagggaga aggtgaggtc attgaagagg atcttccccg ctcgaggcat 7380
gaagtttctg gtgatgcgaa agggccctgg gaccgaggag cggttgttga tgacctgggc 7440
ggccaggacg atctcgtcaa agccgtttat gttgtggccc acgatgtaga gctccaaaaa 7500
gcggggctgg cccttgatgg aggggagctt tttgagttcc tcgtaggtga gctcctcggg 7560
cgattccagg ccgtgctcct ccagggccca gtcttgcaag tgagggttgg ccgccaggaa 7620
ggatcgccag aggtcgcggg ccatgagggt ctgcaggcgg tcgcggaagg ttctgaactg 7680
tcgccccacg gccatctttt cgggggtgat gcagtagaag gtgagggggt ctttctccca 7740
ggggtcccat ctgagctctc gggcgaggtc gcgcgcggcg gcgaccagag cctcgtcgcc 7800
ccccagtttc atgaccagca tgaagggcac gagctgcttg ccaaaggctc ccatccaagt 7860
gtaggtctct acatcgtagg tgacaaagag gcgctccgtg cgaggatgag agccgatcgg 7920
gaagaactgg atctcccgcc accagttgga ggattggctg ttgatgtggt gaaagtagaa 7980
gtcccgtctg cgggccgagc actcgtgctg gcttttgtaa aagcgaccgc agtactggca 8040
gcgctgcacg ggttgtatat cttgcacgag gtgaacctgg cgacctctga cgaggaagcg 8100
cagcgggaat ctaagtcccc cgcctggggt cccgtgtggc tggtggtctt ctactttggt 8160
tgtctggccg ccagcatctg tctcctggag ggcgatggtg gagcagacca ccacgccgcg 8220
agagccgcag gtccagatct cggcgctcgg cgggcggagt ttgatgacga catcgcgcac 8280
attggagctg tccatggtct ccagctcccg cggcggcagg tcagctggga gttcctggag 8340
gttcacctcg cagagacggg tcaaggcgcg ggcagtgttg agatggtatc tgatttcaag 8400
gggcgtgttg gcggcggagt cgatggcttg caggaggccg cagccccggg gggccacgat 8460

-continued

```
ggttccccgc ggggcgcgag gggaggcgga agctgggggt gtgttcagaa gcggtgacgc   8520
gggcgggccc ccggaggtag ggggggttcc ggccccacag gcatgggcgg caggggcacg   8580
tcttcgccgc gcgcgggcag gggctggtgc tggctccgaa gagcgcttgc gtgcgcgacg   8640
acgcgacggt tggtgtcctg tatctgacgc ctctgagtga agaccacggg tcccgtgacc   8700
ttgaacctga aagagagttc gacagaatca atctcggcat cgttgacagc ggcctggcgc   8760
aggatctcct gcacgtcgcc cgagttgtcc tggtaggcga tctctgccat gaactgctcg   8820
atctcttctt cctggagatc tcctcgtccg gcgcgctcca cggtggccgc caggtcgttg   8880
gagatgcgac ccatgagctg tgagaaggcg ttgagcccgc cctcgttcca gacccggctg   8940
tagaccacgc ccccctcggc gtcgcgagcg cgcatgacca cctgggccag gttgagctcc   9000
acgtgtcgcg tgaagacggc gtagttgcgc aggcgctgga aaaggtagtt cagggtggtg   9060
gcggtgtgct cggcgacgaa gaagtacatg acccagcgcc gcaacgtgga ttcattgatg   9120
tcccccaagg cctccaggcg ctccatggcc tcgtagaagt ccacggcgaa gttgaaaaac   9180
tgggagttgc gagcggacac ggtcaactcc tcctccagaa gacggatgag ctcggcgaca   9240
gtgttgcgca cctcgcgctc gaaggccacg gggggcgctt cttcctcttc cacctcttct   9300
tccatgatcg cttcttcttc ttcctcagcc gggacgggag gggcggcgg cggcgggga   9360
ggggcgcggc ggcggcggcg gcgcaccggg aggcggtcga tgaagcgctc gatcatctcc   9420
ccccgcatgc ggcgcatggt ctcggtgacg gcgcggccgt tctcccgggg gcgcagctcg   9480
aagacgccgc ctctcatctc gccgcggggc gagcggccgt gaggtagcga gacggcgctg   9540
actatgcatc ttaacaattg ctgtgtaggt acaccgccga gggacctgat tgagtccaga   9600
tccaccggat ccgaaaacct ttggaggaaa gcgtctatcc agtcgcagtc gcaaggtagg   9660
ctgagcaccg tggcgggcgg gggcgggtct ggagagttcc tggcggagat gctgctgatg   9720
atgtaattaa agtaggcggt cttgagaagg cggatggtgg acaggagcac catgtctttg   9780
ggtccggcct gttggatgcg gaggcggtcg gccatgcccc aggcctcgtt ctgacaccgg   9840
cgcaggtctt tgtagtagtc ttgcatgagt ctttccaccg gcacctcttc tccttcctct   9900
tctccatctc gccggtggtt tctcgcgccg cccatgcgcg tgaccccaaa gcccctgagc   9960
ggctgcagca gggccaggtc ggcgaccacg cgctcggcca agatggcctg ctgcacctga  10020
gtgagggtcc tctcgaagtc atccatgtcc acgaagcggt ggtaggcgcc cgtgttgatg  10080
gtgtaggtgc agttggccat gacggaccag ttgacggtct ggtgtcccgg ctgcgagagc  10140
tccgtgtacc gcaggcgcga gaaggcgcgg gaatcgaaca cgtagtcgtt gcaagtccgc  10200
accagatact ggtagcccac caggaagtgc ggcggaggtt ggcgatagag ggccagcgc   10260
tgggtggcgg gggcgccggg cgccaggtct tccagcatga ggcggtggta tccgtagatg  10320
tacctggaca tccaggtgat gccggcggcg gtggtggtgg cgcgcgcgta gtcgcggacc  10380
cggttccaga tgtttcgcag gggcgagaag tgttccatgg tcggcacgct ctggccggtg  10440
aggcgcgcgc agtcgttgac gctctataca cacacaaaaa cgaaagcgtt tacagggctt  10500
tcgttctgta gcctggagga aagtaaatgg gttgggttgc ggtgtgcccc ggttcgagac  10560
caagctgagc tcggccggct gaagccgcag ctaacgtggt attggcagtc ccgtctcgac  10620
ccaggccctg tatcctccag gatacggtcg agagcccttt tgctttcttg gccaagcgcc  10680
cgtggcgcga tctgggatag atggtcgcga tgagaggaca aaagcggctc gcttccgtag  10740
tctggagaaa caatcgccag ggttgcgttg cggcgtaccc cggttcgagc ccctatggcg  10800
gcttgaatcg gccggaaccg cggctaacga gggccgtggc agccccgtcc tcaggacccc  10860
```

gccagccgac ttctccagtt acgggagcga gcccctttg tttttattt tttagatgca 10920
tcccgtgctg cggcagatgc gcccctcgcc ccggcccgat cagcagcagc aacagcaggc 10980
atgcagaccc ccctctcccc tttccgcccc ggtcaccacg gccgcggcgg ccgtgtcggg 11040
cgcgggggc gcgctggagt cagatgagcc accgcggcgg cgacctaggc agtatctgga 11100
cttggaagag ggcgagggac tggcgcggct gggggcgaac tctccagagc gccacccgcg 11160
ggtgcagttg aaaagggacg cgcgcgaggc gtacctgccg cggcagaacc tgtttcgcga 11220
ccgcgggggc gaggagcccg aggagatgcg agactgcagg ttccaagcgg ggcgcgagct 11280
gcggcgcggg ctggacagac agcgcctgct gcgcgaggag gactttgagc ccgacacgca 11340
gacgggcatc agccccgcgc gcgcgcacgt agccgcggcc gacctggtga ccgcctacga 11400
gcagacggta aaccaggagc gcaacttcca aaagagcttc aacaaccacg tgcgcacgct 11460
ggtggcgcgc gaggaggtga ccctgggtct catgcatctg tgggacctgg tggaggcgat 11520
cgtgcagaac cccagcagca agcccctgac cgcgcagctg ttcctggtgg tgcagcacag 11580
cagggacaac gaggccttca gggaggcgct gctgaacatc accgagccgg aggggcgctg 11640
gctcctggac ctgataaaca tcctgcagag catagtggtg caggagcgca gcctgagcct 11700
ggccgagaag gtggcggcca tcaactactc tatgctgagc ctgggcaagt tctacgcccg 11760
caagatctac aagacccct acgtgcccat agacaaggag gtgaagatag acagcttcta 11820
catgcgcatg gcgctgaagg tgctgaccct gagcgacgac ctgggagtgt accgcaacga 11880
gcgcatccac aaggccgtga gcgccagccg gcggcgcgag ctgagcgacc gcgagctgat 11940
gcacagtctg cagcgcgcgc tgaccggcgc gggcgagggc gacagggagg tcgagtccta 12000
cttcgacatg gggccgacc tgcactggca gccgagccgc cgcgccctgg aggcggcggg 12060
ggcgtacggc ggcccctgg cggccgatga ccaggaagag gaggactatg agctagagga 12120
gggcgagtac ctggaggact gacctggctg gtggtgtttt ggtatagatg caagatccga 12180
acgtggcgga cccggcggtc cgggcggcgc tgcaaagcca gccgtccggc attaactcct 12240
ctgacgactg ggccgcggcc atgggtcgca tcatggccct gaccgcgcgc aaccccgagg 12300
ctttcaggca gcagcctcag gccaaccggc tggcggccat cttggaagcg gtagtgcccg 12360
cgcgctccaa ccccacccac gagaaggtgc tggccatagt caacgcgctg gcggagagca 12420
gggccatccg cgcggacgag gccggactgg tgtacgatgc gctgctgcag cgggtggcgc 12480
ggtacaacag cggcaacgtg cagaccaacc tggaccgcct ggtgacggac gtgcgcgagg 12540
ccgtggcgca gcgcgagcgc ttgcatcagg acggtaacct gggctcgctg gtggcgctaa 12600
acgccttcct cagcacccag ccggccaacg taccgcgggg gcaggaggac tacaccaact 12660
ttttgagcgc gctgcggctg atggtgaccg aggtccctca gagcgaggtg taccagtcgg 12720
ggcccgacta cttcttccag accagcagac agggcttgca aaccgtgaac ctgagccagg 12780
ctttcaagaa cctgcggggg ctgtggggag tgaaggcgcc caccggcgac cgggctacgg 12840
tgtccagcct gctaaccccc aactcgcgcc tgctgctgct gctgatcgcg cccttcacgg 12900
acagcgggag cgtctcgcgg gagacctatc tgggccacct gctgacgctg taccgcgagg 12960
ccatcgggca ggcgcaggtg gacgagcaca ccttccaaga gatcaccagc gtgagccacg 13020
cgctggggca ggaggacacg ggcagcctgc aggcgaccct gaactacctg ctgaccaaca 13080
ggcggcagaa gattcccacg ctgcacagcc tgacccagga ggaggagcgc atcttgcgct 13140
acgtgcagca gagcgtgagc ctgaacctga tgcgcgacgg cgtgacgccc agcgtggcgc 13200

-continued tggacatgac cgcgcgcaac atggaaccgg gcatgtacgc ctcccaccgg ccgtttatca 13260
accgcctgat ggactacttg catcgggcgg cggccgtgaa ccccgagtac ttcactaatg 13320
ccattctgaa tccccactgg atgccccctc cgggtttcta caacggggac tttgaggtgc 13380
ccgaggtcaa cgacgggttc ctctgggatg acatggatga cagtgtgttc tcacccaacc 13440
cgctgcgcgc cgcgtctctg cgattgaagg agggctctga cagggaagga ccgaggagtc 13500
tggcctcctc cctggctctg ggagcggtgg gcgccacggg cgcggcggcg cggggcagta 13560
gccccttccc cagcctggca gactctctga acagcgggcg ggtgagcagg ccccgcttgc 13620
taggcgagga ggagtatctg aacaactccc tgctgcagcc cgcgagggac aagaacgctc 13680
agcggcagca gtttcccaac aatgggatag agagcctggt ggacaagatg tccagatgga 13740
agacgtatgc gcaggagtac aaggagtggg aggaccgcca gccgcggccc ttgccgcccc 13800
ctaggcagcg ctggcagcgg cgcgcgtcca accgccgctg gaggcagggg cccgaggacg 13860
atgatgactc tgcagatgac agcagcgtgt tggacctggg cgggagcggg aacccctttt 13920
cgcacctgcg cccacgcctg ggcaagatgt tttaaaagaa aaaaaaaaat aaaactcacc 13980
aaggccatgg cgacgagcgt tggttttttg ttcccttcct tagtatgcgg cgcgcggcga 14040
tgttcgagga ggggcctccc ccctcttacg agagcgcgat ggggatttct cctgcggcgc 14100
ccctgcagcc tccctacgtg cctcctcggt acctgcaacc tacagggggg agaaatagca 14160
tctgttactc tgagctgcag cccctgtacg ataccaccag actgtacctg gtggacaaca 14220
agtccgcgga cgtggcctcc ctgaactacc agaacgacca cagcgatttt ttgaccacgg 14280
tgatccaaaa caacgacttc accccaaccg aggccagcac ccagaccata aacctggata 14340
acaggtcgaa ctggggcggc gacctgaaga ccatcttgca caccaacatg cccaacgtga 14400
acgagttcat gttcaccaac tcttttaagg cgcgggtgat ggtggcgcgc gagcaggggg 14460
aggcgaagta cgagtgggtg gacttcacgc tgcccgaggg caactactca gagaccatga 14520
ctctcgacct gatgaacaat gcgatcgtgg aacactatct gaaagtgggc aggcagaacg 14580
gggtgaagga aagcgatatc ggggtcaagt ttgacaccag aaacttccgt ctgggctggg 14640
accccgtgac cgggctggtc atgccggggg tctacaccaa cgaggccttt catcccgaca 14700
tagtgcttct gcccggctgt ggggtggact tcacccagag ccggctgagc aacctgctgg 14760
gcattcgcaa gcggcagcct ttccaggagg gtttcaagat cacctatgag gatctgaagg 14820
ggggcaacat tcccgcgctc cttgatctgg acgcctacga ggagagcttg aaacccgagg 14880
agagcgctgg cgacagcggc gagagtggcg aggagcaagc cggcggcggt ggcggcgcgt 14940
cggtagaaaa cgaaagtacg cccgcagtgg cggcggacgc tgcggaggtc gagccggagg 15000
ccatgcagca ggacgcagag gagggcgcac aggagggcgc gcagaaggac atgaacgatg 15060
gggagatcag gggagacaca ttcgccaccc ggggcgaaga aaaagaggca gaggcggcgg 15120
cggcggcgac ggcggaggcc gaaaccgagg ttgaggcaga ggcagagccc gagaccgaag 15180
ttatggaaga catgaatgat ggagaacgta ggggcgacac gttcgccacc cggggcgaag 15240
agaaggcggc ggaggcagaa gccgcggctg aggaggcggc tgcggctgcg gccaagactg 15300
aggctgcggc taaggctgag gtcgaagcca atgttgcggt tgaggctcag gctgaggagg 15360
aggcggcggc tgaagcagtt aaggaaaagg cccaggcaga gcaggaagag aaaaaacctg 15420
tcattcaacc tctaaaagaa gatagcaaaa agcgcagtta caacgtcatc gagggcagca 15480
cctttaccca gtaccgcagc tggtacctgg cgtacaacta cggcgacccg gtcaaggggg 15540
tgcgctcgtg gaccctgctc tgcacgccgg acgtcacctg cggctccgag cagatgtact 15600

-continued ggtcgctgcc gaacatgatg caagacccgg tgaccttccg ctccacgcgg caggttagca 15660
acttcccggt ggtgggcgcc gaactgctgc ccgtgcactc caagagtttt tacaacgagc 15720
aggccgtcta ctcccagctg atccgccagg ccacctctct gacccacgtg ttcaatcgct 15780
ttcccgagaa ccagattttg gcgcgcccgc cggcccccac catcaccacc gtgagtgaaa 15840
acgttcctgc cctcacagat cacgggacgc taccgctgcg caacagcatc tcaggagtcc 15900
agcgagtgac cattactgac gccagacgcc ggacctgccc ctacgtttac aaggccttgg 15960
gcatagtctc gccgcgcgtc ctctccagtc gcacttttta aaacacatct acccacacgt 16020
tccaaaatca tgtccgtact catctcaccc agcaacaaca ccggctgggg gctgcgcgcg 16080
cccagcaaga tgtttggagg ggcgaggaag cgctccgacc agcaccctgt gcgcgtgcgc 16140
ggccactacc gcgcgccctg gggagcgcac aagcgcgggc gcacagggcg caccactgtg 16200
gacgacgtca ttgactccgt agtggagcaa gcgcgccact acacacccgg cgcgccgacc 16260
gcccccgccg tgtccaccgt ggaccaggcg atcgaaagcg tggtacaggg cgcgcggcac 16320
tatgccaacc ttaaaagtcg ccgccgccgc gtggcccgcc gccatcgccg gagaccccgg 16380
gccaccgccg ccgcgcgcct tactaaggct ctgctcaggc gcgccaggcg aactggccac 16440
cgggccgcca tgagggccgc acggcgggct gccgctgccg caagcgtcgt ggccccgcgg 16500
gcacgaaggc gcgcggccgc tgccgccgcc gccgccattt ccagcttggc ctcgacgcgg 16560
cgcggtaaca tatactgggt gcgcgactcg gtaaccggca cgcgggtacc cgtgcgcttt 16620
cgcccccccgc ggaattagca caagacaaca tacacactga gtctcctgct gttgtgtatc 16680
ccagcggcga ccgtcagcag cggcgacatg tccaagcgca aaattaaaga agagatgctc 16740
caggtcatcg cgccggagat ctatgggccc ccgaagaagg aggaggatga ttacaagccc 16800
cgcaagctaa agcgggtcaa aaagaaaaag aaagatgatg atgacgaggc ggtggagttt 16860
gtccgccgca tggcacccag gcgccccgtg cagtggaagg gccggcgcgt gcagcgcgtt 16920
ttgcgccccg gcaccgcggt ggtcttcacg cccggcgagc gctccacgcg cactttcaag 16980
cgggtgtacg atgaggtgta cggcgacgag gacctgttgg agcaggccaa ccagcgcttt 17040
ggggagtttg catatgggaa acggccccgc gagagtctaa aagaggacct gctggcgcta 17100
ccgctggacg agggcaatcc caccccgagt ctgaagccgg taaccctgca acaggtgctg 17160
cctttgagcg cgcccagcga gcataagcga gggttgaagc gcgaaggcgg ggacctggcg 17220
cccaccgtgc agttgatggt gcccaagcgg cagaagctgg aggacgtgct ggagaaaatg 17280
aaagtagagc ccgggatcca gcccgagatc aaggtccgcc ccatcaagca ggtggcgccc 17340
ggcgtgggag tccagaccgt ggacgttagg attcccacgg aggagatgga aacccaaacc 17400
gccactccct cttcggcggc cagcgccacc accggcaccg cttcggtaga ggtgcagacg 17460
gacccctggc tacccgccac cgctgttgcc gccgccgccc cccgttcgcg cgggcgcaag 17520
agaaattatc cagcggccag cgcgctcatg ccccagtacg cactgcatcc atccatcgtg 17580
cccacccccg gctaccgcgg gtactcgtac cgcccgcgca gatcagccgg cactcgcggc 17640
cgccgccgcc gtgcgaccac aaccagccgc cgccgtcgcc gccgccgcca gccagtgctg 17700
acccccgtgt ctgtaaggaa ggtggctcgc tcggggagca cgctggtggt gcccagagcg 17760
cgctaccacc ccagcatcgt ttaaagccgg tctctgtatg gttcttgcag atatggccct 17820
cacttgtcgc ctccgcttcc cggtgccggg ataccgagga agaactcacc gccgcagagg 17880
catggcgggc agcggtctcc gcggcggccg tcgccatcgc cggcgcgcaa aaagcaggcg 17940

-continued catgcgcggc ggtgtgctgc ctctgctaat cccgctaatc gccgcggcga tcggtgccgt 18000
acccgggatc gcctccgtgg ccctgcaggc gtcccagaaa cgttgactct tgcaaccttg 18060
caagcttgca ttttttggag gaaaaaataa aaaaaaagtc tagactctca cgctcgcttg 18120
gtcctgtgac tattttgtag aaaaaaagat ggaagacatc aactttgcgt cgctggcccc 18180
gcgtcacggc tcgcgcccgt tcatgggaga ctggacagat atcggcacca gcaatatgag 18240
cggtggcgcc ttcagctggg gcagtctgtg gagcggcctt aaaaattttg gttccaccat 18300
taagaactat ggcaacaaag cgtggaacag cagcacgggc cagatgctga gagacaagtt 18360
gaaagagcag aacttccagg agaaggtggc gcagggcctg gcctctggca tcagcggggt 18420
ggtggacata gctaaccagg ccgtgcagaa aaagataaac agtcatctgg acccccgtcc 18480
tcaggtggag gaaatgcctc cagcgatgga gacggtgtct cccgagggca aaggcgaaaa 18540
gcgcccgcgg cccgacagag aagagaccct ggtgtcacac accgaggagc cgccctctta 18600
cgaggaggca gtcaaggccg gcctgcccac cactcgcccc atagccccca tggccaccgg 18660
tgtggtgggc cacaggcaac acactcccgc aacactagat ctgcccccgc cgtccgagcc 18720
gccgcgccag ccaaaggcgg cgacggtgcc cgctccctcc acttccgccg ccaacagagt 18780
gcccctgcgc cgcgccgcga gcggcccccg ggcctcgcga gttagcggca actggcagag 18840
cacactgaac agcatcgtgg gcctgggagt gaggagtgtg aagcgccgcc gttgctactg 18900
aatgagcaag ctagctaacg tgttgtatgt gtgtatgcgt cctatgtcgc cgccagagga 18960
gctgttgagc cgccggcgcc gtctgcactc cagcgaattt caagatggcg accccatcga 19020
tgatgcctca gtggtcgtac atgcacatct cgggccagga cgcttcggag tacctgagcc 19080
ccgggctggt gcagttcgcc cgcgccacag acacctactt caacatgagt aacaagttca 19140
ggaaccccac tgtggcgccc acccacgatg tgaccacgga ccggtcgcag cgcctgacgc 19200
tgcggttcat ccccgtggat cgggaggaca ccgcctactc ttacaaggcg cggttcacgc 19260
tggccgtggg cgacaaccgc gtgctggaca tggcctccac ttactttgac atcagggggg 19320
tgctggacag gggccccacc ttcaagccct actcgggtac tgcctacaac tccctggccc 19380
ccaagggcgc tcccaattct tgcgagtggg aacaagatga accagctcag gcagcaatag 19440
ctgaagatga agaagaactt gaagaagaac aagctcagga cgaacaggcg cccactaaga 19500
aaacccatgt atacgcccag gcacctcttt ctggtgaaaa aattactaag gatggtttgc 19560
aaataggtgt ggatgccaca caggcgggag ataaccctat atatgctgat aaaacattcc 19620
aacccgaacc tcagataggt gagtctcagt ggaacgaggc tgatgccaca gtagcaggag 19680
gcagagtctt aaaaaagacc acccctatga gaccttgcta tggatcctat gccaaaccta 19740
ctaatgccaa tggcggtcaa gggatcatgg tggccaatga tcagggagcg cttgaatcta 19800
aagttgagat gcaatttttc tccaccacaa cgtctcttaa tgtaagggaa ggtgaaaaca 19860
atcttcagcc aaaagtagtg ctatacagcg aagatgttaa cttggaatcc cctgacactc 19920
atttgtctta caaacctaaa aaggatgaca ccaactctaa aatcatgttg ggtcagcaag 19980
ccatgcccaa cagacccaac ctcattgctt ttagggacaa ctttattgga cttatgtact 20040
acaacagcac aggcaacatg ggagtgctgg caggacaggc ctcccagcta aacgctgtgg 20100
tagacttgca agacagaaac acagagctgt cataccaact gatgcttgat tccattggag 20160
acagatcaag atacttttcc atgtggaacc aggcagtgga cagctatgac ccagatgtca 20220
gaatcattga aaaccatggg gttgaagatg agctgcccaa ctattgcttt cccctgggcg 20280
gtattggaat tacagacaca taccagtgca taaaaccaac cgcagctgct aataacacta 20340
catggtctaa ggatgaagaa tttagtgatc gcaatgaaat aggggtggga aacaacttcg 20400
ccatggagat caacatccag gccaacctct ggaggaactt cctctatgcg aacgtggggc 20460
tctacctgcc agacaagctc aagtacaacc ccaccaacgt ggacatctct gacaacccca 20520
acacctatga ctacatgaac aagcgtgtgg tggctcccgg cctggtggac tgctttgtca 20580
atgtgggagc caggtggtcc ctggactaca tggacaacgt caaccccttc aaccaccacc 20640
gcaatgcggg tctgcgctac cgctccatga tcctgggcaa cgggcgctac gtgcccttcc 20700
acattcaggt gccccagaag ttctttgcca tcaagaacct cctcctcctg ccgggctcct 20760
acacttacga gtggaacttc aggaaggatg tcaacatggt cctgcagagc tctctgggca 20820
atgaccttag ggtggacggg gccagcatca agtttgacag cgtcaccctc tatgctacct 20880
tcttccccat ggctcacaac accgcctcca cgctcgaggc catgctgagg aacgacacca 20940
acgaccagtc cttcaatgac tacctctctg ggccaacat gctctacccc atccccgcca 21000
aggccaccaa cgtgcccatc tccattccct ctcgcaactg ggccgccttc agaggctggg 21060
cctttacccg ccttaagacc aaggaaaccc cctccctggg ctcgggtttt gacccctact 21120
ttgtctactc gggatccatc ccctacctgg atggcacctt ctacctcaac cacactttta 21180
agaagatatc catcatgtat gactcctccg tcagctggcc gggcaatgac cgcctgctca 21240
cccccaatga gttcgaggtc aagcgcgccg tggacggcga gggctacaac gtggcccagt 21300
gcaacatgac caaggactgg ttcctggtgc agatgctggc caactacaac ataggctacc 21360
agggcttcta catcccagag agctacaagg acaggatgta ctccttcttc agaaatttcc 21420
aacccatgag caggcaggtg gtggacgaga ccaaatacaa ggactatcag gccattggca 21480
tcactcacca gcacaacaac tcgggattcg tgggctacct ggctcccacc atgcgcgagg 21540
ggcaggccta ccccgccaac ttcccctacc cgttgatagg caaaaccgcg gtcgacagcg 21600
tcacccagaa aaagttcctc tgcgaccgca ccctctggcg catccccttc tctagcaact 21660
tcatgtccat gggtgcgctc acggacctgg gccagaacct gctctatgcc aactccgccc 21720
atgcgctgga catgactttt gaggtggacc ccatggacga gcccaccctt ctctatattg 21780
tgtttgaagt gttcgacgtg gtcagagtgc accagccgca ccgcggtgtc atcgagaccg 21840
tgtacctgcg cacgcccttc tcggccggca acgccaccac ctaaggagac agcgccgccg 21900
cctgcatgac gggttccacc gagcaagagc tcagggccat cgccagagac ctgggatgcg 21960
gaccctattt tttgggcacc tatgacaaac gcttcccggg cttcatctcc cgagacaagc 22020
tcgcctgcgc catcgtcaac acggccgcgc gcgagaccgg gggcgtgcac tggctggcct 22080
ttggctggga cccgcgctcc aaaacctgct acctcttcga cccctttggc ttctccgatc 22140
agcgcctcag acagatctat gagtttgagt acgaggggct gctgcgccgc agcgcgcttg 22200
cctcctcgcc cgaccgctgc atcacccttg agaagtccac cgagaccgtg caggggcccc 22260
actcggccgc ctgcggtctc ttctgctgca tgtttttgca cgcctttgtg cgctggcccc 22320
agagtcccat ggatcgcaac ccccaccatga acttgctcaa gggagtgccc aacgccatgc 22380
tccagagccc ccaggtccag cccaccctgc gccacaacca ggaacagctc taccgcttcc 22440
tggagcgcca ctccccctac ttccgcagtc acagcgcgca catccggggg gccacctctt 22500
tctgccactt gcaagaaaac atgcaagacg gaaaatgatg tacagctcgc tttttaataa 22560
atgtaaagac tgtgcacttt atttatacac gggctctttc tggttattta ttcaacaccg 22620
ccgtcgccat ctagaaatcg aaagggttct gccgcgcgtc gccgtgcgcc acgggcagag 22680

-continued

```
acacgttgcg atactggaag cggctcgccc acttaaactc gggcaccacc atgcggggca  22740
gtggttcctc ggggaagttc tcgccccaca gggtgcgggt cagctgcagc gcgctcagga  22800
ggtcgggagc cgagatcttg aagtcgcagt tggggccgga accctgcgcg cgcgagttgc  22860
ggtacacggg gttgcagcac tggaacacca gcagggccgg attatgcacg ctggccagca  22920
ggctctcgtc gctgatcatg tcgctgtcca gatcctccgc gttgctcagg gcgaacgggg  22980
tcatcttgca gacctgcctg cccaggaaag gcggcagccc gggcttgccg ttgcagtcgc  23040
agcgcagggg catcagcagg tgcccgcggc ccgactgcgc ctgcgggtac agcgcgcgca  23100
tgaaggcttc gatctgcctg aaagccacct gcgtcttggc tccctccgaa aagaacatcc  23160
cacaggactt gctggagaac tggttcgcgg gacagctggc atcgtgcagg cagcagcgcg  23220
cgtcggtgtt ggcgatctgc accacgttgc gaccccaccg gttcttcact atcttggcct  23280
tggaagcctg ctccttcagc gcgcgctggc cgttctcgct ggtcacatcc atctctatca  23340
cctgctcctt gttgatcatg tttgtaccgt gcagacactt caggtcgccc tccgtctggg  23400
tgcagcggtg ctcccacagc gcgcaaccgg tgggctccca atttttgtgg gtcacccccg  23460
cgtaggcctg caggtaggcc tgcaagaagc gccccatcat ggccacaaag gtcttctggc  23520
tcgtaaaggt cagctgcagg ccgcgatgct cttcgttcag ccaggtcttg cagatggcgg  23580
ccagcgcctc ggtctgctcg ggcagcatcc taaaatttgt cttcaggtcg ttatccacgt  23640
ggtacttgtc catcatggcg cgcgccgcct ccatgccctt ctcccaggcg gacaccatgg  23700
gcaggcttag gggtttatc acttccaccg gcgaggacac cgtactttcg atttcttctt  23760
cctcccctc ttcccggcgc gcgcccacgc tgctgcgcgc tctcaccgcc tgcaccaagg  23820
ggtcgtcttc aggcaagcgc cgcaccgagc gcttgccgcc cttgacctgc ttaatcagca  23880
ccggcgggtt gctgaagccc accatggtca gcgccgcctg ctcttcttcg tcttcgctgt  23940
ctaccactat ctctggggaa gggcttctcc gctctgcggc ggcgcgcttc tttttttct  24000
tgggagcggc cgtgatggag tccgccacgg cgacggaggt cgagggcgtg gggctggggg  24060
tgcgcggtac cagggcctcg tcgccctcgg actcttcctc tgactccagg cggcggcgga  24120
gtcgcttctt tgggggcgcg cgcgtcagcg gcggcggaga cggggacggg gacggggacg  24180
ggacgccctc cacaggggt ggtcttcgcg cagacccgcg gccgcgctcg gggtcttct  24240
cgagctggtc ttggtcccga ctggccattg tatcctcctc ctcctaggca gagagacata  24300
aggagtctat catgcaagtc gagaaggagg agagcttaac cacccctct gagaccgccg  24360
atgcgcccgc cgtcgccgtc gccccgctg ccgccgacgc gcccgccaca ccgagcgaca  24420
cccccgcgga cccccccgcc gacgcacccc tgttcgagga agcggccgtg gagcaggacc  24480
cgggctttgt ctcggcagag gaggatttgc gagaggagga ggataaggag aagaagccct  24540
cagtgccaaa agatgataaa gagcaagacg agcacgacgc agatgcacac cagggtgaag  24600
tcgggcgggg ggacggaggg catgacggcg ccgactacct agacgaaggg aacgacgtgc  24660
tcttgaagca cctgcatcgt cagtgcgcca ttgtttgcga cgctctgcag gagcgcagcg  24720
aagtgcccct cagcgtggcg gaggtcagcc acgcctacga gctcagcctc ttctcccccc  24780
gggtgccccc ccgccgccgc gaaaacggca catgcgagcc caacccgcgc ctcaacttct  24840
accccgcctt tgtggtaccc gaggtcctgg ccacctatca catcttcttt caaaattgca  24900
agatcccct ctcgtgccgc gccaaccgta gccgcgccga taagatgctg gccctgcgcc  24960
agggcgacca catacctgat atcgccgctt tggaagatgt accaaagatc ttcgagggtc  25020
tgggtcgcaa cgagaagcgg gcagcaaact ctctgcaaca ggaaaacagc gaaaatgaga  25080
```

```
gtcacaccgg ggtactggtg gagctcgagg gcgacaacgc ccgcctggcg gtggtcaagc  25140
gcagcatcga ggtcacccac tttgcctacc ccgcgctaaa cctgcccccc aaagtcatga  25200
acgcggccat ggacgggctg atcatgcgcc gcggccggcc cctcgctcca gatgcaaact  25260
tgcatgagga gaccgaggac ggccagcccg tggtcagcga cgagcagctg gcgcgctggc  25320
tggagaccgc ggaccccgcc gaactggagg agcggcgcaa gatgatgatg gccgtggtgc  25380
tggtcaccgt agagctggag tgtctgcagc gcttcttcgg cgaccccgag atgcagagaa  25440
aggtcgagga gaccctgcac tacaccttcc gccagggcta cgtgcgccag gcttgcaaga  25500
tctccaacgt ggagctcagc aacctggtgt cctacctggg catcttgcat gagaaccgcc  25560
tcgggcagag cgtgctgcac tccaccctgc gcggggaggc gcgccgcgac tacgtgcgcg  25620
actgcgttta cctcttcctc tgctacacct ggcagacggc catgggggtc tggcagcagt  25680
gcctggagga gcgcaacctc aaggagctgg agaagctcct gcagcgcgcg ctcaaagatc  25740
tctggacggg ctacaacgag cgctcggtgg ccgccgcgct ggccgacctc atcttccccg  25800
agcgcctgct caaaaccctc cagcaggggc tgcccgactt caccagccaa agcatgttgc  25860
aaaacttcag gaactttatc ctggagcgtt ctggcatcct acccgccacc tgctgcgccc  25920
tgcccagcga ctttgtcccc ctcgtgtacc gcgagtgccc cccgccgctg tggggtcact  25980
gctacctgtt ccaactggcc aactacctgt cctaccacgc ggacctcatg gaggactcca  26040
gcggcgaggg gctcatggag tgccactgcc gctgcaacct ctgcacgccc caccgctccc  26100
tggtctgcaa cacccaactg ctcagcgaga gtcagattat cggtaccttc gagctacagg  26160
gtccgtcctc ctcagacgag aagtccgcgg ctccggggct aaaactcact ccggggctgt  26220
ggacttccgc ctacctgcgc aaatttgtac ctgaagacta ccacgcccac gagatcaggt  26280
tttacgaaga ccaatcccgc ccgcccaagg cggagctgac cgcctgcgtc atcacccagg  26340
gcgagatcct aggccaattg caagccatcc aaaaagcccg ccaagacttt ttgctgaaga  26400
agggtcgggg ggtgtatctg gacccccagt cgggtgagga gctcaacccg gttcccccgc  26460
tgccgccgcc gcgggacctt gcttcccagg ataagcatcg ccatggctcc cagaaagaag  26520
cagcagcggc cgccactgcc gccaccccac atgctggagg aagaggagga atactgggac  26580
agtcaggcag aggaggtttc ggacgaggag gagccggaga cggagatgga agagtgggag  26640
gaggacagct tagacgagga ggcttccgaa gccgaagagg cagacgcaac accgtcaccc  26700
tcggccgcag cccccctcgca ggcgcccccg aagtccgctc ccagcatcag cagcaacagc  26760
agcgctataa cctccgctcc tccaccgccg cgacccacgg ccgaccgcag acccaaccgt  26820
agatgggaca ccaccggaac cggggccggt aagtcctccg ggagaggcaa gcaagcgcag  26880
cgccaaggct accgctcgtg gcgcgctcac aagaacgcca tagtcgcttg cttgcaagac  26940
tgcgggggga acatctcctt cgcccgccgc ttcctgctct tccaccacgg tgtggccttc  27000
ccccgtaacg tcctgcatta ctaccgtcat ctctacagcc cctactgcgg cggcagtgag  27060
ccagagacgg tcggcggcgg cggcggcgcc cgtttcggcg cctaggaaga cccagggcaa  27120
gacttcagcc aagaaactcg cggcggccgc ggcgaacgcg gtcgcggggg ccctgcgcct  27180
gacggtgaac gaacccctgt cgacccgcga actgaggaac cgaatcttcc ccactctcta  27240
tgccatcttc cagcagagca gagggcagga tcaggaactg aaagtaaaaa acaggtctct  27300
gcgctccctc acccgcagct gtctgtatca caagagcgaa gaccagcttc ggcgcacgct  27360
ggaggacgct gaggcactct tcagcaaata ctgcgcgctc actcttaagg actagctccg  27420
```

-continued

```
cgcccttctc gaatttaggc gggaacgcct acgtcatcgc agcgccgccg tcatgagcaa  27480
ggacattccc acgccataca tgtggagcta tcagccgcag atgggactcg cggcgggcgc  27540
ctcccaagac tactccaccc gcatgaactg gctcagtgcc ggcccacaca tgatctcaca  27600
ggttaatgat atccgcaccc atcgaaacca aatattggtg gagcaggcgg caattaccac  27660
cacgccccgc aataatccca accccaggga gtggcccgcg tccctggtgt atcaggaaat  27720
tcccggcccc accaccgtac tacttccgcg tgattcccag gccgaagtcc aaatgactaa  27780
ctcaggggca cagctcgcgg gcggctgtcg tcacagggtg cggcctcctc gccagggtat  27840
aactcacctg gagatccgag gcagaggtat tcagctcaac gacgagtcgg tgagctcctc  27900
gctcggtctc agacctgacg ggaccttcca gatagccgga gccggccgat cttccttcac  27960
gccccgccag gcgtacctga ctctgcaaag ctcgtcctcg gcgccgcgct cgggcggcat  28020
cgggactctc cagttcgtgc aggagtttgt gccctcggtc tacttcaacc ccttctcggg  28080
ctctcccggt cgctacccgg accagttcat ctcgaacttt gacgccgcga gggactcggt  28140
ggacggctac gactgaatgt cgggtggacc cggtgcagag caacttcgcc tgaagcacct  28200
cgaccactgc cgccgccctc agtgctttgc ccgctgtcag accggtgagt tccagtactt  28260
ttccctgccc gactcgcacc cggacggccc ggcgcacggg gtgcgctttt tcatcccgag  28320
tcaggtgcgc tctaccctaa tcagggagtt taccgcccgt cccctactgg cggagttgga  28380
aaaggggcct tctatcctaa ccattgcctg catctgctct aaccctggat tgcaccaaga  28440
tctttgctgt catttgtgtg ctgagtataa taaaggctga gatcagaatc tactcgggct  28500
cctgtcgcca tcctgtcaac gccaccgtcc aagcccggcc cgatcagccc gaggtgaacc  28560
tcacctgcgg tctgcaccgg cgcctgagga aatacctagc ttggtactac aacagcactc  28620
cctttgtggt ttacaacagc tttgaccagg acggggtctc actgagggat aacctctcga  28680
acctgagcta ctccatcagg aagaacagca ccctcgagct acttcctcct tacctgcccg  28740
ggacttacca gtgtgtcacc ggtccctgca cccacaccca cctgttgatc gtaaacgact  28800
ctcttccgag aacagacctc aataactcct cttcgcagtt ccccagaaca ggaggtgagc  28860
tcaggaaacc ccgggtaaag aagggtggac gagagttaac acttgtgggg tttctggtgt  28920
atgtgacgct ggtggtggct cttttgatta aggcttttcc ttccatgtct gaactctccc  28980
tcttctttta tgaacaactc gactagtgct aacgggaccc tacccaacga atcgggattg  29040
aatatcggta accaggttgc agtttcactt ttgattacct tcatagtcct cttcctgcta  29100
gtgctgtcgc ttctgtgcct gcggatcggg ggctgctgca tccacgttta tatctggtgc  29160
tggctgttta gaaggttcgg agaccatcgc aggtagaata aacatgctgc tgcttaccct  29220
ctttgtcctg gcgctggccg ccagctgcca agccttttcc gaggctgact ttatagagcc  29280
ccagtgtaat gtgactttta aagcccatgc acagcgttgt catactataa tcaaatgtgc  29340
caccgaacac gatgaatacc ttatccagta taaagataaa tcacacaaag tggcacttgt  29400
tgacatctgg aaacccgaag acccctttgga atacaatgtg accgttttcc agggtgacct  29460
cttcaaaatt tacaattaca ctttcccatt tgaccagatg tgtgactttg tcatgtacat  29520
ggaaaagcag cacaagctgt ggcctccgac tccccagggc tgtgtggaaa atccaggctc  29580
tttctgcatg atctctctct gtgtaactgt gctggcacta atactcacgc ttttgtatat  29640
cagatttaaa tcaaggcaaa gcttcattga tgaaaagaaa atgccttaat cgctttcacg  29700
cttgattgct aacaccgggt ttttatccgc agaatgattg gaatcaccct actaatcacc  29760
tccctccttg cgattgccca tgggttggaa cgaatcgaag tccctgtggg ggccaatgtt  29820
```

accctggtgg ggcctgtcgg caatgctaca ttaatgtggg aaaaatatac taaaaatcaa 29880
tgggtctctt actgcactaa caaaaatagc cacaagccca gagccatctg cgatgggcaa 29940
aatctaacct tgattgatgt tcaattgctg gatgcgggct actattatgg gcagctgggt 30000
acaatgatta attactggag accccacaga gattacatgc tccacgtagt aaagggtccc 30060
cttagcagcc cacccactac cacctctact acccccacta ccaccactac tcccaccacc 30120
agcactgccg cccagcctcc tcatagcaga acaaccactt ttatcaattc caagtcccac 30180
tccccccaca ttgccggcgg gccctccgcc tcagactccg aaaccaccga gatctgcttc 30240
tgcaaatgct ctgacgccat tgcccaggat ttggaagatc acgaggaaga tgagcatgac 30300
ttcgcagatg catgccaggc atcagagcca gaagcgctgc cggtggccct caaacagtat 30360
gcagaccccc acaccacccc cgaccttcct ccaccttccc agaagccaag tttcctgggg 30420
gaaaatgaaa ctctgcctct ctccatactc gctctgacat ctgttgctat gttgaccgct 30480
ctgctggtgc ttctatgctc tatatgctac ctgatctgct gcagaaagaa aaaatctcac 30540
ggccatgctc accagcccct catgcacttc ccttaccctc cagagctggg cgaccacaaa 30600
ctttaagtct gcagtaacta tctgcccatc ccttgtcagt cgacagcgat gagccccact 30660
aatctaacgg cctctggact tacaacatcg tctcttaatg agaccaccgc tcctcaagac 30720
ctgtacgatg gtgtctccgc gctggttaac cagtgggatc acctgggcat atggtggctc 30780
ctcataggag cagtgaccct gtgcctaatc ctggtctgga tcatctgctg catcaaaagc 30840
agaagaccca ggcggcggcc catctacagg cccctttgtca tcacacctga agatgatgat 30900
gacaccactt ccaggctgca gaggctaaag cagctactct tctcttttac agcatggtaa 30960
attgaatcat gcctcgcatt ttcatctact tgtctctcct tccacttttt ctgggctctt 31020
ctacattggc cgctgtgtcc cacatcgagg tagactgcct cacgcccttc acagtctacc 31080
tgcttttcgg ctttgtcatc tgcacctttg tctgcagcgt tatcactgta gtgatctgct 31140
tcatacagtg catcgactac gtctgcgtgc gggtggctta ctttagacac cacccccagt 31200
atcgcaacag ggacatagcg gctctcctaa gacttgttta aaatcatggc caaattaact 31260
gtgattggtc ttctgatcat ctgctgcgtc ctagccgcga ttgggactca agctcctacc 31320
accaccagcg ctcccagaaa gagacatgta tcctgcagct tcaagcgtcc ctggaatata 31380
ccccaatgct ttactgatga acctgaaatc tctttggctt ggtacttcag cgtcaccgcc 31440
cttcttatct tctgcagtac ggttattgcc cttgccatct acccttccct tgacctgggc 31500
tggaatgctg tcaactctat ggaatatccc accttcccag aaccagacct gccagacctg 31560
gttgttctaa acgcgtttcc tcctcctgct cccgttcaaa atcagtttcg ccctccgtcc 31620
cccacgccca ctgaggtcag ctactttaat ctaacaggcg gagatgactg aaaacctaga 31680
cctagaaatg gacggtctct gcagcgagca acgcacacta gagaggcgcc ggcaaaaaga 31740
gctcgagcgt cttaaacaag agctccaaga cgcggtggcc atacaccagt gcaaaaaagg 31800
tgtcttctgt ctggtaaaac aggccacgct cacctatgaa aaaacaggtg acacccaccg 31860
cctaggatac aagctgccca cacagcgcca aaagttcgcc ctcatgatag gcgaacaacc 31920
catcaccgtg acccagcact ccgtggagac agaaggctgc atacatgctc cctgtagggg 31980
cgctgactgc ctctacacct tgatcaaaac cctctgcggt ctcagagacc ttatcccttt 32040
caattaatca taactgtaat caataaaaaa tcacttactt gaaatctgat agcaagcctc 32100
tgtccaattt tttcagcaac acttccttcc cctcctccca actctggtac tctaggcgcc 32160

```
tcctagctgc aaacttcctc cacagtctga agggaatgtc agattcctcc tcctgtccct  32220

ccgcacccac gatcttcatg ttgttgcaga tgaaacgcgc gagatcgtct gacgagacct  32280

tcaaccccgt gtacccctac gataccgaga tcgctccgac ttctgtccct ttccttaccc  32340

ctccctttgt gtcatccgca ggaatgcaag aaaatccagc tggggtgctg tccctgcact  32400

tgtcagagcc ccttaccacc cacaatgggg ccctgactct aaaaatgggg ggcggcctga  32460

ccctggacaa ggaagggaat ctcacttccc aaaacatcac cagtgtcgat ccccctctca  32520

aaaaaagcaa gaacaacatc agccttcaga ccgccgcacc cctcgccgtc agctccgggg  32580

ccctaacact ttttgccact cccccccctag cggtcagtgg tgacaacctt actgtgcagt  32640

ctcaggcccc tctcactttg gaagactcaa aactaactct ggccaccaaa ggacccctaa  32700

ctgtgtccga aggcaaactt gtcctaga                                     32728
```

<210> SEQ ID NO 25
<211> LENGTH: 32728
<212> TYPE: DNA
<213> ORGANISM: Artificial sequence
<220> FEATURE:
<223> OTHER INFORMATION: Adenovirus vector nucleotide sequences

<400> SEQUENCE: 25

```
catcatcaat aatatacctt attttggatt gtggccaata tgataatgag gtgggcgggg     60

agaggcgggg cgggtgacgt aggacgcgcg agtagggttg ggaggtgtgg cggaagtgtg    120

gcatttgcaa gtgggaggag ctcacatgca agcttccgtc gcggaaaatg tgacgttttt    180

gatgagcgcc gcctacctcc ggaagtgcca attttcgcgc gcttttcacc ggatatcgta    240

gtaattttgg gcgggaccat gtaagatttg gccattttcg cgcgaaaagt gaaacgggga    300

agtgaaaact gaataatagg gcgttagtca tagtgcgtaa tatttaccga gggccgaggg    360

actttgaccg attacgtgga ggactcgccc aggtgttttt tacgtgaatt tccgcgttcc    420

gggtcaaagt ctccgtttta ttgtcaccgt catttgacgc ttaggcctga ccatctggtg    480

ctggcctgca ccagggccga gtttgggtct agcgatgagg ataccgattg aggtgggtaa    540

ggtgggcgtg gctagaaggg tggggcgtgt ataaattggg ggtctaaggg tctctctgtt    600

ttgtcttgca acagccgccg ccatgagcga caccggcaac agctttgatg gaagcatctt    660

tagcccctat ctgacagtgc gcatgcctca ctgggctgga gtgcgtcaga atgtgatggg    720

ttccaacgtg gatggacgcc ccgttctgcc ttcaaattcg tctacaatgg cctacgcgac    780

cgtgggagga actccgctgg acgccgcgac ctccgccgcc gcctccgccg ccgccgcgac    840

cgcgcgcagc atggctacgg acctttacag ctctttggtg gcgagcggcg cggcctctcg    900

cgcgtctgct cgggatgaga aactgaccgc tctgctgctt aaactggaag acttgacccg    960

ggagctgggt caactgaccc agcaggtctc cagcttgcgt gagagcagcc ttgcctcccc   1020

ctaatggccc ataatataaa taaaagccag tctgtttgga ttaagcaagt gtatgttctt   1080

tatttaactc tccgcgcgcg gtaagcccgg gaccagcggt ctcggtcgtt tagggtgcgg   1140

tggattcttt ccaacacgtg gtacaggtgg ctctggatgt ttagatacat gggcatgagt   1200

ccatccctgg ggtggaggta gcaccactgc agagcttcgt gctcgggggt ggtgttgtat   1260

atgatccagt cgtagcagga gcgctgggcg tggtgctgaa aaatgtcctt aagcaagagg   1320

cttatagcta gggggaggcc cttggtgtaa gtgtttacaa atctgctcag ttgggagggg   1380

tgcatccggg gggatataat gtgcatcttg gactggattt ttaggttggc tatgttccca   1440

cccagatccc ttctgggatt catgttgtgc aggaccacca gcacggtata tccagtgcac   1500
```

-continued

```
ttgggaaatt tatcgtggag cttagacggg aatgcatgga agaacttgga gacgcccttg   1560
tggcctccca gattttccat acattcgtcc atgatgatgg caatgggccc gtgggaagct   1620
gcctgagcaa aaatgtttct gggatcgctc acatcgtagt tatgttccag ggtgaggtca   1680
tcataggaca tctttacgaa tcgggggcgg agggtcccgg actggggat gatggtaccc   1740
tcgggccccg gggcgtagtt cccctcacag atctgcatct cccaggcttt catttcagag   1800
ggagggatca tatccacctg cggagcgatg aaaaacacag tttctggcgc aggggagatt   1860
aactgggatg agagcaggtt tctgagcagc tgtgactttc cacagccggt gggcccatat   1920
atcacgccta tcaccggctg cagctggtag ttaagagagc tgcagctgcc gtcctcccgg   1980
agcagggggg ccacctcgtt cagcatatcc ctgacgtgga tgttctccct gaccaattcc   2040
gccagaaggc gctcgccgcc cagcgaaagc agctcttgca aggaagcaaa atttttcagc   2100
ggttttaggc cgtcggccgt gggcatgttt ttcagcgtct gggtcagcag ttccagcctg   2160
tcccacagct cggtgatgtg ctctacggca tctcgatcca gcagatctcc tcgtttcgcg   2220
ggttggggcg gctttcgctg tagggcacca gccgatgggc gtccagcggg gccagagtca   2280
tgtccttcca tgggcgcagg gtcctcgtca gggtggtctg ggtcacggtg aaggggtgcg   2340
ctccgggttg ggcgctggcc agggtgcgct tgaggctggt tctgctggtg ctgaatcgct   2400
gccgctcttc gccctgcgcg tcggccaggt agcatttgac catggtctcg tagtcgagac   2460
cctcggcggc gtgccccttg gcgcggagct ttcccttgga ggtggcgccg cacgaggggc   2520
actgcaggct cttcagggcg tagagcttgg gagcgagaaa cacggactct ggggagtagg   2580
cgtccgcgcc gcaggaagcg cagaccgtct cgcattccac cagccaagtg agctccgggc   2640
ggtcagggtc aaaaaccagg ttgcccccat gctttttgat gcgtttctta cctcggctct   2700
ccatgaggcg gtgtcccttc tcggtgacga agaggctgtc cgtgtccccg tagaccgact   2760
tcaggggcct gtcttccagc ggagtgcctc tgtcctcctc gtagagaaac tctgaccact   2820
ctgagacgaa ggcccgcgtc caggccagga cgaaggaggc cacgtgggag gggtagcggt   2880
cgttgtccac tagcgggtcc accttctcca gggtgtgcag gcacatgtcc ccctcctccg   2940
cgtccagaaa agtgattggc ttgtaggtgt aggacacgtg accgggggtt cccgacgggg   3000
gggtataaaa gggggtgggc gccctttcat cttcactctc ttccgcatcg ctgtctgcga   3060
gggccagctg ctggggtaag tattccctct cgaaggcggg catgacctca gcgctcaggt   3120
tgtcagtttc taaaaatgag gaggatttga tgttcacctg tccggaggtg ataccttga    3180
gggtacctgg gtccatctgg tcagaaaaca ctattttttt gttgtcaagc ttggtggcga   3240
acgacccgta gagggcgttg gagagcagct tggcgatgga gcgcagggtc tggtttttgt   3300
cgcggtcggc tcgctccttg gccgcgatgt tgagttgcac gtactcgcgg gccacgcact   3360
tccactcggg gaagacggtg gtgcgctcgt ctgggattag gcgcaccctc cagcctcggt   3420
tgtgcagggt gaccatgtcg acgctggtgg cgacctcgcc gcgcaggcgc tcgttggtcc   3480
agcagaggcg gccgcccttg cgcgagcaga aggggggtag ggggtccagc tggtcctcgt   3540
ttgggggggtc cgcgtcgatg gtgaagaccc cggggagcaa gcgcgggtca aagtagtcga   3600
tcttgcaagc ttgcatgtcc agagcccgct gccattcgcg ggcggcgagc gcgcgctcgt   3660
aggggttgag ggcgggcccc cagggcatgg ggtgggtgag cgcggaggcg tacatgccgc   3720
agatgtcata cacgtacagg ggttccctga ggatgccgag gtaggtgggg tagcagcgcc   3780
ccccgcggat gctggcgcgc acgtagtcat agagctcgtg ggagggggcc agcatgttgg   3840
```

-continued

```
gcccgaggtt ggtgcgctgg gggcgctcgg cgcggaaggc gatctgcctg aagatggcat   3900
gggagttgga ggagatggtg ggccgctgga agacgttgaa gcttgcttct tgcaagccca   3960
ccgagtccct gacgaaggag gcgtaggact cgcgcagctt gtgcaccagc tcggcggtga   4020
cctggacgtc gagcgcgcag tagtcgaggg tctcgcggat gatgtcatac ttatcctccc   4080
ccttcttttt ccacagctcg cggttgagga cgaactcttc gcggtctttc cagtactctt   4140
ggaggggaaa cccgtccgtg tccgaacggt aagagcctag catgtagaac tggttgacgg   4200
cctggtaggg gcaacagccc ttctccacgg gcagcgcgta ggcctgcgcc gccttgcgga   4260
gggaggtgtg ggtgagggcg aaagtgtccc tgaccatgac tttgaggtat tgatgtttga   4320
agtctgtgtc atcgcagccg ccctgttccc acagggtgta gtccgtgcgc tttttggagc   4380
gcgggttggg cagggagaag gtgaggtcat tgaagaggat cttccccgct cgaggcatga   4440
agtttctggt gatgcgaaag ggccctggga ccgaggagcg gttgttgatg acctgggcgg   4500
ccaggacgat ctcgtcaaag ccgtttatgt tgtggcccac gatgtagagc tccaaaaagc   4560
ggggctggcc cttgatggag gggagctttt tgagttcctc gtaggtgagc tcctcgggcg   4620
attccaggcc gtgctcctcc agggcccagt cttgcaagtg agggttggcc gccaggaagg   4680
atcgccagag gtcgcgggcc atgagggtct gcaggcggtc gcggaaggtt ctgaactgtc   4740
gccccacggc catcttttcg ggggtgatgc agtagaaggt gagggggtct ttctcccagg   4800
ggtcccatct gagctctcgg gcgaggtcgc gcgcggcggc gaccagagcc tcgtcgcccc   4860
ccagtttcat gaccagcatg aagggcacga gctgcttgcc aaaggctccc atccaagtgt   4920
aggtctctac atcgtaggtg acaaagaggc gctccgtgcg aggatgagag ccgatcggga   4980
agaactggat ctcccgccac cagttggagg attggctgtt gatgtggtga aagtagaagt   5040
cccgtctgcg ggccgagcac tcgtgctggc ttttgtaaaa gcgaccgcag tactggcagc   5100
gctgcacggg ttgtatatct tgcacgaggt gaacctggcg acctctgacg aggaagcgca   5160
gcgggaatct aagtcccccg cctggggtcc cgtgtggctg gtggtcttct actttggttg   5220
tctggccgcc agcatctgtc tcctggaggg cgatggtgga gcagaccacc acgccgcgag   5280
agccgcaggt ccagatctcg gcgctcggcg ggcggagttt gatgacgaca tcgcgcacat   5340
tggagctgtc catggtctcc agctcccgcg gcggcaggtc agctgggagt tcctggaggt   5400
tcacctcgca gagacgggtc aaggcgcggg cagtgttgag atggtatctg atttcaaggg   5460
gcgtgttggc ggcggagtcg atggcttgca ggaggccgca gccccggggg gccacgatgg   5520
ttccccgcgg ggcgcgaggg gaggcggaag ctgggggtgt gttcagaagc ggtgacgcgg   5580
gcgggccccc ggaggtaggg ggggttccgg ccccacaggc atgggcggca ggggcacgtc   5640
ttcgccgcgc gcgggcaggg gctggtgctg gctccgaaga gcgcttgcgt gcgcgacgac   5700
gcgacggttg gtgtcctgta tctgacgcct ctgagtgaag accacgggtc ccgtgacctt   5760
gaacctgaaa gagagttcga cagaatcaat ctcggcatcg ttgacagcgg cctggcgcag   5820
gatctcctgc acgtcgcccg agttgtcctg gtaggcgatc tctgccatga actgctcgat   5880
ctcttcttcc tggagatctc ctcgtccggc gcgctccacg gtggccgcca ggtcgttgga   5940
gatgcgaccc atgagctgtg agaaggcgtt gagcccgccc tcgttccaga cccggctgta   6000
gaccacgccc ccctcggcgt cgcgagcgcg catgaccacc tgggccaggt tgagctccac   6060
gtgtcgcgtg aagacggcgt agttgcgcag gcgctggaaa aggtagttca gggtggtggc   6120
ggtgtgctcg gcgacgaaga agtacatgac ccagcgccgc aacgtggatt cattgatgtc   6180
ccccaaggcc tccaggcgct ccatggcctc gtagaagtcc acggcgaagt tgaaaaactg   6240
```

-continued

```
ggagttgcga gcggacacgg tcaactcctc ctccagaaga cggatgagct cggcgacagt   6300
gttgcgcacc tcgcgctcga aggccacggg gggcgcttct tcctcttcca cctcttcttc   6360
catgatcgct tcttcttctt cctcagccgg gacgggaggg ggcggcggcg gcgggggagg   6420
ggcgcggcgg cggcggcggc gcaccgggag gcggtcgatg aagcgctcga tcatctcccc   6480
ccgcatgcgg cgcatggtct cggtgacggc gcggccgttc tcccgggggc gcagctcgaa   6540
gacgccgcct ctcatctcgc cgcggggcga gcggccgtga ggtagcgaga cggcgctgac   6600
tatgcatctt aacaattgct gtgtaggtac accgccgagg gacctgattg agtccagatc   6660
caccggatcc gaaaaccttt ggaggaaagc gtctatccag tcgcagtcgc aaggtaggct   6720
gagcaccgtg gcgggcgggg gcgggtctgg agagttcctg gcggagatgc tgctgatgat   6780
gtaattaaag taggcggtct tgagaaggcg gatggtggac aggagcacca tgtctttggg   6840
tccggcctgt tggatgcgga ggcggtcggc catgccccag gcctcgttct gacaccggcg   6900
caggtctttg tagtagtctt gcatgagtct ttccaccggc acctcttctc cttcctcttc   6960
tccatctcgc cggtggtttc tcgcgccgcc catgcgcgtg accccaaagc ccctgagcgg   7020
ctgcagcagg gccaggtcgg cgaccacgcg ctcggccaag atggcctgct gcacctgagt   7080
gagggtcctc tcgaagtcat ccatgtccac gaagcggtgg taggcgcccg tgttgatggt   7140
gtaggtgcag ttggccatga cggaccagtt gacggtctgg tgtcccggct gcgagagctc   7200
cgtgtaccgc aggcgcgaga aggcgcggga atcgaacacg tagtcgttgc aagtccgcac   7260
cagatactgg tagcccacca ggaagtgcgg cggaggttgg cgatagaggg gccagcgctg   7320
ggtggcgggg gcgccgggcg ccaggtcttc cagcatgagg cggtggtatc cgtagatgta   7380
cctggacatc caggtgatgc cggcggcggt ggtggtggcg cgcgcgtagt cgcggacccg   7440
gttccagatg tttcgcaggg gcgagaagtg ttccatggtc ggcacgctct ggccggtgag   7500
gcgcgcgcag tcgttgacgc tctatacaca cacaaaaacg aaagcgttta cagggctttc   7560
gttctgtagc ctggaggaaa gtaaatgggt tgggttgcgg tgtgccccgg ttcgagacca   7620
agctgagctc ggccggctga agccgcagct aacgtggtat tggcagtccc gtctcgaccc   7680
aggccctgta tcctccagga tacggtcgag agccctttg ctttcttggc caagcgcccg   7740
tggcgcgatc tgggatagat ggtcgcgatg agaggacaaa agcggctcgc ttccgtagtc   7800
tggagaaaca atcgccaggg ttgcgttgcg gcgtaccccg gttcgagccc ctatggcggc   7860
ttgaatcggc cggaaccgcg gctaacgagg gccgtggcag ccccgtcctc aggaccccgc   7920
cagccgactt ctccagttac gggagcgagc cccttttgtt ttttattttt tagatgcatc   7980
ccgtgctgcg gcagatgcgc ccctcgcccc ggcccgatca gcagcagcaa cagcaggcat   8040
gcagaccccc ctctcccctt tccgccccgg tcaccacggc cgcggcggcc gtgtcgggcg   8100
cggggggcgc gctggagtca gatgagccac cgcggcggcg acctaggcag tatctggact   8160
tggaagaggg cgagggactg gcgcggctgg gggcgaactc tccagagcgc cacccgcggg   8220
tgcagttgaa aagggacgcg cgcgaggcgt acctgccgcg gcagaacctg tttcgcgacc   8280
gcgggggcga ggagcccgag gagatgcgag actgcaggtt ccaagcgggg cgcgagctgc   8340
ggcgcgggct ggacagacag cgcctgctgc gcgaggagga ctttgagccc gacacgcaga   8400
cgggcatcag ccccgcgcgc gcgcacgtag ccgcggccga cctggtgacc gcctacgagc   8460
agacggtaaa ccaggagcgc aacttccaaa agagcttcaa caaccacgtg cgcacgctgg   8520
tggcgcgcga ggaggtgacc ctgggtctca tgcatctgtg ggacctggtg gaggcgatcg   8580
```

-continued

```
tgcagaaccc cagcagcaag cccctgaccg cgcagctgtt cctggtggtg cagcacagca   8640
gggacaacga ggccttcagg gaggcgctgc tgaacatcac cgagccggag gggcgctggc   8700
tcctggacct gataaacatc ctgcagagca tagtggtgca ggagcgcagc ctgagcctgg   8760
ccgagaaggt ggcggccatc aactactcta tgctgagcct gggcaagttc tacgcccgca   8820
agatctacaa gacccccctac gtgcccatag acaaggaggt gaagatagac agcttctaca   8880
tgcgcatggc gctgaaggtg ctgaccctga gcgacgacct gggagtgtac cgcaacgagc   8940
gcatccacaa ggccgtgagc gccagccggc ggcgcgagct gagcgaccgc gagctgatgc   9000
acagtctgca gcgcgcgctg accggcgcgg gcgagggcga cagggaggtc gagtcctact   9060
tcgacatggg ggccgacctg cactggcagc cgagccgccg cgccctggag gcggcggggg   9120
cgtacggcgg cccccctggcg gccgatgacc aggaagagga ggactatgag ctagaggagg   9180
gcgagtacct ggaggactga cctggctggt ggtgttttgg tatagatgca agatccgaac   9240
gtggcggacc cggcggtccg ggcggcgctg caaagccagc cgtccggcat taactcctct   9300
gacgactggg ccgcggccat gggtcgcatc atggccctga ccgcgcgcaa ccccgaggct   9360
ttcaggcagc agcctcaggc caaccggctg gcggccatct tggaagcggt agtgcccgcg   9420
cgctccaacc ccacccacga gaaggtgctg gccatagtca acgcgctggc ggagagcagg   9480
gccatccgcg cggacgaggc cggactggtg tacgatgcgc tgctgcagcg ggtggcgcgg   9540
tacaacagcg gcaacgtgca gaccaacctg gaccgcctgg tgacggacgt gcgcgaggcc   9600
gtggcgcagc gcgagcgctt gcatcaggac ggtaacctgg gctcgctggt ggcgctaaac   9660
gccttcctca gcacccagcc ggccaacgta ccgcgggggc aggaggacta caccaacttt   9720
ttgagcgcgc tgcggctgat ggtgaccgag gtccctcaga gcgaggtgta ccagtcgggg   9780
cccgactact tcttccagac cagcagacag ggcttgcaaa ccgtgaacct gagccaggct   9840
ttcaagaacc tgcgggggct gtggggagtg aaggcgccca ccggcgaccg ggctacggtg   9900
tccagcctgc taacccccaa ctcgcgcctg ctgctgctgc tgatcgcgcc cttcacggac   9960
agcgggagcg tctcgcggga gacctatctg ggccacctgc tgacgctgta ccgcgaggcc  10020
atcgggcagg cgcaggtgga cgagcacacc ttccaagaga tcaccagcgt gagccacgcg  10080
ctggggcagg aggacacggg cagcctgcag gcgaccctga actacctgct gaccaacagg  10140
cggcagaaga ttcccacgct gcacagcctg acccaggagg aggagcgcat cttgcgctac  10200
gtgcagcaga gcgtgagcct gaacctgatg cgcgacggcg tgacgcccag cgtggcgctg  10260
gacatgaccg cgcgcaacat ggaaccgggc atgtacgcct cccaccggcc gtttatcaac  10320
cgcctgatgg actacttgca tcgggcggcg gccgtgaacc ccgagtactt cactaatgcc  10380
attctgaatc cccactggat gcccctccg ggtttctaca acggggactt tgaggtgccc  10440
gaggtcaacg acgggttcct ctgggatgac atggatgaca gtgtgttctc acccaacccg  10500
ctgcgcgccg cgtctctgcg attgaaggag ggctctgaca gggaaggacc gaggagtctg  10560
gcctcctccc tggctctggg agcggtgggc gccacgggcg cggcggcgcg gggcagtagc  10620
cccttcccca gcctggcaga ctctctgaac agcgggcggg tgagcaggcc ccgcttgcta  10680
ggcgaggagg agtatctgaa caactccctg ctgcagcccg cgagggacaa gaacgctcag  10740
cggcagcagt ttcccaacaa tgggatagag agcctggtgg acaagatgtc cagatggaag  10800
acgtatgcgc aggagtacaa ggagtgggag gaccgccagc cgcggccctt gccgcccccct  10860
aggcagcgct ggcagcggcg cgcgtccaac cgccgctgga ggcaggggcc cgaggacgat  10920
gatgactctg cagatgacag cagcgtgttg gacctgggcg ggagcgggaa cccctttttcg  10980
```

-continued

```
cacctgcgcc cacgcctggg caagatgttt taaaagaaaa aaaaaataaa actcaccaag  11040
gccatggcga cgagcgttgg ttttttgttc ccttccttag tatgcggcgc gcggcgatgt  11100
tcgaggaggg gcctcccccc tcttacgaga gcgcgatggg gatttctcct gcggcgcccc  11160
tgcagcctcc ctacgtgcct cctcggtacc tgcaacctac aggggggaga aatagcatct  11220
gttactctga gctgcagccc ctgtacgata ccaccagact gtacctggtg gacaacaagt  11280
ccgcggacgt ggcctccctg aactaccaga acgaccacag cgatttttttg accacggtga  11340
tccaaaacaa cgacttcacc ccaaccgagg ccagcaccca gaccataaac ctggataaca  11400
ggtcgaactg ggcggcgac ctgaagacca tcttgcacac caacatgccc aacgtgaacg  11460
agttcatgtt caccaactct tttaaggcgc gggtgatggt ggcgcgcgag caggggggagg  11520
cgaagtacga gtgggtggac ttcacgctgc ccgagggcaa ctactcagag accatgactc  11580
tcgacctgat gaacaatgcg atcgtggaac actatctgaa agtgggcagg cagaacgggg  11640
tgaaggaaag cgatatcggg gtcaagtttg acaccagaaa cttccgtctg ggctgggacc  11700
ccgtgaccgg gctggtcatg ccgggggtct acaccaacga ggcctttcat cccgacatag  11760
tgcttctgcc cggctgtggg gtggacttca cccagagccg gctgagcaac ctgctgggca  11820
ttcgcaagcg gcagcctttc caggagggtt tcaagatcac ctatgaggat ctgaaggggg  11880
gcaacattcc cgcgctcctt gatctggacg cctacgagga gagcttgaaa cccgaggaga  11940
gcgctggcga cagcggcgag agtggcgagg agcaagccgg cggcggtggc ggcgcgtcgg  12000
tagaaaacga aagtacgccc gcagtggcgg cggacgctgc ggaggtcgag ccggaggcca  12060
tgcagcagga cgcagaggag ggcgcacagg agggcgcgca gaaggacatg aacgatgggg  12120
agatcagggg agacacattc gccacccggg gcgaagaaaa agaggcagag gcggcggcgg  12180
cggcgacggc ggaggccgaa accgaggttg aggcagaggc agagcccgag accgaagtta  12240
tggaagacat gaatgatgga gaacgtaggg gcgacacgtt cgccacccgg ggcgaagaga  12300
aggcggcgga ggcagaagcc gcggctgagg aggcggctgc ggctgcggcc aagactgagg  12360
ctgcggctaa ggctgaggtc gaagccaatg ttgcggttga ggctcaggct gaggaggagg  12420
cggcggctga agcagttaag gaaaaggccc aggcagagca ggaagagaaa aaacctgtca  12480
ttcaacctct aaaagaagat agcaaaaagc gcagttacaa cgtcatcgag ggcagcacct  12540
ttacccagta ccgcagctgg tacctggcgt acaactacgg cgacccggtc aagggggtgc  12600
gctcgtggac cctgctctgc acgccggacg tcacctgcgg ctccgagcag atgtactggt  12660
cgctgccgaa catgatgcaa gacccggtga ccttccgctc cacgcggcag gttagcaact  12720
tcccggtggt gggcgccgaa ctgctgcccg tgcactccaa gagtttttac aacgagcagg  12780
ccgtctactc ccagctgatc cgccaggcca cctctctgac ccacgtgttc aatcgctttc  12840
ccgagaacca gattttggcg cgcccgccgg cccccaccat caccaccgtg agtgaaaacg  12900
ttcctgccct cacagatcac gggacgctac cgctgcgcaa cagcatctca ggagtccagc  12960
gagtgaccat tactgacgcc agacgccgga cctgccccta cgtttacaag gccttgggca  13020
tagtctcgcc gcgcgtcctc tccagtcgca ctttttaaaa cacatctacc cacacgttcc  13080
aaaatcatgt ccgtactcat ctcacccagc aacaacaccg gctgggggct gcgcgcgccc  13140
agcaagatgt ttggaggggc gaggaagcgc tccgaccagc accctgtgcg cgtgcgcggc  13200
cactaccgcg cgccctgggg agcgcacaag cgcgggcgca cagggcgcac cactgtggac  13260
gacgtcattg actccgtagt ggagcaagcg cgccactaca cacccggcgc gccgaccgcc  13320
```

-continued

```
cccgccgtgt ccaccgtgga ccaggcgatc gaaagcgtgg tacagggcgc gcggcactat  13380
gccaacctta aaagtcgccg ccgccgcgtg gcccgccgcc atcgccggag accccgggcc  13440
accgccgccg cgcgccttac taaggctctg ctcaggcgcg ccaggcgaac tggccaccgg  13500
gccgccatga gggccgcacg gcgggctgcc gctgccgcaa gcgtcgtggc cccgcgggca  13560
cgaaggcgcg cggccgctgc cgccgccgcc gccatttcca gcttggcctc gacgcggcgc  13620
ggtaacatat actgggtgcg cgactcggta accggcacgc gggtacccgt gcgctttcgc  13680
cccccgcgga attagcacaa gacaacatac acactgagtc tcctgctgtt gtgtatccca  13740
gcggcgaccg tcagcagcgg cgacatgtcc aagcgcaaaa ttaaagaaga gatgctccag  13800
gtcatcgcgc cggagatcta tgggcccccg aagaaggagg aggatgatta caagccccgc  13860
aagctaaagc gggtcaaaaa gaaaaagaaa gatgatgatg acgaggcggt ggagtttgtc  13920
cgccgcatgg cacccaggcg ccccgtgcag tggaagggcc ggcgcgtgca gcgcgttttg  13980
cgccccggca ccgcggtggt cttcacgccc ggcgagcgct ccacgcgcac tttcaagcgg  14040
gtgtacgatg aggtgtacgg cgacgaggac ctgttggagc aggccaacca gcgctttggg  14100
gagtttgcat atgggaaacg gccccgcgag agtctaaaag aggacctgct ggcgctaccg  14160
ctggacgagg gcaatcccac cccgagtctg aagccggtaa ccctgcaaca ggtgctgcct  14220
ttgagcgcgc ccagcgagca taagcgaggg ttgaagcgcg aaggcgggga cctggcgccc  14280
accgtgcagt tgatggtgcc caagcggcag aagctggagg acgtgctgga gaaaatgaaa  14340
gtagagcccg ggatccagcc cgagatcaag gtccgcccca tcaagcaggt ggcgcccggc  14400
gtgggagtcc agaccgtgga cgttaggatt cccacggagg agatggaaac ccaaaccgcc  14460
actccctctt cggcggccag cgccaccacc ggcaccgctt cggtagaggt gcagacggac  14520
ccctggctac ccgccaccgc tgttgccgcc gccgcccccc gttcgcgcgg gcgcaagaga  14580
aattatccag cggccagcgc gctcatgccc cagtacgcac tgcatccatc catcgtgccc  14640
acccccggct accgcgggta ctcgtaccgc ccgcgcagat cagccggcac tcgcggccgc  14700
cgccgccgtg cgaccacaac cagccgccgc cgtcgccgcc gccgccagcc agtgctgacc  14760
cccgtgtctg taaggaaggt ggctcgctcg gggagcacgc tggtggtgcc cagagcgcgc  14820
taccacccca gcatcgttta aagccggtct ctgtatggtt cttgcagata tggccctcac  14880
ttgtcgcctc cgcttcccgg tgccgggata ccgaggaaga actcaccgcc gcagaggcat  14940
ggcgggcagc ggtctccgcg gcggccgtcg ccatcgccgg cgcgcaaaaa gcaggcgcat  15000
gcgcggcggt gtgctgcctc tgctaatccc gctaatcgcc gcggcgatcg gtgccgtacc  15060
cgggatcgcc tccgtggccc tgcaggcgtc ccagaaacgt tgactcttgc aaccttgcaa  15120
gcttgcattt tttggaggaa aaataaaaaa aagtctagac tctcacgctc gcttggtcct  15180
gtgactattt tgtagaaaaa aagatggaag acatcaactt tgcgtcgctg gccccgcgtc  15240
acggctcgcg cccgttcatg ggagactgga cagatatcgg caccagcaat atgagcggtg  15300
gcgccttcag ctggggcagt ctgtggagcg gccttaaaaa ttttggttcc accattaaga  15360
actatggcaa caaagcgtgg aacagcagca cgggccagat gctgagagac aagttgaaag  15420
agcagaactt ccaggagaag gtggcgcagg gcctggcctc tggcatcagc ggggtggtgg  15480
acatagctaa ccaggccgtg cagaaaaaga taaacagtca tctggacccc cgtcctcagg  15540
tggaggaaat gcctccagcg atggagacgg tgtctcccga gggcaaaggc gaaaagcgcc  15600
cgcggcccga cagagaagag accctggtgt cacacaccga ggagccgccc tcttacgagg  15660
aggcagtcaa ggccggcctg cccaccactc gccccatagc ccccatggcc accggtgtgg  15720
```

-continued

```
tgggccacag gcaacacact cccgcaacac tagatctgcc cccgccgtcc gagccgccgc  15780
gccagccaaa ggcggcgacg gtgcccgctc cctccacttc cgccgccaac agagtgcccc  15840
tgcgccgcgc cgcgagcggc ccccgggcct cgcgagttag cggcaactgg cagagcacac  15900
tgaacagcat cgtgggcctg ggagtgagga gtgtgaagcg ccgccgttgc tactgaatga  15960
gcaagctagc taacgtgttg tatgtgtgta tgcgtcctat gtcgccgcca gaggagctgt  16020
tgagccgccg gcgccgtctg cactccagcg aatttcaaga tggcgacccc atcgatgatg  16080
cctcagtggt cgtacatgca catctcgggc caggacgctt cggagtacct gagccccggg  16140
ctggtgcagt tcgcccgcgc cacagacacc tacttcaaca tgagtaacaa gttcaggaac  16200
cccactgtgg cgcccaccca cgatgtgacc acggaccggt cgcagcgcct gacgctgcgg  16260
ttcatccccg tggatcggga ggacaccgcc tactcttaca aggcgcggtt cacgctggcc  16320
gtgggcgaca accgcgtgct ggacatggcc tccacttact ttgacatcag gggggtgctg  16380
gacaggggcc ccaccttcaa gccctactcg ggtactgcct acaactccct ggcccccaag  16440
ggcgctccca attcttgcga gtgggaacaa gatgaaccag ctcaggcagc aatagctgaa  16500
gatgaagaag aacttgaaga agaacaagct caggacgaac aggcgcccac taagaaaacc  16560
catgtatacg cccaggcacc tctttctggt gaaaaaatta ctaaggatgg tttgcaaata  16620
ggtgtggatg ccacacaggc gggagataac cctatatatg ctgataaaac attccaaccc  16680
gaacctcaga taggtgagtc tcagtggaac gaggctgatg ccacagtagc aggaggcaga  16740
gtcttaaaaa agaccacccc tatgagacct tgctatggat cctatgccaa acctactaat  16800
gccaatggcg gtcaagggat catggtggcc aatgatcagg gagcgcttga atctaaagtt  16860
gagatgcaat tttctccac cacaacgtct cttaatgtaa gggaaggtga aaacaatctt  16920
cagccaaaag tagtgctata cagcgaagat gttaacttgg aatcccctga cactcatttg  16980
tcttacaaac ctaaaaagga tgacaccaac tctaaaatca tgttgggtca gcaagccatg  17040
cccaacagac ccaacctcat tgcttttagg gacaacttta ttggacttat gtactacaac  17100
agcacaggca acatgggagt gctggcagga caggcctccc agctaaacgc tgtggtagac  17160
ttgcaagaca gaaacacaga gctgtcatac caactgatgc ttgattccat tggagacaga  17220
tcaagatact tttccatgtg gaaccaggca gtggacagct atgacccaga tgtcagaatc  17280
attgaaaacc atggggttga agatgagctg cccaactatt gctttcccct gggcggtatt  17340
ggaattacag acacatacca gtgcataaaa ccaaccgcag ctgctaataa cactacatgg  17400
tctaaggatg aagaatttag tgatcgcaat gaaatagggg tgggaaacaa cttcgccatg  17460
gagatcaaca tccaggccaa cctctggagg aacttcctct atgcgaacgt ggggctctac  17520
ctgccagaca agctcaagta caaccccacc aacgtggaca tctctgacaa ccccaacacc  17580
tatgactaca tgaacaagcg tgtggtggct cccggcctgg tggactgctt tgtcaatgtg  17640
ggagccaggt ggtccctgga ctacatggac aacgtcaacc ccttcaacca ccaccgcaat  17700
gcgggtctgc gctaccgctc catgatcctg ggcaacgggc gctacgtgcc cttccacatt  17760
caggtgcccc agaagttctt tgccatcaag aacctcctcc tcctgccggg ctcctacact  17820
tacgagtgga acttcaggaa ggatgtcaac atggtcctgc agagctctct gggcaatgac  17880
cttagggtgg acggggccag catcaagttt gacagcgtca ccctctatgc taccttcttc  17940
cccatggctc acaacaccgc ctccacgctc gaggccatgc tgaggaacga caccaacgac  18000
cagtccttca atgactacct ctctggggcc aacatgctct accccatccc cgccaaggcc  18060
```

-continued

```
accaacgtgc ccatctccat tccctctcgc aactgggccg ccttcagagg ctgggccttt  18120
acccgcctta agaccaagga aaccccctcc ctgggctcgg gttttgaccc ctactttgtc  18180
tactcgggat ccatccccta cctggatggc accttctacc tcaaccacac ttttaagaag  18240
atatccatca tgtatgactc ctccgtcagc tggccgggca atgaccgcct gctcaccccc  18300
aatgagttcg aggtcaagcg cgccgtggac ggcgagggct acaacgtggc ccagtgcaac  18360
atgaccaagg actggttcct ggtgcagatg ctggccaact acaacatagg ctaccagggc  18420
ttctacatcc cagagagcta caaggacagg atgtactcct tcttcagaaa tttccaaccc  18480
atgagcaggc aggtggtgga cgagaccaaa tacaaggact atcaggccat tggcatcact  18540
caccagcaca acaactcggg attcgtgggc tacctggctc ccaccatgcg cgaggggcag  18600
gcctaccccg ccaacttccc ctacccgttg ataggcaaaa ccgcggtcga cagcgtcacc  18660
cagaaaaagt tcctctgcga ccgcaccctc tggcgcatcc ccttctctag caacttcatg  18720
tccatgggtg cgctcacgga cctgggccag aacctgctct atgccaactc cgcccatgcg  18780
ctggacatga cttttgaggt ggaccccatg gacgagccca cccttctcta tattgtgttt  18840
gaagtgttcg acgtggtcag agtgcaccag ccgcaccgcg gtgtcatcga gaccgtgtac  18900
ctgcgcacgc ccttctcggc cggcaacgcc accacctaag gagacagcgc cgccgcctgc  18960
atgacgggtt ccaccgagca agagctcagg gccatcgcca gagacctggg atgcggaccc  19020
tatttttgg gcacctatga caaacgcttc ccgggcttca tctcccgaga caagctcgcc  19080
tgcgccatcg tcaacacggc cgcgcgcgag accgggggcg tgcactggct ggcctttggc  19140
tgggacccgc gctccaaaac ctgctacctc ttcgacccct ttggcttctc cgatcagcgc  19200
ctcagacaga tctatgagtt tgagtacgag gggctgctgc gccgcagcgc gcttgcctcc  19260
tcgcccgacc gctgcatcac ccttgagaag tccaccgaga ccgtgcaggg gccccactcg  19320
gccgcctgcg gtctcttctg ctgcatgttt ttgcacgcct ttgtgcgctg gccccagagt  19380
cccatggatc gcaaccccac catgaacttg ctcaagggag tgcccaacgc catgctccag  19440
agcccccagg tccagcccac cctgcgccac aaccaggaac agctctaccg cttcctggag  19500
cgccactccc cctacttccg cagtcacagc gcgcacatcc ggggggccac ctctttctgc  19560
cacttgcaag aaaacatgca agacggaaaa tgatgtacag ctcgcttttt aataaatgta  19620
aagactgtgc actttattta tacacgggct ctttctggtt atttattcaa caccgccgtc  19680
gccatctaga aatcgaaagg gttctgccgc gcgtcgccgt gcgccacggg cagagacacg  19740
ttgcgatact ggaagcggct cgcccactta aactcgggca ccaccatgcg gggcagtggt  19800
tcctcgggga agttctcgcc ccacagggtg cgggtcagct gcagcgcgct caggaggtcg  19860
ggagccgaga tcttgaagtc gcagttgggg ccggaaccct gcgcgcgcga gttgcggtac  19920
acggggttgc agcactggaa caccagcagg gccggattat gcacgctggc cagcaggctc  19980
tcgtcgctga tcatgtcgct gtccagatcc tccgcgttgc tcagggcgaa cggggtcatc  20040
ttgcagacct gcctgcccag gaaaggcggc agcccgggct tgccgttgca gtcgcagcgc  20100
aggggcatca gcaggtgccc gcggcccgac tgcgcctgcg ggtacagcgc gcgcatgaag  20160
gcttcgatct gcctgaaagc cacctgcgtc ttggctccct ccgaaaagaa catcccacag  20220
gacttgctgg agaactggtt cgcgggacag ctggcatcgt gcaggcagca gcgcgcgtcg  20280
gtgttggcga tctgcaccac gttgcgaccc caccggttct tcactatctt ggccttggaa  20340
gcctgctcct tcagcgcgcg ctggccgttc tcgctggtca catccatctc tatcacctgc  20400
tccttgttga tcatgtttgt accgtgcaga cacttcaggt cgccctccgt ctgggtgcag  20460
```

```
cggtgctccc acagcgcgca accggtgggc tcccaatttt tgtgggtcac ccccgcgtag  20520
gcctgcaggt aggcctgcaa gaagcgcccc atcatggcca caaaggtctt ctggctcgta  20580
aaggtcagct gcaggccgcg atgctcttcg ttcagccagg tcttgcagat ggcggccagc  20640
gcctcggtct gctcgggcag catcctaaaa tttgtcttca ggtcgttatc cacgtggtac  20700
ttgtccatca tggcgcgcgc cgcctccatg cccttctccc aggcggacac catgggcagg  20760
cttagggggt ttatcacttc caccggcgag gacaccgtac tttcgatttc ttcttcctcc  20820
ccctcttccc ggcgcgcgcc cacgctgctg cgcgctctca ccgcctgcac caaggggtcg  20880
tcttcaggca agcgccgcac cgagcgcttg ccgcccttga cctgcttaat cagcaccggc  20940
gggttgctga agcccaccat ggtcagcgcc gcctgctctt cttcgtcttc gctgtctacc  21000
actatctctg gggaagggct tctccgctct gcggcggcgc gcttcttttt tttcttggga  21060
gcggccgtga tggagtccgc cacggcgacg gaggtcgagg gcgtggggct gggggtgcgc  21120
ggtaccaggg cctcgtcgcc ctcggactct tcctctgact ccaggcggcg gcggagtcgc  21180
ttctttgggg gcgcgcgcgt cagcggcggc ggagacgggg acggggacgg ggacgggacg  21240
ccctccacag gggtggtctt cgcgcagacc ccgcggccgc gctcgggggt cttctcgagc  21300
tggtcttggt cccgactggc cattgtatcc tcctcctcct aggcagagag acataaggag  21360
tctatcatgc aagtcgagaa ggaggagagc ttaaccaccc cctctgagac cgccgatgcg  21420
cccgccgtcg ccgtcgcccc cgctgccgcc gacgcgcccg ccacaccgag cgacaccccc  21480
gcggaccccc ccgccgacgc acccctgttc gaggaagcgg ccgtggagca ggacccgggc  21540
tttgtctcgg cagaggagga tttgcgagag gaggaggata aggagaagaa gccctcagtg  21600
ccaaaagatg ataaagagca agacgagcac gacgcagatg cacaccaggg tgaagtcggg  21660
cggggggacg gagggcatga cggcgccgac tacctagacg aagggaacga cgtgctcttg  21720
aagcacctgc atcgtcagtg cgccattgtt tgcgacgctc tgcaggagcg cagcgaagtg  21780
cccctcagcg tggcggaggt cagccacgcc tacgagctca gcctcttctc cccccgggtg  21840
ccccccccgcc gccgcgaaaa cggcacatgc gagcccaacc cgcgcctcaa cttctacccc  21900
gcctttgtgg tacccgaggt cctggccacc tatcacatct tctttcaaaa ttgcaagatc  21960
cccctctcgt gccgcgccaa ccgtagccgc gccgataaga tgctggccct gcgccagggc  22020
gaccacatac ctgatatcgc cgctttggaa gatgtaccaa agatcttcga gggtctgggt  22080
cgcaacgaga agcgggcagc aaactctctg caacaggaaa acagcgaaaa tgagagtcac  22140
accggggtac tggtggagct cgagggcgac aacgcccgcc tggcggtggt caagcgcagc  22200
atcgaggtca cccactttgc ctaccccgcg ctaaacctgc cccccaaagt catgaacgcg  22260
gccatggacg ggctgatcat gcgccgcggc cggcccctcg ctccagatgc aaacttgcat  22320
gaggagaccg aggacggcca gcccgtggtc agcgacgagc agctggcgcg ctggctggag  22380
accgcggacc ccgccgaact ggaggagcgg cgcaagatga tgatggccgt ggtgctggtc  22440
accgtagagc tggagtgtct gcagcgcttc ttcggcgacc ccgagatgca gagaaaggtc  22500
gaggagaccc tgcactacac cttccgccag ggctacgtgc gccaggcttg caagatctcc  22560
aacgtggagc tcagcaacct ggtgtcctac ctgggcatct tgcatgagaa ccgcctcggg  22620
cagagcgtgc tgcactccac cctgcgcggg gaggcgcgcc gcgactacgt gcgcgactgc  22680
gtttacctct tcctctgcta cacctggcag acggccatgg gggtctggca gcagtgcctg  22740
gaggagcgca acctcaagga gctggagaag ctcctgcagc gcgcgctcaa agatctctgg  22800
```

-continued

```
acgggctaca acgagcgctc ggtggccgcc gcgctggccg acctcatctt ccccgagcgc  22860
ctgctcaaaa ccctccagca ggggctgccc gacttcacca gccaaagcat gttgcaaaac  22920
ttcaggaact ttatcctgga gcgttctggc atcctacccg ccacctgctg cgccctgccc  22980
agcgactttg tcccccctcgt gtaccgcgag tgcccccccgc cgctgtgggg tcactgctac  23040
ctgttccaac tggccaacta cctgtcctac cacgcggacc tcatggagga ctccagcggc  23100
gaggggctca tggagtgcca ctgccgctgc aacctctgca cgccccaccg ctccctggtc  23160
tgcaacaccc aactgctcag cgagagtcag attatcggta ccttcgagct acagggtccg  23220
tcctcctcag acgagaagtc cgcggctccg gggctaaaac tcactccggg gctgtggact  23280
tccgcctacc tgcgcaaatt tgtacctgaa gactaccacg cccacgagat caggttttac  23340
gaagaccaat cccgcccgcc caaggcggag ctgaccgcct gcgtcatcac ccagggcgag  23400
atcctaggcc aattgcaagc catccaaaaa gcccgccaag actttttgct gaagaagggt  23460
cggggggtgt atctggaccc ccagtcgggt gaggagctca acccggttcc cccgctgccg  23520
ccgccgcggg accttgcttc ccaggataag catcgccatg gctcccagaa agaagcagca  23580
gcggccgcca ctgccgccac ccccacatgct ggaggaagag gaggaatact gggacagtca  23640
ggcagaggag gtttcggacg aggaggagcc ggagacggag atggaagagt gggaggagga  23700
cagcttagac gaggaggctt ccgaagccga agaggcagac gcaacaccgt caccctcggc  23760
cgcagccccc tcgcaggcgc ccccgaagtc cgctcccagc atcagcagca acagcagcgc  23820
tataacctcc gctcctccac cgccgcgacc cacggccgac cgcagaccca accgtagatg  23880
ggacaccacc ggaaccgggg ccggtaagtc ctccgggaga ggcaagcaag cgcagcgcca  23940
aggctaccgc tcgtggcgcg ctcacaagaa cgccatagtc gcttgcttgc aagactgcgg  24000
ggggaacatc tccttcgccc gccgcttcct gctcttccac cacggtgtgg ccttcccccg  24060
taacgtcctg cattactacc gtcatctcta cagcccctac tgcggcggca gtgagccaga  24120
gacggtcggc ggcggcggcg gcgcccgttt cggcgcctag gaagacccag ggcaagactt  24180
cagccaagaa actcgcggcg gccgcggcga acgcggtcgc gggggccctg cgcctgacgg  24240
tgaacgaacc cctgtcgacc cgcgaactga ggaaccgaat cttccccact ctctatgcca  24300
tcttccagca gagcagaggg caggatcagg aactgaaagt aaaaaacagg tctctgcgct  24360
ccctcacccg cagctgtctg tatcacaaga gcgaagacca gcttcggcgc acgctggagg  24420
acgctgaggc actcttcagc aaatactgcg cgctcactct taaggactag ctccgcgccc  24480
ttctcgaatt taggcgggaa cgcctacgtc atcgcagcgc cgccgtcatg agcaaggaca  24540
ttcccacgcc atacatgtgg agctatcagc cgcagatggg actcgcggcg ggcgcctccc  24600
aagactactc cacccgcatg aactggctca gtgccggccc acacatgatc tcacaggtta  24660
atgatatccg cacccatcga aaccaaatat tggtggagca ggcggcaatt accaccacgc  24720
cccgcaataa tcccaacccc agggagtggc ccgcgtccct ggtgtatcag gaaattcccg  24780
gccccaccac cgtactactt ccgcgtgatt cccaggccga agtccaaatg actaactcag  24840
gggcacagct cgcgggcggc tgtcgtcaca gggtgcggcc tcctcgccag ggtataactc  24900
acctggagat ccgaggcaga ggtattcagc tcaacgacga gtcggtgagc tcctcgctcg  24960
gtctcagacc tgacgggacc ttccagatag ccggagccgg ccgatcttcc ttcacgcccc  25020
gccaggcgta cctgactctg caaagctcgt cctcggcgcc gcgctcgggc ggcatcggga  25080
ctctccagtt cgtgcaggag tttgtgccct cggtctactt caaccccttc tcgggctctc  25140
ccggtcgcta cccggaccag ttcatctcga actttgacgc cgcgagggac tcggtggacg  25200
```

-continued gctacgactg aatgtcgggt ggacccggtg cagagcaact tcgcctgaag cacctcgacc 25260
actgccgccg ccctcagtgc tttgcccgct gtcagaccgg tgagttccag tacttttccc 25320
tgcccgactc gcacccggac ggcccggcgc acggggtgcg ctttttcatc ccgagtcagg 25380
tgcgctctac cctaatcagg gagtttaccg cccgtcccct actggcggag ttggaaaagg 25440
ggccttctat cctaaccatt gcctgcatct gctctaaccc tggattgcac caagatcttt 25500
gctgtcattt gtgtgctgag tataataaag gctgagatca gaatctactc gggctcctgt 25560
cgccatcctg tcaacgccac cgtccaagcc cggcccgatc agcccgaggt gaacctcacc 25620
tgcggtctgc accggcgcct gaggaaatac ctagcttggt actacaacag cactcccttt 25680
gtggtttaca acagctttga ccaggacggg gtctcactga gggataacct ctcgaacctg 25740
agctactcca tcaggaagaa cagcaccctc gagctacttc ctccttacct gcccgggact 25800
taccagtgtg tcaccggtcc ctgcacccac acccacctgt tgatcgtaaa cgactctctt 25860
ccgagaacag acctcaataa ctcctcttcg cagttcccca gaacaggagg tgagctcagg 25920
aaaccccggg taaagaaggg tggacgagag ttaacacttg tggggtttct ggtgtatgtg 25980
acgctggtgg tggctctttt gattaaggct tttccttcca tgtctgaact ctccctcttc 26040
ttttatgaac aactcgacta gtgctaacgg gaccctaccc aacgaatcgg gattgaatat 26100
cggtaaccag gttgcagttt cacttttgat taccttcata gtcctcttcc tgctagtgct 26160
gtcgcttctg tgcctgcgga tcgggggctg ctgcatccac gtttatatct ggtgctggct 26220
gtttagaagg ttcggagacc atcgcaggta gaataaacat gctgctgctt accctctttg 26280
tcctggcgct ggccgccagc tgccaagcct tttccgaggc tgactttata gagccccagt 26340
gtaatgtgac ttttaaagcc catgcacagc gttgtcatac tataatcaaa tgtgccaccg 26400
aacacgatga ataccttatc cagtataaag ataaatcaca caaagtggca cttgttgaca 26460
tctggaaacc cgaagaccct ttggaataca atgtgaccgt tttccagggt gacctcttca 26520
aaatttacaa ttacactttc ccatttgacc agatgtgtga ctttgtcatg tacatggaaa 26580
agcagcacaa gctgtggcct ccgactcccc agggctgtgt ggaaaatcca ggctctttct 26640
gcatgatctc tctctgtgta actgtgctgg cactaatact cacgcttttg tatatcagat 26700
ttaaatcaag gcaaagcttc attgatgaaa agaaaaatgcc ttaatcgctt tcacgcttga 26760
ttgctaacac cgggttttta tccgcagaat gattggaatc accctactaa tcacctccct 26820
ccttgcgatt gcccatgggt tggaacgaat cgaagtccct gtgggggcca atgttaccct 26880
ggtggggcct gtcggcaatg ctacattaat gtgggaaaaa tatactaaaa atcaatgggt 26940
ctcttactgc actaacaaaa atagccacaa gcccagagcc atctgcgatg ggcaaaatct 27000
aaccttgatt gatgttcaat tgctggatgc gggctactat tatgggcagc tgggtacaat 27060
gattaattac tggagacccc acagagatta catgctccac gtagtaaagg gtccccttag 27120
cagcccaccc actaccacct ctactacccc cactaccacc actactccca ccaccagcac 27180
tgccgcccag cctcctcata gcagaacaac cacttttatc aattccaagt cccactcccc 27240
ccacattgcc ggcgggccct ccgcctcaga ctccgaaacc accgagatct gcttctgcaa 27300
atgctctgac gccattgccc aggatttgga agatcacgag gaagatgagc atgacttcgc 27360
agatgcatgc caggcatcag agccagaagc gctgccggtg gccctcaaac agtatgcaga 27420
cccccacacc acccccgacc ttcctccacc ttcccagaag ccaagtttcc tgggggaaaa 27480
tgaaactctg cctctctcca tactcgctct gacatctgtt gctatgttga ccgctctgct 27540

```
ggtgcttcta tgctctatat gctacctgat ctgctgcaga aagaaaaaat ctcacggcca  27600
tgctcaccag cccctcatgc acttccctta ccctccagag ctgggcgacc acaaacttta  27660
agtctgcagt aactatctgc ccatcccttg tcagtcgaca gcgatgagcc ccactaatct  27720
aacggcctct ggacttacaa catcgtctct taatgagacc accgctcctc aagacctgta  27780
cgatggtgtc tccgcgctgg ttaaccagtg ggatcacctg ggcatatggt ggctcctcat  27840
aggagcagtg accctgtgcc taatcctggt ctggatcatc tgctgcatca aaagcagaag  27900
acccaggcgg cggcccatct acaggcccct tgtcatcaca cctgaagatg atgatgacac  27960
cacttccagg ctgcagaggc taaagcagct actcttctct tttacagcat ggtaaattga  28020
atcatgcctc gcattttcat ctacttgtct ctccttccac tttttctggg ctcttctaca  28080
ttggccgctg tgtcccacat cgaggtagac tgcctcacgc ccttcacagt ctacctgctt  28140
ttcggctttg tcatctgcac ctttgtctgc agcgttatca ctgtagtgat ctgcttcata  28200
cagtgcatcg actacgtctg cgtgcgggtg gcttacttta gacaccaccc ccagtatcgc  28260
aacagggaca tagcggctct cctaagactt gtttaaaatc atggccaaat taactgtgat  28320
tggtcttctg atcatctgct gcgtcctagc cgcgattggg actcaagctc ctaccaccac  28380
cagcgctccc agaaagagac atgtatcctg cagcttcaag cgtccctgga atatacccca  28440
atgctttact gatgaacctg aaatctcttt ggcttggtac ttcagcgtca ccgcccttct  28500
tatcttctgc agtacggtta ttgcccttgc catctaccct tcccttgacc tgggctggaa  28560
tgctgtcaac tctatggaat atcccacctt cccagaacca gacctgccag acctggttgt  28620
tctaaacgcg tttcctcctc ctgctcccgt tcaaaatcag tttcgccctc cgtcccccac  28680
gcccactgag gtcagctact ttaatctaac aggcggagat gactgaaaac ctagacctag  28740
aaatggacgg tctctgcagc gagcaacgca cactagagag gcgccggcaa aaagagctcg  28800
agcgtcttaa acaagagctc caagacgcgg tggccataca ccagtgcaaa aaaggtgtct  28860
tctgtctggt aaaacaggcc acgctcacct atgaaaaaac aggtgacacc caccgcctag  28920
gatacaagct gcccacacag cgccaaaagt tcgccctcat gataggcgaa caacccatca  28980
ccgtgaccca gcactccgtg gagacagaag gctgcataca tgctccctgt aggggcgctg  29040
actgcctcta caccttgatc aaaaccctct gcggtctcag agaccttatc cctttcaatt  29100
aatcataact gtaatcaata aaaaatcact tacttgaaat ctgatagcaa gcctctgtcc  29160
aatttttca gcaacacttc cttcccctcc tcccaactct ggtactctag gcgcctccta  29220
gctgcaaact tcctccacag tctgaaggga atgtcagatt cctcctcctg tccctccgca  29280
cccacgatct tcatgttgtt gcagatgaaa cgcgcgagat cgtctgacga gaccttcaac  29340
cccgtgtacc cctacgatac cgagatcgct ccgacttctg tccctttcct tacccctccc  29400
tttgtgtcat ccgcaggaat gcaagaaaat ccagctgggg tgctgtccct gcacttgtca  29460
gagcccctta ccacccacaa tggggccctg actctaaaaa tggggggcgg cctgaccctg  29520
gacaaggaag ggaatctcac ttcccaaaac atcaccagtg tcgatccccc tctcaaaaaa  29580
agcaagaaca acatcagcct tcagaccgcc gcacccctcg ccgtcagctc cggggcccta  29640
acactttttg ccactccccc cctagcggtc agtggtgaca accttactgt gcagtctcag  29700
gcccctctca ctttggaaga ctcaaaacta actctggcca ccaaaggacc cctaactgtg  29760
tccgaaggca aacttgtcct agaaacagag gctcccctgc atgcaagtga cagcagcagc  29820
ctgggcctta gcgttacggc ccccacttagc attaacaatg acagcctagg actagatctg  29880
caggcaccca ttgtctctca aaatggaaaa ctggctctaa atgtagcagg cccccctagct  29940
```

-continued gtggccaatg gcattaatgc tttgacagta ggcacaggca aaggtattgg tctaaatgaa 30000
accagcactc acttgcaagc aaagttggtc gcccccctag gctttgatac caatggcaac 30060
attaagctaa gcgttgcagg aggcatgaga ctaaataatg acacacttat actagatgta 30120
aactacccat ttgaagctca aggccaacta agtctaagag tgggccaggg tccgctgtat 30180
gtagattcta gcagccataa cctgaccatt agatgcctta gaggattata cataacatcg 30240
tctaataacc aaaccggtct agaggccaac ataaaactaa caaaaggcct tgtctatgat 30300
ggaaatgcca tagcagtcaa tgttggtcaa ggattgcaat acagcactac tgccacatcg 30360
gaaggtgtgt atcctataca gtctaagata ggtttgggaa tggaatatga taccaacgga 30420
gccatgatga caaaactagg ctctggacta agctttgaca attcaggagc cattgtagtg 30480
ggaaacaaaa atgatgacag gcttactctg tggactacac cagacccatc tcctaactgt 30540
agaatttatt ctgaaaaaga tactaaacta accttggtgc tgactaagtg tggcagccaa 30600
atcctaggca cagtatctgc ccttgctgtc agaggcagcc ttgcgcccat cactaatgca 30660
tccagcatag tccaaatatt tctaagattt gatgaaaatg gactattgat gagcaactca 30720
tcgctagacg gtgattactg gaattacaga aatggggact ccactaatag cacaccatat 30780
acaaatgcag taggctttat gcctaatcta gcagcctatc ctaaaggtca ggctacagct 30840
gcaaaaagca gtattgtaag ccaggtatac atggatggtg acactactaa acctataaca 30900
ctaaaaataa acttcaatgg cattgatgaa acaacagaaa ataccccctgt tagtaaatat 30960 tccatgacat tctcatggag ctggcccacc gcaagctaca taggccacac ttttgcaaca 31020
aactctttta ctttctccta catcgcccaa gaataaagaa agcacagaga tgcttgtttt 31080
gatttcaaaa ttgtgtgctt ttatttattt tcagcttaca gtatttccag tagtcattcg 31140
aataaagctt aatcaaactg catgagaacc cttccacata gcttaaatta gcaccagtgc 31200
aaatggagaa aagcctcgag gtcgttgcgc ggccgggatc ggtgatcacc gatccagaca 31260
tgataagata cattgatgag tttggacaaa ccacaactag aatgcagtga aaaaaatgct 31320
ttatttgtga aatttgtgat gctattgctt tatttgtaac cattataagc tgcaataaac 31380
aagttcccgg atcgcgatcc ggcccgaggc tgtagccgac gatggtgcgc caggagagtt 31440
gttgattcat tgtttgcctc cctgctgcgg tttttcaccg aagttcatgc cagtccagcg 31500
tttttgcagc agaaaagccg ccgacttcgg tttgcggtcg cgagtgaaga tccctttctt 31560
gttaccgcca acgcgcaata tgccttgcga ggtcgcaaaa tcggcgaaat tccatacctg 31620
ttcaccgacg acggcgctga cgcgatcaaa gacgcggtga tacatatcca gccatgcaca 31680
ctgatactct tcactccaca tgtcggtgta cattgagtgc agcccggcta acgtatccac 31740
gccgtattcg gtgatgataa tcggctgatg cagtttctcc tgccaggcca gaagttcttt 31800
ttccagtacc ttctctgccg tttccaaatc gccgctttgg acataccatc cgtaataacg 31860
gttcaggcac agcacatcaa agagatcgct gatggtatcg gtgtgagcgt cgcagaacat 31920
tacattgacg caggtgatcg gacgcgtcgg gtcgagttta cgcgttgctt ccgccagtgg 31980
cgcgaaatat tcccgtgcac cttgcggacg ggtatccggt tcgttggcaa tactccacat 32040
caccacgctt gggtggtttt tgtcacgcgc tatcagctct ttaatcgcct gtaagtgcgc 32100
ttgctgagtt tccccgttga ctgcctcttc gctgtacagt tctttcggct tgttgcccgc 32160
ttcgaaacca atgcctaaag agaggttaaa gccgacagca gcagtttcat caatcaccac 32220
gatgccatgt tcatctgccc agtcgagcat ctcttcagcg taagggtaat gcgaggtacg 32280

```
gtaggagttg gccccaatcc agtccattaa tgcgtggtcg tgcaccatca gcacgttatc  32340

gaatcctttg ccacgcaagt ccgcatcttc atgacgacca aagccagtaa agtagaacgg  32400

tttgtggtta atcaggaact gttcgccctt cactgccact gaccggatgc cgacgcgaag  32460

cgggtagata tcacactctg tctggctttt ggctgtgacg cacagttcat agagataacc  32520

ttcacccggt tgccagaggt gcggattcac cacttgcaaa gtcccgctag tgccttgtcc  32580

agttgcaacc acctgttgat ccgcatcacg cagttcaacg ctgacatcac cattggccac  32640

cacctgccag tcaacagacg cgtggttaca gtcttgcgcg acatgcgtca ccacggtgat  32700

atcgtccacc caggtgttcg gcgtggtg                                     32728
```

```
<210> SEQ ID NO 26
<211> LENGTH: 114
<212> TYPE: DNA
<213> ORGANISM: Artificial sequence
<220> FEATURE:
<223> OTHER INFORMATION: IL-2 core promoter

<400> SEQUENCE: 26

acattttgac acccccataa tatttttcca gaattaacag tataaattgc atctcttgtt     60

caagagttcc ctatcactct ctttaatcac tactcacagt aacctcaact cctg          114
```

```
<210> SEQ ID NO 27
<211> LENGTH: 55
<212> TYPE: DNA
<213> ORGANISM: Artificial sequence
<220> FEATURE:
<223> OTHER INFORMATION: IL-2 minimal promoter

<400> SEQUENCE: 27

tcaagagttc cctatcactc tctttaatca ctactcacag taacctcaac tcctg          55
```

```
<210> SEQ ID NO 28
<211> LENGTH: 380
<212> TYPE: DNA
<213> ORGANISM: Artificial sequence
<220> FEATURE:
<223> OTHER INFORMATION: IL-2 enhancer and promoter variant

<400> SEQUENCE: 28

tgatatcttt tctgagttac ttttgtatcc ccaccccctt aaagaaagga ggaaaaactg     60

tttcatacag aaggcgttaa ttgcatgaat tagagctatc acctaagtgt gggctaatgt    120

aacaaagagg gatttcacct acatccattc agtcagtctt tgggggttta aagaaattcc    180

aaagagtcat cagaagagga aaaatgaagg taatgttttt tcagactggt aaagtctttg    240

aaaatatgtg taatatgtaa aacattttga cacccccata atatttttcc agaattaaca    300

gtataaattg catctcttgt tcaagagttc cctatcactc tctttaatca ctactcacag    360

taacctcaac tcctgccaca                                                380
```

```
<210> SEQ ID NO 29
<211> LENGTH: 373
<212> TYPE: DNA
<213> ORGANISM: Artificial sequence
<220> FEATURE:
<223> OTHER INFORMATION: L-2 enhancer and promoter variant

<400> SEQUENCE: 29

ttttctgagt tacttttgta tccccacccc cttaaagaaa ggaggaaaaa ctgtttcata     60

cagaaggcgt taattgcatg aattagagct atcacctaag tgtgggctaa tgtaacaaag    120
```

agggatttca cctacatcca ttcagtcagt ctttgggggt ttaaagaaat tccaaagagt 180
catcagaaga ggaaaaatga aggtaatgtt ttttcagact ggtaaagtct ttgaaaatat 240
gtgtaatatg taaaacattt tgacaccccc ataatatttt tccagaatta acagtataaa 300
ttgcatctct tgttcaagag ttccctatca ctctctttaa tcactactca cagtaacctc 360
aactcctgcc aca 373

<210> SEQ ID NO 30
<211> LENGTH: 161
<212> TYPE: DNA
<213> ORGANISM: Artificial sequence
<220> FEATURE:
<223> OTHER INFORMATION: (NF-?B)1-IL2 promoter variant

<400> SEQUENCE: 30
aattggtccc atcgaagagg gatttcacct acataattgg tcccgggaca ttttgacacc 60
cccataatat ttttccagaa ttaacagtat aaattgcatc tcttgttcaa gagttcccta 120
tcactctctt taatcactac tcacagtaac ctcaactcct g 161

<210> SEQ ID NO 31
<211> LENGTH: 201
<212> TYPE: DNA
<213> ORGANISM: Artificial sequence
<220> FEATURE:
<223> OTHER INFORMATION: (NF-?B)3-IL2 promoter variant

<400> SEQUENCE: 31
aattggtccc atcgaagagg gatttcacct acataagagg gatttcacct acataagagg 60
gatttcacct acataattgg tcccgggaca ttttgacacc cccataatat ttttccagaa 120
ttaacagtat aaattgcatc tcttgttcaa gagttcccta tcactctctt taatcactac 180
tcacagtaac ctcaactcct g 201

<210> SEQ ID NO 32
<211> LENGTH: 268
<212> TYPE: DNA
<213> ORGANISM: Artificial sequence
<220> FEATURE:
<223> OTHER INFORMATION: (NF-?B)6-IL2 promoter variant

<400> SEQUENCE: 32
aattggtccc atcgaagagg gatttcacct acataagagg gatttcacct acataagagg 60
gatttcacct acataattgg taagagggat ttcacctaca taagagggat ttcacctaca 120
taagagggat ttcacctaca taattggtcc cgggacattt tgacaccccc ataatatttt 180
tccagaatta acagtataaa ttgcatctct tgttcaagag ttccctatca ctctctttaa 240
tcactactca cagtaacctc aactcctg 268

<210> SEQ ID NO 33
<211> LENGTH: 177
<212> TYPE: DNA
<213> ORGANISM: Artificial sequence
<220> FEATURE:
<223> OTHER INFORMATION: 1X NFAT response elements-IL2 promoter variant

<400> SEQUENCE: 33
aattggtccc atcgaattag gaggaaaaac tgtttcatac agaaggcgtc aattggtccc 60
gggacatttt gacaccccca taatattttt ccagaattaa cagtataaat tgcatctctt 120
gttcaagagt tccctatcac tctctttaat cactactcac agtaacctca actcctg 177

<210> SEQ ID NO 34
<211> LENGTH: 256
<212> TYPE: DNA
<213> ORGANISM: Artificial sequence
<220> FEATURE:
<223> OTHER INFORMATION: 3X NFAT response elements-IL2 promoter variant

<400> SEQUENCE: 34
tgatatcaat tggtcccatc gaattaggag gaaaaactgt ttcatacaga aggcgtcaat 60
taggaggaaa aactgtttca tacagaaggc gtcaattagg aggaaaaact gtttcataca 120
gaaggcgtca attggtcccg ggacattttg acacccccat aatatttttc cagaattaac 180
agtataaatt gcatctcttg ttcaagagtt ccctatcact ctctttaatc actactcaca 240
gtaacctcaa ctcctg 256

<210> SEQ ID NO 35
<211> LENGTH: 249
<212> TYPE: DNA
<213> ORGANISM: Artificial sequence
<220> FEATURE:
<223> OTHER INFORMATION: 3X NFAT response elements-IL2 promoter variant

<400> SEQUENCE: 35
aattggtccc atcgaattag gaggaaaaac tgtttcatac agaaggcgtc aattaggagg 60
aaaaactgtt tcatacagaa ggcgtcaatt aggaggaaaa actgtttcat acagaaggcg 120
tcaattggtc ccgggacatt ttgacacccc cataatattt ttccagaatt aacagtataa 180
attgcatctc ttgttcaaga gttccctatc actctcttta atcactactc acagtaacct 240
caactcctg 249

<210> SEQ ID NO 36
<211> LENGTH: 358
<212> TYPE: DNA
<213> ORGANISM: Artificial sequence
<220> FEATURE:
<223> OTHER INFORMATION: 6X NFAT response elements-IL2 promoter variant

<400> SEQUENCE: 36
gaattaggag gaaaaactgt ttcatacaga aggcgtcaat taggaggaaa aactgtttca 60
tacagaaggc gtcaattagg aggaaaaact gtttcataca gaaggcgtca attggtccca 120
tcgaattagg aggaaaaact gtttcataca gaaggcgtca attaggagga aaaactgttt 180
catacagaag gcgtcaatta ggaggaaaaa ctgtttcata cagaaggcgt caattggtcc 240
cgggacattt tgacaccccc ataatatttt tccagaatta acagtataaa ttgcatctct 300
tgttcaagag ttccctatca ctctccttaa tcactactca cagtaacctc aactcctg 358

<210> SEQ ID NO 37
<211> LENGTH: 374
<212> TYPE: DNA
<213> ORGANISM: Artificial sequence
<220> FEATURE:
<223> OTHER INFORMATION: 6X NFAT response elements-IL2 promoter variant

<400> SEQUENCE: 37
tgatatcgaa ttaggaggaa aaactgtttc atacagaagg cgtcaattag gaggaaaaac 60
tgtttcatac agaaggcgtc aattaggagg aaaaactgtt tcatacagaa ggcgtcaatt 120
ggtcccatcg aattaggagg aaaaactgtt tcatacagaa ggcgtcaatt aggaggaaaa 180

-continued actgtttcat acagaaggcg tcaattagga ggaaaaactg tttcatacag aaggcgtcaa 240
ttggtcccgg gacattttga cacccccata atatttttcc agaattaaca gtataaattg 300
catctcttgt tcaagagttc cctatcactc tctttaatca ctactcacag taacctcaac 360
tcctgaattc catg 374

<210> SEQ ID NO 38
<211> LENGTH: 358
<212> TYPE: DNA
<213> ORGANISM: Artificial sequence
<220> FEATURE:
<223> OTHER INFORMATION: 6X NFAT response elements-IL2 promoter variant

<400> SEQUENCE: 38
gaattaggag gaaaaactgt ttcatacaga aggcgtcaat taggaggaaa aactgtttca 60
tacagaaggc gtcaattagg aggaaaaact gtttcataca gaaggcgtca attggtccca 120
tcgaattagg aggaaaaact gtttcataca gaaggcgtca attaggagga aaaactgttt 180
catacagaag gcgtcaatta ggaggaaaaa ctgtttcata cagaaggcgt caattggtcc 240
cgggacattt tgacaccccc ataatatttt tccagaatta acagtataaa ttgcatctct 300
tgttcaagag ttccctatca ctctctttaa tcactactca cagtaacctc aactcctg 358

<210> SEQ ID NO 39
<211> LENGTH: 365
<212> TYPE: DNA
<213> ORGANISM: Artificial sequence
<220> FEATURE:
<223> OTHER INFORMATION: 6X NFAT response elements-IL2 promoter variant

<400> SEQUENCE: 39
tgatatcgaa ttaggaggaa aaactgtttc atacagaagg cgtcaattag gaggaaaaac 60
tgtttcatac agaaggcgtc aattaggagg aaaaactgtt tcatacagaa ggcgtcaatt 120
ggtcccatcg aattaggagg aaaaactgtt tcatacagaa ggcgtcaatt aggaggaaaa 180
actgtttcat acagaaggcg tcaattagga ggaaaaactg tttcatacag aaggcgtcaa 240
ttggtcccgg gacattttga cacccccata atatttttcc agaattaaca gtataaattg 300
catctcttgt tcaagagttc cctatcactc tctttaatca ctactcacag taacctcaac 360
tcctg 365

<210> SEQ ID NO 40
<211> LENGTH: 244
<212> TYPE: DNA
<213> ORGANISM: Artificial sequence
<220> FEATURE:
<223> OTHER INFORMATION: human EEF1A1 promoter variant

<400> SEQUENCE: 40
gagcgtgcgt gaggctccgg tgcccgtcag tgggcagagc gcacatcgcc cacagtcccc 60
gagaagttgg ggggaggggg tcggcgattg aaccggtgcc tagagaaggt ggcgcggggt 120
aaactgggaa agtgatgtcg tgtactggct ccgccttttt cccgagggtg ggggagaacc 180
gtatataagt gcagtagtcg ccgtgaacgt tctttttcgc aacgggtttg ccgccagaac 240
acag 244

<210> SEQ ID NO 41
<211> LENGTH: 236
<212> TYPE: DNA

<213> ORGANISM: Artificial sequence
<220> FEATURE:
<223> OTHER INFORMATION: human EEF1A1 promoter variant

<400> SEQUENCE: 41
gcgtgaggct ccggtgcccg tcagtgggca gagcgcacat cgcccacagt ccccgagaag 60
ttggggggag gggtcggcaa ttgaaccggt gcctagagaa ggtggcgcgg ggtaaactgg 120
gaaagtgatg tcgtgtactg gctccgcctt tttcccgagg gtgggggaga accgtatata 180
agtgcagtag tcgccgtgaa cgttcttttt cgcaacgggt ttgccgccag aacaca 236

<210> SEQ ID NO 42
<211> LENGTH: 1266
<212> TYPE: DNA
<213> ORGANISM: Artificial sequence
<220> FEATURE:
<223> OTHER INFORMATION: human EEF1A1 promoter and enhancer

<400> SEQUENCE: 42
gagctttgca aagatggata aagttttaaa cagagaggaa tctttgcagc taatggacct 60
tctaggtctt gaaaggagtg ggaattggct ccggtgcccg tcagtgggca gagcgcacat 120
cgcccacagt ccccgagaag ttggggggag gggtcggcaa ttgaaccggt gcctagagaa 180
ggtggcgcgg ggtaaactgg gaaagtgatg tcgtgtactg gctccgcctt tttcccgagg 240
gtgggggaga accgtatata agtgcagtag tcgccgtgaa cgttcttttt cgcaacgggt 300
ttgccgccag aacacaggta agtgccgtgt gtggttcccg cgggcctggc ctctttacgg 360
gttatggccc ttgcgtgcct tgaattactt ccacctggct gcagtacgtg attcttgatc 420
ccgagcttcg ggttggaagt gggtgggaga gttcgaggcc ttgcgcttaa ggagcccctt 480
cgcctcgtgc ttgagttgag gcctggcctg ggcgctgggg ccgccgcgtg cgaatctggt 540
ggcaccttcg cgcctgtctc gctgctttcg ataagtctct agccatttaa aatttttgat 600
gacctgctgc gacgcttttt ttctggcaag atagtcttgt aaatgcgggc caagatctgc 660
acactggtat ttcggttttt ggggccgcgg gcggcgacgg ggcccgtgcg tcccagcgca 720
catgttcggc gaggcggggc ctgcgagcgc ggccaccgag aatcggacgg gggtagtctc 780
aagctggccg gcctgctctg gtgcctggcc tcgcgccgcc gtgtatcgcc ccgccctggg 840
cggcaaggct ggcccggtcg gcaccagttg cgtgagcgga aagatggccg cttcccggcc 900
ctgctgcagg gagctcaaaa tggaggacgc ggcgctcggg agagcgggcg ggtgagtcac 960
ccacacaaag gaaaagggcc tttccgtcct cagccgtcgc ttcatgtgac tccacggagt 1020
accgggcgcc gtccaggcac ctcgattagt tctcgagctt ttggagtacg tcgtctttag 1080
gttgggggga ggggttttat gcgatggagt ttccccacac tgagtgggtg gagactgaag 1140
ttaggccagc ttggcacttg atgtaattct ccttggaatt tgcccttttt gagtttggat 1200
cttggttcat tctcaagcct cagacagtgg ttcaaagttt ttttcttcca tttcaggtgt 1260
cgtgag 1266

<210> SEQ ID NO 43
<211> LENGTH: 571
<212> TYPE: DNA
<213> ORGANISM: Artificial sequence
<220> FEATURE:
<223> OTHER INFORMATION: human UBC promoter

<400> SEQUENCE: 43
ggcctccgcg ccgggttttg gcgcctcccg cgggcgcccc cctcctcacg gcgagcgctg 60

```
ccacgtcaga cgaagggcgc agcgagcgtc ctgatccttc cgcccggacg ctcaggacag    120

cggcccgctg ctcataagac tcggccttag aaccccagta tcagcagaag gacattttag    180

gacgggactt gggtgactct agggcactgg ttttctttcc agagagcgga acaggcgagg    240

aaaagtagtc ccttctcggc gattctgcgg agggatctcc gtggggcggt gaacgccgat    300

gattatataa ggacgcgccg ggtgtggcac agctagttcc gtcgcagccg ggatttgggt    360

cgcggttctt gtttgtggat cgctgtgatc gtcacttggt gagtagcggg ctgctgggct    420

gggtacgtgc gctcggggtt ggcgagtgtg ttttgtgaag ttttttaggc accttttgaa    480

atgtaatcat ttgggtcaat atgtaatttt cagtgttaga ctagtaaatt gtccgctaaa    540

ttctggccgt ttttggcttt tttgttagac g                                   571
```

<210> SEQ ID NO 44
<211> LENGTH: 81
<212> TYPE: DNA
<213> ORGANISM: Artificial sequence
<220> FEATURE:
<223> OTHER INFORMATION: synthetic minimal promoter 1

<400> SEQUENCE: 44

```
aggtctatat aagcagagct cgtttagtga accctcattc tggagacgga tcccgagccg    60

agtgttttga cctccataga a                                              81
```

<210> SEQ ID NO 45
<211> LENGTH: 151
<212> TYPE: PRT
<213> ORGANISM: Artificial sequence
<220> FEATURE:
<223> OTHER INFORMATION: HPV antigen design 1 HPV16 E6 amino acids

<400> SEQUENCE: 45

```
Met Phe Gln Asp Pro Gln Glu Arg Pro Arg Lys Leu Pro Gln Leu Cys
1               5                   10                  15

Thr Ala Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Gly Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg His Tyr Cys
65                  70                  75                  80

Tyr Ser Leu Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Ala Ala Ala Ala
145                 150
```

<210> SEQ ID NO 46
<211> LENGTH: 98
<212> TYPE: PRT
<213> ORGANISM: Artificial sequence
<220> FEATURE:

```
<223> OTHER INFORMATION: HPV antigen design 1 HPV16 E7 amino acids

<400> SEQUENCE: 46

Met Pro Gly Asp Thr Pro Thr Leu His Glu Tyr Met Leu Asp Leu Gln
1               5                   10                  15

Pro Glu Thr Thr Asp Leu Tyr Gly Tyr Glu Gln Leu Asn Asp Ser Ser
            20                  25                  30

Glu Glu Glu Asp Glu Ile Asp Gly Pro Ala Gly Gln Ala Ala Pro Asp
        35                  40                  45

Arg Ala His Tyr Asn Ile Val Thr Phe Cys Cys Lys Cys Asp Ser Thr
    50                  55                  60

Leu Arg Arg Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro


<210> SEQ ID NO 47
<211> LENGTH: 58
<212> TYPE: PRT
<213> ORGANISM: Artificial sequence
<220> FEATURE:
<223> OTHER INFORMATION: HPV antigen design 1 HPV16 E5 amino acids

<400> SEQUENCE: 47

Met Thr Asn Leu Asp Thr Ala Ser Thr Thr Leu Leu Ala Cys Phe Leu
1               5                   10                  15

Leu Cys Phe Cys Val Leu Leu Cys Val Cys Leu Leu Ile Arg Pro Leu
            20                  25                  30

Leu Leu Ser Val Ser Thr Tyr Thr Arg Cys Phe Ile Val Tyr Ile Ile
        35                  40                  45

Phe Val Tyr Ile Pro Leu Phe Leu Ile His
    50                  55


<210> SEQ ID NO 48
<211> LENGTH: 120
<212> TYPE: PRT
<213> ORGANISM: Artificial sequence
<220> FEATURE:
<223> OTHER INFORMATION: HPV antigen design 1 HPV18 E6 amino acids

<400> SEQUENCE: 48

Met Ala Arg Phe Glu Asp Pro Thr Arg Arg Pro Tyr Lys Leu Pro Asp
1               5                   10                  15

Leu Cys Thr Ala Leu Asn Thr Ser Leu Gln Asp Ile Glu Ile Thr Cys
            20                  25                  30

Val Tyr Cys Lys Thr Val Leu Glu Leu Thr Glu Val Phe Glu Phe Ala
        35                  40                  45

Phe Lys Asp Gly Phe Val Val Tyr Arg Asp Ser Ile Pro His Ala Ala
    50                  55                  60

Cys His Lys Cys Ile Asp Phe Tyr Ser Arg Ile Arg Glu Leu Arg His
65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
            100                 105                 110

Asn Pro Ala Glu Lys Leu Arg His
        115                 120
```

<210> SEQ ID NO 49
<211> LENGTH: 66
<212> TYPE: PRT
<213> ORGANISM: Artificial sequence
<220> FEATURE:
<223> OTHER INFORMATION: HPV antigen design 1 HPV18 E7 amino acids

<400> SEQUENCE: 49

```
Glu Ile Asp Gly Val Asn His Gln His Leu Pro Ala Arg Arg Ala Ala
1               5                   10                  15

Pro Gln Arg His Thr Met Leu Cys Met Cys Cys Lys Cys Glu Ala Arg
            20                  25                  30

Ile Glu Arg Val Val Glu Ser Ser Ala Asp Asp Leu Arg Ala Phe Gln
        35                  40                  45

Gln Leu Phe Leu Asn Thr Leu Ser Phe Val Cys Pro Trp Cys Ala Ser
    50                  55                  60

Gln Gln
65
```

<210> SEQ ID NO 50
<211> LENGTH: 53
<212> TYPE: PRT
<213> ORGANISM: Artificial sequence
<220> FEATURE:
<223> OTHER INFORMATION: HPV antigen design 1 HPV18 E5 amino acids

<400> SEQUENCE: 50

```
Met Leu Ser Leu Ile Phe Leu Phe Cys Phe Cys Val Cys Met Tyr Val
1               5                   10                  15

Cys Cys His Val Pro Leu Leu Pro Ser Val Val Val Ile Thr Ser Pro
            20                  25                  30

Ala Thr Ala Phe Thr Val Tyr Leu Leu Pro Met Leu Leu Leu His Ile
        35                  40                  45

His Ala Ile Leu Ser
    50
```

<210> SEQ ID NO 51
<211> LENGTH: 547
<212> TYPE: PRT
<213> ORGANISM: Artificial sequence
<220> FEATURE:
<223> OTHER INFORMATION: HPV antigen design 1 amino acids

<400> SEQUENCE: 51

```
Met Met Phe Gln Asp Pro Gln Glu Arg Pro Arg Lys Leu Pro Gln Leu
1               5                   10                  15

Cys Thr Ala Leu Gln Thr Thr Ile His Asp Ile Ile Leu Glu Cys Val
            20                  25                  30

Tyr Cys Lys Gln Gln Leu Leu Arg Arg Glu Val Tyr Asp Phe Ala Phe
        35                  40                  45

Arg Asp Gly Cys Ile Val Tyr Arg Asp Gly Asn Pro Tyr Ala Val Cys
    50                  55                  60

Asp Lys Cys Leu Lys Phe Tyr Ser Lys Ile Ser Glu Tyr Arg His Tyr
65                  70                  75                  80

Cys Tyr Ser Leu Tyr Gly Thr Thr Leu Glu Gln Gln Tyr Asn Lys Pro
                85                  90                  95

Leu Cys Asp Leu Leu Ile Arg Cys Ile Asn Cys Gln Lys Pro Leu Cys
            100                 105                 110
```

-continued

```
Pro Glu Glu Lys Gln Arg His Leu Asp Lys Lys Gln Arg Phe His Asn
        115                 120                 125

Ile Arg Gly Arg Trp Thr Gly Arg Cys Met Ser Cys Cys Arg Ser Ser
    130                 135                 140

Arg Thr Arg Arg Ala Ala Ala Ala Met Pro Gly Asp Thr Pro Thr Leu
145                 150                 155                 160

His Glu Tyr Met Leu Asp Leu Gln Pro Glu Thr Thr Asp Leu Tyr Gly
                165                 170                 175

Tyr Glu Gln Leu Asn Asp Ser Ser Glu Glu Glu Asp Glu Ile Asp Gly
            180                 185                 190

Pro Ala Gly Gln Ala Ala Pro Asp Arg Ala His Tyr Asn Ile Val Thr
        195                 200                 205

Phe Cys Cys Lys Cys Asp Ser Thr Leu Arg Arg Cys Val Gln Ser Thr
    210                 215                 220

His Val Asp Ile Arg Thr Leu Glu Asp Leu Leu Met Gly Thr Leu Gly
225                 230                 235                 240

Ile Val Cys Pro Ile Cys Ser Gln Lys Pro Met Thr Asn Leu Asp Thr
                245                 250                 255

Ala Ser Thr Thr Leu Leu Ala Cys Phe Leu Leu Cys Phe Cys Val Leu
            260                 265                 270

Leu Cys Val Cys Leu Leu Ile Arg Pro Leu Leu Leu Ser Val Ser Thr
        275                 280                 285

Tyr Thr Arg Cys Phe Ile Val Tyr Ile Ile Phe Val Tyr Ile Pro Leu
    290                 295                 300

Phe Leu Ile His Met Ala Arg Phe Glu Asp Pro Thr Arg Arg Pro Tyr
305                 310                 315                 320

Lys Leu Pro Asp Leu Cys Thr Ala Leu Asn Thr Ser Leu Gln Asp Ile
                325                 330                 335

Glu Ile Thr Cys Val Tyr Cys Lys Thr Val Leu Glu Leu Thr Glu Val
            340                 345                 350

Phe Glu Phe Ala Phe Lys Asp Gly Phe Val Val Tyr Arg Asp Ser Ile
        355                 360                 365

Pro His Ala Ala Cys His Lys Cys Ile Asp Phe Tyr Ser Arg Ile Arg
    370                 375                 380

Glu Leu Arg His Tyr Ser Asp Ser Val Tyr Gly Asp Thr Leu Glu Lys
385                 390                 395                 400

Leu Thr Asn Thr Gly Leu Tyr Asn Leu Leu Ile Arg Cys Leu Arg Cys
                405                 410                 415

Gln Lys Pro Leu Asn Pro Ala Glu Lys Leu Arg His Glu Ile Asp Gly
            420                 425                 430

Val Asn His Gln His Leu Pro Ala Arg Arg Ala Ala Pro Gln Arg His
        435                 440                 445

Thr Met Leu Cys Met Cys Cys Lys Cys Glu Ala Arg Ile Glu Arg Val
    450                 455                 460

Val Glu Ser Ser Ala Asp Asp Leu Arg Ala Phe Gln Gln Leu Phe Leu
465                 470                 475                 480

Asn Thr Leu Ser Phe Val Cys Pro Trp Cys Ala Ser Gln Gln Met Leu
                485                 490                 495

Ser Leu Ile Phe Leu Phe Cys Phe Cys Val Cys Met Tyr Val Cys Cys
            500                 505                 510

His Val Pro Leu Leu Pro Ser Val Val Val Ile Thr Ser Pro Ala Thr
        515                 520                 525

Ala Phe Thr Val Tyr Leu Leu Pro Met Leu Leu Leu His Ile His Ala
```

530 535 540

Ile Leu Ser
545

<210> SEQ ID NO 52
<211> LENGTH: 563
<212> TYPE: PRT
<213> ORGANISM: Artificial sequence
<220> FEATURE:
<223> OTHER INFORMATION: HPV antigen design 2 amino acids

<400> SEQUENCE: 52

Met Gln Thr Asp Arg Thr Gly Glu Thr Ala Leu His Leu Ala Ala Arg
1 5 10 15

Tyr Ser Arg Ser Asp His Leu Asp Lys Lys Gln Arg Phe His Asn Ile
20 25 30

Ala Asp Ala Arg Trp Thr Gly Arg Cys Met Ser Cys Cys Asp Asn Met
35 40 45

Thr Thr Leu Glu Gln Gln Tyr Asn Lys Pro Leu Cys Asp Leu Leu Pro
50 55 60

Leu His Ala Ala Val Ser Ala Asp Ile Ser Glu Tyr Arg His Tyr Cys
65 70 75 80

Tyr Arg Asn Arg Ala Thr Asp Leu Val Tyr Asp Phe Ala Phe Arg Asp
85 90 95

Leu Met His Asp Thr Ile His Asp Ile Ile Leu Glu Cys Val Pro Leu
100 105 110

Ile Leu Ala Ala Arg Leu Ala Val Lys Leu Pro Gln Leu Cys Thr Glu
115 120 125

Leu Ser His Ala Asp Val Phe Ala Phe Arg Asp Leu Cys Ile Val Tyr
130 135 140

Asp Asp Leu Leu Cys Ile Val Tyr Arg Asp Gly Asn Pro Tyr Ala Val
145 150 155 160

Cys Asp Ala Leu His Trp Ala Ala Ala Val Asn Asn Val Leu Cys Val
165 170 175

Gln Ser Thr His Val Asp Ile Gly Ala Asn Lys Arg Thr Leu Glu Asp
180 185 190

Leu Leu Met Gly Thr Asn Asn Arg Thr Leu Gly Ile Val Cys Pro Ile
195 200 205

Pro Leu Phe Leu Ala Ala Arg Glu Gly Ser Tyr Glu Leu Leu Met Gly
210 215 220

Thr Leu Gly Ile Val Ala Asn Arg Thr Leu His Glu Tyr Met Leu Asp
225 230 235 240

Leu Asp His Met Ala His Tyr Asn Ile Val Thr Phe Cys Cys Pro Arg
245 250 255

Asp Tyr Met Leu Asp Leu Gln Pro Glu Thr Thr Ile Val Arg Leu Leu
260 265 270

Asp Leu Glu Val Ser Gln Thr Ser Lys Leu Thr Arg Gln Thr Asp Arg
275 280 285

Thr Gly Glu Thr Ala Leu His Leu Ala Ala Arg Tyr Ser Arg Ser Asp
290 295 300

Cys Asp Ser Thr Leu Arg Leu Cys Val Ala Asp Ala Lys Leu Thr Asn
305 310 315 320

Thr Gly Leu Tyr Asn Leu Asp Asn Met Lys Cys Ile Asp Phe Tyr Ser
325 330 335

Arg Ile Pro Leu His Ala Ala Val Ser Ala Asp Phe Ala Phe Lys Asp

```
            340                 345                 350

Leu Phe Val Val Arg Asn Arg Ala Thr Asp Leu Asn Leu Leu Ile Arg
        355                 360                 365

Cys Leu Arg Cys Met His Asp Lys Leu Pro Asp Leu Cys Thr Glu Leu
    370                 375                 380

Pro Leu Ile Leu Ala Ala Arg Leu Ala Val Glu Leu Thr Glu Val Phe
385                 390                 395                 400

Glu Phe Ala Ser His Ala Asp Val Ser Leu Gln Asp Ile Glu Ile Thr
                405                 410                 415

Cys Val Asp Asp Leu Lys Thr Val Leu Glu Leu Thr Glu Val Leu His
            420                 425                 430

Trp Ala Ala Ala Val Asn Asn Val Asp Asp Leu Arg Ala Phe Gln Gln
        435                 440                 445

Leu Phe Leu Asn Thr Leu Ser Gly Ala Asn Lys Phe Gln Gln Leu Phe
    450                 455                 460

Leu Asn Thr Leu Asn Asn Arg Gln Leu Phe Leu Asn Thr Leu Ser Phe
465                 470                 475                 480

Val Pro Leu Phe Leu Ala Ala Arg Glu Gly Ser Tyr Glu Leu Phe Leu
                485                 490                 495

Asn Thr Leu Ser Phe Val Cys Pro Trp Cys Ala Ser Ala Asn Arg Thr
            500                 505                 510

Leu Gln Asp Ile Val Leu His Leu Asp His Met Ser Glu Glu Glu Asn
        515                 520                 525

Asp Glu Ile Asp Gly Val Asn His Gln His Leu Pro Ala Arg Arg Pro
    530                 535                 540

Arg Asp Tyr Ile Ile Phe Val Tyr Ile Pro Leu Ile Val Arg Leu Leu
545                 550                 555                 560

Asp Leu Glu


<210> SEQ ID NO 53
<211> LENGTH: 605
<212> TYPE: PRT
<213> ORGANISM: Artificial sequence
<220> FEATURE:
<223> OTHER INFORMATION: HPV antigen design 3 amino acids

<400> SEQUENCE: 53

Met Lys Leu Pro Gln Leu Cys Thr Glu Val Met Phe Gln Asp Pro Gln
1               5                   10                  15

Glu Arg Pro Arg Lys Leu Pro Gln Leu Cys Thr Ala Leu Gln Thr Thr
            20                  25                  30

Ile His Asp Ile Ile Leu Glu Cys Val Tyr Cys Lys Gln Gln Leu Leu
        35                  40                  45

Arg Arg Glu Val Tyr Asp Phe Ala Phe Arg Asp Gly Cys Ile Val Tyr
    50                  55                  60

Arg Asp Gly Asn Pro Tyr Ala Val Cys Asp Lys Cys Leu Lys Phe Tyr
65                  70                  75                  80

Ser Lys Ile Ser Glu Tyr Arg His Tyr Cys Tyr Ser Leu Tyr Gly Thr
                85                  90                  95

Thr Leu Glu Gln Gln Tyr Asn Lys Pro Leu Cys Asp Leu Leu Ile Arg
            100                 105                 110

Cys Ile Asn Cys Gln Lys Pro Leu Cys Pro Glu Glu Lys Gln Arg His
        115                 120                 125

Leu Asp Lys Lys Gln Arg Phe His Asn Ile Arg Gly Arg Trp Thr Gly
    130                 135                 140
```

-continued

```
Arg Cys Met Ser Cys Cys Arg Ser Ser Arg Thr Arg Arg Ala Ala Ala
145                 150                 155                 160

Ala Gln Leu Tyr Asn Lys Pro Leu Cys Asp Val Met Pro Gly Asp Thr
                165                 170                 175

Pro Thr Leu His Glu Tyr Met Leu Asp Leu Gln Pro Glu Thr Thr Asp
            180                 185                 190

Leu Tyr Gly Tyr Glu Gln Leu Asn Asp Ser Ser Glu Glu Glu Asp Glu
        195                 200                 205

Ile Asp Gly Pro Ala Gly Gln Ala Ala Pro Asp Arg Ala His Tyr Asn
    210                 215                 220

Ile Val Thr Phe Cys Cys Lys Cys Asp Ser Thr Leu Arg Arg Cys Val
225                 230                 235                 240

Gln Ser Thr His Val Asp Ile Arg Thr Leu Glu Asp Leu Leu Met Gly
                245                 250                 255

Thr Leu Gly Ile Val Cys Pro Ile Cys Ser Gln Lys Pro Arg Thr Leu
            260                 265                 270

Glu Asp Leu Leu Met Gly Val Met Thr Asn Leu Asp Thr Ala Ser Thr
        275                 280                 285

Thr Leu Leu Ala Cys Phe Leu Leu Cys Phe Cys Val Leu Leu Cys Val
    290                 295                 300

Cys Leu Leu Ile Arg Pro Leu Leu Leu Ser Val Ser Thr Tyr Thr Arg
305                 310                 315                 320

Cys Phe Ile Val Tyr Ile Ile Phe Val Tyr Ile Pro Leu Phe Leu Ile
                325                 330                 335

His Lys Leu Pro Asp Leu Cys Thr Glu Val Met Ala Arg Phe Glu Asp
            340                 345                 350

Pro Thr Arg Arg Pro Tyr Lys Leu Pro Asp Leu Cys Thr Ala Leu Asn
        355                 360                 365

Thr Ser Leu Gln Asp Ile Glu Ile Thr Cys Val Tyr Cys Lys Thr Val
    370                 375                 380

Leu Glu Leu Thr Glu Val Phe Glu Phe Ala Phe Lys Asp Gly Phe Val
385                 390                 395                 400

Val Tyr Arg Asp Ser Ile Pro His Ala Ala Cys His Lys Cys Ile Asp
                405                 410                 415

Phe Tyr Ser Arg Ile Arg Glu Leu Arg His Tyr Ser Asp Ser Val Tyr
            420                 425                 430

Gly Asp Thr Leu Glu Lys Leu Thr Asn Thr Gly Leu Tyr Asn Leu Leu
        435                 440                 445

Ile Arg Cys Leu Arg Cys Gln Lys Pro Leu Asn Pro Ala Glu Lys Leu
    450                 455                 460

Arg His Lys Leu Thr Asn Thr Gly Leu Tyr Asn Val Glu Ile Asp Gly
465                 470                 475                 480

Val Asn His Gln His Leu Pro Ala Arg Arg Ala Ala Pro Gln Arg His
                485                 490                 495

Thr Met Leu Cys Met Cys Cys Lys Cys Glu Ala Arg Ile Glu Arg Val
            500                 505                 510

Val Glu Ser Ser Ala Asp Asp Leu Arg Ala Phe Gln Gln Leu Phe Leu
        515                 520                 525

Asn Thr Leu Ser Phe Val Cys Pro Trp Cys Ala Ser Gln Gln Arg Ala
    530                 535                 540

Phe Gln Gln Leu Phe Leu Asn Val Met Leu Ser Leu Ile Phe Leu Phe
545                 550                 555                 560
```

-continued

Cys Phe Cys Val Cys Met Tyr Val Cys Cys His Val Pro Leu Leu Pro
565 570 575

Ser Val Val Val Ile Thr Ser Pro Ala Thr Ala Phe Thr Val Tyr Leu
580 585 590

Leu Pro Met Leu Leu Leu His Ile His Ala Ile Leu Ser
595 600 605

<210> SEQ ID NO 54
<211> LENGTH: 572
<212> TYPE: PRT
<213> ORGANISM: Artificial sequence
<220> FEATURE:
<223> OTHER INFORMATION: HPV antigen design 4 amino acids

<400> SEQUENCE: 54

Met Gln Thr Asp Arg Glu Leu Thr Glu Val Phe Glu Phe Ala Ala Arg
1 5 10 15

Tyr Ser Arg Ser Asp Tyr Ile Ile Phe Val Tyr Ile Pro Leu Ala Asp
20 25 30

Ala Lys Leu Pro Gln Leu Cys Thr Glu Val Asp Asn Met Leu Leu Met
35 40 45

Gly Thr Leu Gly Ile Val Pro Leu His Ala Ala Val Ser Ala Asp Thr
50 55 60

Leu His Glu Tyr Met Leu Asp Leu Arg Asn Arg Ala Thr Asp Leu Ser
65 70 75 80

Glu Glu Glu Asn Asp Glu Ile Asp Gly Val Asn His Gln His Leu Pro
85 90 95

Ala Arg Arg Met His Asp Asn Leu Leu Ile Arg Cys Leu Arg Cys Pro
100 105 110

Leu Ile Leu Ala Ala Arg Leu Ala Val Leu Phe Leu Asn Thr Leu Ser
115 120 125

Phe Val Cys Pro Trp Cys Ala Ser Ser His Ala Asp Val Lys Cys Ile
130 135 140

Asp Phe Tyr Ser Arg Ile Asp Asp Leu Lys Leu Pro Asp Leu Cys Thr
145 150 155 160

Glu Leu Ala Leu His Trp Ala Ala Ala Val Asn Asn Val Gln Leu Phe
165 170 175

Leu Asn Thr Leu Ser Phe Val Gly Ala Asn Lys Phe Gln Gln Leu Phe
180 185 190

Leu Asn Thr Leu Asn Asn Arg Val Tyr Asp Phe Ala Phe Arg Asp Leu
195 200 205

Pro Leu Phe Leu Ala Ala Arg Glu Gly Ser Tyr Glu Lys Leu Thr Asn
210 215 220

Thr Gly Leu Tyr Asn Leu Ala Asn Arg Leu Cys Ile Val Tyr Arg Asp
225 230 235 240

Gly Asn Pro Tyr Ala Val Cys Asp Asp His Met Tyr Met Leu Asp Leu
245 250 255

Gln Pro Glu Thr Thr Pro Arg Asp Phe Ala Phe Arg Asp Leu Cys Ile
260 265 270

Val Tyr Ile Val Arg Leu Leu Asp Leu Glu Val Ser Gln Thr Ser Lys
275 280 285

Leu Thr Arg Gln Thr Asp Arg Thr Leu Gly Ile Val Cys Pro Ile Ala
290 295 300

Ala Arg Tyr Ser Arg Ser Asp Arg Thr Leu Glu Asp Leu Leu Met Gly
305 310 315 320

```
Val Ala Asp Ala Thr Ile His Asp Ile Ile Leu Glu Cys Val Asp Asn
                325                 330                 335

Met His Leu Asp Lys Lys Gln Arg Phe His Asn Ile Pro Leu His Ala
            340                 345                 350

Ala Val Ser Ala Asp Thr Thr Leu Glu Gln Gln Tyr Asn Lys Pro Leu
        355                 360                 365

Cys Asp Leu Leu Arg Asn Arg Ala Thr Asp Leu Cys Asp Ser Thr Leu
    370                 375                 380

Arg Leu Cys Val Met His Asp Arg Trp Thr Gly Arg Cys Met Ser Cys
385                 390                 395                 400

Cys Pro Leu Ile Leu Ala Ala Arg Leu Ala Val Ser Leu Gln Asp Ile
                405                 410                 415

Glu Ile Thr Cys Val Ser His Ala Asp Val Leu Cys Val Gln Ser Thr
            420                 425                 430

His Val Asp Ile Asp Asp Leu Ala His Tyr Asn Ile Val Thr Phe Cys
        435                 440                 445

Cys Leu His Trp Ala Ala Ala Val Asn Asn Val Asp Asp Leu Arg Ala
    450                 455                 460

Phe Gln Gln Leu Phe Leu Asn Thr Leu Ser Gly Ala Asn Lys Ile Ser
465                 470                 475                 480

Glu Tyr Arg His Tyr Cys Tyr Asn Asn Arg Lys Leu Pro Gln Leu Cys
                485                 490                 495

Thr Glu Leu Pro Leu Phe Leu Ala Ala Arg Glu Gly Ser Tyr Glu Lys
            500                 505                 510

Thr Val Leu Glu Leu Thr Glu Val Ala Asn Arg Arg Thr Leu Glu Asp
        515                 520                 525

Leu Leu Met Gly Thr Asp His Met Phe Ala Phe Lys Asp Leu Phe Val
    530                 535                 540

Val Pro Arg Asp Gln Leu Tyr Asn Lys Pro Leu Cys Asp Val Ile Val
545                 550                 555                 560

Arg Thr Leu Gln Asp Ile Val Leu His Leu Leu Glu
                565                 570
```

<210> SEQ ID NO 55
<211> LENGTH: 436
<212> TYPE: PRT
<213> ORGANISM: Artificial sequence
<220> FEATURE:
<223> OTHER INFORMATION: HPV antigen design 5 amino acids

<400> SEQUENCE: 55

```
Met Lys Lys Glu Leu Thr Glu Val Phe Glu Phe Ala Lys Lys Tyr Ile
1               5                   10                  15

Ile Phe Val Tyr Ile Pro Leu Lys Lys Lys Leu Pro Gln Leu Cys Thr
            20                  25                  30

Glu Val Lys Lys Leu Leu Met Gly Thr Leu Gly Ile Val Lys Lys Thr
        35                  40                  45

Leu His Glu Tyr Met Leu Asp Leu Lys Lys Ser Glu Glu Glu Asn Asp
    50                  55                  60

Glu Ile Asp Gly Val Asn His Gln His Leu Pro Ala Arg Arg Lys Lys
65                  70                  75                  80

Asn Leu Leu Ile Arg Cys Leu Arg Cys Lys Lys Leu Phe Leu Asn Thr
                85                  90                  95

Leu Ser Phe Val Cys Pro Trp Cys Ala Ser Lys Lys Lys Cys Ile Asp
            100                 105                 110
```

```
Phe Tyr Ser Arg Ile Lys Lys Lys Leu Pro Asp Leu Cys Thr Glu Leu
        115                 120                 125

Lys Lys Gln Leu Phe Leu Asn Thr Leu Ser Phe Val Lys Lys Phe Gln
    130                 135                 140

Gln Leu Phe Leu Asn Thr Leu Lys Lys Val Tyr Asp Phe Ala Phe Arg
145                 150                 155                 160

Asp Leu Lys Lys Lys Leu Thr Asn Thr Gly Leu Tyr Asn Leu Lys Lys
                165                 170                 175

Leu Cys Ile Val Tyr Arg Asp Gly Asn Pro Tyr Ala Val Cys Asp Lys
            180                 185                 190

Lys Tyr Met Leu Asp Leu Gln Pro Glu Thr Thr Lys Lys Phe Ala Phe
        195                 200                 205

Arg Asp Leu Cys Ile Val Tyr Lys Lys Thr Leu Gly Ile Val Cys Pro
    210                 215                 220

Ile Lys Lys Arg Thr Leu Glu Asp Leu Leu Met Gly Val Lys Lys Thr
225                 230                 235                 240

Ile His Asp Ile Ile Leu Glu Cys Val Lys Lys His Leu Asp Lys Lys
                245                 250                 255

Gln Arg Phe His Asn Ile Lys Lys Thr Thr Leu Glu Gln Gln Tyr Asn
            260                 265                 270

Lys Pro Leu Cys Asp Leu Leu Lys Lys Cys Asp Ser Thr Leu Arg Leu
        275                 280                 285

Cys Val Lys Lys Arg Trp Thr Gly Arg Cys Met Ser Cys Cys Lys Lys
    290                 295                 300

Ser Leu Gln Asp Ile Glu Ile Thr Cys Val Lys Lys Leu Cys Val Gln
305                 310                 315                 320

Ser Thr His Val Asp Ile Lys Lys Ala His Tyr Asn Ile Val Thr Phe
                325                 330                 335

Cys Cys Lys Lys Asp Asp Leu Arg Ala Phe Gln Gln Leu Phe Leu Asn
            340                 345                 350

Thr Leu Ser Lys Lys Ile Ser Glu Tyr Arg His Tyr Cys Tyr Lys Lys
        355                 360                 365

Lys Leu Pro Gln Leu Cys Thr Glu Leu Lys Lys Lys Thr Val Leu Glu
    370                 375                 380

Leu Thr Glu Val Lys Lys Arg Thr Leu Glu Asp Leu Leu Met Gly Thr
385                 390                 395                 400

Lys Lys Phe Ala Phe Lys Asp Leu Phe Val Val Lys Lys Gln Leu Tyr
                405                 410                 415

Asn Lys Pro Leu Cys Asp Val Lys Lys Thr Leu Gln Asp Ile Val Leu
            420                 425                 430

His Leu Lys Lys
        435
```

<210> SEQ ID NO 56
<211> LENGTH: 6380
<212> TYPE: DNA
<213> ORGANISM: Artificial sequence
<220> FEATURE:
<223> OTHER INFORMATION: HPV antigen design 1 full nucleotide sequences of gorilla adenovirus shuttle plasmid

<400> SEQUENCE: 56

```
gacgaaaggg cctcgtgata cgcctatttt tataggttaa tgtcatgata ataatggttt      60

cttagacgtc aggtggcact tttcggggaa atgtgcgcgg aacccctatt tgtttatttt     120

tctaaataca ttcaaatatg tatccgctca tgagacaata accctgataa atgcttcaat     180
```

-continued

```
aatattgaaa aaggaagagt atgagtattc aacatttccg tgtcgccctt attccctttt    240
ttgcggcatt ttgccttcct gtttttgctc acccagaaac gctggtgaaa gtaaaagatg    300
ctgaagatca gttgggtgca cgagtgggtt acatcgaact ggatctcaac agcggtaaga    360
tccttgagag ttttcgcccc gaagaacgtt ttccaatgat gagcactttt aaagttctgc    420
tatgtggcgc ggtattatcc cgtattgacg ccgggcaaga gcaactcggt cgccgcatac    480
actattctca gaatgacttg gttgagtact caccagtcac agaaaagcat cttacggatg    540
gcatgacagt aagagaatta tgcagtgctg ccataaccat gagtgataac actgcggcca    600
acttacttct gacaacgatc ggaggaccga aggagctaac cgcttttttg cacaacatgg    660
gggatcatgt aactcgcctt gatcgttggg aaccggagct gaatgaagcc ataccaaacg    720
acgagcgtga caccacgatg cctgtagcaa tggcaacaac gttgcgcaaa ctattaactg    780
gcgaactact tactctagct tcccggcaac aattaataga ctggatggag gcggataaag    840
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc atttttaatt taaaaggatc taggtgaaga   1140
tcctttttga taatctcatg accaaaatcc cttaacgtga gttttcgttc cactgagcgt   1200
cagaccccgt agaaaagatc aaaggatctt cttgagatcc tttttttctg cgcgtaatct   1260
gctgcttgca aacaaaaaaa ccaccgctac cagcggtggt ttgtttgccg gatcaagagc   1320
taccaactct ttttccgaag gtaactggct tcagcagagc gcagatacca aatactgttc   1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg gtcgggctga acggggggtt   1560
cgtgcacaca gcccagcttg gagcgaacga cctacaccga actgagatac ctacagcgtg   1620
agctatgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg atttttgtga tgctcgtcag   1800
gggggcggag cctatggaaa aacgccagca acgcggcctt tttacggttc ctggcctttt   1860
gctggccttt tgctcacatg ttctttcctg cgttatcccc tgattctgtg gataaccgta   1920
ttaccgcctt tgagtgagct gataccgctc gccgcagccg aacgaccgag cgcagcgagt   1980
cagtgagcga ggaagcggaa gagcgcccaa tacgcaaacc gcctctcccc gcgcgttggc   2040
cgattcatta atgcagctgg cacgacaggt ttcccgactg gaaagcgggc agtgagcgca   2100
acgcaattaa tgtgagttag ctcactcatt aggcacccca ggctttacac tttatgcttc   2160
cggctcgtat gttgtgtgga attgtgagcg gataacaatt tcacacagga aacagctatg   2220
accatgatta cgccaagctg ggtcaagtct tccagtttaa gcagcagagc ggtcagtttc   2280
tcatcccgag cagacgcgcg agaggccgcg ccgctcgcca ccaaagagct gtaaaggtcc   2340
gtagccatgc tgcgcgcggt cgcggcggcg gcggaggcgg cggcggaggt cgcggcgtcc   2400
agcggagttc ctcccacggt cgcgtaggcc attgtagacg aatttgaagg cagaacgggg   2460
cgtccatcca cgttggaacc catcacattc tgacgcactc cagcccagtg aggcatgcgc   2520
```

```
actgtcagat aggggctaaa gatgcttcca tcaaagctgt tgccggtgtc gctcatggcg   2580
gcggctgttg caagacaaaa cagagagacc cttagacccc caatttatac acgccccacc   2640
cttctagcca cgcccacctt acccacctca atcggtatcc tcatcgctag acccaaactc   2700
ggccctggtg caggccagca ccagatggtc aggcctctag ttattaatag taatcaatta   2760
cggggtcatt agttcatagc ccatatatgg agttccgcgt tacataactt acggtaaatg   2820
gcccgcctgg ctgaccgccc aacgaccccc gcccattgac gtcaataatg acgtatgttc   2880
ccatagtaac gccaataggg actttccatt gacgtcaatg ggtggagtat ttacggtaaa   2940
ctgcccactt ggcagtacat caagtgtatc atatgccaag tacgccccct attgacgtca   3000
atgacggtaa atggcccgcc tggcattatg cccagtacat gaccttatgg gactttccta   3060
cttggcagta catctacgta ttagtcatcg ctattaccat ggtgatgcgg ttttggcagt   3120
acatcaatgg gcgtggatag cggtttgact cacggggatt tccaagtctc caccccattg   3180
acgtcaatgg gagtttgttt tggcaccaaa atcaacggga ctttccaaaa tgtcgtaaca   3240
actccgcccc attgacgcaa atgggcggta ggcgtgtacg gtgggaggtc tatataagca   3300
gagctctccc tatcagtgat agagatctcc ctatcagtga tagagatcgt cgacgagctc   3360
gtttagtgaa ccgtcagatc gcctggagac gccatccacg ctgttttgac ctccatagaa   3420
gacaccggga ccgatccagc ctccgcggcc gggaacggtg cattggaacg cggattcccc   3480
gtgccaagag tgacgtaagt accgcctata gagtctatag gcccaccccc ttggcttcac   3540
ttgaggtgtg gcaggcttga gatctggcca tacacttgag tgacaatgac atccactttg   3600
cctttctctc cacaggtgtc cactcccagg tccaactgca gccggatccg gtaccgccac   3660
catgatgttc caggatcctc aagaacggcc tcggaaacta cctcagctgt gtacagcctt   3720
acagacaaca atacatgata taatcctgga gtgcgtctac tgtaaacagc aactgttgcg   3780
tcgcgaggtc tatgatttcg ccttcaggga tggttgtatt gtatacagag acggcaatcc   3840
gtatgcagtg tgtgataagt gtctcaagtt ctatagcaaa atcagtgaat accggcacta   3900
ttgctatagc ctgtatggaa ctacactaga gcagcagtat aacaagccac tctgtgacct   3960
gctaattaga tgtatcaact gccagaagcc tctgtgcccc gaagagaagc agcggcacct   4020
tgacaagaag cagcggtttc ataatatcag agggaggtgg accgggcggt gtatgtcctg   4080
ctgccgcagc agcaggaccc gtcgggccgc ggcggcaatg ccaggggaca cgcccacact   4140
ccacgagtac atgctcgacc ttcagccgga aaccaccgat ctctacggct atgaacagtt   4200
gaacgacagc tccgaagagg aagatgagat cgacggccca gcaggacagg cggcccctga   4260
cagagcacac tacaatattg ttaccttctg ctgcaagtgc gacagcacgc tgcgccgatg   4320
cgtacaatct acgcatgtgg acattaggac ccttgaggat ctgcttatgg ggacactcgg   4380
aattgtttgt cccatatgca gtcagaaacc tatgaccaac ctagacaccg cgagcacgac   4440
tcttctggct tgcttcctgc tatgtttttg cgtgctgctt tgtgtttgcc tactcattcg   4500
gcccctgctg ctgtctgtga gcacgtacac gaggtgcttc attgtctata ttatcttcgt   4560
ttacataccg ctgttcctga ttcacatggc aagatttgaa gatcccacgc ggcggccata   4620
caaactccct gatctctgca cggcactgaa cacttcgttg caggacatag aaatcacttg   4680
cgtgtactgc aagactgtgc tagagctgac cgaggtgttt gagtttgcct tcaaggacgg   4740
ttttgtggtg tatcgggata gcatccccca tgccgcctgc cataaatgta ttgatttcta   4800
ttcgagaatt agagaactca ggcattattc cgactccgta tacggcgaca ccctagaaaa   4860
actgaccaac accggcttgt ataacctcct catccgctgc ctccgatgcc agaagccact   4920
```

```
taacccagcc gagaaattac gccacgagat cgacggggtc aaccatcagc acctgccggc   4980

cagacgagcc gcccctcagc gccataccat gctgtgcatg tgttgcaagt gcgaagccag   5040

gatcgaaagg gtggtggaat ctagcgctga cgacttaagg gcattccaac aactctttct   5100

taacaccctg agcttcgtgt gtccttggtg tgcttcccaa cagatgctta gtctgatttt   5160

tctgttttgc ttttgcgtgt gtatgtatgt ctgctgccac gtgcctctcc taccatctgt   5220

agtggtgatt acatcccccg cgactgcctt caccgtgtac ctgttgccaa tgctcctcct   5280

tcacatacac gccatcctga gctaagcggc cgctctcgag tctagctagt ctagactagc   5340

tagaaagatc cgggaacttg tttattgcag cttataatgg ttacaaataa agcaatagca   5400

tcacaaattt cacaaataaa gcattttttt cactgcattc tagttgtggt ttgtccaaac   5460

tcatcaatgt atcttatcat gtctggatcg gtgatcaccg atcccgatct gtcaaatgac   5520

ggtgacaata aaacggagac tttgacccgg aacgcggaaa ttcacgtaaa aaacacctgg   5580

gcgagtcctc cacgtaatcg gtcaaagtcc ctcggccctc ggtaaatatt acgcactatg   5640

actaacgccc tattattcag ttttcacttc cccgtttcac ttttcgcgcg aaaatggcca   5700

aatcttacat ggtcccgccc aaaattacta cgatatccgg tgaaaagcgc gcgaaaattg   5760

gcacttccgg aggtaggcgg cgctcatcaa aaacgtcaca ttttccgcga cggaagcttg   5820

catgtgagct cctcccactt gcaaatgcca cacttccgcc acacctccca accctactcg   5880

cgcgtcctac gtcacccgcc ccgcctctcc ccgcccacct cattatcata ttggccacaa   5940

tccaaaataa ggtatattat tgatgatggt ttaaacgccc aattcactgg ccgtcgtttt   6000

acaacgtcgt gactgggaaa accctggcgt tacccaactt aatcgccttg cagcacatcc   6060

ccctttcgcc agctggcgta atagcgaaga ggcccgcacc gatcgccctt cccaacagtt   6120

gcgcagcctg aatggcgaat ggcgcctgat gcggtatttt ctccttacgc atctgtgcgg   6180

tatttcacac cgcatatggt gcactctcag tacaatctgc tctgatgccg catagttaag   6240

ccagccccga cacccgccaa cacccgctga cgcgccctga cgggcttgtc tgctcccggc   6300

atccgcttac agacaagctg tgaccgtctc cgggagctgc atgtgtcaga ggttttcacc   6360

gtcatcaccg aaacgcgcga                                               6380
```

<210> SEQ ID NO 57
<211> LENGTH: 6428
<212> TYPE: DNA
<213> ORGANISM: Artificial sequence
<220> FEATURE:
<223> OTHER INFORMATION: HPV antigen design 2 full nucleotide sequences of gorilla adenovirus shuttle plasmid

<400> SEQUENCE: 57

```
gacgaaaggg cctcgtgata cgcctatttt tataggttaa tgtcatgata ataatggttt     60

cttagacgtc aggtggcact tttcggggaa atgtgcgcgg aacccctatt tgtttatttt    120

tctaaataca ttcaaatatg tatccgctca tgagacaata accctgataa atgcttcaat    180

aatattgaaa aaggaagagt atgagtattc aacatttccg tgtcgccctt attccctttt    240

ttgcggcatt ttgccttcct gtttttgctc acccagaaac gctggtgaaa gtaaaagatg    300

ctgaagatca gttgggtgca cgagtgggtt acatcgaact ggatctcaac agcggtaaga    360

tccttgagag ttttcgcccc gaagaacgtt ttccaatgat gagcactttt aaagttctgc    420

tatgtggcgc ggtattatcc cgtattgacg ccgggcaaga gcaactcggt cgccgcatac    480

actattctca gaatgacttg gttgagtact caccagtcac agaaaagcat cttacggatg    540
```

gcatgacagt aagagaatta tgcagtgctg ccataaccat gagtgataac actgcggcca 600
acttacttct gacaacgatc ggaggaccga aggagctaac cgcttttttg cacaacatgg 660
gggatcatgt aactcgcctt gatcgttggg aaccggagct gaatgaagcc ataccaaacg 720
acgagcgtga caccacgatg cctgtagcaa tggcaacaac gttgcgcaaa ctattaactg 780
gcgaactact tactctagct tcccggcaac aattaataga ctggatggag gcggataaag 840
ttgcaggacc acttctgcgc tcggcccttc cggctggctg gtttattgct gataaatctg 900
gagccggtga gcgtgggtct cgcggtatca ttgcagcact ggggccagat ggtaagccct 960
cccgtatcgt agttatctac acgacgggga gtcaggcaac tatggatgaa cgaaatagac 1020
agatcgctga gataggtgcc tcactgatta agcattggta actgtcagac caagtttact 1080
catatatact ttagattgat ttaaaacttc atttttaatt taaaaggatc taggtgaaga 1140
tcctttttga taatctcatg accaaaatcc cttaacgtga gttttcgttc cactgagcgt 1200
cagaccccgt agaaaagatc aaaggatctt cttgagatcc tttttttctg cgcgtaatct 1260
gctgcttgca aacaaaaaaa ccaccgctac cagcggtggt ttgtttgccg gatcaagagc 1320
taccaactct ttttccgaag gtaactggct tcagcagagc gcagatacca aatactgttc 1380
ttctagtgta gccgtagtta ggccaccact tcaagaactc tgtagcaccg cctacatacc 1440
tcgctctgct aatcctgtta ccagtggctg ctgccagtgg cgataagtcg tgtcttaccg 1500
ggttggactc aagacgatag ttaccggata aggcgcagcg gtcgggctga acggggggtt 1560
cgtgcacaca gcccagcttg gagcgaacga cctacaccga actgagatac ctacagcgtg 1620
agctatgaga aagcgccacg cttcccgaag ggagaaaggc ggacaggtat ccggtaagcg 1680
gcagggtcgg aacaggagag cgcacgaggg agcttccagg gggaaacgcc tggtatcttt 1740
atagtcctgt cgggtttcgc cacctctgac ttgagcgtcg atttttgtga tgctcgtcag 1800
gggggcggag cctatggaaa aacgccagca acgcggcctt tttacggttc ctggcctttt 1860
gctggccttt tgctcacatg ttctttcctg cgttatcccc tgattctgtg gataaccgta 1920
ttaccgcctt tgagtgagct gataccgctc gccgcagccg aacgaccgag cgcagcgagt 1980
cagtgagcga ggaagcggaa gagcgcccaa tacgcaaacc gcctctcccc gcgcgttggc 2040
cgattcatta atgcagctgg cacgacaggt ttcccgactg gaaagcgggc agtgagcgca 2100
acgcaattaa tgtgagttag ctcactcatt aggcacccca ggctttacac tttatgcttc 2160
cggctcgtat gttgtgtgga attgtgagcg gataacaatt tcacacagga aacagctatg 2220
accatgatta cgccaagctg ggtcaagtct tccagtttaa gcagcagagc ggtcagtttc 2280
tcatcccgag cagacgcgcg agaggccgcg ccgctcgcca ccaaagagct gtaaaggtcc 2340
gtagccatgc tgcgcgcggt cgcggcggcg gcggaggcgg cggcggaggt cgcggcgtcc 2400
agcggagttc ctcccacggt cgcgtaggcc attgtagacg aatttgaagg cagaacgggg 2460
cgtccatcca cgttggaacc catcacattc tgacgcactc cagcccagtg aggcatgcgc 2520
actgtcagat aggggctaaa gatgcttcca tcaaagctgt tgccggtgtc gctcatggcg 2580
gcggctgttg caagacaaaa cagagagacc cttagacccc caatttatac acgccccacc 2640
cttctagcca cgcccacctt acccacctca atcggtatcc tcatcgctag acccaaactc 2700
ggccctggtg caggccagca ccagatggtc aggcctctag ttattaatag taatcaatta 2760
cggggtcatt agttcatagc ccatatatgg agttccgcgt tacataactt acggtaaatg 2820
gcccgcctgg ctgaccgccc aacgaccccc gcccattgac gtcaataatg acgtatgttc 2880

-continued

```
ccatagtaac gccaataggg actttccatt gacgtcaatg ggtggagtat ttacggtaaa   2940
ctgcccactt ggcagtacat caagtgtatc atatgccaag tacgccccct attgacgtca   3000
atgacggtaa atggcccgcc tggcattatg cccagtacat gaccttatgg gactttccta   3060
cttggcagta catctacgta ttagtcatcg ctattaccat ggtgatgcgg ttttggcagt   3120
acatcaatgg gcgtggatag cggtttgact cacggggatt tccaagtctc caccccattg   3180
acgtcaatgg gagtttgttt tggcaccaaa atcaacggga ctttccaaaa tgtcgtaaca   3240
actccgcccc attgacgcaa atgggcggta ggcgtgtacg gtgggaggtc tatataagca   3300
gagctctccc tatcagtgat agagatctcc ctatcagtga tagagatcgt cgacgagctc   3360
gtttagtgaa ccgtcagatc gcctggagac gccatccacg ctgttttgac ctccatagaa   3420
gacaccggga ccgatccagc ctccgcggcc gggaacggtg cattggaacg cggattcccc   3480
gtgccaagag tgacgtaagt accgcctata gagtctatag gcccaccccc ttggcttcac   3540
ttgaggtgtg gcaggcttga gatctggcca tacacttgag tgacaatgac atccactttg   3600
cctttctctc cacaggtgtc cactcccagg tccaactgca gccggatccg gtaccgccac   3660
catgcagact gatagaaccg gcgaaaccgc tctacacctt gccgcccgtt atagtcgaag   3720
cgaccacctc gataagaaac agcgattcca caacatcgca gacgcaagat ggaccgggcg   3780
gtgtatgtcc tgctgtgaca atatgacaac actggaacag cagtataaca agcccctgtg   3840
tgacctgttg cccctgcacg ccgccgtgtc agccgacata tccgagtatc ggcattactg   3900
ctaccggaac cgtgccaccg acctcgtgta cgactttgca tttagagacc tgatgcacga   3960
taccatccat gacatcatcc tggaatgtgt cccactgatc ctggctgctc ggcttgcagt   4020
gaagctaccc cagctatgca ctgagctatc acacgcagac gtgttcgcct tcagggatct   4080
gtgcattgtt tacgatgacc tgttgtgtat tgtgtacaga gatggcaacc cttatgcagt   4140
gtgtgacgcc ctgcattggg ctgccgccgt gaataatgtc ctttgtgtcc agagcaccca   4200
cgtcgatata ggcgctaata agcggacact ggaggacctg ttgatgggga ctaataatag   4260
aaccctggga atcgtgtgcc ccattccatt attcctggcc gcccgcgagg gatcttatga   4320
actcctgatg ggcacactag gcatcgtggc caataggaca ttgcacgagt atatgctaga   4380
cttagaccac atggctcact ataacattgt cacattttgt tgccccccgcg attacatgct   4440
tgatttacag cccgaaacaa ccatcgtgag actgctcgat ctggaggtat ctcagacaag   4500
taagctcaca agacaaacag acagaaccgg cgagactgct ttgcatctgg ctgcacgata   4560
ttccaggtcc gactgtgata gcaccctgcg gttatgtgtg gcagacgcaa aacttaccaa   4620
taccggccta tataacctcg acaacatgaa gtgcatcgac ttctacagca gaatccccct   4680
ccatgccgcc gtgagcgccg attttgcctt caaggacctg ttcgtggtga gaaaccgagc   4740
caccgacctg aacctgttga ttcggtgttt acgctgtatg cacgacaagc tgcccgattt   4800
gtgtactgag ctgcctctca ttctggccgc acggctcgca gttgaactaa ccgaagtgtt   4860
cgagttcgcc tcccacgccg acgtgtccct acaggacatc gagatcacat gcgtagacga   4920
tctgaaaacc gttctcgaac tcacagaagt gcttcattgg gccgccgcag tcaacaacgt   4980
ggacgatctc cgggcattcc agcaactgtt cctgaataca ctgtctggcg ctaacaagtt   5040
tcagcagtta tttttgaaca cacttaataa ccgccagcta ttcttgaata ccctgtcatt   5100
cgtgccgctg ttcttggctg cgcgcgaggg gtcctacgag ctgtttctga atacgctctc   5160
cttcgtgtgt ccctggtgcg cctccgctaa taggaccctg caagacatcg tacttcacct   5220
ggatcacatg tcagaggagg agaacgatga gatcgacggt gtcaaccacc agcacctccc   5280
```

```
cgcccggagg ccccgagatt acatcatttt tgtatatatt cccttaatcg taagattact   5340

cgacctggag taagcggccg ctctcgagtc tagctagtct agactagcta gaaagatccg   5400

ggaacttgtt tattgcagct tataatggtt acaaataaag caatagcatc acaaatttca   5460

caaataaagc atttttttca ctgcattcta gttgtggttt gtccaaactc atcaatgtat   5520

cttatcatgt ctggatcggt gatcaccgat cccgatctgt caaatgacgg tgacaataaa   5580

acggagactt tgacccggaa cgcggaaatt cacgtaaaaa acacctgggc gagtcctcca   5640

cgtaatcggt caaagtccct cggccctcgg taaatattac gcactatgac taacgcccta   5700

ttattcagtt ttcacttccc cgtttcactt ttcgcgcgaa aatggccaaa tcttacatgg   5760

tcccgcccaa aattactacg atatccggtg aaaagcgcgc gaaaattggc acttccggag   5820

gtaggcggcg ctcatcaaaa acgtcacatt ttccgcgacg gaagcttgca tgtgagctcc   5880

tcccacttgc aaatgccaca cttccgccac acctcccaac cctactcgcg cgtcctacgt   5940

cacccgcccc gcctctcccc gcccacctca ttatcatatt ggccacaatc caaaataagg   6000

tatattattg atgatggttt aaacgcccaa ttcactggcc gtcgttttac aacgtcgtga   6060

ctgggaaaac cctggcgtta cccaacttaa tcgccttgca gcacatcccc ctttcgccag   6120

ctggcgtaat agcgaagagg cccgcaccga tcgcccttcc caacagttgc gcagcctgaa   6180

tggcgaatgg cgcctgatgc ggtattttct ccttacgcat ctgtgcggta tttcacaccg   6240

catatggtgc actctcagta caatctgctc tgatgccgca tagttaagcc agccccgaca   6300

cccgccaaca cccgctgacg cgccctgacg ggcttgtctg ctcccggcat ccgcttacag   6360

acaagctgtg accgtctccg ggagctgcat gtgtcagagg ttttcaccgt catcaccgaa   6420

acgcgcga                                                            6428
```

<210> SEQ ID NO 58
<211> LENGTH: 6554
<212> TYPE: DNA
<213> ORGANISM: Artificial sequence
<220> FEATURE:
<223> OTHER INFORMATION: HPV antigen design 3 full nucleotide sequences of gorilla adenovirus shuttle plasmid

<400> SEQUENCE: 58

```
gacgaaaggg cctcgtgata cgcctatttt tataggttaa tgtcatgata ataatggttt     60

cttagacgtc aggtggcact tttcggggaa atgtgcgcgg aacccctatt tgtttatttt    120

tctaaataca ttcaaatatg tatccgctca tgagacaata accctgataa atgcttcaat    180

aatattgaaa aaggaagagt atgagtattc aacatttccg tgtcgccctt attccctttt    240

ttgcggcatt ttgccttcct gtttttgctc acccagaaac gctggtgaaa gtaaaagatg    300

ctgaagatca gttgggtgca cgagtgggtt acatcgaact ggatctcaac agcggtaaga    360

tccttgagag ttttcgcccc gaagaacgtt ttccaatgat gagcactttt aaagttctgc    420

tatgtggcgc ggtattatcc cgtattgacg ccgggcaaga gcaactcggt cgccgcatac    480

actattctca gaatgacttg gttgagtact caccagtcac agaaaagcat cttacggatg    540

gcatgacagt aagagaatta tgcagtgctg ccataaccat gagtgataac actgcggcca    600

acttacttct gacaacgatc ggaggaccga aggagctaac cgcttttttg cacaacatgg    660

gggatcatgt aactcgcctt gatcgttggg aaccggagct gaatgaagcc ataccaaacg    720

acgagcgtga caccacgatg cctgtagcaa tggcaacaac gttgcgcaaa ctattaactg    780

gcgaactact tactctagct tcccggcaac aattaataga ctggatggag gcggataaag    840
```

-continued

```
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc atttttaatt taaaaggatc taggtgaaga   1140
tcctttttga taatctcatg accaaaatcc cttaacgtga gttttcgttc cactgagcgt   1200
cagaccccgt agaaaagatc aaaggatctt cttgagatcc tttttttctg cgcgtaatct   1260
gctgcttgca aacaaaaaaa ccaccgctac cagcggtggt ttgtttgccg gatcaagagc   1320
taccaactct ttttccgaag gtaactggct tcagcagagc gcagatacca aatactgttc   1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg gtcgggctga acggggggtt   1560
cgtgcacaca gcccagcttg gagcgaacga cctacaccga actgagatac ctacagcgtg   1620
agctatgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg atttttgtga tgctcgtcag   1800
gggggcggag cctatggaaa aacgccagca acgcggcctt tttacggttc ctggcctttt   1860
gctggccttt tgctcacatg ttctttcctg cgttatcccc tgattctgtg gataaccgta   1920
ttaccgcctt tgagtgagct gataccgctc gccgcagccg aacgaccgag cgcagcgagt   1980
cagtgagcga ggaagcggaa gagcgcccaa tacgcaaacc gcctctcccc gcgcgttggc   2040
cgattcatta atgcagctgg cacgacaggt ttcccgactg gaaagcgggc agtgagcgca   2100
acgcaattaa tgtgagttag ctcactcatt aggcacccca ggctttacac tttatgcttc   2160
cggctcgtat gttgtgtgga attgtgagcg gataacaatt tcacacagga aacagctatg   2220
accatgatta cgccaagctg ggtcaagtct tccagtttaa gcagcagagc ggtcagtttc   2280
tcatcccgag cagacgcgcg agaggccgcg ccgctcgcca ccaaagagct gtaaaggtcc   2340
gtagccatgc tgcgcgcggt cgcggcggcg gcggaggcgg cggcggaggt cgcggcgtcc   2400
agcggagttc ctcccacggt cgcgtaggcc attgtagacg aatttgaagg cagaacgggg   2460
cgtccatcca cgttggaacc catcacattc tgacgcactc cagcccagtg aggcatgcgc   2520
actgtcagat aggggctaaa gatgcttcca tcaaagctgt tgccggtgtc gctcatggcg   2580
gcggctgttg caagacaaaa cagagagacc cttagacccc caatttatac acgccccacc   2640
cttctagcca cgcccacctt acccacctca atcggtatcc tcatcgctag acccaaactc   2700
ggccctggtg caggccagca ccagatggtc aggcctctag ttattaatag taatcaatta   2760
cggggtcatt agttcatagc ccatatatgg agttccgcgt tacataactt acggtaaatg   2820
gcccgcctgg ctgaccgccc aacgaccccc gcccattgac gtcaataatg acgtatgttc   2880
ccatagtaac gccaataggg actttccatt gacgtcaatg ggtggagtat ttacggtaaa   2940
ctgcccactt ggcagtacat caagtgtatc atatgccaag tacgccccct attgacgtca   3000
atgacggtaa atggcccgcc tggcattatg cccagtacat gaccttatgg gactttccta   3060
cttggcagta catctacgta ttagtcatcg ctattaccat ggtgatgcgg ttttggcagt   3120
acatcaatgg gcgtggatag cggtttgact cacggggatt tccaagtctc caccccattg   3180
```

acgtcaatgg gagtttgttt tggcaccaaa atcaacggga ctttccaaaa tgtcgtaaca 3240
actccgcccc attgacgcaa atgggcggta ggcgtgtacg gtgggaggtc tatataagca 3300
gagctctccc tatcagtgat agagatctcc ctatcagtga tagagatcgt cgacgagctc 3360
gtttagtgaa ccgtcagatc gcctggagac gccatccacg ctgttttgac ctccatagaa 3420
gacaccggga ccgatccagc ctccgcggcc gggaacggtg cattggaacg cggattcccc 3480
gtgccaagag tgacgtaagt accgcctata gagtctatag gcccaccccc ttggcttcac 3540
ttgaggtgtg gcaggcttga gatctggcca tacacttgag tgacaatgac atccactttg 3600
cctttctctc cacaggtgtc cactcccagg tccaactgca gccggatccg gtaccgccac 3660
catgaagcta ccgcagctct gtacagaagt gatgttccag gatcctcaag aacggcctcg 3720
gaaactacct cagctgtgta cagccttaca gacaacaata catgatataa tcctggagtg 3780
cgtctactgt aaacagcaac tgttgcgtcg cgaggtctat gatttcgcct tcagggatgg 3840
ttgtattgta tacagagacg gcaatccgta tgcagtgtgt gataagtgtc tcaagttcta 3900
tagcaaaatc agtgaatacc ggcactattg ctatagcctg tatggaacta cactagagca 3960
gcagtataac aagccactct gtgacctgct aattagatgt atcaactgcc agaagcctct 4020
gtgccccgaa gagaagcagc ggcaccttga caagaagcag cggtttcata atatcagagg 4080
gaggtggacc gggcggtgta tgtcctgctg ccgcagcagc aggacccgtc gggccgcggc 4140
ggcacagctg tacaacaaac cactgtgtga cgtgatgcca ggggacacgc ccacactcca 4200
cgagtacatg ctcgaccttc agccggaaac caccgatctc tacggctatg aacagttgaa 4260
cgacagctcc gaagaggaag atgagatcga cggcccagca ggacaggcgg cccctgacag 4320
agcacactac aatattgtta ccttctgctg caagtgcgac agcacgctgc gccgatgcgt 4380
acaatctacg catgtggaca ttaggaccct tgaggatctg cttatgggga cactcggaat 4440
tgtttgtccc atatgcagtc agaaacctcg gacactggaa gatttgctca tgggcgttat 4500
gaccaaccta gacaccgcga gcacgactct tctggcttgc ttcctgctat gtttttgcgt 4560
gctgctttgt gtttgcctac tcattcggcc cctgctgctg tctgtgagca cgtacacgag 4620
gtgcttcatt gtctatatta tcttcgttta cataccgctg ttcctgattc acaagctgcc 4680
cgatttgtgc acagaggtga tggcaagatt tgaagatccc acgcggcggc catacaaact 4740
ccctgatctc tgcacggcac tgaacacttc gttgcaggac atagaaatca cttgcgtgta 4800
ctgcaagact gtgctagagc tgaccgaggt gtttgagttt gccttcaagg acggttttgt 4860
ggtgtatcgg gatagcatcc cccatgccgc ctgccataaa tgtattgatt tctattcgag 4920
aattagagaa ctcaggcatt attccgactc cgtatacggc gacaccctag aaaaactgac 4980
caacaccggc ttgtataacc tcctcatccg ctgcctccga tgccagaagc cacttaaccc 5040
agccgagaaa ttacgccaca agctgacgaa caccggtttg tacaatgtgg agatcgacgg 5100
ggtcaaccat cagcacctgc cggccagacg agccgcccct cagcgccata ccatgctgtg 5160
catgtgttgc aagtgcgaag ccaggatcga aagggtggtg gaatctagcg ctgacgactt 5220
aagggcattc caacaactct ttcttaacac cctgagcttc gtgtgtcctt ggtgtgcttc 5280
ccaacagcgc gccttccaac aattgttcct caatgtaatg cttagtctga tttttctgtt 5340
ttgcttttgc gtgtgtatgt atgtctgctg ccacgtgcct ctcctaccat ctgtagtggt 5400
gattacatcc cccgcgactg ccttcaccgt gtacctgttg ccaatgctcc tccttcacat 5460
acacgccatc ctgagctaag cggccgctct cgagtctagc tagtctagac tagctagaaa 5520
gatccgggaa cttgtttatt gcagcttata atggttacaa ataaagcaat agcatcacaa 5580
atttcacaaa taaagcattt ttttcactgc attctagttg tggtttgtcc aaactcatca 5640
atgtatctta tcatgtctgg atcggtgatc accgatcccg atctgtcaaa tgacggtgac 5700
aataaaacgg agactttgac ccggaacgcg gaaattcacg taaaaaacac ctgggcgagt 5760
cctccacgta atcggtcaaa gtccctcggc cctcggtaaa tattacgcac tatgactaac 5820
gccctattat tcagttttca cttccccgtt tcacttttcg cgcgaaaatg gccaaatctt 5880
acatggtccc gcccaaaatt actacgatat ccggtgaaaa gcgcgcgaaa attggcactt 5940
ccggaggtag gcggcgctca tcaaaaacgt cacattttcc gcgacggaag cttgcatgtg 6000
agctcctccc acttgcaaat gccacacttc cgccacacct cccaacccta ctcgcgcgtc 6060
ctacgtcacc cgccccgcct ctccccgccc acctcattat catattggcc acaatccaaa 6120
ataaggtata ttattgatga tggtttaaac gcccaattca ctggccgtcg ttttacaacg 6180
tcgtgactgg gaaaaccctg gcgttaccca acttaatcgc cttgcagcac atcccccttt 6240
cgccagctgg cgtaatagcg aagaggcccg caccgatcgc ccttcccaac agttgcgcag 6300
cctgaatggc gaatggcgcc tgatgcggta ttttctcctt acgcatctgt gcggtatttc 6360
acaccgcata tggtgcactc tcagtacaat ctgctctgat gccgcatagt taagccagcc 6420
ccgacacccg ccaacacccg ctgacgcgcc ctgacgggct tgtctgctcc cggcatccgc 6480
ttacagacaa gctgtgaccg tctccgggag ctgcatgtgt cagaggtttt caccgtcatc 6540
accgaaacgc gcga 6554

<210> SEQ ID NO 59
<211> LENGTH: 6455
<212> TYPE: DNA
<213> ORGANISM: Artificial sequence
<220> FEATURE:
<223> OTHER INFORMATION: HPV antigen design 4 full nucleotide sequences of gorilla adenovirus shuttle plasmid

<400> SEQUENCE: 59
gacgaaaggg cctcgtgata cgcctatttt tataggttaa tgtcatgata ataatggttt 60
cttagacgtc aggtggcact tttcggggaa atgtgcgcgg aacccctatt tgtttatttt 120
tctaaataca ttcaaatatg tatccgctca tgagacaata accctgataa atgcttcaat 180
aatattgaaa aaggaagagt atgagtattc aacatttccg tgtcgccctt attccctttt 240
ttgcggcatt ttgccttcct gtttttgctc acccagaaac gctggtgaaa gtaaaagatg 300
ctgaagatca gttgggtgca cgagtgggtt acatcgaact ggatctcaac agcggtaaga 360
tccttgagag ttttcgcccc gaagaacgtt ttccaatgat gagcactttt aaagttctgc 420
tatgtggcgc ggtattatcc cgtattgacg ccgggcaaga gcaactcggt cgccgcatac 480
actattctca gaatgacttg gttgagtact caccagtcac agaaaagcat cttacggatg 540
gcatgacagt aagagaatta tgcagtgctg ccataaccat gagtgataac actgcggcca 600
acttacttct gacaacgatc ggaggaccga aggagctaac cgcttttttg cacaacatgg 660
gggatcatgt aactcgcctt gatcgttggg aaccggagct gaatgaagcc ataccaaacg 720
acgagcgtga caccacgatg cctgtagcaa tggcaacaac gttgcgcaaa ctattaactg 780
gcgaactact tactctagct tcccggcaac aattaataga ctggatggag gcggataaag 840
ttgcaggacc acttctgcgc tcggcccttc cggctggctg gtttattgct gataaatctg 900
gagccggtga gcgtgggtct cgcggtatca ttgcagcact ggggccagat ggtaagccct 960
cccgtatcgt agttatctac acgacgggga gtcaggcaac tatggatgaa cgaaatagac 1020

```
agatcgctga gataggtgcc tcactgatta agcattggta actgtcagac caagtttact   1080
catatatact ttagattgat ttaaaacttc atttttaatt taaaaggatc taggtgaaga   1140
tcctttttga taatctcatg accaaaatcc cttaacgtga gttttcgttc cactgagcgt   1200
cagaccccgt agaaaagatc aaaggatctt cttgagatcc tttttttctg cgcgtaatct   1260
gctgcttgca aacaaaaaaa ccaccgctac cagcggtggt ttgtttgccg gatcaagagc   1320
taccaactct ttttccgaag gtaactggct tcagcagagc gcagatacca aatactgttc   1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg gtcgggctga acggggggtt   1560
cgtgcacaca gcccagcttg gagcgaacga cctacaccga actgagatac ctacagcgtg   1620
agctatgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg atttttgtga tgctcgtcag   1800
gggggcggag cctatggaaa aacgccagca acgcggcctt tttacggttc ctggcctttt   1860
gctggccttt tgctcacatg ttctttcctg cgttatcccc tgattctgtg gataaccgta   1920
ttaccgcctt tgagtgagct gataccgctc gccgcagccg aacgaccgag cgcagcgagt   1980
cagtgagcga ggaagcggaa gagcgcccaa tacgcaaacc gcctctcccc gcgcgttggc   2040
cgattcatta atgcagctgg cacgacaggt ttcccgactg gaaagcgggc agtgagcgca   2100
acgcaattaa tgtgagttag ctcactcatt aggcacccca ggctttacac tttatgcttc   2160
cggctcgtat gttgtgtgga attgtgagcg gataacaatt tcacacagga aacagctatg   2220
accatgatta cgccaagctg ggtcaagtct tccagtttaa gcagcagagc ggtcagtttc   2280
tcatcccgag cagacgcgcg agaggccgcg ccgctcgcca ccaaagagct gtaaaggtcc   2340
gtagccatgc tgcgcgcggt cgcggcggcg gcggaggcgg cggcggaggt cgcggcgtcc   2400
agcggagttc ctcccacggt cgcgtaggcc attgtagacg aatttgaagg cagaacgggg   2460
cgtccatcca cgttggaacc catcacattc tgacgcactc cagcccagtg aggcatgcgc   2520
actgtcagat aggggctaaa gatgcttcca tcaaagctgt tgccggtgtc gctcatggcg   2580
gcggctgttg caagacaaaa cagagagacc cttagacccc caatttatac acgccccacc   2640
cttctagcca cgcccacctt acccacctca atcggtatcc tcatcgctag acccaaactc   2700
ggccctggtg caggccagca ccagatggtc aggcctctag ttattaatag taatcaatta   2760
cggggtcatt agttcatagc ccatatatgg agttccgcgt tacataactt acggtaaatg   2820
gcccgcctgg ctgaccgccc aacgaccccc gcccattgac gtcaataatg acgtatgttc   2880
ccatagtaac gccaataggg actttccatt gacgtcaatg ggtggagtat ttacggtaaa   2940
ctgcccactt ggcagtacat caagtgtatc atatgccaag tacgccccct attgacgtca   3000
atgacggtaa atggcccgcc tggcattatg cccagtacat gaccttatgg gactttccta   3060
cttggcagta catctacgta ttagtcatcg ctattaccat ggtgatgcgg ttttggcagt   3120
acatcaatgg gcgtggatag cggtttgact cacggggatt tccaagtctc caccccattg   3180
acgtcaatgg gagtttgttt tggcaccaaa atcaacggga ctttccaaaa tgtcgtaaca   3240
actccgcccc attgacgcaa atgggcggta ggcgtgtacg gtgggaggtc tatataagca   3300
gagctctccc tatcagtgat agagatctcc ctatcagtga tagagatcgt cgacgagctc   3360
```

-continued gtttagtgaa ccgtcagatc gcctggagac gccatccacg ctgttttgac ctccatagaa 3420
gacaccggga ccgatccagc ctccgcggcc gggaacggtg cattggaacg cggattcccc 3480
gtgccaagag tgacgtaagt accgcctata gagtctatag gcccaccccc ttggcttcac 3540
ttgaggtgtg gcaggcttga gatctggcca tacacttgag tgacaatgac atccactttg 3600
cctttctctc cacaggtgtc cactcccagg tccaactgca gccggatccg gtaccgccac 3660
catgcaaacc gacagagagc ttaccgaggt tttcgagttt gcagcccggt actcccggag 3720
cgactacatt atttttgtct atatccctct cgcagacgca aagctgcctc aactgtgtac 3780
agaggttgat aatatgctac tgatgggcac tctcggcatc gtgccgctcc acgccgccgt 3840
gagcgccgac accctgcatg aatacatgct ggacctgaga aatcgggcaa ccgacttatc 3900
cgaggaggag aacgacgaaa ttgatggagt taatcaccag cacctaccag caagacgaat 3960
gcacgacaac ctactgatta gatgcttgag gtgtcccctt attttggcag ccagactcgc 4020
cgttctgttc ctgaacaccc tgagctttgt atgcccctgg tgtgccagct cgcacgcaga 4080
cgtgaaatgt attgacttct attccagaat cgacgaccta aaactgcctg atctctgtac 4140
agagcttgcg ttgcactggg cagccgccgt gaacaacgtg cagttgtttc tgaacacctt 4200
atccttcgtg ggcgctaaca aattccagca actttttcttg aacaccctaa acaacagagt 4260
ttatgacttt gctttcagag acctcccccct gttccttgct gccagagagg gatcatacga 4320
gaaactgaca aatacgggcc tctacaattt ggccaacaga ctgtgcatcg tgtacagaga 4380
tggcaatccc tacgccgttt gcgacgacca catgtacatg ctcgacctcc agccggagac 4440
aactcccaga gacttcgctt ttcgggacct gtgtatcgtg tatattgtaa gactcctgga 4500
cctggaagtg agccaaacaa gtaagctaac cagacaaaca gacagaacac ttgggatcgt 4560
gtgtcctatt gcagcccggt atagtaggtc agaccggact ctggaggacc tgttaatggg 4620
ggtggcggac gcaacaatcc acgacattat cttggagtgt gttgacaata tgcacctgga 4680
caagaaacag agattccaca acatacccct gcacgcagcc gtcagcgcgg atactactct 4740
ggagcagcaa tataacaagc ccctgtgcga cctcctgcgg aatcgggcaa ctgatctctg 4800
tgacagtacc cttcgtttgt gcgttatgca cgacaggtgg actgggagat gtatgtcttg 4860
ctgtcctctc attctggccg caagactggc cgttagtctg caagacatcg agatcacctg 4920
tgtcagtcac gccgatgtgc tatgcgtgca gagcacccac gttgatattg atgacctagc 4980
acactacaac atcgttactt tttgctgtct acactgggcc gcagccgtga ataacgtgga 5040
cgacctacgc gctttccaac aactgttcct taacaccctg agcggcgcaa acaagatcag 5100
cgagtaccgc cactactgtt ataataaccg gaagctgcca cagctatgca cagagttgcc 5160
actgttcctg gcagcaagag agggatctta tgaaaagacc gtgctggagc tgacagaggt 5220
ggctaatcgc cgcacactgg aggacctgtt gatgggaacc gatcacatgt tcgcctttaa 5280
ggaccttttc gttgttccca gagaccagct ttacaacaaa cctctatgcg acgtaatagt 5340
gaggaccttg caggatattg tgctccatct gctggaataa gcggccgctc tcgagtctag 5400
ctagtctaga ctagctagaa agatccggga acttgtttat tgcagcttat aatggttaca 5460
aataaagcaa tagcatcaca aatttcacaa ataaagcatt tttttcactg cattctagtt 5520
gtggtttgtc caaactcatc aatgtatctt atcatgtctg gatcggtgat caccgatccc 5580
gatctgtcaa atgacggtga caataaaacg gagactttga cccggaacgc ggaaattcac 5640
gtaaaaaaca cctgggcgag tcctccacgt aatcggtcaa agtccctcgg ccctcggtaa 5700
atattacgca ctatgactaa cgccctatta ttcagttttc acttccccgt ttcacttttc 5760

-continued gcgcgaaaat ggccaaatct tacatggtcc cgcccaaaat tactacgata tccggtgaaa 5820
agcgcgcgaa aattggcact tccggaggta ggcggcgctc atcaaaaacg tcacattttc 5880
cgcgacggaa gcttgcatgt gagctcctcc cacttgcaaa tgccacactt ccgccacacc 5940
tcccaaccct actcgcgcgt cctacgtcac ccgccccgcc tctccccgcc cacctcatta 6000
tcatattggc cacaatccaa aataaggtat attattgatg atggtttaaa cgcccaattc 6060
actggccgtc gttttacaac gtcgtgactg ggaaaaccct ggcgttaccc aacttaatcg 6120
ccttgcagca catccccctt tcgccagctg gcgtaatagc gaagaggccc gcaccgatcg 6180
cccttcccaa cagttgcgca gcctgaatgg cgaatggcgc ctgatgcggt attttctcct 6240
tacgcatctg tgcggtattt cacaccgcat atggtgcact ctcagtacaa tctgctctga 6300
tgccgcatag ttaagccagc cccgacaccc gccaacaccc gctgacgcgc cctgacgggc 6360
ttgtctgctc ccggcatccg cttacagaca agctgtgacc gtctccggga gctgcatgtg 6420
tcagaggttt tcaccgtcat caccgaaacg cgcga 6455

<210> SEQ ID NO 60
<211> LENGTH: 6047
<212> TYPE: DNA
<213> ORGANISM: Artificial sequence
<220> FEATURE:
<223> OTHER INFORMATION: HPV antigen design 5 full nucleotide sequences of gorilla adenovirus shuttle plasmid

<400> SEQUENCE: 60
gacgaaaggg cctcgtgata cgcctatttt tataggttaa tgtcatgata ataatggttt 60
cttagacgtc aggtggcact tttcggggaa atgtgcgcgg aacccctatt tgtttatttt 120
tctaaataca ttcaaatatg tatccgctca tgagacaata accctgataa atgcttcaat 180
aatattgaaa aaggaagagt atgagtattc aacatttccg tgtcgccctt attccctttt 240
ttgcggcatt ttgccttcct gtttttgctc acccagaaac gctggtgaaa gtaaaagatg 300
ctgaagatca gttgggtgca cgagtgggtt acatcgaact ggatctcaac agcggtaaga 360
tccttgagag ttttcgcccc gaagaacgtt ttccaatgat gagcactttt aaagttctgc 420
tatgtggcgc ggtattatcc cgtattgacg ccgggcaaga gcaactcggt cgccgcatac 480
actattctca gaatgacttg gttgagtact caccagtcac agaaaagcat cttacggatg 540
gcatgacagt aagagaatta tgcagtgctg ccataaccat gagtgataac actgcggcca 600
acttacttct gacaacgatc ggaggaccga aggagctaac cgcttttttg cacaacatgg 660
gggatcatgt aactcgcctt gatcgttggg aaccggagct gaatgaagcc ataccaaacg 720
acgagcgtga caccacgatg cctgtagcaa tggcaacaac gttgcgcaaa ctattaactg 780
gcgaactact tactctagct tcccggcaac aattaataga ctggatggag gcggataaag 840
ttgcaggacc acttctgcgc tcggcccttc cggctggctg gtttattgct gataaatctg 900
gagccggtga gcgtgggtct cgcggtatca ttgcagcact ggggccagat ggtaagccct 960
cccgtatcgt agttatctac acgacgggga gtcaggcaac tatggatgaa cgaaatagac 1020
agatcgctga gataggtgcc tcactgatta agcattggta actgtcagac caagtttact 1080
catatatact ttagattgat ttaaaacttc atttttaatt taaaaggatc taggtgaaga 1140
tcctttttga taatctcatg accaaaatcc cttaacgtga gttttcgttc cactgagcgt 1200
cagaccccgt agaaaagatc aaaggatctt cttgagatcc tttttttctg cgcgtaatct 1260
gctgcttgca aacaaaaaaa ccaccgctac cagcggtggt ttgtttgccg gatcaagagc 1320
taccaactct ttttccgaag gtaactggct tcagcagagc gcagatacca aatactgttc 1380
ttctagtgta gccgtagtta ggccaccact tcaagaactc tgtagcaccg cctacatacc 1440
tcgctctgct aatcctgtta ccagtggctg ctgccagtgg cgataagtcg tgtcttaccg 1500
ggttggactc aagacgatag ttaccggata aggcgcagcg gtcgggctga acggggggtt 1560
cgtgcacaca gcccagcttg gagcgaacga cctacaccga actgagatac ctacagcgtg 1620
agctatgaga aagcgccacg cttcccgaag ggagaaaggc ggacaggtat ccggtaagcg 1680
gcagggtcgg aacaggagag cgcacgaggg agcttccagg gggaaacgcc tggtatcttt 1740
atagtcctgt cgggtttcgc cacctctgac ttgagcgtcg atttttgtga tgctcgtcag 1800
gggggcggag cctatggaaa aacgccagca acgcggcctt tttacggttc ctggcctttt 1860
gctggccttt tgctcacatg ttctttcctg cgttatcccc tgattctgtg gataaccgta 1920
ttaccgcctt tgagtgagct gataccgctc gccgcagccg aacgaccgag cgcagcgagt 1980
cagtgagcga ggaagcggaa gagcgcccaa tacgcaaacc gcctctcccc gcgcgttggc 2040
cgattcatta atgcagctgg cacgacaggt ttcccgactg gaaagcgggc agtgagcgca 2100
acgcaattaa tgtgagttag ctcactcatt aggcacccca ggctttacac tttatgcttc 2160
cggctcgtat gttgtgtgga attgtgagcg gataacaatt tcacacagga aacagctatg 2220
accatgatta cgccaagctg ggtcaagtct tccagtttaa gcagcagagc ggtcagtttc 2280
tcatcccgag cagacgcgcg agaggccgcg ccgctcgcca ccaaagagct gtaaaggtcc 2340
gtagccatgc tgcgcgcggt cgcggcggcg gcggaggcgg cggcggaggt cgcggcgtcc 2400
agcggagttc ctcccacggt cgcgtaggcc attgtagacg aatttgaagg cagaacgggg 2460
cgtccatcca cgttggaacc catcacattc tgacgcactc cagcccagtg aggcatgcgc 2520
actgtcagat aggggctaaa gatgcttcca tcaaagctgt tgccggtgtc gctcatggcg 2580
gcggctgttg caagacaaaa cagagagacc cttagacccc caatttatac acgccccacc 2640
cttctagcca cgcccacctt acccacctca atcggtatcc tcatcgctag acccaaactc 2700
ggccctggtg caggccagca ccagatggtc aggcctctag ttattaatag taatcaatta 2760
cggggtcatt agttcatagc ccatatatgg agttccgcgt tacataactt acggtaaatg 2820
gcccgcctgg ctgaccgccc aacgaccccc gcccattgac gtcaataatg acgtatgttc 2880
ccatagtaac gccaataggg actttccatt gacgtcaatg ggtggagtat ttacggtaaa 2940
ctgcccactt ggcagtacat caagtgtatc atatgccaag tacgccccct attgacgtca 3000
atgacggtaa atggcccgcc tggcattatg cccagtacat gaccttatgg gactttccta 3060
cttggcagta catctacgta ttagtcatcg ctattaccat ggtgatgcgg ttttggcagt 3120
acatcaatgg gcgtggatag cggtttgact cacggggatt tccaagtctc caccccattg 3180
acgtcaatgg gagtttgttt tggcaccaaa atcaacggga ctttccaaaa tgtcgtaaca 3240
actccgcccc attgacgcaa atgggcggta ggcgtgtacg gtgggaggtc tatataagca 3300
gagctctccc tatcagtgat agagatctcc ctatcagtga tagagatcgt cgacgagctc 3360
gtttagtgaa ccgtcagatc gcctggagac gccatccacg ctgttttgac ctccatagaa 3420
gacaccggga ccgatccagc ctccgcggcc gggaacggtg cattggaacg cggattcccc 3480
gtgccaagag tgacgtaagt accgcctata gagtctatag gcccaccccc ttggcttcac 3540
ttgaggtgtg gcaggcttga gatctggcca tacacttgag tgacaatgac atccactttg 3600
cctttctctc cacaggtgtc cactcccagg tccaactgca gccggatccg gtaccgccac 3660

-continued

```
catgaagaaa gaattgaccg aagtatttga atttgccaag aagtacatca tctttgttta   3720
catacccctg aagaagaaat taccccagct gtgtacagag gtgaagaagt tattgatggg   3780
aacactcgga attgtgaaaa agaccctgca cgaatatatg ctagatttga agaagtctga   3840
ggaggagaac gacgagatcg acggggtgaa ccaccagcac ctccccgcca ggagaaagaa   3900
gaatcttctc atacggtgtc tgcggtgcaa aaagctgttc ctgaacaccc tgtcgttcgt   3960
atgtccctgg tgcgcttcca agaagaagtg catcgacttt tactctcgga tcaagaagaa   4020
gctgcccgat ctgtgtactg agctgaagaa gcaactgttc ctgaacacgc tgtcgtttgt   4080
gaagaagttt cagcagctgt tcctgaacac tctaaagaag gtgtacgatt ttgctttcag   4140
agacctgaaa aagaagttga caaatacggg gctgtataat ctgaagaaac tctgtatcgt   4200
ttacagggac ggtaaccctt acgctgtgtg tgacaaaaag tacatgctag acctccagcc   4260
cgaaacgacc aagaagttcg cgttcagaga cctgtgtatc gtctacaaga aaacactagg   4320
catcgtgtgt cccattaaga aacggactct tgaggaccta ttgatgggtg tgaaaaagac   4380
aattcatgac attatcttgg agtgtgtgaa gaaacatctc gataagaaac aaagattcca   4440
taacatcaaa aagacaaccc tggaacagca gtataacaag cctctttgcg atctgctaaa   4500
gaaatgtgac tccaccttga ggctgtgcgt aaagaagcga tggaccggaa gatgtatgtc   4560
ttgttgtaaa aagagtctcc aagatattga gattacttgc gtgaaaaagt tgtgcgttca   4620
gagtacacat gttgatatta agaaagccca ttataatatc gtgacatttt gctgtaagaa   4680
ggatgacctg agagcttttc agcagctgtt tctgaataca ctgagcaaga agatcagcga   4740
gtaccgacac tattgttaca agaaaaagct gccccagctg tgtaccgaat tgaagaagaa   4800
aaccgtccta gagcttaccg aagtgaagaa gcgtaccctg gaggacctgt taatgggcac   4860
gaagaagttt gcattcaagg acctgtttgt cgtgaaaaag cagctgtaca ataagcccct   4920
gtgcgacgtt aaaaagacac tccaagacat cgtcttacac ctgaaaaagt aagcggccgc   4980
tctcgagtct agctagtcta gactagctag aaagatccgg gaacttgttt attgcagctt   5040
ataatggtta caaataaagc aatagcatca caaatttcac aaataaagca tttttttcac   5100
tgcattctag ttgtggtttg tccaaactca tcaatgtatc ttatcatgtc tggatcggtg   5160
atcaccgatc ccgatctgtc aaatgacggt gacaataaaa cggagacttt gacccggaac   5220
gcggaaattc acgtaaaaaa cacctgggcg agtcctccac gtaatcggtc aaagtccctc   5280
ggccctcggt aaatattacg cactatgact aacgccctat tattcagttt tcacttcccc   5340
gtttcacttt tcgcgcgaaa atggccaaat cttacatggt cccgcccaaa attactacga   5400
tatccggtga aagcgcgcg aaaattggca cttccggagg taggcggcgc tcatcaaaaa   5460
cgtcacattt tccgcgacgg aagcttgcat gtgagctcct cccacttgca aatgccacac   5520
ttccgccaca cctcccaacc ctactcgcgc gtcctacgtc acccgccccg cctctccccg   5580
cccacctcat tatcatattg gccacaatcc aaaataaggt atattattga tgatggttta   5640
aacgcccaat tcactggccg tcgttttaca acgtcgtgac tgggaaaacc ctggcgttac   5700
ccaacttaat cgccttgcag cacatccccc tttcgccagc tggcgtaata gcgaagaggc   5760
ccgcaccgat cgcccttccc aacagttgcg cagcctgaat ggcgaatggc gcctgatgcg   5820
gtattttctc cttacgcatc tgtgcggtat ttcacaccgc atatggtgca ctctcagtac   5880
aatctgctct gatgccgcat agttaagcca gccccgacac ccgccaacac ccgctgacgc   5940
gccctgacgg gcttgtctgc tcccggcatc cgcttacaga caagctgtga ccgtctccgg   6000
gagctgcatg tgtcagaggt tttcaccgtc atcaccgaaa cgcgcga                6047
```

<210> SEQ ID NO 61
<211> LENGTH: 10410
<212> TYPE: DNA
<213> ORGANISM: Artificial sequence
<220> FEATURE:
<223> OTHER INFORMATION: GCAd-RTS-IL12 design 1

<400> SEQUENCE: 61
ttcaaatatg tatccgctca tgagacaata accctgataa atgcttcaat aatattgaaa 60
aaggaagagt atgagtattc aacatttccg tgtcgccctt attccctttt ttgcggcatt 120
ttgccttcct gtttttgctc acccagaaac gctggtgaaa gtaaaagatg ctgaagatca 180
gttgggtgca cgagtgggtt acatcgaact ggatctcaac agcggtaaga tccttgagag 240
ttttcgcccc gaagaacgtt ttccaatgat gagcactttt aaagttctgc tatgtggcgc 300
ggtattatcc cgtattgacg ccgggcaaga gcaactcggt cgccgcatac actattctca 360
gaatgacttg gttgagtact caccagtcac agaaaagcat cttacggatg gcatgacagt 420
aagagaatta tgcagtgctg ccataaccat gagtgataac actgcggcca acttacttct 480
gacaacgatc ggaggaccga aggagctaac cgcttttttg cacaacatgg gggatcatgt 540
aactcgcctt gatcgttggg aaccggagct gaatgaagcc ataccaaacg acgagcgtga 600
caccacgatg cctgtagcaa tggcaacaac gttgcgcaaa ctattaactg gcgaactact 660
tactctagct tcccggcaac aattaataga ctggatggag gcggataaag ttgcaggacc 720
acttctgcgc tcggcccttc cggctggctg gtttattgct gataaatctg gagccggtga 780
gcgtgggtct cgcggtatca ttgcagcact ggggccagat ggtaagccct cccgtatcgt 840
agttatctac acgacgggga gtcaggcaac tatggatgaa cgaaatagac agatcgctga 900
gataggtgcc tcactgatta agcattggta actgtcagac caagtttact catatatact 960
ttagattgat ttaaaacttc atttttaatt taaaaggatc taggtgaaga tcctttttga 1020
taatctcatg accaaaatcc cttaacgtga gttttcgttc cactgagcgt cagaccccgt 1080
agaaaagatc aaaggatctt cttgagatcc tttttttctg cgcgtaatct gctgcttgca 1140
aacaaaaaaa ccaccgctac cagcggtggt ttgtttgccg gatcaagagc taccaactct 1200
ttttccgaag gtaactggct tcagcagagc gcagatacca aatactgttc ttctagtgta 1260
gccgtagtta ggccaccact tcaagaactc tgtagcaccg cctacatacc tcgctctgct 1320
aatcctgtta ccagtggctg ctgccagtgg cgataagtcg tgtcttaccg ggttggactc 1380
aagacgatag ttaccggata aggcgcagcg gtcgggctga acggggggtt cgtgcacaca 1440
gcccagcttg gagcgaacga cctacaccga actgagatac ctacagcgtg agctatgaga 1500
aagcgccacg cttcccgaag ggagaaaggc ggacaggtat ccggtaagcg gcagggtcgg 1560
aacaggagag cgcacgaggg agcttccagg gggaaacgcc tggtatcttt atagtcctgt 1620
cgggtttcgc cacctctgac ttgagcgtcg atttttgtga tgctcgtcag gggggcggag 1680
cctatggaaa aacgccagca acgcggcctt tttacggttc ctggcctttt gctggccttt 1740
tgctcacatg ttctttcctg cgttatcccc tgattctgtg gataaccgta ttaccgcctt 1800
tgagtgagct gataccgctc gccgcagccg aacgaccgag cgcagcgagt cagtgagcga 1860
ggaagcggaa gagcgcccaa tacgcaaacc gcctctcccc gcgcgttggc cgattcatta 1920
atgcagctgg cacgacaggt ttcccgactg gaaagcgggc agtgagcgca acgcaattaa 1980
tgtgagttag ctcactcatt aggcacccca ggctttacac tttatgcttc cggctcgtat 2040

-continued

```
gttgtgtgga attgtgagcg gataacaatt tcacacagga aacagctatg accatgatta   2100
cgccaagctg ggtcaagtct tccagtttaa gcagcagagc ggtcagtttc tcatcccgag   2160
cagacgcgcg agaggccgcg ccgctcgcca ccaaagagct gtaaaggtcc gtagccatgc   2220
tgcgcgcggt cgcggcggcg gcggaggcgg cggcggaggt cgcggcgtcc agcggagttc   2280
ctcccacggt cgcgtaggcc attgtagacg aatttgaagg cagaacgggg cgtccatcca   2340
cgttggaacc catcacattc tgacgcactc cagcccagtg aggcatgcgc actgtcagat   2400
aggggctaaa gatgcttcca tcaaagctgt tgccggtgtc gctcatggcg gcggctgttg   2460
caagacaaaa cagagagacc cttagacccc caatttatac acgccccacc cttctagcca   2520
cgcccacctt acccacctca atcggtatcc tcatcgctag acccaaactc ggccctggtg   2580
caggccagca ccagatggtc aggcctgcag gccgcaataa aatatcttta ttttcattac   2640
atctgtgtgt tggttttttg tgtgaatcga tagtactaac atacgctctc catcaaaaca   2700
aaacgaaaca aaacaaacta gcaaaatagg ctgtccccag tgcaagtgca ggtgccagaa   2760
catttctcta tcgataatgc aggtcggagt actgtcctcc gagcggagta ctgtcctccg   2820
agcggagtac tgtcctccga gcggagtact gtcctccgag cggagtactg tcctccgagc   2880
ggagtactgt cctccgagcg gagactcttc gaaggaagag ggcggggtc gatcgacccc    2940
gcccctcttc cttcgaagga agagggggcgg ggtcgaagac ctagagggta tataatgggt  3000
gccttagctg gtgtgtgagc tcatcttcct gtagatcacg cgtgccacca tgggtcacca   3060
gcagttggtc atctcttggt ttccctggt ttttctggca tctcccctcg tggccatatg    3120
ggaactgaag aaagatgttt atgtcgtaga attggattgg tatccggatg cccctggaga   3180
aatggtggtc ctcacctgtg acacccctga agaagatggt atcacctgga ccttggacca   3240
gagcagtgag gtcttaggct ctggcaaaac cctgaccatc caagtcaaag agtttggaga   3300
tgctggccag tacacctgtc acaaaggagg cgaggttcta agccattcgc tcctgctgct   3360
tcacaaaaag gaagatggaa tttggtccac tgatatttta aaggaccaga aagaacccaa   3420
aaataagacc tttctaagat gcgaggccaa gaattattct ggacgtttca cctgctggtg   3480
gctgacgaca atcagtactg atttgacatt cagtgtcaaa agcagcagag gctcttctga   3540
cccccaaggg gtgacgtgcg gagctgctac actctctgca gagagagtca gaggggacaa   3600
caaggagtat gagtactcag tggagtgcca ggaggacagt gcctgcccag ctgctgagga   3660
gagtctgccc attgaggtca tggtggatgc cgttcacaag ctcaagtatg aaaactacac   3720
cagcagcttc ttcatcaggg acatcatcaa acctgaccca cccaagaact tgcagctgaa   3780
gccattaaag aattctcggc aggtggaggt cagctgggag taccctgaca cctggagtac   3840
tccacattcc tacttctccc tgacattctg cgttcaggtc cagggcaaga gcaagagaga   3900
aaagaaagat agagtcttca cggacaagac ctcagccacg gtcatctgcc gcaaaaatgc   3960
cagcattagc gtgcgggccc aggaccgcta ctatagctca tcttggagcg aatgggcatc   4020
tgtgccctgc agttaggttg ggcgagctcg aattcattga tcccccgggc tgcaggaatt   4080
cgatatcaag ctcgggatcc gaattccgcc cccccccccc ccccccccct aacgttactg   4140
gccgaagccg cttggaataa ggccggtgtg cgtttgtcta tatgttattt tccaccatat   4200
tgccgtcttt tggcaatgtg agggcccgga aacctggccc tgtcttcttg acgagcattc   4260
ctaggggtct ttcccctctc gccaaaggaa tgcaaggtct gttgaatgtc gtgaaggaag   4320
cagttcctct ggaagcttct tgaagacaaa caacgtctgt agcgaccctt tgcaggcagc   4380
ggaaccccc acctggcgac aggtgcctct gcggccaaaa gccacgtgta taagatacac    4440
```

ctgcaaaggc ggcacaaccc cagtgccacg ttgtgagttg gatagttgtg gaaagagtca 4500
aatggctctc ctcaagcgta ttcaacaagg ggctgaagga tgcccagaag gtaccccatt 4560
gtatgggatc tgatctgggg cctcggtgca catgctttac atgtgtttag tcgaggttaa 4620
aaaaacgtct aggccccccg aaccacgggg acgtggtttt cctttgaaaa acacgatgat 4680
aatatggcca caaccatggg tccagcgcgc agcctcctcc ttgtggctac cctggtcctc 4740
ctggaccacc tcagtttggc cagaaacctc cccgtggcca ctccagaccc aggaatgttc 4800
ccatgccttc accactccca aaacctgctg agggccgtca gcaacatgct ccagaaggcc 4860
agacaaactc tagaatttta cccttgcact tctgaagaga ttgatcatga agatatcaca 4920
aaagataaaa ccagcacagt ggaggcctgt ttaccattgg aattaaccaa gaatgagagt 4980
tgcctaaatt ccagagagac ctctttcata actaatggga gttgcctggc ctccagaaag 5040
acctctttta tgatggccct gtgccttagt agtatttatg aagacttgaa gatgtaccag 5100
gtggagttca agaccatgaa tgcaaagctt ctgatggatc ctaagaggca gatctttcta 5160
gatcaaaaca tgctggcagt tattgatgag ctgatgcagg ccctgaattt caacagtgag 5220
actgtgccac aaaaatcctc ccttgaagaa ccggattttt ataaaactaa aatcaagctc 5280
tgcatacttc ttcatgcttt cagaattcgg gcagtgacta ttgatagagt gatgagctat 5340
ctgaatgctt cctaacgtac gtcgacatcg agaacttgtt tattgcagct tataatggtt 5400
acaaataaag caatagcatc acaaatttca caaataaagc atttttttca ctgcattcta 5460
gttgtggttt gtccaaactc atcaatgtat cttatcatgt ctgggcgcgc cggcctccgc 5520
gccgggtttt ggcgcctccc gcgggcgccc ccctcctcac ggcgagcgct gccacgtcag 5580
acgaagggcg cagcgagcgt cctgatcctt ccgcccggac gctcaggaca gcggcccgct 5640
gctcataaga ctcggcctta gaaccccagt atcagcagaa ggacatttta ggacgggact 5700
tgggtgactc tagggcactg gttttctttc cagagagcgg aacaggcgag gaaaagtagt 5760
cccttctcgg cgattctgcg gagggatctc cgtggggcgg tgaacgccga tgattatata 5820
aggacgcgcc gggtgtggca cagctagttc cgtcgcagcc gggatttggg tcgcggttct 5880
tgtttgtgga tcgctgtgat cgtcacttgg tgagtagcgg gctgctgggc tgggtacgtg 5940
cgctcggggt tggcgagtgt gttttgtgaa gttttttagg caccttttga aatgtaatca 6000
tttgggtcaa tatgtaattt tcagtgttag actagtaaat tgtccgctaa attctggccg 6060
tttttggctt ttttgttaga cgagctagcg ccgccaccat gggccctaaa aagaagcgta 6120
aagtcgcccc cccgaccgat gtcagcctgg gggacgagct ccacttagac ggcgaggacg 6180
tggcgatggc gcatgccgac gcgctagacg atttcgatct ggacatgttg ggggacgggg 6240
attccccggg tccgggattt accccccacg actccgcccc ctacggcgct ctggatatgg 6300
ccgacttcga gtttgagcag atgtttaccg atgcccttgg aattgacgag tacggtgggg 6360
aattcgagat gcctgtggac aggatcctgg aggcagagct tgctgtggaa cagaagagtg 6420
accagggcgt tgagggtcct gggggaaccg gggtagcgg cagcagccca aatgaccctg 6480
tgactaacat ctgtcaggca gctgacaaac agctattcac gcttgttgag tgggcgaaga 6540
ggatcccaca cttttcctcc ttgcctctgg atgatcaggt catattgctg cgggcaggct 6600
ggaatgaact cctcattgcc tccttttcac accgatccat tgatgttcga gatggcatcc 6660
tccttgccac aggtcttcac gtgcaccgca actcagccca ttcagcagga gtaggagcca 6720
tctttgatcg ggtgctgaca gagctagtgt ccaaaatgcg tgacatgagg atggacaaga 6780

```
cagagcttgg ctgcctgagg gcaatcattc tgtttaatcc agaggtgagg ggtttgaaat   6840
ccgcccagga agttgaactt ctacgtgaaa aagtatatgc cgctttggaa gaatatacta   6900
gaacaacaca tcccgatgaa ccaggaagat ttgcaaaact tttgcttcgt ctgccttctt   6960
tacgttccat aggccttaag tgtttggagc atttgttttt ctttcgcctt attggagatg   7020
ttccaattga tacgttcctg atggagatgc ttgaatcacc ttctgattca taatctagcc   7080
tagcccccct ctccctcccc ccccccctaac gttactggcc gaagccgctt ggaataaggc   7140
cggtgtgcgt ttgtctatat gttattttcc accatattgc cgtcttttgg caatgtgagg   7200
gcccggaaac ctggccctgt cttcttgacg agcattccta ggggtctttc ccctctcgcc   7260
aaaggaatgc aaggtctgtt gaatgtcgtg aaggaagcag ttcctctgga agcttcttga   7320
agacaaacaa cgtctgtagc gaccctttgc aggcagcgga acccccccacc tggcgacagg   7380
tgcctctgcg gccaaaagcc acgtgtataa gatacacctg caaaggcggc acaaccccag   7440
tgccacgttg tgagttggat agttgtggaa agagtcaaat ggctctcctc aagcgtattc   7500
aacaaggggc tgaaggatgc ccagaaggta ccccattgta tgggatctga tctggggcct   7560
cggtgcacat gctttacatg tgtttagtcg aggttaaaaa acgtctaggc cccccgaacc   7620
acggggacgt ggttttcctt tgaaaaacac gatctctagg cgccaccatg aagctactgt   7680
cttctatcga acaagcatgc gatatttgcc gacttaaaaa gctcaagtgc tccaaagaaa   7740
aaccgaagtg cgccaagtgt ctgaagaaca actgggagtg tcgctactct cccaaaacca   7800
aaaggtctcc gctgactagg gcacatctga cagaagtgga atcaaggcta gaaagactgg   7860
aacagctatt tctactgatt tttcctcgag aagaccttga catgattttg aaaatggatt   7920
ctttacagga tataaaagca ttgttaacag gattatttgt acaagataat gtgaataaag   7980
atgccgtcac agatagattg gcttcagtgg agactgatat gcctctaaca ttgagacagc   8040
atagaataag tgcgacatca tcatcggaag agagtagtaa caaaggtcaa agacagttga   8100
ctgtatcgcc ggaattcccg gggatccggc ctgagtgcgt agtacccgag actcagtgcg   8160
ccatgaagcg gaaagagaag aaagcacaga aggagaagga caaactgcct gtcagcacga   8220
cgacggtgga cgaccacatg ccgcccatta tgcagtgtga acctccacct cctgaagcag   8280
caaggattca cgaagtggtc ccaaggtttc tctccgacaa gctgttggtg acaaaccggc   8340
agaaaaacat cccccagttg acagccaacc agcagttcct tatcgccagg ctcatctggt   8400
accaggacgg gtacgagcag ccttctgatg aagatttgaa gaggattacg cagacgtggc   8460
agcaagcgga cgatgaaaac gaagagtcgg acactccctt ccgccagatc acagagatga   8520
ctatcctcac ggtccaactt atcgtggagt tcgcgaaggg attgccaggg ttcgccaaga   8580
tctcgcagcc tgatcaaatt acgctgctta aggcttgctc aagtgaggta atgatgctcc   8640
gagtcgcgcg acgatacgat gcggcctcag acagtattct gttcgcgaac aaccaagcgt   8700
acactcgcga caactaccgc aaggctggca tggccgaggt catcgaggat ctactgcact   8760
tctgccggtg catgtactct atggcgttgg acaacatcca ttacgcgctg ctcacggctg   8820
tcgtcatctt ttctgaccgg ccagggttgg agcagccgca actggtggaa gagatccagc   8880
ggtactacct gaatacgctc cgcatctata tcctgaacca gctgagcggg tcggcgcgtt   8940
cgtccgtcat atacggcaag atcctctcaa tcctctctga gctacgcacg ctcggcatgc   9000
aaaactccaa catgtgcatc tccctcaagc tcaagaacag aaagctgccg cctttcctcg   9060
aggagatctg ggatgtggcg gacatgtcgc acacccaacc gccgcctatc ctcgagtccc   9120
ccacgaatct ctaggcggcc tctagagcgg ccgccaccgc ggggagatcc agacatgata   9180
```

```
agatacattg atgagtttgg acaaaccaca actagaatgc agtgaaaaaa atgctttatt   9240
tgtgaaattt gtgatgctat tgctttattt gtaaccatta taagctgcaa taaacaagtt   9300
aacaacaaca attgcattca ttttatgttt caggttcagg gggaggtgtg ggaggttttt   9360
taaagcaagt aaaacctcta caaatgtggt atggctgatt atgatcaccg gtcaaatgac   9420
ggtgacaata aaacggagac tttgacccgg aacgcggaaa ttcacgtaaa aaacacctgg   9480
gcgagtcctc cacgtaatcg gtcaaagtcc ctcggccctc ggtaaatatt acgcactatg   9540
actaacgccc tattattcag ttttcacttc cccgtttcac ttttcgcgcg aaaatggcca   9600
aatcttacat ggtcccgccc aaaattacta cgatatccgg tgaaaagcgc gcgaaaattg   9660
gcacttccgg aggtaggcgg cgctcatcaa aaacgtcaca ttttccgcga cggaagcttg   9720
catgtgagct cctcccactt gcaaatgcca cacttccgcc acacctccca accctactcg   9780
cgcgtcctac gtcacccgcc ccgcctctcc ccgcccacct cattatcata ttggccacaa   9840
tccaaaataa ggtatattat tgatgatggt ttaaacgccc aattcactgg ccgtcgtttt   9900
acaacgtcgt gactgggaaa accctggcgt tacccaactt aatcgccttg cagcacatcc   9960
ccctttcgcc agctggcgta atagcgaaga ggcccgcacc gatcgccctt cccaacagtt  10020
gcgcagcctg aatggcgaat ggcgcctgat gcggtatttt ctccttacgc atctgtgcgg  10080
tatttcacac cgcatatggt gcactctcag tacaatctgc tctgatgccg catagttaag  10140
ccagccccga cacccgccaa cacccgctga cgcgccctga cgggcttgtc tgctcccggc  10200
atccgcttac agacaagctg tgaccgtctc cgggagctgc atgtgtcaga ggttttcacc  10260
gtcatcaccg aaacgcgcga gacgaaaggg cctcgtgata cgcctatttt tataggttaa  10320
tgtcatgata ataatggttt cttagacgtc aggtggcact tttcggggaa atgtgcgcgg  10380
aacccctatt tgtttatttt tctaaataca                                  10410
```

<210> SEQ ID NO 62
<211> LENGTH: 10040
<212> TYPE: DNA
<213> ORGANISM: Artificial sequence
<220> FEATURE:
<223> OTHER INFORMATION: GCAd-RTS-IL12 design 2

<400> SEQUENCE: 62

```
ttcaaatatg tatccgctca tgagacaata accctgataa atgcttcaat aatattgaaa     60
aaggaagagt atgagtattc aacatttccg tgtcgccctt attccctttt ttgcggcatt    120
ttgccttcct gtttttgctc acccagaaac gctggtgaaa gtaaaagatg ctgaagatca    180
gttgggtgca cgagtgggtt acatcgaact ggatctcaac agcggtaaga tccttgagag    240
ttttcgcccc gaagaacgtt ttccaatgat gagcactttt aaagttctgc tatgtggcgc    300
ggtattatcc cgtattgacg ccgggcaaga gcaactcggt cgccgcatac actattctca    360
gaatgacttg gttgagtact caccagtcac agaaaagcat cttacggatg gcatgacagt    420
aagagaatta tgcagtgctg ccataaccat gagtgataac actgcggcca acttacttct    480
gacaacgatc ggaggaccga aggagctaac cgcttttttg cacaacatgg gggatcatgt    540
aactcgcctt gatcgttggg aaccggagct gaatgaagcc ataccaaacg acgagcgtga    600
caccacgatg cctgtagcaa tggcaacaac gttgcgcaaa ctattaactg gcgaactact    660
tactctagct tcccggcaac aattaataga ctggatggag gcggataaag ttgcaggacc    720
acttctgcgc tcggcccttc cggctggctg gtttattgct gataaatctg gagccggtga    780
```

-continued

```
gcgtgggtct cgcggtatca ttgcagcact ggggccagat ggtaagccct cccgtatcgt    840
agttatctac acgacgggga gtcaggcaac tatggatgaa cgaaatagac agatcgctga    900
gataggtgcc tcactgatta agcattggta actgtcagac caagtttact catatatact    960
ttagattgat ttaaaacttc atttttaatt taaaaggatc taggtgaaga tcctttttga   1020
taatctcatg accaaaatcc cttaacgtga gttttcgttc cactgagcgt cagaccccgt   1080
agaaaagatc aaaggatctt cttgagatcc tttttttctg cgcgtaatct gctgcttgca   1140
aacaaaaaaa ccaccgctac cagcggtggt ttgtttgccg gatcaagagc taccaactct   1200
ttttccgaag gtaactggct tcagcagagc gcagatacca aatactgttc ttctagtgta   1260
gccgtagtta ggccaccact tcaagaactc tgtagcaccg cctacatacc tcgctctgct   1320
aatcctgtta ccagtggctg ctgccagtgg cgataagtcg tgtcttaccg ggttggactc   1380
aagacgatag ttaccggata aggcgcagcg gtcgggctga acggggggtt cgtgcacaca   1440
gcccagcttg gagcgaacga cctacaccga actgagatac ctacagcgtg agctatgaga   1500
aagcgccacg cttcccgaag ggagaaaggc ggacaggtat ccggtaagcg gcagggtcgg   1560
aacaggagag cgcacgaggg agcttccagg gggaaacgcc tggtatcttt atagtcctgt   1620
cgggtttcgc cacctctgac ttgagcgtcg atttttgtga tgctcgtcag gggggcggag   1680
cctatggaaa aacgccagca acgcggcctt tttacggttc ctggcctttt gctggccttt   1740
tgctcacatg ttctttcctg cgttatcccc tgattctgtg gataaccgta ttaccgcctt   1800
tgagtgagct gataccgctc gccgcagccg aacgaccgag cgcagcgagt cagtgagcga   1860
ggaagcggaa gagcgcccaa tacgcaaacc gcctctcccc gcgcgttggc cgattcatta   1920
atgcagctgg cacgacaggt ttcccgactg gaaagcgggc agtgagcgca acgcaattaa   1980
tgtgagttag ctcactcatt aggcacccca ggctttacac tttatgcttc cggctcgtat   2040
gttgtgtgga attgtgagcg gataacaatt tcacacagga aacagctatg accatgatta   2100
cgccaagctg ggtcaagtct tccagtttaa gcagcagagc ggtcagtttc tcatcccgag   2160
cagacgcgcg agaggccgcg ccgctcgcca ccaaagagct gtaaaggtcc gtagccatgc   2220
tgcgcgcggt cgcggcggcg gcggaggcgg cggcggaggt cgcggcgtcc agcggagttc   2280
ctcccacggt cgcgtaggcc attgtagacg aatttgaagg cagaacgggg cgtccatcca   2340
cgttggaacc catcacattc tgacgcactc cagcccagtg aggcatgcgc actgtcagat   2400
aggggctaaa gatgcttcca tcaaagctgt tgccggtgtc gctcatggcg gcggctgttg   2460
caagacaaaa cagagagacc cttagacccc caatttatac acgccccacc cttctagcca   2520
cgcccacctt acccacctca atcggtatcc tcatcgctag acccaaactc ggccctggtg   2580
caggccagca ccagatggtc aggcctgcag gtacgtagcc gcaataaaat atctttattt   2640
tcattacatc tgtgtgttgg tttttttgtgt gaatccatag tactaacata cgctctccat   2700
caaaacaaaa cgaaacaaaa caaactagca aaataggctg tccccagtgc aagtccaggt   2760
gccagaacat ttctctatcc ataatgcagg ggtaccggaa ggaagagggg cggggtcgat   2820
cgaccccgcc cctcttcctt cgaaggaaga ggggcggggt ccaattgcgg agtactgtcc   2880
tccgagcgga gtactgtcct ccgagcggag tactgtcctc cgagcggagt actgtcctcc   2940
gagcggagta ctgtcctccg agcggagtac tgtcctccga gcggagagtc cccggggacc   3000
tagagggtat ataatgggtg ccttagctgg tgtgtgacct catcttcctg tacgcccctg   3060
caggagatca cgcgtgccac catgggtcac cagcagttgg tcatctcttg gttttccctg   3120
gtttttctgg catctcccct cgtggccata tgggaactga agaaagatgt ttatgtcgta   3180
```

-continued

```
gaattggatt ggtatccgga tgcccctgga gaaatggtgg tcctcacctg tgacacccct   3240
gaagaagatg gtatcacctg gaccttggac cagagcagtg aggtcttagg ctctggcaaa   3300
accctgacca tccaagtcaa agagtttgga gatgctggcc agtacacctg tcacaaagga   3360
ggcgaggttc taagccattc gctcctgctg cttcacaaaa aggaagatgg aatttggtcc   3420
actgatattt taaaggacca gaaagaaccc aaaaataaga cctttctaag atgcgaggcc   3480
aagaattatt ctggacgttt cacctgctgg tggctgacga caatcagtac tgatttgaca   3540
ttcagtgtca aaagcagcag aggctcttct gacccccaag ggtgacgtg cggagctgct   3600
acactctctg cagagagagt cagaggggac aacaaggagt atgagtactc agtggagtgc   3660
caggaggaca gtgcctgccc agctgctgag gagagtctgc ccattgaggt catggtggat   3720
gccgttcaca agctcaagta tgaaaactac accagcagct tcttcatcag ggacatcatc   3780
aaacctgacc cacccaagaa cttgcagctg aagccattaa agaattctcg gcaggtggag   3840
gtcagctggg agtaccctga cacctggagt actccacatt cctacttctc cctgacattc   3900
tgcgttcagg tccagggcaa gagcaagaga gaaaagaaag atagagtctt cacggacaag   3960
acctcagcca cggtcatctg ccgcaaaaat gccagcatta gcgtgcgggc ccaggaccgc   4020
tactatagct catcttggag cgaatgggca tctgtgccct gcagtctcga gggcggcgga   4080
gagggcagag gaagtcttct aacatgcggt gacgtggagg agaatcccgg ccctaggatg   4140
ggtccagcgc gcagcctcct ccttgtggct accctggtcc tcctggacca cctcagtttg   4200
gccagaaacc tccccgtggc cactccagac ccaggaatgt tcccatgcct tcaccactcc   4260
caaaacctgc tgagggccgt cagcaacatg ctccagaagg ccagacaaac tctagaattt   4320
tacccttgca cttctgaaga gattgatcat gaagatatca caaaagataa aaccagcaca   4380
gtggaggcct gtttaccatt ggaattaacc aagaatgaga gttgcctaaa ttccagagag   4440
acctctttca taactaatgg gagttgcctg gcctccagaa agacctcttt tatgatggcc   4500
ctgtgcctta gtagtattta tgaagacttg aagatgtacc aggtggagtt caagaccatg   4560
aatgcaaagc ttctgatgga tcctaagagg cagatctttc tagatcaaaa catgctggca   4620
gttattgatg agctgatgca ggccctgaat ttcaacagtg agactgtgcc acaaaaatcc   4680
tcccttgaag aaccggattt ttataaaact aaaatcaagc tctgcatact tcttcatgct   4740
ttcagaattc gggcagtgac tattgataga gtgatgagct atctgaatgc ttcctaaatc   4800
gatttattta tcggcataaa taattttttt gaagaagtaa tactattttt cttttttttt   4860
gtaaataaat gggttaaggg atgtaacatt gtttgttgtt tggtgggggt tggggcctcc   4920
gcgccgggtt ttggcgcctc ccgcgggcgc ccccctcctc acggcgagcg ctgccacgtc   4980
agacgaaggg cgcagcgagc gtcctgatcc ttccgcccgg acgctcagga cagcggcccg   5040
ctgctcataa gactcggcct tagaacccca gtatcagcag aaggacattt taggacggga   5100
cttgggtgac tctagggcac tggttttctt tccagagagc ggaacaggcg aggaaaagta   5160
gtcccttctc ggcgattctg cggagggatc tccgtggggc ggtgaacgcc gatgattata   5220
taaggacgcg ccgggtgtgg cacagctagt tccgtcgcag ccgggatttg ggtcgcggtt   5280
cttgtttgtg gatcgctgtg atcgtcactt ggtgagtagc gggctgctgg gctgggtacg   5340
tgcgctcggg gttggcgagt gtgttttgtg aagtttttta ggcacctttt gaaatgtaat   5400
catttgggtc aatatgtaat tttcagtgtt agactagtaa attgtccgct aaattctggc   5460
cgtttttggc tttttgtta gacgagctag cgccgccacc atgggcccta aaaagaagcg   5520
```

-continued taaagtcgcc cccccgaccg atgtcagcct gggggacgag ctccacttag acggcgagga 5580
cgtggcgatg gcgcatgccg acgcgctaga cgatttcgat ctggacatgt tgggggacgg 5640
ggattccccg ggtccgggat ttacccccca cgactccgcc ccctacggcg ctctggatat 5700
ggccgacttc gagtttgagc agatgtttac cgatgccctt ggaattgacg agtacggtgg 5760
ggaattcgag atgcctgtgg acaggatcct ggaggcagag cttgctgtgg aacagaagag 5820
tgaccagggc gttgagggtc ctgggggaac cgggggtagc ggcagcagcc caaatgaccc 5880
tgtgactaac atctgtcagg cagctgacaa acagctattc acgcttgttg agtgggcgaa 5940
gaggatccca cacttttcct ccttgcctct ggatgatcag gtcatattgc tgcgggcagg 6000
ctggaatgaa ctcctcattg cctccttttc acaccgatcc attgatgttc gagatggcat 6060
cctccttgcc acaggtcttc acgtgcaccg caactcagcc cattcagcag gagtaggagc 6120
catctttgat cgggtgctga cagagctagt gtccaaaatg cgtgacatga ggatggacaa 6180
gacagagctt ggctgcctga gggcaatcat tctgtttaat ccagaggtga ggggtttgaa 6240
atccgcccag gaagttgaac ttctacgtga aaaagtatat gccgctttgg aagaatatac 6300
tagaacaaca catcccgatg aaccaggaag atttgcaaaa cttttgcttc gtctgccttc 6360
tttacgttcc ataggcctta agtgtttgga gcatttgttt ttctttcgcc ttattggaga 6420
tgttccaatt gatacgttcc tgatggagat gcttgaatca ccttctgatt cataatctag 6480
cctagccccc ctctccctcc cccccccta acgttactgg ccgaagccgc ttggaataag 6540
gccggtgtgc gtttgtctat atgttatttt ccaccatatt gccgtctttt ggcaatgtga 6600
gggcccggaa acctggccct gtcttcttga cgagcattcc taggggtctt tcccctctcg 6660
ccaaaggaat gcaaggtctg ttgaatgtcg tgaaggaagc agttcctctg gaagcttctt 6720
gaagacaaac aacgtctgta gcgacccttt gcaggcagcg gaacccccca cctggcgaca 6780
ggtgcctctg cggccaaaag ccacgtgtat aagatacacc tgcaaaggcg gcacaacccc 6840
agtgccacgt tgtgagttgg atagttgtgg aaagagtcaa atggctctcc tcaagcgtat 6900
tcaacaaggg gctgaaggat gcccagaagg taccccattg tatgggatct gatctggggc 6960
ctcggtgcac atgctttaca tgtgtttagt cgaggttaaa aaacgtctag gccccccgaa 7020
ccacggggac gtggttttcc tttgaaaaac acgatctcta ggcgccacca tgaagctact 7080
gtcttctatc gaacaagcat gcgatatttg ccgacttaaa aagctcaagt gctccaaaga 7140
aaaaccgaag tgcgccaagt gtctgaagaa caactgggag tgtcgctact ctcccaaaac 7200
caaaaggtct ccgctgacta gggcacatct gacagaagtg gaatcaaggc tagaaagact 7260
ggaacagcta tttctactga tttttcctcg agaagacctt gacatgattt tgaaaatgga 7320
ttctttacag gatataaaag cattgttaac aggattattt gtacaagata atgtgaataa 7380
agatgccgtc acagatagat tggcttcagt ggagactgat atgcctctaa cattgagaca 7440
gcatagaata agtgcgacat catcatcgga agagagtagt aacaaaggtc aaagacagtt 7500
gactgtatcg ccggaattcc cggggatccg gcctgagtgc gtagtacccg agactcagtg 7560
cgccatgaag cggaaagaga agaaagcaca gaaggagaag gacaaactgc ctgtcagcac 7620
gacgacggtg gacgaccaca tgccgcccat tatgcagtgt gaacctccac ctcctgaagc 7680
agcaaggatt cacgaagtgg tcccaaggtt tctctccgac aagctgttgg tgacaaaccg 7740
gcagaaaaac atcccccagt tgacagccaa ccagcagttc cttatcgcca ggctcatctg 7800
gtaccaggac gggtacgagc agccttctga tgaagatttg aagaggatta cgcagacgtg 7860
gcagcaagcg gacgatgaaa acgaagagtc ggacactccc ttccgccaga tcacagagat 7920

```
gactatcctc acggtccaac ttatcgtgga gttcgcgaag ggattgccag ggttcgccaa   7980
gatctcgcag cctgatcaaa ttacgctgct taaggcttgc tcaagtgagg taatgatgct   8040
ccgagtcgcg cgacgatacg atgcggcctc agacagtatt ctgttcgcga acaaccaagc   8100
gtacactcgc gacaactacc gcaaggctgg catggccgag gtcatcgagg atctactgca   8160
cttctgccgg tgcatgtact ctatggcgtt ggacaacatc cattacgcgc tgctcacggc   8220
tgtcgtcatc ttttctgacc ggccagggtt ggagcagccg caactggtgg aagagatcca   8280
gcggtactac ctgaatacgc tccgcatcta tatcctgaac cagctgagcg ggtcggcgcg   8340
ttcgtccgtc atatacggca agatcctctc aatcctctct gagctacgca cgctcggcat   8400
gcaaaactcc aacatgtgca tctccctcaa gctcaagaac agaaagctgc cgcctttcct   8460
cgaggagatc tgggatgtgg cggacatgtc gcacacccaa ccgccgccta tcctcgagtc   8520
ccccacgaat ctctaaatcg attacgctcc tctactcttt gagacatcac tggcctataa   8580
taaatgggtt aatttatgta acaaaattgc cttggcttgt taactttatt agacattctg   8640
atgtttgcat tgtgtaaata ctgttgtatt ggaaaagcgt gccaagatgg attattgtaa   8700
ttcagtgtct tttttagtag cgtcacgtgc caaacactgt tagtcacaga gggcatgaga   8760
cagcctgtgc tggaacagct cagttcatag ggctatggag atggggagaa aggggcgctt   8820
ctgtcagaga caagctgtgg tctgggaagg ccttagcact aaaagcacca caatgagaag   8880
caaccgccag aagcagggcc cgcaggcctt tgttccagct gcaaagagaa aggaaaaagt   8940
ggggaataag agttggggct gcggaggggg tggggagcat tgtgcaggtt ccgtacttga   9000
acagaaagca gggaccaaca caaggaaggg cgcgccaccg gtcaaatgac ggtgacaata   9060
aaacggagac tttgacccgg aacgcggaaa ttcacgtaaa aaacacctgg gcgagtcctc   9120
cacgtaatcg gtcaaagtcc ctcggccctc ggtaaatatt acgcactatg actaacgccc   9180
tattattcag ttttcacttc cccgtttcac ttttcgcgcg aaaatggcca aatcttacat   9240
ggtcccgccc aaaattacta cgatatccgg tgaaaagcgc gcgaaaattg gcacttccgg   9300
aggtaggcgg cgctcatcaa aaacgtcaca ttttccgcga cggaagcttg catgtgagct   9360
cctcccactt gcaaatgcca cacttccgcc acacctccca accctactcg cgcgtcctac   9420
gtcacccgcc ccgcctctcc ccgcccacct cattatcata ttggccacaa tccaaaataa   9480
ggtatattat tgatgatggt ttaaacgccc aattcactgg ccgtcgtttt acaacgtcgt   9540
gactgggaaa accctggcgt tacccaactt aatcgccttg cagcacatcc ccctttcgcc   9600
agctggcgta atagcgaaga ggcccgcacc gatcgccctt cccaacagtt gcgcagcctg   9660
aatggcgaat ggcgcctgat gcggtatttt ctccttacgc atctgtgcgg tatttcacac   9720
cgcatatggt gcactctcag tacaatctgc tctgatgccg catagttaag ccagccccga   9780
cacccgccaa cacccgctga cgcgccctga cgggcttgtc tgctcccggc atccgcttac   9840
agacaagctg tgaccgtctc cgggagctgc atgtgtcaga ggttttcacc gtcatcaccg   9900
aaacgcgcga gacgaaaggg cctcgtgata cgcctatttt tataggttaa tgtcatgata   9960
ataatggttt cttagacgtc aggtggcact tttcggggaa atgtgcgcgg aacccctatt  10020
tgtttatttt tctaaataca                                             10040
```

<210> SEQ ID NO 63
<211> LENGTH: 9949
<212> TYPE: DNA
<213> ORGANISM: Artificial sequence
<220> FEATURE:

-continued

<223> OTHER INFORMATION: GCAd-RTS-IL12 design 3

<400> SEQUENCE: 63

```
ttcaaatatg tatccgctca tgagacaata accctgataa atgcttcaat aatattgaaa     60
aaggaagagt atgagtattc aacatttccg tgtcgccctt attccctttt ttgcggcatt    120
ttgccttcct gtttttgctc acccagaaac gctggtgaaa gtaaaagatg ctgaagatca    180
gttgggtgca cgagtgggtt acatcgaact ggatctcaac agcggtaaga tccttgagag    240
ttttcgcccc gaagaacgtt ttccaatgat gagcactttt aaagttctgc tatgtggcgc    300
ggtattatcc cgtattgacg ccgggcaaga gcaactcggt cgccgcatac actattctca    360
gaatgacttg gttgagtact caccagtcac agaaaagcat cttacggatg gcatgacagt    420
aagagaatta tgcagtgctg ccataaccat gagtgataac actgcggcca acttacttct    480
gacaacgatc ggaggaccga aggagctaac cgcttttttg cacaacatgg gggatcatgt    540
aactcgcctt gatcgttggg aaccggagct gaatgaagcc ataccaaacg acgagcgtga    600
caccacgatg cctgtagcaa tggcaacaac gttgcgcaaa ctattaactg gcgaactact    660
tactctagct tcccggcaac aattaataga ctggatggag gcggataaag ttgcaggacc    720
acttctgcgc tcggcccttc cggctggctg gtttattgct gataaatctg gagccggtga    780
gcgtgggtct cgcggtatca ttgcagcact ggggccagat ggtaagccct cccgtatcgt    840
agttatctac acgacgggga gtcaggcaac tatggatgaa cgaaatagac agatcgctga    900
gataggtgcc tcactgatta agcattggta actgtcagac caagtttact catatatact    960
ttagattgat ttaaaacttc atttttaatt taaaaggatc taggtgaaga tcctttttga   1020
taatctcatg accaaaatcc cttaacgtga gttttcgttc cactgagcgt cagaccccgt   1080
agaaaagatc aaaggatctt cttgagatcc tttttttctg cgcgtaatct gctgcttgca   1140
aacaaaaaaa ccaccgctac cagcggtggt ttgtttgccg gatcaagagc taccaactct   1200
ttttccgaag gtaactggct tcagcagagc gcagatacca aatactgttc ttctagtgta   1260
gccgtagtta ggccaccact tcaagaactc tgtagcaccg cctacatacc tcgctctgct   1320
aatcctgtta ccagtggctg ctgccagtgg cgataagtcg tgtcttaccg ggttggactc   1380
aagacgatag ttaccggata aggcgcagcg gtcgggctga acggggggtt cgtgcacaca   1440
gcccagcttg gagcgaacga cctacaccga actgagatac ctacagcgtg agctatgaga   1500
aagcgccacg cttcccgaag ggagaaaggc ggacaggtat ccggtaagcg gcagggtcgg   1560
aacaggagag cgcacgaggg agcttccagg gggaaacgcc tggtatcttt atagtcctgt   1620
cgggtttcgc cacctctgac ttgagcgtcg atttttgtga tgctcgtcag gggggcggag   1680
cctatggaaa aacgccagca acgcggcctt tttacggttc ctggcctttt gctggccttt   1740
tgctcacatg ttctttcctg cgttatcccc tgattctgtg gataaccgta ttaccgcctt   1800
tgagtgagct gataccgctc gccgcagccg aacgaccgag cgcagcgagt cagtgagcga   1860
ggaagcggaa gagcgcccaa tacgcaaacc gcctctcccc gcgcgttggc cgattcatta   1920
atgcagctgg cacgacaggt ttcccgactg gaaagcgggc agtgagcgca acgcaattaa   1980
tgtgagttag ctcactcatt aggcacccca ggctttacac tttatgcttc cggctcgtat   2040
gttgtgtgga attgtgagcg gataacaatt tcacacagga aacagctatg accatgatta   2100
cgccaagctg ggtcaagtct tccagtttaa gcagcagagc ggtcagtttc tcatcccgag   2160
cagacgcgcg agaggccgcg ccgctcgcca ccaaagagct gtaaaggtcc gtagccatgc   2220
tgcgcgcggt cgcggcggcg gcggaggcgg cggcggaggt cgcggcgtcc agcggagttc   2280
```

-continued

```
ctcccacggt cgcgtaggcc attgtagacg aatttgaagg cagaacgggg cgtccatcca   2340
cgttggaacc catcacattc tgacgcactc cagcccagtg aggcatgcgc actgtcagat   2400
aggggctaaa gatgcttcca tcaaagctgt tgccggtgtc gctcatggcg gcggctgttg   2460
caagacaaaa cagagagacc cttagacccc caatttatac acgccccacc cttctagcca   2520
cgcccacctt acccacctca atcggtatcc tcatcgctag acccaaactc ggccctggtg   2580
caggccagca ccagatggtc aggcctgcag gtacgtagcc gcaataaaat atctttattt   2640
tcattacatc tgtgtgttgg tttttttgtgt gaatccatag tactaacata cgctctccat   2700
caaaacaaaa cgaaacaaaa caaactagca aaataggctg tccccagtgc aagtccaggt   2760
gccagaacat ttctctatcc ataatgcagg ggtaccggaa ggaagagggg cggggtcgat   2820
cgaccccgcc cctcttcctt cgaaggaaga ggggcggggt ccaattgcgg agtactgtcc   2880
tccgagcgga gtactgtcct ccgagcggag tactgtcctc cgagcggagt actgtcctcc   2940
gagcggagta ctgtcctccg agcggagtac tgtcctccga gcggagagtc cccggggacc   3000
tagagggtat ataatgggtg ccttagctgg tgtgtgacct catcttcctg tacgcccctg   3060
caggcagccg ctaaatccaa ggtaaggtca gaagagctag cgccaccatg tgtcaccagc   3120
agttggtcat ctcttggttc agcctggttt ttctggcatc tcccctcgtg gccatctggg   3180
aactgaagaa agatgtttat gtcgtagaat tggattggta tcccgacgcc cctggagaaa   3240
tggtggtcct gacatgtgac acccctgaag aagatggtat cacctggacc ttggaccaga   3300
gcagtgaggt cttaggctct ggcaagaccc tgaccatcca agtcaaagag tttggagatg   3360
ctggccagta cacctgtcac aaaggaggcg aggttctaag ccattcgctc ctgctgcttc   3420
acaaaaagga agatggaatt tggtccactg acattctgaa ggaccagaaa gaacccaaga   3480
ataagacctt tctaagatgc gaggccaaga attattctgg acgtttcacc tgctggtggc   3540
tgacgacaat cagtactgat ttgacattca gtgtcaaaag cagcagaggc tcttctgacc   3600
cccaaggggt gacgtgcgga gctgctacac tcagcgccga gagagtcaga ggggacaaca   3660
aggagtatga gtactcagtg gagtgccagg aggacagtgc ctgcccagct gctgaggaga   3720
gtctgcccat tgaggtcatg gtggatgccg ttcacaagct caagtatgaa aactacacca   3780
gcagcttctt catcagggac atcatcaaac ctgacccacc caagaacttg cagctgaagc   3840
ccctgaagaa cagcagacag gtggaggtca gctgggagta ccctgacacc tggagtactc   3900
cacattccta cttctccctg acattctgcg ttcaggtcca gggcaagagc aagagagaaa   3960
agaaagatag agtcttcacg gacaagacct cagccacggt catctgccgc aaaaatgcca   4020
gcattagcgt gcgggcccag gaccgctact atagctcatc ttggagcgaa tgggcatctg   4080
tgccctgctc cggtggcggt ggcggcggat ctagaaacct ccccgtggcc actccagacc   4140
caggaatgtt cccatgcctt caccacagcc agaacctgct gagggccgtc agcaacatgc   4200
tccagaaggc cagacaaact ctagaatttt acccttgcac ttctgaagag attgatcatg   4260
aagatatcac aaaagataaa accagcacag tggaggcctg tttaccattg gaattaacca   4320
agaatgagag ttgcctaaat tccagagaga cctctttcat aactaatggg agttgcctgg   4380
cctccagaaa gacctctttt atgatggccc tgtgccttag tagtatttat gaagacttga   4440
agatgtacca ggtggagttc aagaccatga atgcaaagct gctgatggac cccaagaggc   4500
agatctttct agatcaaaac atgctggcag ttattgatga gctgatgcag gccctgaatt   4560
tcaacagtga gactgtgcca caaaaatcct cccttgaaga accggatttt tataaaacta   4620
```

-continued

```
aaatcaagct ctgcatactt cttcatgctt tcagaatcag agcagtgact attgatagag   4680
tgatgagcta tctgaatgct tcctaaatcg atttatttat cggcataaat aatttttttg   4740
aagaagtaat actattttc tttttttttg taaataaatg ggttaaggga tgtaacattg   4800
tttgttgttt ggtgggggtt ggggcctccg cgccgggttt tggcgcctcc cgcgggcgcc   4860
cccctcctca cggcgagcgc tgccacgtca gacgaagggc gcagcgagcg tcctgatcct   4920
tccgcccgga cgctcaggac agcggcccgc tgctcataag actcggcctt agaaccccag   4980
tatcagcaga aggacatttt aggacgggac ttgggtgact ctagggcact ggtttctttt   5040
ccagagagcg gaacaggcga ggaaaagtag tcccttctcg gcgattctgc ggagggatct   5100
ccgtggggcg gtgaacgccg atgattatat aaggacgcgc cgggtgtggc acagctagtt   5160
ccgtcgcagc cgggatttgg gtcgcggttc ttgtttgtgg atcgctgtga tcgtcacttg   5220
gtgagtagcg ggctgctggg ctgggtacgt gcgctcgggg ttggcgagtg tgttttgtga   5280
agtttttag gcacctttg aaatgtaatc atttgggtca atatgtaatt ttcagtgtta   5340
gactagtaaa ttgtccgcta aattctggcc gtttttggct tttttgttag acgagctagc   5400
gccgccacca tgggccctaa aaagaagcgt aaagtcgccc ccccgaccga tgtcagcctg   5460
ggggacgagc tccacttaga cggcgaggac gtggcgatgg cgcatgccga cgcgctagac   5520
gatttcgatc tggacatgtt gggggacggg gattccccgg gtccgggatt tacccccac   5580
gactccgccc cctacggcgc tctggatatg gccgacttcg agtttgagca gatgtttacc   5640
gatgcccttg gaattgacga gtacggtggg gaattcgaga tgcctgtgga caggatcctg   5700
gaggcagagc ttgctgtgga acagaagagt gaccagggcg ttgagggtcc tgggggaacc   5760
gggggtagcg gcagcagccc aaatgaccct gtgactaaca tctgtcaggc agctgacaaa   5820
cagctattca cgcttgttga gtgggcgaag aggatcccac acttttcctc cttgcctctg   5880
gatgatcagg tcatattgct gcgggcaggc tggaatgaac tcctcattgc ctccttttca   5940
caccgatcca ttgatgttcg agatggcatc ctccttgcca caggtcttca cgtgcaccgc   6000
aactcagccc attcagcagg agtaggagcc atctttgatc gggtgctgac agagctagtg   6060
tccaaaatgc gtgacatgag gatggacaag acagagcttg gctgcctgag ggcaatcatt   6120
ctgtttaatc cagaggtgag ggtttgaaa tccgcccagg aagttgaact tctacgtgaa   6180
aaagtatatg ccgctttgga agaatatact agaacaacac atcccgatga accaggaaga   6240
tttgcaaaac ttttgcttcg tctgccttct ttacgttcca taggccttaa gtgtttggag   6300
catttgtttt tctttcgcct tattggagat gttccaattg atacgttcct gatggagatg   6360
cttgaatcac cttctgattc ataatctagc ctagcccccc tctccctccc cccccctaa   6420
cgttactggc cgaagccgct tggaataagg ccggtgtgcg tttgtctata tgttattttc   6480
caccatattg ccgtcttttg gcaatgtgag ggcccggaaa cctggccctg tcttcttgac   6540
gagcattcct aggggtcttt cccctctcgc caaaggaatg caaggtctgt tgaatgtcgt   6600
gaaggaagca gttcctctgg aagcttcttg aagacaaaca acgtctgtag cgaccctttg   6660
caggcagcgg aacccccac ctggcgacag gtgcctctgc ggccaaaagc cacgtgtata   6720
agatacacct gcaaaggcgg cacaacccca gtgccacgtt gtgagttgga tagttgtgga   6780
aagagtcaaa tggctctcct caagcgtatt caacaagggg ctgaaggatg cccagaaggt   6840
accccattgt atgggatctg atctggggcc tcggtgcaca tgctttacat gtgtttagtc   6900
gaggttaaaa aacgtctagg ccccccgaac cacggggacg tggttttcct ttgaaaaaca   6960
cgatctctag gcgccaccat gaagctactg tcttctatcg aacaagcatg cgatatttgc   7020
```

```
cgacttaaaa agctcaagtg ctccaaagaa aaaccgaagt gcgccaagtg tctgaagaac   7080
aactgggagt gtcgctactc tcccaaaacc aaaaggtctc cgctgactag ggcacatctg   7140
acagaagtgg aatcaaggct agaaagactg gaacagctat ttctactgat ttttcctcga   7200
gaagaccttg acatgatttt gaaaatggat tctttacagg atataaaagc attgttaaca   7260
ggattatttg tacaagataa tgtgaataaa gatgccgtca cagatagatt ggcttcagtg   7320
gagactgata tgcctctaac attgagacag catagaataa gtgcgacatc atcatcggaa   7380
gagagtagta acaaaggtca aagacagttg actgtatcgc cggaattccc ggggatccgg   7440
cctgagtgcg tagtacccga gactcagtgc gccatgaagc ggaaagagaa gaaagcacag   7500
aaggagaagg acaaactgcc tgtcagcacg acgacggtgg acgaccacat gccgcccatt   7560
atgcagtgtg aacctccacc tcctgaagca gcaaggattc acgaagtggt cccaaggttt   7620
ctctccgaca agctgttggt gacaaaccgg cagaaaaaca tcccccagtt gacagccaac   7680
cagcagttcc ttatcgccag gctcatctgg taccaggacg ggtacgagca gccttctgat   7740
gaagatttga agaggattac gcagacgtgg cagcaagcgg acgatgaaaa cgaagagtcg   7800
gacactccct tccgccagat cacagagatg actatcctca cggtccaact tatcgtggag   7860
ttcgcgaagg gattgccagg gttcgccaag atctcgcagc ctgatcaaat tacgctgctt   7920
aaggcttgct caagtgaggt aatgatgctc cgagtcgcgc gacgatacga tgcggcctca   7980
gacagtattc tgttcgcgaa caaccaagcg tacactcgcg acaactaccg caaggctggc   8040
atggccgagg tcatcgagga tctactgcac ttctgccggt gcatgtactc tatggcgttg   8100
gacaacatcc attacgcgct gctcacggct gtcgtcatct tttctgaccg gccagggttg   8160
gagcagccgc aactggtgga agagatccag cggtactacc tgaatacgct ccgcatctat   8220
atcctgaacc agctgagcgg gtcggcgcgt tcgtccgtca tatacggcaa gatcctctca   8280
atcctctctg agctacgcac gctcggcatg caaaactcca acatgtgcat ctccctcaag   8340
ctcaagaaca gaaagctgcc gcctttcctc gaggagatct gggatgtggc ggacatgtcg   8400
cacacccaac cgccgcctat cctcgagtcc cccacgaatc tctaaatcga ttacgctcct   8460
ctactctttg agacatcact ggcctataat aaatgggtta atttatgtaa caaaattgcc   8520
ttggcttgtt aactttatta gacattctga tgtttgcatt gtgtaaatac tgttgtattg   8580
gaaaagcgtg ccaagatgga ttattgtaat tcagtgtctt ttttagtagc gtcacgtgcc   8640
aaacactgtt agtcacagag ggcatgagac agcctgtgct ggaacagctc agttcatagg   8700
gctatggaga tggggagaaa ggggcgcttc tgtcagagac aagctgtggt ctgggaaggc   8760
cttagcacta aaagcaccac aatgagaagc aaccgccaga agcagggccc gcaggccttt   8820
gttccagctg caaagagaaa ggaaaaagtg gggaataaga gttggggctg cggagggggt   8880
ggggagcatt gtgcaggttc cgtacttgaa cagaaagcag ggaccaacac aaggaagggc   8940
gcgccaccgg tcaaatgacg gtgacaataa aacggagact ttgacccgga acgcggaaat   9000
tcacgtaaaa aacacctggg cgagtcctcc acgtaatcgg tcaaagtccc tcggccctcg   9060
gtaaatatta cgcactatga ctaacgccct attattcagt tttcacttcc ccgtttcact   9120
tttcgcgcga aaatggccaa atcttacatg gtcccgccca aaattactac gatatccggt   9180
gaaaagcgcg cgaaaattgg cacttccgga ggtaggcggc gctcatcaaa aacgtcacat   9240
tttccgcgac ggaagcttgc atgtgagctc ctcccacttg caaatgccac acttccgcca   9300
cacctcccaa ccctactcgc gcgtcctacg tcacccgccc cgcctctccc cgcccacctc   9360
```

-continued

```
attatcatat tggccacaat ccaaaataag gtatattatt gatgatggtt taaacgccca   9420

attcactggc cgtcgtttta caacgtcgtg actgggaaaa ccctggcgtt acccaactta   9480

atcgccttgc agcacatccc cctttcgcca gctggcgtaa tagcgaagag gcccgcaccg   9540

atcgcccttc ccaacagttg cgcagcctga atggcgaatg gcgcctgatg cggtattttc   9600

tccttacgca tctgtgcggt atttcacacc gcatatggtg cactctcagt acaatctgct   9660

ctgatgccgc atagttaagc cagccccgac acccgccaac acccgctgac gcgccctgac   9720

gggcttgtct gctcccggca tccgcttaca gacaagctgt gaccgtctcc gggagctgca   9780

tgtgtcagag gttttcaccg tcatcaccga aacgcgcgag acgaaagggc ctcgtgatac   9840

gcctattttt ataggttaat gtcatgataa taatggtttc ttagacgtca ggtggcactt   9900

ttcggggaaa tgtgcgcgga acccctattt gtttattttt ctaaataca               9949


<210> SEQ ID NO 64
<211> LENGTH: 54
<212> TYPE: DNA
<213> ORGANISM: Artificial sequence
<220> FEATURE:
<223> OTHER INFORMATION: Whitlow Linker

<400> SEQUENCE: 64

ggcagcacct ccggcagcgg caagcctggc agcggcgagg gcagcaccaa gggc           54


<210> SEQ ID NO 65
<211> LENGTH: 78
<212> TYPE: DNA
<213> ORGANISM: Artificial sequence
<220> FEATURE:
<223> OTHER INFORMATION: Linker

<400> SEQUENCE: 65

tctggcggag gatctggagg aggcggatct ggaggaggag gcagtggagg cggaggatct     60

ggcggaggat ctctgcag                                                   78


<210> SEQ ID NO 66
<211> LENGTH: 9
<212> TYPE: DNA
<213> ORGANISM: Artificial sequence
<220> FEATURE:
<223> OTHER INFORMATION: GSG linker

<400> SEQUENCE: 66

ggaagcgga                                                              9


<210> SEQ ID NO 67
<211> LENGTH: 12
<212> TYPE: DNA
<213> ORGANISM: Artificial sequence
<220> FEATURE:
<223> OTHER INFORMATION: SGSG linker

<400> SEQUENCE: 67

agtggcagcg gc                                                         12


<210> SEQ ID NO 68
<211> LENGTH: 45
<212> TYPE: DNA
<213> ORGANISM: Artificial sequence
<220> FEATURE:
<223> OTHER INFORMATION: (G4S)3 linker

<400> SEQUENCE: 68
```

ggtggcggtg gctcgggcgg tggtgggtcg ggtggcggcg gatct 45

<210> SEQ ID NO 69
<211> LENGTH: 12
<212> TYPE: DNA
<213> ORGANISM: Artificial sequence
<220> FEATURE:
<223> OTHER INFORMATION: Furin cleavage site/ Furinlink1

<400> SEQUENCE: 69
cgtgcaaagc gt 12

<210> SEQ ID NO 70
<211> LENGTH: 84
<212> TYPE: DNA
<213> ORGANISM: Artificial sequence
<220> FEATURE:
<223> OTHER INFORMATION: Fmdv

<400> SEQUENCE: 70
agagccaaga gggcaccggt gaaacagact ttgaattttg accttctgaa gttggcagga 60
gacgttgagt ccaaccctgg gccc 84

<210> SEQ ID NO 71
<211> LENGTH: 54
<212> TYPE: DNA
<213> ORGANISM: Artificial sequence
<220> FEATURE:
<223> OTHER INFORMATION: Thosea asigna virus 2A region (T2A)

<400> SEQUENCE: 71
gagggcagag gaagtctgct aacatgcggt gacgtcgagg agaatcctgg acct 54

<210> SEQ ID NO 72
<211> LENGTH: 75
<212> TYPE: DNA
<213> ORGANISM: Artificial sequence
<220> FEATURE:
<223> OTHER INFORMATION: Furin-GSG-T2A

<400> SEQUENCE: 72
agagctaaga ggggaagcgg agagggcaga ggaagtctgc taacatgcgg tgacgtcgag 60
gagaatcctg gacct 75

<210> SEQ ID NO 73
<211> LENGTH: 78
<212> TYPE: DNA
<213> ORGANISM: Artificial sequence
<220> FEATURE:
<223> OTHER INFORMATION: Furin-SGSG-T2A

<400> SEQUENCE: 73
agggccaaga ggagtggcag cggcgagggc agaggaagtc ttctaacatg cggtgacgtg 60
gaggagaatc ccggccct 78

<210> SEQ ID NO 74
<211> LENGTH: 57
<212> TYPE: DNA
<213> ORGANISM: Artificial sequence
<220> FEATURE:
<223> OTHER INFORMATION: Porcine teschovirus-1 2A region (P2A)

<400> SEQUENCE: 74
gcaacgaact tctctctcct aaaacaggct ggtgatgtgg aggagaatcc tggtcca 57

<210> SEQ ID NO 75
<211> LENGTH: 66
<212> TYPE: DNA
<213> ORGANISM: Artificial sequence
<220> FEATURE:
<223> OTHER INFORMATION: GSG-P2A

<400> SEQUENCE: 75
ggaagcggag ctactaactt cagcctgctg aagcaggctg gagacgtgga ggagaaccct 60
ggacct 66

<210> SEQ ID NO 76
<211> LENGTH: 60
<212> TYPE: DNA
<213> ORGANISM: Artificial sequence
<220> FEATURE:
<223> OTHER INFORMATION: Equine rhinitis A virus 2A region (E2A)

<400> SEQUENCE: 76
cagtgtacta attatgctct cttgaaattg gctggagatg ttgagagcaa ccctggacct 60

<210> SEQ ID NO 77
<211> LENGTH: 66
<212> TYPE: DNA
<213> ORGANISM: Artificial sequence
<220> FEATURE:
<223> OTHER INFORMATION: Foot-and-mouth disease virus 2A region (F2A)

<400> SEQUENCE: 77
gtcaaacaga ccctaaactt tgatctgcta aaactggccg gggatgtgga aagtaatccc 60
ggcccc 66

<210> SEQ ID NO 78
<211> LENGTH: 93
<212> TYPE: DNA
<213> ORGANISM: Artificial sequence
<220> FEATURE:
<223> OTHER INFORMATION: FP2A

<400> SEQUENCE: 78
cgtgcaaagc gtgcaccggt gaaacaggga agcggagcta ctaacttcag cctgctgaag 60
caggctggag acgtggagga gaaccctgga cct 93

<210> SEQ ID NO 79
<211> LENGTH: 24
<212> TYPE: DNA
<213> ORGANISM: Artificial sequence
<220> FEATURE:
<223> OTHER INFORMATION: Linker-GSG

<400> SEQUENCE: 79
gcaccggtga aacagggaag cgga 24

<210> SEQ ID NO 80
<211> LENGTH: 15
<212> TYPE: DNA
<213> ORGANISM: Artificial sequence
<220> FEATURE:
<223> OTHER INFORMATION: Linker

<400> SEQUENCE: 80
gcaccggtga aacag 15

```
<210> SEQ ID NO 81
<211> LENGTH: 18
<212> TYPE: PRT
<213> ORGANISM: Artificial sequence
<220> FEATURE:
<223> OTHER INFORMATION: Whitlow Linker Amino Acid Sequence

<400> SEQUENCE: 81

Gly Ser Thr Ser Gly Ser Gly Lys Pro Gly Ser Gly Glu Gly Ser Thr
1               5                   10                  15

Lys Gly


<210> SEQ ID NO 82
<211> LENGTH: 26
<212> TYPE: PRT
<213> ORGANISM: Artificial sequence
<220> FEATURE:
<223> OTHER INFORMATION: Linker Amino Acid Sequence

<400> SEQUENCE: 82

Ser Gly Gly Gly Ser Gly Gly Gly Gly Ser Gly Gly Gly Gly Ser Gly
1               5                   10                  15

Gly Gly Gly Ser Gly Gly Gly Ser Leu Gln
            20                  25


<210> SEQ ID NO 83
<211> LENGTH: 3
<212> TYPE: PRT
<213> ORGANISM: Artificial sequence
<220> FEATURE:
<223> OTHER INFORMATION: GSG Linker Amino Acid Sequence

<400> SEQUENCE: 83

Gly Ser Gly
1


<210> SEQ ID NO 84
<211> LENGTH: 4
<212> TYPE: PRT
<213> ORGANISM: Artificial sequence
<220> FEATURE:
<223> OTHER INFORMATION: SGSG  Linker Amino Acid Sequence

<400> SEQUENCE: 84

Ser Gly Ser Gly
1


<210> SEQ ID NO 85
<211> LENGTH: 15
<212> TYPE: PRT
<213> ORGANISM: Artificial sequence
<220> FEATURE:
<223> OTHER INFORMATION: (G4S) 3 Linker Amino Acid sequence

<400> SEQUENCE: 85

Gly Gly Gly Gly Ser Gly Gly Gly Gly Ser Gly Gly Gly Gly Ser
1               5                   10                  15


<210> SEQ ID NO 86
<211> LENGTH: 4
<212> TYPE: PRT
<213> ORGANISM: Artificial sequence
<220> FEATURE:
<223> OTHER INFORMATION: Linker Polypeptide component
```

<400> SEQUENCE: 86

Arg Ala Lys Arg
1

<210> SEQ ID NO 87
<211> LENGTH: 28
<212> TYPE: PRT
<213> ORGANISM: Artificial sequence
<220> FEATURE:
<223> OTHER INFORMATION: Fmdv Amino Acid Sequence

<400> SEQUENCE: 87

Arg Ala Lys Arg Ala Pro Val Lys Gln Thr Leu Asn Phe Asp Leu Leu
1 5 10 15

Lys Leu Ala Gly Asp Val Glu Ser Asn Pro Gly Pro
20 25

<210> SEQ ID NO 88
<211> LENGTH: 18
<212> TYPE: PRT
<213> ORGANISM: Artificial sequence
<220> FEATURE:
<223> OTHER INFORMATION: Furin-GSG-T2A Amino Acid Sequence

<400> SEQUENCE: 88

Glu Gly Arg Gly Ser Leu Leu Thr Cys Gly Asp Val Glu Glu Asn Pro
1 5 10 15

Gly Pro

<210> SEQ ID NO 89
<211> LENGTH: 25
<212> TYPE: PRT
<213> ORGANISM: Artificial sequence
<220> FEATURE:
<223> OTHER INFORMATION: Furin-SGSG-T2A Amino Acid Sequence

<400> SEQUENCE: 89

Arg Ala Lys Arg Gly Ser Gly Glu Gly Arg Gly Ser Leu Leu Thr Cys
1 5 10 15

Gly Asp Val Glu Glu Asn Pro Gly Pro
20 25

<210> SEQ ID NO 90
<211> LENGTH: 26
<212> TYPE: PRT
<213> ORGANISM: Artificial sequence
<220> FEATURE:
<223> OTHER INFORMATION: Furin-SGSG-T2A

<400> SEQUENCE: 90

Arg Ala Lys Arg Ser Gly Ser Gly Glu Gly Arg Gly Ser Leu Leu Thr
1 5 10 15

Cys Gly Asp Val Glu Glu Asn Pro Gly Pro
20 25

<210> SEQ ID NO 91
<211> LENGTH: 19
<212> TYPE: PRT
<213> ORGANISM: Artificial sequence
<220> FEATURE:
<223> OTHER INFORMATION: Porcine teschovirus-1 2A region (P2A)

<400> SEQUENCE: 91

Ala Thr Asn Phe Ser Leu Leu Lys Gln Ala Gly Asp Val Glu Glu Asn 1 5 10 15

Pro Gly Pro

<210> SEQ ID NO 92
<211> LENGTH: 22
<212> TYPE: PRT
<213> ORGANISM: Artificial sequence
<220> FEATURE:
<223> OTHER INFORMATION: GSG-P2A Amino Acid Sequence

<400> SEQUENCE: 92

Gly Ser Gly Ala Thr Asn Phe Ser Leu Leu Lys Gln Ala Gly Asp Val
1 5 10 15

Glu Glu Asn Pro Gly Pro
20

<210> SEQ ID NO 93
<211> LENGTH: 20
<212> TYPE: PRT
<213> ORGANISM: Artificial sequence
<220> FEATURE:
<223> OTHER INFORMATION: Equine rhinitis A virus 2A region (E2A) Amino Acid Sequence

<400> SEQUENCE: 93

Gln Cys Thr Asn Tyr Ala Leu Leu Lys Leu Ala Gly Asp Val Glu Ser
1 5 10 15

Asn Pro Gly Pro
20

<210> SEQ ID NO 94
<211> LENGTH: 22
<212> TYPE: PRT
<213> ORGANISM: Artificial sequence
<220> FEATURE:
<223> OTHER INFORMATION: Foot-and-mouth disease virus 2A region (F2A) Amino Acid Sequence

<400> SEQUENCE: 94

Val Lys Gln Thr Leu Asn Phe Asp Leu Leu Lys Leu Ala Gly Asp Val
1 5 10 15

Glu Ser Asn Pro Gly Pro
20

<210> SEQ ID NO 95
<211> LENGTH: 31
<212> TYPE: PRT
<213> ORGANISM: Artificial sequence
<220> FEATURE:
<223> OTHER INFORMATION: FP2A Amino Acid Sequence

<400> SEQUENCE: 95

Arg Ala Lys Arg Ala Pro Val Lys Gln Gly Ser Gly Ala Thr Asn Phe
1 5 10 15

Ser Leu Leu Lys Gln Ala Gly Asp Val Glu Glu Asn Pro Gly Pro
20 25 30

<210> SEQ ID NO 96
<211> LENGTH: 8
<212> TYPE: PRT
<213> ORGANISM: Artificial sequence
<220> FEATURE:
<223> OTHER INFORMATION: Linker-GSG Amino Acid

<400> SEQUENCE: 96

Ala Pro Val Lys Gln Gly Ser Gly
1 5

<210> SEQ ID NO 97
<211> LENGTH: 5
<212> TYPE: PRT
<213> ORGANISM: Artificial sequence
<220> FEATURE:
<223> OTHER INFORMATION: Linker Amino Acid

<400> SEQUENCE: 97

Ala Pro Val Lys Gln
1 5

<210> SEQ ID NO 98
<211> LENGTH: 154
<212> TYPE: PRT
<213> ORGANISM: Artificial sequence
<220> FEATURE:
<223> OTHER INFORMATION: HBV HBx domain of HBV design 1

<400> SEQUENCE: 98

Met Ala Ala Arg Leu Cys Cys Gln Leu Asp Pro Ala Arg Asp Val Leu
1 5 10 15

Cys Leu Arg Pro Val Gly Ala Glu Ser Arg Gly Arg Pro Phe Ser Gly
20 25 30

Pro Leu Gly Ala Leu Ser Ser Ser Ser Pro Pro Ala Val Pro Thr Asp
35 40 45

His Gly Ala His Leu Ser Leu Arg Gly Leu Pro Val Cys Ala Phe Ser
50 55 60

Ser Ala Gly Pro Cys Ala Leu Arg Phe Thr Ser Ala Arg Arg Met Glu
65 70 75 80

Thr Thr Val Asn Ala His Gln Phe Leu Pro Lys Val Leu His Lys Arg
85 90 95

Thr Leu Gly Leu Ser Ala Met Ser Thr Thr Asp Leu Glu Ala Tyr Phe
100 105 110

Lys Asp Cys Leu Phe Lys Asp Trp Glu Glu Leu Gly Glu Glu Leu Arg
115 120 125

Leu Lys Val Phe Val Leu Gly Gly Cys Arg His Lys Leu Val Cys Ala
130 135 140

Pro Ala Pro Cys Asn Phe Phe Thr Ser Ala
145 150

<210> SEQ ID NO 99
<211> LENGTH: 454
<212> TYPE: PRT
<213> ORGANISM: Artificial sequence
<220> FEATURE:
<223> OTHER INFORMATION: HBV Pol domain of HBV design 1

<400> SEQUENCE: 99

Gly Pro Cys Ala Glu His Gly Glu His His Ile Arg Ile Pro Arg Thr
1 5 10 15

Pro Ala Arg Val Thr Gly Gly Val Phe Leu Val Asp Lys Asn Pro His
20 25 30

Asn Thr Ala Glu Ser Arg Leu Val Val Asp Phe Ser Gln Phe Ser Arg
35 40 45

Gly Asn Tyr Arg Val Ser Trp Pro Lys Phe Ala Val Pro Asn Leu Gln
50 55 60

```
Ser Leu Thr Asn Leu Leu Ser Ser Asn Leu Cys Trp Leu Ser Leu Asp
65                  70                  75                  80

Val Ser Ala Ala Phe Tyr His Leu Pro Leu His Pro Ala Ala Met Pro
                85                  90                  95

His Leu Leu Val Gly Ser Ser Gly Leu Ser Arg Tyr Val Ala Arg Leu
            100                 105                 110

Ser Ser Asn Ser Arg Ile Ile Asn His Gln His Gly Thr Leu Gln Asn
        115                 120                 125

Leu His Asp Ser Cys Ser Arg Asn Leu Tyr Val Ser Leu Leu Leu Leu
    130                 135                 140

Tyr Lys Thr Phe Gly Trp Lys Leu His Leu Tyr Ser His Pro Ile Ile
145                 150                 155                 160

Leu Gly Phe Arg Lys Ile Pro Met Gly Val Gly Leu Ser Pro Phe Leu
                165                 170                 175

Leu Ala Gln Phe Thr Ser Ala Ile Cys Ser Val Val Arg Arg Ala Phe
            180                 185                 190

Pro His Cys Leu Ala Phe Ser Gly Ala Lys Ser Val Gln His Leu Glu
        195                 200                 205

Ser Leu Phe Thr Ala Val Thr Asn Phe Leu Leu Ser Leu Gly Ile His
    210                 215                 220

Leu Asn Pro Asn Lys Thr Lys Arg Trp Gly Tyr Ser Leu Asn Phe Met
225                 230                 235                 240

Gly Tyr Val Ile Gly Ser Trp Gly Ser Leu Pro Gln Asp His Ile Arg
                245                 250                 255

His Lys Ile Lys Glu Cys Phe Arg Lys Leu Pro Val His Arg Pro Ile
            260                 265                 270

Asp Trp Lys Val Cys Gln Arg Ile Val Gly Leu Leu Gly Phe Ala Ala
        275                 280                 285

Pro Phe Thr Gln Cys Gly Tyr Pro Ala Leu Met Pro Leu Tyr Ala Cys
    290                 295                 300

Ile Gln Ser Lys Gln Ala Phe Thr Phe Ser Pro Thr Tyr Lys Ala Phe
305                 310                 315                 320

Leu Cys Lys Gln Tyr Leu Asn Leu Tyr Pro Val Ala Arg Gln Arg Pro
                325                 330                 335

Gly Leu Cys Gln Val Phe Ala Asp Ala Thr Pro Thr Gly Trp Gly Leu
            340                 345                 350

Val Met Gly His Gln Arg Met Arg Gly Thr Phe Ser Ser Arg Lys Tyr
        355                 360                 365

Thr Ser Phe Pro Trp Leu Leu Gly Cys Ala Ala Asn Trp Ile Leu Arg
    370                 375                 380

Gly Thr Ser Phe Val Tyr Val Pro Ser Ala Leu Asn Pro Ala Asp Asp
385                 390                 395                 400

Pro Ser Arg Gly Arg Leu Gly Pro Cys Arg Pro Leu Leu His Leu Pro
                405                 410                 415

Phe Arg Pro Thr Thr Gly Arg Thr Ser Leu Tyr Ala Asp Ser Pro Ser
            420                 425                 430

Val Pro Ser His Leu Pro Asp Arg Val His Phe Ala Ser Pro Leu His
        435                 440                 445

Val Ala Trp Arg Pro Pro
    450
```

<210> SEQ ID NO 100
<211> LENGTH: 226
<212> TYPE: PRT

<213> ORGANISM: Artificial sequence
<220> FEATURE:
<223> OTHER INFORMATION: HBV Surface (Env1) domain of HBV domain 1

<400> SEQUENCE: 100

Met Glu Asn Ile Thr Ser Gly Phe Leu Gly Pro Leu Leu Val Leu Gln
1 5 10 15

Ala Gly Phe Phe Leu Leu Thr Arg Ile Leu Thr Ile Pro Gln Ser Leu
20 25 30

Asp Ser Trp Trp Thr Ser Leu Ser Phe Leu Gly Gly Thr Thr Val Cys
35 40 45

Leu Gly Gln Asn Ser Gln Ser Pro Thr Ser Asn His Ser Pro Thr Ser
50 55 60

Cys Pro Pro Thr Cys Val Gly Tyr Arg Trp Met Cys Leu Arg Arg Phe
65 70 75 80

Ile Ile Phe Leu Phe Ile Leu Leu Leu Cys Leu Ile Phe Leu Leu Val
85 90 95

Leu Leu Asp Tyr Gln Gly Met Leu Pro Val Cys Pro Leu Ile Pro Gly
100 105 110

Ser Ser Thr Thr Ser Thr Gly Pro Cys Arg Thr Cys Thr Thr Pro Ala
115 120 125

Gln Gly Thr Ser Met Tyr Pro Ser Cys Cys Cys Thr Lys Pro Ser Asp
130 135 140

Gly Asn Cys Thr Cys Ile Pro Ile Pro Ser Ser Trp Ala Phe Gly Lys
145 150 155 160

Phe Leu Trp Glu Trp Ala Ser Ala Arg Phe Ser Trp Leu Ser Leu Leu
165 170 175

Val Pro Phe Val Gln Trp Phe Val Gly Leu Ser Pro Thr Val Trp Leu
180 185 190

Ser Val Ile Trp Met Met Trp Tyr Trp Gly Pro Ser Leu Tyr Asn Thr
195 200 205

Leu Ser Pro Phe Leu Pro Leu Leu Pro Ile Phe Phe Tyr Leu Trp Val
210 215 220

Tyr Ile
225

<210> SEQ ID NO 101
<211> LENGTH: 180
<212> TYPE: PRT
<213> ORGANISM: Artificial sequence
<220> FEATURE:
<223> OTHER INFORMATION: HBV Core domain of HBV design 1

<400> SEQUENCE: 101

Met Gln Leu Phe His Leu Cys Leu Ile Ile Ser Cys Ser Cys Pro Thr
1 5 10 15

Val Gln Ala Ser Lys Leu Cys Leu Gly Trp Leu Trp Asp Met Asp Ile
20 25 30

Asp Pro Tyr Lys Glu Phe Gly Ala Ser Val Glu Leu Leu Ser Phe Leu
35 40 45

Pro Ser Asp Phe Phe Pro Ser Val Arg Asp Leu Leu Asp Thr Ala Thr
50 55 60

Ala Leu Tyr Arg Asp Ala Leu Glu Ser Pro Glu His Cys Thr Pro His
65 70 75 80

His Thr Ala Leu Arg His Val Cys Leu Cys Trp Gly Asp Leu Met Asn
85 90 95

```
Leu Ala Thr Trp Val Gly Thr Asn Leu Glu Asp Gln Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Asp Leu Val
    130                 135                 140

Leu Glu Tyr Leu Val Ser Phe Gly Val Trp Ile Arg Thr Pro Pro Ala
145                 150                 155                 160

Tyr Arg Pro Ser Asn Ala Pro Ile Leu Ser Thr Leu Pro Glu Thr Thr
                165                 170                 175

Val Val Arg Gln
            180
```

<210> SEQ ID NO 102
<211> LENGTH: 226
<212> TYPE: PRT
<213> ORGANISM: Artificial sequence
<220> FEATURE:
<223> OTHER INFORMATION: SHB(Env) domain

<400> SEQUENCE: 102

```
Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Ser Phe Leu Gly Gly Thr Thr Val Cys
        35                  40                  45

Leu Gly Gln Asn Ser Gln Ser Pro Thr Ser Asn His Ser Pro Thr Ser
    50                  55                  60

Cys Pro Pro Thr Cys Val Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Ser Thr Thr Ser Thr Gly Pro Cys Arg Thr Cys Thr Thr Pro Ala
        115                 120                 125

Gln Gly Thr Ser Met Tyr Pro Ser Cys Cys Cys Thr Lys Pro Ser Asp
    130                 135                 140

Gly Asn Cys Thr Cys Ile Pro Ile Pro Ser Ser Trp Ala Phe Gly Lys
145                 150                 155                 160

Phe Leu Trp Glu Trp Ala Ser Ala Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Asn Thr
        195                 200                 205

Leu Ser Pro Phe Leu Pro Leu Leu Pro Ile Phe Phe Tyr Leu Trp Val
    210                 215                 220

Tyr Ile
225
```

<210> SEQ ID NO 103
<211> LENGTH: 180
<212> TYPE: PRT
<213> ORGANISM: Artificial sequence
<220> FEATURE:

<223> OTHER INFORMATION: HBeAg domain

<400> SEQUENCE: 103

```
Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Asp Met Asp Ile
            20                  25                  30

Asp Pro Tyr Lys Glu Phe Gly Ala Ser Val Glu Leu Leu Ser Phe Leu
        35                  40                  45

Pro Ser Asp Phe Phe Pro Ser Val Arg Asp Leu Leu Asp Thr Ala Thr
    50                  55                  60

Ala Leu Tyr Arg Asp Ala Leu Glu Ser Pro Glu His Cys Thr Pro His
65                  70                  75                  80

His Thr Ala Leu Arg His Val Cys Leu Cys Trp Gly Asp Leu Met Asn
                85                  90                  95

Leu Ala Thr Trp Val Gly Thr Asn Leu Glu Asp Gln Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Asp Leu Val
    130                 135                 140

Leu Glu Tyr Leu Val Ser Phe Gly Val Trp Ile Arg Thr Pro Pro Ala
145                 150                 155                 160

Tyr Arg Pro Ser Asn Ala Pro Ile Leu Ser Thr Leu Pro Glu Thr Thr
                165                 170                 175

Val Val Arg Gln
            180
```

<210> SEQ ID NO 104
<211> LENGTH: 154
<212> TYPE: PRT
<213> ORGANISM: Artificial sequence
<220> FEATURE:
<223> OTHER INFORMATION: HBx domain

<400> SEQUENCE: 104

```
Met Ala Ala Arg Leu Cys Cys Gln Leu Asp Pro Ala Arg Asp Val Leu
1               5                   10                  15

Cys Leu Arg Pro Val Gly Ala Glu Ser Arg Gly Arg Pro Phe Ser Gly
            20                  25                  30

Pro Leu Gly Ala Leu Ser Ser Ser Ser Pro Pro Ala Val Pro Thr Asp
        35                  40                  45

His Gly Ala His Leu Ser Leu Arg Gly Leu Pro Val Cys Ala Phe Ser
    50                  55                  60

Ser Ala Gly Pro Cys Ala Leu Arg Phe Thr Ser Ala Arg Arg Met Glu
65                  70                  75                  80

Thr Thr Val Asn Ala His Gln Phe Leu Pro Lys Val Leu His Lys Arg
                85                  90                  95

Thr Leu Gly Leu Ser Ala Met Ser Thr Thr Asp Leu Glu Ala Tyr Phe
            100                 105                 110

Lys Asp Cys Leu Phe Lys Asp Trp Glu Glu Leu Gly Glu Glu Leu Arg
        115                 120                 125

Leu Lys Val Phe Val Leu Gly Gly Cys Arg His Lys Leu Val Cys Ala
    130                 135                 140

Pro Ala Pro Cys Asn Phe Phe Thr Ser Ala
145                 150
```

<210> SEQ ID NO 105
<211> LENGTH: 454
<212> TYPE: PRT
<213> ORGANISM: Artificial sequence
<220> FEATURE:
<223> OTHER INFORMATION: Pol domain

<400> SEQUENCE: 105

Gly Pro Cys Ala Glu His Gly Glu His His Ile Arg Ile Pro Arg Thr
1               5                   10                  15

Pro Ala Arg Val Thr Gly Gly Val Phe Leu Val Asp Lys Asn Pro His
            20                  25                  30

Asn Thr Ala Glu Ser Arg Leu Val Val Asp Phe Ser Gln Phe Ser Arg
        35                  40                  45

Gly Asn Tyr Arg Val Ser Trp Pro Lys Phe Ala Val Pro Asn Leu Gln
    50                  55                  60

Ser Leu Thr Asn Leu Leu Ser Ser Asn Leu Cys Trp Leu Ser Leu Asp
65                  70                  75                  80

Val Ser Ala Ala Phe Tyr His Leu Pro Leu His Pro Ala Ala Met Pro
                85                  90                  95

His Leu Leu Val Gly Ser Ser Gly Leu Ser Arg Tyr Val Ala Arg Leu
            100                 105                 110

Ser Ser Asn Ser Arg Ile Ile Asn His Gln His Gly Thr Leu Gln Asn
        115                 120                 125

Leu His Asp Ser Cys Ser Arg Asn Leu Tyr Val Ser Leu Leu Leu Leu
    130                 135                 140

Tyr Lys Thr Phe Gly Trp Lys Leu His Leu Tyr Ser His Pro Ile Ile
145                 150                 155                 160

Leu Gly Phe Arg Lys Ile Pro Met Gly Val Gly Leu Ser Pro Phe Leu
                165                 170                 175

Leu Ala Gln Phe Thr Ser Ala Ile Cys Ser Val Val Arg Arg Ala Phe
            180                 185                 190

Pro His Cys Leu Ala Phe Ser Gly Ala Lys Ser Val Gln His Leu Glu
        195                 200                 205

Ser Leu Phe Thr Ala Val Thr Asn Phe Leu Leu Ser Leu Gly Ile His
    210                 215                 220

Leu Asn Pro Asn Lys Thr Lys Arg Trp Gly Tyr Ser Leu Asn Phe Met
225                 230                 235                 240

Gly Tyr Val Ile Gly Ser Trp Gly Ser Leu Pro Gln Asp His Ile Arg
                245                 250                 255

His Lys Ile Lys Glu Cys Phe Arg Lys Leu Pro Val His Arg Pro Ile
            260                 265                 270

Asp Trp Lys Val Cys Gln Arg Ile Val Gly Leu Leu Gly Phe Ala Ala
        275                 280                 285

Pro Phe Thr Gln Cys Gly Tyr Pro Ala Leu Met Pro Leu Tyr Ala Cys
    290                 295                 300

Ile Gln Ser Lys Gln Ala Phe Thr Phe Ser Pro Thr Tyr Lys Ala Phe
305                 310                 315                 320

Leu Cys Lys Gln Tyr Leu Asn Leu Tyr Pro Val Ala Arg Gln Arg Pro
                325                 330                 335

Gly Leu Cys Gln Val Phe Ala Asp Ala Thr Pro Thr Gly Trp Gly Leu
            340                 345                 350

Val Met Gly His Gln Arg Met Arg Gly Thr Phe Ser Ser Arg Lys Tyr
        355                 360                 365

Thr Ser Phe Pro Trp Leu Leu Gly Cys Ala Ala Asn Trp Ile Leu Arg
    370                 375                 380

Gly Thr Ser Phe Val Tyr Val Pro Ser Ala Leu Asn Pro Ala Asp Asp
385                 390                 395                 400

Pro Ser Arg Gly Arg Leu Gly Pro Cys Arg Pro Leu Leu His Leu Pro
                405                 410                 415

Phe Arg Pro Thr Thr Gly Arg Thr Ser Leu Tyr Ala Asp Ser Pro Ser
            420                 425                 430

Val Pro Ser His Leu Pro Asp Arg Val His Phe Ala Ser Pro Leu His
        435                 440                 445

Val Ala Trp Arg Pro Pro
    450

<210> SEQ ID NO 106
<211> LENGTH: 1014
<212> TYPE: PRT
<213> ORGANISM: Artificial sequence
<220> FEATURE:
<223> OTHER INFORMATION: HBV design 1

<400> SEQUENCE: 106

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Ser Phe Leu Gly Gly Thr Thr Val Cys
        35                  40                  45

Leu Gly Gln Asn Ser Gln Ser Pro Thr Ser Asn His Ser Pro Thr Ser
    50                  55                  60

Cys Pro Pro Thr Cys Val Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Ser Thr Thr Ser Thr Gly Pro Cys Arg Thr Cys Thr Thr Pro Ala
        115                 120                 125

Gln Gly Thr Ser Met Tyr Pro Ser Cys Cys Cys Thr Lys Pro Ser Asp
    130                 135                 140

Gly Asn Cys Thr Cys Ile Pro Ile Pro Ser Ser Trp Ala Phe Gly Lys
145                 150                 155                 160

Phe Leu Trp Glu Trp Ala Ser Ala Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Asn Thr
        195                 200                 205

Leu Ser Pro Phe Leu Pro Leu Leu Pro Ile Phe Phe Tyr Leu Trp Val
    210                 215                 220

Tyr Ile Met Gln Leu Phe His Leu Cys Leu Ile Ile Ser Cys Ser Cys
225                 230                 235                 240

Pro Thr Val Gln Ala Ser Lys Leu Cys Leu Gly Trp Leu Trp Asp Met
                245                 250                 255

Asp Ile Asp Pro Tyr Lys Glu Phe Gly Ala Ser Val Glu Leu Leu Ser
            260                 265                 270

```
Phe Leu Pro Ser Asp Phe Phe Pro Ser Val Arg Asp Leu Leu Asp Thr
        275                 280                 285

Ala Thr Ala Leu Tyr Arg Asp Ala Leu Glu Ser Pro Glu His Cys Thr
    290                 295                 300

Pro His His Thr Ala Leu Arg His Val Cys Leu Cys Trp Gly Asp Leu
305                 310                 315                 320

Met Asn Leu Ala Thr Trp Val Gly Thr Asn Leu Glu Asp Gln Ala Ser
                325                 330                 335

Arg Asp Leu Val Val Ser Tyr Val Asn Thr Asn Met Gly Leu Lys Phe
            340                 345                 350

Arg Gln Leu Leu Trp Phe His Ile Ser Cys Leu Thr Phe Gly Arg Asp
        355                 360                 365

Leu Val Leu Glu Tyr Leu Val Ser Phe Gly Val Trp Ile Arg Thr Pro
    370                 375                 380

Pro Ala Tyr Arg Pro Ser Asn Ala Pro Ile Leu Ser Thr Leu Pro Glu
385                 390                 395                 400

Thr Thr Val Val Arg Gln Met Ala Ala Arg Leu Cys Cys Gln Leu Asp
                405                 410                 415

Pro Ala Arg Asp Val Leu Cys Leu Arg Pro Val Gly Ala Glu Ser Arg
            420                 425                 430

Gly Arg Pro Phe Ser Gly Pro Leu Gly Ala Leu Ser Ser Ser Ser Pro
        435                 440                 445

Pro Ala Val Pro Thr Asp His Gly Ala His Leu Ser Leu Arg Gly Leu
    450                 455                 460

Pro Val Cys Ala Phe Ser Ser Ala Gly Pro Cys Ala Leu Arg Phe Thr
465                 470                 475                 480

Ser Ala Arg Arg Met Glu Thr Thr Val Asn Ala His Gln Phe Leu Pro
                485                 490                 495

Lys Val Leu His Lys Arg Thr Leu Gly Leu Ser Ala Met Ser Thr Thr
            500                 505                 510

Asp Leu Glu Ala Tyr Phe Lys Asp Cys Leu Phe Lys Asp Trp Glu Glu
        515                 520                 525

Leu Gly Glu Glu Leu Arg Leu Lys Val Phe Val Leu Gly Gly Cys Arg
    530                 535                 540

His Lys Leu Val Cys Ala Pro Ala Pro Cys Asn Phe Phe Thr Ser Ala
545                 550                 555                 560

Gly Pro Cys Ala Glu His Gly Glu His His Ile Arg Ile Pro Arg Thr
                565                 570                 575

Pro Ala Arg Val Thr Gly Gly Val Phe Leu Val Asp Lys Asn Pro His
            580                 585                 590

Asn Thr Ala Glu Ser Arg Leu Val Val Asp Phe Ser Gln Phe Ser Arg
        595                 600                 605

Gly Asn Tyr Arg Val Ser Trp Pro Lys Phe Ala Val Pro Asn Leu Gln
    610                 615                 620

Ser Leu Thr Asn Leu Leu Ser Ser Asn Leu Cys Trp Leu Ser Leu Asp
625                 630                 635                 640

Val Ser Ala Ala Phe Tyr His Leu Pro Leu His Pro Ala Ala Met Pro
                645                 650                 655

His Leu Leu Val Gly Ser Ser Gly Leu Ser Arg Tyr Val Ala Arg Leu
            660                 665                 670

Ser Ser Asn Ser Arg Ile Ile Asn His Gln His Gly Thr Leu Gln Asn
        675                 680                 685
```

Leu His Asp Ser Cys Ser Arg Asn Leu Tyr Val Ser Leu Leu Leu Leu
690 695 700

Tyr Lys Thr Phe Gly Trp Lys Leu His Leu Tyr Ser His Pro Ile Ile
705 710 715 720

Leu Gly Phe Arg Lys Ile Pro Met Gly Val Gly Leu Ser Pro Phe Leu
725 730 735

Leu Ala Gln Phe Thr Ser Ala Ile Cys Ser Val Val Arg Arg Ala Phe
740 745 750

Pro His Cys Leu Ala Phe Ser Gly Ala Lys Ser Val Gln His Leu Glu
755 760 765

Ser Leu Phe Thr Ala Val Thr Asn Phe Leu Leu Ser Leu Gly Ile His
770 775 780

Leu Asn Pro Asn Lys Thr Lys Arg Trp Gly Tyr Ser Leu Asn Phe Met
785 790 795 800

Gly Tyr Val Ile Gly Ser Trp Gly Ser Leu Pro Gln Asp His Ile Arg
805 810 815

His Lys Ile Lys Glu Cys Phe Arg Lys Leu Pro Val His Arg Pro Ile
820 825 830

Asp Trp Lys Val Cys Gln Arg Ile Val Gly Leu Leu Gly Phe Ala Ala
835 840 845

Pro Phe Thr Gln Cys Gly Tyr Pro Ala Leu Met Pro Leu Tyr Ala Cys
850 855 860

Ile Gln Ser Lys Gln Ala Phe Thr Phe Ser Pro Thr Tyr Lys Ala Phe
865 870 875 880

Leu Cys Lys Gln Tyr Leu Asn Leu Tyr Pro Val Ala Arg Gln Arg Pro
885 890 895

Gly Leu Cys Gln Val Phe Ala Asp Ala Thr Pro Thr Gly Trp Gly Leu
900 905 910

Val Met Gly His Gln Arg Met Arg Gly Thr Phe Ser Ser Arg Lys Tyr
915 920 925

Thr Ser Phe Pro Trp Leu Leu Gly Cys Ala Ala Asn Trp Ile Leu Arg
930 935 940

Gly Thr Ser Phe Val Tyr Val Pro Ser Ala Leu Asn Pro Ala Asp Asp
945 950 955 960

Pro Ser Arg Gly Arg Leu Gly Pro Cys Arg Pro Leu Leu His Leu Pro
965 970 975

Phe Arg Pro Thr Thr Gly Arg Thr Ser Leu Tyr Ala Asp Ser Pro Ser
980 985 990

Val Pro Ser His Leu Pro Asp Arg Val His Phe Ala Ser Pro Leu His
995 1000 1005

Val Ala Trp Arg Pro Pro
1010

<210> SEQ ID NO 107
<211> LENGTH: 1021
<212> TYPE: PRT
<213> ORGANISM: Artificial sequence
<220> FEATURE:
<223> OTHER INFORMATION: HBV design 2

<400> SEQUENCE: 107

Ser Val Glu Leu Leu Ser Phe Leu Pro Ser Asp Phe Phe Pro Ser Val
1 5 10 15

Arg Asp Leu Leu Asp Thr Ala Thr Ala Leu Tyr Arg Asp Ala Leu Glu
20 25 30

-continued

```
Ser Pro Glu His Cys Thr Pro His His Thr Ala Leu Arg His Val Cys
        35                  40                  45

Leu Cys Trp Gly Asp Leu Met Asn Leu Ala Thr Trp Val Gly Thr Asn
    50                  55                  60

Leu Glu Asp Gln Ala Ser Arg Asp Leu Val Val Ser Tyr Val Asn Thr
65                  70                  75                  80

Asn Met Gly Leu Lys Phe Arg Gln Leu Leu Trp Phe His Ile Ser Cys
                85                  90                  95

Leu Thr Phe Gly Arg Asp Leu Val Leu Glu Tyr Leu Val Ser Phe Gly
            100                 105                 110

Val Trp Ile Arg Thr Pro Pro Ala Tyr Arg Pro Ser Asn Ala Pro Ile
        115                 120                 125

Leu Ser Thr Leu Pro Glu Thr Thr Val Val Arg Gln Arg Gly Arg Thr
    130                 135                 140

Ile Val Leu His Lys Arg Thr Leu Gly Leu Met Gly Gln Asn Leu Ser
145                 150                 155                 160

Thr Ser Asn Pro Leu Gly Phe Phe Pro Asp His Gln Leu Asp Pro Ala
                165                 170                 175

Phe Arg Ala Asn Thr Asn Asn Pro Asp Trp Asp Phe Asn Pro Asn Lys
            180                 185                 190

Asp Thr Trp Pro Asp Ala Asn Lys Val Gly Ala Gly Ala Phe Gly Leu
        195                 200                 205

Gly Phe Thr Pro Pro His Gly Gly Leu Leu Gly Trp Ser Pro Gln Ala
    210                 215                 220

Gln Gly Ile Met Gln Thr Leu Pro Ala Asn Pro Pro Pro Ala Ser Thr
225                 230                 235                 240

Asn Arg Gln Ser Gly Arg Gln Pro Thr Pro Leu Leu Pro Lys Val Leu
                245                 250                 255

His Lys Arg Thr Leu Met Pro Leu Ser Tyr Gln His Phe Arg Lys Leu
            260                 265                 270

Leu Leu Leu Asp Asn Glu Ala Gly Pro Leu Glu Glu Glu Leu Pro Arg
        275                 280                 285

Leu Ala Asp Glu Asp Leu Asn Arg Arg Val Ala Glu Asp Leu Asn Leu
    290                 295                 300

Gly Asn Leu Asn Val Ser Ile Pro Trp Thr His Lys Val Gly Asn Phe
305                 310                 315                 320

Thr Gly Leu Tyr Ser Ser Ser Val Pro Val Phe Asn Pro His Trp Lys
                325                 330                 335

Thr Pro Ser Phe Pro Asn Ile His Leu His Gln Asp Ile Ile Lys Lys
            340                 345                 350

Cys Glu Gln Phe Val Gly Pro Leu Thr Val Asn Glu Lys Arg Arg Leu
        355                 360                 365

Lys Leu Ile Met Pro Ala Arg Phe Tyr Pro Asn Phe Thr Lys Tyr Leu
    370                 375                 380

Pro Leu Asp Lys Gly Ile Lys Pro Tyr Tyr Pro Glu His Leu Val Asn
385                 390                 395                 400

His Tyr Phe His Thr Arg His Tyr Leu His Thr Leu Trp Lys Ala Gly
                405                 410                 415

Ile Leu Tyr Lys Arg Val Ser Thr His Ser Ala Ser Phe Cys Gly Ser
            420                 425                 430

Pro Tyr Ser Trp Glu Gln Glu Leu Gln His Gly Ala Glu Ser Phe His
        435                 440                 445

Gln Gln Ser Ser Gly Ile Leu Ser Arg Pro Ser Val Gly Ser Ser Leu
```

```
    450                 455                 460

Gln Ser Lys His Gln Gln Ser Arg Leu Gly Leu Gln Ser Gln Gln Gly
465                 470                 475                 480

His Leu Ala Arg Arg Gln Gln Gly Arg Ser Trp Ser Ile Arg Thr Arg
                485                 490                 495

Val His Pro Thr Ala Arg Arg Pro Ser Gly Val Glu Pro Ser Gly Ser
            500                 505                 510

Gly His Asn Ala Asn Leu Ala Ser Lys Ser Ala Ser Cys Leu Tyr Gln
        515                 520                 525

Ser Thr Val Arg Thr Ala Ala Tyr Pro Ala Val Ser Thr Ser Glu Asn
    530                 535                 540

His Ser Ser Ser Gly His Ala Val Glu Leu His Asn Leu Pro Pro Asn
545                 550                 555                 560

Ser Ala Arg Ser Gln Ser Glu Arg Pro Val Ser Pro Cys Trp Trp Leu
                565                 570                 575

Gln Phe Arg Asn Ser Lys Pro Cys Ser Asp Tyr Cys Leu Ser His Ile
            580                 585                 590

Val Asn Leu Leu Glu Asp Trp Gly Pro Cys His Lys Arg Thr Leu Gly
        595                 600                 605

Leu Ser Ala Met Ser Pro Pro Leu Arg Thr Thr His Pro Gln Ala Met
    610                 615                 620

Gln Trp Asn Ser Thr Thr Phe His Gln Thr Leu Gln Asp Pro Arg Val
625                 630                 635                 640

Arg Gly Leu Tyr Leu Pro Ala Gly Gly Ser Ser Ser Gly Thr Val Asn
                645                 650                 655

Pro Val Pro Thr Thr Ala Ser Pro Thr Leu Ser Thr Ser Ser Arg Ile
            660                 665                 670

Gly Asp Pro Ala Leu Asn Gln Phe Leu Pro Lys Val Leu His Lys Arg
        675                 680                 685

Ser Arg Gly Asn Tyr Arg Val Ser Trp Pro Lys Phe Ala Val Pro Asn
    690                 695                 700

Leu Gln Ser Leu Thr Asn Leu Leu Ser Ser Asn Leu Cys Trp Leu Ser
705                 710                 715                 720

Leu Asp Val Ser Ala Ala Phe Tyr His Leu Pro Leu His Pro Ala Ala
                725                 730                 735

Met Pro His Leu Leu Val Gly Ser Ser Gly Leu Ser Arg Tyr Val Ala
            740                 745                 750

Arg Leu Ser Ser Asn Ser Arg Ile Ile Asn His Gln His Gly Thr Leu
        755                 760                 765

Gln Asn Leu His Asp Ser Cys Ser Arg Asn Leu Tyr Val Ser Leu Leu
    770                 775                 780

Leu Leu Tyr Lys Thr Phe Gly Trp Lys Leu His Leu Tyr Ser His Pro
785                 790                 795                 800

Ile Ile Leu Gly Phe Arg Lys Ile Pro Met Gly Val Gly Leu Ser Pro
                805                 810                 815

Phe Leu Leu Ala Gln Phe Thr Ser Ala Ile Thr Val Asn Ala His Gln
            820                 825                 830

Phe Leu Pro Lys Gln Asn Ser Gln Ser Pro Thr Ser Asn His Ser Pro
        835                 840                 845

Thr Ser Cys Pro Pro Thr Cys Val Gly Tyr Arg Trp Met Cys Leu Arg
    850                 855                 860

Arg Phe Ile Ile Phe Leu Phe Ile Leu Leu Leu Cys Leu Ile Phe Leu
865                 870                 875                 880
```

Leu Val Leu Leu Asp Tyr Gln Gly Met Leu Pro Val Cys Pro Leu Ile
885 890 895

Pro Gly Ser Ser Thr Thr Ser Thr Gly Pro Cys Arg Thr Cys Thr Thr
900 905 910

Pro Ala Gln Gly Thr Ser Met Tyr Pro Ser Cys Cys Cys Thr Lys Pro
915 920 925

Ser Asp Gly Asn Cys Thr Cys Ile Pro Ile Pro Ser Ser Trp Ala Phe
930 935 940

Gly Lys Phe Leu Trp Glu Trp Ala Ser Ala Arg Phe Ser Trp Leu Ser
945 950 955 960

Leu Leu Val Pro Phe Val Gln Trp Phe Val Gly Leu Ser Pro Thr Val
965 970 975

Trp Leu Ser Val Ile Trp Met Met Trp Tyr Trp Gly Pro Ser Leu Tyr
980 985 990

Asn Thr Leu Ser Pro Phe Leu Pro Leu Leu Pro Ile Phe Phe Tyr Leu
995 1000 1005

Trp Val Tyr Ile Leu Ser Ala Met Ser Thr Thr Asp Leu
1010 1015 1020

<210> SEQ ID NO 108
<211> LENGTH: 532
<212> TYPE: PRT
<213> ORGANISM: Artificial sequence
<220> FEATURE:
<223> OTHER INFORMATION: HBV design 3

<400> SEQUENCE: 108

Met Gln Thr Asp Arg Thr Gly Glu Thr Ala Leu His Leu Ala Ala Arg
1 5 10 15

Tyr Ser Arg Ser Asp Phe Leu Pro Ser Asp Phe Phe Pro Ser Val Ala
20 25 30

Asp Ala Gly Val Trp Ile Arg Thr Pro Pro Ala Asp Asn Met Glu Tyr
35 40 45

Leu Val Ser Phe Gly Val Trp Pro Leu His Ala Ala Val Ser Ala Asp
50 55 60

Cys Trp Gly Glu Leu Met Thr Leu Arg Asn Arg Ala Thr Asp Leu Gly
65 70 75 80

Gly Pro Asn Leu Asp Asn Ile Leu Met His Asp Ile Leu Arg Ser Phe
85 90 95

Ile Pro Leu Leu Pro Leu Ile Leu Ala Ala Arg Leu Ala Val Ser Thr
100 105 110

Leu Pro Glu Thr Thr Val Val Arg Arg Ser His Ala Asp Val Phe Leu
115 120 125

Gly Gly Pro Pro Val Cys Leu Asp Asp Leu Phe Leu Leu Thr Arg Ile
130 135 140

Leu Thr Ile Ala Leu His Trp Ala Ala Ala Val Asn Asn Val Leu Thr
145 150 155 160

Phe Gly Arg Glu Thr Val Leu Glu Tyr Gly Ala Asn Lys Trp Leu Ser
165 170 175

Leu Leu Val Pro Phe Val Asn Asn Arg Phe Leu Lys Gln Gln Tyr Met
180 185 190

Asn Leu Pro Leu Phe Leu Ala Ala Arg Glu Gly Ser Tyr Glu Asp Leu
195 200 205

Leu Asp Thr Ala Ser Ala Leu Tyr Ala Asn Arg Phe Leu Ser Lys Gln
210 215 220

Tyr Met Asp Leu Asp His Met Thr Val Ser Thr Lys Leu Cys Lys Ile
225 230 235 240

Pro Arg Asp Leu Trp Phe His Ile Ser Cys Leu Thr Phe Ile Val Arg
245 250 255

Leu Leu Asp Leu Glu Val Ser Gln Thr Ser Lys Leu Thr Arg Gln Thr
260 265 270

Asp Arg Thr Gly Glu Thr Ala Leu His Leu Ala Ala Arg Tyr Ser Arg
275 280 285

Ser Asp Leu Thr Thr Val Pro Ala Ala Ser Leu Leu Ala Ala Asp Ala
290 295 300

Gly Leu Ser Arg Tyr Val Ala Arg Leu Asp Asn Met Lys Leu His Leu
305 310 315 320

Tyr Ser His Pro Ile Pro Leu His Ala Ala Val Ser Ala Asp Gly Leu
325 330 335

Ser Pro Thr Val Trp Leu Ser Val Arg Asn Arg Ala Thr Asp Leu Phe
340 345 350

Leu Leu Ser Leu Gly Ile His Leu Met His Asp Ser Leu Tyr Ala Asp
355 360 365

Ser Pro Ser Val Pro Leu Ile Leu Ala Ala Arg Leu Ala Val His Lys
370 375 380

Arg Thr Leu Gly Leu Ser Ala Met Ser His Ala Asp Val Thr Leu Cys
385 390 395 400

Ile Pro His Val Ala Val Asp Asp Leu Leu Leu Leu Lys Ala Thr Leu
405 410 415

Cys Ile Ala Leu His Trp Ala Ala Ala Val Asn Asn Val Gln Phe Leu
420 425 430

Pro Lys Val Leu His Lys Arg Gly Ala Asn Lys Ala Leu Met Pro Leu
435 440 445

Tyr Ala Cys Ile Asn Asn Arg Thr Val Asn Ala His Gln Phe Leu Pro
450 455 460

Lys Pro Leu Phe Leu Ala Ala Arg Glu Gly Ser Tyr Glu Leu Pro Lys
465 470 475 480

Val Leu His Lys Arg Thr Leu Ala Asn Arg Val Leu His Lys Arg Thr
485 490 495

Leu Gly Leu Asp His Met Leu Ser Ala Met Ser Thr Thr Asp Leu Pro
500 505 510

Arg Asp Leu Leu Val Pro Phe Val Gln Trp Phe Val Ile Val Arg Leu
515 520 525

Leu Asp Leu Glu
530

<210> SEQ ID NO 109
<211> LENGTH: 368
<212> TYPE: PRT
<213> ORGANISM: Artificial sequence
<220> FEATURE:
<223> OTHER INFORMATION: HBV design 4

<400> SEQUENCE: 109

Lys Lys Phe Leu Pro Ser Asp Phe Phe Pro Ser Val Lys Lys Cys Trp
1 5 10 15

Gly Glu Leu Met Thr Leu Lys Lys Gly Val Trp Ile Arg Thr Pro Pro
20 25 30

Ala Lys Lys Ser Thr Leu Pro Glu Thr Thr Val Val Arg Arg Lys Lys
35 40 45

```
Leu Thr Phe Gly Arg Glu Thr Val Leu Glu Tyr Lys Lys Asp Leu Leu
    50                  55                  60

Asp Thr Ala Ser Ala Leu Tyr Lys Lys Leu Trp Phe His Ile Ser Cys
65                  70                  75                  80

Leu Thr Phe Lys Lys Glu Tyr Leu Val Ser Phe Gly Val Trp Lys Lys
                85                  90                  95

Gly Gly Pro Asn Leu Asp Asn Ile Leu Lys Lys Leu Thr Thr Val Pro
            100                 105                 110

Ala Ala Ser Leu Leu Ala Lys Lys Ile Leu Arg Ser Phe Ile Pro Leu
        115                 120                 125

Leu Lys Lys Phe Leu Gly Gly Pro Pro Val Cys Leu Lys Lys Phe Leu
    130                 135                 140

Leu Thr Arg Ile Leu Thr Ile Lys Lys Trp Leu Ser Leu Leu Val Pro
145                 150                 155                 160

Phe Val Lys Lys Gly Leu Ser Pro Thr Val Trp Leu Ser Val Lys Lys
                165                 170                 175

Leu Leu Val Pro Phe Val Gln Trp Phe Val Lys Lys Phe Leu Lys Gln
            180                 185                 190

Gln Tyr Met Asn Leu Lys Lys Phe Leu Ser Lys Gln Tyr Met Asp Leu
        195                 200                 205

Lys Lys Thr Val Ser Thr Lys Leu Cys Lys Ile Lys Lys Gly Leu Ser
    210                 215                 220

Arg Tyr Val Ala Arg Leu Lys Lys Lys Leu His Leu Tyr Ser His Pro
225                 230                 235                 240

Ile Lys Lys Phe Leu Leu Ser Leu Gly Ile His Leu Lys Lys Ser Leu
                245                 250                 255

Tyr Ala Asp Ser Pro Ser Val Lys Lys Ala Leu Met Pro Leu Tyr Ala
            260                 265                 270

Cys Ile Lys Lys Leu Leu Leu Lys Ala Thr Leu Cys Ile Lys Lys Thr
        275                 280                 285

Leu Cys Ile Pro His Val Ala Val Lys Lys Val Leu His Lys Arg Thr
    290                 295                 300

Leu Gly Leu Lys Lys Leu Pro Lys Val Leu His Lys Arg Thr Leu Lys
305                 310                 315                 320

Lys His Lys Arg Thr Leu Gly Leu Ser Ala Met Lys Lys Gln Phe Leu
                325                 330                 335

Pro Lys Val Leu His Lys Arg Lys Lys Thr Val Asn Ala His Gln Phe
            340                 345                 350

Leu Pro Lys Lys Lys Leu Ser Ala Met Ser Thr Thr Asp Leu Lys Lys
        355                 360                 365
```

<210> SEQ ID NO 110
<211> LENGTH: 20
<212> TYPE: DNA
<213> ORGANISM: Artificial sequence
<220> FEATURE:
<223> OTHER INFORMATION: splice primer

<400> SEQUENCE: 110
tgccaagagt gacgtgtcca 20

<210> SEQ ID NO 111
<211> LENGTH: 21
<212> TYPE: DNA
<213> ORGANISM: Artificial sequence
<220> FEATURE:

<223> OTHER INFORMATION: splice probe

<400> SEQUENCE: 111
cccaggtcca actgcagccg g 21

<210> SEQ ID NO 112
<211> LENGTH: 12
<212> TYPE: DNA
<213> ORGANISM: Artificial sequence
<220> FEATURE:
<223> OTHER INFORMATION: Furin linker polypeptide

<400> SEQUENCE: 112
agagctaaga gg 12

<210> SEQ ID NO 113
<211> LENGTH: 11
<212> TYPE: PRT
<213> ORGANISM: Artificial sequence
<220> FEATURE:
<223> OTHER INFORMATION: HPV16-E6

<400> SEQUENCE: 113

His Leu Asp Lys Lys Gln Arg Phe His Asn Ile
1 5 10

<210> SEQ ID NO 114
<211> LENGTH: 10
<212> TYPE: PRT
<213> ORGANISM: Artificial sequence
<220> FEATURE:
<223> OTHER INFORMATION: HPV16-E6

<400> SEQUENCE: 114

Arg Trp Thr Gly Arg Cys Met Ser Cys Cys
1 5 10

<210> SEQ ID NO 115
<211> LENGTH: 15
<212> TYPE: PRT
<213> ORGANISM: Artificial sequence
<220> FEATURE:
<223> OTHER INFORMATION: HPV16-E6

<400> SEQUENCE: 115

Thr Thr Leu Glu Gln Gln Tyr Asn Lys Pro Leu Cys Asp Leu Leu
1 5 10 15

<210> SEQ ID NO 116
<211> LENGTH: 9
<212> TYPE: PRT
<213> ORGANISM: Artificial sequence
<220> FEATURE:
<223> OTHER INFORMATION: HPV16-E6

<400> SEQUENCE: 116

Ile Ser Glu Tyr Arg His Tyr Cys Tyr
1 5

<210> SEQ ID NO 117
<211> LENGTH: 9
<212> TYPE: PRT
<213> ORGANISM: Artificial sequence
<220> FEATURE:
<223> OTHER INFORMATION: HPV16-E6

<400> SEQUENCE: 117

Val Tyr Asp Phe Ala Phe Arg Asp Leu
1 5

<210> SEQ ID NO 118
<211> LENGTH: 10
<212> TYPE: PRT
<213> ORGANISM: Artificial sequence
<220> FEATURE:
<223> OTHER INFORMATION: HPV16-E6

<400> SEQUENCE: 118

Thr Ile His Asp Ile Ile Leu Glu Cys Val
1 5 10

<210> SEQ ID NO 119
<211> LENGTH: 9
<212> TYPE: PRT
<213> ORGANISM: Artificial sequence
<220> FEATURE:
<223> OTHER INFORMATION: HPV16-E6

<400> SEQUENCE: 119

Lys Leu Pro Gln Leu Cys Thr Glu Leu
1 5

<210> SEQ ID NO 120
<211> LENGTH: 10
<212> TYPE: PRT
<213> ORGANISM: Artificial sequence
<220> FEATURE:
<223> OTHER INFORMATION: HPV16-E6

<400> SEQUENCE: 120

Phe Ala Phe Arg Asp Leu Cys Ile Val Tyr
1 5 10

<210> SEQ ID NO 121
<211> LENGTH: 15
<212> TYPE: PRT
<213> ORGANISM: Artificial sequence
<220> FEATURE:
<223> OTHER INFORMATION: HPV16-E6

<400> SEQUENCE: 121

Leu Cys Ile Val Tyr Arg Asp Gly Asn Pro Tyr Ala Val Cys Asp
1 5 10 15

<210> SEQ ID NO 122
<211> LENGTH: 10
<212> TYPE: PRT
<213> ORGANISM: Artificial sequence
<220> FEATURE:
<223> OTHER INFORMATION: HPV16-E7

<400> SEQUENCE: 122

Leu Cys Val Gln Ser Thr His Val Asp Ile
1 5 10

<210> SEQ ID NO 123
<211> LENGTH: 10
<212> TYPE: PRT
<213> ORGANISM: Artificial sequence
<220> FEATURE:
<223> OTHER INFORMATION: HPV16-E7

<400> SEQUENCE: 123

-continued

Arg Thr Leu Glu Asp Leu Leu Met Gly Thr
1 5 10

<210> SEQ ID NO 124
<211> LENGTH: 8
<212> TYPE: PRT
<213> ORGANISM: Artificial sequence
<220> FEATURE:
<223> OTHER INFORMATION: HPV16-E7

<400> SEQUENCE: 124

Thr Leu Gly Ile Val Cys Pro Ile
1 5

<210> SEQ ID NO 125
<211> LENGTH: 9
<212> TYPE: PRT
<213> ORGANISM: Artificial sequence
<220> FEATURE:
<223> OTHER INFORMATION: HPV16-E7

<400> SEQUENCE: 125

Leu Leu Met Gly Thr Leu Gly Ile Val
1 5

<210> SEQ ID NO 126
<211> LENGTH: 9
<212> TYPE: PRT
<213> ORGANISM: Artificial sequence
<220> FEATURE:
<223> OTHER INFORMATION: HPV16-E7

<400> SEQUENCE: 126

Thr Leu His Glu Tyr Met Leu Asp Leu
1 5

<210> SEQ ID NO 127
<211> LENGTH: 10
<212> TYPE: PRT
<213> ORGANISM: Artificial sequence
<220> FEATURE:
<223> OTHER INFORMATION: HPV16-E7

<400> SEQUENCE: 127

Ala His Tyr Asn Ile Val Thr Phe Cys Cys
1 5 10

<210> SEQ ID NO 128
<211> LENGTH: 10
<212> TYPE: PRT
<213> ORGANISM: Artificial sequence
<220> FEATURE:
<223> OTHER INFORMATION: HPV16-E7

<400> SEQUENCE: 128

Tyr Met Leu Asp Leu Gln Pro Glu Thr Thr
1 5 10

<210> SEQ ID NO 129
<211> LENGTH: 9
<212> TYPE: PRT
<213> ORGANISM: Artificial sequence
<220> FEATURE:
<223> OTHER INFORMATION: HPV16-E7

<400> SEQUENCE: 129

Cys Asp Ser Thr Leu Arg Leu Cys Val 1 5

<210> SEQ ID NO 130
<211> LENGTH: 9
<212> TYPE: PRT
<213> ORGANISM: Artificial sequence
<220> FEATURE:
<223> OTHER INFORMATION: HPV16-E5

<400> SEQUENCE: 130

Tyr Ile Ile Phe Val Tyr Ile Pro Leu
1 5

<210> SEQ ID NO 131
<211> LENGTH: 10
<212> TYPE: PRT
<213> ORGANISM: Artificial sequence
<220> FEATURE:
<223> OTHER INFORMATION: HPV16-E5

<400> SEQUENCE: 131

Lys Leu Thr Asn Thr Gly Leu Tyr Asn Leu
1 5 10

<210> SEQ ID NO 132
<211> LENGTH: 9
<212> TYPE: PRT
<213> ORGANISM: Artificial sequence
<220> FEATURE:
<223> OTHER INFORMATION: HPV16-E5

<400> SEQUENCE: 132

Lys Cys Ile Asp Phe Tyr Ser Arg Ile
1 5

<210> SEQ ID NO 133
<211> LENGTH: 9
<212> TYPE: PRT
<213> ORGANISM: Artificial sequence
<220> FEATURE:
<223> OTHER INFORMATION: HPV16-E5

<400> SEQUENCE: 133

Phe Ala Phe Lys Asp Leu Phe Val Val
1 5

<210> SEQ ID NO 134
<211> LENGTH: 9
<212> TYPE: PRT
<213> ORGANISM: Artificial sequence
<220> FEATURE:
<223> OTHER INFORMATION: HPV16-E5

<400> SEQUENCE: 134

Asn Leu Leu Ile Arg Cys Leu Arg Cys
1 5

<210> SEQ ID NO 135
<211> LENGTH: 9
<212> TYPE: PRT
<213> ORGANISM: Artificial sequence
<220> FEATURE:
<223> OTHER INFORMATION: HPV16-E5

<400> SEQUENCE: 135

Lys Leu Pro Asp Leu Cys Thr Glu Leu
1 5

-continued

<210> SEQ ID NO 136
<211> LENGTH: 9
<212> TYPE: PRT
<213> ORGANISM: Artificial sequence
<220> FEATURE:
<223> OTHER INFORMATION: HPV16-E5

<400> SEQUENCE: 136

Glu Leu Thr Glu Val Phe Glu Phe Ala
1               5

<210> SEQ ID NO 137
<211> LENGTH: 10
<212> TYPE: PRT
<213> ORGANISM: Artificial sequence
<220> FEATURE:
<223> OTHER INFORMATION: HPV16-E5

<400> SEQUENCE: 137

Ser Leu Gln Asp Ile Glu Ile Thr Cys Val
1               5                   10

<210> SEQ ID NO 138
<211> LENGTH: 9
<212> TYPE: PRT
<213> ORGANISM: Artificial sequence
<220> FEATURE:
<223> OTHER INFORMATION: HPV16-E5

<400> SEQUENCE: 138

Lys Thr Val Leu Glu Leu Thr Glu Val
1               5

<210> SEQ ID NO 139
<211> LENGTH: 15
<212> TYPE: PRT
<213> ORGANISM: Artificial sequence
<220> FEATURE:
<223> OTHER INFORMATION: HPV18-E7

<400> SEQUENCE: 139

Asp Asp Leu Arg Ala Phe Gln Gln Leu Phe Leu Asn Thr Leu Ser
1               5                   10                  15

<210> SEQ ID NO 140
<211> LENGTH: 9
<212> TYPE: PRT
<213> ORGANISM: Artificial sequence
<220> FEATURE:
<223> OTHER INFORMATION: HPV18-E7

<400> SEQUENCE: 140

Phe Gln Gln Leu Phe Leu Asn Thr Leu
1               5

<210> SEQ ID NO 141
<211> LENGTH: 10
<212> TYPE: PRT
<213> ORGANISM: Artificial sequence
<220> FEATURE:
<223> OTHER INFORMATION: HPV18-E7

<400> SEQUENCE: 141

Gln Leu Phe Leu Asn Thr Leu Ser Phe Val
1               5                   10

-continued

<210> SEQ ID NO 142
<211> LENGTH: 15
<212> TYPE: PRT
<213> ORGANISM: Artificial sequence
<220> FEATURE:
<223> OTHER INFORMATION: HPV18-E7

<400> SEQUENCE: 142

Leu Phe Leu Asn Thr Leu Ser Phe Val Cys Pro Trp Cys Ala Ser
1 5 10 15

<210> SEQ ID NO 143
<211> LENGTH: 9
<212> TYPE: PRT
<213> ORGANISM: Artificial sequence
<220> FEATURE:
<223> OTHER INFORMATION: HPV18-E7

<400> SEQUENCE: 143

Thr Leu Gln Asp Ile Val Leu His Leu
1 5

<210> SEQ ID NO 144
<211> LENGTH: 20
<212> TYPE: PRT
<213> ORGANISM: Artificial sequence
<220> FEATURE:
<223> OTHER INFORMATION: HPV18-E7

<400> SEQUENCE: 144

Ser Glu Glu Glu Asn Asp Glu Ile Asp Gly Val Asn His Gln His Leu
1 5 10 15

Pro Ala Arg Arg
20

<210> SEQ ID NO 145
<211> LENGTH: 9
<212> TYPE: PRT
<213> ORGANISM: Artificial sequence
<220> FEATURE:
<223> OTHER INFORMATION: Agonist peptides

<400> SEQUENCE: 145

Lys Leu Pro Gln Leu Cys Thr Glu Val
1 5

<210> SEQ ID NO 146
<211> LENGTH: 10
<212> TYPE: PRT
<213> ORGANISM: Artificial sequence
<220> FEATURE:
<223> OTHER INFORMATION: Agonist peptides

<400> SEQUENCE: 146

Gln Leu Tyr Asn Lys Pro Leu Cys Asp Val
1 5 10

<210> SEQ ID NO 147
<211> LENGTH: 10
<212> TYPE: PRT
<213> ORGANISM: Artificial sequence
<220> FEATURE:

-continued

<223> OTHER INFORMATION: Agonist peptides

<400> SEQUENCE: 147

```
Arg Thr Leu Glu Asp Leu Leu Met Gly Val
1               5                   10
```